US006248562B1

(12) United States Patent
Dunn et al.

(10) Patent No.: US 6,248,562 B1
(45) **Date of Patent: *Jun. 19, 2001**

(54) CHIMERIC PROTEINS COMPRISING BORRELIA POLYPEPTIDES AND USES THEREFOR

(75) Inventors: John J. Dunn, Bellport; Benjamin J. Luft, Port Jefferson, both of NY (US)

(73) Assignees: Research Foundation State University of New York, Stony Brook; Brookhaven Science Associates, Upton, both of NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/235,836

(22) Filed: Apr. 29, 1994

Related U.S. Application Data

(63) Continuation-in-part of application No. 08/148,191, filed on Nov. 1, 1993, now abandoned.

(51) Int. Cl.[7] .................................................... A61K 39/02

(52) U.S. Cl. .................. 435/69.3; 424/184.1; 424/234.1; 424/185.1; 424/190.1; 424/192.1; 424/203.1; 424/263.1; 435/69.1; 435/69.7; 435/71.1; 530/350

(58) Field of Search ......................... 530/350; 424/263.1, 424/ 184.1, 234.1, 185.1, 190.1, 192.1, 203.1; 435/69.1, 69.3, 69.7, 71.1

(56) References Cited

U.S. PATENT DOCUMENTS

| | | | | |
|---|---|---|---|---|
| 5,217,872 | | 6/1993 | Doward et al. | 435/7.32 |
| 5,523,089 | * | 6/1996 | Bergstrom et al. | 424/262.1 |
| 5,747,294 | * | 5/1998 | Flavell et al. | 435/70.21 |
| 5,777,095 | * | 7/1998 | Barbour et al. | 536/23.7 |

FOREIGN PATENT DOCUMENTS

| | | | | |
|---|---|---|---|---|
| 0 418 827 A1 | | 3/1991 | (DE) | A61K/39/40 |
| 0 492 964 A2 | | 7/1992 | (EP) | C12N/15/31 |
| 0 522 560 A2 | | 1/1993 | (EP) | C12N/15/31 |
| 540457 | * | 5/1993 | (EP) . | |
| WO 94/20536 | | 9/1994 | (EP) | C07K/13/00 |
| WO 90/04411 | | 5/1990 | (WO) | A61K/39/02 |
| WO919870 | * | 7/1991 | (WO) | A61K/39/00 |
| WO 91/09870 | | 7/1991 | (WO) | C01K/13/00 |
| WO 91/13630 | | 9/1991 | (WO) | A61K/39/00 |
| WO 92/00055 | | 1/1992 | (WO) | C12N/15/31 |
| 92/00055 | * | 9/1992 | (WO) | C12N/15/31 |
| 9304175 | * | 3/1993 | (WO) . | |
| WO 93/04175 | | 3/1993 | (WO) | C12N/15/31 |
| WO 93/08286 | | 4/1993 | (WO) | C12N/15/31 |
| WO 93/08299 | | 4/1993 | (WO) | C12P/21/06 |
| WO 93/08306 | | 4/1993 | (WO) | C12Q/1/68 |

(List continued on next page.)

OTHER PUBLICATIONS

McGrath et al Vaccine 93, Presented at the annual meeting Sep. 1992, pp. 365–370, 1993.*
Sears et al J. Immunology 147:1995–2000, 1991.*
Kitten et al J Bacteriology 175:2516–2522, 1993.*
Rosa et al Mol. Microbiology 6:3031–3040, 1992.*
Schubach et al Infection & Immunity 59: 1911–1915, 1991.*
Wilske et al Med. Microbiol Immunol. 181:191–201, 1992.*
Data base Searcher 12 pages.*
Wallich et al Infection & Immunity 60:4856–4866, 1992.*
Wilske et al Journal of Clinical Microbiology 31: 340–350 (Feb. 1993).*
France et al. Biochimica et Biophysica Acta 1202(2) 287–296, 1993.*
Bockenstedt, L. K., et al., "Inability of Truncated Recombinant Osp A Proteins To Elicit Protective Immunity to *Borrelia burgdorferi* in Mice," *J. Immun.*, 151(2):900–906 (1993).
U.S. Ser. No. 664,731, Simpson et al., filed Mar. 5, 1991.
Rosa, P.A., et al., "Recombinant between genes encoding major outer surface proteins A and B of *Borrelia burgdorferi*", Mol. Microbiology 6(20) : 3031–3040.
McGrath, B.C., et al., "Biochemical and biophysical characterization of the major outer surface protein from North American and European isolates of *Borrelia burgdorferi*", Vaccines 93:365–370 (1993).
Kitten, T., et al., "Intragenic recombination and a chimeric outer membrane protein in the relapsing fever agent *Borrelia hermsii*", J. Bacteriology, 175(9): 2516–2522 (1993).

Erdile, L. F. et al., "Role of Attached Lipid in Immunogenicity of *Borrelia burgdorferi* OspA," *Infection and Immunity*, 61(1):81–90 (1993).

Fikrig, E. et al., "Elimination of *Borrelia burgdorferi* from vector ticks feeding on OspA–immunized mice," *Proc. Natl. Acad. Sci. USA*, 89:5418–5421 (1992).

Fikrig, E. et al., "Long–Term Protection of Mice from Lyme Disease by Vaccination with OspA," *Infection and Immunity*, 60(3):773–777 (1992).

Fikrig, E. et al., "Protection of Mice Against the Lyme Disease Agent by Immunizing with Recombinant OspA," *Science*, 250:553–556 (1990).

(List continued on next page.)

*Primary Examiner*—Phuong T. Bui
(74) *Attorney, Agent, or Firm*—Hamilton, Brook, Smith and Reynolds, P.C.

(57) ABSTRACT

Chimeric nucleic acids encoding chimeric Borrelia proteins consisting of at least two antigenic polypeptides from corresponding and/or non-corresponding proteins from the same and/or different species of Borrelia, are disclosed. Chimeric proteins encoded by the nucleic acid sequences are also disclosed. The chimeric proteins are useful as vaccine immunogens against Lyme borreliosis, as well as for immunodiagnostic reagents.

5 Claims, 135 Drawing Sheets

FOREIGN PATENT DOCUMENTS

WO 93/10237    5/1993  (WO) .............................. C12N/15/31

OTHER PUBLICATIONS

Fikrig, E. et al., "*Borrelia burgdorferi* Strain 25015: Characterization of outer Surface Protein A and Vaccination Against Infection," *J. Immunol.*, 148(7):2256–2260 (1992).

France, L. L. et al., "Structural analysis of an outer surface protein from the Lyme disease spirochete, *Borrelia burgdorferi*, using circular dichroism and fluorescence spectroscopy," *Biochimica et Biophysica Acta*, 1120:59–68 (1992).

Howe, T. R. et al., "Organization of Genes Encoding Two Outer Membrane Proteins of the Lyme Disease Agent *Borrelia burgdorferi* within a Single Transcriptional Unit," *Infection and Immunity*, 54(1):207–212 (1986).

Johnson, R. C. et al., "Active Immunization of Hamsters against Experimental Infection with *Borrelia burgdorferi*," *Infection and Immunity*, 54(3):897–898 (1986).

Johnson, R. C., et al., "Passive Immunization of Hamsters against Experimental Infection with the Lyme Disease Spirochete," *Infection and Immunity*, 53(3):713–714 (1986).

Johnson, R. C. et al., "Vaccination of Hamsters Against Experimental Infection with *Borrelia burgdorferi*," *Zbl. Bakt. Hyg. A*, 263:45–48 (1986).

Johnson, R. C. et al., "Experimental Infection of the Hamster with *Borrelia burgdorferi*," *Annals New York Acad. of Sciences*, 539 pp. 258–263 (1988).

Lovrich, S. D. et al., "Seroprotective Groups among Isolates of *Borrelia burgdorferi*," *Infection and Immunity*, 61(10):4367–4374 (1993).

Preac–Mursic, V. et al., "Active Immunization with pC Protein of *Borrelia burgdorferi* Protects Gerbils against B. burgdorferi Infection," *Infection*, 20(6):342–349 (1992).

Schaible, U. E. et al., "Monoclonal antibodies specific for the outer surface protein A (OspA) of *Borrelia burgdorferi* prevent Lyme borreliosis in severe combined immunodeficiency (scid) mice," *Proc. Natl. Acad. Sci. USA*, 87:3768–3772 (1990).

Sears, J. E. et al., "Molecular Mapping of Osp–A Medicated Immunity Against *Borrelia burgdorferi*, The Agent of Lyme Disease," *J. Immunol.*, 147(6):1995–2000 (1991).

Simon, M.M. et al., "A mouse model for *Borrelia burgdorferi* infection: approach to a vaccine against Lyme disease," *Immunology Today*, 12(1):11–16 (1991).

Simon, M. M. et al., "Recombinant Outer Surface Protein A from *Borrelia burgdorferi* Induces Antibodies Protective against Spirochetal Infection in Mice," *J. Infectious Diseases*, 164:123–132 (1991).

Simon, M. et al., "Spirochetes: vaccines, animal models and diagnostics," *Res. Microbiol.*, 143:641–647 (1992).

Stover, C. Kendall et al., "Protective Immunity Elicited by Recombinant Bacille Calmette–Guerin (BCG) Expressing Outer Surface Protein A (OspA) Lipoprotein: A Candidate Lyme Disease Vaccine," *J. Exp. Med.*, 178:197–209 (1993).

Howe, T. R. et al., "A Single Recombinant Plasmid Expressing Two Major Outer Surface Proteins of the Lyme Disease Spirochete," *Science*, 227:645–46 (1985).

\* cited by examiner

Domain 1

| | 34 | 35 | 36 | 37 | 38 | 39 | 40 | 41 |
|---|---|---|---|---|---|---|---|---|
| A-B31    | L | P | G | E | M | K | V | L |
| A-TRo    | L | P | G | E | M | K | V | L |
| A-K48    | L | P | G | G | M | T | V | L |
| A-DK29   | L | P | G | G | M | T | V | L |
| A-P/Gau  | L | P | G | E | M | K | V | L |
| A-PKo    | L | P | G | E | M | K | V | L |
| A-IP3    | L | P | G | E | I | K | V | L |
| A-IP90   | L | P | G | G | M | G | V | L |
| A-25015  | L | P | G | E | M | K | V | L |

Domain 2

| | 65 | 66 | 67 | 68 | 69 | 70 | 71 | 72 | 73 | 74 | 75 |
|---|---|---|---|---|---|---|---|---|---|---|---|
| A-B31    | G | T | S | D | K | N | N | G | S | G | V |
| A-TRo    | G | T | S | D | K | S | N | G | S | G | T |
| A-K48    | G | T | S | D | K | N | N | G | S | G | T |
| A-DK29   | G | T | S | D | K | N | N | G | S | G | T |
| A-P/Gau  | G | T | S | D | K | D | N | G | S | G | T |
| A-PKo    | G | T | S | D | K | D | N | G | S | G | T |
| A-IP3    | G | T | S | D | K | D | N | G | S | G | V |
| A-IP90   | G | T | S | D | K | N | N | G | S | G | T |
| A-25015  | G | T | S | D | K | N | N | G | S | G | V |

Domain 3

| | 190 | 200 | 210 | 220 |
|---|---|---|---|---|
| A-B31    | NISKSGEVSVELNDTDSSAATKKTAAWNSGT |
| A-TRo    | HIPNSGEITVELNDSNSTQATKKTGKWDSNT |
| A-K48    | NILKSGEITVALDDDSDTTQATKKTGKWDSKT |
| A-DK29   | NILKSGEITAALDDSDTTRATKKTGKWDSKT |
| A-P/Gau  | EIAKSGEVTVALNDTNTTQATKKTGAWDSKT |
| A-PKo    | EIAKSGEVTTVALNDTNTTQATKKTGAWDSKT |
| A-IP3    | EIAKSGEVTVALNDTNTTQATKKTGAWDSKT |
| A-IP90   | HISNSGEITVELNDSDTTQATKKTGTWDSKT |
| A-25015  | HISKSGEVTAELNDTDSTQATKKTGKWDAGT |

Domain 4

| | 250 | 260 | 270 |
|---|---|---|---|
| A-B31    | SNGTKLEGSAVEITKLDEIKN |
| A-TRo    | SAGTNLEGNAVEIKTLDELKN |
| A-K48    | SAGTNLEGKAVEITTLKELKN |
| A-DK29   | SAGTNLEGKAVEITTLKELKN |
| A-P/Gau  | SAGTNLEGTAVEITKLDELKN |
| A-PKo    | SAGTNLEGTAVEIKTLDELKN |
| A-IP3    | SAGTNLEGTAVEIKTLDELKN |
| A-IP90   | SAGTNLEGKAVEITTLKELKN |
| A-25015  | SAGTNLEGTAVEIKTLDEIKN |

Figure 2

Fig.4 Protein sequence of OspAs from B31, K48 and the site-directed mutants from amino acids 200-220.

↓

B31:      ELNDTDSSAATKKTAAWNSGT
K48:      ALDDSDTTQATKKTGKWDSKT

613:      ELND__SD__I__SAATKKTAAWNSGT
625:      ELNDTDSSAATKKT__GK__WNSGT
640:      ELNDTDSSAATKKTAAW__DS__K__T
613/625:  ELND__SD__I__SAATKKT__GK__WNSGT
613/640:  ELND__SD__I__SAATKKTAAW__DS__K__T

Figure 4

OSP A B-31
Sequence Range: 1 to 822

```
              10           20           30           40
           .   *     .  *     .  *     .  *     .
     ATG AAA AAA TAT TTA TTG GGA ATA GGT CTA ATA TTA GCC TTA ATA GCA
     TAC TTT TTT ATA AAT AAC CCT TAT CCA GAT TAT AAT CGG AAT TAT CGT
     Met Lys Lys Tyr Leu Leu Gly Ile Gly Leu Ile Leu Ala Leu Ile Ala>

50           60           70           80           90
        *     .  *     .  *     .  *     .  *     .  *
     TGT AAG CAA AAT GTT AGC AGC CTT GAC GAG AAA AAC AGC GTT TCA GTA
     ACA TTC GTT TTA CAA TCG TCG GAA CTG CTC TTT TTG TCG CAA AGT CAT
     Cys Lys Gln Asn Val Ser Ser Leu Asp Glu Lys Asn Ser Val Ser Val>

100          110          120          130          140
        *     .  *     .  *     .  *     .  *     .  *
     GAT TTG CCT GGT GAA ATG AAA GTT CTT GTA AGC AAA GAA AAA AAC AAA
     CTA AAC GGA CCA CTT TAC TTT CAA GAA CAT TCG TTT CTT TTT TTG TTT
     Asp Leu Pro Gly Glu Met Lys Val Leu Val Ser Lys Glu Lys Asn Lys>

150          160          170          180          190
        *     .  *     .  *     .  *     .  *     .  *
     GAC GGC AAG TAC GAT CTA ATT GCA ACA GTA GAC AAG CTT GAG CTT AAA
     CTG CCG TTC ATG CTA GAT TAA CGT TGT CAT CTG TTC GAA CTC GAA TTT
     Asp Gly Lys Tyr Asp Leu Ile Ala Thr Val Asp Lys Leu Glu Leu Lys>

200          210          220          230          240
        *     .  *     .  *     .  *     .  *     .  *
     GGA ACT TCT GAT AAA AAC AAT GGA TCT GGA GTA CTT GAA GGC GTA AAA
     CCT TGA AGA CTA TTT TTG TTA CCT AGA CCT CAT GAA CTT CCG CAT TTT
     Gly Thr Ser Asp Lys Asn Asn Gly Ser Gly Val Leu Glu Gly Val Lys>

250          260          270          280
        *     .  *     .  *     .  *     .  *     .
     GCT GAC AAA AGT AAA GTA AAA TTA ACA ATT TCT GAC GAT CTA GGT CAA
     CGA CTG TTT TCA TTT CAT TTT AAT TGT TAA AGA CTG CTA GAT CCA GTT
     Ala Asp Lys Ser Lys Val Lys Leu Thr Ile Ser Asp Asp Leu Gly Gln>

290          300          310          320          330
        *     .  *     .  *     .  *     .  *     .  *
     ACC ACA CTT GAA GTT TTC AAA GAA GAT GGC AAA ACA CTA GTA TCA AAA
     TGG TGT GAA CTT CAA AAG TTT CTT CTA CCG TTT TGT GAT CAT AGT TTT
     Thr Thr Leu Glu Val Phe Lys Glu Asp Gly Lys Thr Leu Val Ser Lys>

340          350          360          370          380
        *     .  *     .  *     .  *     .  *     .  *
     AAA GTA ACT TCC AAA GAC AAG TCA TCA ACA GAA GAA AAA TTC AAT GAA
     TTT CAT TGA AGG TTT CTG TTC AGT AGT TGT CTT CTT TTT AAG TTA CTT
     Lys Val Thr Ser Lys Asp Lys Ser Ser Thr Glu Glu Lys Phe Asn Glu>
```

Figure 7A

```
      390         400         410         420         430
       *           *           *           *           *
AAA GGT GAA GTA TCT GAA AAA ATA ATA ACA AGA GCA GAC GGA ACC AGA
TTT CCA CTT CAT AGA CTT TTT TAT TAT TGT TCT CGT CTG CCT TGG TCT
Lys Gly Glu Val Ser Glu Lys Ile Ile Thr Arg Ala Asp Gly Thr Arg>

440         450         460         470         480
           *           *           *           *           *
CTT GAA TAC ACA GGA ATT AAA AGC GAT GGA TCT GGA AAA GCT AAA GAG
GAA CTT ATG TGT CCT TAA TTT TCG CTA CCT AGA CCT TTT CGA TTT CTC
Leu Glu Tyr Thr Gly Ile Lys Ser Asp Gly Ser Gly Lys Ala Lys Glu>

490         500         510         520
               *           *           *           *
GTT TTA AAA GGC TAT GTT CTT GAA GGA ACT CTA ACT GCT GAA AAA ACA
CAA AAT TTT CCG ATA CAA GAA CTT CCT TGA GAT TGA CGA CTT TTT TGT
Val Leu Lys Gly Tyr Val Leu Glu Gly Thr Leu Thr Ala Glu Lys Thr>

530         540         550         560         570
  *           *           *           *           *
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser>

580         590         600         610         620
      *           *           *           *           *
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

630         640         650         660         670
          *           *           *           *           *
GCT ACT AAA AAA ACT GCA GCT TGG AAT TCA GGC ACT TCA ACT TTA ACA
CGA TGA TTT TTT TGA CGT CGA ACC TTA AGT CCG TGA AGT TGA AAT TGT
Ala Thr Lys Lys Thr Ala Ala Trp Asn Ser Gly Thr Ser Thr Leu Thr>

680         690         700         710         720
              *           *           *           *           *
ATT ACT GTA AAC AGT AAA AAA ACT AAA GAC CTT GTG TTT ACA AAA GAA
TAA TGA CAT TTG TCA TTT TTT TGA TTT CTG GAA CAC AAA TGT TTT CTT
Ile Thr Val Asn Ser Lys Lys Thr Lys Asp Leu Val Phe Thr Lys Glu>

730         740         750         760
           *           *           *           *
AAC ACA ATT ACA GTA CAA CAA TAC GAC TCA AAT GGC ACC AAA TTA GAG
TTG TGT TAA TGT CAT GTT GTT ATG CTG AGT TTA CCG TGG TTT AAT CTC
Asn Thr Ile Thr Val Gln Gln Tyr Asp Ser Asn Gly Thr Lys Leu Glu>

770         780         790         800         810
 *           *           *           *           *
GGG TCA GCA GTT GAA ATT ACA AAA CTT GAT GAA ATT AAA AAC GCT TTA
CCC AGT CGT CAA CTT TAA TGT TTT GAA CTA CTT TAA TTT TTG CGA AAT
Gly Ser Ala Val Glu Ile Thr Lys Leu Asp Glu Ile Lys Asn Ala Leu>

820
  *
AAA TAA
TTT ATT
Lys ***>
```

Figure 7B

OSPA K48

```
         *    *    *    *    *    *    *    *    *
        ATG  AAA  AAA  TAT  TTA  TTG  GGA  ATA  GGT  CTA  ATA  TTA  GCC  TTA  ATA  GCA
        TAC  TTT  TTT  ATA  AAT  AAC  CCT  TAT  CCA  GAT  TAT  AAT  CGG  AAT  TAT  CGT
        Met  Lys  Lys  Tyr  Leu  Leu  Gly  Ile  Gly  Leu  Ile  Leu  Ala  Leu  Ile  Ala>

50             60             70             80             90
         *    *    *    *    *    *    *    *    *    *
        TGT  AAG  CAA  AAT  GTT  AGC  AGC  CTT  GAT  GAA  AAA  AAT  AGC  GTT  TCA  GTA
        ACA  TTC  GTT  TTA  CAA  TCG  TCG  GAA  CTA  CTT  TTT  TTA  TCG  CAA  AGT  CAT
        Cys  Lys  Gln  Asn  Val  Ser  Ser  Leu  Asp  Glu  Lys  Asn  Ser  Val  Ser  Val>

100            110            120            130            140
         *    *    *    *    *    *    *    *    *
        GAT  TTA  CCT  GGT  GGA  ATG  ACA  GTT  CTT  GTA  AGT  AAA  GAA  AAA  GAC  AAA
        CTA  AAT  GGA  CCA  CCT  TAC  TGT  CAA  GAA  CAT  TCA  TTT  CTT  TTT  CTG  TTT
        Asp  Leu  Pro  Gly  Gly  Met  Thr  Val  Leu  Val  Ser  Lys  Glu  Lys  Asp  Lys>

150            160            170            180            190
         *    *    *    *    *    *    *    *    *    *
        GAC  GGT  AAA  TAC  AGT  CTA  GAG  GCA  ACA  GTA  GAC  AAG  CTT  GAG  CTT  AAA
        CTG  CCA  TTT  ATG  TCA  GAT  CTC  CGT  TGT  CAT  CTG  TTC  GAA  CTC  GAA  TTT
        Asp  Gly  Lys  Tyr  Ser  Leu  Glu  Ala  Thr  Val  Asp  Lys  Leu  Glu  Leu  Lys>

200            210            220            230            240
         *    *    *    *    *    *    *    *    *    *
        GGA  ACT  TCT  GAT  AAA  AAC  AAC  GGT  TCT  GGA  ACA  CTT  GAA  GGT  GAA  AAA
        CCT  TGA  AGA  CTA  TTT  TTG  TTG  CCA  AGA  CCT  TGT  GAA  CTT  CCA  CTT  TTT
        Gly  Thr  Ser  Asp  Lys  Asn  Asn  Gly  Ser  Gly  Thr  Leu  Glu  Gly  Glu  Lys>

250            260            270            280
         *    *    *    *    *    *    *    *    *
        ACT  GAC  AAA  AGT  AAA  GTA  AAA  TTA  ACA  ATT  GCT  GAT  GAC  CTA  AGT  CAA
        TGA  CTG  TTT  TCA  TTT  CAT  TTT  AAT  TGT  TAA  CGA  CTA  CTG  GAT  TCA  GTT
        Thr  Asp  Lys  Ser  Lys  Val  Lys  Leu  Thr  Ile  Ala  Asp  Asp  Leu  Ser  Gln>

290            300            310            320            330
         *    *    *    *    *    *    *    *    *    *
        ACT  AAA  TTT  GAA  ATT  TTC  AAA  GAA  GAT  GCC  AAA  ACA  TTA  GTA  TCA  AAA
        TGA  TTT  AAA  CTT  TAA  AAG  TTT  CTT  CTA  CGG  TTT  TGT  AAT  CAT  AGT  TTT
        Thr  Lys  Phe  Glu  Ile  Phe  Lys  Glu  Asp  Ala  Lys  Thr  Leu  Val  Ser  Lys>

340            350            360            370            380
         *    *    *    *    *    *    *    *    *
        AAA  GTA  ACC  CTT  AAA  GAC  AAG  TCA  TCA  ACA  GAA  GAA  AAA  TTC  AAC  GAA
        TTT  CAT  TGG  GAA  TTT  CTG  TTC  AGT  AGT  TGT  CTT  CTT  TTT  AAG  TTG  CTT
        Lys  Val  Thr  Leu  Lys  Asp  Lys  Ser  Ser  Thr  Glu  Glu  Lys  Phe  Asn  Glu>
```

Figure 8A

OSP A K48

```
        390           400           410           420           430
    *     *       *     *       *     *       *     *       *     *
AAG GGT GAA ACA TCT GAA AAA ACA ATA GTA AGA GCA AAT GGA ACC AGA
TTC CCA CTT TGT AGA CTT TTT TGT TAT CAT TCT CGT TTA CCT TGG TCT
Lys Gly Glu Thr Ser Glu Lys Thr Ile Val Arg Ala Asn Gly Thr Arg>

440           450           460           470           480
    *     *       *     *       *     *       *     *       *     *
CTT GAA TAC ACA GAC ATA AAA AGC GAT GGA TCC GGA AAA GCT AAA GAA
GAA CTT ATG TGT CTG TAT TTT TCG CTA CCT AGG CCT TTT CGA TTT CTT
Leu Glu Tyr Thr Asp Ile Lys Ser Asp Gly Ser Gly Lys Ala Lys Glu>

490           500           510           520
    *     *       *     *       *     *       *     *       *
GTT TTA AAA GAC TTT ACT CTT GAA GGA ACT CTA GCT GCT GAC GGC AAA
CAA AAT TTT CTG AAA TGA GAA CTT CCT TGA GAT CGA CGA CTG CCG TTT
Val Leu Lys Asp Phe Thr Leu Glu Gly Thr Leu Ala Ala Asp Gly Lys>

530       540           550           560           570
    *     *       *     *       *     *       *     *       *
ACA ACA TTG AAA GTT ACA GAA GGC ACT GTT GTT TTA AGC AAG AAC ATT
TGT TGT AAC TTT CAA TGT CTT CCG TGA CAA CAA AAT TCG TTC TTG TAA
Thr Thr Leu Lys Val Thr Glu Gly Thr Val Val Leu Ser Lys Asn Ile>

580           590           600           610           620
    *     *       *     *       *     *       *     *       *     *
TTA AAA TCC GGA GAA ATA ACA GTT GCA CTT GAT GAC TCT GAC ACT ACT
AAT TTT AGG CCT CTT TAT TGT CAA CGT GAA CTA CTG AGA CTG TGA TGA
Leu Lys Ser Gly Glu Ile Thr Val Ala Leu Asp Asp Ser Asp Thr Thr>

630           640           650           660           670
    *     *       *     *       *     *       *     *       *     *
CAG GCT ACT AAA AAA ACT GGA AAA TGG GAT TCA AAA ACT TCC ACT TTA
GTC CGA TGA TTT TTT TGA CCT TTT ACC CTA AGT TTT TGA AGG TGA AAT
Gln Ala Thr Lys Lys Thr Gly Lys Trp Asp Ser Lys Thr Ser Thr Leu>

680           690           700           710           720
    *     *       *     *       *     *       *     *       *     *
ACA ATT AGT GTG AAT AGC CAA AAA ACC AAA AAC CTT GTA TTC ACA AAA
TGT TAA TCA CAC TTA TCG GTT TTT TGG TTT TTG GAA CAT AAG TGT TTT
Thr Ile Ser Val Asn Ser Gln Lys Thr Lys Asn Leu Val Phe Thr Lys>

730           740           750           760
    *     *       *     *       *     *       *     *       *
GAA GAC ACA ATA ACA GTA CAA AAA TAC GAC TCA GCA GGC ACC AAT CTA
CTT CTG TGT TAT TGT CAT GTT TTT ATG CTG AGT CGT CCG TGG TTA GAT
Glu Asp Thr Ile Thr Val Gln Lys Tyr Asp Ser Ala Gly Thr Asn Leu>
```

Figure 8B

Osp A K-48

```
        770         780         790         800         810
          *           *           *           *           *
    *     *     *     *     *     *     *     *     *     *
   GAA GGC AAA GCA GTC GAA ATT ACA ACA CTT AAA GAA CTT AAA AAC GCT
   CTT CCG TTT CGT CAG CTT TAA TGT TGT GAA TTT CTT GAA TTT TTG CGA
   Glu Gly Lys Ala Val Glu Ile Thr Thr Leu Lys Glu Leu Lys Asn Ala>
```

OSP A K48

```
        820
          *     *
   TTA AAA TAA
   AAT TTT ATT
   Leu Lys ***>
```

Figure 8C

OSP A PGAU

```
              10              20              30              40
               *               *               *               *
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50              60              70              80              90
    *               *               *               *               *
TGC AAG CAA AAT GTT AGC AGC CTT GAT GAA AAA AAC AGC GCT TCA GTA
ACG TTC GTT TTA CAA TCG TCG GAA CTA CTT TTT TTG TCG CGA AGT CAT
Cys Lys Gln Asn Val Ser Ser Leu Asp Glu Lys Asn Ser Ala Ser Val>

100             110             120             130             140
       *               *               *               *               *
GAT TTG CCT GGT GAG ATG AAA GTT CTT GTA AGT AAA GAA AAA GAC AAA
CTA AAC GGA CCA CTC TAC TTT CAA GAA CAT TCA TTT CTT TTT CTG TTT
Asp Leu Pro Gly Glu Met Lys Val Leu Val Ser Lys Glu Lys Asp Lys>

150             160             170             180             190
          *               *               *               *               *
GAC GGT AAG TAC AGT CTA AAG GCA ACA GTA GAC AAG ATT GAG CTA AAA
CTG CCA TTC ATG TCA GAT TTC CGT TGT CAT CTG TTC TAA CTC GAT TTT
Asp Gly Lys Tyr Ser Leu Lys Ala Thr Val Asp Lys Ile Glu Leu Lys>

200             210             220             230             240
             *               *               *               *               *
GGA ACT TCT GAT AAA GAC AAT GGT TCT GGA GTG CTT GAA GGT ACA AAA
CCT TGA AGA CTA TTT CTG TTA CCA AGA CCT CAC GAA CTT CCA TGT TTT
Gly Thr Ser Asp Lys Asp Asn Gly Ser Gly Val Leu Glu Gly Thr Lys>

250             260             270             280
                *               *               *               *
GAT GAC AAA AGT AAA GCA AAA TTA ACA ATT GCT GAC GAT CTA AGT AAA
CTA CTG TTT TCA TTT CGT TTT AAT TGT TAA CGA CTG CTA GAT TCA TTT
Asp Asp Lys Ser Lys Ala Lys Leu Thr Ile Ala Asp Asp Leu Ser Lys>

290             300             310             320             330
 *               *               *               *               *
ACC ACA TTC GAA CTT TTA AAA GAA GAT GGC AAA ACA TTA GTG TCA AGA
TGG TGT AAG CTT GAA AAT TTT CTT CTA CCG TTT TGT AAT CAC AGT TCT
Thr Thr Phe Glu Leu Leu Lys Glu Asp Gly Lys Thr Leu Val Ser Arg>

340             350             360             370             380
    *               *               *               *               *
AAA GTA AGT TCT AGA GAC AAA ACA TCA ACA GAT GAA ATG TTC AAT GAA
TTT CAT TCA AGA TCT CTG TTT TGT AGT TGT CTA CTT TAC AAG TTA CTT
Lys Val Ser Ser Arg Asp Lys Thr Ser Thr Asp Glu Met Phe Asn Glu>
```

Figure 9A

OSP A PGAU

```
           390            400            410            420            430
            *              *              *              *              *
       *         *      *         *    *         *    *         *    *         *
     AAA GGT GAA TTG TCT GCA AAA ACC ATG ACA AGA GAA AAT GGA ACC AAA
     TTT CCA CTT AAC AGA CGT TTT TGG TAC TGT TCT CTT TTA CCT TGG TTT
     Lys Gly Glu Leu Ser Ala Lys Thr Met Thr Arg Glu Asn Gly Thr Lys>

440            450            460            470           480
                *              *              *              *              *
         *         *    *         *    *         *    *         *    *         *
         CTT GAA TAT ACA GAA ATG AAA AGC GAT GGA ACC GGA AAA GCT AAA GAA
         GAA CTT ATA TGT CTT TAC TTT TCG CTA CCT TGG CCT TTT CGA TTT CTT
         Leu Glu Tyr Thr Glu Met Lys Ser Asp Gly Thr Gly Lys Ala Lys Glu>

490            500            510            520
                    *         *    *         *    *         *    *         *
             *         *    *         *    *         *    *         *    *         *
             GTT TTA AAA AAG TTT ACT CTT GAA GGA AAA GTA GCT AAT GAT AAA GTA
             CAA AAT TTT TTC AAA TGA GAA CTT CCT TTT CAT CGA TTA CTA TTT CAT
             Val Leu Lys Lys Phe Thr Leu Glu Gly Lys Val Ala Asn Asp Lys Val>

530            540            550            560            570
        *              *              *              *              *
    *         *    *         *    *         *    *         *    *         *
     ACA TTG GAA GTA AAA GAA GGA ACC GTT ACT TTA AGT AAG GAA ATT GCA
     TGT AAC CTT CAT TTT CTT CCT TGG CAA TGA AAT TCA TTC CTT TAA CGT
     Thr Leu Glu Val Lys Glu Gly Thr Val Thr Leu Ser Lys Glu Ile Ala>

580            590            600            610            620
            *              *              *              *              *
       *         *    *         *    *         *    *         *    *         *
       AAA TCT GGA GAA GTA ACA GTT GCT CTT AAT GAC ACT AAC ACT ACT CAG
       TTT AGA CCT CTT CAT TGT CAA CGA GAA TTA CTG TGA TTG TGA TGA GTC
       Lys Ser Gly Glu Val Thr Val Ala Leu Asn Asp Thr Asn Thr Thr Gln>

630            640            650            660            670
                *              *              *              *              *
         *         *    *         *    *         *    *         *    *         *
         GCT ACT AAA AAA ACT GGC GCA TGG GAT TCA AAA ACT TCT ACT TTA ACA
         CGA TGA TTT TTT TGA CCG CGT ACC CTA AGT TTT TGA AGA TGA AAT TGT
         Ala Thr Lys Lys Thr Gly Ala Trp Asp Ser Lys Thr Ser Thr Leu Thr>

680            690            700            710            720
                    *              *              *              *              *
             *         *    *         *    *         *    *         *    *         *
             ATT AGT GTT AAC AGC AAA AAA ACT ACA CAA CTT GTG TTT ACT AAA CAA
             TAA TCA CAA TTG TCG TTT TTT TGA TGT GTT GAA CAC AAA TGA TTT GTT
             Ile Ser Val Asn Ser Lys Lys Thr Thr Gln Leu Val Phe Thr Lys Gln>

730            740            750            760
                        *              *              *              *
                 *         *    *         *    *         *    *         *
                 TAC ACA ATA ACT GTA AAA CAA TAC GAC TCC GCA GGT ACC AAT TTA GAA
                 ATG TGT TAT TGA CAT TTT GTT ATG CTG AGG CGT CCA TGG TTA AAT CTT
                 Tyr Thr Ile Thr Val Lys Gln Tyr Asp Ser Ala Gly Thr Asn Leu Glu>
```

Figure 9B

OSP A PGAU

```
       770           780           790           800           810
        *    *    *    *    *    *    *    *    *    *
       GGC  ACA  GCA  GTC  GAA  ATT  AAA  ACA  CTT  GAT  GAA  CTT  AAA  AAC  GCT  TTA
       CCG  TGT  CGT  CAG  CTT  TAA  TTT  TGT  GAA  CTA  CTT  GAA  TTT  TTG  CGA  AAT
       Gly  Thr  Ala  Val  Glu  Ile  Lys  Thr  Leu  Asp  Glu  Leu  Lys  Asn  Ala  Leu>

820
           *
       AAA  TAA
       TTT  ATT
       Lys  ***>
```

Figure 9C

OSPA 25015

```
           10            20            30            40
    *    *    *    *    *    *    *    *    *    *    *    *
ATG  AAA  AAA  TAT  TTA  TTG  GGA  ATA  GGT  CTA  ATA  TTA  GCC  TTA  ATA  GCA
TAC  TTT  TTT  ATA  AAT  AAC  CCT  TAT  CCA  GAT  TAT  AAT  CGG  AAT  TAT  CGT
Met  Lys  Lys  Tyr  Leu  Leu  Gly  Ile  Gly  Leu  Ile  Leu  Ala  Leu  Ile  Ala>

50            60            70            80            90
   *    *    *    *    *    *    *    *    *    *    *
TGT  AAG  CAA  AAT  GTT  AGC  AGC  CTT  GAC  GAG  AAA  AAC  AGC  GTT  TCA  GTA
ACA  TTC  GTT  TTA  CAA  TCG  TCG  GAA  CTG  CTC  TTT  TTG  TCG  CAA  AGT  CAT
Cys  Lys  Gln  Asn  Val  Ser  Ser  Leu  Asp  Glu  Lys  Asn  Ser  Val  Ser  Val>

100           110           120           130          140
   *    *    *    *    *    *    *    *    *    *    *    *
GAT  TTG  CCT  GGT  GAA  ATG  AAA  GTT  CTT  GTA  AGC  AAA  GAA  AAA  AAC  AAA
CTA  AAC  GGA  CCA  CTT  TAC  TTT  CAA  GAA  CAT  TCG  TTT  CTT  TTT  TTG  TTT
Asp  Leu  Pro  Gly  Glu  Met  Lys  Val  Leu  Val  Ser  Lys  Glu  Lys  Asn  Lys>

150           160           170           180          190
   *    *    *    *    *    *    *    *    *    *    *    *
GAC  GGC  AAG  TAC  GAT  CTA  ATT  GCA  ACA  GTA  GAC  AAG  CTT  GAG  CTT  AAA
CTG  CCG  TTC  ATG  CTA  GAT  TAA  CGT  TGT  CAT  CTG  TTC  GAA  CTC  GAA  TTT
Asp  Gly  Lys  Tyr  Asp  Leu  Ile  Ala  Thr  Val  Asp  Lys  Leu  Glu  Leu  Lys>

200           210           220           230          240
   *    *    *    *    *    *    *    *    *    *    *    *
GGA  ACT  TCT  GAT  AAA  AAC  AAT  GGA  TCT  GGA  GTA  CTT  GAA  GGC  GTA  AAA
CCT  TGA  AGA  CTA  TTT  TTG  TTA  CCT  AGA  CCT  CAT  GAA  CTT  CCG  CAT  TTT
Gly  Thr  Ser  Asp  Lys  Asn  Asn  Gly  Ser  Gly  Val  Leu  Glu  Gly  Val  Lys>

250           260           270           280
   *    *    *    *    *    *    *    *    *    *    *
GCT  GAC  AAA  AGT  AAA  GTA  AAA  TTA  ACA  ATT  TCT  GAC  GAT  CTA  GGT  CAA
CGA  CTG  TTT  TCA  TTT  CAT  TTT  AAT  TGT  TAA  AGA  CTG  CTA  GAT  CCA  GTT
Ala  Asp  Lys  Ser  Lys  Val  Lys  Leu  Thr  Ile  Ser  Asp  Asp  Leu  Gly  Gln>

290           300           310           320          330
   *    *    *    *    *    *    *    *    *    *    *
ACC  ACA  CTT  GAA  GTT  TTC  AAA  GAA  GAT  GGC  AAA  ACA  CTA  GTA  TCA  AAA
TGG  TGT  GAA  CTT  CAA  AAG  TTT  CTT  CTA  CCG  TTT  TGT  GAT  CAT  AGT  TTT
Thr  Thr  Leu  Glu  Val  Phe  Lys  Glu  Asp  Gly  Lys  Thr  Leu  Val  Ser  Lys>

340           350           360           370          380
   *    *    *    *    *    *    *    *    *    *    *
AAA  GTA  ACT  TCC  AAA  GAC  AAG  TCA  TCA  ACA  GAA  GAA  AAA  TTC  AAT  GAA
TTT  CAT  TGA  AGG  TTT  CTG  TTC  AGT  AGT  TGT  CTT  CTT  TTT  AAG  TTA  CTT
Lys  Val  Thr  Ser  Lys  Asp  Lys  Ser  Ser  Thr  Glu  Glu  Lys  Phe  Asn  Glu>
```

Figure 10A

OSP A 25015

```
            390           400           410           420           430
       *      *      *      *      *      *      *      *      *      *
      AAA GGT GAA GTA TCT GAA AAA ATA ATA ACA AGA GCA GAC GGA ACC AGA
      TTT CCA CTT CAT AGA CTT TTT TAT TAT TGT TCT CGT CTG CCT TGG TCT
      Lys Gly Glu Val Ser Glu Lys Ile Ile Thr Arg Ala Asp Gly Thr Arg>

440           450           460           470           480
             *      *      *      *      *      *      *      *      *      *
            CTT GAA TAC ACA GGA ATT AAA AGC GAT GGA TCT GGA AAA GCT AAA GAG
            GAA CTT ATG TGT CCT TAA TTT TCG CTA CCT AGA CCT TTT CGA TTT CTC
            Leu Glu Tyr Thr Gly Ile Lys Ser Asp Gly Ser Gly Lys Ala Lys Glu>

490           500           510           520
                   *      *      *      *      *      *      *      *      *
                  GTT TTA AAA GGC TAT GTT CTT GAA GGA ACT CTA ACT GCT GAA AAA ACA
                  CAA AAT TTT CCG ATA CAA GAA CTT CCT TGA GAT TGA CGA CTT TTT TGT
                  Val Leu Lys Gly Tyr Val Leu Glu Gly Thr Leu Thr Ala Glu Lys Thr>

530           540           550           560           570
        *      *      *      *      *      *      *      *      *      *
      ACA TTG GTG GTT AAA GAA GGA ACT GTT ACT TTA AGC AAA AAT ATT TCA
      TGT AAC CAC CAA TTT CTT CCT TGA CAA TGA AAT TCG TTT TTA TAA AGT
      Thr Leu Val Val Lys Glu Gly Thr Val Thr Leu Ser Lys Asn Ile Ser>

580           590           600           610           620
        *      *      *      *      *      *      *      *      *
      AAA TCT GGG GAA GTT TCA GTT GAA CTT AAT GAC ACT GAC AGT AGT GCT
      TTT AGA CCC CTT CAA AGT CAA CTT GAA TTA CTG TGA CTG TCA TCA CGA
      Lys Ser Gly Glu Val Ser Val Glu Leu Asn Asp Thr Asp Ser Ser Ala>

630           640           650           660           670
             *      *      *      *      *      *      *      *      *      *
            GCT ACT AAA AAA ACT GCA GCT TGG AAT GCA GGC ACT TCA ACT TTA ACA
            CGA TGA TTT TTT TGA CGT CGA ACC TTA CGT CCG TGA AGT TGA AAT TGT
            Ala Thr Lys Lys Thr Ala Ala Trp Asn Ala Gly Thr Ser Thr Leu Thr>

680           690           700           710           720
                   *      *      *      *      *      *      *      *      *      *
                  ATT ACT GTA AAC AAC AAA AAA ACT AAA GCC CTT GTA TTT ACA AAA CAA
                  TAA TGA CAT TTG TTG TTT TTT TGA TTT CGG GAA CAT AAA TGT TTT GTT
                  Ile Thr Val Asn Asn Lys Lys Thr Lys Ala Leu Val Phe Thr Lys Gln>

730           740           750           760
                         *      *      *      *      *      *      *      *      *
                        GAC ACA ATT ACA TCA CAA AAA TAC GAC TCA GCA GGA ACC AAC TTG GAA
                        CTG TGT TAA TGT AGT GTT TTT ATG CTG AGT CGT CCT TGG TTG AAC CTT
                        Asp Thr Ile Thr Ser Gln Lys Tyr Asp Ser Ala Gly Thr Asn Leu Glu>
```

Figure 10B

OSPA 25015

```
      770         780         790         800         810
       *     *     *     *     *     *     *     *     *     *
GGC ACA GCA GTC GAA ATT AAA ACA CTT GAT GAA CTT AAA AAC GCT TTA
CCG TGT CGT CAG CTT TAA TTT TGT GAA CTA CTT GAA TTT TTG CGA AAT
Gly Thr Ala Val Glu Ile Lys Thr Leu Asp Glu Leu Lys Asn Ala Leu>

AGA
TCT
Arg>
```

Figure 10C

OSP B B-31
Sequence Range: 1 to 891

```
              10          20          30          40
               .           .           .           .
     ATG AGA TTA TTA ATA GGA TTT GCT TTA GCG TTA GCT TTA ATA GGA TGT
     TAC TCT AAT AAT TAT CCT AAA CGA AAT CGC AAT CGA AAT TAT CCT ACA
     Met Arg Leu Leu Ile Gly Phe Ala Leu Ala Leu Ala Leu Ile Gly Cys>

50          60          70          80          90
       .           .           .           .           .
     GCA CAA AAA GGT GCT GAG TCA ATT GGT TCT CAA AAA GAA AAT GAT CTA
     CGT GTT TTT CCA CGA CTC AGT TAA CCA AGA GTT TTT CTT TTA CTA GAT
     Ala Gln Lys Gly Ala Glu Ser Ile Gly Ser Gln Lys Glu Asn Asp Leu>

100         110         120         130         140
       .           .           .           .           .
     AAC CTT GAA GAC TCT AGT AAA AAA TCA CAT CAA AAC GCT AAA CAA GAC
     TTG GAA CTT CTG AGA TCA TTT TTT AGT GTA GTT TTG CGA TTT GTT CTG
     Asn Leu Glu Asp Ser Ser Lys Lys Ser His Gln Asn Ala Lys Gln Asp>

150         160         170         180         190
       .           .           .           .           .
     CTT CCT GCG GTG ACA GAA GAC TCA GTG TCT TTG TTT AAT GGT AAT AAA
     GAA GGA CGC CAC TGT CTT CTG AGT CAC AGA AAC AAA TTA CCA TTA TTT
     Leu Pro Ala Val Thr Glu Asp Ser Val Ser Leu Phe Asn Gly Asn Lys>

200         210         220         230         240
       .           .           .           .           .
     ATT TTT GTA AGC AAA GAA AAA AAT AGC TCC GGC AAA TAT GAT TTA AGA
     TAA AAA CAT TCG TTT CTT TTT TTA TCG AGG CCG TTT ATA CTA AAT TCT
     Ile Phe Val Ser Lys Glu Lys Asn Ser Ser Gly Lys Tyr Asp Leu Arg>

250         260         270         280
       .           .           .           .
     GCA ACA ATT GAT CAG GTT GAA CTT AAA GGA ACT TCC GAT AAA AAC AAT
     CGT TGT TAA CTA GTC CAA CTT GAA TTT CCT TGA AGG CTA TTT TTG TTA
     Ala Thr Ile Asp Gln Val Glu Leu Lys Gly Thr Ser Asp Lys Asn Asn>

290         300         310         320         330
       .           .           .           .           .
     GGT TCT GGA ACC CTT GAA GGT TCA AAG CCT GAC AAG AGT AAA GTA AAA
     CCA AGA CCT TGG GAA CTT CCA AGT TTC GGA CTG TTC TCA TTT CAT TTT
     Gly Ser Gly Thr Leu Glu Gly Ser Lys Pro Asp Lys Ser Lys Val Lys>

340         350         360         370         380
       .           .           .           .           .
     TTA ACA GTT TCT GCT GAT TTA AAC ACA GTA ACC TTA GAA GCA TTT GAT
     AAT TGT CAA AGA CGA CTA AAT TTG TGT CAT TGG AAT CTT CGT AAA CTA
     Leu Thr Val Ser Ala Asp Leu Asn Thr Val Thr Leu Glu Ala Phe Asp>
      390         400         410         420         430
```

Figure 11A

```
    *       *       *       *       *       *       *       *       *       *
    GCC     AGC     AAC     CAA     AAA     ATT     TCA     AGT     AAA     GTT     ACT     AAA     AAA     CAG     GGG     TCA
    CGG     TCG     TTG     GTT     TTT     TAA     AGT     TCA     TTT     CAA     TGA     TTT     TTT     GTC     CCC     AGT
    Ala     Ser     Asn     Gln     Lys     Ile     Ser     Ser     Lys     Val     Thr     Lys     Lys     Gln     Gly     Ser>

440             450             460             470             480
            *       *       *       *       *       *       *       *       *       *
    ATA     ACA     GAG     GAA     ACT     CTC     AAA     GCT     AAT     AAA     TTA     GAC     TCA     AAG     AAA     TTA
    TAT     TGT     CTC     CTT     TGA     GAG     TTT     CGA     TTA     TTT     AAT     CTG     AGT     TTC     TTT     AAT
    Ile     Thr     Glu     Glu     Thr     Leu     Lys     Ala     Asn     Lys     Leu     Asp     Ser     Lys     Lys     Leu>

490             500             510             520
            *       *       *       *       *       *       *       *       *       *
    ACA     AGA     TCA     AAC     GGA     ACT     ACA     CTT     GAA     TAC     TCA     CAA     ATA     ACA     GAT     GCT
    TGT     TCT     AGT     TTG     CCT     TGA     TGT     GAA     CTT     ATG     AGT     GTT     TAT     TGT     CTA     CGA
    Thr     Arg     Ser     Asn     Gly     Thr     Thr     Leu     Glu     Tyr     Ser     Gln     Ile     Thr     Asp     Ala>

530             540             550             560             570
            *       *       *       *       *       *       *       *       *       *
    GAC     AAT     GCT     ACA     AAA     GCA     GTA     GAA     ACT     CTA     AAA     AAT     AGC     ATT     AAG     CTT
    CTG     TTA     CGA     TGT     TTT     CGT     CAT     CTT     TGA     GAT     TTT     TTA     TCG     TAA     TTC     GAA
    Asp     Asn     Ala     Thr     Lys     Ala     Val     Glu     Thr     Leu     Lys     Asn     Ser     Ile     Lys     Leu>

580             590             600             610             620
            *       *       *       *       *       *       *       *       *       *
    GAA     GGA     AGT     CTT     GTA     GTC     GGA     AAA     ACA     ACA     GTG     GAA     ATT     AAA     GAA     GGT
    CTT     CCT     TCA     GAA     CAT     CAG     CCT     TTT     TGT     TGT     CAC     CTT     TAA     TTT     CTT     CCA
    Glu     Gly     Ser     Leu     Val     Val     Gly     Lys     Thr     Thr     Val     Glu     Ile     Lys     Glu     Gly>

630             640             650             660             670
            *       *       *       *       *       *       *       *       *       *
    ACT     GTT     ACT     CTA     AAA     AGA     GAA     ATT     GAA     AAA     GAT     GGA     AAA     GTA     AAA     GTC
    TGA     CAA     TGA     GAT     TTT     TCT     CTT     TAA     CTT     TTT     CTA     CCT     TTT     CAT     TTT     CAG
    Thr     Val     Thr     Leu     Lys     Arg     Glu     Ile     Glu     Lys     Asp     Gly     Lys     Val     Lys     Val>

680             690             700             710             720
            *       *       *       *       *       *       *       *       *       *
    TTT     TTG     AAT     GAC     ACT     GCA     GGT     TCT     AAC     AAA     AAA     ACA     GGT     AAA     TGG     GAA
    AAA     AAC     TTA     CTG     TGA     CGT     CCA     AGA     TTG     TTT     TTT     TGT     CCA     TTT     ACC     CTT
    Phe     Leu     Asn     Asp     Thr     Ala     Gly     Ser     Asn     Lys     Lys     Thr     Gly     Lys     Trp     Glu>

730             740             750             760
            *       *       *       *       *       *       *       *       *
    GAC     AGT     ACT     AGC     ACT     TTA     ACA     ATT     AGT     GCT     GAC     AGC     AAA     AAA     ACT     AAA
    CTG     TCA     TGA     TCG     TGA     AAT     TGT     TAA     TCA     CGA     CTG     TCG     TTT     TTT     TGA     TTT
    Asp     Ser     Thr     Ser     Thr     Leu     Thr     Ile     Ser     Ala     Asp     Ser     Lys     Lys     Thr     Lys>

770             780             790             800             810
            *       *       *       *       *       *       *       *       *       *
    GAT     TTG     GTG     TTC     TTA     ACA     GAT     GGT     ACA     ATT     ACA     GTA     CAA     CAA     TAC     AAC
    CTA     AAC     CAC     AAG     AAT     TGT     CTA     CCA     TGT     TAA     TGT     CAT     GTT     GTT     ATG     TTG
    Asp     Leu     Val     Phe     Leu     Thr     Asp     Gly     Thr     Ile     Thr     Val     Gln     Gln     Tyr     Asn>
```

Figure 11B

```
         820           830           840           850           860
          *    *    *    *    *    *    *    *    *
         ACA  GCT  GGA  ACC  AGC  CTA  GAA  GGA  TCA  GCA  AGT  GAA  ATT  AAA  AAT  CTT
         TGT  CGA  CCT  TGG  TCG  GAT  CTT  CCT  AGT  CGT  TCA  CTT  TAA  TTT  TTA  GAA
         Thr  Ala  Gly  Thr  Ser  Leu  Glu  Gly  Ser  Ala  Ser  Glu  Ile  Lys  Asn  Leu>

870           880           890
          *    *    *    *    *    *
         TCA  GAG  CTT  AAA  AAC  GCT  TTA  AAA  TAA
         AGT  CTC  GAA  TTT  TTG  CGA  AAT  TTT  ATT
         Ser  Glu  Leu  Lys  Asn  Ala  Leu  Lys  ***>
```

Figure 11C

OspC-B31
Sequence Range: 1 to 633

```
              10            20            30            40
         *    *    *    *    *    *    *    *    *
     ATG  AAA  AAG  AAT  ACA  TTA  AGT  GCG  ATA  TTA  ATG  ACT  TTA  TTT  TTA  TTT
     TAC  TTT  TTC  TTA  TGT  AAT  TCA  CGC  TAT  AAT  TAC  TGA  AAT  AAA  AAT  AAA
     Met  Lys  Lys  Asn  Thr  Leu  Ser  Ala  Ile  Leu  Met  Thr  Leu  Phe  Leu  Phe>

50            60            70            80            90
     *     *    *    *    *    *    *    *    *    *
     ATA  TCT  TGT  AAT  AAT  TCA  GGG  AAA  GAT  GGG  AAT  ACA  TCT  GCA  AAT  TCT
     TAT  AGA  ACA  TTA  TTA  AGT  CCC  TTT  CTA  CCC  TTA  TGT  AGA  CGT  TTA  AGA
     Ile  Ser  Cys  Asn  Asn  Ser  Gly  Lys  Asp  Gly  Asn  Thr  Ser  Ala  Asn  Ser>

100           110           120           130           140
         *    *    *    *    *    *    *    *    *
     GCT  GAT  GAG  TCT  GTT  AAA  GGG  CCT  AAT  CTT  ACA  GAA  ATA  AGT  AAA  AAA
     CGA  CTA  CTC  AGA  CAA  TTT  CCC  GGA  TTA  GAA  TGT  CTT  TAT  TCA  TTT  TTT
     Ala  Asp  Glu  Ser  Val  Lys  Gly  Pro  Asn  Leu  Thr  Glu  Ile  Ser  Lys  Lys>

150           160           170           180           190
         *    *    *    *    *    *    *    *    *    *
     ATT  ACG  GAT  TCT  AAT  GCG  GTT  TTA  CTT  GCT  GTG  AAA  GAG  GTT  GAA  GCG
     TAA  TGC  CTA  AGA  TTA  CGC  CAA  AAT  GAA  CGA  CAC  TTT  CTC  CAA  CTT  CGC
     Ile  Thr  Asp  Ser  Asn  Ala  Val  Leu  Leu  Ala  Val  Lys  Glu  Val  Glu  Ala>

200           210           220           230           240
         *    *    *    *    *    *    *    *    *    *
     TTG  CTG  TCA  TCT  ATA  GAT  GAA  ATT  GCT  GCT  AAA  GCT  ATT  GGT  AAA  AAA
     AAC  GAC  AGT  AGA  TAT  CTA  CTT  TAA  CGA  CGA  TTT  CGA  TAA  CCA  TTT  TTT
     Leu  Leu  Ser  Ser  Ile  Asp  Glu  Ile  Ala  Ala  Lys  Ala  Ile  Gly  Lys  Lys>

250           260           270           280
         *    *    *    *    *    *    *    *    *
     ATA  CAC  CAA  AAT  AAT  GGT  TTG  GAT  ACC  GAA  TAT  AAT  CAC  AAT  GGA  TCA
     TAT  GTG  GTT  TTA  TTA  CCA  AAC  CTA  TGG  CTT  ATA  TTA  GTG  TTA  CCT  AGT
     Ile  His  Gln  Asn  Asn  Gly  Leu  Asp  Thr  Glu  Tyr  Asn  His  Asn  Gly  Ser>

290           300           310           320           330
         *    *    *    *    *    *    *    *    *    *
     TTG  TTA  GCG  GGA  CGT  TAT  GCA  ATA  TCA  ACC  CTA  ATA  AAA  CAA  AAA  TTA
     AAC  AAT  CGC  CCT  GCA  ATA  CGT  TAT  AGT  TGG  GAT  TAT  TTT  GTT  TTT  AAT
     Leu  Leu  Ala  Gly  Arg  Tyr  Ala  Ile  Ser  Thr  Leu  Ile  Lys  Gln  Lys  Leu>

340           350           360           370           380
         *    *    *    *    *    *    *    *    *
     GAT  GGA  TTG  AAA  AAT  GAA  GGA  TTA  AAG  GAA  AAA  ATT  GAT  GCG  GCT  AAG
     CTA  CCT  AAC  TTT  TTA  CTT  CCT  AAT  TTC  CTT  TTT  TAA  CTA  CGC  CGA  TTC
     Asp  Gly  Leu  Lys  Asn  Glu  Gly  Leu  Lys  Glu  Lys  Ile  Asp  Ala  Ala  Lys>
```

Figure 12A

OspC-B31

```
           390         400         410         420         430
       *  *    *    *    *    *    *    *    *    *
       AAA TGT TCT GAA ACA TTT ACT AAT AAA TTA AAA GAA AAA CAC ACA GAT
       TTT ACA AGA CTT TGT AAA TGA TTA TTT AAT TTT CTT TTT GTG TGT CTA
       Lys Cys Ser Glu Thr Phe Thr Asn Lys Leu Lys Glu Lys His Thr Asp>

440         450         460         470         480
           *    *    *    *    *    *    *    *    *    *
       CTT GGT AAA GAA GGT GTT ACT GAT GCT GAT GCA AAA GAA GCC ATT TTA
       GAA CCA TTT CTT CCA CAA TGA CTA CGA CTA CGT TTT CTT CGG TAA AAT
       Leu Gly Lys Glu Gly Val Thr Asp Ala Asp Ala Lys Glu Ala Ile Leu>

490         500         510         520
           *    *    *    *    *    *    *    *    *
       AAA ACA AAT GGT ACT AAA ACT AAA GGT GCT GAA GAA CTT GGA AAA TTA
       TTT TGT TTA CCA TGA TTT TGA TTT CCA CGA CTT CTT GAA CCT TTT AAT
       Lys Thr Asn Gly Thr Lys Thr Lys Gly Ala Glu Glu Leu Gly Lys Leu>

530         540         550         560         570
       *    *    *    *    *    *    *    *    *    *
       TTT GAA TCA GTA GAG GTC TTG TCA AAA GCA GCT AAA GAG ATG CTT GCT
       AAA CTT AGT CAT CTC CAG AAC AGT TTT CGT CGA TTT CTC TAC GAA CGA
       Phe Glu Ser Val Glu Val Leu Ser Lys Ala Ala Lys Glu Met Leu Ala>

580         590         600         610         620
           *    *    *    *    *    *    *    *    *
       AAT TCA GTT AAA GAG CTT ACA AGC CCT GTT GTG GCA GAA AGT CCA AAA
       TTA AGT CAA TTT CTC GAA TGT TCG GGA CAA CAC CGT CTT TCA GGT TTT
       Asn Ser Val Lys Glu Leu Thr Ser Pro Val Val Ala Glu Ser Pro Lys>

630
           *    *
       AAA CCT TAA
       TTT GGA ATT
       Lys Pro ***>
```

Figure 12B

OspC-K48
Sequence Range: 1 to 630

```
            10           20           30           40
             *            *            *            *
ATG AAA AAG AAT ACA TTA AGT GCG ATA TTA ATG ACT TTA TTT TTA TTT
TAC TTT TTC TTA TGT AAT TCA CGC TAT AAT TAC TGA AAT AAA AAT AAA
Met Lys Lys Asn Thr Leu Ser Ala Ile Leu Met Thr Leu Phe Leu Phe>

50           60           70           80           90
      *            *            *            *            *
ATA TCT TGT AAT AAT TCA GGT GGG GAT ACC GCA TCT ACT AAT CCT GAT
TAT AGA ACA TTA TTA AGT CCA CCC CTA TGG CGT AGA TGA TTA GGA CTA
Ile Ser Cys Asn Asn Ser Gly Gly Asp Thr Ala Ser Thr Asn Pro Asp>

100          110          120          130          140
      *            *            *            *            *
GAG TCT GCA AAA GGA CCT AAT CTT ACA GTA ATA AGC AAA AAA ATT ACA
CTC AGA CGT TTT CCT GGA TTA GAA TGT CAT TAT TCG TTT TTT TAA TGT
Glu Ser Ala Lys Gly Pro Asn Leu Thr Val Ile Ser Lys Lys Ile Thr>

150          160          170          180          190
      *            *            *            *            *
GAT TCT AAT GCA TTT GTA CTG GCT GTG AAA GAA GTT GAG GCT TTG ATC
CTA AGA TTA CGT AAA CAT GAC CGA CAC TTT CTT CAA CTC CGA AAC TAG
Asp Ser Asn Ala Phe Val Leu Ala Val Lys Glu Val Glu Ala Leu Ile>

200          210          220          230          240
      *            *            *            *            *
TCA TCT ATA GAT GAA CTT GCT AAT AAA GCT ATT GGT AAA GTA ATA CAT
AGT AGA TAT CTA CTT GAA CGA TTA TTT CGA TAA CCA TTT CAT TAT GTA
Ser Ser Ile Asp Glu Leu Ala Asn Lys Ala Ile Gly Lys Val Ile His>

250          260          270          280
      *            *            *            *
CAA AAT AAT GGT TTA AAT GCT AAT GCG GGT CAA AAC GGA TCA TTG TTA
GTT TTA TTA CCA AAT TTA CGA TTA CGC CCA GTT TTG CCT AGT AAC AAT
Gln Asn Asn Gly Leu Asn Ala Asn Ala Gly Gln Asn Gly Ser Leu Leu>

290          300          310          320          330
  *            *            *            *            *
GCA GGA GCC TAT GCA ATA TCA ACC CTA ATA ACA GAA AAA TTA AGT AAA
CGT CCT CGG ATA CGT TAT AGT TGG GAT TAT TGT CTT TTT AAT TCA TTT
Ala Gly Ala Tyr Ala Ile Ser Thr Leu Ile Thr Glu Lys Leu Ser Lys>

340          350          360          370          380
     *            *            *            *            *
TTG AAA AAT TCA GAA GAG TTA AAT AAA AAA ATT GAA GAG GCT AAG AAC
AAC TTT TTA AGT CTT CTC AAT TTA TTT TTT TAA CTT CTC CGA TTC TTG
Leu Lys Asn Ser Glu Glu Leu Asn Lys Lys Ile Glu Glu Ala Lys Asn>
```

Figure 13A

OspC-K48

```
         390         400         410         420         430
          *           *           *           *           *
CAT TCT GAA GCA TTT ACT AAT AGA CTA AAA GGT TCT CAT GCA CAA CTT
GTA AGA CTT CGT AAA TGA TTA TCT GAT TTT CCA AGA GTA CGT GTT GAA
His Ser Glu Ala Phe Thr Asn Arg Leu Lys Gly Ser His Ala Gln Leu>

440         450         460         470         480
          *           *           *           *           *
GGA GTT GCT GCT GCT ACT GAT GAT CAT GCA AAA GAA GCT ATT TTA AAG
CCT CAA CGA CGA CGA TGA CTA CTA GTA CGT TTT CTT CGA TAA AAT TTC
Gly Val Ala Ala Ala Thr Asp Asp His Ala Lys Glu Ala Ile Leu Lys>

490         500         510         520
          *           *           *           *
TCA AAT CCT ACT AAA GAT AAG GGT GCT AAA GCA CTT AAA GAC TTA TCT
AGT TTA GGA TGA TTT CTA TTC CCA CGA TTT CGT GAA TTT CTG AAT AGA
Ser Asn Pro Thr Lys Asp Lys Gly Ala Lys Ala Leu Lys Asp Leu Ser>

530         540         550         560         570
  *           *           *           *           *
GAA TCA GTA GAA AGC TTG GCA AAA GCA GCG CAA GAA GCA TTA GCT AAT
CTT AGT CAT CTT TCG AAC CGT TTT CGT CGC GTT CTT CGT AAT CGA TTA
Glu Ser Val Glu Ser Leu Ala Lys Ala Ala Gln Glu Ala Leu Ala Asn>

580         590         600         610         620
          *           *           *           *           *
TCA GTT AAA GAA CTT ACA AAT CCT GTT GTG GCA GAA AGT CCA AAA AAA
AGT CAA TTT CTT GAA TGT TTA GGA CAA CAC CGT CTT TCA GGT TTT TTT
Ser Val Lys Glu Leu Thr Asn Pro Val Val Ala Glu Ser Pro Lys Lys>

630
          *
CCT TAA
GGA ATT
Pro ***>
```

Figure 13B

OspC-PKO
Sequence Range: 1 to 639

```
                10              20              30              40
                 *               *               *               *
        ATG AAA AAG AAT ACA TTA AGT GCG ATA TTA ATG ACT TTA TTT TTA TTT
        TAC TTT TTC TTA TGT AAT TCA CGC TAT AAT TAC TGA AAT AAA AAT AAA
        Met Lys Lys Asn Thr Leu Ser Ala Ile Leu Met Thr Leu Phe Leu Phe>

50              60              70              80              90
              *               *               *               *               *
        ATA TCT TGT AGT AAT TCA GGG AAA GGT GGG GAT TCT GCA TCT ACT AAT
        TAT AGA ACA TCA TTA AGT CCC TTT CCA CCC CTA AGA CGT AGA TGA TTA
        Ile Ser Cys Ser Asn Ser Gly Lys Gly Gly Asp Ser Ala Ser Thr Asn>

100             110             120             130             140
                 *               *               *               *               *
        CCT GCT GAC GAG TCT GCG AAA GGG CCT AAT CTT ACA GAA ATA AGC AAA
        GGA CGA CTG CTC AGA CGC TTT CCC GGA TTA GAA TGT CTT TAT TCG TTT
        Pro Ala Asp Glu Ser Ala Lys Gly Pro Asn Leu Thr Glu Ile Ser Lys>

150             160             170             180             190
                     *               *               *               *               *
        AAA ATT ACA GAT TCT AAT GCA TTT GTA CTT GCT GTT AAA GAA GTT GAG
        TTT TAA TGT CTA AGA TTA CGT AAA CAT GAA CGA CAA TTT CTT CAA CTC
        Lys Ile Thr Asp Ser Asn Ala Phe Val Leu Ala Val Lys Glu Val Glu>

200             210             220             230             240
                     *               *               *               *               *
        ACT TTG GTT TTA TCT ATA GAT GAA CTT GCT AAG AAA GCT ATT GGT CAA
        TGA AAC CAA AAT AGA TAT CTA CTT GAA CGA TTC TTT CGA TAA CCA GTT
        Thr Leu Val Leu Ser Ile Asp Glu Leu Ala Lys Lys Ala Ile Gly Gln>

250             260             270             280
                         *               *               *               *
        AAA ATA GAC AAT AAT AAT GGT TTA GCT GCT TTA AAT AAT CAG AAT GGA
        TTT TAT CTG TTA TTA TTA CCA AAT CGA CGA AAT TTA TTA GTC TTA CCT
        Lys Ile Asp Asn Asn Asn Gly Leu Ala Ala Leu Asn Asn Gln Asn Gly>

290             300             310             320             330
         *               *               *               *               *
        TCG TTG TTA GCA GGA GCC TAT GCA ATA TCA ACC CTA ATA ACA GAA AAA
        AGC AAC AAT CGT CCT CGG ATA CGT TAT AGT TGG GAT TAT TGT CTT TTT
        Ser Leu Leu Ala Gly Ala Tyr Ala Ile Ser Thr Leu Ile Thr Glu Lys>

340             350             360             370             380
             *               *               *               *               *
        TTG AGT AAA TTG AAA AAT TTA GAA GAA TTA AAG ACA GAA ATT GCA AAG
        AAC TCA TTT AAC TTT TTA AAT CTT CTT AAT TTC TGT CTT TAA CGT TTC
        Leu Ser Lys Leu Lys Asn Leu Glu Glu Leu Lys Thr Glu Ile Ala Lys>
```

Figure 14A

OspC-PKO

```
          390           400           410           420           430
       *     *       *     *       *     *       *     *       *     *
GCT AAG AAA TGT TCC GAA GAA TTT ACT AAT AAA CTA AAA AGT GGT CAT
CGA TTC TTT ACA AGG CTT CTT AAA TGA TTA TTT GAT TTT TCA CCA GTA
Ala Lys Lys Cys Ser Glu Glu Phe Thr Asn Lys Leu Lys Ser Gly His>

440           450           460           470           480
       *     *       *     *       *     *       *     *       *     *
GCA GAT CTT GGC AAA CAG GAT GCT ACC GAT GAT CAT GCA AAA GCA GCT
CGT CTA GAA CCG TTT GTC CTA CGA TGG CTA CTA GTA CGT TTT CGT CGA
Ala Asp Leu Gly Lys Gln Asp Ala Thr Asp Asp His Ala Lys Ala Ala>

490           500           510           520
       *     *       *     *       *     *       *     *
ATT TTA AAA ACA CAT GCA ACT ACC GAT AAA GGT GCT AAA GAA TTT AAA
TAA AAT TTT TGT GTA CGT TGA TGG CTA TTT CCA CGA TTT CTT AAA TTT
Ile Leu Lys Thr His Ala Thr Thr Asp Lys Gly Ala Lys Glu Phe Lys>

530           540           550           560           570
    *       *     *       *     *       *     *       *     *       *
GAT TTA TTT GAA TCA GTA GAA GGT TTG TTA AAA GCA GCT CAA GTA GCA
CTA AAT AAA CTT AGT CAT CTT CCA AAC AAT TTT CGT CGA GTT CAT CGT
Asp Leu Phe Glu Ser Val Glu Gly Leu Leu Lys Ala Ala Gln Val Ala>

580           590           600           610           620
       *     *       *     *       *     *       *     *       *
CTA ACT AAT TCA GTT AAA GAA CTT ACA AGT CCT GTT GTA GCA GAA AGT
GAT TGA TTA AGT CAA TTT CTT GAA TGT TCA GGA CAA CAT CGT CTT TCA
Leu Thr Asn Ser Val Lys Glu Leu Thr Ser Pro Val Val Ala Glu Ser>

630
       *     *       *
CCA AAA AAA CCT TAA
GGT TTT TTT GGA ATT
Pro Lys Lys Pro ***>
```

Figure 14B

OspC-TRO
Sequence Range: 1 to 624

```
              10           20           30           40
               *            *            *            *
       *   *      *    *       *    *       *    *       *   *
    ATG AAA AAG AAT ACA TTA AGT GCG ATA TTA ATG ACT TTA TTT TTA TTT
    TAC TTT TTC TTA TGT AAT TCA CGC TAT AAT TAC TGA AAT AAA AAT AAA
    Met Lys Lys Asn Thr Leu Ser Ala Ile Leu Met Thr Leu Phe Leu Phe>

50           60           70           80           90
        *            *            *            *            *
    *       *    *       *    *       *    *       *    *       *
    ATA TCT TGT AAT AAT TCA GGT GGG GAT TCT GCA TCT ACT AAT CCT GAT
    TAT AGA ACA TTA TTA AGT CCA CCC CTA AGA CGT AGA TGA TTA GGA CTA
    Ile Ser Cys Asn Asn Ser Gly Gly Asp Ser Ala Ser Thr Asn Pro Asp>

100          110          120          130          140
            *            *            *            *            *
        *       *    *       *    *.      *    *       *    *       *
    GAG TCT GCA AAA GGA CCT AAT CTT ACC GTA ATA AGC AAA AAA ATT ACA
    CTC AGA CGT TTT CCT GGA TTA GAA TGG CAT TAT TCG TTT TTT TAA TGT
    Glu Ser Ala Lys Gly Pro Asn Leu Thr Val Ile Ser Lys Lys Ile Thr>

150          160          170          180          190
            *            *            *.           *            *
        *       *    *       *    *       *    *       *    *       *
    GAT TCT AAT GCA TTT TTA CTG GCT GTG AAA GAA GTT GAG GCT TTG CTT
    CTA AGA TTA CGT AAA AAT GAC CGA CAC TTT CTT CAA CTC CGA AAC GAA
    Asp Ser Asn Ala Phe Leu Leu Ala Val Lys Glu Val Glu Ala Leu Leu>

200          210          220          230          .240
            *            *            *            *            *
        *       *    *       *    *       *    *       *    *       *
    TCA TCT ATA GAT GAA CTT TCT AAA GCT ATT GGT AAA AAA ATA AAA AAT
    AGT AGA TAT CTA CTT GAA AGA TTT CGA TAA CCA TTT TTT TAT TTT TTA
    Ser Ser Ile Asp Glu Leu Ser Lys Ala Ile Gly Lys Lys Ile Lys Asn>

250          260          270          280
            *            *            *            *
        *       *    *       *    *       *    *       *    *       *
    GAT GGT ACT TTA GAT AAC GAA GCA AAT CGA AAC GAA TCA TTG ATA GCA
    CTA CCA TGA AAT CTA TTG CTT CGT TTA GCT TTG CTT AGT AAC TAT CGT
    Asp Gly Thr Leu Asp Asn Glu Ala Asn Arg Asn Glu Ser Leu Ile Ala>

290          300          310          320          330
     *            *            *            *            *
 *       *    *       *    *       *    *       *    *       *
    GGA GCT TAT GAA ATA TCA AAA CTA ATA ACA CAA AAA TTA AGT GTA TTG
    CCT CGA ATA CTT TAT AGT TTT GAT TAT TGT GTT TTT AAT TCA CAT AAC
    Gly Ala Tyr Glu Ile Ser Lys Leu Ile Thr Gln Lys Leu Ser Val Leu>

340          350          360          370          380
     *            *            *            *            *
 *       *    *       *    *       *    *       *    *
    AAT TCA GAA GAA TTA AAG AAA AAA ATT AAA GAG GCT AAG GAT TGT TCC
    TTA AGT CTT CTT AAT TTC TTT TTT TAA TTT CTC CGA TTC CTA ACA AGG
    Asn Ser Glu Glu Leu Lys Lys Lys Ile Lys Glu Ala Lys Asp Cys Ser>
```

Figure 15A

OspC-TRO

```
          390         400         410         420         430
           *           *           *           *           *
      *       *       *       *       *       *       *       *       *
     GAA AAA TTT ACT ACT AAG CTA AAA GAT AGT CAT GCA GAG CTT GGT ATA
     CTT TTT AAA TGA TGA TTC GAT TTT CTA TCA GTA CGT CTC GAA CCA TAT
     Glu Lys Phe Thr Thr Lys Leu Lys Asp Ser His Ala Glu Leu Gly Ile>

440         450         460         470         480
           *           *           *           *           *
      *       *       *       *       *       *       *       *       *
     CAA AGC GTT CAG GAT GAT AAT GCA AAA AAA GCT ATT TTA AAA ACA CAT
     GTT TCG CAA GTC CTA CTA TTA CGT TTT TTT CGA TAA AAT TTT TGT GTA
     Gln Ser Val Gln Asp Asp Asn Ala Lys Lys Ala Ile Leu Lys Thr His>

490         500         510         520
           *           *           *           *
      *       *       *       *       *       *       *       *       *
     GGA ACT AAA GAC AAG GGT GCT AAA GAA CTT GAA GAG TTA TTT AAA TCA
     CCT TGA TTT CTG TTC CCA CGA TTT CTT GAA CTT CTC AAT AAA TTT AGT
     Gly Thr Lys Asp Lys Gly Ala Lys Glu Leu Glu Glu Leu Phe Lys Ser>

530         540         550         560         570
      *           *           *           *           *
      *       *       *       *       *       *       *       *       *
     CTA GAA AGC TTG TCA AAA GCA GCG CAA GCA GCA TTA ACT AAT TCA GTT
     GAT CTT TCG AAC AGT TTT CGT CGC GTT CGT CGT AAT TGA TTA AGT CAA
     Leu Glu Ser Leu Ser Lys Ala Ala Gln Ala Ala Leu Thr Asn Ser Val>

580         590         600         610         620
          *           *           *           *           *
      *       *       *       *       *       *       *       *
     AAA GAG CTT ACA AAT CCT GTT GTG GCA GAA AGT CCA AAA AAA CCT TAA
     TTT CTC GAA TGT TTA GGA CAA CAC CGT CTT TCA GGT TTT TTT GGA ATT
     Lys Glu Leu Thr Asn Pro Val Val Ala Glu Ser Pro Lys Lys Pro ***>
```

Figure 15B

P93
Sequence Range: 1 to 2102

```
                  10             20             30             40
          *        *     *        *     *        *     *        *     *
         ATG AAA AAA ATG TTA CTA ATC TTT AGT TTT TTT CTT ATT TTC TTG AAT
         TAC TTT TTT TAC AAT GAT TAG AAA TCA AAA AAA GAA TAA AAG AAC TTA
         Met Lys Lys Met Leu Leu Ile Phe Ser Phe Phe Leu Ile Phe Leu Asn>

50             60             70             80             90
          *        *     *        *     *        *     *        *     *
         GGA TTT CCT GTT AGT GCA AGA GAA GTT GAT AGG GAA AAA TTA AAG GAC
         CCT AAA GGA CAA TCA CGT TCT CTT CAA CTA TCC CTT TTT AAT TTC CTG
         Gly Phe Pro Val Ser Ala Arg Glu Val Asp Arg Glu Lys Leu Lys Asp>

100            110            120            130            140
          *        *     *        *     *        *     *        *     *
         TTT GTT AAT ATG GAT CTT GAG TTT GTA AAT TAT AAA GGC CCT TAT GAT
         AAA CAA TTA TAC CTA GAA CTC  A CAT TTA ATA TTT CCG GGA ATA CTA
         Phe Val Asn Met Asp Leu Glu Phe Val Asn Tyr Lys Gly Pro Tyr Asp>

150            160            170            180            190
          *        *     *        *     *        *     *        *     *
         TCT ACA AAT ACA TAT GAA CAA ATA GTG GGT ATT GGG GAG TTT TTA GCA
         AGA TGT TTA TGT ATA CTT GTT TAT CAC CCA TAA CCC CTC AAA AAT CGT
         Ser Thr Asn Thr Tyr Glu Gln Ile Val Gly Ile Gly Glu Phe Leu Ala>

200            210            220            230            240
          *        *     *        *     *        *     *        *     *
         AGA CCG TTG ACC AAT TCC AAT AGC AAC TCA AGT TAT TAT GGT AAA TAT
         TCT GGC AAC TGG TTA AGG TTA TCG TTG AGT TCA ATA ATA CCA TTT ATA
         Arg Pro Leu Thr Asn Ser Asn Ser Asn Ser Ser Tyr Tyr Gly Lys Tyr>

250            260            270            280
          *        *     *        *     *        *     *        *     *
         TTT ATT AAT AGA TTT ATT GAT GAT CAA GAT AAA AAA GCA AGC GTT GAT
         AAA TAA TTA TCT AAA TAA CTA CTA GTT CTA TTT TTT CGT TCG CAA CTA
         Phe Ile Asn Arg Phe Ile Asp Asp Gln Asp Lys Lys Ala Ser Val Asp>

290            300            310            320            330
          *        *     *        *     *        *     *        *     *
         GTT TTT TCT ATT GGT AGT AAG TCA GAG CTT GAC AGT ATA TTG AAT TTA
         CAA AAA AGA TAA CCA TCA TTC AGT CTC GAA CTG TCA TAT AAC TTA AAT
         Val Phe Ser Ile Gly Ser Lys Ser Glu Leu Asp Ser Ile Leu Asn Leu>

340            350            360            370            380
          *        *     *        *     *        *     *        *     *
         AGA AGA ATT CTT ACA GGG TAT TTA ATA AAG TCT TTC GAT TAT GAC AGG
         TCT TCT TAA GAA TGT CCC ATA AAT TAT TTC AGA AAG CTA ATA CTG TCC
         Arg Arg Ile Leu Thr Gly Tyr Leu Ile Lys Ser Phe Asp Tyr Asp Arg>
```

Figure 16A

```
          390           400           410           420           430
   *   *     *     *     *     *     *     *     *     *
TCT AGT GCA GAA TTA ATT GCT AAG GTT ATT ACA ATA TAT AAT GCT GTT
AGA TCA CGT CTT AAT TAA CGA TTC CAA TAA TGT TAT ATA TTA CGA CAA
Ser Ser Ala Glu Leu Ile Ala Lys Val Ile Thr Ile Tyr Asn Ala Val>

440            450           460           470           480
   *   *     *     *     *     *     *     *     *     *
TAT AGA GGA GAT TTG GAT TAT TAT AAA GGG TTT TAT ATT GAG GCT GCT
ATA TCT CCT CTA AAC CTA ATA ATA TTT CCC AAA ATA TAA CTC CGA CGA
Tyr Arg Gly Asp Leu Asp Tyr Tyr Lys Gly Phe Tyr Ile Glu Ala Ala>

490           500           510           520
   *   *     *     *     *     *     *     *     *
TTA AAG TCT TTA AGT AAA GAA AAT GCA GGT CTT TCT AGG GTT TAT AGT
AAT TTC AGA AAT TCA TTT CTT TTA CGT CCA GAA AGA TCC CAA ATA TCA
Leu Lys Ser Leu Ser Lys Glu Asn Ala Gly Leu Ser Arg Val Tyr Ser>

530           540           550           560           570
  *    *     *     *     *     *     *     *     *     *
CAG TGG GCT GGA AAG ACA CAA ATA TTT ATT CCT CTT AAA AAG GAT ATT
GTC ACC CGA CCT TTC TGT GTT TAT AAA TAA GGA GAA TTT TTC CTA TAA
Gln Trp Ala Gly Lys Thr Gln Ile Phe Ile Pro Leu Lys Lys Asp Ile>

580           590           600           610           620
   *   *     *     *     *     *     *     *     *     *
TTG TCT GGA AAT ATT GAG TCT GAC ATT GAT ATT GAC AGT TTA GTT ACA
AAC AGA CCT TTA TAA CTC AGA CTG TAA CTA TAA CTG TCA AAT CAA TGT
Leu Ser Gly Asn Ile Glu Ser Asp Ile Asp Ile Asp Ser Leu Val Thr>

630           640           650           660           670
   *   *     *     *     *     *     *     *     *     *
GAT AAG GTG GTG GCA GCT CTT TTA AGT GAA AAT GAA GCA GGT GTT AAC
CTA TTC CAC CAC CGT CGA GAA AAT TCA CTT TTA CTT CGT CCA CAA TTG
Asp Lys Val Val Ala Ala Leu Leu Ser Glu Asn Glu Ala Gly Val Asn>

680           690           700           710           722
   *   *     *     *     *     *     *     *     *     *
TTT GCA AGA GAT ATT ACA GAT ATT CAA GGC GAA ACT CAT AAG GCA GAT
AAA CGT TCT CTA TAA TGT CTA TAA GTT CCG CTT TGA GTA TTC CGT CTA
Phe Ala Arg Asp Ile Thr Asp Ile Gln Gly Glu Thr His Lys Ala Asp>

730           740           750           760
   *   *     *     *     *     *     *     *     *
CAA GAT AAA ATT GAT ATT GAA TTA GAC AAT ATT CAT GAA AGT GAT TCC
GTT CTA TTT TAA CTA TAA CTT AAT CTG TTA TAA GTA CTT TCA CTA AGG
Gln Asp Lys Ile Asp Ile Glu Leu Asp Asn Ile His Glu Ser Asp Ser>

770           780           790           800           810
  *    *     *     *     *     *     *     *     *     *
AAT ATA ACA GAA ACT ATT GAA AAT TTA AGG GAT CAG CTT GAA AAA GCT
TTA TAT TGT CTT TGA TAA CTT TTA AAT TCC CTA GTC GAA CTT TTT CGA
Asn Ile Thr Glu Thr Ile Glu Asn Leu Arg Asp Gln Leu Glu Lys Ala>
```

Figure 16B

```
         820         830         840         850         860
          *           *           *           *           *
     *         *           *           *          *          *
ACA GAT GAA GAG CAT AAA AAA GAG ATT GAA AGT CAG GTT GAT GCT AAA
TGT CTA CTT CTC GTA TTT TTT CTC TAA CTT TCA GTC CAA CTA CGA TTT
Thr Asp Glu Glu His Lys Lys Glu Ile Glu Ser Gln Val Asp Ala Lys>

870         880         890         900         910
          *           *           *           *           *
     *         *           *           *          *          *
AAG AAA CAA AAG GAA GAG CTA GAT AAA AAG GCA ATA AAT CTT GAT AAA
TTC TTT GTT TTC CTT CTC GAT CTA TTT TTC CGT TAT TTA GAA CTA TTT
Lys Lys Gln Lys Glu Glu Leu Asp Lys Lys Ala Ile Asn Leu Asp Lys>

920         930         940         950         960
          *           *           *           *           *
     *         *           *           *          *          *
GCT CAG CAA AAA TTA GAT TCT GCT GAA GAT AAT TTA GAT GTT CAA AGA
CGA GTC GTT TTT AAT CTA AGA CGA CTT CTA TTA AAT CTA CAA GTT TCT
Ala Gln Gln Lys Leu Asp Ser Ala Glu Asp Asn Leu Asp Val Gln Arg>

970         980         990        1000
          *           *           *           *           *
     *         *           *           *          *          *
AAT ACT GTT AGA GAG AAA ATT CAA GAG GAT ATT AAC GAA ATT AAC AAG
TTA TGA CAA TCT CTC TTT TAA GTT CTC CTA TAA TTG CTT TAA TTG TTC
Asn Thr Val Arg Glu Lys Ile Gln Glu Asp Ile Asn Glu Ile Asn Lys>

1010        1020        1030        1040        1050
          *           *           *           *           *
     *         *           *           *          *          *
GAA AAG AAT TTA CCA AAG CCT GGT GAT GTA AGT TCT CCT AAA GTT GAT
CTT TTC TTA AAT GGT TTC GGA CCA CTA CAT TCA AGA GGA TTT CAA CTA
Glu Lys Asn Leu Pro Lys Pro Gly Asp Val Ser Ser Pro Lys Val Asp>

1060        1070        1080        1090        1100
          *           *           *           *           *
     *         *           *           *          *          *
AAG CAA CTA CAA ATA AAA GAG AGC CTG GAA GAT TTG CAG GAG CAG CTT
TTC GTT GAT GTT TAT TTT CTC TCG GAC CTT CTA AAC GTC CTC GTC GAA
Lys Gln Leu Gln Ile Lys Glu Ser Leu Glu Asp Leu Gln Glu Gln Leu>

1110        1120        1130        1140        1150
          *           *           *           *           *
     *         *           *           *          *          *
AAA GAA ACT GGT GAT GAA AAT CAG AAA AGA GAA ATT GAA AAG CAA ATT
TTT CTT TGA CCA CTA CTT TTA GTC TTT TCT CTT TAA CTT TTC GTT TAA
Lys Glu Thr Gly Asp Glu Asn Gln Lys Arg Glu Ile Glu Lys Gln Ile>

1160        1170        1180        1190        1200
          *           *           *           *           *
     *         *           *           *          *          *
GAA ATC AAA AAA AGT GAT GAA AAG CTT TTA AAA AGT AAA GAT GAT AAA
CTT TAG TTT TTT TCA CTA CTT TTC GAA AAT TTT TCA TTT CTA CTA TTT
Glu Ile Lys Lys Ser Asp Glu Lys Leu Leu Lys Ser Lys Asp Asp Lys>

1210        1220        1230        1240
          *           *           *           *           *
     *         *           *           *          *          *
GCA AGT AAA GAT GGT AAA GCC TTG GAT CTT GAT CGA GAA TTA AAT TCT
CGT TCA TTT CTA CCA TTT CGG AAC CTA GAA CTA GCT CTT AAT TTA AGA
Ala Ser Lys Asp Gly Lys Ala Leu Asp Leu Asp Arg Glu Leu Asn Ser>
```

Figure 16C

```
     1250         1260         1270         1280         1290
      *    *    *    *    *    *    *    *    *    *
     AAA  GCT  TCT  AGC  AAA  GAA  AAA  AGT  AAA  GCC  AAG  GAA  GAA  GAA  ATA  ACC
     TTT  CGA  AGA  TCG  TTT  CTT  TTT  TCA  TTT  CGG  TTC  CTT  CTT  CTT  TAT  TGG
     Lys  Ala  Ser  Ser  Lys  Glu  Lys  Ser  Lys  Ala  Lys  Glu  Glu  Glu  Ile  Thr>

1300         1310         1320         1330         1340
      *    *    *    *    *    *    *    *    *    *
     AAG  GGT  AAG  TCA  CAG  AAA  AGC  TTA  GGC  GAT  TTG  AAT  AAT  GAT  GAA  AAT
     TTC  CCA  TTC  AGT  GTC  TTT  TCG  AAT  CCG  CTA  AAC  TTA  TTA  CTA  CTT  TTA
     Lys  Gly  Lys  Ser  Gln  Lys  Ser  Leu  Gly  Asp  Leu  Asn  Asn  Asp  Glu  Asn>

1350         1360         1370         1380         1390
      *    *    *    *    *    *    *    *    *    *
     CTT  ATG  ATG  CCA  GAA  GAT  CAA  AAA  TTA  CCT  GAG  GTT  AAA  AAA  TTA  GAT
     GAA  TAC  TAC  GGT  CTT  CTA  GTT  TTT  AAT  GGA  CTC  CAA  TTT  TTT  AAT  CTA
     Leu  Met  Met  Pro  Glu  Asp  Gln  Lys  Leu  Pro  Glu  Val  Lys  Lys  Leu  Asp>

1400         1410         1420         1430         1440
      *    *    *    *    *    *    *    *    *    *
     AGC  AAA  AAA  GAA  TTT  AAA  CCT  GTT  TCT  GAG  GTT  GAG  AAA  TTA  GAT  AAG
     TCG  TTT  TTT  CTT  AAA  TTT  GGA  CAA  AGA  CTC  CAA  CTC  TTT  AAT  CTA  TTC
     Ser  Lys  Lys  Glu  Phe  Lys  Pro  Val  Ser  Glu  Val  Glu  Lys  Leu  Asp  Lys>

1450         1460         1470         1480
      *    *    *    *    *    *    *    *    *
     ATT  TTC  AAG  TCT  AAT  AAC  AAT  GTT  GGA  GAA  TTA  TCA  CCG  TTA  GAT  AAA
     TAA  AAG  TTC  AGA  TTA  TTG  TTA  CAA  CCT  CTT  AAT  AGT  GGC  AAT  CTA  TTT
     Ile  Phe  Lys  Ser  Asn  Asn  Asn  Val  Gly  Glu  Leu  Ser  Pro  Leu  Asp  Lys>

1490         1500         1510         1520         1530
      *    *    *    *    *    *    *    *    *    *
     TCT  TCT  TAT  AAA  GAC  ATT  GAT  TCA  AAA  GAG  GAG  ACA  GTT  AAT  AAA  GAT
     AGA  AGA  ATA  TTT  CTG  TAA  CTA  AGT  TTT  CTC  CTC  TGT  CAA  TTA  TTT  CTA
     Ser  Ser  Tyr  Lys  Asp  Ile  Asp  Ser  Lys  Glu  Glu  Thr  Val  Asn  Lys  Asp>

1540         1550         1560         1570         1580
      *    *    *    *    *    *    *    *    *
     GTT  AAT  TTG  CAA  AAG  ACT  AAG  CCT  CAG  GTT  AAA  GAC  CAA  GTT  ACT  TCT
     CAA  TTA  AAC  GTT  TTC  TGA  TTC  GGA  GTC  CAA  TTT  CTG  GTT  CAA  TGA  AGA
     Val  Asn  Leu  Gln  Lys  Thr  Lys  Pro  Gln  Val  Lys  Asp  Gln  Val  Thr  Ser>

1590         1600         1610         1620         1630
      *    *    *    *    *    *    *    *    *    *
     TTG  AAT  GAA  GAT  TTG  ACT  ACT  ATG  TCT  ATA  GAT  TCC  AGT  AGT  CCT  GTA
     AAC  TTA  CTT  CTA  AAC  TGA  TGA  TAC  AGA  TAT  CTA  AGG  TCA  TCA  GGA  CAT
     Leu  Asn  Glu  Asp  Leu  Thr  Thr  Met  Ser  Ile  Asp  Ser  Ser  Ser  Pro  Val>

1640         1650         1660         1670         1680
      *    *    *    *    *    *    *    *    *    *
     TTT  TTA  GAG  GTT  ATT  GAT  CCA  ATT  ACA  AAT  TTA  GGA  ACT  CTT  CAA  CTT
     AAA  AAT  CTC  CAA  TAA  CTA  GGT  TAA  TGT  TTA  AAT  CCT  TGA  GAA  GTT  GAA
     Phe  Leu  Glu  Val  Ile  Asp  Pro  Ile  Thr  Asn  Leu  Gly  Thr  Leu  Gln  Leu>
```

Figure 16D

```
                1690              1700              1710              1720
         *         *         *         *         *         *         *
ATT GAT TTA AAT ACT GGT GTT AGG CTT AAA GAA AGC ACT CAG CAA GGC
TAA CTA AAT TTA TGA CCA CAA TCC GAA TTT CTT TCG TGA GTC GTT CCG
Ile Asp Leu Asn Thr Gly Val Arg Leu Lys Glu Ser Thr Gln Gln Gly>

1730              1740              1750              1760              1770
       *         *         *         *         *         *         *         *         *         *
ATT CAG CGG TAT GGA ATT TAT GAA CGT GAA AAA GAT TTG GTT GTT ATT
TAA GTC GCC ATA CCT TAA ATA CTT GCA CTT TTT CTA AAC CAA CAA TAA
Ile Gln Arg Tyr Gly Ile Tyr Glu Arg Glu Lys Asp Leu Val Val Ile>

1780              1790              1800              1810              1820
            *         *         *         *         *         *         *         *         *
AAA ATG GAT TCA GGA AAA GCT AAG CTT CAG ATA CTT GAT AAA CTT GAA
TTT TAC CTA AGT CCT TTT CGA TTC GAA GTC TAT GAA CTA TTT GAA CTT
Lys Met Asp Ser Gly Lys Ala Lys Leu Gln Ile Leu Asp Lys Leu Glu>

1830              1840              1850              1860              1870
              *         *         *         *         *         *         *         *         *         *
AAT TTA AAA GTG GTA TCA GAG TCT AAT TTT GAG ATT AAT AAA AAT TCA
TTA AAT TTT CAC CAT AGT CTC AGA TTA AAA CTC TAA TTA TTT TTA AGT
Asn Leu Lys Val Val Ser Glu Ser Asn Phe Glu Ile Asn Lys Asn Ser>

1880              1890              1900              1910              1920
              *         *         *         *         *         *         *         *         *         *
TCT CTT TAT GTT GAT TCT AAA ATG ATT TTA GTA GCT GTT AGG GAT AAA
AGA GAA ATA CAA CTA AGA TTT TAC TAA AAT CAT CGA CAA TCC CTA TTT
Ser Leu Tyr Val Asp Ser Lys Met Ile Leu Val Ala Val Arg Asp Lys>

1930              1940              1950              1960
                *         *         *         *         *         *         *         *         *
GAT AGT AGT AAT GAT TGG AGA TTG GCC AAA TTT TCT CCT AAA AAT TTA
CTA TCA TCA TTA CTA ACC TCT AAC CGG TTT AAA AGA GGA TTT TTA AAT
Asp Ser Ser Asn Asp Trp Arg Leu Ala Lys Phe Ser Pro Lys Asn Leu>

1970              1980              1990              2000              2010
       *         *         *         *         *         *         *         *         *         *
GAT GAG TTT ATT CTT TCA GAG AAT AAA ATT ATG CCT TTT ACT AGC TTT
CTA CTC AAA TAA GAA AGT CTC TTA TTT TAA TAC GGA AAA TGA TCG AAA
Asp Glu Phe Ile Leu Ser Glu Asn Lys Ile Met Pro Phe Thr Ser Phe>

2020              2030              2040              2050              2060
            *         *         *         *         *         *         *         *         *
TCT GTG AGA AAA AAT TTT ATT TAT TTG CAA GAT GAG TTT AAA AGT CTA
AGA CAC TCT TTT TTA AAA TAA ATA AAC GTT CTA CTC AAA TTT TCA GAT
Ser Val Arg Lys Asn Phe Ile Tyr Leu Gln Asp Glu Phe Lys Ser Leu>

2070              2080              2090              2100
              *         *         *         *         *         *         *
GTT ATT TTA GAT GTA AAT ACT TTA AAA AAA GTT AAG TA
CAA TAA AAT CTA CAT TTA TGA AAT TTT TTT CAA TTC AT
Val Ile Leu Asp Val Asn Thr Leu Lys Lys Val Lys Xxx>
```

Figure 16E p93 - K48

```
   1 ATGAAAAAAT TGTTACTAAT CTTTAGTTTT TTTCTTATTT CTTTGAATGG ATTTCCTCTT
  61 AATTCAAGGG AAGTTGATAA GGAAAAATTA AAGGATTTTG TTAATATGGA TCTTGAGTTT
 121 GTAAACTATA AAGGTCCTTA TGATTCTACA AATACATATG AACAAATAGT AGGTATTGGT
 181 GAGTTTTTAG CAAGACCATT GATTAATTCC AATAGCAACT CAATTTATTA TGGTAAATAT
 241 TTTATTAATA GATTTATTGA TGATCAAGAT AAAAAAGCAA GCGTTGATGT TTTTTCTATT
 301 GGTAGTAGGT CACAGCTTGA CAGTATATTG AATCTAAGAA GAATTCTTAC AGGGTATTTG
 361 ATAAAGTCTT TTGATTATGA AAGATCTAGT GCTGAATTAA TTGCTAAGGT TATTACAATA
 421 CATAATGCTG TTTATAGAGG GGATTTAAAT TATTATAAAG AGGTTTATAT TGAGGCTGCT
 481 TTAAAGTCTT TAACTAAAGA AAATGCAGGT CTTTCTAGAG TGTACAGTCA ATGGGCTGGA
 541 AAGCACACAA TATTTATTCC TCTTAAAAAG AATATTTTAT CTGGAAAAGT TGAGTCTGAC
 601 ATTGATATTG ACAGTTTGGT TACAGATAAG GTTGTGGCAG GTCTTTTAAG CGAGAATGAA
 661 GCAGGTGTTA ACTTTGCAAG AGATATTACA GATATTCAAG GCGAAACTCA TAAAGCAGAT
 721 CAAGATAAAA TTGATATTGA ATTAGATAAT GTTCATAAAA GTGATTCCAA TATAACAGAG
 781 ACTATTGAGA ATTTAAGAGA TCAGCTTGAA AAGGCTACAG ATGAAGAGCA TAGAAAAGAG
 841 ATTGAAAGTC AGGTTGATGC TAAAAAGAAA CAAAAGAAG AACTAGATAA AAAGGCAATC
 901 GATCTTGATA AAGCCCAACA AAAATTAGAT TCTTCTGAAG ATAATTTAGA TATTCAAAGG
 961 GATACTGTTA GAGAGAAGAT TCAAGAGGAT ATTGACGAGA TTAATAAAGA AAAGAATTTG
1021 CCAAAACCTG TGATGTAAG TTCTCCTAAA GTTGATAAGC AGCTACAAAT AAAAGAGAGT
1081 CTAGAAGACT TGCAGGAACA GCTTAAAGAA ACTAGCGATG AAAATCAAAA AAGAGAAATT
1141 GAAAAGCAAA TTGAAATCAA AAAAAGTGAT GAAGAACTTT TAAAAAGTAA AGATCCTAAA
1201 GCATTAGATC TTAATGGAGA TTTAAATTCT AAAGTTTCTA GTAAAGAAAA AATTAAAGGC
1261 AAAGAAGGAG AAATAGTCAA AGAGGAATCA AAGGCAAGTT TAGCTGATTT GAATAATGAC
1321 GAAAATCTTA TGAGGCCGGA AGATCAAAAA TTATCTGAGG ATAAAAAATT AGATAGTAAA
1381 AAAAATTTAA AACCTGTTTC TGAGATTGAG AGAGTAAATG AAATTTCGAA GTCTAACAAC
1441 AATGAGATTA GTGAATCATC ACCATTATAT AAGCCTTCTT ATAGCGATAT GGATTCAAAA
1501 GAGGGTATAG ATAATAAAGA TGTTAACTTG CAAGAAACCA AGTCTCAAAC TAAAAGTCAA
1561 CCTACTTCTT TAAATCAAGA TTTGACTACT ATGTCTATAG ATTCTAGTAA TCCTGTATTT
1621 TTAGAGGTTA TTGATCCTAT TACAAATTTA GGAACGCTTC AACTTATTGA TTTGAATACC
1681 GGTGTTAGAC TTAAAGAAAG TACTCAGCAA GGCATTCAGC GGTATGGAAT TTATGAACGT
1741 GAAAAAGATT TAGTTGTTAT TAAAATGGAT TCAGGAAAAG CCAAGCTTCA AATACTTAAT
1801 AAACTTGAGA ATTTAAAGT GATATCGGAG TCTAATTTTG AGATTAATAA AAATTCATCT
1861 CTTTATGTTG ACTCTAAAAT GATTTTAGTA GTTGTGAGAG ATAGTGGTAA TGTTTGGAGA
1921 TTGGCTAAAT TTTCTCCTAA AAATTTAAAT GAGTTTATTC TTTCAGAGAA TAAAATTTTG
1981 CCTTTTACTA GCTTTTCTGT GAGAAAGAAT TTTATTTATT TGCAGGATGA GTTAAAAGT
2041 CTTATTACTT TAGATGTAAA TACTTTAAAA AAAGTTAAGT A
```

Figure 17 p93 - B0

```
   1 ATGAAAAAAA TGTTACTAAT CTTTAGTTTT TTTCTTGTTT TTTTAAATGG ATTTCCTCTT
  61 AATGCAAGGG AAGTTGATAA GGAAAAATTA AAGGACTTTG TTAATATGGA TCTTGAATTT
 121 GTTAATTACA AGGGTCCTTA TGATTCTACA GATACATATG AACAAATAGT AGGTATTGGG
 181 GAGTTTTTAG CAAGGCCGTT GAACAATTCC AATAGTAATT CAAGTTATTA TGGTAAATAT
 241 TTTGTTAATA GATTTATTGA CGATCAAGAT AAAAAAGCAA GTGTTGATAT TTTTTCTATT
 301 GGTAGTAAGT CAGAGCTTGA TAGTATATTA AATCTAAGAA GAATTCTTAC AGGGTATTTA
 361 ATGAAGTCTT TTGATTATGA GAGGTCTAGT GCGGAATTAA TTGCTAAAGC TATTACAATA
 421 TATAATGCTG TTTATAGAGG AGATTTAGAT TATTACAAAG AGTTTTATAT TGAGGCTTCT
 481 TTGAAGTCTT TGACTAAAGA AAATGCAGGT CTTTCTAGGG TGTACAGTCA ATGGGCTGGG
 541 AAGACACAAA TATTTATTCC TCTTAAAAAG AATATTTTAT CTGGAAATGT TGAGTCTGAC
 601 ATTGATATTG ATAGTTTGGT TACAGATAAG GTGGTGGCAG CTCTTTTAAG TGAGAATGAA
 661 TCAGGTGTTA ACTTTGCAAG AGATATTACA GACATTCAAG GCGAAACTCA TAAAGCAGAT
 721 CAAGATAAAA TTGATATTGA ATTAGATAAT TTTCATGAAA GTGATTCCAA TATAACAGAA
 781 ACTATTGAGA ATTTAAGGGA TCAGCTTGAA AAAGCTACAG ATGAAGAGCA TAAAAAAGAG
 841 ATTGAAAGTC AGGTTGATGC TAAAAAGAAA CAAAAGGAAG AATTAGATAA AAAGGCAATT
 901 GATCTTGATA AAGCTCAACA AAAATTAGAT TTTGCTGAAG ATAATCTAGA TATTCAAAGG
 961 GATACTGTTA GAGAGAAGCT TCAAGAAAAT ATTAACGAGA CTAATAAGGA AAAGAATTTA
1021 CCAAAGCCTG GTGATGTAAG TTCTCCTAAG GTTGATAAGC AGTTGCAGAT AAAAGAGAGT
1081 CTAGAAGATT TGCAAGAGCA GCTTAAAGAA GCTAGTGATG AAAATCAAAA AAGAGAAATA
1141 GAAAAGCAAA TTGAAATCAA AAAAAATGAT GAAGAACTTT TTAAAAATAA AGATCATAAA
1201 GCATTAGATC TTAAGCAAGA ATTAAATTCT AAAGCTTCTA GTAAAGAAAA AATTGAAGGC
1261 GAAGAAGAGG ATAAAGAATT AGATAGTAAA AAAAATTTAG AGCCTGTTTC TGAGGCTGAT
1321 AAAGTAGATA AAATTTCCAA GTCTAACAAC AATGAGGTTA GTAAATTATC CCCGTTAGAT
1381 GAGCCTTCTT ATAGCGACAT TGATTCGAAA GAGGGTGTAG ATAACAAAGA TGTTGATTTG
1441 CAAAAAACTA ACCCCAAGT TGAAAGTCAA CCTACTTCGT TAAATGAAGA TTTGATTGAT
1501 GTGTCTATAG ATTCCAGTAA TCCTGTCTTT TTAGAGGTTA TCGATCCGAT TACAAATTTA
1561 GGAACGCTTC AACTTATTGA TTTGAATACC GGTGTTAGAC TTAAAGAAAG TGCTCAACAA
1621 GGTATTCAGC GATATGGAAT TTATGAACGT GAAAAGATT TGGTTGTTAT TAAAATAGAT
1681 TCAGGAAAAG CTAAGCTTCA GATACTTGAT AAACTCGAGA ATTTAAAAGT GATATCAGAG
1741 TCTAATTTTG AGATTAATAA AAATTCATCT CTTTATGTTG ACTCTAGAAT GATTTAGTA
1801 GTTGTTAAGG ACGATAGTAA TGCTTGGAGA TTGGCTAAAT TTTCTCCTAA AAATTTAGAT
1861 GAATTTATTC TGTCAGAAAA TAAAATTTTG CCTTTTACTA GCTTGCTGT GAGAAAGAAT
1921 TTTATTTATT TGCAAGATGA ACTTAAAAGC TTAGTTACTT TAGATGTAAA TACTTTAAAA
1981 AAAGTTAAGT A
```

Figure 18 p93 - pIRO

```
   1 ATGAAAAAAA TGTTACTAAT CTTTAGTTTT TTTCTTATTT CTTTGAATGG ATTTCCCCTT
  61 AATGCAAGGG AAGTTGATAA GGAAAAATTA AAGGACTTTG TTAATATGGA TCTTGAGTTT
 121 GTAAACTATA AAGGTCCTTA TGATTCTACA AATACATATG AACAAATAGT AGGTATTGGT
 181 GAGTTTTTAG CAAGACCATT GATTAATTTC AATAGCAACT CAAGTTATTA TGGTAAATAT
 241 TTTATTAATA GATTTATTGA CGATCAAGAT AAAAAAGCAA GCGTTGATGT TTTTTCTATT
 301 AGTAGTAAGT CACAGCTTGA CAGTATATTG AATTTAAGAA GAATTCTTAC AGGGTATTTG
 361 ATAAAGTCTT TTGATTATGA AAGATCTAGT GCTGAATTAA TTGCCAAGGT TATTACAATA
 421 CATAATGCTG TTTATAGAGG TGATTTAAAT TATTATAAAG AGTTTTATAT TGAGTCTGCT
 481 TTAAAGTCTT TAACTAAAGA AAATGCAGGT CTTTCTAGAG TGTACAGTCA ATGGGCTGGA
 541 AAGACACAAA TATTTATTCC TCTTAAAAAG AATATTTTAT CTGGAAAAAT TGAGTCTGAC
 601 ATTGATATTG ATAGTTTGGT TACAGATAAG GTTGTGGCAG GTCTTTTAAG CGAAAATGAA
 661 GCAGGTGTTA ACTTTGCAAG GGATATTACA GATATTCAAG GAGAAACTCA TAAAGCAGAT
 721 CAAGATAAAA TTGATATTGA ATTAGATAAT GTTCATGAAA GTGATTCCAA TATAACAGAA
 781 ACTATTGAGA ATTTAAGAGA TCAGCTTGAA AAGGCTACAG ATGAAGAGCA TAGAAAAGAG
 841 ATTGAAAGTC AAGTTGATGC TAAAAAGAAA CAAAAAGAAG AACTAGATAA AAAGGCAATC
 901 GATCTTGATA AAGCCCAACA AAAATTAGAT TTTTCTGAAG ATAATTTAGA TATTCAAAGG
 961 GATACTGTTA GAGAGAAGAT TCAAGAGGAT ATTAACGAGA TTAATAAGGA AAAGAATTTA
1021 CCAAAACCTG GTGATGTAAG TTCTCCTAAA GTTGATAAGC AGCTACAAAT AAAAGAGAGT
1081 CTAGAAGACT TGCAGGAGCA GCTTAAAGAA ACTAGCGATG AAAATCAAAA AAGAGAAATT
1141 GAAAAGCAAA TTGAAATCAA AAAAAGTGAT GAAGAACTTT TAAAAAGCAA AGATCCTAAA
1201 GCATTAGATC TTAATCGAGA TTTAAATTCT AAAGCTTCTA GTAAAGAAAA AATTAAAGGC
1261 AAAGAAAAAG AAATAGTCAA AGAGAAATCA AAGGTAAGTT TAGGTGATTT GGATAATGAC
1321 GAAACCCTTA TGACGCCGGA AGATCAAAAA TTATCTGAGG ATAAAAAATT AGATAGTAAA
1381 AAAAATTTAA AACCTGTTTC TGAGATTGAG AGAGTAAATG AAATTTCAAA GTCTAACAAC
1441 AATGAGGTTA GCAAATCATC ACCATTAGAT AAGCCTTCTT ATAGTGATAT CGATTCAAAA
1501 GAGGTTGTAG ATAATAAAGA TGTTAATTTG CAAGAAACCA AGCCTCAAGC TAAAAGTCAA
1561 TCTACTTCTT TAAATCAAGA TTTGATTACT ATGTCTATAG ATTCTAGTAA TCCTGTATTT
1621 TTAGAGGTTA TTGATCCTAT TACAAATTTA GGAATGCTTC AACTTATTGA TTTAAATACT
1681 GGTGTTAGAC TTAAAGAAAG CACTCAGCAA GGCATTCAGC GTTATGGAAT TTATGAACGT
1741 GAAAAAGATT TAGTTGTTAT TAAATGGAT TCAGGAAAAG CTAAGCTTCA AATACTTAAT
1801 AAACTTGAGA ATTTAAAAGT GATATCAGAG TCTAATTTTG AGATTAATAA AAATTCATCT
1861 CTTTATGTTG ACTCTAAAAT GATTTTAGTA GCTGTGAAAG ATAGTGGTAA TGTTTGGAGA
1921 TTGGCTAAAT TTTCTCCTAA AAATTTAGAT GAGTTTATTC TTTCAGAGAA TAAAATTTTG
1981 CCTTTTACTA GCTTTTCTGT GAGAAAGAAT TTATTTATT TGCAAGATGA GTTAAAAGT
2041 CTTATTACTT TAGATGTAAA TACTTTAAAA AAAGTTAAGT A
```

Figure 19 p93 - pGau

```
   1 ATGAAAAAAA TGTTACTAAT CTTTAGTTTT TTTCTTGTTT TTTTAAATGG ATTTCCTCTT
  61 AATGCAAGGG AAGTTGATAA GGAAAAATTA AAGGACTTTG TTAATATGGA TCTTGAATTT
 121 GTTAATTACA AGGGTCCTTA TGATTCTACA AATACATATG AACAAATAGT AGGTATTGGG
 181 GAGTTTTTAG CAAGGCCGTT GATCAATTCC AATAGTAATT CAAGTTATTA TGGTAAATAT
 241 TTTGTTAATA GATTTATTGA CGATCAAGAT AAAAAAGCAA GTGTTGATAT TTTTTCTATT
 301 GGTAGTAAGT CAGAGCTTGA TAGTATATTA AATCTAAGAA GAATTCTTAC AGGGTATTTA
 361 ATGAAGTCTT TTGATTATGA GAGGTCTAGT GCGGAATTAA TTGCTAAAGC TATTACAATA
 421 TATAATGCTG TTTATAGAGG AGATTTAGAT TATTACAAAG AGTTTTATAT TGAGGCTTCT
 481 TTGAAGTCTT TGACTAAAGA AAATGCAGGT CTTTCTAGGG TGTACAGTCA ATGGGCTGGG
 541 AAGACACAAA TATTTATTCC TCTTAAAAAG AATATTTTAT CTGGAAATGT TGAGTCTGAC
 601 ATTGATATTG ATAGTTTGGT TACAGATAAG GTGGTGGCAG CTCTTTTAAG TGAGAATGAA
 661 TCAGGTGTTA ACTTTGCAAG AGATATTACA GACATTCAAG GCGAAACTCA TAAAGCAGAT
 721 CAAGATAAAA TTGATATTGA ATTAGATAAT ATTCATGAAA GTGATTCCAA TATAACAGAA
 781 ACTATTGAGA ATTTAAGGGA TCAGCTTGAA AAAGCTACAG ATGAAGAGCA TAAAAAGAG
 841 ATTGAAAGTC AGGTTGATGC TAAAAAGAAA CAAAAGGAAG AATTAGATAA AAAGGCAATT
 901 GATCTTGATA AAGCTCAACA AAAATTAGAT TTTGCTGAAG ATAATCTAGA TATTCAAAGG
 961 GATACTGTTA GAGAGAAGCT TCAAGAGAAT ATTAACGAGA CTAATAAGGA AAAGAATTTA
1021 CCAAAGCCTG GTGATGTAAG TTCTCCTAAA GTTGATAAGC AACTACAAAT AAAAGAGAGC
1081 CTGGAAGATT TGCAGGAGCA GCTTAAAGAA ACTGGTGATG AAAATCAGAA AAGAGAAATT
1141 GAAAAGCAAA TTGAAATCAA AAAAAGTGAT GAAAAGCTTT TAAAAAGTAA AGATGATAAA
1201 GCAAGTAAAG ATGGTAAAGC CTTGGATCTT GATCGAGAAT TAAATTCTAA AGCTTCTAGC
1261 AAAGAAAAAA GTAAAGCCAA GGAAGAAGAA ATAACCAAGG GTAAGTCACA GAAAAGCTTA
1321 GGCGATTTGA ATAATGATGA AAATCTTATG ATGCCAGAAG ATCAAAAATT ACCTGAGGTT
1381 AAAAAATTAG ATAGCAAAAA AGAATTTAAA CCTGTTTCTG AGGTTGAGAA ATTAGATAAG
1441 ATTTTCAAGT CTAATAACAA TGTTGGAGAA TTATCACCGT TAGATAAATC TTCTTATAAA
1501 GACATTGATT CAAAAGAGGA GACAGTTAAT AAAGATGTTA ATTTGCAAAA GACTAAGCCT
1561 CAGGTTAAAG ACCAAGTTAC TTCTTTGAAT GAAGATTTGA CTACTATGTC TATAGATTCC
1621 AGTAGTCCTG TATTTTTAGA GGTTATTGAT CCAATTACAA ATTAGGAAC TCTTCAACTT
1681 ATTGATTTAA ATACTGGTGT TAGGCTTAAA GAAAGCACTC AGCAAGGCAT TCAGCGGTAT
1741 GGAATTTATG AACGTGAAAA AGATTTGGTT GTTATTAAAA TGGATTCAGG AAAAGCTAAG
1801 CTTCAGATAC TTGATAAACT TGAAAATTTA AAAGTGGTAT CAGAGTCTAA TTTTGAGATT
1861 AATAAAAATT CATCTCTTTA TGTTGATTCT AAAATGATTT TAGTAGCTGT TAGGGATAAA
1921 GATAGTAGTA ATGATTGGAG ATTGGCCAAA TTTTCTCCTA AAAATTTAGA TGAGTTTATT
1981 CTTTCAGAGA ATAAAATTAT GCCTTTTACT AGCTTTTCTG TGAGAAAAAA TTTTATTTAT
2041 TTGCAAGATG AGTTTAAAAG TCTAGTTATT TTAGATGTAA ATACTTTAAA AAAAGTTAAG
2101 TAAAGCC
```

Figure 20 p93 - 25015

```
   1 ATGAAAAAAA TGTTACTAAT CTTTAGTTTT TTTCTTATTT TTTTGAATGG ATTTCCTCTT
  61 AATGCAAGGA AAGTTGATAA GGAAAAATTA AAGGATTTTG TTAATATGGA TCTTGAGTTT
 121 GTAAATTATA AAGGTCCTTA TGATTCTACA AATACGTATG AACAAATAGT GGGTATTGGG
 181 GAGTTTTTAG CAAGACCGCT GACCAATTCC AATAGCAACT CAAGTTATTA TGGCAAATAT
 241 TTTATTAATA GATTTATTGA TGATCAAGAT AAAAAAGCAA GTGTTGATGT TTTTTCTATA
 301 AGCAGCAAAT CAGAGCTTGA CAGTATATTG AATTTAAGAA GAATTCTTAC AGGGTATATA
 361 ATAAAGTCTT TCGATTATGA CAGGTCTAGT GCAGAATTAA TTGCTAAGGT TATTACAATA
 421 TATAATGCTG TTTATAGAGG AGATTTGGAT TATTATAAAG GGTTTTATAT TGAGCCTGCT
 481 TTGAAGTCTT TAACTAAAGA AAACGCAGGT CTTTCTAGGG TTTACAGTCA GTGGGCTGGA
 541 AAGACTCAAA TATTTATTCC TCTTAAAAAG GATATTTTGT CTGGAAATAT TGAATCTGAC
 601 ATTGATATTG ACAGTTGGT TACAGATAAG GTGATAGCAG CTCTTTTAAG CGAAAATGAA
 661 GCAGGCGTTA ACTTTGCAAG AGATATTACA GATATTCAAG GCGAAACTCA TAAGGCAGAT
 721 CAAGATAAGA TTGATACTGA ATTAGACAAT ATCCATGAAA GCGATTCTAA TATAACAGAA
 781 ACTATTGAAA ATTTAAGGGA TCAGCTTGAA AAAGCTACAG ATGAAGAGCA TAAAAAAGAG
 841 ATTGAAAGTC AGGTTGATGC TAAAAAGAAA GAAAAGGAAG AGCTAGATAA AAAGGCAATC
 901 AATCTTGATA AAGCTCAGCA AAAATTAGAC TCTGCTGAAG ATAATTTAGA TGTTCAAAGA
 961 GATACTGTTA GAGAGAAAAT TCAAGAGGAT ATTAATGAGA TTAATAAGGA AAGAATTTG
1021 CCAAAACCTG GTGATGTAAG TTCTCCTAAA GTTGATAAGC AACTGCAAAT AAAAGAGAGT
1081 CTAGAAGATT TGCAGGAGCA GCTTAAAGAA GCTGGTGATG AAAATCAGAA AAGAGAAATT
1141 GAGAAGCAAA TTGAAATCAA AAAAAGGGAC GAAGAACTTT TAAAAAGTAA AGATGGCAAA
1201 GTAAGTAAAG ATTATGAAGC ATTAGATCTT GATCGAGAAT TATCCAAAGC TTCTAGTAAA
1261 GAAAAAAGTA AGGTCAAGGA AGAAGAAATA ACTAAAGGTA AATCACGGGC AAGCTTAGGC
1321 GATTTGAATA ATGATAAAAA CCTTATGTTG CCAGAAGATC AAAAATTACC TGAAGATAAA
1381 AAATTGGATA GTAAATTAGA TGGTAAAAAA GAATTTAAAC CAGTTTCTGA GGTGAAAAAA
1441 TTAGATAAGA TTTCCAAGTC TAATAACAAT GAGGTTGGCA AGTTATCACC ATTAGATAAG
1501 CCTTCTTATG ATGATATTGA TTCAAAAGAG GAGGTAGATA ATAAAGCTAT TAATTTGCAA
1561 AAGATCGACC CTAAAGTTAA AGACCAAACT ACTTCTTTGA ATGAAGATTT GGATAAAGAT
1621 TTGACTACTA TGTCTATAGA TTCCAGCAGT CCTGTATTTC TAGAGGTTAT TGATCCTATT
1681 ACAAATTTAG GAACCCTGCA GCTTATTGAT TTAAATACTG GGTTAGGCT TAAGGAAAGC
1741 ACTCAGCAAG GCATTCAGCG GTATGGAATT TATGAACGTG AAAAAGATTT GGTTGTTATT
1801 AAAATGGATT CAGGAAAGGC TAAGCTTCAA ATACTTAATA AGCTTGAAAA TTTGAAAGTG
1861 GTATCAGAGT CTAATTTTGA GATCAATAAA AATTCATCTC TTTATGTTGA CTCTAAAATG
1921 ATTTTGGCAG CTGTTAGAGA TAAGGATGAT AGCAATGCTT GGAGATTGGC TAAATTTTCT
1981 CCTAAAAATT TGGATGAGTT TATTCTTTCA GAGAATAAAA TTTGCCTTTT TACTAGCTTT
2041 TCTGTGAGAA AAAATTTATT TTATTTGCAA GATGAGCTTA AAAATCTAGT TATTTTAGAT
2101 GTAAATACTT TAAAAAAAGT TAAGTA
```

Figure 21 p93 - pKO

```
   1 ATGAAAAAAA TGTTACTAAT CTTTAGTTTT TTTCTTGTTT TTTTAAATGG ATTTCCTCTT
  61 AATGCAAGGG AAGTTGATAA GGAAAAATTA AAGGACTTTG TTAATATGGA TCTTGAATTT
 121 GTTAATTACA AGGGTCCTTA TGATTCTACA AATACATATG AACAAATAGT AGGTATTGGG
 181 GAGTTTTTAG CAAGGCCGTT GATCAATTCC AATAGTAATT CAAGTTATTA TGGTAAATAT
 241 TTTGTTAATA GATTTATTGA CGATCAAGAT AAAAAAGCAA GTGTTGATAT TTTTTCTATT
 301 GGTAGTAAGT CAGAGCTTGA TAGTATATTA AATCTAAGAA GAATTCTTAC AGGGTATTTA
 361 ATGAAGTCTT TTGATTATGA GAGGTCTAGT GCGGAATTAA TTGCTAAAGC TATTACAATA
 421 TATAATGCTG TTTATAGAGG AGATTTAGAT TATTCAAAAG AGTTTTATAT TGAGGCTTCT
 481 TTGAAGTCTT TGACTAAAGA AAATGCAGGT CTTTCTAGGG TGTACAGTCA ATGGGCTGGG
 541 AAGACACAAA TATTTATTCC TCTTAAAAAG AATATTTTAT CTGGAAATGT TGAGTCTGAC
 601 ATTGATATTG ATAGTTTGGT TACAGATAAG GTGGTGGCAG CTCTTTTAAG TGAGAATGAA
 661 TCAGGTGTTA ACTTTGCAAG AGATATTACA GACATTCAAG GCGAAACTCA TAAAGCAGAT
 721 CAAGATAAAA TTGATATTGA ATTAGATAAT TTTCATGAAA GTGATTCCAA TATAACAGAA
 781 ACTATTGAGA ATTTAAGGGA TCAGCTTGAA AAAGCTACAG ATGAAGAGCA TAAAAAAGAG
 841 ATTGAAAGTC AGGTTGATGC TAAAAAGAAA CAAAGGAAG AATTAGATAA AAAGGCAATT
 901 GATCTTGATA AAGCTCAACA AAAATTAGAT TTTGCTGAAG ATAATCTAGA TATTCAAAGG
 961 GATACTGTTA GAGAGAAGCT TCAAGAAAAT ATTAACGAGA CTAATAAGGA AAAGAATTTA
1021 CCAAAGCCTG GTGATGTAAG TTCTCCTAAG GTTGATAAGC AGTTGCAGAT AAAAGAGAGT
1081 CTAGAAGATT TGCAAGAGCA GCTTAAAGAA GCTAGTGATG AAAATCAAAA AAGAGAAATA
1141 GAAAAGCAAA TTGAAATCAA AAAAAATGAT GAAGAACTTT TTAAAAATAA AGATCATAAA
1201 GCATTAGATC TTAAGCAAGA ATTAAATTCT AAAGCTTCTA GTAAAGAAAA AATTGAAGGC
1261 GAAGAAGAGG ATAAAGAATT AGATAGTAAA AAAAATTTAG AGCCTGTTTC TGAGGCTGAT
1321 AAAGTAGATA AATTTCCAA GTCTAACAAC AATGAGGTTA GTAAATTATC CCCGTTAGAT
1381 GAGCCTTCTT ATAGCCGACAT TGATTCGAAA GAGGGTGTAG ATAACAAAGA TGTTGATTTG
1441 CAAAAAACTA AACCCCAAGT TGAAAGTCAA CCTACTTCGT TAAATGAAGA CTTGATTGAT
1501 GTGTCTATAG ATTCCAGTAA TCCTGTCTTT TTAGAGGTTA TCGATCCGAT TACAAATTTA
1561 GGAACGCTTC AACTTATTGA TTTGAATACC GGTGTTAGAC TTAAAGAAAG TGCTCAACAA
1621 GGTATTCAGC GATATGGAAT TTATGAACGT GAAAAGATT TGGTTGTTAT TAAAATAGAT
1681 TCAGGAAAAG CTAAGCTTCA GATACTTGAT AAACTCGAGA ATTTAAAAGT GATATCAGAG
1741 TCTAATTTTG AGATTAATAA AAATTCATCT CTTTATGTTG ACTCTAGAAT GATTTTAGTA
1801 GTTGTTAAGG ACGATAGTAA TGCTTGGAGA TTGGCTAAAT TTTCTCCTAA AAATTTAGAT
1861 GAATTTATTC TGTCAGAAAA TAAATTTTTG CCTTTTACTA GCTTTGCTGT GAGAAAGAAT
1921 TTTATTTATT TGCAAGATGA ACTTAAAAGC TTAGTTACTT TAGATGTAAA TACTTTAAAA
1981 AAAGTTAAGT A
```

Figure 22

K48 OSP A/ PGAU OSP A FUSION

```
              10                  20                  30                  40
       *           *           *           *           *           *           *           *
ATG   AAA   AAA   TAT   TTA   TTG   GGA   ATA   GGT   CTA   ATA   TTA   GCC   TTA   ATA   GCA
TAC   TTT   TTT   ATA   AAT   AAC   CCT   TAT   CCA   GAT   TAT   AAT   CGG   AAT   TAT   CGT
Met   Lys   Lys   Tyr   Leu   Leu   Gly   Ile   Gly   Leu   Ile   Leu   Ala   Leu   Ile   Ala>

50                  60                  70                  80                  90
       *           *           *           *           *           *           *           *           *
TGT   AAG   CAA   AAT   GTT   AGC   AGC   CTT   GAT   GAA   AAA   AAT   AGC   GTT   TCA   GTA
ACA   TTC   GTT   TTA   CAA   TCG   TCG   GAA   CTA   CTT   TTT   TTA   TCG   CAA   AGT   CAT
Cys   Lys   Gln   Asn   Val   Ser   Ser   Leu   Asp   Glu   Lys   Asn   Ser   Val   Ser   Val>

100                 110                 120                 130                 140
       *           *           *           *           *           *           *           *
GAT   TTA   CCT   GGT   GGA   ATG   ACA   GTT   CTT   GTA   AGT   AAA   GAA   AAA   GAC   AAA
CTA   AAT   GGA   CCA   CCT   TAC   TGT   CAA   GAA   CAT   TCA   TTT   CTT   TTT   CTG   TTT
Asp   Leu   Pro   Gly   Gly   Met   Thr   Val   Leu   Val   Ser   Lys   Glu   Lys   Asp   Lys>

150                 160                 170                 180                 190
       *           *           *           *           *           *           *           *           *
GAC   GGT   AAA   TAC   AGT   CTA   GAG   GCA   ACA   GTA   GAC   AAG   CTT   GAG   CTT   AAA
CTG   CCA   TTT   ATG   TCA   GAT   CTC   CGT   TGT   CAT   CTG   TTC   GAA   CTC   GAA   TTT
Asp   Gly   Lys   Tyr   Ser   Leu   Glu   Ala   Thr   Val   Asp   Lys   Leu   Glu   Leu   Lys>

200                 210                 220                 230                 240
       *           *           *           *           *           *           *           *
GGA   ACT   TCT   GAT   AAA   AAC   AAC   GGT   TCT   GGA   ACA   CTT   GAA   GGT   GAA   AAA
CCT   TGA   AGA   CTA   TTT   TTG   TTG   CCA   AGA   CCT   TGT   GAA   CTT   CCA   CTT   TTT
Gly   Thr   Ser   Asp   Lys   Asn   Asn   Gly   Ser   Gly   Thr   Leu   Glu   Gly   Glu   Lys>

250                 260                 270                 280
       *           *           *           *           *           *           *           *
ACT   GAC   AAA   AGT   AAA   GTA   AAA   TTA   ACA   ATT   GCT   GAT   GAC   CTA   AGT   CAA
TGA   CTG   TTT   TCA   TTT   CAT   TTT   AAT   TGT   TAA   CGA   CTA   CTG   GAT   TCA   GTT
Thr   Asp   Lys   Ser   Lys   Val   Lys   Leu   Thr   Ile   Ala   Asp   Asp   Leu   Ser   Gln>

290                 300                 310                 320                 330
       *           *           *           *           *           *           *           *           *
ACT   AAA   TTT   GAA   ATT   TTC   AAA   GAA   GAT   GCC   AAA   ACA   TTA   GTA   TCA   AAA
TGA   TTT   AAA   CTT   TAA   AAG   TTT   CTT   CTA   CGG   TTT   TGT   AAT   CAT   AGT   TTT
Thr   Lys   Phe   Glu   Ile   Phe   Lys   Glu   Asp   Ala   Lys   Thr   Leu   Val   Ser   Lys>

340                 350                 360                 370                 380
       *           *           *           *           *           *           *           *
AAA   GTA   ACC   CTT   AAA   GAC   AAG   TCA   TCA   ACA   GAA   GAA   AAA   TTC   AAC   GAA
TTT   CAT   TGG   GAA   TTT   CTG   TTC   AGT   AGT   TGT   CTT   CTT   TTT   AAG   TTG   CTT
Lys   Val   Thr   Leu   Lys   Asp   Lys   Ser   Ser   Thr   Glu   Glu   Lys   Phe   Asn   Glu>
```

Figure 23A

K48 OSP A/ PGAU OSPA FUSION

```
         390           400           410           420           430
          *     *       *     *       *     *       *     *       *
AAG GGT GAA ACA TCT GAA AAA ACA ATA GTA AGA GCA AAT GGA ACC AGA
TTC CCA CTT TGT AGA CTT TTT TGT TAT CAT TCT CGT TTA CCT TGG TCT
Lys Gly Glu Thr Ser Glu Lys Thr Ile Val Arg Ala Asn Gly Thr Arg>

440           450           460           470           480
               *     *       *     *       *     *       *     *       *
CTT GAA TAC ACA GAC ATA AAA AGC GAT GGA TCC GGA AAA GCT AAA GAA
GAA CTT ATG TGT CTG TAT TTT TCG CTA CCT AGG CCT TTT CGA TTT CTT
Leu Glu Tyr Thr Asp Ile Lys Ser Asp Gly Ser Gly Lys Ala Lys Glu>

490           500           510           520
                     *     *       *     *       *     *       *     *
GTT TTA AAA GAC TTT ACT CTT GAA GGA ACT CTA GCT GCT GAC GGC AAA
CAA AAT TTT CTG AAA TGA GAA CTT CCT TGA GAT CGA CGA CTG CCG TTT
Val Leu Lys Asp Phe Thr Leu Glu Gly Thr Leu Ala Ala Asp Gly Lys>

530           540           550           560           570
     *     *       *     *       *     *       *     *       *     *
ACA ACA TTG AAA GTT ACA GAA GGC ACT GTT GTT TTA AGC AAG AAC ATT
TGT TGT AAC TTT CAA TGT CTT CCG TGA CAA CAA AAT TCG TTC TTG TAA
Thr Thr Leu Lys Val Thr Glu Gly Thr Val Val Leu Ser Lys Asn Ile>

580           590           600           610           620
         *     *       *     *       *     *       *     *       *
TTA AAA TCC GGA GAA ATA ACA GTT GCA CTT GAT GAC TCT GAC ACT ACT
AAT TTT AGG CCT CTT TAT TGT CAA CGT GAA CTA CTG AGA CTG TGA TGA
Leu Lys Ser Gly Glu Ile Thr Val Ala Leu Asp Asp Ser Asp Thr Thr>

630           640           650           660           670
             *     *       *     *       *     *       *     *       *
CAG GCT ACT AAA AAA ACT GGA AAA TGG GAT TCA AAA ACT TCT ACT TTA
GTC CGA TGA TTT TTT TGA CCT TTT ACC CTA AGT TTT TGA AGA TGA AAT
Gln Ala Thr Lys Lys Thr Gly Lys Trp Asp Ser Lys Thr Ser Thr Leu>

680           690           700           710           720
                 *     *       *     *       *     *       *     *       *
ACA ATT AGT GTT AAC AGC AAA AAA ACT ACA CAA CTT GTG TTT ACT AAA
TGT TAA TCA CAA TTG TCG TTT TTT TGA TGT GTT GAA CAC AAA TGA TTT
Thr Ile Ser Val Asn Ser Lys Lys Thr Thr Gln Leu Val Phe Thr Lys>

730           740           750           760
                     *     *       *     *       *     *       *     *
CAA TAC ACA ATA ACT GTA AAA CAA TAC GAC TCC GCA GGT ACC AAT TTA
GTT ATG TGT TAT TGA CAT TTT GTT ATG CTG AGG CGT CCA TGG TTA AAT
Gln Tyr Thr Ile Thr Val Lys Gln Tyr Asp Ser Ala Gly Thr Asn Leu>
```

Figure 23B

K48 OSPA / PGAU OSP A FUSION

```
770         780         790         800         810
 *     *     *     *     *     *     *     *     *     *
GAA GGC ACA GCA GTC GAA ATT AAA ACA CTT GAT GAA CTT AAA AAC GCT
CTT CCG TGT CGT CAG CTT TAA TTT TGT GAA CTA CTT GAA TTT TTG CGA
Glu Gly Thr Ala Val Glu Ile Lys Thr Leu Asp Glu Leu Lys Asn Ala>

820
     *     *
TTA AAA TAA
AAT TTT ATT
Leu Lys ***>
```

Figure 23C

B-31 OSP A /PGAU OSP A FUSION

```
                10                  20                  30                  40
                 *         *         *         *         *         *         *         *
      ATG AAA AAA TAT TTA TTG GGA ATA GGT CTA ATA TTA GCC TTA ATA GCA
      TAC TTT TTT ATA AAT AAC CCT TAT CCA GAT TAT AAT CGG AAT TAT CGT
      Met Lys Lys Tyr Leu Leu Gly Ile Gly Leu Ile Leu Ala Leu Ile Ala>

50                  60                  70                  80                  90
              *         *         *         *         *         *         *         *         *         *
      TGC AAG CAA AAT GTT AGC AGC CTT GAT GAA AAA AAC AGC GCT TCA GTA
      ACG TTC GTT TTA CAA TCG TCG GAA CTA CTT TTT TTG TCG CGA AGT CAT
      Cys Lys Gln Asn Val Ser Ser Leu Asp Glu Lys Asn Ser Ala Ser Val>

100                 110                 120                 130                 140
                   *         *        ·*         *         *         *         *         *         *
      GAT TTG CCT GGT GAG ATG AAA GTT CTT GTA AGT AAA GAA AAA GAC AAA
      CTA AAC GGA CCA CTC TAC TTT CAA GAA CAT TCA TTT CTT TTT CTG TTT
      Asp Leu Pro Gly Glu Met Lys Val Leu Val Ser Lys Glu Lys Asp Lys>

150                 160                 170                 180                 190
                  *         *         *         *         *         *         *         *         *         *
      GAC GGT AAG TAC AGT CTA AAG GCA ACA GTA GAC AAG ATT GAG CTA AAA
      CTG CCA TTC ATG TCA GAT TTC CGT TGT CAT CTG TTC TAA CTC GAT TTT
      Asp Gly Lys Tyr Ser Leu Lys Ala Thr Val Asp Lys Ile Glu Leu Lys>

200                 210                 220                 230                 240
              *         *         *         *         *         *         *         *         *         *
      GGA ACT TCT GAT AAA GAC AAT GGT TCT GGA GTG CTT GAA GGT ACA AAA
      CCT TGA AGA CTA TTT CTG TTA CCA AGA CCT CAC GAA CTT CCA TGT TTT
      Gly Thr Ser Asp Lys Asp Asn Gly Ser Gly Val Leu Glu Gly Thr Lys>

250                 260                 270                 280
                   *         *         *         *         *         *         *         *
      GAT GAC AAA AGT AAA GCA AAA TTA ACA ATT GCT GAC GAT CTA AGT AAA
      CTA CTG TTT TCA TTT CGT TTT AAT TGT TAA CGA CTG CTA GAT TCA TTT
      Asp Asp Lys Ser Lys Ala Lys Leu Thr Ile Ala Asp Asp Leu Ser Lys>

290                 300                 310                 320                 330
       *         *         *         *         *         *         *         *         *         *
      ACC ACA TTC GAA CTT TTA AAA GAA GAT GGC AAA ACA TTA GTG TCA AGA
      TGG TGT AAG CTT GAA AAT TTT CTT CTA CCG TTT TGT AAT CAC AGT TCT
      Thr Thr Phe Glu Leu Leu Lys Glu Asp Gly Lys Thr Leu Val Ser Arg>

340                 350                 360                 370                 380
         *         *         *         *         *         *         *         *         *
      AAA GTA AGT TCT AGA GAC AAA ACA TCA ACA GAT GAA ATG TTC AAT GAA
      TTT CAT TCA AGA TCT CTG TTT TGT AGT TGT CTA CTT TAC AAG TTA CTT
      Lys Val Ser Ser Arg Asp Lys Thr Ser Thr Asp Glu Met Phe Asn Glu>
```

Figure 24A

B-31 OSP A/ PGAU OSP A FUSION

```
       390         400         410         420         430
  *      *     *      *     *      *     *      *     *      *
AAA GGT GAA TTG TCT GCA AAA ACC ATG ACA AGA GAA AAT GGA ACC AAA
TTT CCA CTT AAC AGA CGT TTT TGG TAC TGT TCT CTT TTA CCT TGG TTT
Lys Gly Glu Leu Ser Ala Lys Thr Met Thr Arg Glu Asn Gly Thr Lys>

440         450         460         470         480
  *      *     *      *     *      *     *      *     *      *
CTT GAA TAT ACA GAA ATG AAA AGC GAT GGA ACC GGA AAA GCT AAA GAA
GAA CTT ATA TGT CTT TAC TTT TCG CTA CCT TGG CCT TTT CGA TTT CTT
Leu Glu Tyr Thr Glu Met Lys Ser Asp Gly Thr Gly Lys Ala Lys Glu>

490         500         510         520
  *      *     *      *     *      *     *      *     *
GTT TTA AAA AAG TTT ACT CTT GAA GGA AAA GTA GCT AAT GAT AAA GTA
CAA AAT TTT TTC AAA TGA GAA CTT CCT TTT CAT CGA TTA CTA TTT CAT
Val Leu Lys Lys Phe Thr Leu Glu Gly Lys Val Ala Asn Asp Lys Val>

530         540         550         560         570
  *      *     *      *     *      *     *      *     *      *
ACA TTG GAA GTA AAA GAA GGA ACC GTT ACT TTA AGT AAG GAA ATT GCA
TGT AAC CTT CAT TTT CTT CCT TGG CAA TGA AAT TCA TTC CTT TAA CGT
Thr Leu Glu Val Lys Glu Gly Thr Val Thr Leu Ser Lys Glu Ile Ala>

580         590         600         610         620
  *      *     *      *     *      *     *      *     *
AAA TCT GGA GAA GTA ACA GTT GCT CTT AAT GAC ACT AAC ACT ACT CAG
TTT AGA CCT CTT CAT TGT CAA CGA GAA TTA CTG TGA TTG TGA TGA GTC
Lys Ser Gly Glu Val Thr Val Ala Leu Asn Asp Thr Asn Thr Thr Gln>

630         640         650         660         670
  *      *     *      *     *      *     *      *     *      *
GCT ACT AAA AAA ACT GGC GCA TGG GAT TCA AAA ACT TCT ACT TTA ACA
CGA TGA TTT TTT TGA CCG CGT ACC CTA AGT TTT TGA AGA TGA AAT TGT
Ala Thr Lys Lys Thr Gly Ala Trp Asp Ser Lys Thr Ser Thr Leu Thr>

680         690         700         710         720
  *      *     *      *     *      *     *      *     *      *
ATT AGT GTT AAC AGC AAA AAA ACT ACA CAA CTT GTG TTT ACT AAA CAA
TAA TCA CAA TTG TCG TTT TTT TGA TGT GTT GAA CAC AAA TGA TTT GTT
Ile Ser Val Asn Ser Lys Lys Thr Thr Gln Leu Val Phe Thr Lys Gln>

730         740         750         760
  *      *     *      *     *      *     *      *
TAC ACA ATA ACT GTA AAA CAA TAC GAC TCC GCA GGT ACC AAT TTA GAA
ATG TGT TAT TGA CAT TTT GTT ATG CTG AGG CGT CCA TGG TTA AAT CTT
Tyr Thr Ile Thr Val Lys Gln Tyr Asp Ser Ala Gly Thr Asn Leu Glu>
```

Figure 24B

B-31 OSP A /PGAU OSP A FUSION

```
        770           780           790           800           810
         *         *   *         *   *         *   *         *   *         *
        GGC ACA GCA GTC GAA ATT AAA ACA CTT GAT GAA CTT AAA AAC GCT TTA
        CCG TGT CGT CAG CTT TAA TTT TGT GAA CTA CTT GAA TTT TTG CGA AAT
        Gly Thr Ala Val Glu Ile Lys Thr Leu Asp Glu Leu Lys Asn Ala Leu>

820
             *
        AAA TAA
        TTT ATT
        Lys ***>
```

Figure 24C

B31/K48 fusion

```
              10              20              30              40
               *               *               *               *
     ATG AAA AAA TAT TTA TTG GGA ATA GGT CTA ATA TTA GCC TTA ATA GCA
     TAC TTT TTT ATA AAT AAC CCT TAT CCA GAT TAT AAT CGG AAT TAT CGT
     Met Lys Lys Tyr Leu Leu Gly Ile Gly Leu Ile Leu Ala Leu Ile Ala>

50              60              70              80              90
          *               *               *               *               *
     TGT AAG CAA AAT GTT AGC AGC CTT GAC GAG AAA AAC AGC GTT TCA GTA
     ACA TTC GTT TTA CAA TCG TCG GAA CTG CTC TTT TTG TCG CAA AGT CAT
     Cys Lys Gln Asn Val Ser Ser Leu Asp Glu Lys Asn Ser Val Ser Val>

100             110             120             130             140
              *               *               *               *               *
     GAT TTG CCT GGT GAA ATG AAA GTT CTT GTA AGC AAA GAA AAA AAC AAA
     CTA AAC GGA CCA CTT TAC TTT CAA GAA CAT TCG TTT CTT TTT TTG TTT
     Asp Leu Pro Gly Glu Met Lys Val Leu Val Ser Lys Glu Lys Asn Lys>

150             160             170             180             190
             *               *               *               *               *
     GAC GGC AAG TAC GAT CTA ATT GCA ACA GTA GAC AAG CTT GAG CTT AAA
     CTG CCG TTC ATG CTA GAT TAA CGT TGT CAT CTG TTC GAA CTC GAA TTT
     Asp Gly Lys Tyr Asp Leu Ile Ala Thr Val Asp Lys Leu Glu Leu Lys>

200             210             220             230             240
              *               *               *               *               *
     GGA ACT TCT GAT AAA AAC AAT GGA TCT GGA GTA CTT GAA GGC GTA AAA
     CCT TGA AGA CTA TTT TTG TTA CCT AGA CCT CAT GAA CTT CCG CAT TTT
     Gly Thr Ser Asp Lys Asn Asn Gly Ser Gly Val Leu Glu Gly Val Lys>

250             260             270             280
              *               *               *               *               *
     GCT GAC AAA AGT AAA GTA AAA TTA ACA ATT TCT GAC GAT CTA GGT CAA
     CGA CTG TTT TCA TTT CAT TTT AAT TGT TAA AGA CTG CTA GAT CCA GTT
     Ala Asp Lys Ser Lys Val Lys Leu Thr Ile Ser Asp Asp Leu Gly Gln>

290             300             310             320             330
         *               *               *               *               *
     ACC ACA CTT GAA GTT TTC AAA GAA GAT GGC AAA ACA CTA GTA TCA AAA
     TGG TGT GAA CTT CAA AAG TTT CTT CTA CCG TTT TGT GAT CAT AGT TTT
     Thr Thr Leu Glu Val Phe Lys Glu Asp Gly Lys Thr Leu Val Ser Lys>

340             350             360             370            .380
           *               *               *               *               *
     AAA GTA ACT TCC AAA GAC AAG TCA TCA ACA GAA GAA AAA TTC AAT GAA
     TTT CAT TGA AGG TTT CTG TTC AGT AGT TGT CTT CTT TTT AAG TTA CTT
     Lys Val Thr Ser Lys Asp Lys Ser Ser Thr Glu Glu Lys Phe Asn Glu>

390             400             410             420             430
             *               *               *               *               *
     AAA GGT GAA GTA TCT GAA AAA ATA ATA ACA AGA GCA GAC GGA ACC AGA
     TTT CCA CTT CAT AGA CTT TTT TAT TAT TGT TCT CGT CTG CCT TGG TCT
     Lys Gly Glu Val Ser Glu Lys Ile Ile Thr Arg Ala Asp Gly Thr Arg>
```

Figure 25A

B31/K48 fusion

```
            440         450         460         470         480
             *           *           *           *           *
         CTT GAA TAC ACA GGA ATT AAA AGC GAT GGA TCT GGA AAA GCT AAA GAG
         GAA CTT ATG TGT CCT TAA TTT TCG CTA CCT AGA CCT TTT CGA TTT CTC
         Leu Glu Tyr Thr Gly Ile Lys Ser Asp Gly Ser Gly Lys Ala Lys Glu>

490         500         510         520
                     *           *           *           *
         GTT TTA AAA GGC TAT GTT CTT GAA GGA ACT CTA ACT GCT GAA AAA ACA
         CAA AAT TTT CCG ATA CAA GAA CTT CCT TGA GAT TGA CGA CTT TTT TGT
         Val Leu Lys Gly Tyr Val Leu Glu Gly Thr Leu Thr Ala Glu Lys Thr>

530         540         550         560         570
    *           *           *           *           *
   ACA TTG GTG GTT AAA GAA GGA ACT GTT ACT TTA AGC AAA AAT ATT TCA
   TGT AAC CAC CAA TTT CTT CCT TGA CAA TGA AAT TCG TTT TTA TAA AGT
   Thr Leu Val Val Lys Glu Gly Thr Val Thr Leu Ser Lys Asn Ile Ser>

580         590         600         610         620
             *           *           *           *           *
         AAA TCT GGG GAA GTT TCA GTT GAA CTT AAT GAC ACT GAC AGT AGT GCT
         TTT AGA CCC CTT CAA AGT CAA CTT GAA TTA CTG TGA CTG TCA TCA CGA
         Lys Ser Gly Glu Val Ser Val Glu Leu Asn Asp Thr Asp Ser Ser Ala>

630         640         650         660         670
                     *           *           *           *           *
         GCT ACT AAA AAA ACT GCA GCT TGG AAT TCA AAA ACT TCC ACT TTA ACA
         CGA TGA TTT TTT TGA CGT CGA ACC TTA AGT TTT TGA AGG TGA AAT TGT
         Ala Thr Lys Lys Thr Ala Ala Trp Asn Ser Lys Thr Ser Thr Leu Thr>

680         690         700         710         720
                     *           *           *           *           *
         ATT AGT GTG AAT AGC CAA AAA ACC AAA AAC CTT GTA TTC ACA AAA GAA
         TAA TCA CAC TTA TCG GTT TTT TGG TTT TTG GAA CAT AAG TGT TTT CTT
         Ile Ser Val Asn Ser Gln Lys Thr Lys Asn Leu Val Phe Thr Lys Glu>

730         740         750         760
                     *           *           *           *
         GAC ACA ATA ACA GTA CAA AAA TAC GAC TCA GCA GGC ACC AAT CTA GAA
         CTG TGT TAT TGT CAT GTT TTT ATG CTG AGT CGT CCG TGG TTA GAT CTT
         Asp Thr Ile Thr Val Gln Lys Tyr Asp Ser Ala Gly Thr Asn Leu Glu>

770         780         790         800         810
    *           *           *           *           *
   GGC AAA GCA GTC GAA ATT ACA ACA CTT AAA GAA CTT AAA AAC GCT TTA
   CCG TTT CGT CAG CTT TAA TGT TGT GAA TTT CTT GAA TTT TTG CGA AAT
   Gly Lys Ala Val Glu Ile Thr Thr Leu Lys Glu Leu Lys Asn Ala Leu>

820
    *
   AAA TAA
   TTT ATT
   Lys ***>
```

Figure 25B

B-31 OSP A/ 25015 OSP A FUSION

```
           10          20          30          40
            *     *     *     *     *     *     *     *     *
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50          60          70          80          90
      *     *     *     *     *     *     *     *     *     *
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

100         110         120         130         140
       *     *     *     *     *     *     *     *     *
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

150         160         170         180         190
       *     *     *     *     *     *     *     *     *     *
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

200         210         220         230         240
            *     *     *     *     *     *     *     *     *     *
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

250         260         270         280
                 *     *     *     *     *     *     *     *     *
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290         300         310         320         330
 *     *     *     *     *     *     *     *     *     *
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

340         350         360         370         380
       *     *     *     *     *     *     *     *     *
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

Figure 26A

B-31 OSP A/ 25015 OSP A FUSION

```
            390            400            410            420            430
             *              *              *              *              *
       AAA GGT GAA GTA TCT GAA AAA ATA ATA ACA AGA GCA GAC GGA ACC AGA
       TTT CCA CTT CAT AGA CTT TTT TAT TAT TGT TCT CGT CTG CCT TGG TCT
       Lys Gly Glu Val Ser Glu Lys Ile Ile Thr Arg Ala Asp Gly Thr Arg>

440            450            460            470            480
                    *              *              *              *              *
       CTT GAA TAC ACA GGA ATT AAA AGC GAT GGA TCT GGA AAA GCT AAA GAG
       GAA CTT ATG TGT CCT TAA TTT TCG CTA CCT AGA CCT TTT CGA TTT CTC
       Leu Glu Tyr Thr Gly Ile Lys Ser Asp Gly Ser Gly Lys Ala Lys Glu>

490            500            510            520
                    *              *              *              *              *
       GTT TTA AAA GGC TAT GTT CTT GAA GGA ACT CTA ACT GCT GAA AAA ACA
       CAA AAT TTT CCG ATA CAA GAA CTT CCT TGA GAT TGA CGA CTT TTT TGT
       Val Leu Lys Gly Tyr Val Leu Glu Gly Thr Leu Thr Ala Glu Lys Thr>

530            540            550            560            570
        *              *              *              *              *
       ACA TTG GTG GTT AAA GAA GGA ACT GTT ACT TTA AGC AAA AAT ATT TCA
       TGT AAC CAC CAA TTT CTT CCT TGA CAA TGA AAT TCG TTT TTA TAA AGT
       Thr Leu Val Val Lys Glu Gly Thr Val Thr Leu Ser Lys Asn Ile Ser>

580            590            600            610            620
              *              *              *              *              *
       AAA TCT GGG GAA GTT TCA GTT GAA CTT AAT GAC ACT GAC AGT AGT GCT
       TTT AGA CCC CTT CAA AGT CAA CTT GAA TTA CTG TGA CTG TCA TCA CGA
       Lys Ser Gly Glu Val Ser Val Glu Leu Asn Asp Thr Asp Ser Ser Ala>

630            640            650            660            670
              *              *              *              *              *
       GCT ACT AAA AAA ACT GCA GCT TGG AAT GCA GGC ACT TCA ACT TTA ACA
       CGA TGA TTT TTT TGA CGT CGA ACC TTA CGT CCG TGA AGT TGA AAT TGT
       Ala Thr Lys Lys Thr Ala Ala Trp Asn Ala Gly Thr Ser Thr Leu Thr>

680            690            700            710            720
                    *              *              *              *              *
       ATT ACT GTA AAC AAC AAA AAA ACT AAA GCC CTT GTA TTT ACA AAA CAA
       TAA TGA CAT TTG TTG TTT TTT TGA TTT CGG GAA CAT AAA TGT TTT GTT
       Ile Thr Val Asn Asn Lys Lys Thr Lys Ala Leu Val Phe Thr Lys Gln>

730            740            750            760
                    *              *              *              *
       GAC ACA ATT ACA TCA CAA AAA TAC GAC TCA GCA GGA ACC AAC TTG GAA
       CTG TGT TAA TGT AGT GTT TTT ATG CTG AGT CGT CCT TGG TTG AAC CTT
       Asp Thr Ile Thr Ser Gln Lys Tyr Asp Ser Ala Gly Thr Asn Leu Glu>
```

Figure 26B

B-31 OSP A/ 25015 OSP A FUSION

```
770           780             790             800             810
 *        *    *        *        *      *        *        *     *        *
GGC ACA GCA GTC GAA ATT AAA ACA CTT GAT GAA CTT AAA AAC GCT TTA
CCG TGT CGT CAG CTT TAA TTT TGT GAA CTA CTT GAA TTT TTG CGA AAT
Gly Thr Ala Val Glu Ile Lys Thr Leu Asp Glu Leu Lys Asn Ala Leu>

AGA
TCT
Arg>
```

Figure 26C

K48 OSP A/ B-31 OSP A/ K48 OSP A FUSION

```
              10             20             30             40
               *              *              *              *         *
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50             60             70             80             90
        *              *              *              *              *         *
TGT AAG CAA AAT GTT AGC AGC CTT GAT GAA AAA AAT AGC GTT TCA GTA
ACA TTC GTT TTA CAA TCG TCG GAA CTA CTT TTT TTA TCG CAA AGT CAT
Cys Lys Gln Asn Val Ser Ser Leu Asp Glu Lys Asn Ser Val Ser Val>

100            110            120            130            140
        *              *              *              *              *
GAT TTA CCT GGT GGA ATG ACA GTT CTT GTA AGT AAA GAA AAA GAC AAA
CTA AAT GGA CCA CCT TAC TGT CAA GAA CAT TCA TTT CTT TTT CTG TTT
Asp Leu Pro Gly Gly Met Thr Val Leu Val Ser Lys Glu Lys Asp Lys>

150            160            170            180            190
   *    *         *              *              *              *         *
GAC GGT AAA TAC AGT CTA GAG GCA ACA GTA GAC AAG CTT GAG CTT AAA
CTG CCA TTT ATG TCA GAT CTC CGT TGT CAT CTG TTC GAA CTC GAA TTT
Asp Gly Lys Tyr Ser Leu Glu Ala Thr Val Asp Lys Leu Glu Leu Lys>

200            210            220            230            240
               *              *              *              *              *         *
GGA ACT TCT GAT AAA AAC AAC GGT TCT GGA ACA CTT GAA GGT GAA AAA
CCT TGA AGA CTA TTT TTG TTG CCA AGA CCT TGT GAA CTT CCA CTT TTT
Gly Thr Ser Asp Lys Asn Asn Gly Ser Gly Thr Leu Glu Gly Glu Lys>

250            260            270            280
               *         *    *              *              *              *         *
ACT GAC AAA AGT AAA GTA AAA TTA ACA ATT GCT GAT GAC CTA AGT CAA
TGA CTG TTT TCA TTT CAT TTT AAT TGT TAA CGA CTA CTG GAT TCA GTT
Thr Asp Lys Ser Lys Val Lys Leu Thr Ile Ala Asp Asp Leu Ser Gln>

290            300            310            320            330
 *              *    *         *              *              *         *
ACT AAA TTT GAA ATT TTC AAA GAA GAT GCC AAA ACA TTA GTA TCA AAA
TGA TTT AAA CTT TAA AAG TTT CTT CTA CGG TTT TGT AAT CAT AGT TTT
Thr Lys Phe Glu Ile Phe Lys Glu Asp Ala Lys Thr Leu Val Ser Lys>

340            350            360            370            380
        *    *         *              *    *              *              *
AAA GTA ACC CTT AAA GAC AAG TCA TCA ACA GAA GAA AAA TTC AAC GAA
TTT CAT TGG GAA TTT CTG TTC AGT AGT TGT CTT CTT TTT AAG TTG CTT
Lys Val Thr Leu Lys Asp Lys Ser Ser Thr Glu Glu Lys Phe Asn Glu>
```

Figure 27A

K48 OSP A/ B-31 OSP A/ K48 OSP A FUSION

```
       390          400          410          420          430
        *            *            *            *            *
   *         *            *   *         *   *         *   *         *
AAG GGT GAA ACA TCT GAA AAA ACA ATA GTA AGA GCA AAT GGA ACC AGA
TTC CCA CTT TGT AGA CTT TTT TGT TAT CAT TCT CGT TTA CCT TGG TCT
Lys Gly Glu Thr Ser Glu Lys Thr Ile Val Arg Ala Asn Gly Thr Arg>

440          450          460          470          480
             *            *            *            *            *
   *    *         *   *         *   *         *   *         *   *
CTT GAA TAC ACA GAC ATA AAA AGC GAT GGA TCC GGA AAA GCT AAA GAA
GAA CTT ATG TGT CTG TAT TTT TCG CTA CCT AGG CCT TTT CGA TTT CTT
Leu Glu Tyr Thr Asp Ile Lys Ser Asp Gly Ser Gly Lys Ala Lys Glu>

490          500          510          520
                  *            *            *            *
        *    *         *   *         *   *         *   *         *
GTT TTA AAA GAC TTT ACT CTT GAA GGA ACT CTA GCT GCT GAC GGC AAA
CAA AAT TTT CTG AAA TGA GAA CTT CCT TGA GAT CGA CGA CTG CCG TTT
Val Leu Lys Asp Phe Thr Leu Glu Gly Thr Leu Ala Ala Asp Gly Lys>

530          540          550          560          570
 *            *            *            *            *
   *    *         *   *         *   *         *   * .        *   *
ACA ACA TTG AAA GTT ACA GAA GGC ACT GTT GTT TTA AGC AAG ATT TCA
TGT TGT AAC TTT CAA TGT CTT CCG TGA CAA CAA AAT TCG TTC TAA AGT
Thr Thr Leu Lys Val Thr Glu Gly Thr Val Val Leu Ser Lys Ile Ser>

580          590          600          610          620
       *            *            *            *            *
   *         *   *         *   *         *   *         *   *
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

630          640          650          660          670
             *            *            *            *            *
   *    *         *   *    *    *         *   *         *   *
GCT ACT AAA AAA ACT GCA GCT TGG AAT TCA AAA ACT TCC ACT TTA ACA
CGA TGA TTT TTT TGA CGT CGA ACC TTA AGT TTT TGA AGG TGA AAT TGT
Ala Thr Lys Lys Thr Ala Ala Trp Asn Ser Lys Thr Ser Thr Leu Thr>

680          690          700          710          720
             *            *.           *            *            *   *
   *    *         *   *         *   *         *   *         *
ATT AGT GTG AAT AGC CAA AAA ACC AAA AAC CTT GTA TTC ACA AAA GAA
TAA TCA CAC TTA TCG GTT TTT TGG TTT TTG GAA CAT AAG TGT TTT CTT
Ile Ser Val Asn Ser Gln Lys Thr Lys Asn Leu Val Phe Thr Lys Glu>

730          740          750          760
             *    *         *            *    *         *
   *    *              *   *         *              *   *         *
GAC ACA ATA ACA GTA CAA AAA TAC GAC TCA GCA GGC ACC AAT CTA GAA
CTG TGT TAT TGT CAT GTT TTT ATG CTG AGT CGT CCG TGG TTA GAT CTT
Asp Thr Ile Thr Val Gln Lys Tyr Asp Ser Ala Gly Thr Asn Leu Glu>
```

Figure 27B

K48 OSP A / B-31 OSP A/ K48 OSP A FUSION

```
       770           780           790           800           810
         *             *             *             *             *
          *             *             *             *             *
       GGC AAA GCA GTC GAA ATT ACA ACA CTT AAA GAA CTT AAA AAC GCT TTA
       CCG TTT CGT CAG CTT TAA TGT TGT GAA TTT CTT GAA TTT TTG CGA AAT
       Gly Lys Ala Val Glu Ile Thr Thr Leu Lys Glu Leu Lys Asn Ala Leu>

820
            *
       AAA TAA
       TTT ATT
       Lys ***>
```

Figure 27C

B-31 OSP A/K48 OSP A/ B-31 OSP A/ K48 OSP A FUSION

```
              10              20              30              40
               *               *               *               *
    ATG AAA AAA TAT TTA TTG GGA ATA GGT CTA ATA TTA GCC TTA ATA GCA
    TAC TTT TTT ATA AAT AAC CCT TAT CCA GAT TAT AAT CGG AAT TAT CGT
    Met Lys Lys Tyr Leu Leu Gly Ile Gly Leu Ile Leu Ala Leu Ile Ala>

50              60              70              80              90
         *               *               *               *               *
    TGT AAG CAA AAT GTT AGC AGC CTT GAT GAA AAA AAT AGC GTT TCA GTA
    ACA TTC GTT TTA CAA TCG TCG GAA CTA CTT TTT TTA TCG CAA AGT CAT
    Cys Lys Gln Asn Val Ser Ser Leu Asp Glu Lys Asn Ser Val Ser Val>

100             110             120             130             140
           *               *               *               *               *
    GAT TTA CCT GGT GGA ATG ACA GTT CTT GTA AGT AAA GAA AAA GAC AAA
    CTA AAT GGA CCA CCT TAC TGT CAA GAA CAT TCA TTT CTT TTT CTG TTT
    Asp Leu Pro Gly Gly Met Thr Val Leu Val Ser Lys Glu Lys Asp Lys>

150             160             170             180             190
           *               *               *               *               *
    GAC GGT AAA TAC AGT CTA GAG GCA ACA GTA GAC AAG CTT GAG CTT AAA
    CTG CCA TTT ATG TCA GAT CTC CGT TGT CAT CTG TTC GAA CTC GAA TTT
    Asp Gly Lys Tyr Ser Leu Glu Ala Thr Val Asp Lys Leu Glu Leu Lys>

200             210             220             230             240
           *               *               *               *               *
    GGA ACT TCT GAT AAA AAC AAC GGT TCT GGA ACA CTT GAA GGT GAA AAA
    CCT TGA AGA CTA TTT TTG TTG CCA AGA CCT TGT GAA CTT CCA CTT TTT
    Gly Thr Ser Asp Lys Asn Asn Gly Ser Gly Thr Leu Glu Gly Glu Lys>

250             260             270             280
           *               *               *               *
    ACT GAC AAA AGT AAA GTA AAA TTA ACA ATT GCT GAT GAC CTA AGT CAA
    TGA CTG TTT TCA TTT CAT TTT AAT TGT TAA CGA CTA CTG GAT TCA GTT
    Thr Asp Lys Ser Lys Val Lys Leu Thr Ile Ala Asp Asp Leu Ser Gln>

290             300             310             320             330
       *               *               *               *               *
    ACT AAA TTT GAA ATT TTC AAA GAA GAT GCC AAA ACA TTA GTA TCA AAA
    TGA TTT AAA CTT TAA AAG TTT CTT CTA CGG TTT TGT AAT CAT AGT TTT
    Thr Lys Phe Glu Ile Phe Lys Glu Asp Ala Lys Thr Leu Val Ser Lys>

340             350             360             370             380
           *               *               *               *               *
    AAA GTA ACC CTT AAA GAC AAG TCA TCA ACA GAA GAA AAA TTC AAC GAA
    TTT CAT TGG GAA TTT CTG TTC AGT AGT TGT CTT CTT TTT AAG TTG CTT
    Lys Val Thr Leu Lys Asp Lys Ser Ser Thr Glu Glu Lys Phe Asn Glu>
```

Figure 28A

B-31 OSP A/K48 OSP A/ B-31 OSP A/ K48 OSP A FUSION

```
          390         400         410         420         430
           *           *           *           *           *
AAG GGT GAA ACA TCT GAA AAA ACA ATA GTA AGA GCA AAT GGA ACC AGA
TTC CCA CTT TGT AGA CTT TTT TGT TAT CAT TCT CGT TTA CCT TGG TCT
Lys Gly Glu Thr Ser Glu Lys Thr Ile Val Arg Ala Asn Gly Thr Arg>

440         450         460         470         480
                 *           *           *           *           *
CTT GAA TAC ACA GAC ATA AAA AGC GAT GGA TCC GGA AAA GCT AAA GAA
GAA CTT ATG TGT CTG TAT TTT TCG CTA CCT AGG CCT TTT CGA TTT CTT
Leu Glu Tyr Thr Asp Ile Lys Ser Asp Gly Ser Gly Lys Ala Lys Glu>

490         500         510         520
                         *           *           *           *
GTT TTA AAA GAC TTT ACT CTT GAA GGA ACT CTA GCT GCT GAC GGC AAA
CAA AAT TTT CTG AAA TGA GAA CTT CCT TGA GAT CGA CGA CTG CCG TTT
Val Leu Lys Asp Phe Thr Leu Glu Gly Thr Leu Ala Ala Asp Gly Lys>

530         540         550         560         570
  *           *           *           *           *
ACA ACA TTG AAA GTT ACA GAA GGC ACT GTT GTT TTA AGC AAG ATT TCA
TGT TGT AAC TTT CAA TGT CTT CCG TGA CAA CAA AAT TCG TTC TAA AGT
Thr Thr Leu Lys Val Thr Glu Gly Thr Val Val Leu Ser Lys Ile Ser>

580         590         600         610         620
          *           *           *           *           *
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

630         640         650         660         670
             *           *           *           *           *
GCT ACT AAA AAA ACT GCA GCT TGG AAT TCA AAA ACT TCC ACT TTA ACA
CGA TGA TTT TTT TGA CGT CGA ACC TTA AGT TTT TGA AGG TGA AAT TGT
Ala Thr Lys Lys Thr Ala Ala Trp Asn Ser Lys Thr Ser Thr Leu Thr>

680         690         700         710         720
                 *           *           *           *           *
ATT AGT GTG AAT AGC CAA AAA ACC AAA AAC CTT GTA TTC ACA AAA GAA
TAA TCA CAC TTA TCG GTT TTT TGG TTT TTG GAA CAT AAG TGT TTT CTT
Ile Ser Val Asn Ser Gln Lys Thr Lys Asn Leu Val Phe Thr Lys Glu>

730         740         750         760
                         *           *           *           *
GAC ACA ATA ACA GTA CAA AAA TAC GAC TCA GCA GGC ACC AAT CTA GAA
CTG TGT TAT TGT CAT GTT TTT ATG CTG AGT CGT CCG TGG TTA GAT CTT
Asp Thr Ile Thr Val Gln Lys Tyr Asp Ser Ala Gly Thr Asn Leu Glu>
```

Figure 28B

B-31 OSP A/K48 OSP A/ B-31 OSP A/ K48 OSP A FUSION

```
        770         780         790         800         810
         *     *     *     *     *     *     *     *     *     *
        GGC   AAA   GCA   GTC   GAA   ATT   ACA   ACA   CTT   AAA   GAA   CTT   AAA   AAC   GCT   TTA
        CCG   TTT   CGT   CAG   CTT   TAA   TGT   TGT   GAA   TTT   CTT   GAA   TTT   TTG   CGA   AAT
        Gly   Lys   Ala   Val   Glu   Ile   Thr   Thr   Leu   Lys   Glu   Leu   Lys   Asn   Ala   Leu>

820
            *
        AAA   TAA
        TTT   ATT
        Lys   ***>
```

Figure 28C

B-31 OSPA/ B-31 OSPB FUSION

```
          10             20             30             40
           *    *    *    *    *    *    *    *    *    *
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50             60             70             80             90
           *    *    *    *    *    *    *    *    *    *
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

100            110            120            130            140
           *    *    *    *    *    *    *    *    *
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

150            160            170            180            190
           *    *    *    *    *    *    *    *    *    *
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

200            210            220            230            240
           *    *    *    *    *    *    *    *    *    *
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

250            260            270            280
           *    *    *    *    *    *    *    *    *
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290            300            310            320            330
  *    *    *    *    *    *    *    *    *    *
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

340            350            360            370            380
           *    *    *    *    *    *    *    *    *
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

Figure 29A

B-31 OSP A/ B-31 OSP B FUSION

```
           390            400            410            420            430
            *      *       *      *       *      *       *      *       *      *
          AAA GGT GAA GTA TCT GAA AAA ATA ATA ACA AGA GCA GAC GGA ACC AGA
          TTT CCA CTT CAT AGA CTT TTT TAT TAT TGT TCT CGT CTG CCT TGG TCT
          Lys Gly Glu Val Ser Glu Lys Ile Ile Thr Arg Ala Asp Gly Thr Arg>

440            450            460            470            480
                  *      *       *      *       *      *       *      *       *      *
               CTT GAA TAC ACA GGA ATT AAA AGC GAT GGA TCT GGA AAA GCT AAA GAG
               GAA CTT ATG TGT CCT TAA TTT TCG CTA CCT AGA CCT TTT CGA TTT CTC
               Leu Glu Tyr Thr Gly Ile Lys Ser Asp Gly Ser Gly Lys Ala Lys Glu>

490            500            510            520
                         *      *       *      *       *      *       *      *      *
                      GTT TTA AAA GGC TAT GTT CTT GAA GGA ACT CTA ACT GCT GAA AAA ACA
                      CAA AAT TTT CCG ATA CAA GAA CTT CCT TGA GAT TGA CGA CTT TTT TGT
                      Val Leu Lys Gly Tyr Val Leu Glu Gly Thr Leu Thr Ala Glu Lys Thr>

530            540            550            560            570
           *      *       *      *       *      *       *      *       *      *
         ACA TTG GTG GTT AAA GAA GGA ACT GTT ACT TTA AGC AAA AAT ATT TCA
         TGT AAC CAC CAA TTT CTT CCT TGA CAA TGA AAT TCG TTT TTA TAA AGT
         Thr Leu Val Val Lys Glu Gly Thr Val Thr Leu Ser Lys Asn Ile Ser>

580            590            600            610            620
                  *      *       *      *       *      *       *      *       *      *
               AAA TCT GGG GAA GTT TCA GTT GAA CTT AAT GAC ACT GAC AGT AGT GCT
               TTT AGA CCC CTT CAA AGT CAA CTT GAA TTA CTG TGA CTG TCA TCA CGA
               Lys Ser Gly Glu Val Ser Val Glu Leu Asn Asp Thr Asp Ser Ser Ala>

630            640            650            660            670
                         *      *       *      *       *      *       *      *       *      *
                      GCT ACT AAA AAA ACT GCA GCT TGG AAT GAC AGT ACT AGC ACT TTA ACA
                      CGA TGA TTT TTT TGA CGT CGA ACC TTA CTG TCA TGA TCG TGA AAT TGT
                      Ala Thr Lys Lys Thr Ala Ala Trp Asn Asp Ser Thr Ser Thr Leu Thr>

680            690            700            710            720
                                *      *       *      *       *      *       *      *       *      *
                             ATT AGT GCT GAC AGC AAA AAA ACT AAA GAT TTG GTG TTC TTA ACA GAT
                             TAA TCA CGA CTG TCG TTT TTT TGA TTT CTA AAC CAC AAG AAT TGT CTA
                             Ile Ser Ala Asp Ser Lys Lys Thr Lys Asp Leu Val Phe Leu Thr Asp>

730            740            750            760
                                       *      *       *      *       *      *       *      *       *
                                    GGT ACA ATT ACA GTA CAA CAA TAC AAC ACA GCT GGA ACC AGC CTA GAA
                                    CCA TGT TAA TGT CAT GTT GTT ATG TTG TGT CGA CCT TGG TCG GAT CTT
                                    Gly Thr Ile Thr Val Gln Gln Tyr Asn Thr Ala Gly Thr Ser Leu Glu>
```

Figure 29B

B-31 OSP A/ B-31 OSP B FUSION

```
    770         780         790         800         810
     *           *           *           *           *
GGA TCA GCA AGT GAA ATT AAA AAT CTT TCA GAG CTT AAA AAC GCT TTA
CCT AGT CGT TCA CTT TAA TTT TTA GAA AGT CTC GAA TTT TTG CGA AAT
Gly Ser Ala Ser Glu Ile Lys Asn Leu Ser Glu Leu Lys Asn Ala Leu>

820
     *
AAA TAA
TTT ATT
Lys ***>
```

Figure 29C

B-31 OSP A/ B-31 OSP B / B-31 OSP C FUSION nce Range: 1 to 1401

```
                10           20           30           40
                 *            *            *            *
        ATG AAA AAA TAT TTA TTG GGA ATA GGT CTA ATA TTA GCC TTA ATA GCA
        TAC TTT TTT ATA AAT AAC CCT TAT CCA GAT TAT AAT CGG AAT TAT CGT
        Met Lys Lys Tyr Leu Leu Gly Ile Gly Leu Ile Leu Ala Leu Ile Ala>

50           60           70           80           90
          *            *            *            *            *
        TGT AAG CAA AAT GTT AGC AGC CTT GAC GAG AAA AAC AGC GTT TCA GTA
        ACA TTC GTT TTA CAA TCG TCG GAA CTG CTC TTT TTG TCG CAA AGT CAT
        Cys Lys Gln Asn Val Ser Ser Leu Asp Glu Lys Asn Ser Val Ser Val>

100          110          120          130          140
          *            *            *            *            *
        GAT TTG CCT GGT GAA ATG AAA GTT CTT GTA AGC AAA GAA AAA AAC AAA
        CTA AAC GGA CCA CTT TAC TTT CAA GAA CAT TCG TTT CTT TTT TTG TTT
        Asp Leu Pro Gly Glu Met Lys Val Leu Val Ser Lys Glu Lys Asn Lys>

150          160          170          180          190
            *            *            *            *            *
        GAC GGC AAG TAC GAT CTA ATT GCA ACA GTA GAC AAG CTT GAG CTT AAA
        CTG CCG TTC ATG CTA GAT TAA CGT TGT CAT CTG TTC GAA CTC GAA TTT
        Asp Gly Lys Tyr Asp Leu Ile Ala Thr Val Asp Lys Leu Glu Leu Lys>

200          210          220          230          240
             *            *            *            *            *
        GGA ACT TCT GAT AAA AAC AAT GGA TCT GGA GTA CTT GAA GGC GTA AAA
        CCT TGA AGA CTA TTT TTG TTA CCT AGA CCT CAT GAA CTT CCG CAT TTT
        Gly Thr Ser Asp Lys Asn Asn Gly Ser Gly Val Leu Glu Gly Val Lys>

250          260          270          280
               *            *            *            *            *
        GCT GAC AAA AGT AAA GTA AAA TTA ACA ATT TCT GAC GAT CTA GGT CAA
        CGA CTG TTT TCA TTT CAT TTT AAT TGT TAA AGA CTG CTA GAT CCA GTT
        Ala Asp Lys Ser Lys Val Lys Leu Thr Ile Ser Asp Asp Leu Gly Gln>

290          300          310          320          330
         *            *            *            *            *
        ACC ACA CTT GAA GTT TTC AAA GAA GAT GGC AAA ACA CTA GTA TCA AAA
        TGG TGT GAA CTT CAA AAG TTT CTT CTA CCG TTT TGT GAT CAT AGT TTT
        Thr Thr Leu Glu Val Phe Lys Glu Asp Gly Lys Thr Leu Val Ser Lys>

340          350          360          370          380
          *            *            *            *            *
        AAA GTA ACT TCC AAA GAC AAG TCA TCA ACA GAA GAA AAA TTC AAT GAA
        TTT CAT TGA AGG TTT CTG TTC AGT AGT TGT CTT CTT TTT AAG TTA CTT
        Lys Val Thr Ser Lys Asp Lys Ser Ser Thr Glu Glu Lys Phe Asn Glu>
```

Figure 30A

B-31 OAP A/ B-31 OSP B / B-31 OSPC FUSION

```
              390         400         410         420         430
               *           *           *           *           *
         AAA GGT GAA GTA TCT GAA AAA ATA ATA ACA AGA GCA GAC GGA ACC AGA
         TTT CCA CTT CAT AGA CTT TTT TAT TAT TGT TCT CGT CTG CCT TGG TCT
         Lys Gly Glu Val Ser Glu Lys Ile Ile Thr Arg Ala Asp Gly Thr Arg>

440         450         460         470         480
                    *           *           *           *           *
         CTT GAA TAC ACA GGA ATT AAA AGC GAT GGA TCT GGA AAA GCT AAA GAG
         GAA CTT ATG TGT CCT TAA TTT TCG CTA CCT AGA CCT TTT CGA TTT CTC
         Leu Glu Tyr Thr Gly Ile Lys Ser Asp Gly Ser Gly Lys Ala Lys Glu>

490         500         510         520
                         *           *           *           *           *
         GTT TTA AAA GGC TAT GTT CTT GAA GGA ACT CTA ACT GCT GAA AAA ACA
         CAA AAT TTT CCG ATA CAA GAA CTT CCT TGA GAT TGA CGA CTT TTT TGT
         Val Leu Lys Gly Tyr Val Leu Glu Gly Thr Leu Thr Ala Glu Lys Thr>

530         540         550         560         570
          *           *           *           *           *
         ACA TTG GTG GTT AAA GAA GGA ACT GTT ACT TTA AGC AAA AAT ATT TCA
         TGT AAC CAC CAA TTT CTT CCT TGA CAA TGA AAT TCG TTT TTA TAA AGT
         Thr Leu Val Val Lys Glu Gly Thr Val Thr Leu Ser Lys Asn Ile Ser>

580         590         600         610         620
               *           *           *           *           *
         AAA TCT GGG GAA GTT TCA GTT GAA CTT AAT GAC ACT GAC AGT AGT GCT
         TTT AGA CCC CTT CAA AGT CAA CTT GAA TTA CTG TGA CTG TCA TCA CGA
         Lys Ser Gly Glu Val Ser Val Glu Leu Asn Asp Thr Asp Ser Ser Ala>

630         640         650         660         670
                    *           *           *           *           *
         GCT ACT AAA AAA ACT GCA GCT TGG AAT GAC AGT ACT AGC ACT TTA ACA
         CGA TGA TTT TTT TGA CGT CGA ACC TTA CTG TCA TGA TCG TGA AAT TGT
         Ala Thr Lys Lys Thr Ala Ala Trp Asn Asp Ser Thr Ser Thr Leu Thr>

680         690         700         710         720
                         *           *           *           *           *
         ATT AGT GCT GAC AGC AAA AAA ACT AAA GAT TTG GTG TTC TTA ACA GAT
         TAA TCA CGA CTG TCG TTT TTT TGA TTT CTA AAC CAC AAG AAT TGT CTA
         Ile Ser Ala Asp Ser Lys Lys Thr Lys Asp Leu Val Phe Leu Thr Asp>

730         740         750         760
                    *           *           *           *           *
         GGT ACA ATT ACA GTA CAA CAA TAC AAC ACA GCT GGA ACC AGC CTA GAA
         CCA TGT TAA TGT CAT GTT GTT ATG TTG TGT CGA CCT TGG TCG GAT CTT
         Gly Thr Ile Thr Val Gln Gln Tyr Asn Thr Ala Gly Thr Ser Leu Glu>
```

Figure 30B

B-31 OSP A/ B-31 OSP B / B-31 OSP C FUSION

```
         770           780           790          800           810
          *     *       *     *       *     *      *     *       *     *
       GGA TCA GCA AGT GAA ATT AAA AAT CTT TCA GAG CTT AAA AAC GCT TTA
       CCT AGT CGT TCA CTT TAA TTT TTA GAA AGT CTC GAA TTT TTG CGA AAT
       Gly Ser Ala Ser Glu Ile Lys Asn Leu Ser Glu Leu Lys Asn Ala Leu>

820           830           840          850           860
          *     *       *     *       *     *      *     *       *     *
       AAA ATG GCT AAT AAT TCA GGG AAA GAT GGG AAT ACA TCT GCA AAT TCT
       TTT TAC CGA TTA TTA AGT CCC TTT CTA CCC TTA TGT AGA CGT TTA AGA
       Lys Met Ala Asn Asn Ser Gly Lys Asp Gly Asn Thr Ser Ala Asn Ser>

870           880           890          900           910
          *     *       *     *       *     *      *     *       *     *
       GCT GAT GAG TCT GTT AAA GGG CCT AAT CTT ACA GAA ATA AGT AAA AAA
       CGA CTA CTC AGA CAA TTT CCC GGA TTA GAA TGT CTT TAT TCA TTT TTT
       Ala Asp Glu Ser Val Lys Gly Pro Asn Leu Thr Glu Ile Ser Lys Lys>

920           930           940          950           960
          *     *       *     *       *     *      *     *       *     *
       ATT ACG GAT TCT AAT GCG GTT TTA CTT GCT GTG AAA GAG GTT GAA GCG
       TAA TGC CTA AGA TTA CGC CAA AAT GAA CGA CAC TTT CTC CAA CTT CGC
       Ile Thr Asp Ser Asn Ala Val Leu Leu Ala Val Lys Glu Val Glu Ala>

970           980           990         1000
          *     *       *     *       *     *      *     *       *
       TTG CTG TCA TCT ATA GAT GAA ATT GCT GCT AAA GCT ATT GGT AAA AAA
       AAC GAC AGT AGA TAT CTA CTT TAA CGA CGA TTT CGA TAA CCA TTT TTT
       Leu Leu Ser Ser Ile Asp Glu Ile Ala Ala Lys Ala Ile Gly Lys Lys>

1010          1020          1030         1040          1050
          *     *       *     *       *     *      *     *       *     *
       ATA CAC CAA AAT AAT GGT TTG GAT ACC GAA TAT AAT CAC AAT GGA TCA
       TAT GTG GTT TTA TTA CCA AAC CTA TGG CTT ATA TTA GTG TTA CCT AGT
       Ile His Gln Asn Asn Gly Leu Asp Thr Glu Tyr Asn His Asn Gly Ser>

1060          1070          1080         1090          1100
          *     *       *     *       *     *      *     *       *
       TTG TTA GCG GGA CGT TAT GCA ATA TCA ACC CTA ATA AAA CAA AAA TTA
       AAC AAT CGC CCT GCA ATA CGT TAT AGT TGG GAT TAT TTT GTT TTT AAT
       Leu Leu Ala Gly Arg Tyr Ala Ile Ser Thr Leu Ile Lys Gln Lys Leu>

1110          1120          1130         1140          1150
          *     *       *     *       *     *      *     *       *     *
       GAT GGA TTG AAA AAT GAA GGA TTA AAG GAA AAA ATT GAT GCG GCT AAG
       CTA CCT AAC TTT TTA CTT CCT AAT TTC CTT TTT TAA CTA CGC CGA TTC
       Asp Gly Leu Lys Asn Glu Gly Leu Lys Glu Lys Ile Asp Ala Ala Lys>
```

Figure 30C

B-31 OSP A / B-31 OSP B/ B-31 OSP C FUSION

```
        1160          1170         1180         1190         1200
          *       *     *      *     *      *     *      *     *      *
        AAA TGT TCT GAA ACA TTT ACT AAT AAA TTA AAA GCA AAA CAC ACA GAT
        TTT ACA AGA CTT TGT AAA TGA TTA TTT AAT TTT CGT TTT GTG TGT CTA
        Lys Cys Ser Glu Thr Phe Thr Asn Lys Leu Lys Ala Lys His Thr Asp>

1210          1220         1230         1240
          *     *      *     *      *     *      *     *      *
        CTT GGT AAA GAA GGT GTT ACT GAT GCT GAT GCA AAA GAA GCC ATT TTA
        GAA CCA TTT CTT CCA CAA TGA CTA CGA CTA CGT TTT CTT CGG TAA AAT
        Leu Gly Lys Glu Gly Val Thr Asp Ala Asp Ala Lys Glu Ala Ile Leu>

1250          1260         1270         1280         1290
     *      *     *     *      *     *      *     *      *     *
    AAA ACA AAT GGT ACT AAA ACT AAA GGT GCT GAA GAA CTT GGA AAA TTA
    TTT TGT TTA CCA TGA TTT TGA TTT CCA CGA CTT CTT GAA CCT TTT AAT
    Lys Thr Asn Gly Thr Lys Thr Lys Gly Ala Glu Glu Leu Gly Lys Leu>

1300          1310         1320         1330         1340
          *     *      *     *     *      *     *      *     *
        TTT GAA TCA GTA GAG GTC TTG TCA AAA GCA GCT AAA GAG ATG CTT GCT
        AAA CTT AGT CAT CTC CAG AAC AGT TTT CGT CGA TTT CTC TAC GAA CGA
        Phe Glu Ser Val Glu Val Leu Ser Lys Ala Ala Lys Glu Met Leu Ala>

1350          1360         1370         1380         1390
          *     *      *     *      *     * .     *     *      *     *
        AAT TCA GTT AAA GAG CTT ACA AGC CCT GTT GTG GCA GAA AGT CCA AAA
        TTA AGT CAA TTT CTC GAA TGT TCG GGA CAA CAC CGT CTT TCA GGT TTT
        Asn Ser Val Lys Glu Leu Thr Ser Pro Val Val Ala Glu Ser Pro Lys>

1400
          *     *
        AAA CCT TAA
        TTT GGA ATT
        Lys Pro ***>
```

Figure 30D

B-31 OSP C/ B-31 OSP A/ B-31 OSP B FUSION

```
          10              20              30              40
           *               *               *               *
ATG AAA AAG AAT ACA TTA AGT GCG ATA TTA ATG ACT TTA TTT TTA TTT
TAC TTT TTC TTA TGT AAT TCA CGC TAT AAT TAC TGA AAT AAA AAT AAA
Met Lys Lys Asn Thr Leu Ser Ala Ile Leu Met Thr Leu Phe Leu Phe>

50              60              70              80              90
   *               *               *               *               *
ATA TCT TGT AAT AAT TCA GGG AAA GAT GGG AAT ACA TCT GCA AAT TCT
TAT AGA ACA TTA TTA AGT CCC TTT CTA CCC TTA TGT AGA CGT TTA AGA
Ile Ser Cys Asn Asn Ser Gly Lys Asp Gly Asn Thr Ser Ala Asn Ser>

100             110             120             130             140
       *               *               *               *               *
GCT GAT GAG TCT GTT AAA GGG CCT AAT CTT ACA GAA ATA AGT AAA AAA
CGA CTA CTC AGA CAA TTT CCC GGA TTA GAA TGT CTT TAT TCA TTT TTT
Ala Asp Glu Ser Val Lys Gly Pro Asn Leu Thr Glu Ile Ser Lys Lys>

150             160             170             180             190
          *               *               *               *               *
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
Ile Thr Asp Ser Asn Ala Val Leu Leu Ala Val Lys Glu Val Glu Ala>

200             210             220             230             240
            *               *               *               *               *
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
Leu Leu Ser Ser Ile Asp Glu Ile Ala Ala Lys Ala Ile Gly Lys Lys>

250             260             270             280
              *               *               *               *
ATA CAC CAA AAT AAT GGT TTG GAT ACC GAA TAT AAT CAC AAT GGA TCA
TAT GTG GTT TTA TTA CCA AAC CTA TGG CTT ATA TTA GTG TTA CCT AGT
Ile His Gln Asn Asn Gly Leu Asp Thr Glu Tyr Asn His Asn Gly Ser>

290             300             310             320             330
  *               *               *               *               *
TTG TTA GCG GGA CGT TAT GCA ATA TCA ACC CTA ATA AAA CAA AAA TTA
AAC AAT CGC CCT GCA ATA CGT TAT AGT TGG GAT TAT TTT GTT TTT AAT
Leu Leu Ala Gly Arg Tyr Ala Ile Ser Thr Leu Ile Lys Gln Lys Leu>

340             350             360             370             380
    *               *               *               *               *
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
Asp Gly Leu Lys Asn Glu Gly Leu Lys Glu Lys Ile Asp Ala Ala Lys>
```

Figure 31A

B-31 OSP C/ B-31 OSP A/ B-31 OSP B FUSION

```
         390         400         410         420         430
          *           *           *           *           *
AAA TGT TCT GAA ACA TTT ACT AAT AAA TTA AAA GCA AAA CAC ACA GAT
TTT ACA AGA CTT TGT AAA TGA TTA TTT AAT TTT CGT TTT GTG TGT CTA
Lys Cys Ser Glu Thr Phe Thr Asn Lys Leu Lys Ala Lys His Thr Asp>

440         450         460         470         480
          *           *           *           *           *
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
Leu Gly Lys Glu Gly Val Thr Asp Ala Asp Ala Lys Glu Ala Ile Leu>

490         500         510         520
          *           *           *           *
AAA ACA AAT GGT ACT AAA ACT AAA GGT GCT GAA GAA CTT GGA AAA TTA
TTT TGT TTA CCA TGA TTT TGA TTT CCA CGA CTT CTT GAA CCT TTT AAT
Lys Thr Asn Gly Thr Lys Thr Lys Gly Ala Glu Glu Leu Gly Lys Leu>

530         540         550         560         570
  *           *           *           *           *
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
Phe Glu Ser Val Glu Val Leu Ser Lys Ala Ala Lys Glu Met Leu Ala>

580         590         600         610         620
          *           *           *           *           *
AAT TCA GTT AAA GAG CTT ACA AGC CCT GTT GTG GCA GAA AGT CCA AAA
TTA AGT CAA TTT CTC GAA TGT TCG GGA CAA CAC CGT CTT TCA GGT TTT
Asn Ser Val Lys Glu Leu Thr Ser Pro Val Val Ala Glu Ser Pro Lys>

630         640         650         660         670
          *           *           *           *           *
AAA CCT AAG CAA AAT GTT AGC AGC CTT GAC GAG AAA AAC AGC GTT TCA
TTT GGA TTC GTT TTA CAA TCG TCG GAA CTG CTC TTT TTG TCG CAA AGT
Lys Pro Lys Gln Asn Val Ser Ser Leu Asp Glu Lys Asn Ser Val Ser>

680         690         700         710         720
          *           *           *           *           *
GTA GAT TTG CCT GGT GAA ATG AAA GTT CTT GTA AGC AAA GAA AAA AAC
CAT CTA AAC GGA CCA CTT TAC TTT CAA GAA CAT TCG TTT CTT TTT TTG
Val Asp Leu Pro Gly Glu Met Lys Val Leu Val Ser Lys Glu Lys Asn>

730         740         750         760
          *           *           *           *
AAA GAC GGC AAG TAC GAT CTA ATT GCA ACA GTA GAC AAG CTT GAG CTT
TTT CTG CCG TTC ATG CTA GAT TAA CGT TGT CAT CTG TTC GAA CTC GAA
Lys Asp Gly Lys Tyr Asp Leu Ile Ala Thr Val Asp Lys Leu Glu Leu>
```

Figure 31B

B-31 OSP C/ B-31 OSP A/ B-31 OSP B FUSION

```
         770         780         790         800         810
          *           *           *           *           *
   AAA GGA ACT TCT GAT AAA AAC AAT GGA TCT GGA GTA CTT GAA GGC GTA
   TTT CCT TGA AGA CTA TTT TTG TTA CCT AGA CCT CAT GAA CTT CCG CAT
   Lys Gly Thr Ser Asp Lys Asn Asn Gly Ser Gly Val Leu Glu Gly Val>

820         830         840         850         860
          *           *           *           *           *
   AAA GCT GAC AAA AGT AAA GTA AAA TTA ACA ATT TCT GAC GAT CTA GGT
   TTT CGA CTG TTT TCA TTT CAT TTT AAT TGT TAA AGA CTG CTA GAT CCA
   Lys Ala Asp Lys Ser Lys Val Lys Leu Thr Ile Ser Asp Asp Leu Gly>

870         880         890         900         910
          *           *           *           *           *
   CAA ACC ACA CTT GAA GTT TTC AAA GAA GAT GGC AAA ACA CTA GTA TCA
   GTT TGG TGT GAA CTT CAA AAG TTT CTT CTA CCG TTT TGT GAT CAT AGT
   Gln Thr Thr Leu Glu Val Phe Lys Glu Asp Gly Lys Thr Leu Val Ser>

920         930         940         950         960
          *           *           *           *           *
   AAA AAA GTA ACT TCC AAA GAC AAG TCA TCA ACA GAA GAA AAA TTC AAT
   TTT TTT CAT TGA AGG TTT CTG TTC AGT AGT TGT CTT CTT TTT AAG TTA
   Lys Lys Val Thr Ser Lys Asp Lys Ser Ser Thr Glu Glu Lys Phe Asn>

970         980         990        1000
          *           *           *           *           *
   GAA AAA GGT GAA GTA TCT GAA AAA ATA ATA ACA AGA GCA GAC GGA ACC
   CTT TTT CCA CTT CAT AGA CTT TTT TAT TAT TGT TCT CGT CTG CCT TGG
   Glu Lys Gly Glu Val Ser Glu Lys Ile Ile Thr Arg Ala Asp Gly Thr>

1010        1020        1030        1040        1050
    *           *           *           *           *
   AGA CTT GAA TAC ACA GGA ATT AAA AGC GAT GGA TCT GGA AAA GCT AAA
   TCT GAA CTT ATG TGT CCT TAA TTT TCG CTA CCT AGA CCT TTT CGA TTT
   Arg Leu Glu Tyr Thr Gly Ile Lys Ser Asp Gly Ser Gly Lys Ala Lys>

1060        1070        1080        1090        1100
          *           *           *           *           *
   GAG GTT TTA AAA GGC TAT GTT CTT GAA GGA ACT CTA ACT GCT GAA AAA
   CTC CAA AAT TTT CCG ATA CAA GAA CTT CCT TGA GAT TGA CGA CTT TTT
   Glu Val Leu Lys Gly Tyr Val Leu Glu Gly Thr Leu Thr Ala Glu Lys>

1110        1120        1130        1140        1150
          *           *           *           *           *
   ACA ACA TTG GTG GTT AAA GAA GGA ACT GTT ACT TTA AGC AAA AAT ATT
   TGT TGT AAC CAC CAA TTT CTT CCT TGA CAA TGA AAT TCG TTT TTA TAA
   Thr Thr Leu Val Val Lys Glu Gly Thr Val Thr Leu Ser Lys Asn Ile>
```

Figure 31C

B-31 OSP C/ B-31 OSP A / B-31 OSP B FUSION

```
            1160            1170            1180            1190            1200
             *               *               *               *               *
     *               *               *               *               *
    TCA AAA TCT GGG GAA GTT TCA GTT GAA CTT AAT GAC ACT GAC AGT AGT
    AGT TTT AGA CCC CTT CAA AGT CAA CTT GAA TTA CTG TGA CTG TCA TCA
    Ser Lys Ser Gly Glu Val Ser Val Glu Leu Asn Asp Thr Asp Ser Ser>

1210            1220            1230            1240
             *               *               *               *
     *               *               *               *               *
    GCT GCT ACT AAA AAA ACT GCA GCT TGG AAT GAC AGT ACT AGC ACT TTA
    CGA CGA TGA TTT TTT TGA CGT CGA ACC TTA CTG TCA TGA TCG TGA AAT
    Ala Ala Thr Lys Lys Thr Ala Ala Trp Asn Asp Ser Thr Ser Thr Leu>

1250            1260            1270            1280            1290
    *               *               *               *               *
             *               *               *               *               *
    ACA ATT AGT GCT GAC AGC AAA AAA ACT AAA GAT TTG GTG TTC TTA ACA
    TGT TAA TCA CGA CTG TCG TTT TTT TGA TTT CTA AAC CAC AAG AAT TGT
    Thr Ile Ser Ala Asp Ser Lys Lys Thr Lys Asp Leu Val Phe Leu Thr>

1300            1310            1320            1330            1340
             *               *               *               *               *
     *               *               *               *               *
    GAT GGT ACA ATT ACA GTA CAA CAA TAC AAC ACA GCT GGA ACC AGC CTA
    CTA CCA TGT TAA TGT CAT GTT GTT ATG TTG TGT CGA CCT TGG TCG GAT
    Asp Gly Thr Ile Thr Val Gln Gln Tyr Asn Thr Ala Gly Thr Ser Leu>

1350            1360            1370            1380            1390
             *               *               *               *               *
     *               *               *               *               *
    GAA GGA TCA GCA AGT GAA ATT AAA AAT CTT TCA GAG CTT AAA AAC GCT
    CTT CCT AGT CGT TCA CTT TAA TTT TTA GAA AGT CTC GAA TTT TTG CGA
    Glu Gly Ser Ala Ser Glu Ile Lys Asn Leu Ser Glu Leu Lys Asn Ala>

1400
             *               *
    TTA AAA TAA
    AAT TTT ATT
    Leu Lys ***>
```

Figure 31D

FUSION SEQUENCE

B-31 OSP A/ B-31 P-93 (1168-2100)
Sequence Range: 1 to 1720

```
          10           20           30           40
           *            *            *            *
AAG CAA AAT GTT AGC AGC CTT GAC GAG AAA AAC AGC GTT TCA GTA GAT
TTC GTT TTA CAA TCG TCG GAA CTG CTC TTT TTG TCG CAA AGT CAT CTA
 K   Q   N   V   S   S   L   D   E   K   N   S   V   S   V   D>

50           60           70           80           90
    *            *            *            *            *
TTG CCT GGT GAA ATG AAA GTT CTT GTA AGC AAA GAA AAA AAC AAA GAC
AAC GGA CCA CTT TAC TTT CAA GAA CAT TCG TTT CTT TTT TTG TTT CTG
 L   P   G   E   M   K   V   L   V   S   K   E   K   N   K   D>

100          110          120          130          140
       *            *            *            *            *
GGC AAG TAC GAT CTA ATT GCA ACA GTA GAC AAG CTT GAG CTT AAA GGA
CCG TTC ATG CTA GAT TAA CGT TGT CAT CTG TTC GAA CTC GAA TTT CCT
 G   K   Y   D   L   I   A   T   V   D   K   L   E   L   K   G>

150          160          170          180          190
      *            *            *            *            *
ACT TCT GAT AAA AAC AAT GGA TCT GGA GTA CTT GAA GGC GTA AAA GCT
TGA AGA CTA TTT TTG TTA CCT AGA CCT CAT GAA CTT CCG CAT TTT CGA
 T   S   D   K   N   N   G   S   G   V   L   E   G   V   K   A>

200          210          220          230          240
           *            *            *            *            *
GAC AAA AGT AAA GTA AAA TTA ACA ATT TCT GAC GAT CTA GGT CAA ACC
CTG TTT TCA TTT CAT TTT AAT TGT TAA AGA CTG CTA GAT CCA GTT TGG
 D   K   S   K   V   K   L   T   I   S   D   D   L   G   Q   T>

250          260          270          280
              *            *            *            *
ACA CTT GAA GTT TTC AAA GAA GAT GGC AAA ACA CTA GTA TCA AAA AAA
TGT GAA CTT CAA AAG TTT CTT CTA CCG TTT TGT GAT CAT AGT TTT TTT
 T   L   E   V   F   K   E   D   G   K   T   L   V   S   K   K>

290          300          310          320          330
    *            *            *            *            *
GTA ACT TCC AAA GAC AAG TCA TCA ACA GAA GAA AAA TTC AAT GAA AAA
CAT TGA AGG TTT CTG TTC AGT AGT TGT CTT CTT TTT AAG TTA CTT TTT
 V   T   S   K   D   K   S   S   T   E   E   K   F   N   E   K>

340          350          360          370          380
       *            *            *            *            *
GGT GAA GTA TCT GAA AAA ATA ATA ACA AGA GCA GAC GGA ACC AGA CTT
CCA CTT CAT AGA CTT TTT TAT TAT TGT TCT CGT CTG CCT TGG TCT GAA
 G   E   V   S   E   K   I   I   T   R   A   D   G   T   R   L>
```

Figure 32A

B-31 OSP A/ B-31 P93

```
         390           400           410           420           430
          *             *             *             *             *
GAA TAC ACA GGA ATT AAA AGC GAT GGA TCT GGA AAA GCT AAA GAG GTT
CTT ATG TGT CCT TAA TTT TCG CTA CCT AGA CCT TTT CGA TTT CTC CAA
 E   Y   T   G   I   K   S   D   G   S   G   K   A   K   E   V>

440           450           460           470           480
               *             *             *             *             *
TTA AAA GGC TAT GTT CTT GAA GGA ACT CTA ACT GCT GAA AAA ACA ACA
AAT TTT CCG ATA CAA GAA CTT CCT TGA GAT TGA CGA CTT TTT TGT TGT
 L   K   G   Y   V   L   E   G   T   L   T   A   E   K   T   T>

490           500           510           520
                    *             *             *             *
TTG GTG GTT AAA GAA GGA ACT GTT ACT TTA AGC AAA AAT ATT TCA AAA
AAC CAC CAA TTT CTT CCT TGA CAA TGA AAT TCG TTT TTA TAA AGT TTT
 L   V   V   K   E   G   T   V   T   L   S   K   N   I   S   K>

530           540           550           560           570
 *             *             *             *             *
TCT GGG GAA GTT TCA GTT GAA CTT AAT GAC ACT GAC AGT AGT GCT GCT
AGA CCC CTT CAA AGT CAA CTT GAA TTA CTG TGA CTG TCA TCA CGA CGA
 S   G   E   V   S   V   E   L   N   D   T   D   S   S   A   A>

580           590           600           610           620
      *             *             *             *             *
ACT AAA AAA ACT GCA GCT TGG AAT TCA GGC ACT TCA ACT TTA ACA ATT
TGA TTT TTT TGA CGT CGA ACC TTA AGT CCG TGA AGT TGA AAT TGT TAA
 T   K   K   T   A   A   W   N   S   G   T   S   T   L   T   I>

630           640           650           660           670
           *             *             *             *             *
ACT GTA AAC AGT AAA AAA ACT AAA GAC CTT GTG TTT ACA AAA GAA AAC
TGA CAT TTG TCA TTT TTT TGA TTT CTG GAA CAC AAA TGT TTT CTT TTG
 T   V   N   S   K   K   T   K   D   L   V   F   T   K   E   N>

680           690           700           710           720
                *             *             *             *             *
ACA ATT ACA GTA CAA CAA TAC GAC TCA AAT GGC ACC AAA TTA GAG GGG
TGT TAA TGT CAT GTT GTT ATG CTG AGT TTA CCG TGG TTT AAT CTC CCC
 T   I   T   V   Q   Q   Y   D   S   N   G   T   K   L   E   G>

730           740           750           760
                     *             *             *             *
TCA GCA GTT GAA ATT ACA AAA CTT GAT GAA ATT AAA AAC GCT TTA AAA
AGT CGT CAA CTT TAA TGT TTT GAA CTA CTT TAA TTT TTG CGA AAT TTT
 S   A   V   E   I   T   K   L   D   E   I   K   N   A   L   K>
```

Figure 32B

B-31 OSP A/ B-31 P-93

```
      770            780            790            800            810
       *        *     *         *    *         *    *         *    *         *
     GGT CAC CCC ATG GAT GAA AAG CTT TTA AAA AGT AAA GAT GAT AAA GCA
     CCA GTG GGG TAC CTA CTT TTC GAA AAT TTT TCA TTT CTA CTA TTT CGT
      G   H   P   M   D   E   K   L   L   K   S   K   D   D   K   A>

820            830            840            850            860
       *        *     *         *    *         *    *         *    *
     AGT AAA GAT GGT AAA GCC TTG GAT CTT GAT CGA GAA TTA AAT TCT AAA
     TCA TTT CTA CCA TTT CGG AAC CTA GAA CTA GCT CTT AAT TTA AGA TTT
      S   K   D   G   K   A   L   D   L   D   R   E   L   N   S   K>

870            880            890            900            910
           *        *    *         *    *         *    *         *    *    *
     GCT TCT AGC AAA GAA AAA AGT AAA GCC AAG GAA GAA GAA ATA ACC AAG
     CGA AGA TCG TTT CTT TTT TCA TTT CGG TTC CTT CTT CTT TAT TGG TTC
      A   S   S   K   E   K   S   K   A   E   E   E   I   T   K>

920            930            940            950            960
               *        *    *         *    *         *    *         *    *    *
     GGT AAG TCA CAG AAA AGC TTA GGC GAT TTG AAT AAT GAT GAA AAT CTT
     CCA TTC AGT GTC TTT TCG AAT CCG CTA AAC TTA TTA CTA CTT TTA GAA
      G   K   S   Q   K   S   L   G   D   L   N   N   D   E   N   L>

970            980            990            1000
                   *        *    *         *    *         *    *         *    *
     ATG ATG CCA GAA GAT CAA AAA TTA CCT GAG GTT AAA AAA TTA GAT AGC
     TAC TAC GGT CTT CTA GTT TTT AAT GGA CTC CAA TTT TTT AAT CTA TCG
      M   M   P   E   D   Q   K   L   P   E   V   K   K   L   D   S>

1010           1020           1030           1040           1050
       *        *    *         *    *         *    *         *    *         *
     AAA AAA GAA TTT AAA CCT GTT TCT GAG GTT GAG AAA TTA GAT AAG ATT
     TTT TTT CTT AAA TTT GGA CAA AGA CTC CAA CTC TTT AAT CTA TTC TAA
      K   K   E   F   K   P   V   S   E   V   E   K   L   D   K   I>

1060           1070           1080           1090           1100
           *        *    *         *    *         *    *         *    *
     TTC AAG TCT AAT AAC AAT GTT GGA GAA TTA TCA CCG TTA GAT AAA TCT
     AAG TTC AGA TTA TTG TTA CAA CCT CTT AAT AGT GGC AAT CTA TTT AGA
      F   K   S   N   N   N   V   G   E   L   S   P   L   D   K   S>

1110           1120           1130           1140           1150
               *        *    *         *    *         *    *         *    *    *
     TCT TAT AAA GAC ATT GAT TCA AAA GAG GAG ACA GTT AAT AAA GAT GTT
     AGA ATA TTT CTG TAA CTA AGT TTT CTC CTC TGT CAA TTA TTT CTA CAA
      S   Y   K   D   I   D   S   K   E   E   T   V   N   K   D   V>
```

Figure 32C

B-31 OSP / B-31 P-93

```
           1160        1170        1180        1190        1200
            *           *           *           *           *
       AAT TTG CAA AAG ACT AAG CCT CAG GTT AAA GAC CAA GTT ACT TCT TTG
       TTA AAC GTT TTC TGA TTC GGA GTC CAA TTT CTG GTT CAA TGA AGA AAC
        N   L   Q   K   T   K   P   Q   V   K   D   Q   V   T   S   L>

1210        1220        1230        1240
                  *           *           *           *           *
       AAT GAA GAT TTG ACT ACT ATG TCT ATA GAT TCC AGT AGT CCT GTA TTT
       TTA CTT CTA AAC TGA TGA TAC AGA TAT CTA AGG TCA TCA GGA CAT AAA
        N   E   D   L   T   T   M   S   I   D   S   S   S   P   V   F>

1250        1260        1270        1280        1290
     *           *           *           *           *
  TTA GAG GTT ATT GAT CCA ATT ACA AAT TTA GGA ACT CTT CAA CTT ATT
  AAT CTC CAA TAA CTA GGT TAA TGT TTA AAT CCT TGA GAA GTT GAA TAA
   L   E   V   I   D   P   I   T   N   L   G   T   L   Q   L   I>

1300        1310        1320        1330        1340
        *           *           *           *           *
   GAT TTA AAT ACT GGT GTT AGG CTT AAA GAA AGC ACT CAG CAA GGC ATT
   CTA AAT TTA TGA CCA CAA TCC GAA TTT CTT TCG TGA GTC GTT CCG TAA
    D   L   N   T   G   V   R   L   K   E   S   T   Q   Q   G   I>

1350        1360        1370        1380        1390
             *           *           *           *           *
       CAG CGG TAT GGA ATT TAT GAA CGT GAA AAA GAT TTG GTT GTT ATT AAA
       GTC GCC ATA CCT TAA ATA CTT GCA CTT TTT CTA AAC CAA CAA TAA TTT
        Q   R   Y   G   I   Y   E   R   E   K   D   L   V   V   I   K>

1400        1410        1420        1430        1440
                  *           *           *           *           *
       ATG GAT TCA GGA AAA GCT AAG CTT CAG ATA CTT GAT AAA CTT GAA AAT
       TAC CTA AGT CCT TTT CGA TTC GAA GTC TAT GAA CTA TTT GAA CTT TTA
        M   D   S   G   K   A   K   L   Q   I   L   D   K   L   E   N>

1450        1460        1470        1480
                  *           *           *           *           *
       TTA AAA GTG GTA TCA GAG TCT AAT TTT GAG ATT AAT AAA AAT TCA TCT
       AAT TTT CAC CAT AGT CTC AGA TTA AAA CTC TAA TTA TTT TTA AGT AGA
        L   K   V   V   S   E   S   N   F   E   I   N   K   N   S   S>

1490        1500        1510        1520        1530
     *           *           *           *           *
  CTT TAT GTT GAT TCT AAA ATG ATT TTA GTA GCT GTT AGG GAT AAA GAT
  GAA ATA CAA CTA AGA TTT TAC TAA AAT CAT CGA CAA TCC CTA TTT CTA
   L   Y   V   D   S   K   M   I   L   V   A   V   R   D   K   D>
```

Figure 32D

B-31 OSP A/ B-31 P-93

```
     1540          1550          1560          1570          1580
      *             *             *             *             *
AGT AGT AAT GAT TGG AGA TTG GCC AAA TTT TCT CCT AAA AAT TTA GAT
TCA TCA TTA CTA ACC TCT AAC CGG TTT AAA AGA GGA TTT TTA AAT CTA
 S   S   N   D   W   R   L   A   K   F   S   P   K   N   L   D>

1590          1600          1610          1620          1630
      *             *             *             *             *
GAG TTT ATT CTT TCA GAG AAT AAA ATT ATG CCT TTT ACT AGC TTT TCT
CTC AAA TAA GAA AGT CTC TTA TTT TAA TAC GGA AAA TGA TCG AAA AGA
 E   F   I   L   S   E   N   K   I   M   P   F   T   S   F   S>

1640          1650          1660          1670          1680
      *             *             *             *             *
GTG AGA AAA AAT TTT ATT TAT TTG CAA GAT GAG TTT AAA AGT CTA GTT
CAC TCT TTT TTA AAA TAA ATA AAC GTT CTA CTC AAA TTT TCA GAT CAA
 V   R   K   N   F   I   Y   L   Q   D   E   F   K   S   L   V>

1690          1700          1710          1720
      *             *             *             *
ATT TTA GAT GTA AAT ACT TTA AAA AAA GTT AAG GGT CAC C
TAA AAT CTA CAT TTA TGA AAT TTT TTT CAA TTC CCA GTG G
 I   L   D   V   N   T   L   K   K   V   K   G   H   X>
```

Figure 32E

B-31 OSP B/ B-31 P41 (122-234)

OSPB/Fla122-234
Sequence Range: 1 to 1180

```
              10              20              30              40
               *               *               *               *
GCA CAA AAA GGT GCT GAG TCA ATT GGT TCT CAA AAA GAA AAT GAT CTA
CGT GTT TTT CCA CGA CTC AGT TAA CCA AGA GTT TTT CTT TTA CTA GAT
 A   Q   K   G   A   E   S   I   G   S   Q   K   E   N   D   L>

50              60              70              80              90
      *               *               *               *               *
AAC CTT GAA GAC TCT AGT AAA AAA TCA CAT CAA AAC GCT AAA CAA GAC
TTG GAA CTT CTG AGA TCA TTT TTT AGT GTA GTT TTG CGA TTT GTT CTG
 N   L   E   D   S   S   K   K   S   H   Q   N   A   K   Q   D>

100             110             120             130             140
      *               *               *               *               *
CTT CCT GCG GTG ACA GAA GAC TCA GTG TCT TTG TTT AAT GGT AAT AAA
GAA GGA CGC CAC TGT CTT CTG AGT CAC AGA AAC AAA TTA CCA TTA TTT
 L   P   A   V   T   E   D   S   V   S   L   F   N   G   N   K>

150             160             170             180             190
      *               *               *               *               *
ATT TTT GTA AGC AAA GAA AAA AAT AGC TCC GGC AAA TAT GAT TTA AGA
TAA AAA CAT TCG TTT CTT TTT TTA TCG AGG CCG TTT ATA CTA AAT TCT
 I   F   V   S   K   E   K   N   S   S   G   K   Y   D   L   R>

200             210             220             230             240
      *               *               *               *               *
GCA ACA ATT GAT CAG GTT GAA CTT AAA GGA ACT TCC GAT AAA AAC AAT
CGT TGT TAA CTA GTC CAA CTT GAA TTT CCT TGA AGG CTA TTT TTG TTA
 A   T   I   D   Q   V   E   L   K   G   T   S   D   K   N   N>

250             260             270             280
      *               *               *               *
GGT TCT GGA ACC CTT GAA GGT TCA AAG CCT GAC AAG AGT AAA GTA AAA
CCA AGA CCT TGG GAA CTT CCA AGT TTC GGA CTG TTC TCA TTT CAT TTT
 G   S   G   T   L   E   G   S   K   P   D   K   S   K   V   K>

290             300             310             320             330
 *               *               *               *               *
TTA ACA GTT TCT GCT GAT TTA AAC ACA GTA ACC TTA GAA GCA TTT GAT
AAT TGT CAA AGA CGA CTA AAT TTG TGT CAT TGG AAT CTT CGT AAA CTA
 L   T   V   S   A   D   L   N   T   V   T   L   E   A   F   D>

340             350             360             370             380
      *               *               *               *               *
GCC AGC AAC CAA AAA ATT TCA AGT AAA GTT ACT AAA AAA CAG GGG TCA
CGG TCG TTG GTT TTT TAA AGT TCA TTT CAA TGA TTT TTT GTC CCC AGT
 A   S   N   Q   K   I   S   S   K   V   T   K   K   Q   G   S>
```

Figure 33A

B-31 OSP B/ B-31 P41 (122-234)

```
         390         400         410         420         430
          *           *           *           *           *
ATA ACA GAG GAA ACT CTC AAA GCT AAT AAA TTA GAC TCA AAG AAA TTA
TAT TGT CTC CTT TGA GAG TTT CGA TTA TTT AAT CTG AGT TTC TTT AAT
 I   T   E   E   T   L   K   A   N   K   L   D   S   K   K   L>

440         450         460         470         480
          *           *           *           *           *
ACA AGA TCA AAC GGA ACT ACA CTT GAA TAC TCA CAA ATA ACA GAT GCT
TGT TCT AGT TTG CCT TGA TGT GAA CTT ATG AGT GTT TAT TGT CTA CGA
 T   R   S   N   G   T   T   L   E   Y   S   Q   I   T   D   A>

490         500         510         520
          *           *           *           *
GAC AAT GCT ACA AAA GCA GTA GAA ACT CTA AAA AAT AGC ATT AAG CTT
CTG TTA CGA TGT TTT CGT CAT CTT TGA GAT TTT TTA TCG TAA TTC GAA
 D   N   A   T   K   A   V   E   T   L   K   N   S   I   K   L>

530         540         550         560         570
  *           *           *           *           *
GAA GGA AGT CTT GTA GTC GGA AAA ACA ACA GTG AAA ATT AAA GAA GGT
CTT CCT TCA GAA CAT CAG CCT TTT TGT TGT CAC TTT TAA TTT CTT CCA
 E   G   S   L   V   V   G   K   T   T   V   E   I   K   E   G>

580         590         600         610         620
          *           *           *           *           *
ACT GTT ACT CTA AAA AGA GAA ATT GAA AAA GAT GGA AAA GTA AAA GTC
TGA CAA TGA GAT TTT TCT CTT TAA CTT TTT CTA CCT TTT CAT TTT CAG
 T   V   T   L   K   R   E   I   E   K   D   G   K   V   K   V>

630         640         650         660         670
          *           *           *           *           *
TTT TTG AAT GAC ACT GCA GGT TCT AAC AAA AAA ACA GGT AAA TGG GAA
AAA AAC TTA CTG TGA CGT CCA AGA TTG TTT TTT TGT CCA TTT ACC CTT
 F   L   N   D   T   A   G   S   N   K   K   T   G   K   W   E>

680         690         700         710         720
          *           *           *           *           *
GAC AGT ACT AGC ACT TTA ACA ATT AGT GCT GAC AGC AAA AAA ACT AAA
CTG TCA TGA TCG TGA AAT TGT TAA TCA CGA CTG TCG TTT TTT TGA TTT
 D   S   T   S   T   L   T   I   S   A   D   S   K   K   T   K>

730         740         750         760
          *           *           *           *
GAT TTG GTG TTC TTA ACA GAT GGT ACA ATT ACA GTA CAA CAA TAC AAC
CTA AAC CAC AAG AAT TGT CTA CCA TGT TAA TGT CAT GTT GTT ATG TTG
 D   L   V   F   L   T   D   G   T   I   T   V   Q   Q   Y   N>
```

Figure 33B

B-31 OSP B/ B-31 P41 (122-234)

```
        770           780           790           800           810
         *             *             *             *             *
   ACA GCT GGA ACC AGC CTA GAA GGA TCA GCA AGT GAA ATT AAA AAT CTT
   TGT CGA CCT TGG TCG GAT CTT CCT AGT CGT TCA CTT TAA TTT TTA GAA
    T   A   G   T   S   L   E   G   S   A   S . E   I   K   N   L>

820           830           840           850           860
         *             *             *             *             *
   TCA GAG CTT AAA AAC GCT TTA AAA GGT CAC CCC ATG GCT CAA TAT AAC
   AGT CTC GAA TTT TTG CGA AAT TTT CCA GTG GGG TAC CGA GTT ATA TTG
    S   E   L   K   N   A   L   K   G   H   P   M   A   Q   Y   N>

870           880           890           900           910
         *             *             *             *             *
   CAA ATG CAC ATG TTA TCA AAC AAA TCT GCT TCT CAA AAT GTA AGA ACA
   GTT TAC GTG TAC AAT AGT TTG TTT AGA CGA AGA GTT TTA CAT TCT TGT
    Q   M   H   M   L   S   N   K   S   A   S   Q   N   V   R   T>

920           930           940           950           960
         *             *             *             *             *
   GCT GAA GAG CTT GGA ATG CAG CCT GCA AAA ATT AAC ACA CCA GCA TCA
   CGA CTT CTC GAA CCT TAC GTC GGA CGT TTT TAA TTG TGT GGT CGT AGT
    A   E   E   L   G   M   Q   P   A   K   I   N   T   P   A   S>

970           980           990          1000
         *             *             *             *             *
   CTT TCA GGG CTT CAA GCG TCT TGG ACT TTA AGA GTT CAT GTT GGA GCA
   GAA AGT CCC GAA GTT CGC AGA ACC TGA AAT TCT CAA GTA CAA CCT CGT
    L   S   G   L   Q   A   S   W   T   L   R   V   H   V   G   A>

1010          1020          1030          1040          1050
     *             *             *             *             *
   ACC CAA GAT GAA GCT ATT GCT GTA AAT ATT TAT GCA GCT AAT GTT GCA
   TGG GTT CTA CTT CGA TAA CGA CAT TTA TAA ATA CGT CGA TTA CAA CGT
    T   Q   D   E   A   I   A   V   N   I   Y   A   A   N   V   A>

1060          1070          1080          1090          1100
         *             *             *             *             *
   AAT CTT TTC TCT GGT GAG GGA GCT CAA ACT GCT CAG GCT GCA CCG GTT
   TTA GAA AAG AGA CCA CTC CCT CGA GTT TGA CGA GTC CGA CGT GGC CAA
    N   L   F   S   G   E   G   A   Q   T   A   Q   A   A   P   V>

1110          1120          1130          1140          1150
         *             *             *             *             *
   CAA GAG GGT GTT CAA CAG GAA GGA GCT CAA CAG CCA GCA CCT GCT ACA
   GTT CTC CCA CAA GTT GTC CTT CCT CGA GTT GTC GGT CGT GGA CGA TGT
    Q   E   G   V   Q   Q   E   G   A   Q   Q   P   A   P   A   T>
```

Figure 33C

B-31 OSP B/ B-31 P41 (122-234)

```
         1160           1170          1180
   *       *       *       *       *       *
GCA CCT TCT CAA GGC GGA GTT GGT CAC C
CGT GGA AGA GTT CCG CCT CAA CCA GTG G
 A   P   S   Q   G   G   V   G   H  X>
```

Figure 33D

B-31 OSP B / B-31 P41 (122-295)

Sequence Range: 1 to 1363

```
              10          20          30          40
               *           *           *           *
    GCA CAA AAA GGT GCT GAG TCA ATT GGT TCT CAA AAA GAA AAT GAT CTA
    CGT GTT TTT CCA CGA CTC AGT TAA CCA AGA GTT TTT CTT TTA CTA GAT
     A   Q   K   G   A   E   S   I   G   S   Q   K   E   N   D   L>

50          60          70          80          90
      *           *           *           *           *
    AAC CTT GAA GAC TCT AGT AAA AAA TCA CAT CAA AAC GCT AAA CAA GAC
    TTG GAA CTT CTG AGA TCA TTT TTT AGT GTA GTT TTG CGA TTT GTT CTG
     N   L   E   D   S   S   K   K   S   H   Q   N   A   K   Q   D>

100         110         120         130         140
          *           *           *           *           *
    CTT CCT GCG GTG ACA GAA GAC TCA GTG TCT TTG TTT AAT GGT AAT AAA
    GAA GGA CGC CAC TGT CTT CTG AGT CAC AGA AAC AAA TTA CCA TTA TTT
     L   P   A   V   T   E   D   S   V   S   L   F   N   G   N   K>

150         160         170         180         190
              *           *           *           *           *
    ATT TTT GTA AGC AAA GAA AAA AAT AGC TCC GGC AAA TAT GAT TTA AGA
    TAA AAA CAT TCG TTT CTT TTT TTA TCG AGG CCG TTT ATA CTA AAT TCT
     I   F   V   S   K   E   K   N   S   S   G   K   Y   D   L   R>

200         210         220         230         240
          *           *           *           *           *
    GCA ACA ATT GAT CAG GTT GAA CTT AAA GGA ACT TCC GAT AAA AAC AAT
    CGT TGT TAA CTA GTC CAA CTT GAA TTT CCT TGA AGG CTA TTT TTG TTA
     A   T   I   D   Q   V   E   L   K   G   T   S   D   K   N   N>

250         260         270         280
              *           *           *           *
    GGT TCT GGA ACC CTT GAA GGT TCA AAG CCT GAC AAG AGT AAA GTA AAA
    CCA AGA CCT TGG GAA CTT CCA AGT TTC GGA CTG TTC TCA TTT CAT TTT
     G   S   G   T   L   E   G   S   K   P   D   K   S   K   V   K>

290         300         310         320         330
     *           *           *           *           *
    TTA ACA GTT TCT GCT GAT TTA AAC ACA GTA ACC TTA GAA GCA TTT GAT
    AAT TGT CAA AGA CGA CTA AAT TTG TGT CAT TGG AAT CTT CGT AAA CTA
     L   T   V   S   A   D   L   N   T   V   T   L   E   A   F   D>

340         350         360         370         380
     *           *           *           *           *
    GCC AGC AAC CAA AAA ATT TCA AGT AAA GTT ACT AAA AAA CAG GGG TCA
    CGG TCG TTG GTT TTT TAA AGT TCA TTT CAA TGA TTT TTT GTC CCC AGT
     A   S   N   Q   K   I   S   S   K   V   T   K   K   Q   G   S>
```

Figure 34A

B-31 OSP B / B-31 P41 (122-295)

```
         390            400            410            420            430
          *              *              *              *              *
    ATA ACA GAG GAA ACT CTC AAA GCT AAT AAA TTA GAC TCA AAG AAA TTA
    TAT TGT CTC CTT TGA GAG TTT CGA TTA TTT AAT CTG AGT TTC TTT AAT
     I   T   E   E   T   L   K   A   N   K   L   D   S   K   K   L>

440            450            460            470            480
          *              *              *              *              *
    ACA AGA TCA AAC GGA ACT ACA CTT GAA TAC TCA CAA ATA ACA GAT GCT
    TGT TCT AGT TTG CCT TGA TGT GAA CTT ATG AGT GTT TAT TGT CTA CGA
     T   R   S   N   G   T   T   L   E   Y   S   Q   I   T   D   A>

490            500            510            520
          *              *              *              *              *
    GAC AAT GCT ACA AAA GCA GTA GAA ACT CTA AAA AAT AGC ATT AAG CTT
    CTG TTA CGA TGT TTT CGT CAT CTT TGA GAT TTT TTA TCG TAA TTC GAA
     D   N   A   T   K   A   V   E   T   L   K   N   S   I   K   L>

530            540            550            560            570
     *              *              *              *              *
    GAA GGA AGT CTT GTA GTC GGA AAA ACA ACA GTG GAA ATT AAA GAA GGT
    CTT CCT TCA GAA CAT CAG CCT TTT TGT TGT CAC CTT TAA TTT CTT CCA
     E   G   S   L   V   V   G   K   T   T   V   E   I   K   E   G>

580            590            600            610            620
          *              *              *              *              *
    ACT GTT ACT CTA AAA AGA GAA ATT GAA AAA GAT GGA AAA GTA AAA GTC
    TGA CAA TGA GAT TTT TCT CTT TAA CTT TTT CTA CCT TTT CAT TTT CAG
     T   V   T   L   K   R   E   I   E   K   D   G   K   V   K   V>

630            640            650            660            670
          *              *              *              *              *
    TTT TTG AAT GAC ACT GCA GGT TCT AAC AAA AAA ACA GGT AAA TGG GAA
    AAA AAC TTA CTG TGA CGT CCA AGA TTG TTT TTT TGT CCA TTT ACC CTT
     F   L   N   D   T   A   G   S   N   K   K   T   G   K   W   E>

680            690            700            710            720
          *              *              *              *              *
    GAC AGT ACT AGC ACT TTA ACA ATT AGT GCT GAC AGC AAA AAA ACT AAA
    CTG TCA TGA TCG TGA AAT TGT TAA TCA CGA CTG TCG TTT TTT TGA TTT
     D   S   T   S   T   L   T   I   S   A   D   S   K   K   T   K>

730            740            750            760
          *              *              *              *              *
    GAT TTG GTG TTC TTA ACA GAT GGT ACA ATT ACA GTA CAA CAA TAC AAC
    CTA AAC CAC AAG AAT TGT CTA CCA TGT TAA TGT CAT GTT GTT ATG TTG
     D   L   V   F   L   T   D   G   T   I   T   V   Q   Q   Y   N>
```

Figure 34B

B-31 OSP B / B-31 P41 (122-295)

```
         770         780         790         800         810
          *           *           *           *           *
    ACA GCT GGA ACC AGC CTA GAA GGA TCA GCA AGT GAA ATT AAA AAT CTT
    TGT CGA CCT TGG TCG GAT CTT CCT AGT CGT TCA CTT TAA TTT TTA GAA
     T   A   G   T   S   L   E   G   S   A   S   E   I   K   N   L>

820         830         840         850         860
          *           *           *           *           *
    TCA GAG CTT AAA AAC GCT TTA AAA GGT CAC CCC ATG GCT CAA TAT AAC
    AGT CTC GAA TTT TTG CGA AAT TTT CCA GTG GGG TAC CGA GTT ATA TTG
     S   E   L   K   N   A   L   K   G   H   P   M   A   Q   Y   N>

870         880         890         900         910
          *           *           *           *           *
    CAA ATG CAC ATG TTA TCA AAC AAA TCT GCT TCT CAA AAT GTA AGA ACA
    GTT TAC GTG TAC AAT AGT TTG TTT AGA CGA AGA GTT TTA CAT TCT TGT
     Q   M   H   M   L   S   N   K   S   A   S   Q   N   V   R   T>

920         930         940         950         960
          *           *           *           *           *
    GCT GAA GAG CTT GGA ATG CAG CCT GCA AAA ATT AAC ACA CCA GCA TCA
    CGA CTT CTC GAA CCT TAC GTC GGA CGT TTT TAA TTG TGT GGT CGT AGT
     A   E   E   L   G   M   Q   P   A   K   I   N   T   P   A   S>

970         980         990         1000
          *           *           *           *
    CTT TCA GGG CTT CAA GCG TCT TGG ACT TTA AGA GTT CAT GTT GGA GCA
    GAA AGT CCC GAA GTT CGC AGA ACC TGA AAT TCT CAA GTA CAA CCT CGT
     L   S   G   L   Q   A   S   W   T   L   R   V   H   V   G   A>

1010        1020        1030        1040        1050
     *           *           *           *           *
    ACC CAA GAT GAA GCT ATT GCT GTA AAT ATT TAT GCA GCT AAT GTT GCA
    TGG GTT CTA CTT CGA TAA CGA CAT TTA TAA ATA CGT CGA TTA CAA CGT
     T   Q   D   E   A   I   A   V   N   I   Y   A   A   N   V   A>

1060        1070        1080        1090        1100
          *           *           *           *           *
    AAT CTT TTC TCT GGT GAG GGA GCT CAA ACT GCT CAG GCT GCA CCG GTT
    TTA GAA AAG AGA CCA CTC CCT CGA GTT TGA CGA GTC CGA CGT GGC CAA
     N   L   F   S   G   E   G   A   Q   T   A   Q   A   A   P   V>

1110        1120        1130        1140        1150
          *           *           *           *           *
    CAA GAG GGT GTT CAA CAG GAA GGA GCT CAA CAG CCA GCA CCT GCT ACA
    GTT CTC CCA CAA GTT GTC CTT CCT CGA GTT GTC GGT CGT GGA CGA TGT
     Q   E   G   V   Q   Q   E   G   A   Q   Q   P   A   P   A   T>
```

Figure 34C

B-31 OSP B / B-31 P41 (122-295)

```
          1160        1170        1180        1190        1200
           *           *           *           *           *
GCA CCT TCT CAA GGC GGA GTT AAT TCT CCT GTT AAT GTT ACA ACT ACA
CGT GGA AGA GTT CCG CCT CAA TTA AGA GGA CAA TTA CAA TGT TGA TGT
 A   P   S   Q   G   G   V   N   S   P   V   N   V   T   T   T>

1210        1220        1230        1240
           *           *           *           *
GTT GAT GCT AAT ACA TCA CTT GCT AAA ATT GAA AAT GCT ATT AGA ATG
CAA CTA CGA TTA TGT AGT GAA CGA TTT TAA CTT TTA CGA TAA TCT TAC
 V   D   A   N   T   S   L   A   K   I   E   N   A   I   R   M>

1250       1260        1270        1280        1290
  *           *           *           *           *
ATA AGT GAT CAA AGG GCA AAT TTA GGT GCT TTC CAA AAT AGA CTT GAA
TAT TCA CTA GTT TCC CGT TTA AAT CCA CGA AAG GTT TTA TCT GAA CTT
 I   S   D   Q   R   A   N   L   G   A   F   Q   N   R   L   E>

1300        1310        1320        1330        1340
      *           *           *           *           *
TCT ATA AAG AAT AGT ACT GAG TAT GCA ATT GAA AAT CTA AAA GCA TCT
AGA TAT TTC TTA TCA TGA CTC ATA CGT TAA CTT TTA GAT TTT CGT AGA
 S   I   K   N   S   T   E   Y   A   I   E   N   L   K   A   S>

1350        1360
      *           *
TAT GCT CAA ATA GGT CAC C
ATA CGA GTT TAT CCA GTG G
 Y   A   Q   I   G   H   X>
```

Figure 34D

B-31 OSP B/ B-31 P41 (140-234)
Sequence Range: 1 to 1141

```
              10              20              30              40
         *    *          *    *          *    *          *    *
GCA CAA AAA GGT GCT GAG TCA ATT GGT TCT CAA AAA GAA AAT GAT CTA
CGT GTT TTT CCA CGA CTC AGT TAA CCA AGA GTT TTT CTT TTA CTA GAT
 A   Q   K   G   A   E   S   I   G   S   Q   K   E   N   D   L>

50              60              70              80              90
     *         *    *          *    *          *    *          *    *
AAC CTT GAA GAC TCT AGT AAA AAA TCA CAT CAA AAC GCT AAA CAA GAC
TTG GAA CTT CTG AGA TCA TTT TTT AGT GTA GTT TTG CGA TTT GTT CTG
 N   L   E   D   S   S   K   K   S   H   Q   N   A   K   Q   D>

100             110             120             130             140
    *    *          *    *          *    *          *    *          *
CTT CCT GCG GTG ACA GAA GAC TCA GTG TCT TTG TTT AAT GGT AAT AAA
GAA GGA CGC CAC TGT CTT CTG AGT CAC AGA AAC AAA TTA CCA TTA TTT
 L   P   A   V   T   E   D   S   V   S   L   F   N   G   N   K>

150             160             170             180             190
    *    *          *    *          *    *          *    *          *    *
ATT TTT GTA AGC AAA GAA AAA AAT AGC TCC GGC AAA TAT GAT TTA AGA
TAA AAA CAT TCG TTT CTT TTT TTA TCG AGG CCG TTT ATA CTA AAT TCT
 I   F   V   S   K   E   K   N   S   S   G   K   Y   D   L   R>

200             210             220             230           240
      *    *          *    *          *    *          *    *          *    *
GCA ACA ATT GAT CAG GTT GAA CTT AAA GGA ACT TCC GAT AAA AAC AAT
CGT TGT TAA CTA GTC CAA CTT GAA TTT CCT TGA AGG CTA TTT TTG TTA
 A   T   I   D   Q   V   E   L   K   G   T   S   D   K   N   N>

250             260             270             280
        *    *          *    *          *    *          *    *
GGT TCT GGA ACC CTT GAA GGT TCA AAG CCT GAC AAG AGT AAA GTA AAA
CCA AGA CCT TGG GAA CTT CCA AGT TTC GGA CTG TTC TCA TTT CAT TTT
 G   S   G   T   L   E   G   S   K   P   D   K   S   K   V   K>

290             300             310             320             330
  *        *    *          *    *          *    *          *    *          *
TTA ACA GTT TCT GCT GAT TTA AAC ACA GTA ACC TTA GAA GCA TTT GAT
AAT TGT CAA AGA CGA CTA AAT TTG TGT CAT TGG AAT CTT CGT AAA CTA
 L   T   V   S   A   D   L   N   T   V   T   L   E   A   F   D>

340             350             360             370             380
     *         *    *          *    *          *    *          *    *
GCC AGC AAC CAA AAA ATT TCA AGT AAA GTT ACT AAA AAA CAG GGG TCA
CGG TCG TTG GTT TTT TAA AGT TCA TTT CAA TGA TTT TTT GTC CCC AGT
 A   S   N   Q   K   I   S   S   K   V   T   K   K   Q   G   S>
```

Figure 35A

B-31 OSP B/ B-31 P41 (140-234)

```
            390           400           410           420           430
         *     *       *     *       *     *       *     *       *     *
       ATA ACA GAG GAA ACT CTC AAA GCT AAT AAA TTA GAC TCA AAG AAA TTA
       TAT TGT CTC CTT TGA GAG TTT CGA TTA TTT AAT CTG AGT TTC TTT AAT
        I   T   E   E   T   L   K   A   N   K   L   D   S   K   K   L>

440           450           460           470           480
         *     *       *     *       *     *       *     *       *     *
       ACA AGA TCA AAC GGA ACT ACA CTT GAA TAC TCA CAA ATA ACA GAT GCT
       TGT TCT AGT TTG CCT TGA TGT GAA CTT ATG AGT GTT TAT TGT CTA CGA
        T   R   S   N   G   T   T   L   E   Y   S   Q   I   T   D   A>

490           500           510           520
             *     *       *     *       *     *       *     *
       GAC AAT GCT ACA AAA GCA GTA GAA ACT CTA AAA AAT AGC ATT AAG CTT
       CTG TTA CGA TGT TTT CGT CAT CTT TGA GAT TTT TTA TCG TAA TTC GAA
        D   N   A   T   K   A   V   E   T   L   K   N   S   I   K   L>

530           540           550           560           570
         *     *       *     *       *     *       *     *       *     *
       GAA GGA AGT CTT GTA GTC GGA AAA ACA ACA GTG GAA ATT AAA GAA GGT
       CTT CCT TCA GAA CAT CAG CCT TTT TGT TGT CAC CTT TAA TTT CTT CCA
        E   G   S   L   V   V   G   K   T   T   V   E   I   K   E   G>

580           590           600           610           620
         *     *       *     *       *     *       *     *       *
       ACT GTT ACT CTA AAA AGA GAA ATT GAA AAA GAT GGA AAA GTA AAA GTC
       TGA CAA TGA GAT TTT TCT CTT TAA CTT TTT CTA CCT TTT CAT TTT CAG
        T   V   T   L   K   R   E   I   E   K   D   G   K   V   K   V>

630           640           650           660           670
         *     *       *     *       *     *       *     *       *     *
       TTT TTG AAT GAC ACT GCA GGT TCT AAC AAA AAA ACA GGT AAA TGG GAA
       AAA AAC TTA CTG TGA CGT CCA AGA TTG TTT TTT TGT CCA TTT ACC CTT
        F   L   N   D   T   A   G   S   N   K   K   T   G   K   W   E>

680           690           700           710           720
         *     *       *     *       *     *       *     *       *     *
       GAC AGT ACT AGC ACT TTA ACA ATT AGT GCT GAC AGC AAA AAA ACT AAA
       CTG TCA TGA TCG TGA AAT TGT TAA TCA CGA CTG TCG TTT TTT TGA TTT
        D   S   T   S   T   L   T   I   S   A   D   S   K   K   T   K>

730           740           750           760
            *     *       *     *       *     *       *     *
       GAT TTG GTG TTC TTA ACA GAT GGT ACA ATT ACA GTA CAA CAA TAC AAC
       CTA AAC CAC AAG AAT TGT CTA CCA TGT TAA TGT CAT GTT GTT ATG TTG
        D   L   V   F   L   T   D   G   T   I   T   V   Q   Q   Y   N>
```

Figure 35B

B-31 OSP B/ B-31 P41 (140-234)

```
        770         780         790         800         810
         *           *           *           *           *
ACA GCT GGA ACC AGC CTA GAA GGA TCA GCA AGT GAA ATT AAA AAT CTT
TGT CGA CCT TGG TCG GAT CTT CCT AGT CGT TCA CTT TAA TTT TTA GAA
 T   A   G   T   S   L   E   G   S   A   S   E   I   K   N   L>

820         830         840         850         860
         *           *           *           *           *
TCA GAG CTT AAA AAC GCT TTA AAA GGT CAC CCC ATG GCT TCT CAA AAT
AGT CTC GAA TTT TTG CGA AAT TTT CCA GTG GGG TAC CGA AGA GTT TTA
 S   E   L   K   N   A   L   K   G   H   P   M   A   S   Q   N>

870         880         890         900         910
         *           *           *           *           *
GTA AGA ACA GCT GAA GAG CTT GGA ATG CAG CCT GCA AAA ATT AAC ACA
CAT TCT TGT CGA CTT CTC GAA CCT TAC GTC GGA CGT TTT TAA TTG TGT
 V   R   T   A   E   E   L   G   M   Q   P   A   K   I   N   T>

920         930         940         950         960
         *           *           *           *           *
CCA GCA TCA CTT TCA GGG CTT CAA GCG TCT TGG ACT TTA AGA GTT CAT
GGT CGT AGT GAA AGT CCC GAA GTT CGC AGA ACC TGA AAT TCT CAA GTA
 P   A   S   L   S   G   L   Q   A   S   W   T   L   R   V   H>

970         980         990        1000
         *           *           *           *           *
GTT GGA GCA ACC CAA GAT GAA GCT ATT GCT GTA AAT ATT TAT GCA GCT
CAA CCT CGT TGG GTT CTA CTT CGA TAA CGA CAT TTA TAA ATA CGT CGA
 V   G   A   T   Q   D   E   A   I   A   V   N   I   Y   A   A>

1010        1020        1030        1040        1050.
  *           *           *           *           *
AAT GTT GCA AAT CTT TTC TCT GGT GAG GGA GCT CAA ACT GCT CAG GCT
TTA CAA CGT TTA GAA AAG AGA CCA CTC CCT CGA GTT TGA CGA GTC CGA
 N   V   A   N   L   F   S   G   E   G   A   Q   T   A   Q   A>

1060        1070        1080        1090        1100
         *           *           *           *           *
GCA CCG GTT CAA GAG GGT GTT CAA CAG GAA GGA GCT CAA CAG CCA GCA
CGT GGC CAA GTT CTC CCA CAA GTT GTC CTT CCT CGA GTT GTC GGT CGT
 A   P   V   Q   E   G   V   Q   Q   E   G   A   Q   Q   P   A>

1110        1120        1130        1140
         *           *           *           *
CCT GCT ACA GCA CCT TCT CAA GGC GGA GTT GGT CAC C
GGA CGA TGT CGT GGA AGA GTT CCG CCT CAA CCA GTG G
 P   A   T   A   P   S   Q   G   G   V   G   H   X>
```

Figure 35C

B-31 OSP B/ B-31 P41 (140 -295)

Sequence Range: 1 to 1324

```
          10          20          30          40
           *     *     *     *     *     *     *     *
GCA CAA AAA GGT GCT GAG TCA ATT GGT TCT CAA AAA GAA AAT GAT CTA
CGT GTT TTT CCA CGA CTC AGT TAA CCA AGA GTT TTT CTT TTA CTA GAT
 A   Q   K   G   A   E   S   I   G   S   Q   K   E   N   D   L>

50          60          70          80          90
   *     *     *     *     *     *     *     *     *     *
AAC CTT GAA GAC TCT AGT AAA AAA TCA CAT CAA AAC GCT AAA CAA GAC
TTG GAA CTT CTG AGA TCA TTT TTT AGT GTA GTT TTG CGA TTT GTT CTG
 N   L   E   D   S   S   K   K   S   H   Q   N   A   K   Q   D>

100         110         120         130         140
       *     *     *     *     *     *     *     *     *
CTT CCT GCG GTG ACA GAA GAC TCA GTG TCT TTG TTT AAT GGT AAT AAA
GAA GGA CGC CAC TGT CTT CTG AGT CAC AGA AAC AAA TTA CCA TTA TTT
 L   P   A   V   T   E   D   S   V   S   L   F   N   G   N   K>

150         160         170         180         190
           *     *     *     *     *     *     *     *     *     *
ATT TTT GTA AGC AAA GAA AAA AAT AGC TCC GGC AAA TAT GAT TTA AGA
TAA AAA CAT TCG TTT CTT TTT TTA TCG AGG CCG TTT ATA CTA AAT TCT
 I   F   V   S   K   E   K   N   S   S   G   K   Y   D   L   R>

200         210         220         230         240
       *     *     *     *     *     *     *     *     *     *
GCA ACA ATT GAT CAG GTT GAA CTT AAA GGA ACT TCC GAT AAA AAC AAT
CGT TGT TAA CTA GTC CAA CTT GAA TTT CCT TGA AGG CTA TTT TTG TTA
 A   T   I   D   Q   V   E   L   K   G   T   S   D   K   N   N>

250         260         270         280
           *     *     *     *     *     *     *     *     *
GGT TCT GGA ACC CTT GAA GGT TCA AAG CCT GAC AAG AGT AAA GTA AAA
CCA AGA CCT TGG GAA CTT CCA AGT TTC GGA CTG TTC TCA TTT CAT TTT
 G   S   G   T   L   E   G   S   K   P   D   K   S   K   V   K>

290         300         310         320         330
   *     *     *     *     *     *     *     *     *     *
TTA ACA GTT TCT GCT GAT TTA AAC ACA GTA ACC TTA GAA GCA TTT GAT
AAT TGT CAA AGA CGA CTA AAT TTG TGT CAT TGG AAT CTT CGT AAA CTA
 L   T   V   S   A   D   L   N   T   V   T   L   E   A   F   D>

340         350         360         370         380
   *     *     *     *     *     *     *     *     *     *
GCC AGC AAC CAA AAA ATT TCA AGT AAA GTT ACT AAA AAA CAG GGG TCA
CGG TCG TTG GTT TTT TAA AGT TCA TTT CAA TGA TTT TTT GTC CCC AGT
 A   S   N   Q   K   I   S   S   K   V   T   K   K   Q   G   S>
```

Figure 36A

B-31 OSP B/ B-31 P41 (140 -295)

```
          390            400            410            420            430
           *     *        *     *        *     *        *     *        *
     ATA ACA GAG GAA ACT CTC AAA GCT AAT AAA TTA GAC TCA AAG AAA TTA
     TAT TGT CTC CTT TGA GAG TTT CGA TTA TTT AAT CTG AGT TTC TTT AAT
      I   T   E   E   T   L   K   A   N   K   L   D   S   K   K   L>

440            450            460            470            480
               *     *        *     *        *     *        *     *        *
     ACA AGA TCA AAC GGA ACT ACA CTT GAA TAC TCA CAA ATA ACA GAT GCT
     TGT TCT AGT TTG CCT TGA TGT GAA CTT ATG AGT GTT TAT TGT CTA CGA
      T   R   S   N   G   T   T   L   E   Y   S   Q   I   T   D   A>

490            500            510            520
                   *     *        *     *        *     *        *     *
     GAC AAT GCT ACA AAA GCA GTA GAA ACT CTA AAA AAT AGC ATT AAG CTT
     CTG TTA CGA TGT TTT CGT CAT CTT TGA GAT TTT TTA TCG TAA TTC GAA
      D   N   A   T   K   A   V   E   T   L   K   N   S   I   K   L>

530            540            550            560            570
      *     *        *     *        *     *        *     *        *     *
     GAA GGA AGT CTT GTA GTC GGA AAA ACA ACA GTG GAA ATT AAA GAA GGT
     CTT CCT TCA GAA CAT CAG CCT TTT TGT TGT CAC CTT TAA TTT CTT CCA
      E   G   S   L   V   V   G   K   T   T   V   E   I   K   E   G>

580            590            600            610            620
          *     *        *     *        *     *        *     *        *
     ACT GTT ACT CTA AAA AGA GAA ATT GAA AAA GAT GGA AAA GTA AAA GTC
     TGA CAA TGA GAT TTT TCT CTT TAA CTT TTT CTA CCT TTT CAT TTT CAG
      T   V   T   L   K   R   E   I   E   K   D   G   K   V   K   V>

630            640            650            660            670
              *     *        *     *        *     *        *     *        *
     TTT TTG AAT GAC ACT GCA GGT TCT AAC AAA AAA ACA GGT AAA TGG GAA
     AAA AAC TTA CTG TGA CGT CCA AGA TTG TTT TTT TGT CCA TTT ACC CTT
      F   L   N   D   T   A   G   S   N   K   K   T   G   K   W   E>

680            690            700            710            720
                  *     *        *     *        *     *        *     *        *
     GAC AGT ACT AGC ACT TTA ACA ATT AGT GCT GAC AGC AAA AAA ACT AAA
     CTG TCA TGA TCG TGA AAT TGT TAA TCA CGA CTG TCG TTT TTT TGA TTT
      D   S   T   S   T   L   T   I   S   A   D   S   K   K   T   K>

730            740            750            760
                      *     *        *     *        *     *        *     *
     GAT TTG GTG TTC TTA ACA GAT GGT ACA ATT ACA GTA CAA CAA TAC AAC
     CTA AAC CAC AAG AAT TGT CTA CCA TGT TAA TGT CAT GTT GTT ATG TTG
      D   L   V   F   L   T   D   G   T   I   T   V   Q   Q   Y   N>
```

Figure 36B

B-31 OSP B/ B-31 P41 (140 -295)

```
      770         780         790         800         810
       *     *     *     *     *     *     *     *     *     *
    ACA GCT GGA ACC AGC CTA GAA GGA TCA GCA AGT GAA ATT AAA AAT CTT
    TGT CGA CCT TGG TCG GAT CTT CCT AGT CGT TCA CTT TAA TTT TTA GAA
     T   A   G   T   S   L   E   G   S   A   S   E   I   K   N   L>

820         830         840         850         860
       *     *     *     *     *     *     *     *     *     *
    TCA GAG CTT AAA AAC GCT TTA AAA GGT CAC CCC ATG GCT TCT CAA AAT
    AGT CTC GAA TTT TTG CGA AAT TTT CCA GTG GGG TAC CGA AGA GTT TTA
     S   E   L   K   N   A   L   K   G   H   P   M   A   S   Q   N>

870         880         890         900         910
       *     *     *     *     *     *     *     *     *     *
    GTA AGA ACA GCT GAA GAG CTT GGA ATG CAG CCT GCA AAA ATT AAC ACA
    CAT TCT TGT CGA CTT CTC GAA CCT TAC GTC GGA CGT TTT TAA TTG TGT
     V   R   T   A   E   E   L   G   M   Q   P   A   K   I   N   T>

920         930         940         950         960
       *     *     *     *     *     *     *     *     *     *
    CCA GCA TCA CTT TCA GGG CTT CAA GCG TCT TGG ACT TTA AGA GTT CAT
    GGT CGT AGT GAA AGT CCC GAA GTT CGC AGA ACC TGA AAT TCT CAA GTA
     P   A   S   L   S   G   L   Q   A   S   W   T   L   R   V   H>

970         980         990        1000
       *     *     *     *     *     *     *     *     *     *
    GTT GGA GCA ACC CAA GAT GAA GCT ATT GCT GTA AAT ATT TAT GCA GCT
    CAA CCT CGT TGG GTT CTA CTT CGA TAA CGA CAT TTA TAA ATA CGT CGA
     V   G   A   T   Q   D   E   A   I   A   V   N   I   Y   A   A>

1010         1020        1030        1040        1050
       *     *     *     *     *     *     *     *     *     *
    AAT GTT GCA AAT CTT TTC TCT GGT GAG GGA GCT CAA ACT GCT CAG GCT
    TTA CAA CGT TTA GAA AAG AGA CCA CTC CCT CGA GTT TGA CGA GTC CGA
     N   V   A   N   L   F   S   G   E   G   A   Q   T   A   Q   A>

1060         1070        1080        1090        1100
       *     *     *     *     *     *     *     *     *     *
    GCA CCG GTT CAA GAG GGT GTT CAA CAG GAA GGA GCT CAA CAG CCA GCA
    CGT GGC CAA GTT CTC CCA CAA GTT GTC CTT CCT CGA GTT GTC GGT CGT
     A   P   V   Q   E   G   V   Q   Q   E   G   A   Q   Q   P   A>

1110         1120        1130        1140        1150
       *     *     *     *     *     *     *     *     *     *
    CCT GCT ACA GCA CCT TCT CAA GGC GGA GTT AAT TCT CCT GTT AAT GTT
    GGA CGA TGT CGT GGA AGA GTT CCG CCT CAA TTA AGA GGA CAA TTA CAA
     P   A   T   A   P   S   Q   G   G   V   N   S   P   V   N   V>
```

Figure 36C

B-31 OSP B/ B-31 P41 (140 -295)

```
            1160        1170        1180        1190        1200
              *           *           *           *           *
      ACA ACT ACA GTT GAT GCT AAT ACA TCA CTT GCT AAA ATT GAA AAT GCT
      TGT TGA TGT CAA CTA CGA TTA TGT AGT GAA CGA TTT TAA CTT TTA CGA
       T   T   T   V   D   A   N   T   S   L   A   K   I   E   N   A>

1210        1220        1230        1240
                *           *           *           *           *
      ATT AGA ATG ATA AGT GAT CAA AGG GCA AAT TTA GGT GCT TTC CAA AAT
      TAA TCT TAC TAT TCA CTA GTT TCC CGT TTA AAT CCA CGA AAG GTT TTA
       I   R   M   I   S   D   Q   R   A   N   L   G   A   F   Q   N>

1250        1260        1270        1280        1290
        *           *           *           *           *           *
      AGA CTT GAA TCT ATA AAG AAT AGT ACT GAG TAT GCA ATT GAA AAT CTA
      TCT GAA CTT AGA TAT TTC TTA TCA TGA CTC ATA CGT TAA CTT TTA GAT
       R   L   E   S   I   K   N   S   T   E   Y   A   I   E   N   L>

1300        1310        1320
        *           *           *
      AAA GCA TCT TAT GCT CAA ATA GGT CAC C
      TTT CGT AGA ATA CGA GTT TAT CCA GTG G
       K   A   S   Y   A   Q   I   G   H   X>
```

Figure 36D

Osp b/ fla (122-234) osp c
Sequence Range: 1 to 1765

```
              10          20          30          40
           *     *     *     *     *     *     *     *     *
          GCA AAA AAA GGT GCT GAG TCA ATT GGT TCT CAA AAA GAA AAT GAT CTA
          CGT GTT TTT CCA CGA CTC AGT TAA CCA AGA GTT TTT CTT TTA CTA GAT
           A   Q   K   G   A   E   S   I   G   S   Q   K   E   N   D   L>

50          60          70          80          90
         *     *     *     *     *     *     *     *     *     *
        AAC CTT GAA GAC TCT AGT AAA AAA TCA CAT CAA AAC GCT AAA CAA GAC
        TTG GAA CTT CTG AGA TCA TTT TTT AGT GTA GTT TTG CGA TTT GTT CTG
         N   L   E   D   S   S   K   K   S   H   Q   N   A   K   Q   D>

100         110         120         130         140
         *     *     *     *     *     *     *     *     *     *
        CTT CCT GCG GTG ACA GAA GAC TCA GTG TCT TTG TTT AAT GGT AAT AAA
        GAA GGA CGC CAC TGT CTT CTG AGT CAC AGA AAC AAA TTA CCA TTA TTT
         L   P   A   V   T   E   D   S   V   S   L   F   N   G   N   K>

150         160         170         180         190
         *     *     *     *     *     *     *     *     *     *
        ATT TTT GTA AGC AAA GAA AAA AAT AGC TCC GGC AAA TAT GAT TTA AGA
        TAA AAA CAT TCG TTT CTT TTT TTA TCG AGG CCG TTT ATA CTA AAT TCT
         I   F   V   S   K   E   K   N   S   S   G   K   Y   D   L   R>

200         210         220         230         240
         *     *     *     *     *     *     *     *     *     *
        GCA ACA ATT GAT CAG GTT GAA CTT AAA GGA ACT TCC GAT AAA AAC AAT
        CGT TGT TAA CTA GTC CAA CTT GAA TTT CCT TGA AGG CTA TTT TTG TTA
         A   T   I   D   Q   V   E   L   K   G   T   S   D   K   N   N>

250         260         270         280
         *     *     *     *     *     *     *     *     *
        GGT TCT GGA ACC CTT GAA GGT TCA AAG CCT GAC AAG AGT AAA GTA AAA
        CCA AGA CCT TGG GAA CTT CCA AGT TTC GGA CTG TTC TCA TTT CAT TTT
         G   S   G   T   L   E   G   S   K   P   D   K   S   K   V   K>

290         300         310         320         330
         *     *     *     *     *     *     *     *     *     *
        TTA ACA GTT TCT GCT GAT TTA AAC ACA GTA ACC TTA GAA GCA TTT GAT
        AAT TGT CAA AGA CGA CTA AAT TTG TGT CAT TGG AAT CTT CGT AAA CTA
         L   T   V   S   A   D   L   N   T   V   T   L   E   A   F   D>

340         350         360         370         380
         *     *     *     *     *     *     *     *     *
        GCC AGC AAC CAA AAA ATT TCA AGT AAA GTT ACT AAA AAA CAG GGG TCA
        CGG TCG TTG GTT TTT TAA AGT TCA TTT CAA TGA TTT TTT GTC CCC AGT
         A   S   N   Q   K   I   S   S   K   V   T   K   K   Q   G   S>
```

Figure 37A

Osp b/ fla (122-234) osp c

```
        390         400         410         420         430
         *           *           *           *           *
ATA ACA GAG GAA ACT CTC AAA GCT AAT AAA TTA GAC TCA AAG AAA TTA
TAT TGT CTC CTT TGA GAG TTT CGA TTA TTT AAT CTG AGT TTC TTT AAT
 I   T   E   E   T   L   K   A   N   K   L   D   S   K   K   L>

440         450         460         470         480
         *           *           *           *           *
ACA AGA TCA AAC GGA ACT ACA CTT GAA TAC TCA CAA ATA ACA GAT GCT
TGT TCT AGT TTG CCT TGA TGT GAA CTT ATG AGT GTT TAT TGT CTA CGA
 T   R   S   N   G   T   T   L   E   Y   S   Q   I   T   D   A>

490         500         510         520
         *           *           *           *
GAC AAT GCT ACA AAA GCA GTA GAA ACT CTA AAA AAT AGC ATT AAG CTT
CTG TTA CGA TGT TTT CGT CAT CTT TGA GAT TTT TTA TCG TAA TTC GAA
 D   N   A   T   K   A   V   E   T   L   K   N   S   I   K   L>

530         540         550         560         570
 *           *           *           *           *
GAA GGA AGT CTT GTA GTC GGA AAA ACA ACA GTG GAA ATT AAA GAA GGT
CTT CCT TCA GAA CAT CAG CCT TTT TGT TGT CAC CTT TAA TTT CTT CCA
 E   G   S   L   V   V   G   K   T   T   V   E   I   K   E   G>

580         590         600         610         620
     *           *           *           *           *
ACT GTT ACT CTA AAA AGA GAA ATT GAA AAA GAT GGA AAA GTA AAA GTC
TGA CAA TGA GAT TTT TCT CTT TAA CTT TTT CTA CCT TTT CAT TTT CAG
 T   V   T   L   K   R   E   I   E   K   D   G   K   V   K   V>

630         640         650         660         670
         *           *           *           *           *
TTT TTG AAT GAC ACT GCA GGT TCT AAC AAA AAA ACA GGT AAA TGG GAA
AAA AAC TTA CTG TGA CGT CCA AGA TTG TTT TTT TGT CCA TTT ACC CTT
 F   L   N   D   T   A   G   S   N   K   K   T   G   K   W   E>

680         690         700         710         720
         *           *           *           *           *
GAC AGT ACT AGC ACT TTA ACA ATT AGT GCT GAC AGC AAA AAA ACT AAA
CTG TCA TGA TCG TGA AAT TGT TAA TCA CGA CTG TCG TTT TTT TGA TTT
 D   S   T   S   T   L   T   I   S   A   D   S   K   K   T   K>

730         740         750         760
             *           *           *           *
GAT TTG GTG TTC TTA ACA GAT GGT ACA ATT ACA GTA CAA CAA TAC AAC
CTA AAC CAC AAG AAT TGT CTA CCA TGT TAA TGT CAT GTT GTT ATG TTG
 D   L   V   F   L   T   D   G   T   I   T   V   Q   Q   Y   N>
```

Figure 37B

Osp b/ fla (122-234) osp c

```
         770         780         790         800         810
          *     *     *     *     *     *     *     *     *     *
         ACA GCT GGA ACC AGC CTA GAA GGA TCA GCA AGT GAA ATT AAA AAT CTT
         TGT CGA CCT TGG TCG GAT CTT CCT AGT CGT TCA CTT TAA TTT TTA GAA
          T   A   G   T   S   L   E   G   S   A   S   E   I   K   N   L>

820         830         840         850         860
          *     *     *     *     *     *     *     *     *     *
         TCA GAG CTT AAA AAC GCT TTA AAA GGT CAC CCC ATG GGA AAT AAT TCA
         AGT CTC GAA TTT TTG CGA AAT TTT CCA GTG GGG TAC CCT TTA TTA AGT
          S   E   L   K   N   A   L   K   G   H   P   M   G   N   N   S>

870         880         890         900         910
          *     *     *     *     *     *     *     *     *     *
         GGG AAA GAT GGG AAT ACA TCT GCA AAT TCT GCT GAT GAG TCT GTT AAA
         CCC TTT CTA CCC TTA TGT AGA CGT TTA AGA CGA CTA CTC AGA CAA TTT
          G   K   D   G   N   T   S   A   N   S   A   D   E   S   V   K>

920         930         940         950         960
          *     *     *     *     *     *     *     *     *     *
         GGG CCT AAT CTT ACA GAA ATA AGT AAA AAA ATT ACG GAT TCT AAT GCG
         CCC GGA TTA GAA TGT CTT TAT TCA TTT TTT TAA TGC CTA AGA TTA CGC
          G   P   N   L   T   E   I   S   K   K   I   T   D   S   N   A>

970         980         990         1000
          *     *     *     *     *     *     *     *     *
         GTT TTA CTT GCT GTG AAA GAG GTT GAA GCG TTG CTG TCA TCT ATA GAT
         CAA AAT GAA CGA CAC TTT CTC CAA CTT CGC AAC GAC AGT AGA TAT CTA
          V   L   L   A   V   K   E   V   E   A   L   S   S   I   D>

1010         1020         1030         1040         1050
     *     *     *     *     *     *     *     *     *     *
    GAA ATT GCT GCT AAA GCT ATT GGT AAA AAA ATA CAC CAA AAT AAT GGT
    CTT TAA CGA CGA TTT CGA TAA CCA TTT TTT TAT GTG GTT TTA TTA CCA
     E   I   A   A   K   A   I   G   K   K   I   H   Q   N   N   G>

1060         1070         1080         1090         1100
     *     *     *     *     *     *     *     *     *
    TTG GAT ACC GAA TAT AAT CAC AAT GGA TCA TTG TTA GCG GGA CGT TAT
    AAC CTA TGG CTT ATA TTA GTG TTA CCT AGT AAC AAT CGC CCT GCA ATA
     L   D   T   E   Y   N   H   N   G   S   L   L   A   G   R   Y>

1110         1120         1130         1140         1150
          *     *     *     *     *     *     *     *     *     *
         GCA ATA TCA ACC CTA ATA AAA CAA AAA TTA GAT GGA TTG AAA AAT GAA
         CGT TAT AGT TGG GAT TAT TTT GTT TTT AAT CTA CCT AAC TTT TTA CTT
          A   I   S   T   L   I   K   Q   K   L   D   G   L   K   N   E>
```

Figure 37C

Osp b/ fla (122-234) osp c

```
          1160           1170           1180           1190           1200
           *              *              *              *              *
     GGA TTA AAG GAA AAA ATT GAT GCG GCT AAG AAA TGT TCT GAA ACA TTT
     CCT AAT TTC CTT TTT TAA CTA CGC CGA TTC TTT ACA AGA CTT TGT AAA
      G   L   K   E   K   I   D   A   A   K   K   C   S   E   T   F>

1210           1220           1230           1240
                  *              *              *              *
     ACT AAT AAA TTA AAA GAA AAA CAC ACA GAT CTT GGT AAA GAA GGT GTT
     TGA TTA TTT AAT TTT CTT TTT GTG TGT CTA GAA CCA TTT CTT CCA CAA
      T   N   K   L   K   E   K   H   T   D   L   G   K   E   G   V>

1250           1260           1270           1280           1290
      *              *              *              *              *
     ACT GAT GCT GAT GCA AAA GAA GCC ATT TTA AAA ACA AAT GGT ACT AAA
     TGA CTA CGA CTA CGT TTT CTT CGG TAA AAT TTT TGT TTA CCA TGA TTT
      T   D   A   D   A   K   E   A   I   L   K   T   N   G   T   K>

1300           1310           1320           1330           1340
           *              *              *              *              *
     ACT AAA GGT GCT GAA GAA CTT GGA AAA TTA TTT GAA TCA GTA GAG GTC
     TGA TTT CCA CGA CTT CTT GAA CCT TTT AAT AAA CTT AGT CAT CTC CAG
      T   K   G   A   E   E   L   G   K   L   F   E   S   V   E   V>

1350           1360           1370           1380           1390
             *              *              *              *              *
     TTG TCA AAA GCA GCT AAA GAG ATG CTT GCT AAT TCA GTT AAA GAG CTT
     AAC AGT TTT CGT CGA TTT CTC TAC GAA CGA TTA AGT CAA TTT CTC GAA
      L   S   K   A   A   K   E   M   L   A   N   S   V   K   E   L>

1400           1410           1420           1430           1440
               *              *              *              *              *
     ACA AGC CCT GTT GTG GCA GAA AGT CCA AAA AAA CCT GGT ACC ATG GCT
     TGT TCG GGA CAA CAC CGT CTT TCA GGT TTT TTT GGA CCA TGG TAC CGA
      T   S   P   V   V   A   E   S   P   K   K   P   G   T   M   A>

1450           1460           1470           1480
                  *              *              *              *
     CAA TAT AAC CAA ATG CAC ATG TTA TCA AAC AAA TCT GCT TCT CAA AAT
     GTT ATA TTG GTT TAC GTG TAC AAT AGT TTG TTT AGA CGA AGA GTT TTA
      Q   Y   N   Q   M   H   M   L   S   N   K   S   A   S   Q   N>

1490           1500           1510           1520           1530
      *              *              *              *              *
     GTA AGA ACA GCT GAA GAG CTT GGA ATG CAG CCT GCA AAA ATT AAC ACA
     CAT TCT TGT CGA CTT CTC GAA CCT TAC GTC GGA CGT TTT TAA TTG TGT
      V   R   T   A   E   E   L   G   M   Q   P   A   K   I   N   T>
```

Figure 37D

Osp b/ fla (122-234) osp c

```
        1540          1550          1560          1570          1580
          *     *       *     *       *     *       *     *       *     *
        CCA GCA TCA CTT TCA GGG CTT CAA GCG TCT TGG ACT TTA AGA GTT CAT
        GGT CGT AGT GAA AGT CCC GAA GTT CGC AGA ACC TGA AAT TCT CAA GTA
         P   A   S   L   S   G   L   Q   A   S   W   T   L   R   V   H>

1590          1600          1610          1620          1630
          *     *       *     *       *     *       *     *       *     *
        GTT GGA GCA ACC CAA GAT GAA GCT ATT GCT GTA AAT ATT TAT GCA GCT
        CAA CCT CGT TGG GTT CTA CTT CGA TAA CGA CAT TTA TAA ATA CGT CGA
         V   G   A   T   Q   D   E   A   I   A   V   N   I   Y   A   A>

1640          1650          1660          1670          1680
          *     *       *     *       *     *       *     *       *     *
        AAT GTT GCA AAT CTT TTC TCT GGT GAG GGA GCT CAA ACT GCT CAG GCT
        TTA CAA CGT TTA GAA AAG AGA CCA CTC CCT CGA GTT TGA CGA GTC CGA
         N   V   A   N   L   F   S   G   E   G   A   Q   T   A   Q   A>

1690          1700          1710          1720
                *     *       *     *       *     *       *     *
        GCA CCG GTT CAA GAG GGT GTT CAA CAG GAA GGA GCT CAA CAG CCA GCA
        CGT GGC CAA GTT CTC CCA CAA GTT GTC CTT CCT CGA GTT GTC GGT CGT
         A   P   V   Q   E   G   V   Q   Q   E   G   A   Q   Q   P   A>

1730          1740          1750          1760
    *     *       *     *       *     *       *     *
  CCT GCT ACA GCA CCT TCT CAA GGC GGA GTT GGT CAC C
  GGA CGA TGT CGT GGA AGA GTT CCG CCT CAA CCA GTG G
   P   A   T   A   P   S   Q   G   G   V   G   H   X>
```

Figure 37E

```
Alignment List

Search Analysis for Sequence: OspC-B31        Matrix: DNA database matrix
Search from 1 to 633 where origin = 1         Score Region from 1 to 633
                                              Maximum possible score: 2532

Database: UserFolder: ospC DNA 10          20          30          40
                 *   *       *   *       *   *       *   *       *
OspC-B31    ATG AAA AAG AAT ACA TTA AGT GCG ATA TTA ATG ACT TTA TTT TTA TTT
            TAC TTT TTC TTA TGT AAT TCA CGC TAT AAT TAC TGA AAT AAA AAT AAA 1. OspC-PK            10          20          30          40
  [ 1832 ]    ... ... ... ... ... ... ... ... ... ... ... ... ... ... ...>

2. OspC-TR            10          20          30          40
  [ 1786 ]    ... ... ... ... ... ... ... ... ... ... ... ... ... ... ...>

3. OspC-K4            10          20          30          40
  [ 1774 ]    ... ... ... ... ... ... ... ... ... ... ... ... ... ... ...>

50          60          70          80          90
             *   *       *   *       *   *       *   *       *   *       *
OspC-B31    ATA TCT TGT AAT AAT TCA GGG AAA GAT GGG AAT ACA TCT GCA AAT TCT
            TAT AGA ACA TTA TTA AGT CCC TTT CTA CCC TTA TGT AGA CGT TTA AGA tgc
                                                         |
  1. OspC-PK50          60          70          80       |  90
  [ 1832 ]    ... ... ... .g. ... ... ... ... .g. ... g.. t.. ... a.t ... c..>

2. OspC-TR50          60          70          80          90
  [ 1786 ]    ... ... ... ... ... ... ..t ggg ... --- tc. g.. ... a.t ..- ..->

3. OspC-K450          60          70          80          90
  [ 1774 ]    ... ... ... ... ... ... ..t ggg ... --- .cc g.. ... a.t ..- ..->

100         110         120         130         140
             *   *       *   *       *   *       *   *       *   *       *
OspC-B31    GCT GAT GAG TCT GTT AAA GGG CCT AAT CTT ACA GAA ATA AGT AAA AAA
            CGA CTA CTC AGA CAA TTT CCC GGA TTA GAA TGT CTT TAT TCA TTT TTT

1. OspC-100           110         120         130         140
  [ 1832 ]    ... ..c ... ... .cg ... ... ... ... ... ... ... ... ..c ... ...>

2. OspC-TR            100         110         120         130
  [ 1786 ]    -.. ... ... ... .ca ... ..a ... ... ... ..c .t. ... ..c ... ...>

3. OspC-K4            100         110         120         130
  [ 1774 ]    -.. ... ... ... .ca ... ..a ... ... ... ... .t. ... ..c ... ...>
```

Figure 38A

```
                  150          160           170           180          190
               *    *        *     *       *      *       *    *       *    *
OspC-B31    ATT ACG GAT TCT AAT GCG GTT TTA CTT GCT GTG AAA GAG GTT GAA GCG
            TAA TGC CTA AGA TTA CGC CAA AAT GAA CGA CAC TTT CTC CAA CTT CGC

1. OspC-PK  150          160           170           180          190
[ 1832 ]    ... ..a ... ... ... ..a t.. g.. ... ... ..t ... ..a ... ..g a.t>

2. OspC-T   140          150           160           170          180
[ 1786 ]    ... ..a ... ... ... ..a t.. ... ..g ... ... ... ..a ... ..g ..t>

3. OspC-K   140          150           160           170          180
[ 1774 ]    ... ..a ... ... ... ..a t.. g.. ..g ... ... ... ..a ... ..g ..t>

200          210           220           230          240
               *    *        *     *       *      *       *    *       *    *
OspC-B31    TTG CTG TCA TCT ATA GAT GAA ATT GCT GCT AAA GCT ATT GGT AAA AAA
            AAC GAC AGT AGA TAT CTA CTT TAA CGA CGA TTT CGA TAA CCA TTT TTT

1. OspC-PK  200          210           220           230          240
[ 1832 ]    ... g.t .t. ... ... ... ... c.. ... aag ... ... ... ... c.. ...>

2. OspC-TR  190          200           210           220          230
[ 1786 ]    ... ..t ... ... ... ... ... c.. --. -.. ... ... ... ... ... ...>

3. OspC-K4  190          200           210           220          230
[ 1774 ]    ... a.c ... ... ... ... ... c.. ... aa. ... ... ... ... ... gt.>

250          260           270           280
               *    *        *     *       *      *       *    *       *
OspC-B31    ATA CAC CAA AAT AAT GGT TTG GAT ACC GAA TAT AAT CAC AAT GGA TCA
            TAT GTG GTT TTA TTA CCA AAC CTA TGG CTT ATA TTA GTG TTA CCT AGT

1. OspC-PK  250          260           270           280          290
[ 1832 ]    ... g.. a.t ... ... ... ..a .c. g.t tt. a.. ... ..g ... ... ..g> tac
                                        |
 2. OspC-TR           240              |250          260          270
[ 1786 ]    ... -.- -.. ... g.. ... ... ..a ... .a. ... gca ... .ga ..c .a. ...>

3. OspC-K4  240          250           260           270          280
[ 1774 ]    ... ..t ... ... ... ..a a.. g.t a.t gcg gg. ...a ..c ... ... ...>

290          300           310           320          330
               *    *        *     *       *      *       *    *       *    *
OspC-B31    TTG TTA GCG GGA CGT TAT GCA ATA TCA ACC CTA ATA AAA CAA AAA TTA
            AAC AAT CGC CCT GCA ATA CGT TAT AGT TGG GAT TAT TTT GTT TTT AAT

1. OspC-PK  300          310           320           330
[ 1832 ]    ... ... ..a ... gcc ... ... ... ... ... ... ... .c. g.. ... ..g>

2. OspC-   280          290           300           310          320
[ 1786 ]    ... a.. ..a ... gc. ... .a. ... ... .aa ... ... .c. ... ... ...>
```

Figure 38B

```
3. OspC-K4        290         300         310         320         330
[ 1774 ]    ... ... ..a ... gcc ... ... ... ... ... .c. g.. ... ...>

340         350         360         370         380
                 *           *           *           *           *
OspC-B31    GAT GGA TTG AAA AAT GAA GGA TTA AAG GAA AAA ATT GAT GCG GCT AAG
            CTA CCT AAC TTT TTA CTT CCT AAT TTC CTT TTT TAA CTA CGC CGA TTC ttt
                             |
1. OspC-340       350        | 360         370         380         390
[ 1832 ]    ag. aa. ... ... ..a ... .a. ... ... ac. g.. ... .ca aa. ... ...>

2. OspC-TR330        340         350         360         370
[ 1786 ]    ag. .t. ... ..t tca ... .a. ... ... a.. ... ... a.a .a. ... ...> ttc
                             |
3. OspC-K4        340        | 350         360         370         380
[ 1774 ]    ag. aa. ... ... ..a ... .ag ... ..t a.. ... ... ..a .a. ... ...>

390         400         410         420         430
                 *           *           *           *           *
OspC-B31    AAA TGT TCT GAA ACA TTT ACT AAT AAA TTA AAA GAA AAA CAC ACA GAT
            TTT ACA AGA CTT TGT AAA TGA TTA TTT AAT TTT CTT TTT GTG TGT CTA

1. OspC-PK        400         410         420         430
[ 1832 ]    ... ... ..c ... ga. ... ... ... ... c.. ... agt ggt ..t g.. ...>

2. OspC-TR    380         390         400         410         420
[ 1786 ]    g.t ... ..c ... .a. ... ... .c. ...g c.. ... ..t .gt ..t g.. ...g>

3. OspC-K4        390         400         410         420
[ 1774 ]    ..c ca. ... ... g.. ... ... ... .g. c.. ... .gt tct ..t g.. c.a>

440         450         460         470         480
                 *           *           *           *           *
OspC-B31    CTT GGT AAA GAA GGT GTT ACT GAT GCT GAT GCA AAA GAA GCC ATT TTA
            GAA CCA TTT CTT CCA CAA TGA CTA CGA CTA CGT TTT CTT CGG TAA AAT

1. OspC-P440       450         460         470         480
[ 1832 ]    ... ..c ... c.g .a. .c. ..c ... .a; c.. ... ... .c. ..t ... ...>

2. OspC-TR    430         440         450         460         470
[ 1786 ]    ... ... .t. c.. a.c ... cag ... .a. a.. ... ... a.. ..t ... ...>

3. OspC-430        440         450         460         470
[ 1774 ]    ... ..a gtt .ct .c. .c. ... ... .a. c.. ... ... ... ..t ... ...>

490         500         510         520
                 *           *           *           *
OspC-B31    AAA ACA AAT GGT ACT AAA ACT AAA GGT GCT GAA GAA CTT GGA AAA TTA
            TTT TGT TTA CCA TGA TTT TGA TTT CCA CGA CTT CTT GAA CCT TTT AAT
```

Figure 38C

```
  1. OspC-PK   490           500           510           520           530
[ 1832 ]      ... ... c.. .ca ... .cc ga. ... ... a.. ... t.. aa. g.t ...>

2. OspC-TR   480           490           500           510
[ 1786 ]      ... ... c.. ..a ... ... gac ..g ... ... a.. ... ... .a. g.g ...>

3. OspC-K4  480           490           500           510           520
[ 1774 ]      ..g t.. ... cc. ... ... ga. ..g ... ... a.. .c. ... aa. g.c ...>

530           540           550           560           570
               *     *     *     *     *     *     *     *     *     *
OspC-B31      TTT GAA TCA GTA GAG GTC TTG TCA AAA GCA GCT AAA GAG ATG CTT GCT
              AAA CTT AGT CAT CTC CAG AAC AGT TTT CGT CGA TTT CTC TAC GAA CGA

1. OspC-PK   540           550           560           570           580
[ 1832 ]      ... ... ... ..a .gt ... .t. ... ... ... c.. .ta gca ..a a..>

2. OspC-520               530           540           550           560
[ 1786 ]      ... a.. ... c.. ..a ag. ... ... ... ... ..g c.. .ca gca t.a a..>

3. OspC-K4  530           540           550           560           570
[ 1774 ]      .c. ... ... ..a ag. ... g.. ... ... ..g c.. ..a gca t.a ...>

580           590           600           610           620
               *     *     *     *     *     *     *     *     *     *
OspC-B31      AAT TCA GTT AAA GAG CTT ACA AGC CCT GTT GTG GCA GAA AGT CCA AAA
              TTA AGT CAA TTT CTC GAA TGT TCG GGA CAA CAC CGT CTT TCA GGT TTT

1. OspC-PK                590           600           610           620
[ 1832 ]      ... ... ... ... ..a ... ... ..t ... ... ..a ... ... ... ... ...>

2. OspC-TR570             580           590           600           610
[ 1786 ]      ... ... ... ... ... ... .at ... ... ... ... ... ... ... ...>

3. OspC-K4               580           590           600           610           620
[ 1774 ]      ... ... ... ... ..a ... .at ... ... ... ... ... ... ... ...>

630
               *       *
OspC-B31      AAA CCT TAA
              TTT GGA ATT

1. OspC-PK
[ 1832 ]      ... ... ...>

2. OspC-TR   620
[ 1786 ]      ... ... ...>

3. OspC-K4              630
[ 1774 ]      ... ... ...>
```

Figure 38D

Alignment List

Search Analysis for Sequence: BO ospD    Matrix: DNA database matrix
Search from 1 to 704 where origin = 1    Score Region from 1 to 704
Date: October 22, 1993                   Maximum possible score: 2816
Time: 16:00:00

Database: UserFolder: osp-D DNA

```
                   10          20          30          40
                *           *           *           *           *
BO ospD      CTA CTG TTA AGT TTA TTT TTA TTG CTC TCA ATA TCT TGT TCT TTA GAT
             GAT GAC AAT TCA AAT AAA AAT AAC GAG AGT TAT AGA ACA AGA AAT CTA 1. P-Gau o      10          20          30          40
[ 2804 ]     ... ... ... ... ... ... ... ... ... ... ... ... .a. ... ... ...>

2. DK29 os      10          20          30          40
[ 2786 ]     ... ... c.. ... ... ... ... ... ... ... ... ... g.. ... ... ...>

3. K48 osp      10          20          30          40
[ 2786 ]     ... ... ... ... ... ... ... ... ... ... ... ... ... ... ... ...>

50          60          70          80          90
                *           *           *           *           *           *
BO ospD      AAT GAA GGT GTA AAC TCA AAA GAT TAC GAG TCA AAA AAA CAG AGT ATA
             TTA CTT CCA CAT TTG AGT TTT CTA ATG CTC AGT TTT TTT GTC TCA TAT 1. P-Gau o50          60          70          80          90
[ 2804 ]     ... ... ... ... ... ... ... ... ... ... ... ... ... ... ... ...>

2. DK29 os50          60          70          80          90
[ 2786 ]     ... ... ... ... ... ... ... ... ... ... ... ... ... ... ... ...>

3. K48 osp50          60          70          80          90
[ 2786 ]     ... ... ... ... .g. ... ... ... ... ... ... ... ... ... ... ...>

100         110         120         130         140
                *           *           *           *           *
BO ospD      CTA GGT GAA TTA AAT CAG CTA TTG GGG CAA ACT ACA AAT TCA CTA AAA
             GAT CCA CTT AAT TTA GTC GAT AAC CCC GTT TGA TGT TTA AGT GAT TTT 1. P-Gau o 100         110         120         130         140
[ 2804 ]     ... ... ... ... ... ... ... ... ... ... ... ... ... ... ... ...>

2. DK29 os 100         110         120         130         140
[ 2786 ]     ... ... ... ... ... ... ... ... ... ... ... ... ... ... ... ...>

3. K48 osp 100         110         120         130         140
[ 2786 ]     ... ... ... ... ... ... ... ... ... ... ... ... ... ... ... ...>

```
              *         *         *         *         *         *         *         *         *         *
BO ospD    GAA GCA AAA AAT ACA ACA GAT AAT TTA AAT GCA TCA AAT GAG GCA AAT
           CTT CGT TTT TTA TGT TGT CTA TTA AAT TTA CGT AGT TTA CTC CGT TTA 1. P-Gau o     150       160       170       180       190
 [ 2804 ]       ... ... ... ... ... ... ... ... ... ... ... ... ... ... ...>

2. DK29 os     150       160       170       180       190
 [ 2786 ]       ... ... ... ... ... ... ... ... ... ... ... ... ... ... ...>

3. K48 osp     150       160       170       180       190
 [ 2786 ]       ... ... ... ... ... ... ... ... ... ... ... ... ... ... ...>

200       210       220       230       240
           *    *    *    *    *    *    *    *    *    *
BO ospD    AAA GTT GTA GAA GCA GTT ATA AGT GTG GTT AAT TTA ATT TCA TCT GCT
           TTT CAA CAT CTT CGT CAA TAT TCA CAC CAA TTA AAT TAA AGT AGA CGA 1. P-Gau o     200       210       220       230       240
 [ 2804 ]       ... ... ... ... ... ... ... ... ... ... ... ... ... ... ...>

2. DK29 os     200       210       220       230       240
 [ 2786 ]       ... ... ... ... ... ... ... ... ... ... ... ... ... ... ...>

3. K48 osp     200       210       220       230       240
 [ 2786 ]       ... ... ... ... ... ... ... ... ... ... ... ... ... ... ...>

250       260       270       280
           *    *    *    *    *    *    *    *    *
BO ospD    GCA GAT CAG GTA AAA GGT CAA CAA CAA ATA TGC ACG ATT TAG CTC AAA
           CGT CTA GTC CAT TTT CCA GTT GTT GTT TAT ACG TGC TAA ATC GAG TTT 1. P-Gau o     250       260       270       280
 [ 2804 ]       ... ... ... ... ... ... ... ... ... ... ... ... ... ... ...>

2. DK29 os     250       260       270       280
 [ 2786 ]       ... ... ... ..g ... ... ... ... ... ... ... ... ... ... ...>

3. K48 osp     250       260       270       280
 [ 2786 ]       ... ... ... ..g ... ... ... ... ... ... ... ... ... ... ...>

290       300       310       320       330
           *    *    *    *    *    *    *    *    *    *
BO ospD    TGG CAG AAA TAG ATT TAG AAA AAA TAA AGG AAT CTA GTG ATA AAG TAA
           ACC GTC TTT ATC TAA ATC TTT TTT ATT TCC TTA GAT CAC TAT TTC ATT 1. P-Gau 290       300       310       320       330
 [ 2804 ]       ... ... ... ... ... ... ... ... ... ... ... ... ... ... ...>

```
                340         350         360         370         380
                 *    *      *    *      *    *      *    *      *
BO ospD       TAG TTG CGG CTA ATG TTG CGA AAG AAG CAT ATA ACC TTA CTA AAG CAG
              ATC AAC GCC GAT TAC AAC GCT TTC TTC GTA TAT TGG AAT GAT TTC GTC 1. P-Gau o  340         350         360         370         380
  [ 2804 ]    ... ... ... ... ... ... ... ... ... ... ... ... ... ... ... ...>

2. DK29 os  340         350         360         370         380
  [ 2786 ]    ... ... ... ... ... ... ... ... ... ... ... ... ... ... ... ...>

3. K48 osp  340         350         360         370         380
  [ 2786 ]    ... ... ... ... ... ... ... ... ... ... ... ... ... ... ... ...>

390         400         410         420         430
                 *    *      *    *      *    *      *    *      *    *
BO ospD       TAG AAC AAA ATA TGC AAA AAC TGT ACA AAG AGC AAG AAG AGC AAC TAA
              ATC TTG TTT TAT ACG TTT TTG ACA TGT TTC TCG TTC TTC TCG TTG ATT 1. P-Gau o  390         400         410         420         430
  [ 2804 ]    ... ... ... ... ... ... ... ... ... ... ... ... ... ... ... ...>

2. DK29 os  390         400         410         420         430
  [ 2786 ]    ... ... ... ... ... ... ... ... ... ... ... ... ... ... ... ...>

3. K48 osp  390         400         410         420         430
  [ 2786 ]    ... ... ... ... ... ... ... ... ... ... ... ... ... ... ... ...>

440         450         460         470         480
                 *    *      *    *      *    *      *    *      *    *
BO ospD       AAC ACT ATC TGA TTC TGA TGA AAC AGA ACG AGT TTC TGA TGA AAT AAA
              TTG TGA TAG ACT AAG ACT ACT TTG TCT TGC TCA AAG ACT ACT TTA TTT 1. P-Gau o  440         450         460         470         480
  [ 2804 ]    ... ... ... ... ... ... ... ... ... ... ... ... ... ... ... ...>

2. DK29 os  440         450         460         470         480
  [ 2786 ]    ... ... ... ... ... ... ... .g. ... ... ... ... ... ... ... ...>

3. K48 osp  440         450         460         470         480
  [ 2786 ]    ... ... ... ... ... ... ... .g. ... ... ... ... ... ... ... ...>

490         500         510         520
                             *    *      *    *      *    *      *    *
BO ospD                   ACA AGC TAA AGA GGC TGT AGA AAT AGC TTG GAA AGC CAC AGT AAA AGT
                          TGT TCG ATT TCT CCG ACA TCT TTA TCG AAC CTT TCG GTG TCA TTT TCA 1. P-Gau o              490         500         510         520
  [ 2804 ]                ... ... ... ... ... ... ... ... ... ... ... ... ... ... ... ...>

2. DK29 os              490         500         510         520
  [ 2786 ]                ... ... ... ... ... ... ... ... ... ... ... ... ... ... ... ...>

3. K48 osp              490         500         510         520
```

530         540         550         560         570
                 *     *     *     *     *     *     *     *     *     *
BO ospD     AAA AGA TGA GTT AAT TGA TGT AGA AAA TGC AGT CAA AGA GGC ATT GGA
            TTT TCT ACT CAA TTA ACT ACA TCT TTT ACG TCA GTT TCT CCG TAA CCT 1. P-Gau  530         540         550         560         570
[ 2804 ]    ... ... ... ... ... ... ... ... ... ... ... ... ... ... ... ...>

2. DK29 o 530         540         550         560         570
[ 2786 ]    ... ... ... ... ... ... ... ... ... ... ... ... ... ... ... ...>

3. K48 os 530         540         550         560         570
[ 2786 ]    ... ... ... ... ... ... ... ... ... ... ... ... ... ... ... ...>

580         590         600         610         620
                 *     *     *     *     *     *     *     *     *     *
BO ospD     TAA AAT AAA GAC AGA AAC CGC GAA CAA TAC AAA ACT TAC AGA TAT AGA
            ATT TTA TTT CTG TCT TTG GCG CTT GTT ATG TTT TGA ATG TCT ATA TCT 1. P-Gau o 580        590         600         610         620
[ 2804 ]    ... ... ... ... ... ... ... ... ... ... ... ... ... ... ... ...>

2. DK29 os 580        590         600         610         620
[ 2786 ]    ... ... ... ... ... ... ... ... ... ... ... ... ... ... ... ...>

3. K48 osp 580        590         600         610         620
[ 2786 ]    ... ... ... ... ..g ... ... ... ... ... ... ... ... ... ... ...>

630         640         650         660         670
                 *     *     *     *     *     *     *     *     *     *
BO ospD     AGA AGT AGC AGA GTT AGT ATT ACA GAT AGC CAA AAA TGT AGC GGA AAT
            TCT TCA TCG TCT CAA TCA TAA TGT CTA TCG GTT TTT ACA TCG CCT TTA 1. P-Gau o 630        640         650         660         670
[ 2804 ]    ... ... ... ... ... ... ... ... a.. ... ... ... ... ... ... ...>

2. DK29 os 630        640         650         660         670
[ 2786 ]    ... ... ... ... ... ... ... ... a.. ... ... ... ... ... ... ...>

3. K48 osp 630        640         650         660         670
[ 2786 ]    ... ... ... ... ... ... ... ... a.. ... ... ... ... ... ... ...>

680         690         700
                  *     *     *     *     *     *
BO ospD     AGC GCA AGA AGT TGT GGC CTT GTT AAA TAC TT
            TCG CGT TCT TCA ACA CCG GAA CAA TTT ATG AA 1. P-Gau o  680         690         700
[ 2804 ]     ... ... ... ... ... ... ... ... ... ... ..>

2. DK29 os  680         690         700
[ 2786 ]     ... ... ... ... ... ... ... ... ... ... ..>

3. K48 osp         680         690         700
[ 2786 ]     ... ... ... ... ... ... ... ... ... ... ..>
```

Figure 39D p41
Sequence Range: 1 to 1011

```
              10             20             30             40
               *              *              *              *
       *      *     *      *     *      *     *      *     *      *
ATG ATT ATC AAT CAT AAT ACA TCA GCT ATT AAT GCT TCA AGA AAT AAT
TAC TAA TAG TTA GTA TTA TGT AGT CGA TAA TTA CGA AGT TCT TTA TTA
Met Ile Ile Asn His Asn Thr Ser Ala Ile Asn Ala Ser Arg Asn Asn>

50             60             70             80             90
   *              *              *              *              *
   *      *     *      *     *      *     *      *     *      *
GGC ATT AAC GCT GCT AAT CTT AGT AAA ACT CAA GAA AAG CTT TCT AGT
CCG TAA TTG CGA CGA TTA GAA TCA TTT TGA GTT CTT TTC GAA AGA TCA
Gly Ile Asn Ala Ala Asn Leu Ser Lys Thr Gln Glu Lys Leu Ser Ser>

100            110            120            130            140
        *              *              *              *              *
   *      *     *      *     *      *     *      *     *      *
GGC TAC AGA ATT AAT CGA GCT TCT GAT GAT GCT GCT GGC ATG GGA GTT
CCG ATG TCT TAA TTA GCT CGA AGA CTA CTA CGA CGA CCG TAC CCT CAA
Gly Tyr Arg Ile Asn Arg Ala Ser Asp Asp Ala Ala Gly Met Gly Val>

150            160            170            180            190
        *              *              *              *              *
   *      *     *      *     *      *     *      *     *      *
TCT GGT AAG ATT AAT GCT CAA ATA AGA GGT TTG TCA CAA GCT TCT AGA
AGA CCA TTC TAA TTA CGA GTT TAT TCT CCA AAC AGT GTT CGA AGA TCT
Ser Gly Lys Ile Asn Ala Gln Ile Arg Gly Leu Ser Gln Ala Ser Arg>

200            210            220            230            240
        *              *              *              *              *
   *      *     *      *     *      *     *      *     *      *
AAT ACT TCA AAG GCT ATT AAT TTT ATT CAG ACA ACA GAA GGG AAT TTA
TTA TGA AGT TTC CGA TAA TTA AAA TAA GTC TGT TGT CTT CCC TTA AAT
Asn Thr Ser Lys Ala Ile Asn Phe Ile Gln Thr Thr Glu Gly Asn Leu>

250            260            270            280
        *              *              *              *
   *      *     *      *     *      *     *      *     *      *
AAT GAA GTA GAA AAA GTC TTA GTA AGA ATG AAG GAA TTG GCA GTT CAA
TTA CTT CAT CTT TTT CAG AAT CAT TCT TAC TTC CTT AAC CGT CAA GTT
Asn Glu Val Glu Lys Val Leu Val Arg Met Lys Glu Leu Ala Val Gln>

290            300            310            320            330
   *              *              *              *              *
   *      *     *      *     *      *     *      *     *      *
TCA GGT AAC GGC ACA TAT TCA GAT GCA GAC AGA GGT TCT ATA CAA ATT
AGT CCA TTG CCG TGT ATA AGT CTA CGT CTG TCT CCA AGA TAT GTT TAA
Ser Gly Asn Gly Thr Tyr Ser Asp Ala Asp Arg Gly Ser Ile Gln Ile>

340            350            360            370            380
        *              *              *              *              *
   *      *     *      *     *      *     *      *     *      *
GAA ATA GAG CAA CTT ACA GAC GAA ATT AAT AGA ATT GCT GAT CAA GCT
CTT TAT CTC GTT GAA TGT CTG CTT TAA TTA TCT TAA CGA CTA GTT CGA
Glu Ile Glu Gln Leu Thr Asp Glu Ile Asn Arg Ile Ala Asp Gln Ala>
```

Figure 40A

```
          390           400           410           420           430
 .    *     .    *     .    *     .    *     .    *     .
CAA TAT AAC CAA ATG CAC ATG TTA TCA AAC AAA TCT GCT TCT CAA AAT
GTT ATA TTG GTT TAC GTG TAC AAT AGT TTG TTT AGA CGA AGA GTT TTA
Gln Tyr Asn Gln Met His Met Leu Ser Asn Lys Ser Ala Ser Gln Asn>

440           450           460           470           480
 .    *     .    *     .    *     .    *     .    *     .
GTA AGA ACA GCT GAA GAG CTT GGA ATG CAG CCT GCA AAA ATT AAC ACA
CAT TCT TGT CGA CTT CTC GAA CCT TAC GTC GGA CGT TTT TAA TTG TGT
Val Arg Thr Ala Glu Glu Leu Gly Met Gln Pro Ala Lys Ile Asn Thr>

490           500           510           520
 .    *     .    *     .    *     .    *     .    *     .
CCA GCA TCA CTT TCA GGG CTT CAA GCG TCT TGG ACT TTA AGA GTT CAT
GGT CGT AGT GAA AGT CCC GAA GTT CGC AGA ACC TGA AAT TCT CAA GTA
Pro Ala Ser Leu Ser Gly Leu Gln Ala Ser Trp Thr Leu Arg Val His>

530           540           550           560           570
 .    *     .    *     .    *     .    *     .    *     .
GTT GGA GCA ACC CAA GAT GAA GCT ATT GCT GTA AAT ATT TAT GCA GCT
CAA CCT CGT TGG GTT CTA CTT CGA TAA CGA CAT TTA TAA ATA CGT CGA
Val Gly Ala Thr Gln Asp Glu Ala Ile Ala Val Asn Ile Tyr Ala Ala>

580           590           600           610           620
 .    *     .    *     .    *     .    *     .    *     .
AAT GTT GCA AAT CTT TTC TCT GGT GAG GGA GCT CAA ACT GCT CAG GCT
TTA CAA CGT TTA GAA AAG AGA CCA CTC CCT CGA GTT TGA CGA GTC CGA
Asn Val Ala Asn Leu Phe Ser Gly Glu Gly Ala Gln Thr Ala Gln Ala>

630           640           650           660           670
 .    *     .    *     .    *     .    *     .    *     .
GCA CCG GTT CAA GAG GGT GTT CAA CAG GAA GGA GCT CAA CAG CCA GCA
CGT GGC CAA GTT CTC CCA CAA GTT GTC CTT CCT CGA GTT GTC GGT CGT
Ala Pro Val Gln Glu Gly Val Gln Gln Glu Gly Ala Gln Gln Pro Ala>

680           690           700           710           720
 .    *     .    *     .    *     .    *     .    *     .
CCT GCT ACA GCA CCT TCT CAA GGC GGA GTT AAT TCT CCT GTT AAT GTT
GGA CGA TGT CGT GGA AGA GTT CCG CCT CAA TTA AGA GGA CAA TTA CAA
Pro Ala Thr Ala Pro Ser Gln Gly Gly Val Asn Ser Pro Val Asn Val>

730           740           750           760
 .    *     .    *     .    *     .    *     .    *     .
ACA ACT ACA GTT GAT GCT AAT ACA TCA CTT GCT AAA ATT GAA AAT GCT
TGT TGA TGT CAA CTA CGA TTA TGT AGT GAA CGA TTT TAA CTT TTA CGA
Thr Thr Thr Val Asp Ala Asn Thr Ser Leu Ala Lys Ile Glu Asn Ala>

770           780           790           800           810
 .    *     .    *     .    *     .    *     .    *     .
ATT AGA ATG ATA AGT GAT CAA AGG GCA AAT TTA GGT GCT TTC CAA AAT
TAA TCT TAC TAT TCA CTA GTT TCC CGT TTA AAT CCA CGA AAG GTT TTA
Ile Arg Met Ile Ser Asp Gln Arg Ala Asn Leu Gly Ala Phe Gln Asn>
```

Figure 40B

```
          820           830           840           850           860
           *    *    *    *    *    *    *    *    *    *
          AGA  CTT  GAA  TCT  ATA  AAG  AAT  AGT  ACT  GAG  TAT  GCA  ATT  GAA  AAT  CTA
          TCT  GAA  CTT  AGA  TAT  TTC  TTA  TCA  TGA  CTC  ATA  CGT  TAA  CTT  TTA  GAT
          Arg  Leu  Glu  Ser  Ile  Lys  Asn  Ser  Thr  Glu  Tyr  Ala  Ile  Glu  Asn  Leu>

870           880           890           900           910
           *    *    *    *    *    *    *    *    *    *
          AAA  GCA  TCT  TAT  GCT  CAA  ATA  AAA  GAT  GCT  ACA  ATG  ACA  GAT  GAG  GTT
          TTT  CGT  AGA  ATA  CGA  GTT  TAT  TTT  CTA  CGA  TGT  TAC  TGT  CTA  CTC  CAA
          Lys  Ala  Ser  Tyr  Ala  Gln  Ile  Lys  Asp  Ala  Thr  Met  Thr  Asp  Glu  Val>

920           930           940           950           960
           *    *    *    *    *    *    *    *    *    *
          GTA  GCA  GCA  ACA  ACT  AAT  ATG  ATT  TTA  ACA  CAA  TCT  GCA  ATG  GCA  ATG
          CAT  CGT  CGT  TGT  TGA  TTA  TAC  TAA  AAT  TGT  GTT  AGA  CGT  TAC  CGT  TAC
          Val  Ala  Ala  Thr  Thr  Asn  Met  Ile  Leu  Thr  Gln  Ser  Ala  Met  Ala  Met>

970           980           990           1000
             *    *    *    *    *    *    *    *    *
            ATT  GCG  CAG  GCT  AAT  CAA  GTT  CCC  CAA  TAT  GTT  TTG  TCA  TTG  CTT  AGA
            TAA  CGC  GTC  CGA  TTA  GTT  CAA  GGG  GTT  ATA  CAA  AAC  AGT  AAC  GAA  TCT
            Ile  Ala  Gln  Ala  Asn  Gln  Val  Pro  Gln  Tyr  Val  Leu  Ser  Leu  Leu  Arg>

1010
           *
          TAA
          ATT
          ***>
```

Figure 40C

Alignment List

Search Analysis for Sequence: B31-41kD  Matrix: DNA database matrix
Search from 1 to 1011 where origin = 1  Score Region from 1 to 1011
Date: October 22,1993  Maximum possible score: 4044
Time: 15:03:24

Database: UserFolder: 41 kD Flagellin clones

```
              10          20          30          40
              *           *           *           *     *
B31-41kD  ATG ATT ATC AAT CAT AAT ACA TCA GCT ATT AAT GCT TCA AGA AAT AAT
          TAC TAA TAG TTA GTA TTA TGT AGT CGA TAA TTA CGA AGT TCT TTA TTA

1. KA-41kD       10          20          30          40
[ 3996 ]     ... ... ... ... ... ... ... ... ... ... ... ... ... ... ...>

2. P-Gau-4       10          20          30          40
[ 3696 ]     ... ... ... ... ... ... ... ... ... ... ... ... ... ... ...>

3. BO-41kD       10          20          30          40
[ 3684 ]     ... ... ... ... ... ... ... ... ... ... ... ... ... ... ...>

4. DK29-41       10          20          30          40
[ 3672 ]     ... ... ... ... ... ... ... ... ... ... ... ... ... ... ...>

5. PKO-41k       10          20          30          40
[ 3672 ]     ... ... ... ... ... ... ... ... ... ... ... ... ... ... ...>

50          60          70          80          90
              *     *     *     *     *     *     *     *     *     *
B31-41kD  GGC ATT AAC GCT GCT AAT CTT AGT AAA ACT CAA GAA AAG CTT TCT AGT
          CCG TAA TTG CGA CGA TTA GAA TCA TTT TGA GTT CTT TTC GAA AGA TCA

1. KA-41kD50      60          70          80          90
[ 3996 ]     ... ... ... ... ... ... ... ... ... ... ... ... ... ... ...>

2. P-Gau-450     60          70          80          90
[ 3696 ]     .c. ... ..t ... ... ... ... ... ..c ... ..g ... ... ... ...>

3. BO-41kD50     60          70          80          90
[ 3684 ]     .c. ... ..t ... ... ... ... ... ..c ... ..g ... ... ... ...>

4. DK29-4150     60          70          80          90
[ 3672 ]     ..t ... ..t ... ... ... ... ... ... ... ..g ... ... ... ...>

5. PKO-41k50     60          70          80          90
[ 3672 ]     .c. ... ..t ... ... ... ... ... ..c ... ..g ... .c. ... ...>

100         110         120         130         140
              *     *     *     *     *     *     *     *     *
B31-41kD  GGC TAC AGA ATT AAT CGA GCT TCT GAT GAT GCT GCT GGC ATG GGA GTT
          CCG ATG TCT TAA TTA GCT CGA AGA CTA CTA CGA CGA CCG TAC CCT CAA
```

2. P-Gau-4                 100           110           120           130           140
   [ 3696 ]      ..t ... ... ... ... ... ... ... ... ... ... ..t ... ..g ...>

3. BO-41kD                 100           110           120           130           140
   [ 3684 ]      ..t ... ... ... ... ... ... ... ... ... ... ..t ... ..g ...>

4. DK29-41                 100           110           120           130           140
   [ 3672 ]      ..t ... ... ... ... a.. ... ... ... ... ... ..t ... ..g ...>

5. PKO-41k                 100           110           120           130           140
   [ 3672 ]      ..t ... ... ... ... ... ... ... ... ... ... ..t ... ..g ...>

150           160           170           180           190
                        *             *             *             *             *
   B31-41kD    TCT GGT AAG ATT AAT GCT CAA ATA AGA GGT TTG TCA CAA GCT TCT AGA
               AGA CCA TTC TAA TTA CGA GTT TAT TCT CCA AAC AGT GTT CGA AGA TCT

1. KA-41kD               150           160           170           180           190
   [ 3996 ]      ... ... ... ... ... ... ... ... ... ... ... ... ... ... ... ...>

2. P-Gau-4               150           160           170           180           190
   [ 3696 ]      ... ..c ... ... ... ... ... ... ... .c. ..c ..a ... ... ... ...>

3. BO-41kD               150           160           170           180           190
   [ 3684 ]      ... ..c ... ... ... ... ... ... ... ... ..c ..a ... ... ... ...>

4. DK29-41                150           160           170           180           190
   [ 3672 ]      ... ..g ... ... ... ... ... ... ... ... ... ..a ... ... ... ...>

5. PKO-41k                150           160           170           180           190
   [ 3672 ]      ... ..c ... ... ... ... ... ... ... ... ..c ..a ... ... ... ...>

200           210           220           230           240
                        *             *             *             *             *
   B31-41kD    AAT ACT TCA AAG GCT ATT AAT TTT ATT CAG ACA ACA GAA GGG AAT TTA
               TTA TGA AGT TTC CGA TAA TTA AAA TAA GTC TGT TGT CTT CCC TTA AAT

1. KA-41kD               200           210           220           230           240
   [ 3996 ]      ... ... ... ... ... ... ... ... ... ... ... ... ... ... ... ...>

2. P-Gau-4               200           210           220           230           240
   [ 3696 ]      ..c ... ... ..a ... ..c ... ... ... ... ... ... ... ..a ... ...>

3. BO-41kD               200           210           220           230           240
   [ 3684 ]      ..c ... ... ..a ... ..c ... ... ... ... ... ... ... ..a ... ...>

4. DK29-41                200           210           220           230           240
   [ 3672 ]      ..c ... ... ..a ... ... ... ... ... ... ... ... ... ..a ... ..g>

5. PKO-41k                200           210           220           230           240
   [ 3672 ]      ..c ... ... ..a ... ..c ... ... ... ... ... ... ... ..a ... ...>
```

Figure 41B

```
              250          260         270         280
               *    *    *    *    *    *    *    *    *
B31-41kD   AAT GAA GTA GAA AAA GTC TTA GTA AGA ATG AAG GAA TTG GCA GTT CAA
           TTA CTT CAT CTT TTT CAG AAT CAT TCT TAC TTC CTT AAC CGT CAA GTT

1. KA-41kD      250         260         270         280
   [ 3996 ]    ... ... ... ... ... ... ... ... ... ... ... ... ... ... ...>

2. P-Gau-4      250         260         270         280
   [ 3696 ]    ... ... ... ... ..t ... ... ... ... ... ..a ... ..a ... ...>

3. BO-41kD      250         260         270         280
   [ 3684 ]    ... ... ... ... ..t ... ... ... ... ... ..a ... ..a ... ...>

4. DK29-41      250         260         270         280
   [ 3672 ]    ... ... ... ... ..t ... ... ... ... ... ..a ... ..a ... ...>

5. PKO-41k      250         260         270         280
   [ 3672 ]    ... ... ... ... ..t ... ... ... ... ... ..a ... ..a ... ...>

290         300         310         320         330
               *    *    *    *    *    *    *    *    *    *
B31-41kD   TCA GGT AAC GGC ACA TAT TCA GAT GCA GAC AGA GGT TCT ATA CAA ATT
           AGT CCA TTG CCG TGT ATA AGT CTA CGT CTG TCT CCA AGA TAT GTT TAA

1. KA-41k290    300         310         320         330
   [ 3996 ]    ... ... ... ... ... ... ... ... ... ... ... ... ... ... ...>

2. P-Gau-290    300         310         320         330
   [ 3696 ]    ... ... ... ..a ..g ... ... ... ..c ... ... ... ... ... ..g ...>

3. BO-41k290    300         310         320         330
   [ 3684 ]    ... ... ... ..a ..g ... ... ... ..c t.. ... ... ... ... ..g ...>

4. DK29-4290    300         310         320         330
   [ 3672 ]    ... ... ... ..t ... ... ... ... ..c ... ... ... ... ... ... ...>

5. PKO-41290    300         310         320         330
   [ 3672 ]    ... ... ... ..a ..g ... ... ... ..c t.. ... ... ... ... ..g ...>

340         350         360         370         380
               *    *    *    *    *    *    *    *    *
B31-41kD   GAA ATA GAG CAA CTT ACA GAC GAA ATT AAT AGA ATT GCT GAT CAA GCT
           CTT TAT CTC GTT GAA TGT CTG CTT TAA TTA TCT TAA CGA CTA GTT CGA

1. KA-41kD  340         350         360         370         380
   [ 3996 ]    ... ... ... ... ... ... ... ... ... ... ... ... ... ... ...>

2. P-Gau-4  340         350         360         370         380
   [ 3696 ]    ... ... ... ... ... ... ... ... ... ... ... ... ... ..g ...>

5. PKO-41k  340            350            360            370            380
[ 3672 ]      ...  ...  ...  ...  ...  ...  ...  ...  ...  ...  ...  ...  ..g  ...>

390            400            410            420            430
                *      *      *      *      *      *      *      *      *      *
B31-41kD      CAA  TAT  AAC  CAA  ATG  CAC  ATG  TTA  TCA  AAC  AAA  TCT  GCT  TCT  CAA  AAT
              GTT  ATA  TTG  GTT  TAC  GTG  TAC  AAT  AGT  TTG  TTT  AGA  CGA  AGA  GTT  TTA

1. KA-41kD  390            400            410            420            430
[ 3996 ]      ...  ...  ...  ...  ...  ...  ...  ...  ...  ...  ...  ...  ...  ...  ...  ...>

2. P-Gau-4  390            400            410            420            430
[ 3696 ]      ...  ...  ...  ...  ...  ...  ..g  ...  ...  ...  ...  ...  ..c  ...  ...>

3. BO-41kD  390            400            410            420            430
[ 3684 ]      ...  ...  ...  ...  ...  ...  ..g  ...  ...  ...  ...  ...  ..c  ...  ...>

4. DK29-41  390            400            410            420            430
[ 3672 ]      ...  ...  ...  ...  ...  ...  ..g  ...  ...  ...  ...  ...  ..c  ...  ...>

5. PKO-41k  390            400            410            420            430
[ 3672 ]      ...  ...  ...  ...  ...  ...  ..g  ...  ...  ...  ...  ...  ..c  ...  ...>

440            450            460            470            480
                *      *      *      *      *      *      *      *      *      *
B31-41kD      GTA  AGA  ACA  GCT  GAA  GAG  CTT  GGA  ATG  CAG  CCT  GCA  AAA  ATT  AAC  ACA
              CAT  TCT  TGT  CGA  CTT  CTC  GAA  CCT  TAC  GTC  GGA  CGT  TTT  TAA  TTG  TGT

1. KA-41kD  440            450            460            470            480
[ 3996 ]      ...  ...  ...  ...  ...  ...  ...  ...  ...  ...  ...  ...  ...  ...  ...  ...>

2. P-Gau-4  440            450            460            470            480
[ 3696 ]      ...  .a.  ...  ...  ...  ...  ...  ...  ...  ...  ...  ...  ...  ...  ...>

3. BO-41kD  440            450            460            470            480
[ 3684 ]      ...  .a.  ...  ...  ...  ...  ...  ...  ...  ...  ...  ...  ...  ...  ...>

4. DK29-41  440            450            460            470            480
[ 3672 ]      ...  ...  ...  ...  ...  ..a  ...  ...  ..a  ...  ...  ...  ..c  ...  ...>

5. PKO-41k  440            450            460            470            480
[ 3672 ]      ...  .a.  ...  ...  ...  ...  ...  ...  ...  ...  ...  ...  ...  ...  ...>

490            500            510            520
                *      *      *      *      *      *      *      *      *
B31-41kD      CCA  GCA  TCA  CTT  TCA  GGG  CTT  CAA  GCG  TCT  TGG  ACT  TTA  AGA  GTT  CAT
              GGT  CGT  AGT  GAA  AGT  CCC  GAA  GTT  CGC  AGA  ACC  TGA  AAT  TCT  CAA  GTA

1. KA-41kD  490            500            510            520
[ 3996 ]      ...  ...  ...  ...  ...  ...  tc.  ...  ...  ...  ...  ...  ...  ...  ...>

2. P-Gau-4  490            500            510            520
[ 3696 ]      ...  ...  ...  ...  ..a  tc.  ...  ..t  ...  ...  ...  ...  ...  ...  ...>
```

5. PKO-41k          490           500           510           520
 [ 3672 ]       ... ... ... ... ... ...a tc. ... ..t ... ... ... ... ...>

530           540           550           560           570
             *     *     *     *     *     *     *     *     *     *
 B31-41kD   GTT   GGA   GCA   ACC   CAA   GAT   GAA   GCT   ATT   GCT   GTA   AAT   ATT   TAT   GCA   GCT
            CAA   CCT   CGT   TGG   GTT   CTA   CTT   CGA   TAA   CGA   CAT   TTA   TAA   ATA   CGT   CGA

1. KA-41k530        540           550           560           570
 [ 3996 ]       ... ... ... .a. ... ... ... ... ... ... ... ... ... ... ...>

2. P-Gau-530        540           550           560           570
 [ 3696 ]       ..g ... ... .at ... ... ... ...a ... ... ... ... ... t.. ...>

3. BO-41k530        540           550           560           570
 [ 3684 ]       ..g ... ... .at ... ... ... ...a ... ... ... ... ... t.. ...>

4. DK29-4530        540           550           560           570
 [ 3672 ]       ..g ... ... .at ... ... ... ..g ... ... ... ... ... ..t ...>

5. PKO-41530        540           550           560           570
 [ 3672 ]       ..g ... ... .at ... ... ... ...a ... ... ... ... ... t.. ...>

580           590           600           610           620
             *     *     *     *     *     *     *     *     *     *
 B31-41kD   AAT   GTT   GCA   AAT   CTT   TTC   TCT   GGT   GAG   GGA   GCT   CAA   ACT   GCT   CAG   GCT
            TTA   CAA   CGT   TTA   GAA   AAG   AGA   CCA   CTC   CCT   CGA   GTT   TGA   CGA   GTC   CGA

1. KA-41kD  580         590           600           610           620
 [ 3996 ]       ... ... ... ... ... ... ... ... ... ... ... ... ... ... ... ...>

2. P-Gau-4  580         590           600           610           620
 [ 3696 ]       ... ... ... ... ... ..t g.. ... ... ... ... g.. ... ... ... ...>

3. BO-41kD  580         590           600           610           620
 [ 3684 ]       ... ... ... ... ... ..t g.. ... ... ... ... g.. ... ... ... ...>

4. DK29-41  580         590           600           610           620
 [ 3672 ]       ... ... ... ... ..a ... ... ... ...a ... ..g g.. ... ... a..>

5. PKO-41k  580         590           600           610           620
 [ 3672 ]       ... ... ... ... ... ..t g.. ... ... ... ... g.. ... ... ... ...>

630           640           650           660           670
             *     *     *     *     *     *     *     *     *     *
 B31-41kD   GCA   CCG   GTT   CAA   GAG   GGT   GTT   CAA   CAG   GAA   GGA   GCT   CAA   CAG   CCA   GCA
            CGT   GGC   CAA   GTT   CTC   CCA   CAA   GTT   GTC   CTT   CCT   CGA   GTT   GTC   GGT   CGT
```

2. P-Gau-4     630         640         650         660         670
        [ 3696 ]        ... ..t ... ... ... ... .c. ... g.a ... ... ... ..g ..a ... a..>

3. BO-41kD     630         640         650         660         670
        [ 3684 ]        ... ..t ... ... ... ... .c. ... g.a ... ... ... ..g ..a ... a..>

4. DK29-41     630         640         650         660         670
        [ 3672 ]        ... ..t ... ... ..a ... .c. ... ..a ... ... ... ..a ... ...>

5. PKO-41k     630         640         650         660         670
        [ 3672 ]        ... ..t ... ... ... ... .c. ... g.a ... ... ... ..g ..a ... a..>

680         690         700         710         720
                        *   *       *   *       *   *       *   *       *   *
        B31-41kD    CCT GCT ACA GCA CCT TCT CAA GGC GGA GTT AAT TCT CCT GTT AAT GTT
                    GGA CGA TGT CGT GGA AGA GTT CCG CCT CAA TTA AGA GGA CAA TTA CAA

1. KA-41kD     680         690         700         710         720
        [ 3996 ]        ... ... ... ... ... ... ... ... ... ... ... ... ... ... ...>

2. P-Gau-4     680         690         700         710         720
        [ 3696 ]        ... ... ... ... ... a.. ... ... ..t ... ... ... ... ... ...>

3. BO-41kD     680         690         700         710         720
        [ 3684 ]        ... ... ... ... ... a.. ... ... ..t ... ... ... ... ... ...>

4. DK29-41     680         690         700         710         720
        [ 3672 ]        ... ... ... ..g ... ... ..g ..t ... ... ... ... ... ... ...>

5. PKO-41k     680         690         700         710         720
        [ 3672 ]        ... ... ... ... ... a.. ... ... ..t ... ... ... ... ... ...>

730         740         750         760
                        *   *       *   *       *   *       *   *       *
        B31-41kD    ACA ACT ACA GTT GAT GCT AAT ACA TCA CTT GCT AAA ATT GAA AAT GCT
                    TGT TGA TGT CAA CTA CGA TTA TGT AGT GAA CGA TTT TAA CTT TTA CGA

1. KA-41kD     730         740         750         760
        [ 3996 ]        ... ... ... ... ... ... ... ... ... ... ... ... ... ... ...>

2. P-Gau-4     730         740         750         760
        [ 3696 ]        ... ..c ... ... ... ... ... ... ... ... ... ... ..a ... ...>

3. BO-41kD     730         740         750         760
        [ 3684 ]        ... ..c ... ... ... ... ... ... ... ... ... ... ..a ... ...>

4. DK29-41     730         740         750         760
        [ 3672 ]        ... ... ... ... ..c ... ... ... ... ..t ... ... ..a ... ...>

5. PKO-41k     730         740         750         760
        [ 3672 ]        ... ..c ... ... ... ... ... ... ... ... ... ... ..a ... ...>
```

Figure 41F

```
               770         780         790         800         810
                *           *           *           *           *
B31-41kD   ATT AGA ATG ATA AGT GAT CAA AGG GCA AAT TTA GGT GCT TTC CAA AAT
           TAA TCT TAC TAT TCA CTA GTT TCC CGT TTA AAT CCA CGA AAG GTT TTA

1. KA-41k770      780         790         800         810
[ 3996 ]    ... ... ... ... ... ... ... ... ... ... ... ... ... ... ... ...>

2. P-Gau-770      780         790         800         810
[ 3696 ]    ... ... ... ... ... ... ... ...a... ... ... ... ... ... ... ...>

3. BO-41k770      780         790         800         810
[ 3684 ]    ... ... ... ... ... ... ... ...a... ... ... ... ... ... ... ...>

4. DK29-4770      780         790         800         810
[ 3672 ]    ... ... ... ... ... ... ... ...a... ... ... ... ... ... ... ...>

5. PKO-41770      780         790         800         810
[ 3672 ]    ... ... ... ... ... ... ... ...a... ... ... ... ... ... ... ...>

820         830         840         850         860
                *           *           *           *           *
B31-41kD   AGA CTT GAA TCT ATA AAG AAT AGT ACT GAG TAT GCA ATT GAA AAT CTA
           TCT GAA CTT AGA TAT TTC TTA TCA TGA CTC ATA CGT TAA CTT TTA GAT

1. KA-41kD  820      830         840         850         860
[ 3996 ]    ... ... ... ... ... ... ... ... ... ... ... ... ... ... ... ...>

2. P-Gau-4  820      830         840         850         860
[ 3696 ]    ... ... ... ... ... ... ... ... ..c... ... ..t... ... ... ... ...>

3. BO-41kD  820      830         840         850         860
[ 3684 ]    ... ... ... ... ... ... ... ... ..c... ... ..t... ... ... ... ...>

4. DK29-41  820      830         840         850         860
[ 3672 ]    ... ... ..g... ... ... ... g.. ... ... ... ..t... ... ..c... ...>

5. PKO-41k  820      830         840         850         860
[ 3672 ]    ... ... ... ... ... ... ... ... ..c... ... ..t... ... ... ... ...>

870         880         890         900         910
                *           *           *           *           *
B31-41kD   AAA GCA TCT TAT GCT CAA ATA AAA GAT GCT ACA ATG ACA GAT GAG GTT
           TTT CGT AGA ATA CGA GTT TAT TTT CTA CGA TGT TAC TGT CTA CTC CAA

1. KA-41kD  870      880         890         900         910
[ 3996 ]    ... ... ... ... ... ... ... ... ... ... ... ... ... ... ... ...>

2. P-Gau-4  870      880         890         900         910
[ 3696 ]    ... ... ... ... ... ... ... ... ... ... ... ... ... ... ... ...>

```
     5. PKO-41k     870         880         890         900         910
     [ 3672 ]       ... ... ... ... ... ... ... ... ... ... ... ... ... ... ...>

920         930         940         950         960
                       *   *     *   *     *   *     *   *     *   *     *   *
     B31-41kD     GTA GCA GCA ACA ACT AAT ATG ATT TTA ACA CAA TCT GCA ATG GCA ATG
                  CAT CGT CGT TGT TGA TTA TAC TAA AAT TGT GTT AGA CGT TAC CGT TAC

1. KA-41kD       920         930         940         950         960
     [ 3996 ]       ... ... ... ... ... .gt ... ... ... ... ... ... ... ... ...>

2. P-Gau-4       920         930         940         950         960
     [ 3696 ]       ... ... ..t ... ... ... .gt ... ... ..t ... ... ... ... ...>

3. BO-41kD       920         930         940         950         960
     [ 3684 ]       ... ... ..t ... ... ... .gt ... ... ..t ... ... ... ... ...>

4. DK29-41       920         930         940         950         960
     [ 3672 ]       ... ... ..t ... ... ... .gt ... ... ... ... .g. ... ... ...>

5. PKO-41k       920         930         940         950         960
     [ 3672 ]       ... ... ..t ... ... ..a .gt ... ... ..t ... ... ... ... ...>

970         980         990         1000
                       *   *     *   *     *   *     *   *     *
     B31-41kD     ATT GCG CAG GCT AAT CAA GTT CCC CAA TAT GTT TTG TCA TTG CTT AGA
                  TAA CGC GTC CGA TTA GTT CAA GGG GTT ATA CAA AAC AGT AAC GAA TCT

1. KA-41kD       970         980         990         1000
     [ 3996 ]       ... ... ... ... ... ... ... ... ... ... ... ... ... ... ...>

2. P-Gau-4       970         980         990         1000
     [ 3696 ]       ... ..a ... ... ... ... ... ..t ... ... ... ... ... ... ...>

3. BO-41kD       970         980         990         1000
     [ 3684 ]       ... ..a ... ... ... ... ... ..t ... ... ... ... ... ... ...>

4. DK29-41       970         980         990         1000
     [ 3672 ]       ... ..a ... ... ... ... ... ..t ... ... ... ... ... ... ...>

5. PKO-41k       970         980         990         1000
     [ 3672 ]       ... ..a ... ... ... ... ... ..t ... ... ... ... ... ... ...>

1010
              *
     B31-41kD    TAA
                 ATT

2. P-Gau   1010
     [ 3696 ]    ...>
```

Figure 41H

Sequence Range: 1 to 822

```
                        10              20              30              40
                         *       *       *       *       *       *       *       *       *
OspA-B31        ATG AAA AAA TAT TTA TTG GGA ATA GGT CTA ATA TTA GCC TTA ATA GCA
                TAC TTT TTT ATA AAT AAC CCT TAT CCA GAT TAT AAT CGG AAT TAT CGT

OspA-B31                10              20              30              40
[ 3288 ]        ... ... ... ... ... ... ... ... ... ... ... ... ... ... ... ...>

OspA-KA                 10              20              30              40
[ 3288 ]        ... ... ... ... ... ... ... ... ... ... ... ... ... ... ... ...>

OspA-N40                10              20              30              40
[ 3276 ]        ... ... ... ... ... ... ... ... ... ... ... ... ... ... ... ...>

OspA-ZS7                10              20              30              40
[ 3264 ]        ... ... ... ... ... ... ... ... ... ... ... ... ... ... ... ...>

OspA-25015              10              20              30              40
[ 2802 ]        ... ... ... ... ... ... ... ... ... ... ... ... ..t ... ... ...>

OspA-TRO                10              20              30              40
[ 2648 ]        ... ... ... ... ... ... ... ... ... ... ... ... ... ... ... ...>

OspA-K48                10              20              30              40
[ 2584 ]        ... ... ... ... ... ... ... ... ... ... ... ... ... ... ... ...>

OspA-HE 11              10              20              30              40
[ 2580 ]        ... ... ... ... ... ... ... ... ... ... ... ... ... ... ... ...>

OspA-DK29               10              20              30              40
[ 2566 ]        ... ... ... ... ... ... ... ... ... ... ... ... ... ... ... ...>

OspA-Ip90               10              20              30              40
[ 2562 ]        ... ... ... ... ... ... ... ... ... ... ... ... ..a ... ... ...>

OspA-BO                 10              20              30              40
[ 2558 ]        ... ... ... ... ... ... ... ... ... ... ... ... ... ... ... ...>

OSPA-IP3                10              20              30              40
[ 2558 ]        ... ... ... ... ... ... ... ... ... ... ... ... ... ... ... ...>

OspA-PKO                10              20              30              40
[ 2558 ]        ... ... ... ... ... ... ... ... ... ... ... ... ... ... ... ...>

OspA-ACAI               10              20              30              40
[ 2556 ]        ... ... ... ... ... ... ... ... ... ... ... ... ... ... ... ...> ospA-P-GAU              10              20              30              40
[ 2544 ]        ... ... ... ... ... ... ... ... ... ... ... ... ... ... ... ...>

50              60              70              80              90
                 *       *       *       *       *       *       *       *       *       *
OspA-B31        TGT AAG CAA AAT GTT AGC AGC CTT GAC GAG AAA AAC AGC GTT TCA GTA
                ACA TTC GTT TTA CAA TCG TCG GAA CTG CTC TTT TTG TCG CAA AGT CAT
```

Figure 42A

|  | 50 | 60 | 70 | 80 | 90 |
|---|---|---|---|---|---|
| OspA-B31 [ 3288 ] | ... ... ... | ... ... ... | ... ... ... | ... ... ... | ... ... ... ...> |
| OspA-KA [ 3288 ] | ... ... ... | ... ... ... | ... ... ... | ... ... ... | ... ... ... ...> |
| OspA-N40 [ 3276 ] | ... ... ... | ... ... ... | ... ... ... | ... ... ... | ... ... ... ...> |
| OspA-ZS7 [ 3264 ] | ... ... ... | ... ... ... | ... ... ... | ... ... ... | ... ... ... ...> |
| OspA-25015 [ 2802 ] | ... ... ... | ... ... ... | ... ... ... | ... ... ... | ... ... ... ...> |
| OspA-TRO [ 2648 ] | ... ... ... | ... ... ... | ... ... ... | ..t ... ... | ... ... ... ...> |
| OspA-K48 [ 2584 ] | ... ... ... | ... ... ... | ... ... ... | ..t ..a ... | ..t ... ... ...> |
| OspA-HE 11 [ 2580 ] | ... ... ... | ... ... ... | ... ... ... | ..t ..a ... | ..t ... ... ...> |
| OspA-DK29 [ 2566 ] | ... ... ... | ... ... ... | ... ... ... | ..t ..a ... | ..t ... ... ...> |
| OspA-Ip90 [ 2562 ] | ... ... ... | ... ... ... | ... ... ... | ..t ..a ... | ..t ... ... ...> |
| OspA-BO [ 2558 ] | ..c ... ... | ... ... ... | ... ... ... | ..t ..a ... | .c. ... ...> |
| OSPA-IP3 [ 2558 ] | ..c ... ... | ... ... ... | ... ... ... | ..t ..a ... | .c. ... ...> |
| OspA-PKO [ 2558 ] | ..c ... ... | ... ... ... | ... ... ... | ..t ..a ... | .c. ... ...> |
| OspA-ACAI [ 2556 ] | ..c ... ... | ... ... ... | ... ... ... | ..t ..a ... | .c. ... ...> |
| ospA-P-GAU [ 2544 ] | ..c ... ... | ... ... ... | ... ... ... | ..t ..a ... | .c. ... ...> |

|  | 100 | 110 | 120 | 130 | 140 |
|---|---|---|---|---|---|
| OspA-B31 | GAT TTG CCT CTA AAC GGA | GGT GAA ATG CCA CTT TAC | AAA GTT CTT TTT CAA GAA | GTA AGC AAA CAT TCG TTT | GAA AAA AAC AAA CTT TTT TTG TTT |
| OspA-B31 [ 3288 ] | ... ... ... | ... ... ... | ... ... ... | ... ... ... | ... ... ... ...> |
| OspA-KA [ 3288 ] | ... ... ... | ... ... ... | ... ... ... | ... ... ... | ... ... ... ...> |
| OspA-N40 | 100 | 110 | 120 | 130 | 140 |

OspA-ZS7       100         110         120         130         140
[ 3264 ]       ... ... ... ... ... ... ..c ... ... ... ... ... ... ... ...>

OspA-25015     100         110         120         130         140
[ 2802 ]       ... ... ... ... ... ... ... ... ... ... ... ... ... g.. ...>

OspA-TRO       100         110         120         130         140
[ 2648 ]       ... ..a ... ... ... ... ... ... ... ... ... ... ... g.. ...>

OspA-K48       100         110         120         130         140
[ 2584 ]       ... ..a ... ... .g. ... .c. ... ... ... ..t ... ... g.. ...>

OspA-HE 11     100         110         120         130         140
[ 2580 ]       ... ..a ... ... .g. ... ... ... ... ... ..t ... ... g.. ...>

OspA-DK29      100         110         120         130         140
[ 2566 ]       ... ..a ... ... .g. ... .c. ... ... ... ..t ... ... g.. ...>

OspA-Ip90      100         110         120         130         140
[ 2562 ]       ... ..a ... ... .g. ... c.. ... ... ... ..t ... ... g.. ...>

OspA-BO        100         110         120         130         140
[ 2558 ]       ... ... ... ... ..g ... ... ... ... ... ..t ... ... g.. ...>

OSPA-IP3       100         110         120         130         140
[ 2558 ]       ... ... ... ... ..g ..t ... ... ... ... ..t ... ... g.. ...>

OspA-PKO       100         110         120         130         140
[ 2558 ]       ... ... ... ... ..g ... ... ... ... ... ..t ... ... g.. ...>

OspA-ACAI      100         110         120         130         140
[ 2556 ]       ... ... ... ... ..g ... ... ... ... ... ..t ... ... g.. ...> ospA-P-GAU     100         110         120         130         140
[ 2544 ]       ... ... ... ... ..g ... ... ... ... ... ..t ... ... g.. ...>

150         160         170         180         190
                *      *     *     *     *     *     *     *     *     *
OspA-B31        GAC GGC AAG TAC GAT CTA ATT GCA ACA GTA GAC AAG CTT GAG CTT AAA
                CTG CCG TTC ATG CTA GAT TAA CGT TGT CAT CTG TTC GAA CTC GAA TTT

OspA-B31             150         160         170         180         190
[ 3288 ]       ... ... ... ... ... ... ... ... ... ... ... ... ... ... ...>

OspA-KA              150         160         170         180         190
[ 3288 ]       ... ... ... ... ... ... ... ... ... ... ... ... ... ... ...>

OspA-N40             150         160         170         180         190
[ 3276 ]       ... ... ... ... ... ... ... ... ... ... ... ... ... ... ...>

OspA-ZS7             150         160         170         180         190
[ 3264 ]       ... ... ... ... ... ... ... ... ... ... ... ... ... ... ...>

OspA-25015           150         160         170         180         190
[ 2802 ]       ... ... ... ... ag. ... ..g ... ... ... ... ... ... ... ...>
```

Figure 42C

```
OspA-TRO        150       160       170       180       190
[ 2648 ]     ..t ..t ..a ... ag. ... ..g ... ... ... ..a ... ... ...>

OspA-K48        150       160       170       180       190
[ 2584 ]     ... ..t ..a ... ag. ... gag ... ... ... ... ... ... ...>

OspA-HE 11      150       160       170       180       190
[ 2580 ]     ..t ..t ..a ... ag. ... ..g ... ... ..a ... ... ... ...>

OspA-DK29       150       160       170       180       190
[ 2566 ]     ... ..t ..a ... ag. ... gag ... ... ... ... ... ... ...>

OspA-Ip90       150       160       170       180       190
[ 2562 ]     ..t ..t ..a ... ag. ... ..g ... ... ... ... ... ... ...>

OspA-BO         150       160       170       180       190
[ 2558 ]     ... ..t ... ... ag. ... .ag ... ... ... ... a.. ... ..a ...>

OSPA-IP3        150       160       170       180       190
[ 2558 ]     ... ..t ... ... ag. ... .ag ... ... ... ... a.. ... ..a ...>

OspA-PKO        150       160       170       180       190
[ 2558 ]     ... ..t ... ... ag. ... .ag ... ... ... ... a.. ... ..a ...>

OspA-ACAI       150       160       170       180       190
[ 2556 ]     ... ..t ... ... ag. ... .ag ... ... ... ... a.. ... ..a ...> ospA-P-GAU      150       160       170       180       190
[ 2544 ]     ... ..t ... ... ag. ... .ag ... ... ... ... a.. ... ..a ...>

200       210       220       230       240
                 *         *    *    *    *    *    *    *     *    *
OspA-B31     GGA ACT TCT GAT AAA AAC AAT GGA TCT GGA GTA CTT GAA GGC GTA AAA
             CCT TGA AGA CTA TTT TTG TTA CCT AGA CCT CAT GAA CTT CCG CAT TTT

OspA-B31        200       210       220       230       240
[ 3288 ]     ... ... ... ... ... ... ... ... ... ... ... ... ... ... ...>

OspA-KA         200       210       220       230       240
[ 3288 ]     ... ... ... ... ... ... ... ... ... ... ... ... ... ... ...>

OspA-N40        200       210       220       230       240
[ 3276 ]     ... ... ... ... ... ... ... ... ... ... ... ... ... ... ...>

OspA-ZS7        200       210       220       230       240
[ 3264 ]     ... ... ... ... ... ... ... ... ... ... ... ... ... ... ...>

OspA-25015      200       210       220       230       240
[ 2802 ]     ... ..a ... ... ... ... ... ... ..g ..g ... ... ... ... ...>

OspA-TRO        200       210       220       230       240
[ 2648 ]     ... ... ... ... ... .g. ...c ..t ... ... ac. ... ... ..t .a. ...>

OspA-K48        200       210       220       230       240
[ 2584 ]     ... ... ... ... ... ... ..c ..t ... ... ac. ... ... ..t .a. ...>
```

Figure 42D

```
OspA-HE 11        200       210       220       230       240
[ 2580 ]          ... ... ... ... ... ..c ..t ... ... ac. ... ... ..t .a. ...>

OspA-DK29         200       210       220       230       240
[ 2566 ]          ... ... ... ... ... ..c ..t ... ... ac. ... ... ..t .a. ...>

OspA-Ip90         200       210       220       230       240
[ 2562 ]          ... ... ... ... ... ..c ..t ... ... ac. ... ... ..t .a. ...>

OspA-BO           200       210       220       230       240
[ 2558 ]          ... ... ... ... ... g.. ... ..t ... ..g ..g ... ... ..t ac. ...>

OSPA-IP3          200       210       220       230       240
[ 2558 ]          ... ... ... ... ... g.. ... ..t ... ... ..g ... ... ..t ac. ...>

OspA-PKO          200       210       220       230       240
[ 2558 ]          ... ... ... ... ... g.. ... ..t ... ..g ..g ... ... ..t ac. ...>

OspA-ACAI         200       210       220       230       240
[ 2556 ]          ... ... ... ... ... g.. ... ..t ... ... ..g ... ... ..t ac. ...> ospA-P-GAU        200       210       220       230       240
[ 2544 ]          ... ... ... ... ... g.. ... ..t ... ... ..g ... ... ..t ac. ...>

250         260         270         280
                    *     *     *     *     *     *     *     *     *
OspA-B31         GCT GAC AAA AGT AAA GTA AAA TTA ACA ATT TCT GAC GAT CTA GGT CAA
                 CGA CTG TTT TCA TTT CAT TTT AAT TGT TAA AGA CTG CTA GAT CCA GTT

OspA-B31            250       260       270       280
[ 3288 ]         ... ... ... ... ... ... ... ... ... ... ... ... ... ... ... ...>

OspA-KA             250       260       270       280
[ 3288 ]         ... ... ... ... ... ... ... ... ... ... ... ... ... ... ... ...>

OspA-N40            250       260       270       280
[ 3276 ]         ... ... ... ... ... ... ... ... ... ... ... ... ... ... ... ...>

OspA-ZS7            250       260       270       280
[ 3264 ]         ... ... ... ... ... ... ... ... ... ... ... ... ... ... ... ...>

OspA-25015          250       260       270       280
[ 2802 ]         ... ... ... ..c ... ... ... ... ... g.. ... ... ... ... a..c ac.>

OspA-TRO            250       260       270       280
[ 2648 ]         t.. ... ... ... ... .c. ... ... ... ... ..a ... ... a.. a..>

OspA-K48            250       260       270       280
[ 2584 ]         a.. ... ... ... ... ... ... ... ... g.. ..t ..c ... a.. ...>

OspA-HE 11          250       260       270       280
[ 2580 ]         a.. ... ... ... ... ... ... ... ... g.. ..g ... ... a.. a..>

OspA-DK29           250       260       270       280
[ 2566 ]         a.. ... ... ... ... .c. ... ... ... g.. ..t ..c ... a.. ...>

OspA-Ip90           250       260       270       280
```

OspA-BO              250          260          270          280
[ 2558 ]     .a. ... ... ... ...  .c. ... ... ... ...  g.. ... ... ...  ... a..>

OSPA-IP3             250          260          270          280
[ 2558 ]     .a. ... ... ... ...  .c. ... ... ... ...  g.. ... ... ...  ... a..>

OspA-PKO             250          260          270          280
[ 2558 ]     .a. ... ... ... ...  .c. ... ... ... ...  g.. ... ... ...  ... a..>

OspA-ACAI            250          260          270          280
[ 2556 ]     .a. ... ... ... ...  .c. ... ... ... ...  g.. ... ... ...  a.. a..> ospA-P-GAU           250          260          270.         280
[ 2544 ]     .a. ... ... ... ...  .c. ... ... ... ...  g.. ... ... ...  a.. a..>

290         300         310         320         330
               *           *           *           *           *
OspA-B31     ACC ACA CTT GAA GTT TTC AAA GAA GAT GGC AAA ACA CTA GTA TCA AAA
             TGG TGT GAA CTT CAA AAG TTT CTT CTA CCG TTT TGT GAT CAT AGT TTT

OspA-B31     290         300         310         320         330
[ 3288 ]     ... ... ... ... ... ... ... ... ... ... ... ... ... ... ... ...>

OspA-KA      290         300         310         320         330
[ 3288 ]     ... ... ... ... ... ... ... ... ... ... ... ... ... ... ... ...>

OspA-N40     290         300         310         320         330
[ 3276 ]     ... ... ... ... ... ... ... ... ... ... ... ... ... ... ... ...>

OspA-ZS7     290         300         310         320         330
[ 3264 ]     ... ... ... ... ... ... ... ... ... ... ... ... ... ... ... ...>

OspA-25015   290         300         310         320         330
[ 2802 ]     ... ... ... ... ...  ..a ... ... ... ...  ... ... t.. ..g ... ...>

OspA-TRO     290         300         310         320         330
[ 2648 ]     ... ... t.. ... a..  ... ... ... ... ...  ... ... t.. ... ... ...>

OspA-K48     290         300         310         320         330
[ 2584 ]     ..t .a. t.. ... a..  ... ... ... ... ...  .c. ... t.. ... ... ...>

OspA-HE 11   290         300         310         320         330
[ 2580 ]     ... ... t.. ... a.c  ... ... ... ... ...  ... ... t.. ... ..g ...>

OspA-DK29    290         300         310         320         330
[ 2566 ]     ..t .a. t.. ... a..  ... ... ... ... ...  ... ... t.. ... ... ...>

OspA-Ip90    290         300         310         320         330
[ 2562 ]     ... ... t.. ... a.c  ... ... ... ... ...  ... ... t.. ... ... ...>

OspA-BO      290         300         310         320         330
[ 2558 ]     ... ... t.c ... c..  ... ... ... ... ...  ... ... t.. ..g ... .g.>

OSPA-IP3     290         300         310         320         330
[ 2558 ]     ... ... t.c ... c..  ... ... ... ... ...  ... ... t.. ..g ... .g.>
```

Figure 42F

```
OspA-PKO    290         300         310         320         330
[ 2558 ]    ... ... t.c ... c.. ... ... ... ... ... t.. ..g ... .g.>

OspA-ACAI   290         300         310         320         330
[ 2556 ]    ... ... t.c ... c.. ... ... ... ... ... t.. ..g ... .g.>

OspA-P-GAU  290         300         310         320         330
[ 2544 ]    ... ... t.c ... c.. ..a ... ... ... ... t.. ..g ... .g.>

340         350         360        ·370         380
                   *           *           *           *           *
OspA-B31    AAA GTA ACT TCC AAA GAC AAG TCA TCA ACA GAA GAA AAA TTC AAT GAA
            TTT CAT TGA AGG TTT CTG TTC AGT AGT TGT CTT CTT TTT AAG TTA CTT

OspA-B31    340         350         360         370         380
[ 3288 ]    ... ... ... ... ... ... ... ... ... ... ... ... ... ... ... ...>

OspA-KA     340         350         360         370         380
[ 3288 ]    ... ... ... ... ... ... ... ... ... ... ... ... ... ... ... ...>

OspA-N40    340         350         360         370         380
[ 3276 ]    ... ... ... ... ... ... ... ... ... ... ... ... ... ... ... ...>

OspA-ZS7    340         350         360         370         380
[ 3264 ]    ... ... ... ... ... ... ... ... ... ... ... ... ... ... ... ...>

OspA-25015  340         350         360         370         380
[ 2802 ]    ... ag. ... ..t ... ..t ... ... ... ... ... ..g ... ... ... ...>

OspA-TRO    340         350         360         370         380
[ 2648 ]    ... ... .a. ..t ... ..t ... ... .t. ... ... ... ... ... ..c .c.>

OspA-K48    340         350         360         370         380
[ 2584 ]    ... ... ..c ctt ... ... ... ... ... ... ... ... ... ... ..c ...>

OspA-HE 11  340         350         360         370         380
[ 2580 ]    ... ... ..c ctt ... ... ... ... ... ... ... ... ... ... ..c ...>

OspA-DK29   340         350         360         370         380
[ 2566 ]    ... ... ..c ctt ... ... ... ... ... ... ... ... ... ... ..c .g.>

OspA-Ip90   340         350         360         370         380
[ 2562 ]    ... ... ..c ctt ... ... ... ... ... ... ... ... ... ... ..c .c.>

OspA-BO     340         350         360         370         380
[ 2558 ]    ... ... .g. ..t ... ... ..a a.. ... ... ..t ... .tg ... ... ...>

OSPA-IP3    340         350         360         370         380
[ 2558 ]    ... ... .g. ..t ... ... ..a a.. ... ... ..t ... .tg ... ... ...>

OspA-PKO    340         350         360         370         380
[ 2558 ]    ... ... .g. ..t ... ... ..a a.. ... ... ..t ... .tg ... ... ...>

OspA-ACAI   340         350         360         370         380
[ 2556 ]    ... ... .g. ..t ... ... ..a a.. ... ... ..t ... .tg ... ... ...>
```

Figure 42G

```
ospA-P-GAU     340           350           360           370           380
[ 2544 ]       ... ... .g. ...t .g. ... ...a a.. ... ... ...t ... .tg ... ...>

390           400           410           420           430
               *     *       *     *       *     *       *     *       *     *
OspA-B31       AAA GGT GAA GTA TCT GAA AAA ATA ATA ACA AGA GCA GAC GGA ACC AGA
               TTT CCA CTT CAT AGA CTT TTT TAT TAT TGT TCT CGT CTG CCT TGG TCT

OspA-B31       390           400           410           420           430
[ 3288 ]       ... ... ... ... ... ... ... ... ... ... ... ... ... ... ...>

OspA-KA        390           400           410           420           430
[ 3288 ]       ... ... ... ... ... ... ... ... ... ... ... ... ... ... ...>

OspA-N40       390           400           410           420           430
[ 3276 ]       ... ... ... ... ... ... ... ... ... ... ... ... ... ... ...>

OspA-ZS7       390           400           410           420           430
[ 3264 ]       ... ... ... ... ... ... ... ... ... ... ... ... ... ... ...>

OspA-25015     390           400           410           420           430
[ 2802 ]       ... ..c ... t.. gt. ... ... ... ..g g.. ... ... a.. ... ... .t.>

OspA-TRO       390           400           410           420           430
[ 2648 ]       ... ... ... t.. ... ... ... .c. ... ct. ... ... a.. ... ... ..g>

OspA-K48       390           400           410           420           430
[ 2584 ]       ..g ... ... ac. ... ... ... .c. ... gt. ... ... a.t ... ... ...>

OspA-HE 11     390           400           410           420           430
[ 2580 ]       ..g ... ... a.. ... ... ... .c. ... gt. ... ... a.t ... ... ...>

OspA-DK29      390           400           410           420           430
[ 2566 ]       ..g ... ... ac. ... ... ... .c. ... gt. ... ... a.t ... ... ...>

OspA-Ip90      390           400           410           420           430
[ 2562 ]       ..g ... ... .c. ... ... ... .c. ... gt. ... ... a.t ... ... ...>

OspA-BO        390           400           410           420           430
[ 2558 ]       ... ... ... t.g ... .c. ... .cc ..g ... ... .a. a.t ... ... .a.>

OSPA-IP3       390           400           410           420           430
[ 2558 ]       ... ... ... t.g ... .c. ... .cc ..g ... ... .a. a.t ... ... .a.>

OspA-PKO       390           400           410           420           430
[ 2558 ]       ... ... ... t.g ... .c. ... .cc ..g ... ... .a. a.t ... ... .a.>

OspA-ACAI      390           400           410           420           430
[ 2556 ]       ... ... ... t.g ... .c. ... .cc ..g ... ... .a. a.t ... ... .a.> ospA-P-GAU     390           400           410           420           430
[ 2544 ]       ... ... ... t.g ... .c. ... .cc ..g ... ... .a. a.t ... ... .a.>

440           450           460           470           480
               *     *       *     *       *     *       *     *       *     *
OspA-B31       CTT GAA TAC ACA GGA ATT AAA AGC GAT GGA TCT GGA AAA GCT AAA GAG
```

Figure 42H

```
                    GAA CTT ATG TGT CCT TAA TTT TCG CTA CCT AGA CCT TTT CGA TTT CTC

OspA-B31                440         450         460         470         480
[ 3288 ]        ... ... ... ... ... ... ... ... ... ... ... ... ... ... ...>

OspA-KA                 440         450         460         470         480
[ 3288 ]        ... ... ... ... ... ... ... ... ... ... ... ... ... ... ...>

OspA-N40                440         450         460         470         480
[ 3276 ]        ... ... ... ... .a. ... ... ... ... ... ... ... ... ... ...>

OspA-ZS7                440         450         460         470         480
[ 3264 ]        ... ... ... ... .a. ... ... ... ... ... ... ... ... ... ...>

OspA-25015              440         450         460         470         480
[ 2802 ]        ... ... ... ... ... ... ... ... ... ..c ... ... ... ... ..a>

OspA-TRO                440         450         460         470         480
[ 2648 ]        ... ... ... ... .a. ..a ... ... ... a.c ... ... ... ... ..a>

OspA-K48                440         450         460         470         480
[ 2584 ]        ... ... ... ... .ac ..a ... ... ... ..c ... ... ... ... ..a>

OspA-HE 11              440         450         460         470         480
[ 2580 ]        ... ... ... ... .ac ..a ... ... aa. a.c ... ... ... ... ..a>

OspA-DK29               440         450         460         470         480
[ 2566 ]        ... ... ... ... .ac ..a ... ... ... ..c ... ... ... ... ..a>

OspA-Ip90               440         450         460         470         480
[ 2562 ]        ... ... ... ... .ac ..a ... ... aa. a.c ... ... ... ... ..a>

OspA-BO                 440         450         460         470         480
[ 2558 ]        ... ... ..t ... .a. ..g ... ... ... a.c ... ... ... ... ..a>

OSPA-IP3                440         450         460         470         480
[ 2558 ]        ... ... ..t ... .a. ..g ... ... ... a.c ... ... ... ... ..a>

OspA-PKO                440         450         460         470         480
[ 2558 ]        ... ... ..t ... .a. ..g ... ... ... a.c ... ... ... ... ..a>

OspA-ACAI               440         450         460         470         480
[ 2556 ]        ... ... ..t ... .a. ..g ... ... ... a.c ... ... ... ... ..a> ospA-P-GAU              440         450         460         470         480
[ 2544 ]        ... ... ..t ... .a. ..g ... ... ... a.c ... ... ... ... ..a>

490         500         510         520
                            *           *           *           *
OspA-B31        GTT TTA AAA GGC TAT GTT CTT GAA GGA ACT CTA ACT GCT GAA AAA ACA
                CAA AAT TTT CCG ATA CAA GAA CTT CCT TGA GAT TGA CGA CTT TTT TGT

OspA-B31                490         500         510         520
[ 3288 ]        ... ... ... ... ... ... ... ... ... ... ... ... ... ... ...>

OspA-KA                 490         500         510         520
[ 3288 ]        ... ... ... ... ... ... ... ... ... ... ... ... ... ... ...>
```

Figure 42I

```
OspA-N40           490       500       510       520
[ 3276 ]      ... ... ... ... ... ... ... ... ... ... ... ... ... ...>

OspA-ZS7           490       500       510       520
[ 3264 ]      ... ... ... a.. ... ... ... ... ... ... t.. ... ... ...>

OspA-25015         490       500       510       520
[ 2802 ]      ac. ... ... .aa ... ... ... ... ... ... ... ... ... g..>

OspA-TRO           490       500       510       520
[ 2648 ]      .c. ... ... .a. .t. .c. ... ... ... ... g.. ..c ..c ... ...> cgg
                                                           |
OspA-K48           490       500       510       520|      530
[ 2584 ]      ... ... ... .a. .t. ac. ... ... ... ... g.. ... ..c ... ...> cgg
                                                           |
OspA-HE 11         490       500       510       520|      530
[ 2580 ]      ... ... ... .a. .t. ac. ... ... ... ... g.. ... ..c ... ...> cgg
                                                           |
OspA-DK29          490       500       510       520|      530
[ 2566 ]      ... ... ... .a. .t. ac. ... ... ... ... g.. ... ..c ... ...> cgg
                                                           |
OspA-Ip90          490       500       510       520|      530
[ 2562 ]      ... ... ... .a. .t. .c. ... ... ... ... g.. ... ..c ... ...>

OspA-BO            490       500       510       520
[ 2558 ]      ... ... ... aa. .t. ac. ... ... ... .aa g.. g.. aa. ...t ... gt.>

OSPA-IP3           490       500       510       520
[ 2558 ]      ... ... ... aa. .t. ac. ... ... ... .aa g.. g.. aa. ...t ... gt.>

OspA-PKO           490       500       510       520
[ 2558 ]      ... ... ... aa. .t. ac. ... ... ... .aa g.. g.. aa. ...t ... gt.>

OspA-ACAI          490       500       510       520
[ 2556 ]      ... ... ... aa. .t. ac. ... ... ... .aa g.. g.. aa. ...t ... gt.> ospA-P-GAU         490       500       510       520
[ 2544 ]      ... ... ... aag .t. ac. ... ... ... .aa g.. g.. aa. ...t ... gt.>

530       540       550       560       570
               *    *    *    *    *    *    *    *    *    *
OspA-B31      ACA  TTG  GTG  GTT  AAA  GAA  GGA  ACT  GTT  ACT  TTA  AGC  AAA  AAT  ATT  TCA
              TGT  AAC  CAC  CAA  TTT  CTT  CCT  TGA  CAA  TGA  AAT  TCG  TTT  TTA  TAA  AGT

OspA-B31      530       540       550       560       570
[ 3288 ]      ... ... ... ... ... ... ... ... ... ... ... ... ... ...>

OspA-KA       530       540       550       560       570
```

OspA-N40       530           540            550           560           570
[ 3276 ]        ...  ...  ... ...  ...  ... ...  ... ...  ... ...  ... ...  ...>

OspA-ZS7       530           540            550           560           570
[ 3264 ]        ...  ...  ... ...  ...  ... ...  ... ...  ... ...  ... ...  ...>

OspA-25015     530           540            550           560           570
[ 2802 ]        ...  ...  ... ...  ...  ... ...  ... ...  ... ...  ..t ..g c.c ... ...>

OspA-TRO       530           540            550           560           570
[ 2648 ]        ...  ... aaa ...  .c.  ... ...  ..c ...  ... gt. ...  ... ...  c.c ... c..>

OspA-K48                     540            550           560-          570
[ 2584 ]        ...  ... aaa ...  .c.  ... ...  ..c ...  ... gt. ...  ... ...  ..g ..c ... .t.>

OspA-HE 11                   540            550           560           570
[ 2580 ]        ...  ... aaa ...  .c.  ..g ..c ...  ... ...  ... ...  ... ...  ..g ..c ... ...>

OspA-DK29                    540            550           560           570
[ 2566 ]        ...  ... aaa ...  .c.  ... ..c  ... ...  ... gt. ...  ... ...  ..g ..c ... .t.>

OspA-Ip90                    540            550           560           570
[ 2562 ]        ...  ..a aaa ...  .c.  ... ..c  ... ...  ... gt. ...  ... ...  c.c ... ...>

OspA-BO        530           540            550           560           570
[ 2558 ]        ...  ... .aa ..a  ...  ... ...  ..c ...  ... ...  ..t ..g g.a ... g..>

OSPA-IP3       530           540            550           560           570
[ 2558 ]        ...  ... .aa ..a  ...  ... ...  ..c ...  ... ...  ..t ..g g.a ... g..>

OspA-PKO       530           540            550           560           570
[ 2558 ]        ...  ... .aa ..a  ...  ... ...  ..c ...  ... ...  ..t ..g g.a ... g..>

OspA-ACAI      530           540            550           560           570
[ 2556 ]        ...  ... .aa ..a  ...  ... ...  ..c ...  ... ...  ..t ..g g.a ... g..> ospA-P-GAU     530           540            550           560           570
[ 2544 ]        ...  ... .aa ..a  ...  ... ...  ..c ...  ... ...  ..t ..g g.a ... g..>

580           590           600           610           620
                    *             *             *             *             *
OspA-B31        AAA TCT GGG GAA GTT TCA GTT GAA CTT AAT GAC ACT GAC AGT AGT GCT
                TTT AGA CCC CTT CAA AGT CAA CTT GAA TTA CTG TGA CTG TCA TCA CGA

OspA-B31       580           590           600           610           620
[ 3288 ]        ...  ...  ... ...  ...  ... ...  ... ...  ... ...  ... ...  ...>

OspA-KA        580           590           600           610           620
[ 3288 ]        ...  ...  ... ...  ...  ... ...  ... ...  ... ...  ... ...  ...>

OspA-N40       580           590           600           610           620
[ 3276 ]        ...  ...  ... ...  ...  ... ...  ... ...  ... ...  ... ...  ...>

OspA-ZS7       580           590           600           610           620
[ 3264 ]        ...  ...  ... ...  ...  ... ...  ... ...  ... ...  ... ...  ...>
```

Figure 42K

```
OspA-25015    580         590         600         610         620
[ 2802 ]      ... ... ..a ... ..a a.. .c. ... ... ... ... ... .c. caa>

OspA-TRO      580         590         600         610         620
[ 2648 ]      ..c ... ..a ... a.a a.. ... ..g ... ... ... t.. a.. tc. .c. cag>

OspA-K48      580         590         600         610         620
[ 2584 ]      ... ..c ..a ... a.a a.. ... .c. ... g.. ... t.. ... .c. .c. cag>

OspA-HE 11    580         590         600         610         620
[ 2580 ]      ... ..c ..a ... a.a a.. ... .c. ... g.. ... ... ... tc. .-- ..g>

OspA-DK29     580         590         600         610         620
[ 2566 ]      ... ..c ..a ... a.a a.. .c. .c. ... g.. ... t.. ... .c. .c. cgg>

OspA-Ip90     580         590         600         610         620
[ 2562 ]      ..c ... ..a ... a.a a.. ... ..g ... ... ... t.. ... .c. .c. cag>

OspA-BO       580         590         600         610         620
[ 2558 ]      ... ... ..a ... ..a a.. ... .ct ... ... ... a.. .c. .c. cag>

OSPA-IP3      580         590         600         610         620
[ 2558 ]      ... ... ..a ... ..a a.. ... .ct ... ... ... a.. .c. .c. cag>

OspA-PKO      580         590         600         610         620
[ 2558 ]      ... ... ..a ... ..a a.. ... .ct ... ... ... a.. .c. .c. cag>

OspA-ACAI     580         590         600         610         620
[ 2556 ]      ... ... ..a ... ..a a.. ... .ct ... ... ... a.. .c. .c. cag> ospA-P-GAU    580         590         600         610         620
[ 2544 ]      ... ... ..a ... ..a a.. ... .ct ... ... ... a.. .c. .c. cag>

630         640         650         660         670
              *   *   *   *   *   *   *   *   *   *
OspA-B31      GCT ACT AAA AAA ACT GCA GCT TGG AAT TCA GGC ACT TCA ACT TTA ACA
              CGA TGA TTT TTT TGA CGT CGA ACC TTA AGT CCG TGA AGT TGA AAT TGT

OspA-B31      630         640         650         660         670
[ 3288 ]      ... ... ... ... ... ... ... ... ... ... ... ... ... ... ... ...>

OspA-KA       630         640         650         660         670
[ 3288 ]      ... ... ... ... ... ... ... ... ... ... ... ... ... ... ... ...>

OspA-N40      630         640         650         660         670
[ 3276 ]      ... ... ... ... ... ... ... ... ... ... ... ... ... ... ... ...>

OspA-ZS7      630         640         650         660         670
[ 3264 ]      ... ... ... ... ... ... ... ... ... ... ... ... ... ... ... ...>

OspA-25015    630         640         650         660         670
[ 2802 ]      ... ... ... ... ... .gg aaa ... g.. g.. ... ... ... ... ... ...>

OspA-TRO      630         640         650         660         670
[ 2648 ]      ... ... ... ... ... .g. aaa ... g.. ... aat ... ..c ... ... ...>
```

Figure 42L

```
OspA-K48      630          640          650          660          670
[ 2584 ]      ... ... ... ... ... .g. aaa ... g.. ... aaa ... ..c ... ... ...>

OspA-HE 11    630          640          650          660          670
[ 2580 ]      ..- .a. ... ... t.c .g. a.a ... g.. ... ..t ... ..t ... ... ...>

OspA-DK29     630          640          650          660          670
[ 2566 ]      ... ... ... ... ... .g. aaa ... g.. ... aag ... ..c ... ... ...>

OspA-Ip90     630          640          650          660          670
[ 2562 ]      ... ... ... ... ... .g. a.a ... g.. ... aag ... ..c ... ... ...>

OspA-BO       630          640          650          660          670
[ 2558 ]      ... ... ... ... ... .gc ..a ... g.. ... aaa ... ..t ... ... ...>

OSPA-IP3      630          640          650          660          670
[ 2558 ]      ... ... ... ... ... .gc ..a ... g.. ... aaa ... ..t ... ... ...>

OspA-PKO      630          640          650          660          670
[ 2558 ]      ... ... ... ... ... .gc ..a ... g.. ... aaa ... ..t ... ... ...>

OspA-ACAI     630          640          650          660          670
[ 2556 ]      ... ... ... ... ... .gc ..a ... g.. ... aaa ... ..t ... ... ...> ospA-P-GAU    630          640          650          660          670
[ 2544 ]      ... ... ... ... ... .gc ..a ... g.. ... aaa ... ..t ... ... ...>

680          690          700          710          720
OspA-B31      ATT ACT GTA AAC AGT AAA AAA ACT AAA GAC CTT GTG TTT ACA AAA GAA
              TAA TGA CAT TTG TCA TTT TTT TGA TTT CTG GAA CAC AAA TGT TTT CTT

OspA-B31      680          690          700          710          720
[ 3288 ]      ... ... ... ... ... ... ... ... ... ... ... ... ... ... ... ...>

OspA-KA       680          690          700          710          720
[ 3288 ]      ... ... ... ... ... ... ... ... ... ... ... ... ... ... ... ...>

OspA-N40      680          690          700          710          720
[ 3276 ]      ... ... ... ... ... ... ... ... ... ... ... ... ... ... ... ...>

OspA-ZS7      680          690          700          710          720
[ 3264 ]      ... ... ... ... ... ... ... ... ... ... ... ... ... ... ... ...>

OspA-25015    680          690          700          710          720
[ 2802 ]      ... ... ... ... .ac ... ... ... .c. ... ... ..a ... ... ... c..>

OspA-TRO      680          690          700          710          720
[ 2648 ]      ... .g. ...g ..t ..c ... ... ... ... a.. a.. ..a ... ... ...>

OspA-K48      680          690          700          710          720
[ 2584 ]      ... .g. ...g ..t ..c c.. ... ..c ... a.. ... ..a ..c ... ... ...>

OspA-HE 11    680          690          700          710          720
[ 2580 ]      ... .g. aa. ... ..a c.. ... ... ... c.a ... ..a ..c ... ... ...>

OspA-DK29     680          690          700          710          720
```

Figure 42M

```
[ 2566 ]      ... .g. ...g ..t ..c c..  ...  ..c ... a.. ... ..a ..c ... ... ...>
OspA-Ip90     680      690      700      710      720
[ 2562 ]      ... .g. ...g ..t ..c cg.  ...  ..c ... a.. ... ..a ..c ... ... ...>
OspA-BO       680      690      700      710      720
[ 2558 ]      ... .g. ...t ... ..c ...  ...  ... ... .c. c.a ... ... ... ..t ... c..>
OSPA-IP3      680      690      700      710      720
[ 2558 ]      ... .g. ...t ... ... ...  ...  ... ... .c. c.a ... ... ... ..t ... c..>
OspA-PKO      680      690      700      710      720
[ 2558 ]      ... .g. ...t ... ..c ...  ...  ... ... .c. c.a ... ... ... ..t ... c..>
OspA-ACAI     680      690      700      710      720
[ 2556 ]      ... .g. ...t ... ..c ...  ...  ... ... .c. c.a ... ... ... ..t ... c..>
ospA-P-GAU    680      690      700      710      720
[ 2544 ]      ... .g. ...t ... ..c ...  ...  ... ... .c. c.a ... ... ... ..t ... c..>

730          740          750          760
                               *            *            *            *
OspA-B31      AAC ACA ATT ACA GTA CAA CAA TAC GAC TCA AAT GGC ACC AAA TTA GAG
              TTG TGT TAA TGT CAT GTT GTT ATG CTG AGT TTA CCG TGG TTT AAT CTC

OspA-B31          730          740          750          760
[ 3288 ]      ... ... ... ... ... ... ... ... ... ... ... ... ... ... ... ...>
OspA-KA           730          740          750          760
[ 3288 ]      ... ... ... ... ... ... ... ... ... ... ... ... ... ... ... ...>
OspA-N40          730          740          750          760
[ 3276 ]      ... ... ... ... ... ... ... ... ... ... ... ... ... ... ... ...>
OspA-ZS7          730          740          750          760
[ 3264 ]      ... ... ... ... ... ... ... ... ... ... ... ... ... ... ... ...>
OspA-25015        730          740          750          760
[ 2802 ]      g.. ... ... ... tc. ... a.. ... ... ... gca ..a ... ..c ..g ..a>
OspA-TRO          730          740          750          760
[ 2648 ]      g.. ... ...a ... ... ... a.. ... ... ... gca ... ... ..t c.. ...a>
OspA-K48          730          740          750          760          770
[ 2584 ]      g.. ... ...a ... ... ... a.. ... ... ... gca ... ... ..t c.. ...a>
OspA-HE 11        730          740          750          760
[ 2580 ]      g.. ... ...a ... ... ... a.c ... ... ... gca ... ... ..t c.. ...a>
OspA-DK29         730          740          750          760          770
[ 2566 ]      g.. ... ...a ... ... ... ag. ... ... ... gca ... ... ..t c.. ...a>
OspA-Ip90         730         .740          750          760          770
[ 2562 ]      g.. ... ...a ... ... ... a.. ... ... ... gca ... ... ..t c.. ...a>
OspA-BO           730          740          750          760
[ 2558 ]      g.. ... ...a ..t ... ... a.. ... ... ..c gca ..t ... ..t ... ..a>
```

Figure 42N

| | 730 | 740 | 750 | 760 | |
|---|---|---|---|---|---|
| OSPA-IP3 [ 2558 ] | g.. ... ..a ..t ... | ... a.. ... | ... ..c gca ..t | ... ..t ... | ..a> |
| OspA-PKO [ 2558 ] | g.. ... ..a ..t ... | ... a.. ... | ... ..c gca ..t | ......t ... | ..a> |
| OspA-ACAI [ 2556 ] | g.. ... ..a ..t ... | ... a.. ... | ... ..c gca ..t | ... ..t ... | ..a> |
| ospA-P-GAU [ 2544 ] | t.. ... ..a ..t ... | a.. ... ... | ... ..c gca ..t | ... ..t .... | ..a> |

| | 770 | 780 | 790 | 800 | 810 | |
|---|---|---|---|---|---|---|
| OspA-B31 | GGG TCA GCA | GTT GAA ATT | ACA AAA CTT | GAT GAA ATT | AAA AAC GCT | TTA |
| | CCC AGT CGT | CAA CTT TAA | TGT TTT GAA | CTA CTT TAA | TTT TTG CGA | AAT |
| OspA-B31 [ 3288 ] | 770 ... ... ... | 780 ... ... ... | 790 ... ... ... | 800 ... ... ... | 810 ... ... ... | ...> |
| OspA-KA [ 3288 ] | 770 ... ... ... | 780 ... ... ... | 790 ... ... ... | 800 ... ... ... | 810 ... ... ... | ...> |
| OspA-N40 [ 3276 ] | 770 ... ... ... | 780 ... ... ... | 790 ... ... ... | 800 ... ... ... | 810 ... ... ... | ...> |
| OspA-ZS7 [ 3264 ] | 770 ... ... ... | 780 ... ... ... | 790 ... ... ... | 800 ... ... ... | 810 ... ... ... | ...> |
| OspA-25015 [ 2802 ] | 770 ..c a.. ... | 780 ..c ... ... | 790 .a. .c. ... | 800 ... ... ... | 810 c.. ... ... | ...> |
| OspA-TRO [ 2648 ] | 770 ..c aac ... | 780 ..c ... ... | 790 .a. .c. ... | 800 ... ... ... | 810 c.. ... ... | ...> |
| OspA-K48 [ 2584 ] | ..c aa. ... | 780 ..c ... ... | 790 ... .c. ... | 800 a.a ... | 810 c.. ... ... | ...> |
| OspA-HE 11 [ 2580 ] | 770 ..c aa. ... | 780 ..c ... ... | 790 ... .c. ... | 800 a.a ... | 810 c.. ... ... | ...> |
| OspA-DK29 [ 2566 ] | ..c aa. ... | 780 ..c ... ... | 790 ... .c. ... | 800 a.a ... | 810 c.. ... ... | ...> |
| OspA-Ip90 [ 2562 ] | ..c aa. ... | 780 ..c ... ... | 790 ... .cg ... | 800 a.a ... | 810 c.. ... g.t | ...> |
| OspA-BO [ 2558 ] | 770 ..c a.. ... | 780 ..c ... ... | 790 .a. .c. ... | 800 ... ... ... | 810 c.. ... ... | ...> |
| OSPA-IP3 [ 2558 ] | 770 ..c a.. ... | 780 ..c ... ... | 790 .a. .c. ... | 800 ... ... ... | 810 c.. ... ... | ...> |
| OspA-PKO [ 2558 ] | 770 ..c a.. ... | 780 ..c ... ... | 790 .a. .c. ... | 800 ... ... ... | 810 c.. ... ... | ...> |

Figure 42O

```
OspA-ACAI   770         780         790        800         810
[ 2556 ]    ..c a..  ...  ..c ...  ...  .a.  .c.  ...  ...  ...  c..  ...  ...  ...  ...  ..g> ospA-P-GAU  770         780         790        800         810
[ 2544 ]    ..c a..  ...  ..c ...  ...  .a.  .c.  ...  ...  ...  c..  ...  ...  ...  ...  ...>
```

```
                820
                 *
OspA-B31       AAA TAA
               TTT ATT

OspA-B31        820
[ 3288 ]       ... ...>

OspA-KA         820
[ 3288 ]       ... ...>

OspA-N40        820
[ 3276 ]       ... ...>

OspA-ZS7        820
[ 3264 ]       ... ...>

OspA-25015
[ 2802 ]       .g.>

OspA-TRO        820
[ 2648 ]       ... ..>

OspA-K48   820
[ 2584 ]       ... ...>

OspA-HE 11  820
[ 2580 ]       ... ..>

OspA-DK29 820
[ 2566 ]       ... ...>

OspA-Ip90 820
[ 2562 ]       ... ..>

OspA-BO         820
[ 2558 ]       ... ..>

OSPA-IP3        820
[ 2558 ]       ... ..>

OspA-PKO        820
[ 2558 ]       ... ..>

OspA-ACAI       820
[ 2556 ]       ... ...> ospA-P-GAU      820
[ 2544 ]       ... ...>
```

Figure 42P

K48/Tro OspA

```
              10         20         30         40
               *          *          *          *
ATG AAA AAA TAT TTA TTG GGA ATA GGT CTA ATA TTA GCC TTA ATA
TAC TTT TTT ATA AAT AAC CCT TAT CCA GAT TAT AAT CGG AAT TAT 50         60         70         80         90
               *          *          *          *          *
GCA TGT AAG CAA AAT GTT AGC AGC CTT GAT GAA AAA AAT AGC GTT
CGT ACA TTC GTT TTA CAA TCG TCG GAA CTA CTT TTT TTA TCG CAA 100        110        120        130
               *          *          *          *          *
TCA GTA GAT TTA CCT GGT GGA ATG ACA GTT CTT GTA AGT AAA GAA
AGT CAT CTA AAT GGA CCA CCT TAC TGT CAA GAA CAT TCA TTT CTT 140        150        160        170        180
               *          *          *          *          *
AAA GAC AAA GAC GGT AAA TAC AGT CTA GAG GCA ACA GTA GAC AAG
TTT CTG TTT CTG CCA TTT ATG TCA GAT CTC CGT TGT CAT CTG TTC 190        200        210        220
               *          *          *          *          *
CTT GAG CTT AAA GGA ACT TCT GAT AAA AAC AAC GGT TCT GGA ACA
GAA CTC GAA TTT CCT TGA AGA CTA TTT TTG TTG CCA AGA CCT TGT 230        240        250        260        270
               *          *          *          *          *
CTT GAA GGT GAA AAA ACT GAC AAA AGT AAA GTA AAA TTA ACA ATT
GAA CTT CCA CTT TTT TGA CTG TTT TCA TTT CAT TTT AAT TGT TAA 280        290        300        310
               *          *          *          *          *
GCT GAT GAC CTA AGT CAA ACT AAA TTT GAA ATT TTC AAA GAA GAT
CGA CTA CTG GAT TCA GTT TGA TTT AAA CTT TAA AAG TTT CTT CTA 320        330        340        350        360
               *          *          *          *          *
GCC AAA ACA TTA GTA TCA AAA AAA GTA ACC CTT AAA GAC AAG TCA
CGG TTT TGT AAT CAT AGT TTT TTT CAT TGG GAA TTT CTG TTC AGT 370        380        390        400
               *          *          *          *          *
TCA ACA GAA GAA AAA TTC AAC GAA AAG GGT GAA ACA TCT GAA AAA
AGT TGT CTT CTT TTT AAG TTG CTT TTC CCA CTT TGT AGA CTT TTT 410        420        430        440        450
               *          *          *          *          *
ACA ATA GTA AGA GCA AAT GGA ACC AGA CTT GAA TAC ACA GAC ATA
TGT TAT CAT TCT CGT TTA CCT TGG TCT GAA CTT ATG TGT CTG TAT 460        470        480        490
               *          *          *          *          *
AAA AGC GAT GGA TCC GGA AAA GCT AAA GAA GTT TTA AAA GAC TTT
TTT TCG CTA CCT AGG CCT TTT CGA TTT CTT CAA AAT TTT CTG AAA 500        510        520        530        540
               *          *          *          *          *
ACT CTT GAA GGA ACT CTA GCT GCT GAC GGC AAA ACA ACA TTG AAA
TGA GAA CTT CCT TGA GAT CGA CGA CTG CCG TTT TGT TGT AAC TTT 550        560        570        580
               *          *          *          *          *
GTT ACA GAA GGC ACT GTT GTT TTA AGC AAG AAC ATT TTA AAA TCC
```

Figure 43A

K48/Tro OBDA

```
            CAA TGT CTT CCG TGA CAA CAA AAT TCG TTC TTG TAA AAT TTT AGG
       590         600         610         620         630
         *           *           *           *           *
GGA GAA ATA ACA GTT GCA CTT GAT GAC TCT GAC ACT ACT CAG GCT
CCT CTT TAT TGT CAA CGT GAA CTA CTG AGA CTG TGA TGA GTC CGA 640         650         660         670
         *           *           *           *           *
ACT AAA AAA ACT GGA AAA TGG GAT TCA AAT ACT TCC ACT TTA ACA
TGA TTT TTT TGA CCT TTT ACC CTA AGT TTA TGA AGG TGA AAT TGT 680         690         700         710         720
         *           *           *           *           *
ATT AGT GTG AAT AGC AAA AAA ACT AAA AAC ATT GTA TTT ACA AAA
TAA TCA CAC TTA TCG TTT TTT TGA TTT TTG TAA CAT AAA TGT TTT 730         740         750         760
         *           *           *           *           *
GAA GAC ACA ATA ACA GTA CAA AAA TAC GAC TCA GCA GGC ACC AAT
CTT CTG TGT TAT TGT CAT GTT TTT ATG CTG AGT CGT CCG TGG TTA 770         780         790         800         810
         *           *           *           *           *
CTA GAA GGC AAC GCA GTC GAA ATT AAA ACA CTT GAT GAA CTT AAA
GAT CTT CCG TTG CGT CAG CTT TAA TTT TGT GAA CTA CTT GAA TTT

820
         *           *
AAC GCT TTA AAA TAG
TTG CGA AAT TTT ATC
```

Figure 43B

P-GAU/BO-OBDA

```
              10         20         30         40
               *          *          *          *
    ATG AAA AAA TAT TTA TTG GGA ATA GGT CTA ATA TTA GCC TTA ATA
    TAC TTT TTT ATA AAT AAC CCT TAT CCA GAT TAT AAT CGG AAT TAT 50         60         70         80         90
          *          *          *          *          *
    GCA TGC AAG CAA AAT GTT AGC AGC CTT GAT GAA AAA AAC AGC GCT
    CGT ACG TTC GTT TTA CAA TCG TCG GAA CTA CTT TTT TTG TCG CGA 100        110        120        130
               *          *          *          *
    TCA GTA GAT TTG CCT GGT GAG ATG AAA GTT CTT GTA AGT AAA GAA
    AGT CAT CTA AAC GGA CCA CTC TAC TTT CAA GAA CAT TCA TTT CTT 140        150        160        170        180
          *          *          *          *          *
    AAA GAC AAA GAC GGT AAG TAC AGT CTA AAG GCA ACA GTA GAC AAG
    TTT CTG TTT CTG CCA TTC ATG TCA GAT TTC CGT TGT CAT CTG TTC 190        200        210        220
               *          *          *          *
    ATT GAG CTA AAA GGA ACT TCT GAT AAA GAC AAT GGT TCT GGA GTG
    TAA CTC GAT TTT CCT TGA AGA CTA TTT CTG TTA CCA AGA CCT CAC 230        240        250        260        270
          *          *          *          *          *
    CTT GAA GGT ACA AAA GAT GAC AAA AGT AAA GCA AAA TTA ACA ATT
    GAA CTT CCA TGT TTT CTA CTG TTT TCA TTT CGT TTT AAT TGT TAA 280        290        300        310
               *          *          *          *
    GCT GAC GAT CTA AGT AAA ACC ACA TTC GAA CTT TTA AAA GAA GAT
    CGA CTG CTA GAT TCA TTT TGG TGT AAG CTT GAA AAT TTT CTT CTA 320        330        340        350        360
          *          *          *          *          *
    GGC AAA ACA TTA GTG TCA AGA AAA GTA AGT TCT AGA GAC AAA ACA
    CCG TTT TGT AAT CAC AGT TCT TTT CAT TCA AGA TCT CTG TTT TGT 370        380        390        400
               *          *          *          *
    TCA ACA GAT GAA ATG TTC AAT GAA AAA GGT GAA TTG TCT GCA AAA
    AGT TGT CTA CTT TAC AAG TTA CTT TTT CCA CTT AAC AGA CGT TTT 410        420        430        440        450
          *          *          *          *          *
    ACC ATG ACA AGA GAA AAT GGA ACC AAA CTT GAA TAT ACA GAA ATG
    TGG TAC TGT TCT CTT TTA CCT TGG TTT GAA CTT ATA TGT CTT TAC 460        470        480        490
               *          *          *          *
    AAA AGC GAT GGA ACC GGA AAA GCT AAA GAA GTT TTA AAA AAG TTT
    TTT TCG CTA CCT TGG CCT TTT CGA TTT CTT CAA AAT TTT TTC AAA 500        510        520        530        540
          *          *          *          *          *
    ACT CTT GAA GGA AAA GTA GCT AAT GAT AAA GTA ACA TTG GAA GTA
    TGA GAA CTT CCT TTT CAT CGA TTA CTA TTT CAT TGT AAC CTT CAT 550        560        570        580
               *          *          *          *
    AAA GAA GGA ACC GTT ACT TTA AGT AAG GAA ATT GCA AAA TCT GGA
```

Figure 44A p-GAU/BO-OSDA

```
        TTT CTT CCT TGG CAA TGA AAT TCA TTC CTT TAA CGT TTT AGA CCT 590         600         610         620         630
             *           *           *           *           *
        GAA GTA ACA GTT GCT CTT AAT GAC ACT AAC ACT ACT CAG GCT ACT
        CTT CAT TGT CAA CGA GAA TTA CTG TGA TTG TGA TGA GTC CGA TGA 640         650         660         670
                     *           *           *           *           *
        AAA AAA ACT GGC GCA TGG GAT TCA AAA ACT TCT ACT TTA ACA ATT
        TTT TTT TGA CCG CGT ACC CTA AGT TTT TGA AGA TGA AAT TGT TAA 680         690         700         710         720
             *           *           *           *           *
        AGT GTT AAC AGC AAA AAA ACT ACA CAA CTT GTG TTT ACT AAA CAA
        TCA CAA TTG TCG TTT TTT TGA TGT GTT GAA CAC AAA TGA TTT GTT 730         740         750         760
                     *           *           *           *           *
        GAC ACA ATA ACT GTA CAA AAA TAC GAC TCC GCA GGT ACC AAT TTA
        CTG TGT TAT TGA CAT GTT TTT ATG CTG AGG CGT CCA TGG TTA AAT 770         780         790         800         810
             *           *           *           *           *
        GAA GGC ACA GCA GTC GAA ATT AAA ACA CTT GAT GAA CTT AAA AAC
        CTT CCG TGT CGT CAG CTT TAA TTT TGT GAA CTA CTT GAA TTT TTG

820
                     *           *
        GCT TTA AAA TAG
        CGA AAT TTT ATC
```

Figure 44B

B31-PBK

```
              10           20           30           40
               *     *      *     *      *     *      *     *
      ATG AAA AAA TAT TTA TTG GGA ATA GGT CTA ATA TTA GCC TTA ATA
      TAC TTT TTT ATA AAT AAC CCT TAT CCA GAT TAT AAT CGG AAT TAT 50           60           70           80           90
               *     *      *     *      *     *      *     *      *
      GCA TGT AAG CAA AAT GTT AGC AGC CTT GAC GAG AAA AAC AGC GTT
      CGT ACA TTC GTT TTA CAA TCG TCG GAA CTG CTC TTT TTG TCG CAA 100          110          120          130
               *     *      *     *      *     *      *     *
      TCA GTA GAT TTG CCT GGT GAA ATG AAA GTT CTT GTA AGC AAA GAA
      AGT CAT CTA AAC GGA CCA CTT TAC TTT CAA GAA CAT TCG TTT CTT 140          150          160          170          180
               *     *      *     *      *     *      *     *      *
      AAA AAC AAA GAC GGC AAG TAC GAT CTA ATT GCA ACA GTA GAC AAG
      TTT TTG TTT CTG CCG TTC ATG CTA GAT TAA CGT TGT CAT CTG TTC 190          200          210          220
               *     *      *     *      *     *      *     *
      CTT GAG CTT AAA GGA ACT TCT GAT AAA AAC AAT GGA TCT GGA GTA
      GAA CTC GAA TTT CCT TGA AGA CTA TTT TTG TTA CCT AGA CCT CAT 230          240          250          260          270
               *     *      *     *      *     *      *     *      *
      CTT GAA GGC GTA AAA GCT GAC AAA AGT AAA GTA AAA TTA ACA ATT
      GAA CTT CCG CAT TTT CGA CTG TTT TCA TTT CAT TTT AAT TGT TAA 280          290          300          310
               *     *      *     *      *     *      *     *
      TCT GAC GAT CTA GGT CAA ACC ACA CTT GAA GTT TTC AAA GAA GAT
      AGA CTG CTA GAT CCA GTT TGG TGT GAA CTT CAA AAG TTT CTT CTA 320          330          340          350          360
               *     *      *     *      *     *      *     *      *
      GGC AAA ACA CTA GTA TCA AAA AAA GTA ACT TCC AAA GAC AAG TCA
      CCG TTT TGT GAT CAT AGT TTT TTT CAT TGA AGG TTT CTG TTC AGT 370          380          390          400
               *     *      *     *      *     *      *     *
      TCA ACA GAA GAA AAA TTC AAT GAA AAA GGT GAA GTA TCT GAA AAA
      AGT TGT CTT CTT TTT AAG TTA CTT TTT CCA CTT CAT AGA CTT TTT 410          420          430          440          450
               *     *      *     *      *     *      *     *      *
      ATA ATA ACA AGA GCA AAT GGA ACC AAA CTT GAA TAT ACA GAA ATG
      TAT TAT TGT TCT CGT TTA CCT TGG TTT GAA CTT ATA TGT CTT TAC 460          470          480          490
               *     *      *     *      *     *      *     *
      AAA AGC GAT GGA ACC GGA AAA GCT AAA GAA GTT TTA AAA AAG TTT
      TTT TCG CTA CCT TGG CCT TTT CGA TTT CTT CAA AAT TTT TTC AAA 500          510          520          530          540
               *     *      *     *      *     *      *     *      *
      ACT CTT GAA GGA AAA GTA GCT AAT GAT AAA GTA ACA TTG GAA GTA
      TGA GAA CTT CCT TTT CAT CGA TTA CTA TTT CAT TGT AAC CTT CAT 550          560          570          580
               *     *      *     *      *     *      *     *
      AAA GAA GGA ACC GTT ACT TTA AGT AAG GAA ATT TCA AAA TCT GGG
```

Figure 45A

B31-PBK

```
        TTT CTT CCT TGG CAA TGA AAT TCA TTC CTT TAA AGT TTT AGA CCC
          590         600         610         620         630
           *           *           *           *           *
        GAA GTT TCA GTT GAA CTT AAT GAC ACT GAC AGT AGT GCT GCT ACT
        CTT CAA AGT CAA CTT GAA TTA CTG TGA CTG TCA TCA CGA CGA TGA 640         650         660         670
                       *           *           *           *
        AAA AAA ACT GCA GCT TGG AAT TCA AAA ACT TCC ACT TTA ACA ATT
        TTT TTT TGA CGT CGA ACC TTA AGT TTT TGA AGG TGA AAT TGT TAA 680         690         700         710         720
           *           *           *           *           *
        AGT GTG AAT AGC CAA AAA ACC AAA AAC CTT GTA TTC ACA AAA GAA
        TCA CAC TTA TCG GTT TTT TGG TTT TTG GAA CAT AAG TGT TTT CTT 730         740         750         760
                       *           *           *           *
        GAC ACA ATA ACA GTA CAA AAA TAC GAC TCA GCA GGC ACC AAT CTA
        CTG TGT TAT TGT CAT GTT TTT ATG CTG AGT CGT CCG TGG TTA GAT 770         780         790         800         810
           *           *           *           *           *
        GAA GGC AAA GCA GTC GAA ATT ACA ACA CTT AAA GAA CTT AAA AAC
        CTT CCG TTT CGT CAG CTT TAA TGT TGT GAA TTT CTT GAA TTT TTG

820
                       *
        GCT TTA AAA TAA
        CGA AAT TTT ATT
```

Figure 45B

P grav/B31/K48

```
              10           20           30           40
               *            *            *            *
ATG AAA AAA TAT TTA TTG GGA ATA GGT CTA ATA TTA GCC TTA ATA
TAC TTT TTT ATA AAT AAC CCT TAT CCA GAT TAT AAT CGG AAT TAT
         50           60           70           80           90
          *            *            *            *            *
GCA TGC AAG CAA AAT GTT AGC AGC CTT GAT GAA AAA AAC AGC GCT
CGT ACG TTC GTT TTA CAA TCG TCG GAA CTA CTT TTT TTG TCG CGA
             100          110          120          130
               *            *            *            *
TCA GTA GAT TTG CCT GGT GAG ATG AAA GTT CTT GTA AGT AAA GAA
AGT CAT CTA AAC GGA CCA CTC TAC TTT CAA GAA CAT TCA TTT CTT
        140          150          160          170          180
          *            *            *            *            *
AAA GAC AAA GAC GGT AAG TAC AGT CTA AAG GCA ACA GTA GAC AAG
TTT CTG TTT CTG CCA TTC ATG TCA GAT TTC CGT TGT CAT CTG TTC
             190          200          210          220
               *            *            *            *
ATT GAG CTA AAA GGA ACT TCT GAT AAA GAC AAT GGT TCT GGA GTG
TAA CTC GAT TTT CCT TGA AGA CTA TTT CTG TTA CCA AGA CCT CAC
        230          240          250          260          270
          *            *            *            *            *
CTT GAA GGT ACA AAA GAT GAC AAA AGT AAA GCA AAA TTA ACA ATT
GAA CTT CCA TGT TTT CTA CTG TTT TCA TTT CGT TTT AAT TGT TAA
             280          290          300          310
               *            *            *            *
GCT GAC GAT CTA AGT AAA ACC ACA TTC GAA CTT TTA AAA GAA GAT
CGA CTG CTA GAT TCA TTT TGG TGT AAG CTT GAA AAT TTT CTT CTA
        320          330          340          350          360
          *            *            *            *            *
GGC AAA ACA TTA GTG TCA AGA AAA GTA AGT TCT AGA GAC AAA ACA
CCG TTT TGT AAT CAC AGT TCT TTT CAT TCA AGA TCT CTG TTT TGT
             370          380          390          400
               *            *            *            *
TCA ACA GAT GAA ATG TTC AAT GAA AAA GGT GAA TTG TCT GCA AAA
AGT TGT CTA CTT TAC AAG TTA CTT TTT CCA CTT AAC AGA CGT TTT
        410          420          430          440          450
          *            *            *            *            *
ACC ATG ACA AGA GAA AAT GGA ACC AAA CTT GAA TAT ACA GAA ATG
TGG TAC TGT TCT CTT TTA CCT TGG TTT GAA CTT ATA TGT CTT TAC
             460          470          480          490
               *            *            *            *
AAA AGC GAT GGA ACC GGA AAA GCT AAA GAA GTT TTA AAA AAG TTT
TTT TCG CTA CCT TGG CCT TTT CGA TTT CTT CAA AAT TTT TTC AAA
        500          510          520          530          540
          *            *            *            *            *
ACT CTT GAA GGA AAA GTA GCT AAT GAT AAA GTA ACA TTG GAA GTA
TGA GAA CTT CCT TTT CAT CGA TTA CTA TTT CAT TGT AAC CTT CAT
             550          560          570          580
               *            *            *            *
AAA GAA GGA ACC GTT ACT TTA AGT AAG GAA ATT TCA AAA TCT GGG
```

Figure 46A p oav/B31/K48

```
    TTT CTT CCT TGG CAA TGA AAT TCA TTC CTT TAA AGT TTT AGA CCC
        590         600         610         620         630
         *       *   *       *   *       *   *       *   *
    GAA GTT TCA GTT GAA CTT AAT GAC ACT GAC AGT AGT GCT GCT ACT
    CTT CAA AGT CAA CTT GAA TTA CTG TGA CTG TCA TCA CGA CGA TGA 640         650         660         670
             *   *       *   *       *   *       *   *       *
    AAA AAA ACT GCA GCT TGG AAT TCA AAA ACT TCC ACT TTA ACA ATT
    TTT TTT TGA CGT CGA ACC TTA AGT TTT TGA AGG TGA AAT TGT TAA 680         690         700         710         720
         *       *   *       *   *       *   *       *   *
    AGT GTG AAT AGC CAA AAA ACC AAA AAC CTT GTA TTC ACA AAA GAA
    TCA CAC TTA TCG GTT TTT TGG TTT TTG GAA CAT AAG TGT TTT CTT 730         740         750         760
             *   *       *   *       *   *       *   *       *
    GAC ACA ATA ACA GTA CAA AAA TAC GAC TCA GCA GGC ACC AAT CTA
    CTG TGT TAT TGT CAT GTT TTT ATG CTG AGT CGT CCG TGG TTA GAT 770         780         790         800         810
         *       *   *       *   *       *   *       *   *
    GAA GGC AAA GCA GTC GAA ATT ACA ACA CTT AAA GAA CTT AAA AAC
    CTT CCG TTT CGT CAG CTT TAA TGT TGT GAA TTT CTT GAA TTT TTG

820
             *   *
    GCT TTA AAA TAA
    CGA AAT TTT ATT
```

Figure 46B

SEQUENCE LISTING (1) GENERAL INFORMATION:

(iii) NUMBER OF SEQUENCES: 144

(2) INFORMATION FOR SEQ ID NO:1:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (xi) SEQUENCE DESCRIPTION: SEQ ID NO:1:

CTTAATGACT CTGACACTAG TGC      23

(2) INFORMATION FOR SEQ ID NO:2:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (xi) SEQUENCE DESCRIPTION: SEQ ID NO:2:

GCTACTAAAA AAACCGGGAA ATGGAATTCA      30

(2) INFORMATION FOR SEQ ID NO:3:

(i) SEQUENCE CHARACTERISTICS:
      (A) LENGTH: 33 base pairs
      (B) TYPE: nucleic acid (C) STRANDEDNESS: single
            (D) TOPOLOGY: linear (xi) SEQUENCE DESCRIPTION: SEQ ID NO:3:

GCAGCTTGGG ATTCAAAAAC ATCCACTTTA ACA                                    33

(2) INFORMATION FOR SEQ ID NO:4:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:4:

GGAGAATATA TTATGAAA                                                    18

(2) INFORMATION FOR SEQ ID NO:5:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:5:

CTCCTTATTT TAAAGCG                                                     17

(2) INFORMATION FOR SEQ ID NO:6:

(i) SEQUENCE CHARACTERISTICS:
            (A) LENGTH: 822 base pairs
            (B) TYPE: nucleic acid
            (C) STRANDEDNESS: double
            (D) TOPOLOGY: linear (ii) MOLECULE TYPE: DNA (genomic)

(ix) FEATURE:
            (A) NAME/KEY: CDS
            (B) LOCATION: 1..822

(xi) SEQUENCE DESCRIPTION: SEQ ID NO:6:

```
ATG AAA AAA TAT TTA TTG GGA ATA GGT CTA ATA TTA GCC TTA ATA GCA         48
Met Lys Lys Tyr Leu Leu Gly Ile Gly Leu Ile Leu Ala Leu Ile Ala
 1               5                  10                  15

TGT AAG CAA AAT GTT AGC AGC CTT GAC GAG AAA AAC AGC GTT TCA GTA         96
Cys Lys Gln Asn Val Ser Ser Leu Asp Glu Lys Asn Ser Val Ser Val
            20                  25                  30

GAT TTG CCT GGT GAA ATG AAA GTT CTT GTA AGC AAA GAA AAA AAC AAA        144
Asp Leu Pro Gly Glu Met Lys Val Leu Val Ser Lys Glu Lys Asn Lys
        35                  40                  45

GAC GGC AAG TAC GAT CTA ATT GCA ACA GTA GAC AAG CTT GAG CTT AAA        192
Asp Gly Lys Tyr Asp Leu Ile Ala Thr Val Asp Lys Leu Glu Leu Lys
    50                  55                  60

GGA ACT TCT GAT AAA AAC AAT GGA TCT GGA GTA CTT GAA GGC GTA AAA        240
Gly Thr Ser Asp Lys Asn Asn Gly Ser Gly Val Leu Glu Gly Val Lys
65                  70                  75                  80

GCT GAC AAA AGT AAA GTA AAA TTA ACA ATT TCT GAC GAT CTA GGT CAA        288
Ala Asp Lys Ser Lys Val Lys Leu Thr Ile Ser Asp Asp Leu Gly Gln
                85                  90                  95

ACC ACA CTT GAA GTT TTC AAA GAA GAT GGC AAA ACA CTA GTA TCA AAA        336
Thr Thr Leu Glu Val Phe Lys Glu Asp Gly Lys Thr Leu Val Ser Lys
            100                 105                 110
```

```
AAA GTA ACT TCC AAA GAC AAG TCA TCA ACA GAA GAA AAA TTC AAT GAA        384
Lys Val Thr Ser Lys Asp Lys Ser Ser Thr Glu Glu Lys Phe Asn Glu
        115                 120                 125

AAA GGT GAA GTA TCT GAA AAA ATA ATA ACA AGA GCA GAC GGA ACC AGA        432
Lys Gly Glu Val Ser Glu Lys Ile Ile Thr Arg Ala Asp Gly Thr Arg
130                 135                 140

CTT GAA TAC ACA GGA ATT AAA AGC GAT GGA TCT GGA AAA GCT AAA GAG        480
Leu Glu Tyr Thr Gly Ile Lys Ser Asp Gly Ser Gly Lys Ala Lys Glu
145                 150                 155                 160

GTT TTA AAA GGC TAT GTT CTT GAA GGA ACT CTA ACT GCT GAA AAA ACA        528
Val Leu Lys Gly Tyr Val Leu Glu Gly Thr Leu Thr Ala Glu Lys Thr
                165                 170                 175

ACA TTG GTG GTT AAA GAA GGA ACT GTT ACT TTA AGC AAA AAT ATT TCA        576
Thr Leu Val Val Lys Glu Gly Thr Val Thr Leu Ser Lys Asn Ile Ser
            180                 185                 190

AAA TCT GGG GAA GTT TCA GTT GAA CTT AAT GAC ACT GAC AGT AGT GCT        624
Lys Ser Gly Glu Val Ser Val Glu Leu Asn Asp Thr Asp Ser Ser Ala
        195                 200                 205

GCT ACT AAA AAA ACT GCA GCT TGG AAT TCA GGC ACT TCA ACT TTA ACA        672
Ala Thr Lys Lys Thr Ala Ala Trp Asn Ser Gly Thr Ser Thr Leu Thr
    210                 215                 220

ATT ACT GTA AAC AGT AAA AAA ACT AAA GAC CTT GTG TTT ACA AAA GAA        720
Ile Thr Val Asn Ser Lys Lys Thr Lys Asp Leu Val Phe Thr Lys Glu
225                 230                 235                 240

AAC ACA ATT ACA GTA CAA CAA TAC GAC TCA AAT GGC ACC AAA TTA GAG        768
Asn Thr Ile Thr Val Gln Gln Tyr Asp Ser Asn Gly Thr Lys Leu Glu
                245                 250                 255

GGG TCA GCA GTT GAA ATT ACA AAA CTT GAT GAA ATT AAA AAC GCT TTA        816
Gly Ser Ala Val Glu Ile Thr Lys Leu Asp Glu Ile Lys Asn Ala Leu
            260                 265                 270

AAA TAA                                                                822
Lys
```

(2) INFORMATION FOR SEQ ID NO:7:

(i) SEQUENCE CHARACTERISTICS:
        (A) LENGTH: 273 amino acids
        (B) TYPE: amino acid
        (D) TOPOLOGY: linear (ii) MOLECULE TYPE: protein (xi) SEQUENCE DESCRIPTION: SEQ ID NO:7:

```
Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
                20                  25                  30

Asp Leu Pro Gly Glu Met Lys Val Leu Val Ser Lys Glu Lys Asn Lys
            35                  40                  45

Asp Gly Lys Tyr Asp Leu Ile Ala Thr Val Asp Lys Leu Glu Leu Lys
        50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125
```

```
Lys Gly Glu Val Ser Glu Lys Ile Ile Thr Arg Ala Asp Gly Thr Arg
            130                 135                 140

Leu Glu Tyr Thr Gly Ile Lys Ser Asp Gly Gly Lys Ala Lys Glu
145                 150                 155                 160

Val Leu Lys Gly Tyr Val Leu Glu Gly Thr Leu Thr Ala Glu Lys Thr
                165                 170                 175

Thr Leu Val Val Lys Glu Gly Val Thr Leu Ser Lys Asn Ile Ser
            180                 185                 190

Lys Ser Gly Glu Val Ser Val Glu Leu Asn Asp Thr Asp Ser Ser Ala
            195                 200                 205

Ala Thr Lys Lys Thr Ala Ala Trp Asn Ser Gly Thr Ser Thr Leu Thr
    210                 215                 220

Ile Thr Val Asn Ser Lys Lys Thr Lys Asp Leu Val Phe Thr Lys Glu
225                 230                 235                 240

Asn Thr Ile Thr Val Gln Gln Tyr Asp Ser Asn Gly Thr Lys Leu Glu
                245                 250                 255

Gly Ser Ala Val Glu Ile Thr Lys Leu Asp Glu Ile Lys Asn Ala Leu
                260                 265                 270

Lys
```

(2) INFORMATION FOR SEQ ID NO:8:

(i) SEQUENCE CHARACTERISTICS:
        (A) LENGTH: 825 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..825

(xi) SEQUENCE DESCRIPTION: SEQ ID NO:8:

```
ATG AAA AAA TAT TTA TTG GGA ATA GGT CTA ATA TTA GCC TTA ATA GCA      48
Met Lys Lys Tyr Leu Leu Gly Ile Gly Leu Ile Leu Ala Leu Ile Ala
 1               5                  10                  15

TGT AAG CAA AAT GTT AGC AGC CTT GAT GAA AAA AAT AGC GTT TCA GTA      96
Cys Lys Gln Asn Val Ser Ser Leu Asp Glu Lys Asn Ser Val Ser Val
             20                  25                  30

GAT TTA CCT GGT GGA ATG ACA GTT CTT GTA AGT AAA GAA AAA GAC AAA     144
Asp Leu Pro Gly Gly Met Thr Val Leu Val Ser Lys Glu Lys Asp Lys
         35                  40                  45

GAC GGT AAA TAC AGT CTA GAG GCA ACA GTA GAC AAG CTT GAG CTT AAA     192
Asp Gly Lys Tyr Ser Leu Glu Ala Thr Val Asp Lys Leu Glu Leu Lys
     50                  55                  60

GGA ACT TCT GAT AAA AAC AAC GGT TCT GGA ACA CTT GAA GGT GAA AAA     240
Gly Thr Ser Asp Lys Asn Asn Gly Ser Gly Thr Leu Glu Gly Glu Lys
 65                  70                  75                  80

ACT GAC AAA AGT AAA GTA AAA TTA ACA ATT GCT GAT GAC CTA AGT CAA     288
Thr Asp Lys Ser Lys Val Lys Leu Thr Ile Ala Asp Asp Leu Ser Gln
                 85                  90                  95

ACT AAA TTT GAA ATT TTC AAA GAA GAT GCC AAA ACA TTA GTA TCA AAA     336
Thr Lys Phe Glu Ile Phe Lys Glu Asp Ala Lys Thr Leu Val Ser Lys
            100                 105                 110

AAA GTA ACC CTT AAA GAC AAG TCA TCA ACA GAA GAA AAA TTC AAC GAA     384
Lys Val Thr Leu Lys Asp Lys Ser Ser Thr Glu Glu Lys Phe Asn Glu
        115                 120                 125
```

```
AAG GGT GAA ACA TCT GAA AAA ACA ATA GTA AGA GCA AAT GGA ACC AGA          432
Lys Gly Glu Thr Ser Glu Lys Thr Ile Val Arg Ala Asn Gly Thr Arg
        130                 135                 140

CTT GAA TAC ACA GAC ATA AAA AGC GAT GGA TCC GGA AAA GCT AAA GAA          480
Leu Glu Tyr Thr Asp Ile Lys Ser Asp Gly Ser Gly Lys Ala Lys Glu
145                 150                 155                 160

GTT TTA AAA GAC TTT ACT CTT GAA GGA ACT CTA GCT GCT GAC GGC AAA          528
Val Leu Lys Asp Phe Thr Leu Glu Gly Thr Leu Ala Ala Asp Gly Lys
                165                 170                 175

ACA ACA TTG AAA GTT ACA GAA GGC ACT GTT GTT TTA AGC AAG AAC ATT          576
Thr Thr Leu Lys Val Thr Glu Gly Thr Val Val Leu Ser Lys Asn Ile
        180                 185                 190

TTA AAA TCC GGA GAA ATA ACA GTT GCA CTT GAT GAC TCT GAC ACT ACT          624
Leu Lys Ser Gly Glu Ile Thr Val Ala Leu Asp Asp Ser Asp Thr Thr
195                 200                 205

CAG GCT ACT AAA AAA ACT GGA AAA TGG GAT TCA AAA ACT TCC ACT TTA          672
Gln Ala Thr Lys Lys Thr Gly Lys Trp Asp Ser Lys Thr Ser Thr Leu
        210                 215                 220

ACA ATT AGT GTG AAT AGC CAA AAA ACC AAA AAC CTT GTA TTC ACA AAA          720
Thr Ile Ser Val Asn Ser Gln Lys Thr Lys Asn Leu Val Phe Thr Lys
225                 230                 235                 240

GAA GAC ACA ATA ACA GTA CAA AAA TAC GAC TCA GCA GGC ACC AAT CTA          768
Glu Asp Thr Ile Thr Val Gln Lys Tyr Asp Ser Ala Gly Thr Asn Leu
                245                 250                 255

GAA GGC AAA GCA GTC GAA ATT ACA ACA CTT AAA GAA CTT AAA AAC GCT          816
Glu Gly Lys Ala Val Glu Ile Thr Thr Leu Lys Glu Leu Lys Asn Ala
        260                 265                 270

TTA AAA TAA                                                              825
Leu Lys
    275

(2) INFORMATION FOR SEQ ID NO:9:

(i) SEQUENCE CHARACTERISTICS:
        (A) LENGTH: 274 amino acids
        (B) TYPE: amino acid
        (D) TOPOLOGY: linear (ii) MOLECULE TYPE: protein (xi) SEQUENCE DESCRIPTION: SEQ ID NO:9:

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Gly Met Thr Val Leu Val Ser Lys Glu Lys Asp Lys
        35                  40                  45

Asp Gly Lys Tyr Ser Leu Glu Ala Thr Val Asp Lys Leu Glu Leu Lys
    50                  55                  60

Gly Thr Ser Asp Lys Asn Gly Ser Gly Thr Leu Glu Gly Glu Lys
65                  70                  75                  80

Thr Asp Lys Ser Lys Val Lys Leu Thr Ile Ala Asp Leu Ser Gln
            85                  90                  95

Thr Lys Phe Glu Ile Phe Lys Glu Asp Ala Lys Thr Leu Val Ser Lys
            100                 105                 110

Lys Val Thr Leu Lys Asp Lys Ser Ser Thr Glu Glu Lys Phe Asn Glu
        115                 120                 125

Lys Gly Glu Thr Ser Glu Lys Thr Ile Val Arg Ala Asn Gly Thr Arg
    130                 135                 140
```

```
Leu Glu Tyr Thr Asp Ile Lys Ser Asp Gly Ser Gly Lys Ala Lys Glu
145                 150                 155                 160

Val Leu Lys Asp Phe Thr Leu Glu Gly Thr Leu Ala Ala Asp Gly Lys
                165                 170                 175

Thr Thr Leu Lys Val Thr Glu Gly Thr Val Val Leu Ser Lys Asn Ile
            180                 185                 190

Leu Lys Ser Gly Glu Ile Thr Val Ala Leu Asp Asp Ser Asp Thr Thr
        195                 200                 205

Gln Ala Thr Lys Lys Thr Gly Lys Trp Asp Ser Lys Thr Ser Thr Leu
    210                 215                 220

Thr Ile Ser Val Asn Ser Gln Lys Thr Lys Asn Leu Val Phe Thr Lys
225                 230                 235                 240

Glu Asp Thr Ile Thr Val Gln Lys Tyr Asp Ser Ala Gly Thr Asn Leu
                245                 250                 255

Glu Gly Lys Ala Val Glu Ile Thr Thr Leu Lys Glu Leu Lys Asn Ala
            260                 265                 270

Leu Lys
```

(2) INFORMATION FOR SEQ ID NO:10:

(i) SEQUENCE CHARACTERISTICS:
        (A) LENGTH: 822 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..822

(xi) SEQUENCE DESCRIPTION: SEQ ID NO:10:

```
ATG AAA AAA TAT TTA TTG GGA ATA GGT CTA ATA TTA GCC TTA ATA GCA    48
Met Lys Lys Tyr Leu Leu Gly Ile Gly Leu Ile Leu Ala Leu Ile Ala
 1               5                  10                  15

TGC AAG CAA AAT GTT AGC AGC CTT GAT GAA AAA AAC AGC GCT TCA GTA    96
Cys Lys Gln Asn Val Ser Ser Leu Asp Glu Lys Asn Ser Ala Ser Val
                 20                  25                  30

GAT TTG CCT GGT GAG ATG AAA GTT CTT GTA AGT AAA GAA AAA GAC AAA   144
Asp Leu Pro Gly Glu Met Lys Val Leu Val Ser Lys Glu Lys Asp Lys
             35                  40                  45

GAC GGT AAG TAC AGT CTA AAG GCA ACA GTA GAC AAG ATT GAG CTA AAA   192
Asp Gly Lys Tyr Ser Leu Lys Ala Thr Val Asp Lys Ile Glu Leu Lys
         50                  55                  60

GGA ACT TCT GAT AAA GAC AAT GGT TCT GGA GTG CTT GAA GGT ACA AAA   240
Gly Thr Ser Asp Lys Asp Asn Gly Ser Gly Val Leu Glu Gly Thr Lys
 65                  70                  75                  80

GAT GAC AAA AGT AAA GCA AAA TTA ACA ATT GCT GAC GAT CTA AGT AAA   288
Asp Asp Lys Ser Lys Ala Lys Leu Thr Ile Ala Asp Asp Leu Ser Lys
                 85                  90                  95

ACC ACA TTC GAA CTT TTA AAA GAA GAT GGC AAA ACA TTA GTG TCA AGA   336
Thr Thr Phe Glu Leu Leu Lys Glu Asp Gly Lys Thr Leu Val Ser Arg
                100                 105                 110

AAA GTA AGT TCT AGA GAC AAA ACA TCA ACA GAT GAA ATG TTC AAT GAA   384
Lys Val Ser Ser Arg Asp Lys Thr Ser Thr Asp Glu Met Phe Asn Glu
            115                 120                 125

AAA GGT GAA TTG TCT GCA AAA ACC ATG ACA AGA GAA AAT GGA ACC AAA   432
Lys Gly Glu Leu Ser Ala Lys Thr Met Thr Arg Glu Asn Gly Thr Lys
        130                 135                 140
```

```
CTT GAA TAT ACA GAA ATG AAA AGC GAT GGA ACC GGA AAA GCT AAA GAA    480
Leu Glu Tyr Thr Glu Met Lys Ser Asp Gly Thr Gly Lys Ala Lys Glu
145                 150                 155                 160

GTT TTA AAA AAG TTT ACT CTT GAA GGA AAA GTA GCT AAT GAT AAA GTA    528
Val Leu Lys Lys Phe Thr Leu Glu Gly Lys Val Ala Asn Asp Lys Val
                165                 170                 175

ACA TTG GAA GTA AAA GAA GGA ACC GTT ACT TTA AGT AAG GAA ATT GCA    576
Thr Leu Glu Val Lys Glu Gly Thr Val Thr Leu Ser Lys Glu Ile Ala
            180                 185                 190

AAA TCT GGA GAA GTA ACA GTT GCT CTT AAT GAC ACT AAC ACT ACT CAG    624
Lys Ser Gly Glu Val Thr Val Ala Leu Asn Asp Thr Asn Thr Thr Gln
        195                 200                 205

GCT ACT AAA AAA ACT GGC GCA TGG GAT TCA AAA ACT TCT ACT TTA ACA    672
Ala Thr Lys Lys Thr Gly Ala Trp Asp Ser Lys Thr Ser Thr Leu Thr
    210                 215                 220

ATT AGT GTT AAC AGC AAA AAA ACT ACA CAA CTT GTG TTT ACT AAA CAA    720
Ile Ser Val Asn Ser Lys Lys Thr Thr Gln Leu Val Phe Thr Lys Gln
225                 230                 235                 240

TAC ACA ATA ACT GTA AAA CAA TAC GAC TCC GCA GGT ACC AAT TTA GAA    768
Tyr Thr Ile Thr Val Lys Gln Tyr Asp Ser Ala Gly Thr Asn Leu Glu
                245                 250                 255

GGC ACA GCA GTC GAA ATT AAA ACA CTT GAT GAA CTT AAA AAC GCT TTA    816
Gly Thr Ala Val Glu Ile Lys Thr Leu Asp Glu Leu Lys Asn Ala Leu
            260                 265                 270

AAA TAA                                                            822
Lys
```

(2) INFORMATION FOR SEQ ID NO:11:

(i) SEQUENCE CHARACTERISTICS:
        (A) LENGTH: 273 amino acids
        (B) TYPE: amino acid
        (D) TOPOLOGY: linear (ii) MOLECULE TYPE: protein (xi) SEQUENCE DESCRIPTION: SEQ ID NO:11:

```
Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Ala Ser Val
                20                  25                  30

Asp Leu Pro Gly Glu Met Lys Val Leu Val Ser Lys Glu Lys Asp Lys
            35                  40                  45

Asp Gly Lys Tyr Ser Leu Lys Ala Thr Val Asp Lys Ile Glu Leu Lys
        50                  55                  60

Gly Thr Ser Asp Lys Asp Asn Gly Ser Gly Val Leu Glu Gly Thr Lys
65                  70                  75                  80

Asp Asp Lys Ser Lys Ala Lys Leu Thr Ile Ala Asp Asp Leu Ser Lys
                85                  90                  95

Thr Thr Phe Glu Leu Leu Lys Glu Asp Gly Lys Thr Leu Val Ser Arg
            100                 105                 110

Lys Val Ser Ser Arg Asp Lys Thr Ser Thr Asp Glu Met Phe Asn Glu
        115                 120                 125

Lys Gly Glu Leu Ser Ala Lys Thr Met Thr Arg Glu Asn Gly Thr Lys
    130                 135                 140

Leu Glu Tyr Thr Glu Met Lys Ser Asp Gly Thr Gly Lys Ala Lys Glu
145                 150                 155                 160

Val Leu Lys Lys Phe Thr Leu Glu Gly Lys Val Ala Asn Asp Lys Val
                165                 170                 175
```

-continued

```
Thr Leu Glu Val Lys Glu Gly Thr Val Thr Leu Ser Lys Glu Ile Ala
            180                 185                 190
Lys Ser Gly Glu Val Thr Val Ala Leu Asn Asp Thr Asn Thr Thr Gln
        195                 200                 205
Ala Thr Lys Lys Thr Gly Ala Trp Asp Ser Lys Thr Ser Thr Leu Thr
    210                 215                 220
Ile Ser Val Asn Ser Lys Lys Thr Thr Gln Leu Val Phe Thr Lys Gln
225                 230                 235                 240
Tyr Thr Ile Thr Val Lys Gln Tyr Asp Ser Ala Gly Thr Asn Leu Glu
                245                 250                 255
Gly Thr Ala Val Glu Ile Lys Thr Leu Asp Glu Leu Lys Asn Ala Leu
            260                 265                 270
Lys
```

(2) INFORMATION FOR SEQ ID NO:12:

(i) SEQUENCE CHARACTERISTICS:
        (A) LENGTH: 819 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..819

(xi) SEQUENCE DESCRIPTION: SEQ ID NO:12:

```
ATG AAA AAA TAT TTA TTG GGA ATA GGT CTA ATA TTA GCT TTA ATA GCA      48
Met Lys Lys Tyr Leu Leu Gly Ile Gly Leu Ile Leu Ala Leu Ile Ala
 1               5                  10                  15

TGT AAG CAA AAT GTT AGC AGC CTT GAC GAG AAA AAC AGC GTT TCA GTA      96
Cys Lys Gln Asn Val Ser Ser Leu Asp Glu Lys Asn Ser Val Ser Val
                20                  25                  30

GAT TTG CCT GGT GAA ATG AAA GTT CTT GTA AGC AAA GAA AAA GAC AAA     144
Asp Leu Pro Gly Glu Met Lys Val Leu Val Ser Lys Glu Lys Asp Lys
            35                  40                  45

GAC GGC AAG TAC AGT CTA ATG GCA ACA GTA GAC AAG CTT GAG CTT AAA     192
Asp Gly Lys Tyr Ser Leu Met Ala Thr Val Asp Lys Leu Glu Leu Lys
        50                  55                  60

GGA ACA TCT GAT AAA AAC AAT GGA TCT GGG GTG CTT GAA GGC GTA AAA     240
Gly Thr Ser Asp Lys Asn Asn Gly Ser Gly Val Leu Glu Gly Val Lys
 65                  70                  75                  80

GCT GAC AAA AGC AAA GTA AAA TTA ACA GTT TCT GAC GAT CTA AGC ACA     288
Ala Asp Lys Ser Lys Val Lys Leu Thr Val Ser Asp Asp Leu Ser Thr
                85                  90                  95

ACC ACA CTT GAA GTT TTA AAA GAA GAT GGC AAA ACA TTA GTG TCA AAA     336
Thr Thr Leu Glu Val Leu Lys Glu Asp Gly Lys Thr Leu Val Ser Lys
                100                 105                 110

AAA AGA ACT TCT AAA GAT AAG TCA TCA ACA GAA GAA AAG TTC AAT GAA     384
Lys Arg Thr Ser Lys Asp Lys Ser Ser Thr Glu Glu Lys Phe Asn Glu
            115                 120                 125

AAA GGC GAA TTA GTT GAA AAA ATA ATG GCA AGA GCA AAC GGA ACC ATA     432
Lys Gly Glu Leu Val Glu Lys Ile Met Ala Arg Ala Asn Gly Thr Ile
        130                 135                 140

CTT GAA TAC ACA GGA ATT AAA AGC GAT GGA TCC GGA AAA GCT AAA GAA     480
Leu Glu Tyr Thr Gly Ile Lys Ser Asp Gly Ser Gly Lys Ala Lys Glu
145                 150                 155                 160
```

```
ACT TTA AAA GAA TAT GTT CTT GAA GGA ACT CTA ACT GCT GAA AAA GCA    528
Thr Leu Lys Glu Tyr Val Leu Glu Gly Thr Leu Thr Ala Glu Lys Ala
            165                 170                 175

ACA TTG GTG GTT AAA GAA GGA ACT GTT ACT TTA AGT AAG CAC ATT TCA    576
Thr Leu Val Val Lys Glu Gly Thr Val Thr Leu Ser Lys His Ile Ser
        180                 185                 190

AAA TCT GGA GAA GTA ACA GCT GAA CTT AAT GAC ACT GAC AGT ACT CAA    624
Lys Ser Gly Glu Val Thr Ala Glu Leu Asn Asp Thr Asp Ser Thr Gln
            195                 200                 205

GCT ACT AAA AAA ACT GGG AAA TGG GAT GCA GGC ACT TCA ACT TTA ACA    672
Ala Thr Lys Lys Thr Gly Lys Trp Asp Ala Gly Thr Ser Thr Leu Thr
        210                 215                 220

ATT ACT GTA AAC AAC AAA AAA ACT AAA GCC CTT GTA TTT ACA AAA CAA    720
Ile Thr Val Asn Asn Lys Lys Thr Lys Ala Leu Val Phe Thr Lys Gln
225                 230                 235                 240

GAC ACA ATT ACA TCA CAA AAA TAC GAC TCA GCA GGA ACC AAC TTG GAA    768
Asp Thr Ile Thr Ser Gln Lys Tyr Asp Ser Ala Gly Thr Asn Leu Glu
            245                 250                 255

GGC ACA GCA GTC GAA ATT AAA ACA CTT GAT GAA CTT AAA AAC GCT TTA    816
Gly Thr Ala Val Glu Ile Lys Thr Leu Asp Glu Leu Lys Asn Ala Leu
        260                 265                 270

AGA                                                                819
Arg
```

(2) INFORMATION FOR SEQ ID NO:13:

(i) SEQUENCE CHARACTERISTICS:
        (A) LENGTH: 273 amino acids
        (B) TYPE: amino acid
        (D) TOPOLOGY: linear (ii) MOLECULE TYPE: protein (xi) SEQUENCE DESCRIPTION: SEQ ID NO:13:

```
Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asp Lys
        35                  40                  45

Asp Gly Lys Tyr Ser Leu Met Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Val Ser Asp Asp Leu Ser Thr
                85                  90                  95

Thr Thr Leu Glu Val Leu Lys Glu Asp Gly Lys Thr Leu Val Ser Lys
            100                 105                 110

Lys Arg Thr Ser Lys Asp Lys Ser Ser Thr Glu Glu Lys Phe Asn Glu
        115                 120                 125

Lys Gly Glu Leu Val Glu Lys Ile Met Ala Arg Ala Asn Gly Thr Ile
    130                 135                 140

Leu Glu Tyr Thr Gly Ile Lys Ser Asp Gly Ser Gly Lys Ala Lys Glu
145                 150                 155                 160

Thr Leu Lys Glu Tyr Val Leu Glu Gly Thr Leu Thr Ala Glu Lys Ala
                165                 170                 175

Thr Leu Val Val Lys Glu Gly Thr Val Thr Leu Ser Lys His Ile Ser
            180                 185                 190
```

Lys Ser Gly Glu Val Thr Ala Glu Leu Asn Asp Thr Asp Ser Thr Gln
        195                 200                 205

Ala Thr Lys Lys Thr Gly Lys Trp Asp Ala Gly Thr Ser Thr Leu Thr
        210                 215                 220

Ile Thr Val Asn Asn Lys Lys Thr Lys Ala Leu Val Phe Thr Lys Gln
225                 230                 235                 240

Asp Thr Ile Thr Ser Gln Lys Tyr Asp Ser Ala Gly Thr Asn Leu Glu
            245                 250                 255

Gly Thr Ala Val Glu Ile Lys Thr Leu Asp Glu Leu Lys Asn Ala Leu
            260                 265                 270

Arg (2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:14:

GTCTGCAAAA ACCATGACAA G                                        21

(2) INFORMATION FOR SEQ ID NO:15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:15:

GTCATCAACA GAAGAAAAAT TC                                     22

(2) INFORMATION FOR SEQ ID NO:16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:16:

CCGGATCCAT ATGAAAAAAT ATTTATTGGG                          30

(2) INFORMATION FOR SEQ ID NO:17:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:17:

CCGGGATCCA TATGGCTAAG CAAAATGTTA GC                     32

(2) INFORMATION FOR SEQ ID NO:18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:18:

```
GCGTTCAAGT ACTCCAGA                                                  18

(2) INFORMATION FOR SEQ ID NO:19:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:19:

GATATCTAGA TCTTATTTTA AAGCGTT                                        27

(2) INFORMATION FOR SEQ ID NO:20:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:20:

GGATCCGGTG ACCTTTTAAA GCGTTTTTAA T                                   31

(2) INFORMATION FOR SEQ ID NO:21:

(i) SEQUENCE CHARACTERISTICS:
        (A) LENGTH: 891 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..891

(xi) SEQUENCE DESCRIPTION: SEQ ID NO:21:
```

| | | | | | | | | | | | | | | | | |
|---|---|---|---|---|---|---|---|---|---|---|---|---|---|---|---|---|
| ATG | AGA | TTA | TTA | ATA | GGA | TTT | GCT | TTA | GCG | TTA | GCT | TTA | ATA | GGA | TGT | 48 |
| Met | Arg | Leu | Leu | Ile | Gly | Phe | Ala | Leu | Ala | Leu | Ala | Leu | Ile | Gly | Cys | |
| 1 | | | | 5 | | | | | 10 | | | | | 15 | | |
| GCA | CAA | AAA | GGT | GCT | GAG | TCA | ATT | GGT | TCT | CAA | AAA | GAA | AAT | GAT | CTA | 96 |
| Ala | Gln | Lys | Gly | Ala | Glu | Ser | Ile | Gly | Ser | Gln | Lys | Glu | Asn | Asp | Leu | |
| | | | 20 | | | | | 25 | | | | | 30 | | | |
| AAC | CTT | GAA | GAC | TCT | AGT | AAA | AAA | TCA | CAT | CAA | AAC | GCT | AAA | CAA | GAC | 144 |
| Asn | Leu | Glu | Asp | Ser | Ser | Lys | Lys | Ser | His | Gln | Asn | Ala | Lys | Gln | Asp | |
| | | 35 | | | | | 40 | | | | | 45 | | | | |
| CTT | CCT | GCG | GTG | ACA | GAA | GAC | TCA | GTG | TCT | TTG | TTT | AAT | GGT | AAT | AAA | 192 |
| Leu | Pro | Ala | Val | Thr | Glu | Asp | Ser | Val | Ser | Leu | Phe | Asn | Gly | Asn | Lys | |
| | 50 | | | | | 55 | | | | | 60 | | | | | |
| ATT | TTT | GTA | AGC | AAA | GAA | AAA | AAT | AGC | TCC | GGC | AAA | TAT | GAT | TTA | AGA | 240 |
| Ile | Phe | Val | Ser | Lys | Glu | Lys | Asn | Ser | Ser | Gly | Lys | Tyr | Asp | Leu | Arg | |
| 65 | | | | | 70 | | | | | 75 | | | | | 80 | |
| GCA | ACA | ATT | GAT | CAG | GTT | GAA | CTT | AAA | GGA | ACT | TCC | GAT | AAA | AAC | AAT | 288 |
| Ala | Thr | Ile | Asp | Gln | Val | Glu | Leu | Lys | Gly | Thr | Ser | Asp | Lys | Asn | Asn | |
| | | | | 85 | | | | | 90 | | | | | 95 | | |
| GGT | TCT | GGA | ACC | CTT | GAA | GGT | TCA | AAG | CCT | GAC | AAG | AGT | AAA | GTA | AAA | 336 |
| Gly | Ser | Gly | Thr | Leu | Glu | Gly | Ser | Lys | Pro | Asp | Lys | Ser | Lys | Val | Lys | |
| | | | 100 | | | | | 105 | | | | | 110 | | | |
| TTA | ACA | GTT | TCT | GCT | GAT | TTA | AAC | ACA | GTA | ACC | TTA | GAA | GCA | TTT | GAT | 384 |
| Leu | Thr | Val | Ser | Ala | Asp | Leu | Asn | Thr | Val | Thr | Leu | Glu | Ala | Phe | Asp | |
| | | 115 | | | | | 120 | | | | | 125 | | | | |

```
GCC AGC AAC CAA AAA ATT TCA AGT AAA GTT ACT AAA AAA CAG GGG TCA      432
Ala Ser Asn Gln Lys Ile Ser Ser Lys Val Thr Lys Lys Gln Gly Ser
    130                 135                 140

ATA ACA GAG GAA ACT CTC AAA GCT AAT AAA TTA GAC TCA AAG AAA TTA      480
Ile Thr Glu Glu Thr Leu Lys Ala Asn Lys Leu Asp Ser Lys Lys Leu
145                 150                 155                 160

ACA AGA TCA AAC GGA ACT ACA CTT GAA TAC TCA CAA ATA ACA GAT GCT      528
Thr Arg Ser Asn Gly Thr Thr Leu Glu Tyr Ser Gln Ile Thr Asp Ala
                165                 170                 175

GAC AAT GCT ACA AAA GCA GTA GAA ACT CTA AAA AAT AGC ATT AAG CTT      576
Asp Asn Ala Thr Lys Ala Val Glu Thr Leu Lys Asn Ser Ile Lys Leu
            180                 185                 190

GAA GGA AGT CTT GTA GTC GGA AAA ACA ACA GTG GAA ATT AAA GAA GGT      624
Glu Gly Ser Leu Val Val Gly Lys Thr Thr Val Glu Ile Lys Glu Gly
        195                 200                 205

ACT GTT ACT CTA AAA AGA GAA ATT GAA AAA GAT GGA AAA GTA AAA GTC      672
Thr Val Thr Leu Lys Arg Glu Ile Glu Lys Asp Gly Lys Val Lys Val
    210                 215                 220

TTT TTG AAT GAC ACT GCA GGT TCT AAC AAA AAA ACA GGT AAA TGG GAA      720
Phe Leu Asn Asp Thr Ala Gly Ser Asn Lys Lys Thr Gly Lys Trp Glu
225                 230                 235                 240

GAC AGT ACT AGC ACT TTA ACA ATT AGT GCT GAC AGC AAA AAA ACT AAA      768
Asp Ser Thr Ser Thr Leu Thr Ile Ser Ala Asp Ser Lys Lys Thr Lys
                245                 250                 255

GAT TTG GTG TTC TTA ACA GAT GGT ACA ATT ACA GTA CAA CAA TAC AAC      816
Asp Leu Val Phe Leu Thr Asp Gly Thr Ile Thr Val Gln Gln Tyr Asn
            260                 265                 270

ACA GCT GGA ACC AGC CTA GAA GGA TCA GCA AGT GAA ATT AAA AAT CTT      864
Thr Ala Gly Thr Ser Leu Glu Gly Ser Ala Ser Glu Ile Lys Asn Leu
        275                 280                 285

TCA GAG CTT AAA AAC GCT TTA AAA TAA                                  891
Ser Glu Leu Lys Asn Ala Leu Lys
    290                 295

(2) INFORMATION FOR SEQ ID NO:22:

(i) SEQUENCE CHARACTERISTICS:
        (A) LENGTH: 296 amino acids
        (B) TYPE: amino acid
        (D) TOPOLOGY: linear (ii) MOLECULE TYPE: protein (xi) SEQUENCE DESCRIPTION: SEQ ID NO:22:

Met Arg Leu Leu Ile Gly Phe Ala Leu Ala Leu Ala Leu Ile Gly Cys
  1               5                  10                  15

Ala Gln Lys Gly Ala Glu Ser Ile Gly Ser Gln Lys Glu Asn Asp Leu
                20                  25                  30

Asn Leu Glu Asp Ser Ser Lys Lys Ser His Gln Asn Ala Lys Gln Asp
            35                  40                  45

Leu Pro Ala Val Thr Glu Asp Ser Val Ser Leu Phe Asn Gly Asn Lys
    50                  55                  60

Ile Phe Val Ser Lys Glu Lys Asn Ser Ser Gly Lys Tyr Asp Leu Arg
 65                 70                  75                  80

Ala Thr Ile Asp Gln Val Glu Leu Lys Gly Thr Ser Asp Lys Asn Asn
                85                  90                  95

Gly Ser Gly Thr Leu Glu Gly Ser Lys Pro Asp Lys Ser Lys Val Lys
                100                 105                 110

Leu Thr Val Ser Ala Asp Leu Asn Thr Val Thr Leu Glu Ala Phe Asp
            115                 120                 125
```

```
Ala Ser Asn Gln Lys Ile Ser Ser Lys Val Thr Lys Lys Gln Gly Ser
        130                 135                 140
Ile Thr Glu Glu Thr Leu Lys Ala Asn Lys Leu Asp Ser Lys Lys Leu
145                 150                 155                 160
Thr Arg Ser Asn Gly Thr Thr Leu Glu Tyr Ser Gln Ile Thr Asp Ala
                165                 170                 175
Asp Asn Ala Thr Lys Ala Val Glu Thr Leu Lys Asn Ser Ile Lys Leu
            180                 185                 190
Glu Gly Ser Leu Val Val Gly Lys Thr Val Glu Ile Lys Glu Gly
        195                 200                 205
Thr Val Thr Leu Lys Arg Glu Ile Glu Lys Asp Gly Lys Val Lys Val
    210                 215                 220
Phe Leu Asn Asp Thr Ala Gly Ser Asn Lys Lys Thr Gly Lys Trp Glu
225                 230                 235                 240
Asp Ser Thr Ser Thr Leu Thr Ile Ser Ala Asp Ser Lys Lys Thr Lys
                245                 250                 255
Asp Leu Val Phe Leu Thr Asp Gly Thr Ile Thr Val Gln Gln Tyr Asn
            260                 265                 270
Thr Ala Gly Thr Ser Leu Glu Gly Ser Ala Ser Glu Ile Lys Asn Leu
        275                 280                 285
Ser Glu Leu Lys Asn Ala Leu Lys
    290                 295
```

(2) INFORMATION FOR SEQ ID NO:23:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:23:

GGTACAATTA CAGTACAA                                                      18

(2) INFORMATION FOR SEQ ID NO:24:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:24:

CCGAGAATCT CATATGGCAC AAAAAGGTGC TGAGTCAATT GG                42

(2) INFORMATION FOR SEQ ID NO:25:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:25:

CCGATATCGG ATCCTATTTT AAAGCGTTTT TAAGC                             35

(2) INFORMATION FOR SEQ ID NO:26:

(i) SEQUENCE CHARACTERISTICS:
        (A) LENGTH: 31 base pairs
        (B) TYPE: nucleic acid (C) STRANDEDNESS: single
        (D) TOPOLOGY: linear (xi) SEQUENCE DESCRIPTION: SEQ ID NO:26:

GGATCCGGTG ACCTTTTAAA GCGTTTTTAA G                                31

(2) INFORMATION FOR SEQ ID NO:27:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:27:

GTGCGCGACC ATATGAAAAA GAATACATTA AGTGCG                           36

(2) INFORMATION FOR SEQ ID NO:28:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:28:

GTCGGCGGAT CCTTAAGGTT TTTTTGGACT TTCTGC                           36

(2) INFORMATION FOR SEQ ID NO:29:

(i) SEQUENCE CHARACTERISTICS:
        (A) LENGTH: 633 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..633

(xi) SEQUENCE DESCRIPTION: SEQ ID NO:29:

```
ATG AAA AAG AAT ACA TTA AGT GCG ATA TTA ATG ACT TTA TTT TTA TTT       48
Met Lys Lys Asn Thr Leu Ser Ala Ile Leu Met Thr Leu Phe Leu Phe
 1               5                  10                  15

ATA TCT TGT AAT AAT TCA GGG AAA GAT GGG AAT ACA TCT GCA AAT TCT       96
Ile Ser Cys Asn Asn Ser Gly Lys Asp Gly Asn Thr Ser Ala Asn Ser
                20                  25                  30

GCT GAT GAG TCT GTT AAA GGG CCT AAT CTT ACA GAA ATA AGT AAA AAA      144
Ala Asp Glu Ser Val Lys Gly Pro Asn Leu Thr Glu Ile Ser Lys Lys
            35                  40                  45

ATT ACG GAT TCT AAT GCG GTT TTA CTT GCT GTG AAA GAG GTT GAA GCG      192
Ile Thr Asp Ser Asn Ala Val Leu Leu Ala Val Lys Glu Val Glu Ala
        50                  55                  60

TTG CTG TCA TCT ATA GAT GAA ATT GCT GCT AAA GCT ATT GGT AAA AAA      240
Leu Leu Ser Ser Ile Asp Glu Ile Ala Ala Lys Ala Ile Gly Lys Lys
 65                  70                  75                  80

ATA CAC CAA AAT AAT GGT TTG GAT ACC GAA TAT AAT CAC AAT GGA TCA      288
Ile His Gln Asn Asn Gly Leu Asp Thr Glu Tyr Asn His Asn Gly Ser
                85                  90                  95

TTG TTA GCG GGA CGT TAT GCA ATA TCA ACC CTA ATA AAA CAA AAA TTA      336
Leu Leu Ala Gly Arg Tyr Ala Ile Ser Thr Leu Ile Lys Gln Lys Leu
                100                 105                 110
```

```
GAT GGA TTG AAA AAT GAA GGA TTA AAG GAA AAA ATT GAT GCG GCT AAG       384
Asp Gly Leu Lys Asn Glu Gly Leu Lys Glu Lys Ile Asp Ala Ala Lys
        115                 120                 125

AAA TGT TCT GAA ACA TTT ACT AAT AAA TTA AAA GAA AAA CAC ACA GAT       432
Lys Cys Ser Glu Thr Phe Thr Asn Lys Leu Lys Glu Lys His Thr Asp
130                 135                 140

CTT GGT AAA GAA GGT GTT ACT GAT GCT GAT GCA AAA GAA GCC ATT TTA       480
Leu Gly Lys Glu Gly Val Thr Asp Ala Asp Ala Lys Glu Ala Ile Leu
145                 150                 155                 160

AAA ACA AAT GGT ACT AAA ACT AAA GGT GCT GAA GAA CTT GGA AAA TTA       528
Lys Thr Asn Gly Thr Lys Thr Lys Gly Ala Glu Glu Leu Gly Lys Leu
        165                 170                 175

TTT GAA TCA GTA GAG GTC TTG TCA AAA GCA GCT AAA GAG ATG CTT GCT       576
Phe Glu Ser Val Glu Val Leu Ser Lys Ala Ala Lys Glu Met Leu Ala
            180                 185                 190

AAT TCA GTT AAA GAG CTT ACA AGC CCT GTT GTG GCA GAA AGT CCA AAA       624
Asn Ser Val Lys Glu Leu Thr Ser Pro Val Val Ala Glu Ser Pro Lys
                195                 200                 205

AAA CCT TAA                                                           633
Lys Pro
    210

(2) INFORMATION FOR SEQ ID NO:30:

(i) SEQUENCE CHARACTERISTICS:
        (A) LENGTH: 210 amino acids
        (B) TYPE: amino acid
        (D) TOPOLOGY: linear (ii) MOLECULE TYPE: protein (xi) SEQUENCE DESCRIPTION: SEQ ID NO:30:

Met Lys Lys Asn Thr Leu Ser Ala Ile Leu Met Thr Leu Phe Leu Phe
 1               5                  10                  15

Ile Ser Cys Asn Asn Ser Gly Lys Asp Gly Asn Thr Ser Ala Asn Ser
                20                  25                  30

Ala Asp Glu Ser Val Lys Gly Pro Asn Leu Thr Glu Ile Ser Lys Lys
            35                  40                  45

Ile Thr Asp Ser Asn Ala Val Leu Leu Ala Val Lys Glu Val Glu Ala
        50                  55                  60

Leu Leu Ser Ser Ile Asp Glu Ile Ala Ala Lys Ala Ile Gly Lys Lys
65                  70                  75                  80

Ile His Gln Asn Asn Gly Leu Asp Thr Glu Tyr Asn His Asn Gly Ser
                85                  90                  95

Leu Leu Ala Gly Arg Tyr Ala Ile Ser Thr Leu Ile Lys Gln Lys Leu
            100                 105                 110

Asp Gly Leu Lys Asn Glu Gly Leu Lys Glu Lys Ile Asp Ala Ala Lys
        115                 120                 125

Lys Cys Ser Glu Thr Phe Thr Asn Lys Leu Lys Glu Lys His Thr Asp
130                 135                 140

Leu Gly Lys Glu Gly Val Thr Asp Ala Asp Ala Lys Glu Ala Ile Leu
145                 150                 155                 160

Lys Thr Asn Gly Thr Lys Thr Lys Gly Ala Glu Glu Leu Gly Lys Leu
        165                 170                 175

Phe Glu Ser Val Glu Val Leu Ser Lys Ala Ala Lys Glu Met Leu Ala
            180                 185                 190

Asn Ser Val Lys Glu Leu Thr Ser Pro Val Val Ala Glu Ser Pro Lys
                195                 200                 205
```

Lys Pro
    210

(2) INFORMATION FOR SEQ ID NO:31:

(i) SEQUENCE CHARACTERISTICS:
       (A) LENGTH: 630 base pairs
       (B) TYPE: nucleic acid
       (C) STRANDEDNESS: double
       (D) TOPOLOGY: linear (ii) MOLECULE TYPE: DNA (genomic)

(ix) FEATURE:
       (A) NAME/KEY: CDS
       (B) LOCATION: 1..630

(xi) SEQUENCE DESCRIPTION: SEQ ID NO:31:

```
ATG AAA AAG AAT ACA TTA AGT GCG ATA TTA ATG ACT TTA TTT TTA TTT         48
Met Lys Lys Asn Thr Leu Ser Ala Ile Leu Met Thr Leu Phe Leu Phe
  1               5                  10                  15

ATA TCT TGT AAT AAT TCA GGT GGG GAT ACC GCA TCT ACT AAT CCT GAT         96
Ile Ser Cys Asn Asn Ser Gly Gly Asp Thr Ala Ser Thr Asn Pro Asp
             20                  25                  30

GAG TCT GCA AAA GGA CCT AAT CTT ACA GTA ATA AGC AAA AAA ATT ACA        144
Glu Ser Ala Lys Gly Pro Asn Leu Thr Val Ile Ser Lys Lys Ile Thr
         35                  40                  45

GAT TCT AAT GCA TTT GTA CTG GCT GTG AAA GAA GTT GAG GCT TTG ATC        192
Asp Ser Asn Ala Phe Val Leu Ala Val Lys Glu Val Glu Ala Leu Ile
     50                  55                  60

TCA TCT ATA GAT GAA CTT GCT AAT AAA GCT ATT GGT AAA GTA ATA CAT        240
Ser Ser Ile Asp Glu Leu Ala Asn Lys Ala Ile Gly Lys Val Ile His
 65                  70                  75                  80

CAA AAT AAT GGT TTA AAT GCT AAT GCG GGT CAA AAC GGA TCA TTG TTA        288
Gln Asn Asn Gly Leu Asn Ala Asn Ala Gly Gln Asn Gly Ser Leu Leu
                 85                  90                  95

GCA GGA GCC TAT GCA ATA TCA ACC CTA ATA ACA GAA AAA TTA AGT AAA        336
Ala Gly Ala Tyr Ala Ile Ser Thr Leu Ile Thr Glu Lys Leu Ser Lys
            100                 105                 110

TTG AAA AAT TCA GAA GAG TTA AAT AAA AAA ATT GAA GAG GCT AAG AAC        384
Leu Lys Asn Ser Glu Glu Leu Asn Lys Lys Ile Glu Glu Ala Lys Asn
        115                 120                 125

CAT TCT GAA GCA TTT ACT AAT AGA CTA AAA GGT TCT CAT GCA CAA CTT        432
His Ser Glu Ala Phe Thr Asn Arg Leu Lys Gly Ser His Ala Gln Leu
    130                 135                 140

GGA GTT GCT GCT GCT ACT GAT GAT CAT GCA AAA GAA GCT ATT TTA AAG        480
Gly Val Ala Ala Ala Thr Asp Asp His Ala Lys Glu Ala Ile Leu Lys
145                 150                 155                 160

TCA AAT CCT ACT AAA GAT AAG GGT GCT AAA GCA CTT AAA GAC TTA TCT        528
Ser Asn Pro Thr Lys Asp Lys Gly Ala Lys Ala Leu Lys Asp Leu Ser
                165                 170                 175

GAA TCA GTA GAA AGC TTG GCA AAA GCA GCG CAA GAA GCA TTA GCT AAT        576
Glu Ser Val Glu Ser Leu Ala Lys Ala Ala Gln Glu Ala Leu Ala Asn
            180                 185                 190

TCA GTT AAA GAA CTT ACA AAT CCT GTT GTG GCA GAA AGT CCA AAA AAA        624
Ser Val Lys Glu Leu Thr Asn Pro Val Val Ala Glu Ser Pro Lys Lys
        195                 200                 205

CCT TAA                                                                 630
Pro
    210
```

(2) INFORMATION FOR SEQ ID NO:32:

(i) SEQUENCE CHARACTERISTICS:
        (A) LENGTH: 209 amino acids
        (B) TYPE: amino acid
        (D) TOPOLOGY: linear (ii) MOLECULE TYPE: protein (xi) SEQUENCE DESCRIPTION: SEQ ID NO:32:

```
Met Lys Lys Asn Thr Leu Ser Ala Ile Leu Met Thr Leu Phe Leu Phe
 1               5                  10                  15
Ile Ser Cys Asn Asn Ser Gly Gly Asp Thr Ala Ser Thr Asn Pro Asp
             20                  25                  30
Glu Ser Ala Lys Gly Pro Asn Leu Thr Val Ile Ser Lys Lys Ile Thr
         35                  40                  45
Asp Ser Asn Ala Phe Val Leu Ala Val Lys Glu Val Glu Ala Leu Ile
     50                  55                  60
Ser Ser Ile Asp Glu Leu Ala Asn Lys Ala Ile Gly Lys Val Ile His
 65                  70                  75                  80
Gln Asn Asn Gly Leu Asn Ala Asn Ala Gly Gln Asn Gly Ser Leu Leu
                 85                  90                  95
Ala Gly Ala Tyr Ala Ile Ser Thr Leu Ile Thr Glu Lys Leu Ser Lys
            100                 105                 110
Leu Lys Asn Ser Glu Glu Leu Asn Lys Lys Ile Glu Glu Ala Lys Asn
        115                 120                 125
His Ser Glu Ala Phe Thr Asn Arg Leu Lys Gly Ser His Ala Gln Leu
    130                 135                 140
Gly Val Ala Ala Ala Thr Asp Asp His Ala Lys Glu Ala Ile Leu Lys
145                 150                 155                 160
Ser Asn Pro Thr Lys Asp Lys Gly Ala Lys Ala Leu Lys Asp Leu Ser
                165                 170                 175
Glu Ser Val Glu Ser Leu Ala Lys Ala Ala Gln Glu Ala Leu Ala Asn
            180                 185                 190
Ser Val Lys Glu Leu Thr Asn Pro Val Val Ala Glu Ser Pro Lys Lys
        195                 200                 205
Pro
```

(2) INFORMATION FOR SEQ ID NO:33:

(i) SEQUENCE CHARACTERISTICS:
        (A) LENGTH: 639 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..639

(xi) SEQUENCE DESCRIPTION: SEQ ID NO:33:

```
ATG AAA AAG AAT ACA TTA AGT GCG ATA TTA ATG ACT TTA TTT TTA TTT    48
Met Lys Lys Asn Thr Leu Ser Ala Ile Leu Met Thr Leu Phe Leu Phe
 1               5                  10                  15

ATA TCT TGT AGT AAT TCA GGG AAA GGT GGG GAT TCT GCA TCT ACT AAT    96
Ile Ser Cys Ser Asn Ser Gly Lys Gly Gly Asp Ser Ala Ser Thr Asn
             20                  25                  30
```

```
CCT GCT GAC GAG TCT GCG AAA GGG CCT AAT CTT ACA GAA ATA AGC AAA        144
Pro Ala Asp Glu Ser Ala Lys Gly Pro Asn Leu Thr Glu Ile Ser Lys
        35                  40                  45

AAA ATT ACA GAT TCT AAT GCA TTT GTA CTT GCT GTT AAA GAA GTT GAG        192
Lys Ile Thr Asp Ser Asn Ala Phe Val Leu Ala Val Lys Glu Val Glu
 50                  55                  60

ACT TTG GTT TTA TCT ATA GAT GAA CTT GCT AAG AAA GCT ATT GGT CAA        240
Thr Leu Val Leu Ser Ile Asp Glu Leu Ala Lys Lys Ala Ile Gly Gln
 65                  70                  75                  80

AAA ATA GAC AAT AAT AAT GGT TTA GCT GCT TTA AAT AAT CAG AAT GGA        288
Lys Ile Asp Asn Asn Asn Gly Leu Ala Ala Leu Asn Asn Gln Asn Gly
                 85                  90                  95

TCG TTG TTA GCA GGA GCC TAT GCA ATA TCA ACC CTA ATA ACA GAA AAA        336
Ser Leu Leu Ala Gly Ala Tyr Ala Ile Ser Thr Leu Ile Thr Glu Lys
            100                 105                 110

TTG AGT AAA TTG AAA AAT TTA GAA GAA TTA AAG ACA GAA ATT GCA AAG        384
Leu Ser Lys Leu Lys Asn Leu Glu Glu Leu Lys Thr Glu Ile Ala Lys
        115                 120                 125

GCT AAG AAA TGT TCC GAA GAA TTT ACT AAT AAA CTA AAA AGT GGT CAT        432
Ala Lys Lys Cys Ser Glu Glu Phe Thr Asn Lys Leu Lys Ser Gly His
130                 135                 140

GCA GAT CTT GGC AAA CAG GAT GCT ACC GAT GAT CAT GCA AAA GCA GCT        480
Ala Asp Leu Gly Lys Gln Asp Ala Thr Asp Asp His Ala Lys Ala Ala
145                 150                 155                 160

ATT TTA AAA ACA CAT GCA ACT ACC GAT AAA GGT GCT AAA GAA TTT AAA        528
Ile Leu Lys Thr His Ala Thr Thr Asp Lys Gly Ala Lys Glu Phe Lys
                165                 170                 175

GAT TTA TTT GAA TCA GTA GAA GGT TTG TTA AAA GCA GCT CAA GTA GCA        576
Asp Leu Phe Glu Ser Val Glu Gly Leu Leu Lys Ala Ala Gln Val Ala
            180                 185                 190

CTA ACT AAT TCA GTT AAA GAA CTT ACA AGT CCT GTT GTA GCA GAA AGT        624
Leu Thr Asn Ser Val Lys Glu Leu Thr Ser Pro Val Val Ala Glu Ser
        195                 200                 205

CCA AAA AAA CCT TAA                                                    639
Pro Lys Lys Pro
    210
```

(2) INFORMATION FOR SEQ ID NO:34:

(i) SEQUENCE CHARACTERISTICS:
        (A) LENGTH: 212 amino acids
        (B) TYPE: amino acid
        (D) TOPOLOGY: linear (ii) MOLECULE TYPE: protein (xi) SEQUENCE DESCRIPTION: SEQ ID NO:34:

```
Met Lys Lys Asn Thr Leu Ser Ala Ile Leu Met Thr Leu Phe Leu Phe
 1               5                  10                  15

Ile Ser Cys Ser Asn Ser Gly Lys Gly Gly Asp Ser Ala Ser Thr Asn
            20                  25                  30

Pro Ala Asp Glu Ser Ala Lys Gly Pro Asn Leu Thr Glu Ile Ser Lys
        35                  40                  45

Lys Ile Thr Asp Ser Asn Ala Phe Val Leu Ala Val Lys Glu Val Glu
 50                  55                  60

Thr Leu Val Leu Ser Ile Asp Glu Leu Ala Lys Lys Ala Ile Gly Gln
 65                  70                  75                  80

Lys Ile Asp Asn Asn Asn Gly Leu Ala Ala Leu Asn Asn Gln Asn Gly
                 85                  90                  95
```

```
Ser Leu Leu Ala Gly Ala Tyr Ala Ile Ser Thr Leu Ile Thr Glu Lys
            100                 105                 110

Leu Ser Lys Leu Lys Asn Leu Glu Glu Leu Lys Thr Glu Ile Ala Lys
            115                 120                 125

Ala Lys Lys Cys Ser Glu Glu Phe Thr Asn Lys Leu Lys Ser Gly His
            130                 135                 140

Ala Asp Leu Gly Lys Gln Asp Ala Thr Asp Asp His Ala Lys Ala Ala
145                 150                 155                 160

Ile Leu Lys Thr His Ala Thr Thr Asp Lys Gly Ala Lys Glu Phe Lys
                    165                 170                 175

Asp Leu Phe Glu Ser Val Glu Gly Leu Leu Lys Ala Ala Gln Val Ala
            180                 185                 190

Leu Thr Asn Ser Val Lys Glu Leu Thr Ser Pro Val Val Ala Glu Ser
            195                 200                 205

Pro Lys Lys Pro
    210
```

(2) INFORMATION FOR SEQ ID NO:35:

(i) SEQUENCE CHARACTERISTICS:
        (A) LENGTH: 624 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..624

(xi) SEQUENCE DESCRIPTION: SEQ ID NO:35:

```
ATG AAA AAG AAT ACA TTA AGT GCG ATA TTA ATG ACT TTA TTT TTA TTT        48
Met Lys Lys Asn Thr Leu Ser Ala Ile Leu Met Thr Leu Phe Leu Phe
  1               5                  10                  15

ATA TCT TGT AAT AAT TCA GGT GGG GAT TCT GCA TCT ACT AAT CCT GAT        96
Ile Ser Cys Asn Asn Ser Gly Gly Asp Ser Ala Ser Thr Asn Pro Asp
             20                   25                  30

GAG TCT GCA AAA GGA CCT AAT CTT ACC GTA ATA AGC AAA AAA ATT ACA       144
Glu Ser Ala Lys Gly Pro Asn Leu Thr Val Ile Ser Lys Lys Ile Thr
         35                  40                  45

GAT TCT AAT GCA TTT TTA CTG GCT GTG AAA GAA GTT GAG GCT TTG CTT       192
Asp Ser Asn Ala Phe Leu Leu Ala Val Lys Glu Val Glu Ala Leu Leu
     50                  55                  60

TCA TCT ATA GAT GAA CTT TCT AAA GCT ATT GGT AAA AAA ATA AAA AAT       240
Ser Ser Ile Asp Glu Leu Ser Lys Ala Ile Gly Lys Lys Ile Lys Asn
 65                  70                  75                  80

GAT GGT ACT TTA GAT AAC GAA GCA AAT CGA AAC GAA TCA TTG ATA GCA       288
Asp Gly Thr Leu Asp Asn Glu Ala Asn Arg Asn Glu Ser Leu Ile Ala
                 85                  90                  95

GGA GCT TAT GAA ATA TCA AAA CTA ATA ACA CAA AAA TTA AGT GTA TTG       336
Gly Ala Tyr Glu Ile Ser Lys Leu Ile Thr Gln Lys Leu Ser Val Leu
            100                 105                 110

AAT TCA GAA GAA TTA AAG AAA AAA ATT AAA GAG GCT AAG GAT TGT TCC       384
Asn Ser Glu Glu Leu Lys Lys Lys Ile Lys Glu Ala Lys Asp Cys Ser
            115                 120                 125

GAA AAA TTT ACT ACT AAG CTA AAA GAT AGT CAT GCA GAG CTT GGT ATA       432
Glu Lys Phe Thr Thr Lys Leu Lys Asp Ser His Ala Glu Leu Gly Ile
            130                 135                 140
```

```
CAA AGC GTT CAG GAT GAT AAT GCA AAA AAA GCT ATT TTA AAA ACA CAT        480
Gln Ser Val Gln Asp Asp Asn Ala Lys Lys Ala Ile Leu Lys Thr His
145                 150                 155                 160

GGA ACT AAA GAC AAG GGT GCT AAA GAA CTT GAA GAG TTA TTT AAA TCA        528
Gly Thr Lys Asp Lys Gly Ala Lys Glu Leu Glu Glu Leu Phe Lys Ser
                165                 170                 175

CTA GAA AGC TTG TCA AAA GCA GCG CAA GCA GCA TTA ACT AAT TCA GTT        576
Leu Glu Ser Leu Ser Lys Ala Ala Gln Ala Ala Leu Thr Asn Ser Val
            180                 185                 190

AAA GAG CTT ACA AAT CCT GTT GTG GCA GAA AGT CCA AAA AAA CCT TAA        624
Lys Glu Leu Thr Asn Pro Val Val Ala Glu Ser Pro Lys Lys Pro
        195                 200                 205
```

(2) INFORMATION FOR SEQ ID NO:36:

(i) SEQUENCE CHARACTERISTICS:
        (A) LENGTH: 207 amino acids
        (B) TYPE: amino acid
        (D) TOPOLOGY: linear (ii) MOLECULE TYPE: protein (xi) SEQUENCE DESCRIPTION: SEQ ID NO:36:

```
Met Lys Lys Asn Thr Leu Ser Ala Ile Leu Met Thr Leu Phe Leu Phe
1               5                   10                  15

Ile Ser Cys Asn Asn Ser Gly Gly Asp Ser Ala Ser Thr Asn Pro Asp
            20                  25                  30

Glu Ser Ala Lys Gly Pro Asn Leu Thr Val Ile Ser Lys Lys Ile Thr
        35                  40                  45

Asp Ser Asn Ala Phe Leu Leu Ala Val Lys Glu Val Glu Ala Leu Leu
    50                  55                  60

Ser Ser Ile Asp Glu Leu Ser Lys Ala Ile Gly Lys Lys Ile Lys Asn
65                  70                  75                  80

Asp Gly Thr Leu Asp Asn Glu Ala Asn Arg Asn Glu Ser Leu Ile Ala
                85                  90                  95

Gly Ala Tyr Glu Ile Ser Lys Leu Ile Thr Gln Lys Leu Ser Val Leu
            100                 105                 110

Asn Ser Glu Glu Leu Lys Lys Lys Ile Lys Glu Ala Lys Asp Cys Ser
        115                 120                 125

Glu Lys Phe Thr Thr Lys Leu Lys Asp Ser His Ala Glu Leu Gly Ile
    130                 135                 140

Gln Ser Val Gln Asp Asp Asn Ala Lys Lys Ala Ile Leu Lys Thr His
145                 150                 155                 160

Gly Thr Lys Asp Lys Gly Ala Lys Glu Leu Glu Glu Leu Phe Lys Ser
                165                 170                 175

Leu Glu Ser Leu Ser Lys Ala Ala Gln Ala Ala Leu Thr Asn Ser Val
            180                 185                 190

Lys Glu Leu Thr Asn Pro Val Val Ala Glu Ser Pro Lys Lys Pro
        195                 200                 205
```

(2) INFORMATION FOR SEQ ID NO:37:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:37:

GTGCGCGACC ATATGGCTAA TAATTCAGGG AAAGAT        36

(2) INFORMATION FOR SEQ ID NO:38:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:38:

GTGCGCGACC ATATGGGCTA GTAATTCAGG GAAAGGT    37

(2) INFORMATION FOR SEQ ID NO:39:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:39:

GTGCGCGACC ATATGGCTAA TAATTCAGGT GGGGAT    36

(2) INFORMATION FOR SEQ ID NO:40:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:40:

CTTGGAAAAT TATTTGAA    18

(2) INFORMATION FOR SEQ ID NO:41:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:41:

CACGGTCACC CCATGGGAAA TAATTCAGGG AAAGG    35

(2) INFORMATION FOR SEQ ID NO:42:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:42:

TATAGATGAC AGCAACGC    18

(2) INFORMATION FOR SEQ ID NO:43:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:43:

CCGGTGACCC CATGGTACCA GGTTTTTTTG GACTTTCTGC    40

(2) INFORMATION FOR SEQ ID NO:44:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:44:

CCGGATCCAT ATGGTTAAAA AATAATATT TATTTC                             36

(2) INFORMATION FOR SEQ ID NO:45:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:45:

GATATCTAGA TCTTTAATTG CTCTGCTCAC TCTCTTC                             37

(2) INFORMATION FOR SEQ ID NO:46:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:46:

CCGGGATCCA TATGGCTAGT GCAATTGGTC GTGG                                34

(2) INFORMATION FOR SEQ ID NO:47:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:47:

ATGATTATCA ATCATAAT                                                   18

(2) INFORMATION FOR SEQ ID NO:48:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:48:

TCTGAACAAT GACAAAAC                                                   18

(2) INFORMATION FOR SEQ ID NO:49:

(i) SEQUENCE CHARACTERISTICS:
        (A) LENGTH: 825 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:49:

```
ATGAAAAAAT ATTTATTGGG AATAGGTCTA ATATTAGCCT TAATAGCATG TAAGCAAAAT      60

GTTAGCAGCC TTGATGAAAA AAATAGCGTT TCAGTAGATT TACCTGGTGG AATGACAGTT     120

CTTGTAAGTA AAGAAAAAGA CAAAGACGGT AAATACAGTC TAGAGGCAAC AGTAGACAAG     180

CTTGAGCTTA AGGAACTTC  TGATAAAAAC AACGGTCTG  GAACACTTGA AGGTGAAAAA     240

ACTGACAAAA GTAAAGTAAA ATCAACAATT GCTGATGACC TAAGTCAAAC TAAATTTGAA     300

ATTTTCAAAG AAGATGGCAA ACATTAGTA  TCAAAAAAG  TAACCCTTAA AGACAAGTCA     360

TCAACAGAAG AAAAATTCAA CGGAAAGGGT GAAACATCTG AAAAAACAAT AGTAAGAGCA     420

AATGGAACCA GACTTGAATA CACAGACATA AAAAGCGATG GATCCGGAAA AGCTAAAGAA     480

GTTTTAAAAG ACTTTACTCT TGAAGGAACT CTAGCTGCTG ACGGCAAAAC AACATTGAAA     540

GTTACAGAAG GCACTGTTGT TTTAAGCAAG AACATTTTAA AATCCGGAGA ATAACAGCT     600

GCACTTGATG ACTCTGACAC TACTCGGGCT ACTAAAAAAA CTGGAAAATG GGATTCAAAG     660

ACTTCCACTT TAACAATTAG TGTGAATAGC CAAAAAACCA AAAACCTTGT ATTCACAAAA     720

GAAGACACAA TAACAGTACA AAGATACGAC TCAGCAGGCA CCAATCTAGA AGGCAAAGCA     780

GTCGAAATTA CAACACTTAA AGAACTTAAA AACGCTTTAA AATAA                    825
```

(2) INFORMATION FOR SEQ ID NO:50:

(i) SEQUENCE CHARACTERISTICS:
        (A) LENGTH: 824 base pairs
        (B) TYPE: nucleic acid
        (C) STRANDEDNESS: double
        (D) TOPOLOGY: linear (xi) SEQUENCE DESCRIPTION: SEQ ID NO:50:

```
ATGAAAAAAT ATTTATTGGG AATAGGTCTA ATATTAGCAT TAATAGCATG TAAGCAAAAT      60

GTTAGCAGCC TTGATGAAAA AAATAGCGTT TCAGTAGATT TACCTGGTGG AATGCAAGTT     120

CTTGTAAGTA AAGAAAAAGA CAAAGATGGT AAATACAGTC TAATGGCAAC AGTAGACAAG     180

CTTGAGCTTA AGGAACTTC  TGATAAAAAC AACGGTCTG  GAACACTTGA AGGTGAAAAA     240

ACTGACAAAA GTAAAGCAAA ATTAACAATT GCTGAGGATC TAAGTAAAAC CACATTTGAA     300

ATCTTCAAAG AAGATGGCAA ACATTAGTA  TCAAAAAAG  TAACCCTTAA AGACAAGTCA     360

TCAACAGAAG AAAAATTCAA CGCAAAGGGT GAAGCATCTG AAAAAACAAT AGTAAGAGCA     420

AATGGAACCA GACTTGAATA CACAGACATA AAAAGCGATA AACCGGAAA  AGCTAAAGAA     480

GTTTTAAAAG ACTTTGCTCT TGAAGGAACT CTAGCTGCTG ACGGCAAAAC AACATTAAAA     540

GTTACAGAAG GCACTGTTGT TTTAAGCAAA CACATTTCAA ACTCTGGAGA ATAACAGTT     600

GAGCTTAATG ACTCTGACAC TACTCAGGCT ACTAAAAAAA CTGGAACATG GATTCAAAG     660

ACTTCCACTT TAACAATTAG TGTGAATAGC CGAAAAACCA AAAACCTTGT ATTCACAAAA     720

GAAGACACAA TAACAGTACA AAAATACGAC TCAGCAGGCA CCAATCTAGA AGGCAAAGCA     780

GTCGAAATTA CAACGCTTAA AGAACTTAAA GATGCTTTAA AATA                     824
```

(2) INFORMATION FOR SEQ ID NO:51:

(i) SEQUENCE CHARACTERISTICS:
        (A) LENGTH: 1011 base pairs
        (B) TYPE: nucleic acid
        (C) STRANDEDNESS: double
        (D) TOPOLOGY: linear (ii) MOLECULE TYPE: DNA (genomic)

(ix) FEATURE:
    (A) NAME/KEY: CDS
    (B) LOCATION: 1..1011

(xi) SEQUENCE DESCRIPTION: SEQ ID NO:51:

```
ATG ATT ATC AAT CAT AAT ACA TCA GCT ATT AAT GCT TCA AGA AAT AAT      48
Met Ile Ile Asn His Asn Thr Ser Ala Ile Asn Ala Ser Arg Asn Asn
 1               5                  10                  15

GCC ATT AAT GCT GCT AAT CTT AGT AAA ACC CAA GAG AAG CTT TCT AGT      96
Ala Ile Asn Ala Ala Asn Leu Ser Lys Thr Gln Glu Lys Leu Ser Ser
            20                  25                  30

GGT TAC AGA ATT AAT CGA GCT TCT GAT GAT GCT GCT GGT ATG GGG GTT     144
Gly Tyr Arg Ile Asn Arg Ala Ser Asp Asp Ala Ala Gly Met Gly Val
        35                  40                  45

TCT GGC AAG ATT AAT GCT CAA ATA ACA GGC TTA TCA CAA GCT TCT AGA     192
Ser Gly Lys Ile Asn Ala Gln Ile Thr Gly Leu Ser Gln Ala Ser Arg
 50                  55                  60

AAC ACT TCA AAA GCT ATC AAT TTT ATT CAG ACA ACA GAA GGA AAT TTA     240
Asn Thr Ser Lys Ala Ile Asn Phe Ile Gln Thr Thr Glu Gly Asn Leu
 65                  70                  75                  80

AAT GAA GTA GAA AAA GTT TTA GTA AGA ATG AAA GAA TTA GCA GTT CAA     288
Asn Glu Val Glu Lys Val Leu Val Arg Met Lys Glu Leu Ala Val Gln
                85                  90                  95

TCA GGT AAC GGA ACG TAT TCA GAC GCA GAC AGA GGT TCT ATA CAG ATT     336
Ser Gly Asn Gly Thr Tyr Ser Asp Ala Asp Arg Gly Ser Ile Gln Ile
            100                 105                 110

GAA ATA GAG CAA CTT ACA GAC GAA ATT AAT AGA ATT GCT GAT CAG GCT     384
Glu Ile Glu Gln Leu Thr Asp Glu Ile Asn Arg Ile Ala Asp Gln Ala
        115                 120                 125

CAA TAT AAC CAA ATG CAC ATG TTG TCA AAC AAA TCT GCT TCC CAA AAT     432
Gln Tyr Asn Gln Met His Met Leu Ser Asn Lys Ser Ala Ser Gln Asn
130                 135                 140

GTA AAA ACA GCT GAA GAG CTT GGA ATG CAG CCT GCA AAA ATT AAC ACA     480
Val Lys Thr Ala Glu Glu Leu Gly Met Gln Pro Ala Lys Ile Asn Thr
145                 150                 155                 160

CCA GCA TCA CTT TCA GGA TCT CAA GCT TCT TGG ACT TTA AGA GTT CAT     528
Pro Ala Ser Leu Ser Gly Ser Gln Ala Ser Trp Thr Leu Arg Val His
                165                 170                 175

GTG GGA GCA AAT CAA GAT GAA GCA ATT GCT GTA AAT ATT TAT TCA GCT     576
Val Gly Ala Asn Gln Asp Glu Ala Ile Ala Val Asn Ile Tyr Ser Ala
            180                 185                 190

AAT GTT GCA AAT CTT TTT GCT GGT GAG GGA GCT CAA GCT GCT CAG GCT     624
Asn Val Ala Asn Leu Phe Ala Gly Glu Gly Ala Gln Ala Ala Gln Ala
        195                 200                 205

GCA CCT GTT CAA GAG GGT GCT CAA GAA GAA GGA GCT CAG CAA CCA ACA     672
Ala Pro Val Gln Glu Gly Ala Gln Glu Glu Gly Ala Gln Gln Pro Thr
210                 215                 220

CCT GCT ACA GCA CCT ACT CAA GGT GGA GTT AAT TCT CCT GTT AAT GTT     720
Pro Ala Thr Ala Pro Thr Gln Gly Gly Val Asn Ser Pro Val Asn Val
225                 230                 235                 240

ACA ACC ACA GTT GAT GCT AAT ACA TCA CTT GCT AAA ATA GAA AAT GCT     768
Thr Thr Thr Val Asp Ala Asn Thr Ser Leu Ala Lys Ile Glu Asn Ala
                245                 250                 255

ATT AGA ATG ATA AGT GAT CAA AGA GCA AAT TTA GGT GCT TTC CAA AAT     816
Ile Arg Met Ile Ser Asp Gln Arg Ala Asn Leu Gly Ala Phe Gln Asn
            260                 265                 270

AGA CTT GAA TCT ATA AAG AAT AGC ACT GAG TAT GCT ATT GAA AAT CTA     864
Arg Leu Glu Ser Ile Lys Asn Ser Thr Glu Tyr Ala Ile Glu Asn Leu
        275                 280                 285
```

```
AAA GCA TCT TAT GCT CAA ATA AAA GAT GCT ACA ATG ACA GAT GAG GTT      912
Lys Ala Ser Tyr Ala Gln Ile Lys Asp Ala Thr Met Thr Asp Glu Val
290                 295                 300

GTA GCA GCT ACA ACT AAT AGT ATT TTA ACT CAA TCT GCA ATG GCA ATG      960
Val Ala Ala Thr Thr Asn Ser Ile Leu Thr Gln Ser Ala Met Ala Met
305                 310                 315                 320

ATT GCA CAG GCT AAT CAA GTT CCT CAA TAT GTT TTG TCA TTG CTT AGA     1008
Ile Ala Gln Ala Asn Gln Val Pro Gln Tyr Val Leu Ser Leu Leu Arg
            325                 330                 335

TAA                                                                 1011
```

(2) INFORMATION FOR SEQ ID NO:52:

(i) SEQUENCE CHARACTERISTICS:
        (A) LENGTH: 336 amino acids
        (B) TYPE: amino acid
        (D) TOPOLOGY: linear (ii) MOLECULE TYPE: protein (xi) SEQUENCE DESCRIPTION: SEQ ID NO:52:

```
Met Ile Ile Asn His Asn Thr Ser Ala Ile Asn Ala Ser Arg Asn Asn
 1               5                  10                  15

Ala Ile Asn Ala Ala Asn Leu Ser Lys Thr Gln Glu Lys Leu Ser Ser
             20                  25                  30

Gly Tyr Arg Ile Asn Arg Ala Ser Asp Asp Ala Ala Gly Met Gly Val
         35                  40                  45

Ser Gly Lys Ile Asn Ala Gln Ile Thr Gly Leu Ser Gln Ala Ser Arg
     50                  55                  60

Asn Thr Ser Lys Ala Ile Asn Phe Ile Gln Thr Thr Glu Gly Asn Leu
65                  70                  75                  80

Asn Glu Val Glu Lys Val Leu Val Arg Met Lys Glu Leu Ala Val Gln
                 85                  90                  95

Ser Gly Asn Gly Thr Tyr Ser Asp Ala Asp Arg Gly Ser Ile Gln Ile
            100                 105                 110

Glu Ile Glu Gln Leu Thr Asp Glu Ile Asn Arg Ile Ala Asp Gln Ala
        115                 120                 125

Gln Tyr Asn Gln Met His Met Leu Ser Asn Lys Ser Ala Ser Gln Asn
130                 135                 140

Val Lys Thr Ala Glu Glu Leu Gly Met Gln Pro Ala Lys Ile Asn Thr
145                 150                 155                 160

Pro Ala Ser Leu Ser Gly Ser Gln Ala Ser Trp Thr Leu Arg Val His
                165                 170                 175

Val Gly Ala Asn Gln Asp Glu Ala Ile Ala Val Asn Ile Tyr Ser Ala
            180                 185                 190

Asn Val Ala Asn Leu Phe Ala Gly Glu Gly Ala Gln Ala Ala Gln Ala
        195                 200                 205

Ala Pro Val Gln Glu Gly Ala Gln Glu Gly Ala Gln Gln Pro Thr
210                 215                 220

Pro Ala Thr Ala Pro Thr Gln Gly Gly Val Asn Ser Pro Val Asn Val
225                 230                 235                 240

Thr Thr Thr Val Asp Ala Asn Thr Ser Leu Ala Lys Ile Glu Asn Ala
                245                 250                 255

Ile Arg Met Ile Ser Asp Gln Arg Ala Asn Leu Gly Ala Phe Gln Asn
            260                 265                 270

Arg Leu Glu Ser Ile Lys Asn Ser Thr Glu Tyr Ala Ile Glu Asn Leu
        275                 280                 285
```

```
Lys Ala Ser Tyr Ala Gln Ile Lys Asp Ala Thr Met Thr Asp Glu Val
        290                 295                 300

Val Ala Ala Thr Thr Asn Ser Ile Leu Thr Gln Ser Ala Met Ala Met
305                 310                 315                 320

Ile Ala Gln Ala Asn Gln Val Pro Gln Tyr Val Leu Ser Leu Leu Arg
                325                 330                 335

(2) INFORMATION FOR SEQ ID NO:53:

(i) SEQUENCE CHARACTERISTICS:
        (A) LENGTH: 1008 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..1008

(xi) SEQUENCE DESCRIPTION: SEQ ID NO:53:

ATG ATT ATC AAT CAT AAT ACA TCA GCT ATT AAT GCT TCA AGA AAT AAT        48
Met Ile Ile Asn His Asn Thr Ser Ala Ile Asn Ala Ser Arg Asn Asn
  1               5                  10                  15

GGT ATT AAT GCT GCT AAT CTT AGT AAA ACT CAA GAG AAG CTT TCT AGT        96
Gly Ile Asn Ala Ala Asn Leu Ser Lys Thr Gln Glu Lys Leu Ser Ser
                 20                  25                  30

GGT TAC AGA ATT AAT AGA GCT TCT GAT GAT GCT GCT GGT ATG GGG GTT       144
Gly Tyr Arg Ile Asn Arg Ala Ser Asp Asp Ala Ala Gly Met Gly Val
             35                  40                  45

TCT GGG AAG ATT AAT GCT CAA ATA AGA GGT TTA TCA CAA GCT TCT AGA       192
Ser Gly Lys Ile Asn Ala Gln Ile Arg Gly Leu Ser Gln Ala Ser Arg
 50                  55                  60

AAC ACT TCA AAA GCT ATT AAT TTT ATT CAG ACA ACA GAA GGA AAT TTG       240
Asn Thr Ser Lys Ala Ile Asn Phe Ile Gln Thr Thr Glu Gly Asn Leu
 65                  70                  75                  80

AAT GAA GTA GAA AAA GTT TTA GTA AGA ATG AAA GAA TTA GCA GTT CAA       288
Asn Glu Val Glu Lys Val Leu Val Arg Met Lys Glu Leu Ala Val Gln
                 85                  90                  95

TCA GGT AAC GGT ACA TAT TCA GAC GCA GAC AGA GGT TCT ATA CAA ATT       336
Ser Gly Asn Gly Thr Tyr Ser Asp Ala Asp Arg Gly Ser Ile Gln Ile
                100                 105                 110

GAA ATA GAG CAA CTT ACA GAC GAA ATT AAT AGA ATT GCT GAT CAA GCT       384
Glu Ile Glu Gln Leu Thr Asp Glu Ile Asn Arg Ile Ala Asp Gln Ala
            115                 120                 125

CAA TAT AAC CAA ATG CAC ATG TTG TCA AAC AAA TCT GCT TCC CAA AAT       432
Gln Tyr Asn Gln Met His Met Leu Ser Asn Lys Ser Ala Ser Gln Asn
        130                 135                 140

GTA AGA ACA GCT GAA GAA CTT GGA ATG CAA CCT GCA AAA ATC AAC ACA       480
Val Arg Thr Ala Glu Glu Leu Gly Met Gln Pro Ala Lys Ile Asn Thr
145                 150                 155                 160

CCA GCG TCA CTT TCA GGA TCT CAA GCT TCT TGG ACT TTA AGA GTT CAT       528
Pro Ala Ser Leu Ser Gly Ser Gln Ala Ser Trp Thr Leu Arg Val His
                165                 170                 175

GTG GGA GCA AAT CAA GAT GAA GCG ATT GCT GTA AAT ATT TAT GCT GCT       576
Val Gly Ala Asn Gln Asp Glu Ala Ile Ala Val Asn Ile Tyr Ala Ala
                180                 185                 190

AAT GTT GCA AAT CTA TTC TCT GGT GAA GGA GCT CAG GCT GCT CAG ACT       624
Asn Val Ala Asn Leu Phe Ser Gly Glu Gly Ala Gln Ala Ala Gln Thr
            195                 200                 205
```

```
GCA CCT GTT CAA GAA GGT GCT CAA CAA GAA GGA GCT CAA CAA CCA GCA        672
Ala Pro Val Gln Glu Gly Ala Gln Gln Glu Gly Ala Gln Gln Pro Ala
    210                 215                 220

CCT GCT ACA GCG CCT TCT CAG GGT GGA GTT AAT TCT CCT GTT AAT GTT        720
Pro Ala Thr Ala Pro Ser Gln Gly Gly Val Asn Ser Pro Val Asn Val
225                 230                 235                 240

ACA ACT ACA GTT GAC GCT AAT ACA TCT CTT GCT AAA ATA GAA AAT GCT        768
Thr Thr Thr Val Asp Ala Asn Thr Ser Leu Ala Lys Ile Glu Asn Ala
                245                 250                 255

ATT AGA ATG ATA AGT GAT CAA AGA GCA AAT TTA GGT GCT TTC CAA AAT        816
Ile Arg Met Ile Ser Asp Gln Arg Ala Asn Leu Gly Ala Phe Gln Asn
            260                 265                 270

AGA CTT GAG TCT ATA AAG GAT AGT ACT GAG TAT GCT ATT GAA AAC CTA        864
Arg Leu Glu Ser Ile Lys Asp Ser Thr Glu Tyr Ala Ile Glu Asn Leu
        275                 280                 285

AAA GCA TCT TAT GCT CAA ATA AAA GAT GCT ACA ATG ACA GAT GAG GTT        912
Lys Ala Ser Tyr Ala Gln Ile Lys Asp Ala Thr Met Thr Asp Glu Val
    290                 295                 300

GTA GCA GCT ACA ACT AAT AGT ATT TTA ACA CAA TGT GCA ATG GCA ATG        960
Val Ala Ala Thr Thr Asn Ser Ile Leu Thr Gln Cys Ala Met Ala Met
305                 310                 315                 320

ATT GCG CAA GCT AAT CAA GTT CCT CAA TAT GTT TTG TCA TTG CTT AGA       1008
Ile Ala Gln Ala Asn Gln Val Pro Gln Tyr Val Leu Ser Leu Leu Arg
                325                 330                 335

(2) INFORMATION FOR SEQ ID NO:54:

(i) SEQUENCE CHARACTERISTICS:
        (A) LENGTH: 336 amino acids
        (B) TYPE: amino acid
        (D) TOPOLOGY: linear (ii) MOLECULE TYPE: protein (xi) SEQUENCE DESCRIPTION: SEQ ID NO:54:

Met Ile Ile Asn His Asn Thr Ser Ala Ile Asn Ala Ser Arg Asn Asn
  1               5                  10                  15

Gly Ile Asn Ala Ala Asn Leu Ser Lys Thr Gln Glu Lys Leu Ser Ser
               20                  25                  30

Gly Tyr Arg Ile Asn Arg Ala Ser Asp Asp Ala Ala Gly Met Gly Val
           35                  40                  45

Ser Gly Lys Ile Asn Ala Gln Ile Arg Gly Leu Ser Gln Ala Ser Arg
 50                  55                  60

Asn Thr Ser Lys Ala Ile Asn Phe Ile Gln Thr Thr Glu Gly Asn Leu
 65                  70                  75                  80

Asn Glu Val Glu Lys Val Leu Val Arg Met Lys Glu Leu Ala Val Gln
               85                  90                  95

Ser Gly Asn Gly Thr Tyr Ser Asp Ala Asp Arg Gly Ser Ile Gln Ile
              100                 105                 110

Glu Ile Glu Gln Leu Thr Asp Glu Ile Asn Arg Ile Ala Asp Gln Ala
          115                 120                 125

Gln Tyr Asn Gln Met His Met Leu Ser Asn Lys Ser Ala Ser Gln Asn
    130                 135                 140

Val Arg Thr Ala Glu Glu Leu Gly Met Gln Pro Ala Lys Ile Asn Thr
145                 150                 155                 160

Pro Ala Ser Leu Ser Gly Ser Gln Ala Ser Trp Thr Leu Arg Val His
                165                 170                 175

Val Gly Ala Asn Gln Asp Glu Ala Ile Ala Val Asn Ile Tyr Ala Ala
            180                 185                 190
```

```
Asn Val Ala Asn Leu Phe Ser Gly Glu Gly Ala Gln Ala Ala Gln Thr
            195                 200                 205

Ala Pro Val Gln Glu Gly Ala Gln Gln Glu Gly Ala Gln Gln Pro Ala
    210                 215                 220

Pro Ala Thr Ala Pro Ser Gln Gly Gly Val Asn Ser Pro Val Asn Val
225                 230                 235                 240

Thr Thr Thr Val Asp Ala Asn Thr Ser Leu Ala Lys Ile Glu Asn Ala
                245                 250                 255

Ile Arg Met Ile Ser Asp Gln Arg Ala Asn Leu Gly Ala Phe Gln Asn
            260                 265                 270

Arg Leu Glu Ser Ile Lys Asp Ser Thr Glu Tyr Ala Ile Glu Asn Leu
        275                 280                 285

Lys Ala Ser Tyr Ala Gln Ile Lys Asp Ala Thr Met Thr Asp Glu Val
    290                 295                 300

Val Ala Ala Thr Thr Asn Ser Ile Leu Thr Gln Cys Ala Met Ala Met
305                 310                 315                 320

Ile Ala Gln Ala Asn Gln Val Pro Gln Tyr Val Leu Ser Leu Leu Arg
                325                 330                 335
```

(2) INFORMATION FOR SEQ ID NO:55:

(i) SEQUENCE CHARACTERISTICS:
        (A) LENGTH: 821 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:55:

```
ATGAAAAAAT ATTTATTGGG AATAGGTCTA ATATTAGCCT TAATAGCATG CAAGCAAAAT    60
GTTAGCAGCC TTGATGAAAA AAACAGCGCT TCAGTAGATT TGCCTGGTGA GATGAAAGTT   120
CTTGTAAGTA AAGAAAAAGA CAAAGACGGT AAGTACAGTC TAAAGGCAAC AGTAGACAAG   180
ATTGAGCTAA AAGGAACTTC TGATAAAGAC AATGGTTCTG GGGTGCTTGA AGGTACAAAA   240
GATGACAAAA GTAAAGCAAA ATTAACAATT GCTGACGATC TAGGTAAAAC CACATTCGAA   300
CTTTTCAAAG AAGATGGCAA AACATTAGTG TCAAGAAAAG TAAGTTCTAA AGACAAAACA   360
TCAACAGATG AAATGTTCAA TGAAAAAGGT GAATTGTCTG CAAAAACCAT GACAAGAGAA   420
AATGGAACCA AACTTGAATA TACAGAAATG AAAAGCGATG GAACCGGAAA AGCTAAAGAA   480
GTTTTAAAAA ACTTTACTCT TGAAGGAAAA GTAGCTAATG ATAAAGTAAC ATTGGAAGTA   540
AAAGAAGGAA CCGTTACTTT AAGTAAGGAA ATTGCAAAAT CTGGAGAAGT AACAGTTGCT   600
CTTAATGACA CTAACACTAC TCAGGCTACT AAAAAAACTG GCGCATGGGA TTCAAAAACT   660
TCTACTTTAA CAATTAGTGT TAACAGCAAA AAAACTACAC AACTTGTGTT TACTAAACAA   720
GACACAATAA CTGTACAAAA ATACGACTCC GCAGGTACCA ATTTAGAAGG CACAGCAGTC   780
GAAATTAAAA CACTTGATGA ACTTAAAAAC GCTTTAAAAT A                      821
```

(2) INFORMATION FOR SEQ ID NO:56:

(i) SEQUENCE CHARACTERISTICS:
        (A) LENGTH: 821 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:56:

| | | | | | |
|---|---|---|---|---|---|
| ATGAAAAAAT | ATTTATTGGG | AATAGGTCTA | ATATTAGCCT | TAATAGCATG | CAAGCAAAAT | 60
| GTTAGCAGCC | TTGATGAAAA | AAACAGCGCT | TCAGTAGATT | TGCCTGGTGA | GATTAAAGTT | 120
| CTTGTAAGTA | AAGAAAAAGA | CAAAGACGGT | AAGTACAGTC | TAAAGGCAAC | AGTAGACAAG | 180
| ATTGAGCTAA | AAGGAACTTC | TGATAAAGAC | AATGGTTCTG | GAGTGCTTGA | AGGTACAAAA | 240
| GATGACAAAA | GTAAAGCAAA | ATTAACAATT | GCTGACGATC | TAAGTAAAAC | CACATTCGAA | 300
| CTTTTCAAAG | AAGATGGCAA | ACATTAGTG | TCAAGAAAAG | TAAGTTCTAA | AGACAAAACA | 360
| TCAACAGATG | AAATGTTCAA | TGAAAAAGGT | GAATTGTCTG | CAAAAACCAT | GACAAGAGAA | 420
| AATGGAACCA | AACTTGAATA | TACAGAAATG | AAAGCGATG | GAACCGGAAA | AGCTAAAGAA | 480
| GTTTTAAAAA | ACTTTACTCT | TGAAGGAAAA | GTAGCTAATG | ATAAAGTAAC | ATTGGAAGTA | 540
| AAAGAAGGAA | CCGTTACTTT | AAGTAAGGAA | ATTGCAAAAT | CTGGAGAAGT | AACAGTTGCT | 600
| CTTAATGACA | CTAACACTAC | TCAGGCTACT | AAAAAAACTG | GCGCATGGGA | TTCAAAAACT | 660
| TCTACTTTAA | CAATTAGTGT | TAACAGTAAA | AAAACTACAC | AACTTGTGTT | TACTAAACAA | 720
| GACACAATAA | CTGTACAAAA | ATACGACTCC | GCAGGTACCA | ATTTAGAAGG | CACAGCAGTC | 780
| GAAATTAAAA | CACTTGATGA | ACTTAAAAAC | GCTTTAAAAT | A | | 821

(2) INFORMATION FOR SEQ ID NO:57:

(i) SEQUENCE CHARACTERISTICS:
        (A) LENGTH: 821 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:57:

| | | | | | |
|---|---|---|---|---|---|
| ATGAAAAAAT | ATTTATTGGG | AATAGGTCTA | ATATTAGCCT | TAATAGCATG | CAAGCAAAAT | 60
| GTTAGCAGCC | TTGATGAAAA | AAACAGCGCT | TCAGTAGATT | TGCCTGGTGA | GATGAAAGTT | 120
| CTTGTAAGTA | AAGAAAAAGA | CAAAGACGGT | AAGTACAGTC | TAAAGGCAAC | AGTAGACAAG | 180
| ATTGAGCTAA | AAGGAACTTC | TGATAAAGAC | AATGGTTCTG | GGGTGCTTGA | AGGTACAAAA | 240
| GATGACAAAA | GTAAAGCAAA | ATTAACAATT | GCTGACGATC | TAGGTAAAAC | CACATTCGAA | 300
| CTTTTCAAAG | AAGATGGCAA | ACATTAGTG | TCAAGAAAAG | TAAGTTCTAA | AGACAAAACA | 360
| TCAACAGATG | AAATGTTCAA | TGAAAAAGGT | GAATTGTCTG | CAAAAACCAT | GACAAGAGAA | 420
| AATGGAACCA | AACTTGAATA | TACAGAAATG | AAAGCGATG | GAACCGGAAA | AGCTAAAGAA | 480
| GTTTTAAAAA | ACTTTACTCT | TGAAGGAAAA | GTAGCTAATG | ATAAAGTAAC | ATTGGAAGTA | 540
| AAAGAAGGAA | CCGTTACTTT | AAGTAAGGAA | ATTGCAAAAT | CTGGAGAAGT | AACAGTTGCT | 600
| CTTAATGACA | CTAACACTAC | TCAGGCTACT | AAAAAAACTG | GCGCATGGGA | TTCAAAAACT | 660
| TCTACTTTAA | CAATTAGTGT | TAACAGCAAA | AAAACTACAC | AACTTGTGTT | TACTAAACAA | 720
| GACACAATAA | CTGTACAAAA | ATACGACTCC | GCAGGTACCA | ATTTAGAAGG | CACAGCAGTC | 780
| GAAATTAAAA | CACTTGATGA | ACTTAAAAAC | GCTTTAAAAT | A | | 821

(2) INFORMATION FOR SEQ ID NO:58:

(i) SEQUENCE CHARACTERISTICS:
        (A) LENGTH: 822 base pairs
        (B) TYPE: nucleic acid (C) STRANDEDNESS: double
           (D) TOPOLOGY: linear (ii) MOLECULE TYPE: DNA (genomic)

(xi) SEQUENCE DESCRIPTION: SEQ ID NO:58:

ATGAAAAAAT ATTTATTGGG AATAGGTCTA ATATTAGCCT TAATAGCATG CAAGCAAAAT      60

GTTAGCAGCC TTGATGAAAA AAACAGCGCT TCAGTAGATT TGCCTGGTGA GATGAAAGTT     120

CTTGTAAGTA AAGAAAAAGA CAAAGACGGT AAGTACAGTC TAAAGGCAAC AGTAGACAAG     180

ATTGAGCTAA AAGGAACTTC TGATAAAGAC AATGGTTCTG GAGTGCTTGA AGGTACAAAA     240

GATGACAAAA GTAAAGCAAA ATTAACAATT GCTGACGATC TAAGTAAAAC CACATTCGAA     300

CTTTTCAAAG AAGATGGCAA AACATTAGTG TCAAGAAAAG TAAGTTCTAA AGACAAAACA     360

TCAACAGATG AAATGTTCAA TGAAAAAGGT GAATTGTCTG CAAAAACCAT GACAAGAGAA     420

AATGGAACCA AACTTGAATA TACAGAAATG AAAAGCGATG GAACCGGAAA AGCTAAAGAA     480

GTTTTAAAAA ACTTTACTCT TGAAGGAAAA GTAGCTAATG ATAAAGTAAC ATTGGAAGTA     540

AAAGAAGGAA CCGTTACTTT AAGTAAGGAA ATTGCAAAAT CTGGAGAAGT AACAGTTGCT     600

CTTAATGACA CTAACACTAC TCAGGCTACT AAAAAAACTG GCGCATGGGA TTCAAAAACT     660

TCTACTTTAA CAATTAGTGT TAACAGCAAA AAAACTACAC AACTTGTGTT TACTAAACAA     720

GACACAATAA CTGTACAAAA ATACGACTCC GCAGGTACCA ATTTAGAAGG CACAGCAGTC     780

GAAATTAAAA CACTTGATGA ACTTAAAAAC GCTTTGAAAT AA                        822

(2) INFORMATION FOR SEQ ID NO:59:

(i) SEQUENCE CHARACTERISTICS:
           (A) LENGTH: 37 base pairs
           (B) TYPE: nucleic acid
           (C) STRANDEDNESS: single
           (D) TOPOLOGY: linear (xi) SEQUENCE DESCRIPTION: SEQ ID NO:59:

TTGGATCCGG TCACCCCATG GCTCAATATA ACCAATG                                37

(2) INFORMATION FOR SEQ ID NO:60:

(i) SEQUENCE CHARACTERISTICS:
           (A) LENGTH: 37 base pairs
           (B) TYPE: nucleic acid
           (C) STRANDEDNESS: single
           (D) TOPOLOGY: linear (xi) SEQUENCE DESCRIPTION: SEQ ID NO:60:

TTGGATCCGG TCACCCCATG GCTTCTCAAA ATGTAAG                                37

(2) INFORMATION FOR SEQ ID NO:61:

(i) SEQUENCE CHARACTERISTICS:
           (A) LENGTH: 33 base pairs
           (B) TYPE: nucleic acid
           (C) STRANDEDNESS: single
           (D) TOPOLOGY: linear (xi) SEQUENCE DESCRIPTION: SEQ ID NO:61:

TTGGATCCGG TGACCAACTC CGCCTTGAGA AGG                                    33

(2) INFORMATION FOR SEQ ID NO:62:

(i) SEQUENCE CHARACTERISTICS:
           (A) LENGTH: 33 base pairs (B) TYPE: nucleic acid
(C) STRANDEDNESS: single
(D) TOPOLOGY: linear (xi) SEQUENCE DESCRIPTION: SEQ ID NO:62:

TTGGATCCGG TGACCTATTT GAGCATAAGA TGC    33

(2) INFORMATION FOR SEQ ID NO:63:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:63:

GGTGAATTTA GTTGGTAAGG    20

(2) INFORMATION FOR SEQ ID NO:64:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:64:

CACCAGTTTC TTTAAGCTGC TCCTGC    26

(2) INFORMATION FOR SEQ ID NO:65:

(i) SEQUENCE CHARACTERISTICS:
(A) LENGTH: 2102 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 1..2102

(xi) SEQUENCE DESCRIPTION: SEQ ID NO:65:

```
ATG AAA AAA ATG TTA CTA ATC TTT AGT TTT TTT CTT ATT TTC TTG AAT      48
Met Lys Lys Met Leu Leu Ile Phe Ser Phe Phe Leu Ile Phe Leu Asn
 1               5                  10                  15

GGA TTT CCT GTT AGT GCA AGA GAA GTT GAT AGG GAA AAA TTA AAG GAC      96
Gly Phe Pro Val Ser Ala Arg Glu Val Asp Arg Glu Lys Leu Lys Asp
             20                  25                  30

TTT GTT AAT ATG GAT CTT GAG TTT GTA AAT TAT AAA GGC CCT TAT GAT     144
Phe Val Asn Met Asp Leu Glu Phe Val Asn Tyr Lys Gly Pro Tyr Asp
         35                  40                  45

TCT ACA AAT ACA TAT GAA CAA ATA GTG GGT ATT GGG GAG TTT TTA GCA     192
Ser Thr Asn Thr Tyr Glu Gln Ile Val Gly Ile Gly Glu Phe Leu Ala
     50                  55                  60

AGA CCG TTG ACC AAT TCC AAT AGC AAC TCA AGT TAT TAT GGT AAA TAT     240
Arg Pro Leu Thr Asn Ser Asn Ser Asn Ser Ser Tyr Tyr Gly Lys Tyr
 65                  70                  75                  80

TTT ATT AAT AGA TTT ATT GAT GAT CAA GAT AAA AAA GCA AGC GTT GAT     288
Phe Ile Asn Arg Phe Ile Asp Asp Gln Asp Lys Lys Ala Ser Val Asp
                 85                  90                  95

GTT TTT TCT ATT GGT AGT AAG TCA GAG CTT GAC AGT ATA TTG AAT TTA     336
Val Phe Ser Ile Gly Ser Lys Ser Glu Leu Asp Ser Ile Leu Asn Leu
            100                 105                 110
```

```
AGA AGA ATT CTT ACA GGG TAT TTA ATA AAG TCT TTC GAT TAT GAC AGG        384
Arg Arg Ile Leu Thr Gly Tyr Leu Ile Lys Ser Phe Asp Tyr Asp Arg
        115                 120                 125

TCT AGT GCA GAA TTA ATT GCT AAG GTT ATT ACA ATA TAT AAT GCT GTT        432
Ser Ser Ala Glu Leu Ile Ala Lys Val Ile Thr Ile Tyr Asn Ala Val
    130                 135                 140

TAT AGA GGA GAT TTG GAT TAT TAT AAA GGG TTT TAT ATT GAG GCT GCT        480
Tyr Arg Gly Asp Leu Asp Tyr Tyr Lys Gly Phe Tyr Ile Glu Ala Ala
145                 150                 155                 160

TTA AAG TCT TTA AGT AAA GAA AAT GCA GGT CTT TCT AGG GTT TAT AGT        528
Leu Lys Ser Leu Ser Lys Glu Asn Ala Gly Leu Ser Arg Val Tyr Ser
            165                 170                 175

CAG TGG GCT GGA AAG ACA CAA ATA TTT ATT CCT CTT AAA AAG GAT ATT        576
Gln Trp Ala Gly Lys Thr Gln Ile Phe Ile Pro Leu Lys Lys Asp Ile
        180                 185                 190

TTG TCT GGA AAT ATT GAG TCT GAC ATT GAT ATT GAC AGT TTA GTT ACA        624
Leu Ser Gly Asn Ile Glu Ser Asp Ile Asp Ile Asp Ser Leu Val Thr
    195                 200                 205

GAT AAG GTG GTG GCA GCT CTT TTA AGT GAA AAT GAA GCA GGT GTT AAC        672
Asp Lys Val Val Ala Ala Leu Leu Ser Glu Asn Glu Ala Gly Val Asn
210                 215                 220

TTT GCA AGA GAT ATT ACA GAT ATT CAA GGC GAA ACT CAT AAG GCA GAT        720
Phe Ala Arg Asp Ile Thr Asp Ile Gln Gly Glu Thr His Lys Ala Asp
225                 230                 235                 240

CAA GAT AAA ATT GAT ATT GAA TTA GAC AAT ATT CAT GAA AGT GAT TCC        768
Gln Asp Lys Ile Asp Ile Glu Leu Asp Asn Ile His Glu Ser Asp Ser
            245                 250                 255

AAT ATA ACA GAA ACT ATT GAA AAT TTA AGG GAT CAG CTT GAA AAA GCT        816
Asn Ile Thr Glu Thr Ile Glu Asn Leu Arg Asp Gln Leu Glu Lys Ala
        260                 265                 270

ACA GAT GAA GAG CAT AAA AAA GAG ATT GAA AGT CAG GTT GAT GCT AAA        864
Thr Asp Glu Glu His Lys Lys Glu Ile Glu Ser Gln Val Asp Ala Lys
    275                 280                 285

AAG AAA CAA AAG GAA GAG CTA GAT AAA AAG GCA ATA AAT CTT GAT AAA        912
Lys Lys Gln Lys Glu Glu Leu Asp Lys Lys Ala Ile Asn Leu Asp Lys
290                 295                 300

GCT CAG CAA AAA TTA GAT TCT GCT GAA GAT AAT TTA GAT GTT CAA AGA        960
Ala Gln Gln Lys Leu Asp Ser Ala Glu Asp Asn Leu Asp Val Gln Arg
305                 310                 315                 320

AAT ACT GTT AGA GAG AAA ATT CAA GAG GAT ATT AAC GAA ATT AAC AAG       1008
Asn Thr Val Arg Glu Lys Ile Gln Glu Asp Ile Asn Glu Ile Asn Lys
            325                 330                 335

GAA AAG AAT TTA CCA AAG CCT GGT GAT GTA AGT TCT CCT AAA GTT GAT       1056
Glu Lys Asn Leu Pro Lys Pro Gly Asp Val Ser Ser Pro Lys Val Asp
        340                 345                 350

AAG CAA CTA CAA ATA AAA GAG AGC CTG GAA GAT TTG CAG GAG CAG CTT       1104
Lys Gln Leu Gln Ile Lys Glu Ser Leu Glu Asp Leu Gln Glu Gln Leu
    355                 360                 365

AAA GAA ACT GGT GAT GAA AAT CAG AAA AGA GAA ATT GAA AAG CAA ATT       1152
Lys Glu Thr Gly Asp Glu Asn Gln Lys Arg Glu Ile Glu Lys Gln Ile
370                 375                 380

GAA ATC AAA AAA AGT GAT GAA AAG CTT TTA AAA AGT AAA GAT GAT AAA       1200
Glu Ile Lys Lys Ser Asp Glu Lys Leu Leu Lys Ser Lys Asp Asp Lys
385                 390                 395                 400

GCA AGT AAA GAT GGT AAA GCC TTG GAT CTT GAT CGA GAA TTA AAT TCT       1248
Ala Ser Lys Asp Gly Lys Ala Leu Asp Leu Asp Arg Glu Leu Asn Ser
            405                 410                 415

AAA GCT TCT AGC AAA GAA AAA AGT AAA GCC AAG GAA GAA GAA ATA ACC       1296
Lys Ala Ser Ser Lys Glu Lys Ser Lys Ala Lys Glu Glu Glu Ile Thr
        420                 425                 430
```

```
AAG GGT AAG TCA CAG AAA AGC TTA GGC GAT TTG AAT AAT GAT GAA AAT    1344
Lys Gly Lys Ser Gln Lys Ser Leu Gly Asp Leu Asn Asn Asp Glu Asn
            435                 440                 445

CTT ATG ATG CCA GAA GAT CAA AAA TTA CCT GAG GTT AAA AAA TTA GAT    1392
Leu Met Met Pro Glu Asp Gln Lys Leu Pro Glu Val Lys Lys Leu Asp
        450                 455                 460

AGC AAA AAA GAA TTT AAA CCT GTT TCT GAG GTT GAG AAA TTA GAT AAG    1440
Ser Lys Lys Glu Phe Lys Pro Val Ser Glu Val Glu Lys Leu Asp Lys
465                 470                 475                 480

ATT TTC AAG TCT AAT AAC AAT GTT GGA GAA TTA TCA CCG TTA GAT AAA    1488
Ile Phe Lys Ser Asn Asn Asn Val Gly Glu Leu Ser Pro Leu Asp Lys
                485                 490                 495

TCT TCT TAT AAA GAC ATT GAT TCA AAA GAG GAG ACA GTT AAT AAA GAT    1536
Ser Ser Tyr Lys Asp Ile Asp Ser Lys Glu Glu Thr Val Asn Lys Asp
            500                 505                 510

GTT AAT TTG CAA AAG ACT AAG CCT CAG GTT AAA GAC CAA GTT ACT TCT    1584
Val Asn Leu Gln Lys Thr Lys Pro Gln Val Lys Asp Gln Val Thr Ser
        515                 520                 525

TTG AAT GAA GAT TTG ACT ACT ATG TCT ATA GAT TCC AGT AGT CCT GTA    1632
Leu Asn Glu Asp Leu Thr Thr Met Ser Ile Asp Ser Ser Ser Pro Val
530                 535                 540

TTT TTA GAG GTT ATT GAT CCA ATT ACA AAT TTA GGA ACT CTT CAA CTT    1680
Phe Leu Glu Val Ile Asp Pro Ile Thr Asn Leu Gly Thr Leu Gln Leu
545                 550                 555                 560

ATT GAT TTA AAT ACT GGT GTT AGG CTT AAA GAA AGC ACT CAG CAA GGC    1728
Ile Asp Leu Asn Thr Gly Val Arg Leu Lys Glu Ser Thr Gln Gln Gly
                565                 570                 575

ATT CAG CGG TAT GGA ATT TAT GAA CGT GAA AAA GAT TTG GTT GTT ATT    1776
Ile Gln Arg Tyr Gly Ile Tyr Glu Arg Glu Lys Asp Leu Val Val Ile
            580                 585                 590

AAA ATG GAT TCA GGA AAA GCT AAG CTT CAG ATA CTT GAT AAA CTT GAA    1824
Lys Met Asp Ser Gly Lys Ala Lys Leu Gln Ile Leu Asp Lys Leu Glu
        595                 600                 605

AAT TTA AAA GTG GTA TCA GAG TCT AAT TTT GAG ATT AAT AAA AAT TCA    1872
Asn Leu Lys Val Val Ser Glu Ser Asn Phe Glu Ile Asn Lys Asn Ser
610                 615                 620

TCT CTT TAT GTT GAT TCT AAA ATG ATT TTA GTA GCT GTT AGG GAT AAA    1920
Ser Leu Tyr Val Asp Ser Lys Met Ile Leu Val Ala Val Arg Asp Lys
625                 630                 635                 640

GAT AGT AGT AAT GAT TGG AGA TTG GCC AAA TTT TCT CCT AAA AAT TTA    1968
Asp Ser Ser Asn Asp Trp Arg Leu Ala Lys Phe Ser Pro Lys Asn Leu
                645                 650                 655

GAT GAG TTT ATT CTT TCA GAG AAT AAA ATT ATG CCT TTT ACT AGC TTT    2016
Asp Glu Phe Ile Leu Ser Glu Asn Lys Ile Met Pro Phe Thr Ser Phe
            660                 665                 670

TCT GTG AGA AAA AAT TTT ATT TAT TTG CAA GAT GAG TTT AAA AGT CTA    2064
Ser Val Arg Lys Asn Phe Ile Tyr Leu Gln Asp Glu Phe Lys Ser Leu
        675                 680                 685

GTT ATT TTA GAT GTA AAT ACT TTA AAA AAA GTT AAG TA                 2102
Val Ile Leu Asp Val Asn Thr Leu Lys Lys Val Lys
        690                 695                 700
```

(2) INFORMATION FOR SEQ ID NO:66:

(i) SEQUENCE CHARACTERISTICS:
        (A) LENGTH: 700 amino acids
        (B) TYPE: amino acid
        (D) TOPOLOGY: linear (ii) MOLECULE TYPE: protein (xi) SEQUENCE DESCRIPTION: SEQ ID NO:66:

```
Met Lys Lys Met Leu Leu Ile Phe Ser Phe Phe Leu Ile Phe Leu Asn
  1               5                  10                  15

Gly Phe Pro Val Ser Ala Arg Glu Val Asp Arg Glu Lys Leu Lys Asp
             20                  25                  30

Phe Val Asn Met Asp Leu Glu Phe Val Asn Tyr Lys Gly Pro Tyr Asp
             35                  40                  45

Ser Thr Asn Thr Tyr Glu Gln Ile Val Gly Ile Gly Glu Phe Leu Ala
         50                  55                  60

Arg Pro Leu Thr Asn Ser Asn Ser Asn Ser Ser Tyr Tyr Gly Lys Tyr
 65                  70                  75                  80

Phe Ile Asn Arg Phe Ile Asp Asp Gln Asp Lys Lys Ala Ser Val Asp
                 85                  90                  95

Val Phe Ser Ile Gly Ser Lys Ser Glu Leu Asp Ser Ile Leu Asn Leu
            100                 105                 110

Arg Arg Ile Leu Thr Gly Tyr Leu Ile Lys Ser Phe Asp Tyr Asp Arg
            115                 120                 125

Ser Ser Ala Glu Leu Ile Ala Lys Val Ile Thr Ile Tyr Asn Ala Val
        130                 135                 140

Tyr Arg Gly Asp Leu Asp Tyr Tyr Lys Gly Phe Tyr Ile Glu Ala Ala
145                 150                 155                 160

Leu Lys Ser Leu Ser Lys Glu Asn Ala Gly Leu Ser Arg Val Tyr Ser
                165                 170                 175

Gln Trp Ala Gly Lys Thr Gln Ile Phe Ile Pro Leu Lys Lys Asp Ile
            180                 185                 190

Leu Ser Gly Asn Ile Glu Ser Asp Ile Asp Ile Asp Ser Leu Val Thr
            195                 200                 205

Asp Lys Val Val Ala Ala Leu Leu Ser Glu Asn Glu Ala Gly Val Asn
        210                 215                 220

Phe Ala Arg Asp Ile Thr Asp Ile Gln Gly Glu Thr His Lys Ala Asp
225                 230                 235                 240

Gln Asp Lys Ile Asp Ile Glu Leu Asp Asn Ile His Glu Ser Asp Ser
                245                 250                 255

Asn Ile Thr Glu Thr Ile Glu Asn Leu Arg Asp Gln Leu Glu Lys Ala
            260                 265                 270

Thr Asp Glu Glu His Lys Lys Glu Ile Glu Ser Gln Val Asp Ala Lys
            275                 280                 285

Lys Lys Gln Lys Glu Glu Leu Asp Lys Lys Ala Ile Asn Leu Asp Lys
        290                 295                 300

Ala Gln Gln Lys Leu Asp Ser Ala Glu Asp Asn Leu Asp Val Gln Arg
305                 310                 315                 320

Asn Thr Val Arg Glu Lys Ile Gln Glu Asp Ile Asn Glu Ile Asn Lys
                325                 330                 335

Glu Lys Asn Leu Pro Lys Pro Gly Asp Val Ser Ser Pro Lys Val Asp
            340                 345                 350

Lys Gln Leu Gln Ile Lys Glu Ser Leu Glu Asp Leu Gln Glu Gln Leu
        355                 360                 365

Lys Glu Thr Gly Asp Glu Asn Gln Lys Arg Glu Ile Glu Lys Gln Ile
370                 375                 380

Glu Ile Lys Lys Ser Asp Glu Lys Leu Lys Ser Lys Asp Asp Lys
385                 390                 395                 400
```

```
Ala Ser Lys Asp Gly Lys Ala Leu Asp Leu Asp Arg Glu Leu Asn Ser
            405                 410                 415

Lys Ala Ser Ser Lys Glu Lys Ser Lys Ala Lys Glu Glu Glu Ile Thr
            420                 425                 430

Lys Gly Lys Ser Gln Lys Ser Leu Gly Asp Leu Asn Asn Asp Glu Asn
            435                 440                 445

Leu Met Met Pro Glu Asp Gln Lys Leu Pro Glu Val Lys Lys Leu Asp
        450                 455                 460

Ser Lys Lys Glu Phe Lys Pro Val Ser Glu Val Glu Lys Leu Asp Lys
465                 470                 475                 480

Ile Phe Lys Ser Asn Asn Val Gly Glu Leu Ser Pro Leu Asp Lys
                485                 490                 495

Ser Ser Tyr Lys Asp Ile Asp Ser Lys Glu Glu Thr Val Asn Lys Asp
                500                 505                 510

Val Asn Leu Gln Lys Thr Lys Pro Gln Val Lys Asp Gln Val Thr Ser
            515                 520                 525

Leu Asn Glu Asp Leu Thr Thr Met Ser Ile Asp Ser Ser Pro Val
    530                 535                 540

Phe Leu Glu Val Ile Asp Pro Ile Thr Asn Leu Gly Thr Leu Gln Leu
545                 550                 555                 560

Ile Asp Leu Asn Thr Gly Val Arg Leu Lys Glu Ser Thr Gln Gln Gly
                565                 570                 575

Ile Gln Arg Tyr Gly Ile Tyr Glu Arg Glu Lys Asp Leu Val Val Ile
                580                 585                 590

Lys Met Asp Ser Gly Lys Ala Lys Leu Gln Ile Leu Asp Lys Leu Glu
            595                 600                 605

Asn Leu Lys Val Val Ser Glu Ser Asn Phe Glu Ile Asn Lys Asn Ser
    610                 615                 620

Ser Leu Tyr Val Asp Ser Lys Met Ile Leu Val Ala Val Arg Asp Lys
625                 630                 635                 640

Asp Ser Ser Asn Asp Trp Arg Leu Ala Lys Phe Ser Pro Lys Asn Leu
                645                 650                 655

Asp Glu Phe Ile Leu Ser Glu Asn Lys Ile Met Pro Phe Thr Ser Phe
                660                 665                 670

Ser Val Arg Lys Asn Phe Ile Tyr Leu Gln Asp Glu Phe Lys Ser Leu
            675                 680                 685

Val Ile Leu Asp Val Asn Thr Leu Lys Lys Val Lys
    690                 695                 700

(2) INFORMATION FOR SEQ ID NO:67:

(i) SEQUENCE CHARACTERISTICS:
        (A) LENGTH: 2081 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..2081

(xi) SEQUENCE DESCRIPTION: SEQ ID NO:67:

ATG AAA AAA TTG TTA CTA ATC TTT AGT TTT TTT CTT ATT TCT TTG AAT      48
Met Lys Lys Leu Leu Leu Ile Phe Ser Phe Phe Leu Ile Ser Leu Asn
  1               5                  10                  15
```

| | |
|---|---|
| GGA TTT CCT CTT AAT TCA AGG GAA GTT GAT AAG GAA AAA TTA AAG GAT<br>Gly Phe Pro Leu Asn Ser Arg Glu Val Asp Lys Glu Lys Leu Lys Asp<br>                20                          25                    30 | 96 |
| TTT GTT AAT ATG GAT CTT GAG TTT GTA AAC TAT AAA GGT CCT TAT GAT<br>Phe Val Asn Met Asp Leu Glu Phe Val Asn Tyr Lys Gly Pro Tyr Asp<br>              35                        40                        45 | 144 |
| TCT ACA AAT ACA TAT GAA CAA ATA GTA GGT ATT GGT GAG TTT TTA GCA<br>Ser Thr Asn Thr Tyr Glu Gln Ile Val Gly Ile Gly Glu Phe Leu Ala<br>50                        55                        60 | 192 |
| AGA CCA TTG ATT AAT TCC AAT AGC AAC TCA ATT TAT TAT GGT AAA TAT<br>Arg Pro Leu Ile Asn Ser Asn Ser Asn Ser Ile Tyr Tyr Gly Lys Tyr<br>65                        70                        75                    80 | 240 |
| TTT ATT AAT AGA TTT ATT GAT GAT CAA GAT AAA AAA GCA AGC GTT GAT<br>Phe Ile Asn Arg Phe Ile Asp Asp Gln Asp Lys Lys Ala Ser Val Asp<br>              85                        90                        95 | 288 |
| GTT TTT TCT ATT GGT AGT AGG TCA CAG CTT GAC AGT ATA TTG AAT CTA<br>Val Phe Ser Ile Gly Ser Arg Ser Gln Leu Asp Ser Ile Leu Asn Leu<br>                100                      105                      110 | 336 |
| AGA AGA ATT CTT ACA GGG TAT TTG ATA AAG TCT TTT GAT TAT GAA AGA<br>Arg Arg Ile Leu Thr Gly Tyr Leu Ile Lys Ser Phe Asp Tyr Glu Arg<br>              115                      120                      125 | 384 |
| TCT AGT GCT GAA TTA ATT GCT AAG GTT ATT ACA ATA CAT AAT GCT GTT<br>Ser Ser Ala Glu Leu Ile Ala Lys Val Ile Thr Ile His Asn Ala Val<br>130                        135                      140 | 432 |
| TAT AGA GGG GAT TTA AAT TAT TAT AAA GAG GTT TAT ATT GAG GCT GCT<br>Tyr Arg Gly Asp Leu Asn Tyr Tyr Lys Glu Val Tyr Ile Glu Ala Ala<br>145                        150                      155                    160 | 480 |
| TTA AAG TCT TTA ACT AAA GAA AAT GCA GGT CTT TCT AGA GTG TAC AGT<br>Leu Lys Ser Leu Thr Lys Glu Asn Ala Gly Leu Ser Arg Val Tyr Ser<br>              165                      170                      175 | 528 |
| CAA TGG GCT GGA AAG ACA CAA ATA TTT ATT CCT CTT AAA AAG AAT ATT<br>Gln Trp Ala Gly Lys Thr Gln Ile Phe Ile Pro Leu Lys Lys Asn Ile<br>              180                      185                      190 | 576 |
| TTA TCT GGA AAA GTT GAG TCT GAC ATT GAT ATT GAC AGT TTG GTT ACA<br>Leu Ser Gly Lys Val Glu Ser Asp Ile Asp Ile Asp Ser Leu Val Thr<br>              195                      200                      205 | 624 |
| GAT AAG GTT GTG GCA GCT CTT TTA AGC GAG AAT GAA GCA GGT GTT AAC<br>Asp Lys Val Val Ala Ala Leu Leu Ser Glu Asn Glu Ala Gly Val Asn<br>210                        215                      220 | 672 |
| TTT GCA AGA GAT ATT ACA GAT ATT CAA GGC GAA ACT CAT AAA GCA GAT<br>Phe Ala Arg Asp Ile Thr Asp Ile Gln Gly Glu Thr His Lys Ala Asp<br>225                        230                      235                    240 | 720 |
| CAA GAT AAA ATT GAT ATT GAA TTA GAT AAT GTT CAT AAA AGT GAT TCC<br>Gln Asp Lys Ile Asp Ile Glu Leu Asp Asn Val His Lys Ser Asp Ser<br>              245                      250                      255 | 768 |
| AAT ATA ACA GAG ACT ATT GAG AAT TTA AGA GAT CAG CTT GAA AAG GCT<br>Asn Ile Thr Glu Thr Ile Glu Asn Leu Arg Asp Gln Leu Glu Lys Ala<br>              260                      265                      270 | 816 |
| ACA GAT GAA GAG CAT AGA AAA GAG ATT GAA AGT CAG GTT GAT GCT AAA<br>Thr Asp Glu Glu His Arg Lys Glu Ile Glu Ser Gln Val Asp Ala Lys<br>              275                      280                      285 | 864 |
| AAG AAA CAA AAA GAA GAA CTA GAT AAA AAG GCA ATC GAT CTT GAT AAA<br>Lys Lys Gln Lys Glu Glu Leu Asp Lys Lys Ala Ile Asp Leu Asp Lys<br>          290                      295                      300 | 912 |
| GCC CAA CAA AAA TTA GAT TCT TCT GAA GAT AAT TTA GAT ATT CAA AGG<br>Ala Gln Gln Lys Leu Asp Ser Ser Glu Asp Asn Leu Asp Ile Gln Arg<br>305                        310                      315                    320 | 960 |
| GAT ACT GTT AGA GAG AAG ATT CAA GAG GAT ATT GAC GAG ATT AAT AAA<br>Asp Thr Val Arg Glu Lys Ile Gln Glu Asp Ile Asp Glu Ile Asn Lys<br>              325                      330                      335 | 1008 |

-continued

```
GAA AAG AAT TTG CCA AAA CCT GGT GAT GTA AGT TCT CCT AAA GTT GAT      1056
Glu Lys Asn Leu Pro Lys Pro Gly Asp Val Ser Ser Pro Lys Val Asp
            340             345                 350

AAG CAG CTA CAA ATA AAA GAG AGT CTA GAA GAC TTG CAG GAA CAG CTT      1104
Lys Gln Leu Gln Ile Lys Glu Ser Leu Glu Asp Leu Gln Glu Gln Leu
                355                 360                 365

AAA GAA ACT AGC GAT GAA AAT CAA AAA AGA GAA ATT GAA AAG CAA ATT      1152
Lys Glu Thr Ser Asp Glu Asn Gln Lys Arg Glu Ile Glu Lys Gln Ile
            370                 375                 380

GAA ATC AAA AAA AGT GAT GAA GAA CTT TTA AAA AGT AAA GAT CCT AAA      1200
Glu Ile Lys Lys Ser Asp Glu Glu Leu Leu Lys Ser Lys Asp Pro Lys
385                 390                 395                 400

GCA TTA GAT CTT AAT GGA GAT TTA AAT TCT AAA GTT TCT AGT AAA GAA      1248
Ala Leu Asp Leu Asn Gly Asp Leu Asn Ser Lys Val Ser Ser Lys Glu
                405                 410                 415

AAA ATT AAA GGC AAA GAA GGA GAA ATA GTC AAA GAG GAA TCA AAG GCA      1296
Lys Ile Lys Gly Lys Glu Gly Glu Ile Val Lys Glu Glu Ser Lys Ala
            420                 425                 430

AGT TTA GCT GAT TTG AAT AAT GAC GAA AAT CTT ATG AGG CCG GAA GAT      1344
Ser Leu Ala Asp Leu Asn Asn Asp Glu Asn Leu Met Arg Pro Glu Asp
                435                 440                 445

CAA AAA TTA TCT GAG GAT AAA AAA TTA GAT AGT AAA AAA AAT TTA AAA      1392
Gln Lys Leu Ser Glu Asp Lys Lys Leu Asp Ser Lys Lys Asn Leu Lys
        450                 455                 460

CCT GTT TCT GAG ATT GAG AGA GTA AAT GAA ATT TCG AAG TCT AAC AAC      1440
Pro Val Ser Glu Ile Glu Arg Val Asn Glu Ile Ser Lys Ser Asn Asn
465                 470                 475                 480

AAT GAG ATT AGT GAA TCA TCA CCA TTA TAT AAG CCT TCT TAT AGC GAT      1488
Asn Glu Ile Ser Glu Ser Ser Pro Leu Tyr Lys Pro Ser Tyr Ser Asp
                485                 490                 495

ATG GAT TCA AAA GAG GGT ATA GAT AAT AAA GAT GTT AAC TTG CAA GAA      1536
Met Asp Ser Lys Glu Gly Ile Asp Asn Lys Asp Val Asn Leu Gln Glu
            500                 505                 510

ACC AAG TCT CAA ACT AAA AGT CAA CCT ACT TCT TTA AAT CAA GAT TTG      1584
Thr Lys Ser Gln Thr Lys Ser Gln Pro Thr Ser Leu Asn Gln Asp Leu
        515                 520                 525

ACT ACT ATG TCT ATA GAT TCT AGT AAT CCT GTA TTT TTA GAG GTT ATT      1632
Thr Thr Met Ser Ile Asp Ser Ser Asn Pro Val Phe Leu Glu Val Ile
530                 535                 540

GAT CCT ATT ACA AAT TTA GGA ACG CTT CAA CTT ATT GAT TTG AAT ACC      1680
Asp Pro Ile Thr Asn Leu Gly Thr Leu Gln Leu Ile Asp Leu Asn Thr
545                 550                 555                 560

GGT GTT AGA CTT AAA GAA AGT ACT CAG CAA GGC ATT CAG CGG TAT GGA      1728
Gly Val Arg Leu Lys Glu Ser Thr Gln Gln Gly Ile Gln Arg Tyr Gly
                565                 570                 575

ATT TAT GAA CGT GAA AAA GAT TTA GTT GTT ATT AAA ATG GAT TCA GGA      1776
Ile Tyr Glu Arg Glu Lys Asp Leu Val Val Ile Lys Met Asp Ser Gly
            580                 585                 590

AAA GCC AAG CTT CAA ATA CTT AAT AAA CTT GAG AAT TTA AAA GTG ATA      1824
Lys Ala Lys Leu Gln Ile Leu Asn Lys Leu Glu Asn Leu Lys Val Ile
                595                 600                 605

TCG GAG TCT AAT TTT GAG ATT AAT AAA AAT TCA TCT CTT TAT GTT GAC      1872
Ser Glu Ser Asn Phe Glu Ile Asn Lys Asn Ser Ser Leu Tyr Val Asp
            610                 615                 620

TCT AAA ATG ATT TTA GTA GTT GTG AGA GAT AGT GGT AAT GTT TGG AGA      1920
Ser Lys Met Ile Leu Val Val Val Arg Asp Ser Gly Asn Val Trp Arg
625                 630                 635                 640
```

```
TTG GCT AAA TTT TCT CCT AAA AAT TTA AAT GAG TTT ATT CTT TCA GAG    1968
Leu Ala Lys Phe Ser Pro Lys Asn Leu Asn Glu Phe Ile Leu Ser Glu
            645                 650                 655

AAT AAA ATT TTG CCT TTT ACT AGC TTT TCT GTG AGA AAG AAT TTT ATT    2016
Asn Lys Ile Leu Pro Phe Thr Ser Phe Ser Val Arg Lys Asn Phe Ile
            660                 665                 670

TAT TTG CAG GAT GAG TTT AAA AGT CTT ATT ACT TTA GAT GTA AAT ACT    2064
Tyr Leu Gln Asp Glu Phe Lys Ser Leu Ile Thr Leu Asp Val Asn Thr
            675                 680                 685

TTA AAA AAA GTT AAG TA                                             2081
Leu Lys Lys Val Lys
        690
```

(2) INFORMATION FOR SEQ ID NO:68:

(i) SEQUENCE CHARACTERISTICS:
        (A) LENGTH: 693 amino acids
        (B) TYPE: amino acid
        (D) TOPOLOGY: linear (ii) MOLECULE TYPE: protein (xi) SEQUENCE DESCRIPTION: SEQ ID NO:68:

```
Met Lys Lys Leu Leu Leu Ile Phe Ser Phe Phe Leu Ile Ser Leu Asn
 1               5                  10                  15

Gly Phe Pro Leu Asn Ser Arg Glu Val Asp Lys Glu Lys Leu Lys Asp
                20                  25                  30

Phe Val Asn Met Asp Leu Glu Phe Val Asn Tyr Lys Gly Pro Tyr Asp
            35                  40                  45

Ser Thr Asn Thr Tyr Glu Gln Ile Val Gly Ile Gly Glu Phe Leu Ala
        50                  55                  60

Arg Pro Leu Ile Asn Ser Asn Ser Asn Ser Ile Tyr Tyr Gly Lys Tyr
 65                  70                  75                  80

Phe Ile Asn Arg Phe Ile Asp Asp Gln Asp Lys Lys Ala Ser Val Asp
                85                  90                  95

Val Phe Ser Ile Gly Ser Arg Ser Gln Leu Asp Ser Ile Leu Asn Leu
            100                 105                 110

Arg Arg Ile Leu Thr Gly Tyr Leu Ile Lys Ser Phe Asp Tyr Glu Arg
        115                 120                 125

Ser Ser Ala Glu Leu Ile Ala Lys Val Ile Thr Ile His Asn Ala Val
130                 135                 140

Tyr Arg Gly Asp Leu Asn Tyr Tyr Lys Glu Val Tyr Ile Glu Ala Ala
145                 150                 155                 160

Leu Lys Ser Leu Thr Lys Glu Asn Ala Gly Leu Ser Arg Val Tyr Ser
                165                 170                 175

Gln Trp Ala Gly Lys Thr Gln Ile Phe Ile Pro Leu Lys Lys Asn Ile
            180                 185                 190

Leu Ser Gly Lys Val Glu Ser Asp Ile Asp Ile Asp Ser Leu Val Thr
        195                 200                 205

Asp Lys Val Val Ala Ala Leu Leu Ser Glu Asn Glu Ala Gly Val Asn
210                 215                 220

Phe Ala Arg Asp Ile Thr Asp Ile Gln Gly Glu Thr His Lys Ala Asp
225                 230                 235                 240

Gln Asp Lys Ile Asp Ile Glu Leu Asp Asn Val His Lys Ser Asp Ser
                245                 250                 255

Asn Ile Thr Glu Thr Ile Glu Asn Leu Arg Asp Gln Leu Glu Lys Ala
            260                 265                 270
```

-continued

```
Thr Asp Glu Glu His Arg Lys Glu Ile Glu Ser Gln Val Asp Ala Lys
        275                 280                 285
Lys Lys Gln Lys Glu Glu Leu Asp Lys Ala Ile Asp Leu Asp Lys
290                 295                 300
Ala Gln Gln Lys Leu Asp Ser Ser Glu Asp Asn Leu Asp Ile Gln Arg
305                 310                 315                 320
Asp Thr Val Arg Glu Lys Ile Gln Glu Asp Ile Asp Glu Ile Asn Lys
                325                 330                 335
Glu Lys Asn Leu Pro Lys Pro Gly Asp Val Ser Ser Pro Lys Val Asp
                340                 345                 350
Lys Gln Leu Gln Ile Lys Glu Ser Leu Glu Asp Leu Gln Glu Gln Leu
                355                 360                 365
Lys Glu Thr Ser Asp Glu Asn Gln Lys Arg Glu Ile Glu Lys Gln Ile
                370                 375                 380
Glu Ile Lys Lys Ser Asp Glu Glu Leu Leu Lys Ser Lys Asp Pro Lys
385                 390                 395                 400
Ala Leu Asp Leu Asn Gly Asp Leu Asn Ser Lys Val Ser Ser Lys Glu
                405                 410                 415
Lys Ile Lys Gly Lys Glu Gly Glu Ile Val Lys Glu Ser Lys Ala
                420                 425                 430
Ser Leu Ala Asp Leu Asn Asn Asp Glu Asn Leu Met Arg Pro Glu Asp
                435                 440                 445
Gln Lys Leu Ser Glu Asp Lys Lys Leu Asp Ser Lys Lys Asn Leu Lys
450                 455                 460
Pro Val Ser Glu Ile Glu Arg Val Asn Glu Ile Ser Lys Ser Asn Asn
465                 470                 475                 480
Asn Glu Ile Ser Glu Ser Ser Pro Leu Tyr Lys Pro Ser Tyr Ser Asp
                485                 490                 495
Met Asp Ser Lys Glu Gly Ile Asp Asn Lys Asp Val Asn Leu Gln Glu
                500                 505                 510
Thr Lys Ser Gln Thr Lys Ser Gln Pro Thr Ser Leu Asn Gln Asp Leu
                515                 520                 525
Thr Thr Met Ser Ile Asp Ser Ser Asn Pro Val Phe Leu Glu Val Ile
                530                 535                 540
Asp Pro Ile Thr Asn Leu Gly Thr Leu Gln Leu Ile Asp Leu Asn Thr
545                 550                 555                 560
Gly Val Arg Leu Lys Glu Ser Thr Gln Gln Gly Ile Gln Arg Tyr Gly
                565                 570                 575
Ile Tyr Glu Arg Glu Lys Asp Leu Val Val Ile Lys Met Asp Ser Gly
                580                 585                 590
Lys Ala Lys Leu Gln Ile Leu Asn Lys Leu Glu Asn Leu Lys Val Ile
                595                 600                 605
Ser Glu Ser Asn Phe Glu Ile Asn Lys Asn Ser Ser Leu Tyr Val Asp
                610                 615                 620
Ser Lys Met Ile Leu Val Val Arg Asp Ser Gly Asn Val Trp Arg
625                 630                 635                 640
Leu Ala Lys Phe Ser Pro Lys Asn Leu Asn Glu Phe Ile Leu Ser Glu
                645                 650                 655
Asn Lys Ile Leu Pro Phe Thr Ser Phe Ser Val Arg Lys Asn Phe Ile
                660                 665                 670
Tyr Leu Gln Asp Glu Phe Lys Ser Leu Ile Thr Leu Asp Val Asn Thr
                675                 680                 685
```

```
Leu Lys Lys Val Lys
    690

(2) INFORMATION FOR SEQ ID NO:69:

(i) SEQUENCE CHARACTERISTICS:
        (A) LENGTH: 1991 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..1991

(xi) SEQUENCE DESCRIPTION: SEQ ID NO:69:

ATG AAA AAA ATG TTA CTA ATC TTT AGT TTT TTT CTT GTT TTT TTA AAT        48
Met Lys Lys Met Leu Leu Ile Phe Ser Phe Phe Leu Val Phe Leu Asn
  1               5                  10                  15

GGA TTT CCT CTT AAT GCA AGG GAA GTT GAT AAG GAA AAA TTA AAG GAC        96
Gly Phe Pro Leu Asn Ala Arg Glu Val Asp Lys Glu Lys Leu Lys Asp
             20                  25                  30

TTT GTT AAT ATG GAT CTT GAA TTT GTT AAT TAC AAG GGT CCT TAT GAT       144
Phe Val Asn Met Asp Leu Glu Phe Val Asn Tyr Lys Gly Pro Tyr Asp
         35                  40                  45

TCT ACA GAT ACA TAT GAA CAA ATA GTA GGT ATT GGG GAG TTT TTA GCA       192
Ser Thr Asp Thr Tyr Glu Gln Ile Val Gly Ile Gly Glu Phe Leu Ala
     50                  55                  60

AGG CCG TTG AAC AAT TCC AAT AGT AAT TCA AGT TAT TAT GGT AAA TAT       240
Arg Pro Leu Asn Asn Ser Asn Ser Asn Ser Ser Tyr Tyr Gly Lys Tyr
 65                  70                  75                  80

TTT GTT AAT AGA TTT ATT GAC GAT CAA GAT AAA AAA GCA AGT GTT GAT       288
Phe Val Asn Arg Phe Ile Asp Asp Gln Asp Lys Lys Ala Ser Val Asp
                 85                  90                  95

ATT TTT TCT ATT GGT AGT AAG TCA GAG CTT GAT AGT ATA TTA AAT CTA       336
Ile Phe Ser Ile Gly Ser Lys Ser Glu Leu Asp Ser Ile Leu Asn Leu
            100                 105                 110

AGA AGA ATT CTT ACA GGG TAT TTA ATG AAG TCT TTT GAT TAT GAG AGG       384
Arg Arg Ile Leu Thr Gly Tyr Leu Met Lys Ser Phe Asp Tyr Glu Arg
        115                 120                 125

TCT AGT GCG GAA TTA ATT GCT AAA GCT ATT ACA ATA TAT AAT GCT GTT       432
Ser Ser Ala Glu Leu Ile Ala Lys Ala Ile Thr Ile Tyr Asn Ala Val
    130                 135                 140

TAT AGA GGA GAT TTA GAT TAT TAC AAA GAG TTT TAT ATT GAG GCT TCT       480
Tyr Arg Gly Asp Leu Asp Tyr Tyr Lys Glu Phe Tyr Ile Glu Ala Ser
145                 150                 155                 160

TTG AAG TCT TTG ACT AAA GAA AAT GCA GGT CTT TCT AGG GTG TAC AGT       528
Leu Lys Ser Leu Thr Lys Glu Asn Ala Gly Leu Ser Arg Val Tyr Ser
                165                 170                 175

CAA TGG GCT GGG AAG ACA CAA ATA TTT ATT CCT CTT AAA AAG AAT ATT       576
Gln Trp Ala Gly Lys Thr Gln Ile Phe Ile Pro Leu Lys Lys Asn Ile
            180                 185                 190

TTA TCT GGA AAT GTT GAG TCT GAC ATT GAT ATT GAT AGT TTG GTT ACA       624
Leu Ser Gly Asn Val Glu Ser Asp Ile Asp Ile Asp Ser Leu Val Thr
        195                 200                 205

GAT AAG GTG GTG GCA GCT CTT TTA AGT GAG AAT GAA TCA GGT GTT AAC       672
Asp Lys Val Val Ala Ala Leu Leu Ser Glu Asn Glu Ser Gly Val Asn
    210                 215                 220

TTT GCA AGA GAT ATT ACA GAC ATT CAA GGC GAA ACT CAT AAA GCA GAT       720
Phe Ala Arg Asp Ile Thr Asp Ile Gln Gly Glu Thr His Lys Ala Asp
225                 230                 235                 240
```

```
CAA GAT AAA ATT GAT ATT GAA TTA GAT AAT TTT CAT GAA AGT GAT TCC      768
Gln Asp Lys Ile Asp Ile Glu Leu Asp Asn Phe His Glu Ser Asp Ser
            245                 250                 255

AAT ATA ACA GAA ACT ATT GAG AAT TTA AGG GAT CAG CTT GAA AAA GCT      816
Asn Ile Thr Glu Thr Ile Glu Asn Leu Arg Asp Gln Leu Glu Lys Ala
            260                 265                 270

ACA GAT GAA GAG CAT AAA AAA GAG ATT GAA AGT CAG GTT GAT GCT AAA      864
Thr Asp Glu Glu His Lys Lys Glu Ile Glu Ser Gln Val Asp Ala Lys
            275                 280                 285

AAG AAA CAA AAG GAA GAA TTA GAT AAA AAG GCA ATT GAT CTT GAT AAA      912
Lys Lys Gln Lys Glu Glu Leu Asp Lys Lys Ala Ile Asp Leu Asp Lys
            290                 295                 300

GCT CAA CAA AAA TTA GAT TTT GCT GAA GAT AAT CTA GAT ATT CAA AGG      960
Ala Gln Gln Lys Leu Asp Phe Ala Glu Asp Asn Leu Asp Ile Gln Arg
305             310                 315                 320

GAT ACT GTT AGA GAG AAG CTT CAA GAA AAT ATT AAC GAG ACT AAT AAG     1008
Asp Thr Val Arg Glu Lys Leu Gln Glu Asn Ile Asn Glu Thr Asn Lys
            325                 330                 335

GAA AAG AAT TTA CCA AAG CCT GGT GAT GTA AGT TCT CCT AAG GTT GAT     1056
Glu Lys Asn Leu Pro Lys Pro Gly Asp Val Ser Ser Pro Lys Val Asp
            340                 345                 350

AAG CAG TTG CAG ATA AAA GAG AGT CTA GAA GAT TTG CAA GAG CAG CTT     1104
Lys Gln Leu Gln Ile Lys Glu Ser Leu Glu Asp Leu Gln Glu Gln Leu
            355                 360                 365

AAA GAA GCT AGT GAT GAA AAT CAA AAA AGA GAA ATA GAA AAG CAA ATT     1152
Lys Glu Ala Ser Asp Glu Asn Gln Lys Arg Glu Ile Glu Lys Gln Ile
            370                 375                 380

GAA ATC AAA AAA AAT GAT GAA GAA CTT TTT AAA AAT AAA GAT CAT AAA     1200
Glu Ile Lys Lys Asn Asp Glu Glu Leu Phe Lys Asn Lys Asp His Lys
385             390                 395                 400

GCA TTA GAT CTT AAG CAA GAA TTA AAT TCT AAA GCT TCT AGT AAA GAA     1248
Ala Leu Asp Leu Lys Gln Glu Leu Asn Ser Lys Ala Ser Ser Lys Glu
            405                 410                 415

AAA ATT GAA GGC GAA GAA GAG GAT AAA GAA TTA GAT AGT AAA AAA AAT     1296
Lys Ile Glu Gly Glu Glu Glu Asp Lys Glu Leu Asp Ser Lys Lys Asn
            420                 425                 430

TTA GAG CCT GTT TCT GAG GCT GAT AAA GTA GAT AAA ATT TCC AAG TCT     1344
Leu Glu Pro Val Ser Glu Ala Asp Lys Val Asp Lys Ile Ser Lys Ser
            435                 440                 445

AAC AAC AAT GAG GTT AGT AAA TTA TCC CCG TTA GAT GAG CCT TCT TAT     1392
Asn Asn Asn Glu Val Ser Lys Leu Ser Pro Leu Asp Glu Pro Ser Tyr
            450                 455                 460

AGC GAC ATT GAT TCG AAA GAG GGT GTA GAT AAC AAA GAT GTT GAT TTG     1440
Ser Asp Ile Asp Ser Lys Glu Gly Val Asp Asn Lys Asp Val Asp Leu
465             470                 475                 480

CAA AAA ACT AAA CCC CAA GTT GAA AGT CAA CCT ACT TCG TTA AAT GAA     1488
Gln Lys Thr Lys Pro Gln Val Glu Ser Gln Pro Thr Ser Leu Asn Glu
            485                 490                 495

GAT TTG ATT GAT GTG TCT ATA GAT TCC AGT AAT CCT GTC TTT TTA GAG     1536
Asp Leu Ile Asp Val Ser Ile Asp Ser Ser Asn Pro Val Phe Leu Glu
            500                 505                 510

GTT ATC GAT CCG ATT ACA AAT TTA GGA ACG CTT CAA CTT ATT GAT TTG     1584
Val Ile Asp Pro Ile Thr Asn Leu Gly Thr Leu Gln Leu Ile Asp Leu
            515                 520                 525

AAT ACC GGT GTT AGA CTT AAA GAA AGT GCT CAA CAA GGT ATT CAG CGA     1632
Asn Thr Gly Val Arg Leu Lys Glu Ser Ala Gln Gln Gly Ile Gln Arg
            530                 535                 540
```

```
TAT GGA ATT TAT GAA CGT GAA AAA GAT TTG GTT GTT ATT AAA ATA GAT      1680
Tyr Gly Ile Tyr Glu Arg Glu Lys Asp Leu Val Val Ile Lys Ile Asp
545                 550                 555                 560

TCA GGA AAA GCT AAG CTT CAG ATA CTT GAT AAA CTC GAG AAT TTA AAA      1728
Ser Gly Lys Ala Lys Leu Gln Ile Leu Asp Lys Leu Glu Asn Leu Lys
                565                 570                 575

GTG ATA TCA GAG TCT AAT TTT GAG ATT AAT AAA AAT TCA TCT CTT TAT      1776
Val Ile Ser Glu Ser Asn Phe Glu Ile Asn Lys Asn Ser Ser Leu Tyr
            580                 585                 590

GTT GAC TCT AGA ATG ATT TTA GTA GTT GTT AAG GAC GAT AGT AAT GCT      1824
Val Asp Ser Arg Met Ile Leu Val Val Val Lys Asp Asp Ser Asn Ala
        595                 600                 605

TGG AGA TTG GCT AAA TTT TCT CCT AAA AAT TTA GAT GAA TTT ATT CTG      1872
Trp Arg Leu Ala Lys Phe Ser Pro Lys Asn Leu Asp Glu Phe Ile Leu
610                 615                 620

TCA GAA AAT AAA ATT TTG CCT TTT ACT AGC TTT GCT GTG AGA AAG AAT      1920
Ser Glu Asn Lys Ile Leu Pro Phe Thr Ser Phe Ala Val Arg Lys Asn
625                 630                 635                 640

TTT ATT TAT TTG CAA GAT GAA CTT AAA AGC TTA GTT ACT TTA GAT GTA      1968
Phe Ile Tyr Leu Gln Asp Glu Leu Lys Ser Leu Val Thr Leu Asp Val
                645                 650                 655

AAT ACT TTA AAA AAA GTT AAG TA                                       1991
Asn Thr Leu Lys Lys Val Lys
                660
```

(2) INFORMATION FOR SEQ ID NO:70:

(i) SEQUENCE CHARACTERISTICS:
        (A) LENGTH: 663 amino acids
        (B) TYPE: amino acid
        (D) TOPOLOGY: linear (ii) MOLECULE TYPE: protein (xi) SEQUENCE DESCRIPTION: SEQ ID NO:70:

```
Met Lys Lys Met Leu Leu Ile Phe Ser Phe Phe Leu Val Phe Leu Asn
  1               5                  10                  15

Gly Phe Pro Leu Asn Ala Arg Glu Val Asp Lys Glu Lys Leu Lys Asp
                20                  25                  30

Phe Val Asn Met Asp Leu Glu Phe Val Asn Tyr Lys Gly Pro Tyr Asp
            35                  40                  45

Ser Thr Asp Thr Tyr Glu Gln Ile Val Gly Ile Gly Glu Phe Leu Ala
         50                  55                  60

Arg Pro Leu Asn Asn Ser Asn Ser Asn Ser Ser Tyr Tyr Gly Lys Tyr
 65                  70                  75                  80

Phe Val Asn Arg Phe Ile Asp Asp Gln Asp Lys Lys Ala Ser Val Asp
                85                  90                  95

Ile Phe Ser Ile Gly Ser Lys Ser Glu Leu Asp Ser Ile Leu Asn Leu
            100                 105                 110

Arg Arg Ile Leu Thr Gly Tyr Leu Met Lys Ser Phe Asp Tyr Glu Arg
            115                 120                 125

Ser Ser Ala Glu Leu Ile Ala Lys Ala Ile Thr Ile Tyr Asn Ala Val
            130                 135                 140

Tyr Arg Gly Asp Leu Asp Tyr Lys Glu Phe Tyr Ile Glu Ala Ser
145                 150                 155                 160

Leu Lys Ser Leu Thr Lys Glu Asn Ala Gly Leu Ser Arg Val Tyr Ser
                165                 170                 175

Gln Trp Ala Gly Lys Thr Gln Ile Phe Ile Pro Leu Lys Lys Asn Ile
            180                 185                 190
```

-continued

```
Leu Ser Gly Asn Val Glu Ser Asp Ile Asp Ile Asp Ser Leu Val Thr
            195                 200                 205
Asp Lys Val Val Ala Ala Leu Leu Ser Glu Asn Glu Ser Gly Val Asn
210                 215                 220
Phe Ala Arg Asp Ile Thr Asp Ile Gln Gly Glu Thr His Lys Ala Asp
225                 230                 235                 240
Gln Asp Lys Ile Asp Ile Glu Leu Asp Asn Phe His Glu Ser Asp Ser
                245                 250                 255
Asn Ile Thr Glu Thr Ile Glu Asn Leu Arg Asp Gln Leu Glu Lys Ala
            260                 265                 270
Thr Asp Glu Glu His Lys Lys Glu Ile Glu Ser Gln Val Asp Ala Lys
        275                 280                 285
Lys Lys Gln Lys Glu Glu Leu Asp Lys Lys Ala Ile Asp Leu Asp Lys
290                 295                 300
Ala Gln Gln Lys Leu Asp Phe Ala Glu Asp Asn Leu Asp Ile Gln Arg
305                 310                 315                 320
Asp Thr Val Arg Glu Lys Leu Gln Glu Asn Ile Asn Glu Thr Asn Lys
                325                 330                 335
Glu Lys Asn Leu Pro Lys Pro Gly Asp Val Ser Ser Pro Lys Val Asp
            340                 345                 350
Lys Gln Leu Gln Ile Lys Glu Ser Leu Glu Asp Leu Gln Glu Gln Leu
        355                 360                 365
Lys Glu Ala Ser Asp Glu Asn Gln Lys Arg Glu Ile Glu Lys Gln Ile
        370                 375                 380
Glu Ile Lys Lys Asn Asp Glu Glu Leu Phe Lys Asn Lys Asp His Lys
385                 390                 395                 400
Ala Leu Asp Leu Lys Gln Glu Leu Asn Ser Lys Ala Ser Ser Lys Glu
                405                 410                 415
Lys Ile Glu Gly Glu Glu Glu Asp Glu Leu Asp Ser Lys Lys Asn
            420                 425                 430
Leu Glu Pro Val Ser Glu Ala Asp Lys Val Asp Lys Ile Ser Lys Ser
        435                 440                 445
Asn Asn Asn Glu Val Ser Lys Leu Ser Pro Leu Asp Glu Pro Ser Tyr
    450                 455                 460
Ser Asp Ile Asp Ser Lys Glu Gly Val Asp Asn Lys Asp Val Asp Leu
465                 470                 475                 480
Gln Lys Thr Lys Pro Gln Val Glu Ser Gln Pro Thr Ser Leu Asn Glu
                485                 490                 495
Asp Leu Ile Asp Val Ser Ile Ser Ser Asn Pro Val Phe Leu Glu
            500                 505                 510
Val Ile Asp Pro Ile Thr Asn Leu Gly Thr Leu Gln Leu Ile Asp Leu
        515                 520                 525
Asn Thr Gly Val Arg Leu Lys Glu Ser Ala Gln Gln Gly Ile Gln Arg
    530                 535                 540
Tyr Gly Ile Tyr Glu Arg Glu Lys Asp Leu Val Val Ile Lys Ile Asp
545                 550                 555                 560
Ser Gly Lys Ala Lys Leu Gln Ile Leu Asp Lys Leu Glu Asn Leu Lys
                565                 570                 575
Val Ile Ser Glu Ser Asn Phe Glu Ile Asn Lys Asn Ser Ser Leu Tyr
            580                 585                 590
Val Asp Ser Arg Met Ile Leu Val Val Lys Asp Asp Ser Asn Ala
        595                 600                 605
```

```
Trp Arg Leu Ala Lys Phe Ser Pro Lys Asn Leu Asp Glu Phe Ile Leu
    610             615             620

Ser Glu Asn Lys Ile Leu Pro Phe Thr Ser Phe Ala Val Arg Lys Asn
625             630             635             640

Phe Ile Tyr Leu Gln Asp Glu Leu Lys Ser Leu Val Thr Leu Asp Val
            645             650             655

Asn Thr Leu Lys Lys Val Lys
            660

(2) INFORMATION FOR SEQ ID NO:71:

(i) SEQUENCE CHARACTERISTICS:
        (A) LENGTH: 2081 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..2081

(xi) SEQUENCE DESCRIPTION: SEQ ID NO:71:
```

| | | | | | | | | | | | | | | | | |
|---|---|---|---|---|---|---|---|---|---|---|---|---|---|---|---|---|
| ATG | AAA | AAA | ATG | TTA | CTA | ATC | TTT | AGT | TTT | TTT | CTT | ATT | TCT | TTG | AAT | 48 |
| Met | Lys | Lys | Met | Leu | Leu | Ile | Phe | Ser | Phe | Phe | Leu | Ile | Ser | Leu | Asn | |
| 1 | | | | 5 | | | | | 10 | | | | | 15 | | |
| GGA | TTT | CCC | CTT | AAT | GCA | AGG | GAA | GTT | GAT | AAG | GAA | AAA | TTA | AAG | GAC | 96 |
| Gly | Phe | Pro | Leu | Asn | Ala | Arg | Glu | Val | Asp | Lys | Glu | Lys | Leu | Lys | Asp | |
| | | | 20 | | | | | 25 | | | | | 30 | | | |
| TTT | GTT | AAT | ATG | GAT | CTT | GAG | TTT | GTA | AAC | TAT | AAA | GGT | CCT | TAT | GAT | 144 |
| Phe | Val | Asn | Met | Asp | Leu | Glu | Phe | Val | Asn | Tyr | Lys | Gly | Pro | Tyr | Asp | |
| | | 35 | | | | | 40 | | | | | 45 | | | | |
| TCT | ACA | AAT | ACA | TAT | GAA | CAA | ATA | GTA | GGT | ATT | GGT | GAG | TTT | TTA | GCA | 192 |
| Ser | Thr | Asn | Thr | Tyr | Glu | Gln | Ile | Val | Gly | Ile | Gly | Glu | Phe | Leu | Ala | |
| | 50 | | | | | 55 | | | | | 60 | | | | | |
| AGA | CCA | TTG | ATT | AAT | TTC | AAT | AGC | AAC | TCA | AGT | TAT | TAT | GGT | AAA | TAT | 240 |
| Arg | Pro | Leu | Ile | Asn | Phe | Asn | Ser | Asn | Ser | Ser | Tyr | Tyr | Gly | Lys | Tyr | |
| 65 | | | | | 70 | | | | | 75 | | | | | 80 | |
| TTT | ATT | AAT | AGA | TTT | ATT | GAC | GAT | CAA | GAT | AAA | AAA | GCA | AGC | GTT | GAT | 288 |
| Phe | Ile | Asn | Arg | Phe | Ile | Asp | Asp | Gln | Asp | Lys | Lys | Ala | Ser | Val | Asp | |
| | | | | 85 | | | | | 90 | | | | | 95 | | |
| GTT | TTT | TCT | ATT | AGT | AGT | AAG | TCA | CAG | CTT | GAC | AGT | ATA | TTG | AAT | TTA | 336 |
| Val | Phe | Ser | Ile | Ser | Ser | Lys | Ser | Gln | Leu | Asp | Ser | Ile | Leu | Asn | Leu | |
| | | | | 100 | | | | | 105 | | | | | 110 | | |
| AGA | AGA | ATT | CTT | ACA | GGG | TAT | TTG | ATA | AAG | TCT | TTT | GAT | TAT | GAA | AGA | 384 |
| Arg | Arg | Ile | Leu | Thr | Gly | Tyr | Leu | Ile | Lys | Ser | Phe | Asp | Tyr | Glu | Arg | |
| | | | 115 | | | | | 120 | | | | | 125 | | | |
| TCT | AGT | GCT | GAA | TTA | ATT | GCC | AAG | GTT | ATT | ACA | ATA | CAT | AAT | GCT | GTT | 432 |
| Ser | Ser | Ala | Glu | Leu | Ile | Ala | Lys | Val | Ile | Thr | Ile | His | Asn | Ala | Val | |
| | | 130 | | | | | 135 | | | | | 140 | | | | |
| TAT | AGA | GGT | GAT | TTA | AAT | TAT | TAT | AAA | GAG | TTT | TAT | ATT | GAG | TCT | GCT | 480 |
| Tyr | Arg | Gly | Asp | Leu | Asn | Tyr | Tyr | Lys | Glu | Phe | Tyr | Ile | Glu | Ser | Ala | |
| 145 | | | | | 150 | | | | | 155 | | | | | 160 | |
| TTA | AAG | TCT | TTA | ACT | AAA | GAA | AAT | GCA | GGT | CTT | TCT | AGA | GTG | TAC | AGT | 528 |
| Leu | Lys | Ser | Leu | Thr | Lys | Glu | Asn | Ala | Gly | Leu | Ser | Arg | Val | Tyr | Ser | |
| | | | | 165 | | | | | 170 | | | | | 175 | | |
| CAA | TGG | GCT | GGA | AAG | ACA | CAA | ATA | TTT | ATT | CCT | CTT | AAA | AAG | AAT | ATT | 576 |
| Gln | Trp | Ala | Gly | Lys | Thr | Gln | Ile | Phe | Ile | Pro | Leu | Lys | Lys | Asn | Ile | |
| | | | 180 | | | | | 185 | | | | | 190 | | | |

```
TTA TCT GGA AAA ATT GAG TCT GAC ATT GAT ATT GAT AGT TTG GTT ACA      624
Leu Ser Gly Lys Ile Glu Ser Asp Ile Asp Ile Asp Ser Leu Val Thr
        195                 200                 205

GAT AAG GTT GTG GCA GCT CTT TTA AGC GAA AAT GAA GCA GGT GTT AAC      672
Asp Lys Val Val Ala Ala Leu Leu Ser Glu Asn Glu Ala Gly Val Asn
    210                 215                 220

TTT GCA AGG GAT ATT ACA GAT ATT CAA GGA GAA ACT CAT AAA GCA GAT      720
Phe Ala Arg Asp Ile Thr Asp Ile Gln Gly Glu Thr His Lys Ala Asp
225                 230                 235                 240

CAA GAT AAA ATT GAT ATT GAA TTA GAT AAT GTT CAT GAA AGT GAT TCC      768
Gln Asp Lys Ile Asp Ile Glu Leu Asp Asn Val His Glu Ser Asp Ser
                245                 250                 255

AAT ATA ACA GAA ACT ATT GAG AAT TTA AGA GAT CAG CTT GAA AAG GCT      816
Asn Ile Thr Glu Thr Ile Glu Asn Leu Arg Asp Gln Leu Glu Lys Ala
        260                 265                 270

ACA GAT GAA GAG CAT AGA AAA GAG ATT GAA AGT CAA GTT GAT GCT AAA      864
Thr Asp Glu Glu His Arg Lys Glu Ile Glu Ser Gln Val Asp Ala Lys
    275                 280                 285

AAG AAA CAA AAA GAA GAA CTA GAT AAA AAG GCA ATC GAT CTT GAT AAA      912
Lys Lys Gln Lys Glu Glu Leu Asp Lys Lys Ala Ile Asp Leu Asp Lys
290                 295                 300

GCC CAA CAA AAA TTA GAT TTT TCT GAA GAT AAT TTA GAT ATT CAA AGG      960
Ala Gln Gln Lys Leu Asp Phe Ser Glu Asp Asn Leu Asp Ile Gln Arg
305                 310                 315                 320

GAT ACT GTT AGA GAG AAG ATT CAA GAG GAT ATT AAC GAG ATT AAT AAG     1008
Asp Thr Val Arg Glu Lys Ile Gln Glu Asp Ile Asn Glu Ile Asn Lys
                325                 330                 335

GAA AAG AAT TTA CCA AAA CCT GGT GAT GTA AGT TCT CCT AAA GTT GAT     1056
Glu Lys Asn Leu Pro Lys Pro Gly Asp Val Ser Ser Pro Lys Val Asp
        340                 345                 350

AAG CAG CTA CAA ATA AAA GAG AGT CTA GAA GAC TTG CAG GAG CAG CTT     1104
Lys Gln Leu Gln Ile Lys Glu Ser Leu Glu Asp Leu Gln Glu Gln Leu
    355                 360                 365

AAA GAA ACT AGC GAT GAA AAT CAA AAA AGA GAA ATT GAA AAG CAA ATT     1152
Lys Glu Thr Ser Asp Glu Asn Gln Lys Arg Glu Ile Glu Lys Gln Ile
370                 375                 380

GAA ATC AAA AAA AGT GAT GAA GAA CTT TTA AAA AGC AAA GAT CCT AAA     1200
Glu Ile Lys Lys Ser Asp Glu Glu Leu Leu Lys Ser Lys Asp Pro Lys
385                 390                 395                 400

GCA TTA GAT CTT AAT CGA GAT TTA AAT TCT AAA GCT TCT AGT AAA GAA     1248
Ala Leu Asp Leu Asn Arg Asp Leu Asn Ser Lys Ala Ser Ser Lys Glu
                405                 410                 415

AAA ATT AAA GGC AAA GAA AAA GAA ATA GTC AAA GAG AAA TCA AAG GTA     1296
Lys Ile Lys Gly Lys Glu Lys Glu Ile Val Lys Glu Lys Ser Lys Val
        420                 425                 430

AGT TTA GGT GAT TTG GAT AAT GAC GAA ACC CTT ATG ACG CCG GAA GAT     1344
Ser Leu Gly Asp Leu Asp Asn Asp Glu Thr Leu Met Thr Pro Glu Asp
    435                 440                 445

CAA AAA TTA TCT GAG GAT AAA AAA TTA GAT AGT AAA AAA AAT TTA AAA     1392
Gln Lys Leu Ser Glu Asp Lys Lys Leu Asp Ser Lys Lys Asn Leu Lys
450                 455                 460

CCT GTT TCT GAG ATT GAG AGA GTA AAT GAA ATT TCA AAG TCT AAC AAC     1440
Pro Val Ser Glu Ile Glu Arg Val Asn Glu Ile Ser Lys Ser Asn Asn
465                 470                 475                 480

AAT GAG GTT AGC AAA TCA TCA CCA TTA GAT AAG CCT TCT TAT AGT GAT     1488
Asn Glu Val Ser Lys Ser Ser Pro Leu Asp Lys Pro Ser Tyr Ser Asp
                485                 490                 495

ATC GAT TCA AAA GAG GTT GTA GAT AAT AAA GAT GTT AAT TTG CAA GAA     1536
Ile Asp Ser Lys Glu Val Val Asp Asn Lys Asp Val Asn Leu Gln Glu
        500                 505                 510
```

```
ACC AAG CCT CAA GCT AAA AGT CAA TCT ACT TCT TTA AAT CAA GAT TTG         1584
Thr Lys Pro Gln Ala Lys Ser Gln Ser Thr Ser Leu Asn Gln Asp Leu
        515                 520                 525

ATT ACT ATG TCT ATA GAT TCT AGT AAT CCT GTA TTT TTA GAG GTT ATT         1632
Ile Thr Met Ser Ile Asp Ser Ser Asn Pro Val Phe Leu Glu Val Ile
        530                 535                 540

GAT CCT ATT ACA AAT TTA GGA ATG CTT CAA CTT ATT GAT TTA AAT ACT         1680
Asp Pro Ile Thr Asn Leu Gly Met Leu Gln Leu Ile Asp Leu Asn Thr
545                 550                 555                 560

GGT GTT AGA CTT AAA GAA AGC ACT CAG CAA GGC ATT CAG CGT TAT GGA         1728
Gly Val Arg Leu Lys Glu Ser Thr Gln Gln Gly Ile Gln Arg Tyr Gly
                565                 570                 575

ATT TAT GAA CGT GAA AAA GAT TTA GTT GTT ATT AAA ATG GAT TCA GGA         1776
Ile Tyr Glu Arg Glu Lys Asp Leu Val Val Ile Lys Met Asp Ser Gly
            580                 585                 590

AAA GCT AAG CTT CAA ATA CTT AAT AAA CTT GAG AAT TTA AAA GTG ATA         1824
Lys Ala Lys Leu Gln Ile Leu Asn Lys Leu Glu Asn Leu Lys Val Ile
        595                 600                 605

TCA GAG TCT AAT TTT GAG ATT AAT AAA AAT TCA TCT CTT TAT GTT GAC         1872
Ser Glu Ser Asn Phe Glu Ile Asn Lys Asn Ser Ser Leu Tyr Val Asp
    610                 615                 620

TCT AAA ATG ATT TTA GTA GCT GTG AAA GAT AGT GGT AAT GTT TGG AGA         1920
Ser Lys Met Ile Leu Val Ala Val Lys Asp Ser Gly Asn Val Trp Arg
625                 630                 635                 640

TTG GCT AAA TTT TCT CCT AAA AAT TTA GAT GAG TTT ATT CTT TCA GAG         1968
Leu Ala Lys Phe Ser Pro Lys Asn Leu Asp Glu Phe Ile Leu Ser Glu
                645                 650                 655

AAT AAA ATT TTG CCT TTT ACT AGC TTT TCT GTG AGA AAG AAT TTT ATT         2016
Asn Lys Ile Leu Pro Phe Thr Ser Phe Ser Val Arg Lys Asn Phe Ile
            660                 665                 670

TAT TTG CAA GAT GAG TTT AAA AGT CTT ATT ACT TTA GAT GTA AAT ACT         2064
Tyr Leu Gln Asp Glu Phe Lys Ser Leu Ile Thr Leu Asp Val Asn Thr
        675                 680                 685

TTA AAA AAA GTT AAG TA                                                  2081
Leu Lys Lys Val Lys
        690
```

(2) INFORMATION FOR SEQ ID NO:72:

(i) SEQUENCE CHARACTERISTICS:
        (A) LENGTH: 693 amino acids
        (B) TYPE: amino acid
        (D) TOPOLOGY: linear (ii) MOLECULE TYPE: protein (xi) SEQUENCE DESCRIPTION: SEQ ID NO:72:

```
Met Lys Lys Met Leu Leu Ile Phe Ser Phe Phe Leu Ile Ser Leu Asn
 1               5                  10                  15

Gly Phe Pro Leu Asn Ala Arg Glu Val Asp Lys Glu Lys Leu Lys Asp
                20                  25                  30

Phe Val Asn Met Asp Leu Glu Phe Val Asn Tyr Lys Gly Pro Tyr Asp
            35                  40                  45

Ser Thr Asn Thr Tyr Glu Gln Ile Val Gly Ile Gly Glu Phe Leu Ala
        50                  55                  60

Arg Pro Leu Ile Asn Phe Asn Ser Asn Ser Tyr Tyr Gly Lys Tyr
65                  70                  75                  80

Phe Ile Asn Arg Phe Ile Asp Asp Gln Asp Lys Lys Ala Ser Val Asp
                85                  90                  95
```

-continued

```
Val Phe Ser Ile Ser Ser Lys Ser Gln Leu Asp Ser Ile Leu Asn Leu
            100                 105                 110

Arg Arg Ile Leu Thr Gly Tyr Leu Ile Lys Ser Phe Asp Tyr Glu Arg
            115                 120                 125

Ser Ser Ala Glu Leu Ile Ala Lys Val Ile Thr Ile His Asn Ala Val
            130                 135                 140

Tyr Arg Gly Asp Leu Asn Tyr Lys Glu Phe Tyr Ile Glu Ser Ala
145                 150                 155                 160

Leu Lys Ser Leu Thr Lys Glu Asn Ala Gly Leu Ser Arg Val Tyr Ser
                165                 170                 175

Gln Trp Ala Gly Lys Thr Gln Ile Phe Ile Pro Leu Lys Lys Asn Ile
            180                 185                 190

Leu Ser Gly Lys Ile Glu Ser Asp Ile Asp Ile Asp Ser Leu Val Thr
            195                 200                 205

Asp Lys Val Val Ala Ala Leu Leu Ser Glu Asn Glu Ala Gly Val Asn
    210                 215                 220

Phe Ala Arg Asp Ile Thr Asp Ile Gln Gly Glu Thr His Lys Ala Asp
225                 230                 235                 240

Gln Asp Lys Ile Asp Ile Glu Leu Asp Asn Val His Glu Ser Asp Ser
                245                 250                 255

Asn Ile Thr Glu Thr Ile Glu Asn Leu Arg Asp Gln Leu Glu Lys Ala
            260                 265                 270

Thr Asp Glu Glu His Arg Lys Glu Ile Glu Ser Gln Val Asp Ala Lys
            275                 280                 285

Lys Lys Gln Lys Glu Glu Leu Asp Lys Lys Ala Ile Asp Leu Asp Lys
    290                 295                 300

Ala Gln Gln Lys Leu Asp Phe Ser Glu Asp Asn Leu Asp Ile Gln Arg
305                 310                 315                 320

Asp Thr Val Arg Glu Lys Ile Gln Glu Asp Ile Asn Glu Ile Asn Lys
                325                 330                 335

Glu Lys Asn Leu Pro Lys Pro Gly Asp Val Ser Ser Pro Lys Val Asp
            340                 345                 350

Lys Gln Leu Gln Ile Lys Glu Ser Leu Glu Asp Leu Gln Glu Gln Leu
            355                 360                 365

Lys Glu Thr Ser Asp Glu Asn Gln Lys Arg Glu Ile Glu Lys Gln Ile
            370                 375                 380

Glu Ile Lys Lys Ser Asp Glu Glu Leu Leu Lys Ser Lys Asp Pro Lys
385                 390                 395                 400

Ala Leu Asp Leu Asn Arg Asp Leu Asn Ser Lys Ala Ser Ser Lys Glu
                405                 410                 415

Lys Ile Lys Gly Lys Glu Lys Glu Ile Val Lys Glu Lys Ser Lys Val
            420                 425                 430

Ser Leu Gly Asp Leu Asp Asn Asp Glu Thr Leu Met Thr Pro Glu Asp
            435                 440                 445

Gln Lys Leu Ser Glu Asp Lys Lys Leu Asp Ser Lys Lys Asn Leu Lys
            450                 455                 460

Pro Val Ser Glu Ile Glu Arg Val Asn Glu Ile Ser Lys Ser Asn Asn
465                 470                 475                 480

Asn Glu Val Ser Lys Ser Ser Pro Leu Asp Lys Pro Ser Tyr Ser Asp
                485                 490                 495

Ile Asp Ser Lys Glu Val Val Asp Asn Lys Asp Val Asn Leu Gln Glu
            500                 505                 510
```

```
Thr Lys Pro Gln Ala Lys Ser Gln Ser Thr Ser Leu Asn Gln Asp Leu
        515                 520                 525

Ile Thr Met Ser Ile Asp Ser Ser Asn Pro Val Phe Leu Glu Val Ile
        530                 535                 540

Asp Pro Ile Thr Asn Leu Gly Met Leu Gln Leu Ile Asp Leu Asn Thr
545                 550                 555                 560

Gly Val Arg Leu Lys Glu Ser Thr Gln Gln Gly Ile Gln Arg Tyr Gly
                565                 570                 575

Ile Tyr Glu Arg Glu Lys Asp Leu Val Val Ile Lys Met Asp Ser Gly
            580                 585                 590

Lys Ala Lys Leu Gln Ile Leu Asn Lys Leu Glu Asn Leu Lys Val Ile
        595                 600                 605

Ser Glu Ser Asn Phe Glu Ile Asn Lys Asn Ser Ser Leu Tyr Val Asp
        610                 615                 620

Ser Lys Met Ile Leu Val Ala Val Lys Asp Ser Gly Asn Val Trp Arg
625                 630                 635                 640

Leu Ala Lys Phe Ser Pro Lys Asn Leu Asp Glu Phe Ile Leu Ser Glu
                645                 650                 655

Asn Lys Ile Leu Pro Phe Thr Ser Phe Ser Val Arg Lys Asn Phe Ile
            660                 665                 670

Tyr Leu Gln Asp Glu Phe Lys Ser Leu Ile Thr Leu Asp Val Asn Thr
        675                 680                 685

Leu Lys Lys Val Lys
        690
```

(2) INFORMATION FOR SEQ ID NO:73:

(i) SEQUENCE CHARACTERISTICS:
        (A) LENGTH: 2107 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..2107

(xi) SEQUENCE DESCRIPTION: SEQ ID NO:73:

```
ATG AAA AAA ATG TTA CTA ATC TTT AGT TTT TTT CTT GTT TTT TTA AAT      48
Met Lys Lys Met Leu Leu Ile Phe Ser Phe Phe Leu Val Phe Leu Asn
 1               5                  10                  15

GGA TTT CCT CTT AAT GCA AGG GAA GTT GAT AAG GAA AAA TTA AAG GAC      96
Gly Phe Pro Leu Asn Ala Arg Glu Val Asp Lys Glu Lys Leu Lys Asp
            20                  25                  30

TTT GTT AAT ATG GAT CTT GAA TTT GTT AAT TAC AAG GGT CCT TAT GAT     144
Phe Val Asn Met Asp Leu Glu Phe Val Asn Tyr Lys Gly Pro Tyr Asp
        35                  40                  45

TCT ACA AAT ACA TAT GAA CAA ATA GTA GGT ATT GGG GAG TTT TTA GCA     192
Ser Thr Asn Thr Tyr Glu Gln Ile Val Gly Ile Gly Glu Phe Leu Ala
    50                  55                  60

AGG CCG TTG ATC AAT TCC AAT AGT AAT TCA AGT TAT TAT GGT AAA TAT     240
Arg Pro Leu Ile Asn Ser Asn Ser Asn Ser Ser Tyr Tyr Gly Lys Tyr
65                  70                  75                  80

TTT GTT AAT AGA TTT ATT GAC GAT CAA GAT AAA AAA GCA AGT GTT GAT     288
Phe Val Asn Arg Phe Ile Asp Asp Gln Asp Lys Lys Ala Ser Val Asp
                85                  90                  95
```

```
ATT TTT TCT ATT GGT AGT AAG TCA GAG CTT GAT AGT ATA TTA AAT CTA        336
Ile Phe Ser Ile Gly Ser Lys Ser Glu Leu Asp Ser Ile Leu Asn Leu
            100                 105                 110

AGA AGA ATT CTT ACA GGG TAT TTA ATG AAG TCT TTT GAT TAT GAG AGG        384
Arg Arg Ile Leu Thr Gly Tyr Leu Met Lys Ser Phe Asp Tyr Glu Arg
            115                 120                 125

TCT AGT GCG GAA TTA ATT GCT AAA GCT ATT ACA ATA TAT AAT GCT GTT        432
Ser Ser Ala Glu Leu Ile Ala Lys Ala Ile Thr Ile Tyr Asn Ala Val
130                 135                 140

TAT AGA GGA GAT TTA GAT TAT TAC AAA GAG TTT TAT ATT GAG GCT TCT        480
Tyr Arg Gly Asp Leu Asp Tyr Tyr Lys Glu Phe Tyr Ile Glu Ala Ser
145                 150                 155                 160

TTG AAG TCT TTG ACT AAA GAA AAT GCA GGT CTT TCT AGG GTG TAC AGT        528
Leu Lys Ser Leu Thr Lys Glu Asn Ala Gly Leu Ser Arg Val Tyr Ser
            165                 170                 175

CAA TGG GCT GGG AAG ACA CAA ATA TTT ATT CCT CTT AAA AAG AAT ATT        576
Gln Trp Ala Gly Lys Thr Gln Ile Phe Ile Pro Leu Lys Lys Asn Ile
            180                 185                 190

TTA TCT GGA AAT GTT GAG TCT GAC ATT GAT ATT GAT AGT TTG GTT ACA        624
Leu Ser Gly Asn Val Glu Ser Asp Ile Asp Ile Asp Ser Leu Val Thr
            195                 200                 205

GAT AAG GTG GTG GCA GCT CTT TTA AGT GAG AAT GAA TCA GGT GTT AAC        672
Asp Lys Val Val Ala Ala Leu Leu Ser Glu Asn Glu Ser Gly Val Asn
210                 215                 220

TTT GCA AGA GAT ATT ACA GAC ATT CAA GGC GAA ACT CAT AAA GCA GAT        720
Phe Ala Arg Asp Ile Thr Asp Ile Gln Gly Glu Thr His Lys Ala Asp
225                 230                 235                 240

CAA GAT AAA ATT GAT ATT GAA TTA GAT AAT ATT CAT GAA AGT GAT TCC        768
Gln Asp Lys Ile Asp Ile Glu Leu Asp Asn Ile His Glu Ser Asp Ser
            245                 250                 255

AAT ATA ACA GAA ACT ATT GAG AAT TTA AGG GAT CAG CTT GAA AAA GCT        816
Asn Ile Thr Glu Thr Ile Glu Asn Leu Arg Asp Gln Leu Glu Lys Ala
            260                 265                 270

ACA GAT GAA GAG CAT AAA AAA GAG ATT GAA AGT CAG GTT GAT GCT AAA        864
Thr Asp Glu Glu His Lys Lys Glu Ile Glu Ser Gln Val Asp Ala Lys
            275                 280                 285

AAG AAA CAA AAG GAA GAA TTA GAT AAA AAG GCA ATT GAT CTT GAT AAA        912
Lys Lys Gln Lys Glu Glu Leu Asp Lys Lys Ala Ile Asp Leu Asp Lys
            290                 295                 300

GCT CAA CAA AAA TTA GAT TTT GCT GAA GAT AAT CTA GAT ATT CAA AGG        960
Ala Gln Gln Lys Leu Asp Phe Ala Glu Asp Asn Leu Asp Ile Gln Arg
305                 310                 315                 320

GAT ACT GTT AGA GAG AAG CTT CAA GAG AAT ATT AAC GAG ACT AAT AAG       1008
Asp Thr Val Arg Glu Lys Leu Gln Glu Asn Ile Asn Glu Thr Asn Lys
            325                 330                 335

GAA AAG AAT TTA CCA AAG CCT GGT GAT GTA AGT TCT CCT AAA GTT GAT       1056
Glu Lys Asn Leu Pro Lys Pro Gly Asp Val Ser Ser Pro Lys Val Asp
            340                 345                 350

AAG CAA CTA CAA ATA AAA GAG AGC CTG GAA GAT TTG CAG GAG CAG CTT       1104
Lys Gln Leu Gln Ile Lys Glu Ser Leu Glu Asp Leu Gln Glu Gln Leu
            355                 360                 365

AAA GAA ACT GGT GAT GAA AAT CAG AAA AGA GAA ATT GAA AAG CAA ATT       1152
Lys Glu Thr Gly Asp Glu Asn Gln Lys Arg Glu Ile Glu Lys Gln Ile
            370                 375                 380

GAA ATC AAA AAA AGT GAT GAA AAG CTT TTA AAA AGT AAA GAT GAT AAA       1200
Glu Ile Lys Lys Ser Asp Glu Lys Leu Leu Lys Ser Lys Asp Asp Lys
385                 390                 395                 400

GCA AGT AAA GAT GGT AAA GCC TTG GAT CTT GAT CGA GAA TTA AAT TCT       1248
Ala Ser Lys Asp Gly Lys Ala Leu Asp Leu Asp Arg Glu Leu Asn Ser
            405                 410                 415
```

```
AAA GCT TCT AGC AAA GAA AAA AGT AAA GCC AAG GAA GAA GAA ATA ACC        1296
Lys Ala Ser Ser Lys Glu Lys Ser Lys Ala Lys Glu Glu Glu Ile Thr
            420             425             430

AAG GGT AAG TCA CAG AAA AGC TTA GGC GAT TTG AAT AAT GAT GAA AAT        1344
Lys Gly Lys Ser Gln Lys Ser Leu Gly Asp Leu Asn Asn Asp Glu Asn
            435             440             445

CTT ATG ATG CCA GAA GAT CAA AAA TTA CCT GAG GTT AAA AAA TTA GAT        1392
Leu Met Met Pro Glu Asp Gln Lys Leu Pro Glu Val Lys Lys Leu Asp
    450             455             460

AGC AAA AAA GAA TTT AAA CCT GTT TCT GAG GTT GAG AAA TTA GAT AAG        1440
Ser Lys Lys Glu Phe Lys Pro Val Ser Glu Val Glu Lys Leu Asp Lys
465             470             475             480

ATT TTC AAG TCT AAT AAC AAT GTT GGA GAA TTA TCA CCG TTA GAT AAA        1488
Ile Phe Lys Ser Asn Asn Asn Val Gly Glu Leu Ser Pro Leu Asp Lys
                485             490             495

TCT TCT TAT AAA GAC ATT GAT TCA AAA GAG GAG ACA GTT AAT AAA GAT        1536
Ser Ser Tyr Lys Asp Ile Asp Ser Lys Glu Glu Thr Val Asn Lys Asp
            500             505             510

GTT AAT TTG CAA AAG ACT AAG CCT CAG GTT AAA GAC CAA GTT ACT TCT        1584
Val Asn Leu Gln Lys Thr Lys Pro Gln Val Lys Asp Gln Val Thr Ser
            515             520             525

TTG AAT GAA GAT TTG ACT ACT ATG TCT ATA GAT TCC AGT AGT CCT GTA        1632
Leu Asn Glu Asp Leu Thr Thr Met Ser Ile Asp Ser Ser Ser Pro Val
    530             535             540

TTT TTA GAG GTT ATT GAT CCA ATT ACA AAT TTA GGA ACT CTT CAA CTT        1680
Phe Leu Glu Val Ile Asp Pro Ile Thr Asn Leu Gly Thr Leu Gln Leu
545             550             555             560

ATT GAT TTA AAT ACT GGT GTT AGG CTT AAA GAA AGC ACT CAG CAA GGC        1728
Ile Asp Leu Asn Thr Gly Val Arg Leu Lys Glu Ser Thr Gln Gln Gly
                565             570             575

ATT CAG CGG TAT GGA ATT TAT GAA CGT GAA AAA GAT TTG GTT GTT ATT        1776
Ile Gln Arg Tyr Gly Ile Tyr Glu Arg Glu Lys Asp Leu Val Val Ile
            580             585             590

AAA ATG GAT TCA GGA AAA GCT AAG CTT CAG ATA CTT GAT AAA CTT GAA        1824
Lys Met Asp Ser Gly Lys Ala Lys Leu Gln Ile Leu Asp Lys Leu Glu
            595             600             605

AAT TTA AAA GTG GTA TCA GAG TCT AAT TTT GAG ATT AAT AAA AAT TCA        1872
Asn Leu Lys Val Val Ser Glu Ser Asn Phe Glu Ile Asn Lys Asn Ser
    610             615             620

TCT CTT TAT GTT GAT TCT AAA ATG ATT TTA GTA GCT GTT AGG GAT AAA        1920
Ser Leu Tyr Val Asp Ser Lys Met Ile Leu Val Ala Val Arg Asp Lys
625             630             635             640

GAT AGT AGT AAT GAT TGG AGA TTG GCC AAA TTT TCT CCT AAA AAT TTA        1968
Asp Ser Ser Asn Asp Trp Arg Leu Ala Lys Phe Ser Pro Lys Asn Leu
                645             650             655

GAT GAG TTT ATT CTT TCA GAG AAT AAA ATT ATG CCT TTT ACT AGC TTT        2016
Asp Glu Phe Ile Leu Ser Glu Asn Lys Ile Met Pro Phe Thr Ser Phe
            660             665             670

TCT GTG AGA AAA AAT TTT ATT TAT TTG CAA GAT GAG TTT AAA AGT CTA        2064
Ser Val Arg Lys Asn Phe Ile Tyr Leu Gln Asp Glu Phe Lys Ser Leu
            675             680             685

GTT ATT TTA GAT GTA AAT ACT TTA AAA AAA GTT AAG TAAAGCC               2107
Val Ile Leu Asp Val Asn Thr Leu Lys Lys Val Lys
    690             695             700
```

-continued (2) INFORMATION FOR SEQ ID NO:74:

(i) SEQUENCE CHARACTERISTICS:
        (A) LENGTH: 700 amino acids
        (B) TYPE: amino acid
        (D) TOPOLOGY: linear (ii) MOLECULE TYPE: protein (xi) SEQUENCE DESCRIPTION: SEQ ID NO:74:

```
Met Lys Lys Met Leu Leu Ile Phe Ser Phe Phe Leu Val Phe Leu Asn
  1               5                  10                  15

Gly Phe Pro Leu Asn Ala Arg Glu Val Asp Lys Glu Lys Leu Lys Asp
                 20                  25                  30

Phe Val Asn Met Asp Leu Glu Phe Val Asn Tyr Lys Gly Pro Tyr Asp
             35                  40                  45

Ser Thr Asn Thr Tyr Glu Gln Ile Val Gly Ile Gly Glu Phe Leu Ala
         50                  55                  60

Arg Pro Leu Ile Asn Ser Asn Ser Asn Ser Tyr Tyr Gly Lys Tyr
 65                  70                  75                  80

Phe Val Asn Arg Phe Ile Asp Asp Gln Asp Lys Ala Ser Val Asp
                 85                  90                  95

Ile Phe Ser Ile Gly Ser Lys Ser Glu Leu Asp Ser Ile Leu Asn Leu
                100                 105                 110

Arg Arg Ile Leu Thr Gly Tyr Leu Met Lys Ser Phe Asp Tyr Glu Arg
            115                 120                 125

Ser Ser Ala Glu Leu Ile Ala Lys Ala Ile Thr Ile Tyr Asn Ala Val
        130                 135                 140

Tyr Arg Gly Asp Leu Asp Tyr Tyr Lys Glu Phe Tyr Ile Glu Ala Ser
145                 150                 155                 160

Leu Lys Ser Leu Thr Lys Glu Asn Ala Gly Leu Ser Arg Val Tyr Ser
                165                 170                 175

Gln Trp Ala Gly Lys Thr Gln Ile Phe Ile Pro Leu Lys Lys Asn Ile
                180                 185                 190

Leu Ser Gly Asn Val Glu Ser Asp Ile Asp Ile Asp Ser Leu Val Thr
            195                 200                 205

Asp Lys Val Val Ala Ala Leu Leu Ser Glu Asn Glu Ser Gly Val Asn
        210                 215                 220

Phe Ala Arg Asp Ile Thr Asp Ile Gln Gly Glu Thr His Lys Ala Asp
225                 230                 235                 240

Gln Asp Lys Ile Asp Ile Glu Leu Asp Asn Ile His Glu Ser Asp Ser
                245                 250                 255

Asn Ile Thr Glu Thr Ile Glu Asn Leu Arg Asp Gln Leu Glu Lys Ala
            260                 265                 270

Thr Asp Glu His Lys Lys Glu Ile Glu Ser Gln Val Asp Ala Lys
        275                 280                 285

Lys Lys Gln Lys Glu Glu Leu Asp Lys Ala Ile Asp Leu Asp Lys
290                 295                 300

Ala Gln Gln Lys Leu Asp Phe Ala Glu Asp Asn Leu Asp Ile Gln Arg
305                 310                 315                 320

Asp Thr Val Arg Glu Lys Leu Gln Glu Asn Ile Asn Glu Thr Asn Lys
                325                 330                 335

Glu Lys Asn Leu Pro Lys Pro Gly Asp Val Ser Ser Pro Lys Val Asp
            340                 345                 350

Lys Gln Leu Gln Ile Lys Glu Ser Leu Glu Asp Leu Gln Glu Gln Leu
        355                 360                 365
```

```
Lys Glu Thr Gly Asp Glu Asn Gln Lys Arg Glu Ile Glu Lys Gln Ile
    370                 375                 380
Glu Ile Lys Lys Ser Asp Glu Lys Leu Leu Lys Ser Lys Asp Asp Lys
385                 390                 395                 400
Ala Ser Lys Asp Gly Lys Ala Leu Asp Leu Asp Arg Glu Leu Asn Ser
                405                 410                 415
Lys Ala Ser Ser Lys Glu Lys Ser Lys Ala Lys Glu Glu Ile Thr
                420                 425                 430
Lys Gly Lys Ser Gln Lys Ser Leu Gly Asp Leu Asn Asn Asp Glu Asn
                435                 440                 445
Leu Met Met Pro Glu Asp Gln Lys Leu Pro Glu Val Lys Lys Leu Asp
    450                 455                 460
Ser Lys Lys Glu Phe Lys Pro Val Ser Glu Val Glu Lys Leu Asp Lys
465                 470                 475                 480
Ile Phe Lys Ser Asn Asn Val Gly Glu Leu Ser Pro Leu Asp Lys
                485                 490                 495
Ser Ser Tyr Lys Asp Ile Asp Ser Lys Glu Glu Thr Val Asn Lys Asp
            500                 505                 510
Val Asn Leu Gln Lys Thr Lys Pro Gln Val Lys Asp Gln Val Thr Ser
            515                 520                 525
Leu Asn Glu Asp Leu Thr Thr Met Ser Ile Asp Ser Ser Pro Val
    530                 535                 540
Phe Leu Glu Val Ile Asp Pro Ile Thr Asn Leu Gly Thr Leu Gln Leu
545                 550                 555                 560
Ile Asp Leu Asn Thr Gly Val Arg Leu Lys Glu Ser Thr Gln Gln Gly
                565                 570                 575
Ile Gln Arg Tyr Gly Ile Tyr Glu Arg Glu Lys Asp Leu Val Val Ile
            580                 585                 590
Lys Met Asp Ser Gly Lys Ala Lys Leu Gln Ile Leu Asp Lys Leu Glu
    595                 600                 605
Asn Leu Lys Val Val Ser Glu Ser Asn Phe Glu Ile Asn Lys Asn Ser
    610                 615                 620
Ser Leu Tyr Val Asp Ser Lys Met Ile Leu Val Ala Val Arg Asp Lys
625                 630                 635                 640
Asp Ser Ser Asn Asp Trp Arg Leu Ala Lys Phe Ser Pro Lys Asn Leu
                645                 650                 655
Asp Glu Phe Ile Leu Ser Glu Asn Lys Ile Met Pro Phe Thr Ser Phe
                660                 665                 670
Ser Val Arg Lys Asn Phe Ile Tyr Leu Gln Asp Glu Phe Lys Ser Leu
            675                 680                 685
Val Ile Leu Asp Val Asn Thr Leu Lys Lys Val Lys
    690                 695                 700

(2) INFORMATION FOR SEQ ID NO:75:

(i) SEQUENCE CHARACTERISTICS:
        (A) LENGTH: 2126 base pairs
        (B) TYPE: nucleic acid
        (C) STRANDEDNESS: double
        (D) TOPOLOGY: linear (ii) MOLECULE TYPE: DNA (genomic)
```

-continued

```
    (ix) FEATURE:
         (A) NAME/KEY: CDS
         (B) LOCATION: 1..2126

(xi) SEQUENCE DESCRIPTION: SEQ ID NO:75:

ATG AAA AAA ATG TTA CTA ATC TTT AGT TTT TTT CTT ATT TTT TTG AAT         48
Met Lys Lys Met Leu Leu Ile Phe Ser Phe Phe Leu Ile Phe Leu Asn
 1               5                  10                  15

GGA TTT CCT CTT AAT GCA AGG AAA GTT GAT AAG GAA AAA TTA AAG GAT         96
Gly Phe Pro Leu Asn Ala Arg Lys Val Asp Lys Glu Lys Leu Lys Asp
                 20                  25                  30

TTT GTT AAT ATG GAT CTT GAG TTT GTA AAT TAT AAA GGT CCT TAT GAT        144
Phe Val Asn Met Asp Leu Glu Phe Val Asn Tyr Lys Gly Pro Tyr Asp
             35                  40                  45

TCT ACA AAT ACG TAT GAA CAA ATA GTG GGT ATT GGG GAG TTT TTA GCA        192
Ser Thr Asn Thr Tyr Glu Gln Ile Val Gly Ile Gly Glu Phe Leu Ala
         50                  55                  60

AGA CCG CTG ACC AAT TCC AAT AGC AAC TCA AGT TAT TAT GGC AAA TAT        240
Arg Pro Leu Thr Asn Ser Asn Ser Asn Ser Ser Tyr Tyr Gly Lys Tyr
 65                  70                  75                  80

TTT ATT AAT AGA TTT ATT GAT GAT CAA GAT AAA AAA GCA AGT GTT GAT        288
Phe Ile Asn Arg Phe Ile Asp Asp Gln Asp Lys Lys Ala Ser Val Asp
                 85                  90                  95

GTT TTT TCT ATA AGC AGC AAA TCA GAG CTT GAC AGT ATA TTG AAT TTA        336
Val Phe Ser Ile Ser Ser Lys Ser Glu Leu Asp Ser Ile Leu Asn Leu
                100                 105                 110

AGA AGA ATT CTT ACA GGG TAT ATA ATA AAG TCT TTC GAT TAT GAC AGG        384
Arg Arg Ile Leu Thr Gly Tyr Ile Ile Lys Ser Phe Asp Tyr Asp Arg
            115                 120                 125

TCT AGT GCA GAA TTA ATT GCT AAG GTT ATT ACA ATA TAT AAT GCT GTT        432
Ser Ser Ala Glu Leu Ile Ala Lys Val Ile Thr Ile Tyr Asn Ala Val
130                 135                 140

TAT AGA GGA GAT TTG GAT TAT TAT AAA GGG TTT TAT ATT GAG CCT GCT        480
Tyr Arg Gly Asp Leu Asp Tyr Tyr Lys Gly Phe Tyr Ile Glu Pro Ala
145                 150                 155                 160

TTG AAG TCT TTA ACT AAA GAA AAC GCA GGT CTT TCT AGG GTT TAC AGT        528
Leu Lys Ser Leu Thr Lys Glu Asn Ala Gly Leu Ser Arg Val Tyr Ser
                165                 170                 175

CAG TGG GCT GGA AAG ACT CAA ATA TTT ATT CCT CTT AAA AAG GAT ATT        576
Gln Trp Ala Gly Lys Thr Gln Ile Phe Ile Pro Leu Lys Lys Asp Ile
                180                 185                 190

TTG TCT GGA AAT ATT GAA TCT GAC ATT GAT ATT GAC AGT TTG GTT ACA        624
Leu Ser Gly Asn Ile Glu Ser Asp Ile Asp Ile Asp Ser Leu Val Thr
            195                 200                 205

GAT AAG GTG ATA GCA GCT CTT TTA AGC GAA AAT GAA GCA GGC GTT AAC        672
Asp Lys Val Ile Ala Ala Leu Leu Ser Glu Asn Glu Ala Gly Val Asn
210                 215                 220

TTT GCA AGA GAT ATT ACA GAT ATT CAA GGC GAA ACT CAT AAG GCA GAT        720
Phe Ala Arg Asp Ile Thr Asp Ile Gln Gly Glu Thr His Lys Ala Asp
225                 230                 235                 240

CAA GAT AAG ATT GAT ACT GAA TTA GAC AAT ATC CAT GAA AGC GAT TCT        768
Gln Asp Lys Ile Asp Thr Glu Leu Asp Asn Ile His Glu Ser Asp Ser
                245                 250                 255

AAT ATA ACA GAA ACT ATT GAA AAT TTA AGG GAT CAG CTT GAA AAA GCT        816
Asn Ile Thr Glu Thr Ile Glu Asn Leu Arg Asp Gln Leu Glu Lys Ala
            260                 265                 270

ACA GAT GAA GAG CAT AAA AAA GAG ATT GAA AGT CAG GTT GAT GCT AAA        864
Thr Asp Glu Glu His Lys Lys Glu Ile Glu Ser Gln Val Asp Ala Lys
            275                 280                 285
```

```
AAG AAA GAA AAG GAA GAG CTA GAT AAA AAG GCA ATC AAT CTT GAT AAA        912
Lys Lys Glu Lys Glu Glu Leu Asp Lys Lys Ala Ile Asn Leu Asp Lys
    290                 295                 300

GCT CAG CAA AAA TTA GAC TCT GCT GAA GAT AAT TTA GAT GTT CAA AGA        960
Ala Gln Gln Lys Leu Asp Ser Ala Glu Asp Asn Leu Asp Val Gln Arg
305                 310                 315                 320

GAT ACT GTT AGA GAG AAA ATT CAA GAG GAT ATT AAT GAG ATT AAT AAG       1008
Asp Thr Val Arg Glu Lys Ile Gln Glu Asp Ile Asn Glu Ile Asn Lys
                325                 330                 335

GAA AAG AAT TTG CCA AAA CCT GGT GAT GTA AGT TCT CCT AAA GTT GAT       1056
Glu Lys Asn Leu Pro Lys Pro Gly Asp Val Ser Ser Pro Lys Val Asp
            340                 345                 350

AAG CAA CTG CAA ATA AAA GAG AGT CTA GAA GAT TTG CAG GAG CAG CTT       1104
Lys Gln Leu Gln Ile Lys Glu Ser Leu Glu Asp Leu Gln Glu Gln Leu
        355                 360                 365

AAA GAA GCT GGT GAT GAA AAT CAG AAA AGA GAA ATT GAG AAG CAA ATT       1152
Lys Glu Ala Gly Asp Glu Asn Gln Lys Arg Glu Ile Glu Lys Gln Ile
    370                 375                 380

GAA ATC AAA AAA AGG GAC GAA GAA CTT TTA AAA AGT AAA GAT GGC AAA       1200
Glu Ile Lys Lys Arg Asp Glu Glu Leu Leu Lys Ser Lys Asp Gly Lys
385                 390                 395                 400

GTA AGT AAA GAT TAT GAA GCA TTA GAT CTT GAT CGA GAA TTA TCC AAA       1248
Val Ser Lys Asp Tyr Glu Ala Leu Asp Leu Asp Arg Glu Leu Ser Lys
                405                 410                 415

GCT TCT AGT AAA GAA AAA AGT AAG GTC AAG GAA GAA GAA ATA ACT AAA       1296
Ala Ser Ser Lys Glu Lys Ser Lys Val Lys Glu Glu Glu Ile Thr Lys
            420                 425                 430

GGT AAA TCA CGG GCA AGC TTA GGC GAT TTG AAT AAT GAT AAA AAC CTT       1344
Gly Lys Ser Arg Ala Ser Leu Gly Asp Leu Asn Asn Asp Lys Asn Leu
        435                 440                 445

ATG TTG CCA GAA GAT CAA AAA TTA CCT GAA GAT AAA AAA TTG GAT AGT       1392
Met Leu Pro Glu Asp Gln Lys Leu Pro Glu Asp Lys Lys Leu Asp Ser
    450                 455                 460

AAA TTA GAT GGT AAA AAA GAA TTT AAA CCA GTT TCT GAG GTT GAA AAA       1440
Lys Leu Asp Gly Lys Lys Glu Phe Lys Pro Val Ser Glu Val Glu Lys
465                 470                 475                 480

TTA GAT AAG ATT TCC AAG TCT AAT AAC AAT GAG GTT GGC AAG TTA TCA       1488
Leu Asp Lys Ile Ser Lys Ser Asn Asn Asn Glu Val Gly Lys Leu Ser
                485                 490                 495

CCA TTA GAT AAG CCT TCT TAT GAT GAT ATT GAT TCA AAA GAG GAG GTA       1536
Pro Leu Asp Lys Pro Ser Tyr Asp Asp Ile Asp Ser Lys Glu Glu Val
            500                 505                 510

GAT AAT AAA GCT ATT AAT TTG CAA AAG ATC GAC CCT AAA GTT AAA GAC       1584
Asp Asn Lys Ala Ile Asn Leu Gln Lys Ile Asp Pro Lys Val Lys Asp
        515                 520                 525

CAA ACT ACT TCT TTG AAT GAA GAT TTG GAT AAA GAT TTG ACT ACT ATG       1632
Gln Thr Thr Ser Leu Asn Glu Asp Leu Asp Lys Asp Leu Thr Thr Met
    530                 535                 540

TCT ATA GAT TCC AGC AGT CCT GTA TTT CTA GAG GTT ATT GAT CCT ATT       1680
Ser Ile Asp Ser Ser Ser Pro Val Phe Leu Glu Val Ile Asp Pro Ile
545                 550                 555                 560

ACA AAT TTA GGA ACC CTG CAG CTT ATT GAT TTA AAT ACT GGG GTT AGG       1728
Thr Asn Leu Gly Thr Leu Gln Leu Ile Asp Leu Asn Thr Gly Val Arg
                565                 570                 575

CTT AAG GAA AGC ACT CAG CAA GGC ATT CAG CGG TAT GGA ATT TAT GAA       1776
Leu Lys Glu Ser Thr Gln Gln Gly Ile Gln Arg Tyr Gly Ile Tyr Glu
            580                 585                 590

CGT GAA AAA GAT TTG GTT GTT ATT AAA ATG GAT TCA GGA AAG GCT AAG       1824
Arg Glu Lys Asp Leu Val Val Ile Lys Met Asp Ser Gly Lys Ala Lys
        595                 600                 605
```

```
CTT CAA ATA CTT AAT AAG CTT GAA AAT TTG AAA GTG GTA TCA GAG TCT        1872
Leu Gln Ile Leu Asn Lys Leu Glu Asn Leu Lys Val Val Ser Glu Ser
    610             615                 620

AAT TTT GAG ATC AAT AAA AAT TCA TCT CTT TAT GTT GAC TCT AAA ATG        1920
Asn Phe Glu Ile Asn Lys Asn Ser Ser Leu Tyr Val Asp Ser Lys Met
625             630                 635                 640

ATT TTG GCA GCT GTT AGA GAT AAG GAT GAT AGC AAT GCT TGG AGA TTG        1968
Ile Leu Ala Ala Val Arg Asp Lys Asp Asp Ser Asn Ala Trp Arg Leu
                645                 650                 655

GCT AAA TTT TCT CCT AAA AAT TTG GAT GAG TTT ATT CTT TCA GAG AAT        2016
Ala Lys Phe Ser Pro Lys Asn Leu Asp Glu Phe Ile Leu Ser Glu Asn
                660                 665                 670

AAA ATT TTG CCT TTT ACT AGC TTT TCT GTG AGA AAA AAT TTT ATT TAT        2064
Lys Ile Leu Pro Phe Thr Ser Phe Ser Val Arg Lys Asn Phe Ile Tyr
            675                 680                 685

TTG CAA GAT GAG CTT AAA AAT CTA GTT ATT TTA GAT GTA AAT ACT TTA        2112
Leu Gln Asp Glu Leu Lys Asn Leu Val Ile Leu Asp Val Asn Thr Leu
690                 695                 700

AAA AAA GTT AAG TA                                                      2126
Lys Lys Val Lys
705
```

(2) INFORMATION FOR SEQ ID NO:76:

(i) SEQUENCE CHARACTERISTICS:
        (A) LENGTH: 708 amino acids
        (B) TYPE: amino acid
        (D) TOPOLOGY: linear (ii) MOLECULE TYPE: protein (xi) SEQUENCE DESCRIPTION: SEQ ID NO:76:

```
Met Lys Lys Met Leu Leu Ile Phe Ser Phe Phe Leu Ile Phe Leu Asn
1               5                   10                  15

Gly Phe Pro Leu Asn Ala Arg Lys Val Asp Lys Glu Lys Leu Lys Asp
                20                  25                  30

Phe Val Asn Met Asp Leu Glu Phe Val Asn Tyr Lys Gly Pro Tyr Asp
            35                  40                  45

Ser Thr Asn Thr Tyr Glu Gln Ile Val Gly Ile Gly Glu Phe Leu Ala
        50                  55                  60

Arg Pro Leu Thr Asn Ser Asn Ser Asn Ser Ser Tyr Tyr Gly Lys Tyr
65                  70                  75                  80

Phe Ile Asn Arg Phe Ile Asp Asp Gln Asp Lys Lys Ala Ser Val Asp
                85                  90                  95

Val Phe Ser Ile Ser Ser Lys Ser Glu Leu Asp Ser Ile Leu Asn Leu
                100                 105                 110

Arg Arg Ile Leu Thr Gly Tyr Ile Ile Lys Ser Phe Asp Tyr Asp Arg
            115                 120                 125

Ser Ser Ala Glu Leu Ile Ala Lys Val Ile Thr Ile Tyr Asn Ala Val
        130                 135                 140

Tyr Arg Gly Asp Leu Asp Tyr Tyr Lys Gly Phe Tyr Ile Glu Pro Ala
145                 150                 155                 160

Leu Lys Ser Leu Thr Lys Glu Asn Ala Gly Leu Ser Arg Val Tyr Ser
                165                 170                 175

Gln Trp Ala Gly Lys Thr Gln Ile Phe Ile Pro Leu Lys Lys Asp Ile
            180                 185                 190

Leu Ser Gly Asn Ile Glu Ser Asp Ile Asp Ser Leu Val Thr
        195                 200                 205
```

-continued

```
Asp Lys Val Ile Ala Ala Leu Leu Ser Glu Asn Glu Ala Gly Val Asn
        210                 215                 220
Phe Ala Arg Asp Ile Thr Asp Ile Gln Gly Glu Thr His Lys Ala Asp
225                 230                 235                 240
Gln Asp Lys Ile Asp Thr Glu Leu Asp Asn Ile His Glu Ser Asp Ser
                245                 250                 255
Asn Ile Thr Glu Thr Ile Glu Asn Leu Arg Asp Gln Leu Glu Lys Ala
            260                 265                 270
Thr Asp Glu Glu His Lys Lys Glu Ile Glu Ser Gln Val Asp Ala Lys
        275                 280                 285
Lys Lys Glu Lys Glu Glu Leu Asp Lys Lys Ala Ile Asn Leu Asp Lys
290                 295                 300
Ala Gln Gln Lys Leu Asp Ser Ala Glu Asp Asn Leu Asp Val Gln Arg
305                 310                 315                 320
Asp Thr Val Arg Glu Lys Ile Gln Glu Asp Ile Asn Glu Ile Asn Lys
                325                 330                 335
Glu Lys Asn Leu Pro Lys Pro Gly Asp Val Ser Ser Pro Lys Val Asp
            340                 345                 350
Lys Gln Leu Gln Ile Lys Glu Ser Leu Glu Asp Leu Gln Glu Gln Leu
        355                 360                 365
Lys Glu Ala Gly Asp Glu Asn Gln Lys Arg Glu Ile Glu Lys Gln Ile
        370                 375                 380
Glu Ile Lys Lys Arg Asp Glu Glu Leu Leu Lys Ser Lys Asp Gly Lys
385                 390                 395                 400
Val Ser Lys Asp Tyr Glu Ala Leu Asp Leu Asp Arg Glu Leu Ser Lys
                405                 410                 415
Ala Ser Ser Lys Glu Lys Ser Lys Val Lys Glu Glu Ile Thr Lys
                420                 425                 430
Gly Lys Ser Arg Ala Ser Leu Gly Asp Leu Asn Asn Asp Lys Asn Leu
        435                 440                 445
Met Leu Pro Glu Asp Gln Lys Leu Pro Glu Asp Lys Lys Leu Asp Ser
    450                 455                 460
Lys Leu Asp Gly Lys Lys Glu Phe Lys Pro Val Ser Glu Val Glu Lys
465                 470                 475                 480
Leu Asp Lys Ile Ser Lys Ser Asn Asn Asn Glu Val Gly Lys Leu Ser
                485                 490                 495
Pro Leu Asp Lys Pro Ser Tyr Asp Ile Asp Ser Lys Glu Glu Val
            500                 505                 510
Asp Asn Lys Ala Ile Asn Leu Gln Lys Ile Asp Pro Lys Val Lys Asp
        515                 520                 525
Gln Thr Thr Ser Leu Asn Glu Asp Leu Asp Lys Asp Leu Thr Thr Met
        530                 535                 540
Ser Ile Asp Ser Ser Ser Pro Val Phe Leu Glu Val Ile Asp Pro Ile
545                 550                 555                 560
Thr Asn Leu Gly Thr Leu Gln Leu Ile Asp Leu Asn Thr Gly Val Arg
                565                 570                 575
Leu Lys Glu Ser Thr Gln Gln Gly Ile Gln Arg Tyr Gly Ile Tyr Glu
            580                 585                 590
Arg Glu Lys Asp Leu Val Val Ile Lys Met Asp Ser Gly Lys Ala Lys
        595                 600                 605
Leu Gln Ile Leu Asn Lys Leu Glu Asn Leu Lys Val Val Ser Glu Ser
        610                 615                 620
```

```
Asn Phe Glu Ile Asn Lys Asn Ser Ser Leu Tyr Val Asp Ser Lys Met
625                 630                 635                 640

Ile Leu Ala Ala Val Arg Asp Lys Asp Asp Ser Asn Ala Trp Arg Leu
                645                 650                 655

Ala Lys Phe Ser Pro Lys Asn Leu Asp Glu Phe Ile Leu Ser Glu Asn
                660                 665                 670

Lys Ile Leu Pro Phe Thr Ser Phe Ser Val Arg Lys Asn Phe Ile Tyr
                675                 680                 685

Leu Gln Asp Glu Leu Lys Asn Leu Val Ile Leu Asp Val Asn Thr Leu
                690                 695                 700

Lys Lys Val Lys
705

(2) INFORMATION FOR SEQ ID NO:77:

(i) SEQUENCE CHARACTERISTICS:
        (A) LENGTH: 1991 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..1991

(xi) SEQUENCE DESCRIPTION: SEQ ID NO:77:

ATG AAA AAA ATG TTA CTA ATC TTT AGT TTT TTT CTT GTT TTT TTA AAT      48
Met Lys Lys Met Leu Leu Ile Phe Ser Phe Phe Leu Val Phe Leu Asn
 1               5                  10                  15

GGA TTT CCT CTT AAT GCA AGG GAA GTT GAT AAG GAA AAA TTA AAG GAC      96
Gly Phe Pro Leu Asn Ala Arg Glu Val Asp Lys Glu Lys Leu Lys Asp
                20                  25                  30

TTT GTT AAT ATG GAT CTT GAA TTT GTT AAT TAC AAG GGT CCT TAT GAT     144
Phe Val Asn Met Asp Leu Glu Phe Val Asn Tyr Lys Gly Pro Tyr Asp
                35                  40                  45

TCT ACA AAT ACA TAT GAA CAA ATA GTA GGT ATT GGG GAG TTT TTA GCA     192
Ser Thr Asn Thr Tyr Glu Gln Ile Val Gly Ile Gly Glu Phe Leu Ala
    50                  55                  60

AGG CCG TTG ATC AAT TCC AAT AGT AAT TCA AGT TAT TAT GGT AAA TAT     240
Arg Pro Leu Ile Asn Ser Asn Ser Asn Ser Ser Tyr Tyr Gly Lys Tyr
65                  70                  75                  80

TTT GTT AAT AGA TTT ATT GAC GAT CAA GAT AAA AAA GCA AGT GTT GAT     288
Phe Val Asn Arg Phe Ile Asp Asp Gln Asp Lys Lys Ala Ser Val Asp
                85                  90                  95

ATT TTT TCT ATT GGT AGT AAG TCA GAG CTT GAT AGT ATA TTA AAT CTA     336
Ile Phe Ser Ile Gly Ser Lys Ser Glu Leu Asp Ser Ile Leu Asn Leu
                100                 105                 110

AGA AGA ATT CTT ACA GGG TAT TTA ATG AAG TCT TTT GAT TAT GAG AGG     384
Arg Arg Ile Leu Thr Gly Tyr Leu Met Lys Ser Phe Asp Tyr Glu Arg
            115                 120                 125

TCT AGT GCG GAA TTA ATT GCT AAA GCT ATT ACA ATA TAT AAT GCT GTT     432
Ser Ser Ala Glu Leu Ile Ala Lys Ala Ile Thr Ile Tyr Asn Ala Val
        130                 135                 140

TAT AGA GGA GAT TTA GAT TAT TAC AAA GAG TTT TAT ATT GAG GCT TCT     480
Tyr Arg Gly Asp Leu Asp Tyr Tyr Lys Glu Phe Tyr Ile Glu Ala Ser
145                 150                 155                 160

TTG AAG TCT TTG ACT AAA GAA AAT GCA GGT CTT TCT AGG GTG TAC AGT     528
Leu Lys Ser Leu Thr Lys Glu Asn Ala Gly Leu Ser Arg Val Tyr Ser
                165                 170                 175
```

```
CAA TGG GCT GGG AAG ACA CAA ATA TTT ATT CCT CTT AAA AAG AAT ATT       576
Gln Trp Ala Gly Lys Thr Gln Ile Phe Ile Pro Leu Lys Lys Asn Ile
            180                 185                 190

TTA TCT GGA AAT GTT GAG TCT GAC ATT GAT ATT GAT AGT TTG GTT ACA       624
Leu Ser Gly Asn Val Glu Ser Asp Ile Asp Ile Asp Ser Leu Val Thr
        195                 200                 205

GAT AAG GTG GTG GCA GCT CTT TTA AGT GAG AAT GAA TCA GGT GTT AAC       672
Asp Lys Val Val Ala Ala Leu Leu Ser Glu Asn Glu Ser Gly Val Asn
    210                 215                 220

TTT GCA AGA GAT ATT ACA GAC ATT CAA GGC GAA ACT CAT AAA GCA GAT       720
Phe Ala Arg Asp Ile Thr Asp Ile Gln Gly Glu Thr His Lys Ala Asp
225                 230                 235                 240

CAA GAT AAA ATT GAT ATT GAA TTA GAT AAT TTT CAT GAA AGT GAT TCC       768
Gln Asp Lys Ile Asp Ile Glu Leu Asp Asn Phe His Glu Ser Asp Ser
                245                 250                 255

AAT ATA ACA GAA ACT ATT GAG AAT TTA AGG GAT CAG CTT GAA AAA GCT       816
Asn Ile Thr Glu Thr Ile Glu Asn Leu Arg Asp Gln Leu Glu Lys Ala
            260                 265                 270

ACA GAT GAA GAG CAT AAA AAA GAG ATT GAA AGT CAG GTT GAT GCT AAA       864
Thr Asp Glu Glu His Lys Lys Glu Ile Glu Ser Gln Val Asp Ala Lys
        275                 280                 285

AAG AAA CAA AAG GAA GAA TTA GAT AAA AAG GCA ATT GAT CTT GAT AAA       912
Lys Lys Gln Lys Glu Glu Leu Asp Lys Lys Ala Ile Asp Leu Asp Lys
    290                 295                 300

GCT CAA CAA AAA TTA GAT TTT GCT GAA GAT AAT CTA GAT ATT CAA AGG       960
Ala Gln Gln Lys Leu Asp Phe Ala Glu Asp Asn Leu Asp Ile Gln Arg
305                 310                 315                 320

GAT ACT GTT AGA GAG AAG CTT CAA GAA AAT ATT AAC GAG ACT AAT AAG      1008
Asp Thr Val Arg Glu Lys Leu Gln Glu Asn Ile Asn Glu Thr Asn Lys
                325                 330                 335

GAA AAG AAT TTA CCA AAG CCT GGT GAT GTA AGT TCT CCT AAG GTT GAT      1056
Glu Lys Asn Leu Pro Lys Pro Gly Asp Val Ser Ser Pro Lys Val Asp
            340                 345                 350

AAG CAG TTG CAG ATA AAA GAG AGT CTA GAA GAT TTG CAA GAG CAG CTT      1104
Lys Gln Leu Gln Ile Lys Glu Ser Leu Glu Asp Leu Gln Glu Gln Leu
        355                 360                 365

AAA GAA GCT AGT GAT GAA AAT CAA AAA AGA GAA ATA GAA AAG CAA ATT      1152
Lys Glu Ala Ser Asp Glu Asn Gln Lys Arg Glu Ile Glu Lys Gln Ile
    370                 375                 380

GAA ATC AAA AAA AAT GAT GAA GAA CTT TTT AAA AAT AAA GAT CAT AAA      1200
Glu Ile Lys Lys Asn Asp Glu Glu Leu Phe Lys Asn Lys Asp His Lys
385                 390                 395                 400

GCA TTA GAT CTT AAG CAA GAA TTA AAT TCT AAA GCT TCT AGT AAA GAA      1248
Ala Leu Asp Leu Lys Gln Glu Leu Asn Ser Lys Ala Ser Ser Lys Glu
                405                 410                 415

AAA ATT GAA GGC GAA GAA GAG GAT AAA GAA TTA GAT AGT AAA AAA AAT      1296
Lys Ile Glu Gly Glu Glu Glu Asp Lys Glu Leu Asp Ser Lys Lys Asn
            420                 425                 430

TTA GAG CCT GTT TCT GAG GCT GAT AAA GTA GAT AAA ATT TCC AAG TCT      1344
Leu Glu Pro Val Ser Glu Ala Asp Lys Val Asp Lys Ile Ser Lys Ser
        435                 440                 445

AAC AAC AAT GAG GTT AGT AAA TTA TCC CCG TTA GAT GAG CCT TCT TAT      1392
Asn Asn Asn Glu Val Ser Lys Leu Ser Pro Leu Asp Glu Pro Ser Tyr
    450                 455                 460

AGC GAC ATT GAT TCG AAA GAG GGT GTA GAT AAC AAA GAT GTT GAT TTG      1440
Ser Asp Ile Asp Ser Lys Glu Gly Val Asp Asn Lys Asp Val Asp Leu
465                 470                 475                 480

CAA AAA ACT AAA CCC CAA GTT GAA AGT CAA CCT ACT TCG TTA AAT GAA      1488
Gln Lys Thr Lys Pro Gln Val Glu Ser Gln Pro Thr Ser Leu Asn Glu
                485                 490                 495
```

```
GAC TTG ATT GAT GTG TCT ATA GAT TCC AGT AAT CCT GTC TTT TTA GAG    1536
Asp Leu Ile Asp Val Ser Ile Asp Ser Ser Asn Pro Val Phe Leu Glu
            500                 505                 510

GTT ATC GAT CCG ATT ACA AAT TTA GGA ACG CTT CAA CTT ATT GAT TTG    1584
Val Ile Asp Pro Ile Thr Asn Leu Gly Thr Leu Gln Leu Ile Asp Leu
            515                 520                 525

AAT ACC GGT GTT AGA CTT AAA GAA AGT GCT CAA CAA GGT ATT CAG CGA    1632
Asn Thr Gly Val Arg Leu Lys Glu Ser Ala Gln Gln Gly Ile Gln Arg
            530                 535                 540

TAT GGA ATT TAT GAA CGT GAA AAA GAT TTG GTT GTT ATT AAA ATA GAT    1680
Tyr Gly Ile Tyr Glu Arg Glu Lys Asp Leu Val Val Ile Lys Ile Asp
545                 550                 555                 560

TCA GGA AAA GCT AAG CTT CAG ATA CTT GAT AAA CTC GAG AAT TTA AAA    1728
Ser Gly Lys Ala Lys Leu Gln Ile Leu Asp Lys Leu Glu Asn Leu Lys
            565                 570                 575

GTG ATA TCA GAG TCT AAT TTT GAG ATT AAT AAA AAT TCA TCT CTT TAT    1776
Val Ile Ser Glu Ser Asn Phe Glu Ile Asn Lys Asn Ser Ser Leu Tyr
            580                 585                 590

GTT GAC TCT AGA ATG ATT TTA GTA GTT GTT AAG GAC GAT AGT AAT GCT    1824
Val Asp Ser Arg Met Ile Leu Val Val Val Lys Asp Asp Ser Asn Ala
            595                 600                 605

TGG AGA TTG GCT AAA TTT TCT CCT AAA AAT TTA GAT GAA TTT ATT CTG    1872
Trp Arg Leu Ala Lys Phe Ser Pro Lys Asn Leu Asp Glu Phe Ile Leu
            610                 615                 620

TCA GAA AAT AAA ATT TTG CCT TTT ACT AGC TTT GCT GTG AGA AAG AAT    1920
Ser Glu Asn Lys Ile Leu Pro Phe Thr Ser Phe Ala Val Arg Lys Asn
625                 630                 635                 640

TTT ATT TAT TTG CAA GAT GAA CTT AAA AGC TTA GTT ACT TTA GAT GTA    1968
Phe Ile Tyr Leu Gln Asp Glu Leu Lys Ser Leu Val Thr Leu Asp Val
            645                 650                 655

AAT ACT TTA AAA AAA GTT AAG TA                                     1991
Asn Thr Leu Lys Lys Val Lys
            660
```

(2) INFORMATION FOR SEQ ID NO:78:

(i) SEQUENCE CHARACTERISTICS:
        (A) LENGTH: 663 amino acids
        (B) TYPE: amino acid
        (D) TOPOLOGY: linear (ii) MOLECULE TYPE: protein (xi) SEQUENCE DESCRIPTION: SEQ ID NO:78:

```
Met Lys Lys Met Leu Leu Ile Phe Ser Phe Phe Leu Val Phe Leu Asn
1               5                   10                  15

Gly Phe Pro Leu Asn Ala Arg Glu Val Asp Lys Glu Lys Leu Lys Asp
                20                  25                  30

Phe Val Asn Met Asp Leu Glu Phe Val Asn Tyr Lys Gly Pro Tyr Asp
            35                  40                  45

Ser Thr Asn Thr Tyr Glu Gln Ile Val Gly Ile Gly Glu Phe Leu Ala
        50                  55                  60

Arg Pro Leu Ile Asn Ser Asn Ser Asn Ser Tyr Tyr Gly Lys Tyr
65                  70                  75                  80

Phe Val Asn Arg Phe Ile Asp Asp Gln Asp Lys Lys Ala Ser Val Asp
                85                  90                  95

Ile Phe Ser Ile Gly Ser Lys Ser Glu Leu Asp Ser Ile Leu Asn Leu
            100                 105                 110
```

```
Arg Arg Ile Leu Thr Gly Tyr Leu Met Lys Ser Phe Asp Tyr Glu Arg
        115                 120                 125

Ser Ser Ala Glu Leu Ile Ala Lys Ala Ile Thr Ile Tyr Asn Ala Val
130                 135                 140

Tyr Arg Gly Asp Leu Asp Tyr Tyr Lys Glu Phe Tyr Ile Glu Ala Ser
145                 150                 155                 160

Leu Lys Ser Leu Thr Lys Glu Asn Ala Gly Leu Ser Arg Val Tyr Ser
                165                 170                 175

Gln Trp Ala Gly Lys Thr Gln Ile Phe Ile Pro Leu Lys Lys Asn Ile
                180                 185                 190

Leu Ser Gly Asn Val Glu Ser Asp Ile Asp Ile Asp Ser Leu Val Thr
                195                 200                 205

Asp Lys Val Val Ala Ala Leu Leu Ser Glu Asn Glu Ser Gly Val Asn
210                 215                 220

Phe Ala Arg Asp Ile Thr Asp Ile Gln Gly Glu Thr His Lys Ala Asp
225                 230                 235                 240

Gln Asp Lys Ile Asp Ile Glu Leu Asp Asn Phe His Glu Ser Asp Ser
                245                 250                 255

Asn Ile Thr Glu Thr Ile Glu Asn Leu Arg Asp Gln Leu Glu Lys Ala
                260                 265                 270

Thr Asp Glu Glu His Lys Lys Glu Ile Glu Ser Gln Val Asp Ala Lys
                275                 280                 285

Lys Lys Gln Lys Glu Glu Leu Asp Lys Lys Ala Ile Asp Leu Asp Lys
                290                 295                 300

Ala Gln Gln Lys Leu Asp Phe Ala Glu Asp Asn Leu Asp Ile Gln Arg
305                 310                 315                 320

Asp Thr Val Arg Glu Lys Leu Gln Glu Asn Ile Asn Glu Thr Asn Lys
                325                 330                 335

Glu Lys Asn Leu Pro Lys Pro Gly Asp Val Ser Ser Pro Lys Val Asp
                340                 345                 350

Lys Gln Leu Gln Ile Lys Glu Ser Leu Glu Asp Leu Gln Glu Gln Leu
                355                 360                 365

Lys Glu Ala Ser Asp Glu Asn Gln Lys Arg Glu Ile Glu Lys Gln Ile
370                 375                 380

Glu Ile Lys Lys Asn Asp Glu Glu Leu Phe Lys Asn Lys Asp His Lys
385                 390                 395                 400

Ala Leu Asp Leu Lys Gln Glu Leu Asn Ser Lys Ala Ser Ser Lys Glu
                405                 410                 415

Lys Ile Glu Gly Glu Glu Glu Asp Lys Glu Leu Asp Ser Lys Lys Asn
                420                 425                 430

Leu Glu Pro Val Ser Glu Ala Asp Lys Val Asp Lys Ile Ser Lys Ser
                435                 440                 445

Asn Asn Asn Glu Val Ser Lys Leu Ser Pro Leu Asp Glu Pro Ser Tyr
450                 455                 460

Ser Asp Ile Asp Ser Lys Glu Gly Val Asp Asn Lys Asp Val Asp Leu
465                 470                 475                 480

Gln Lys Thr Lys Pro Gln Val Glu Ser Gln Pro Thr Ser Leu Asn Glu
                485                 490                 495

Asp Leu Ile Asp Val Ser Ile Asp Ser Ser Asn Pro Val Phe Leu Glu
                500                 505                 510

Val Ile Asp Pro Ile Thr Asn Leu Gly Thr Leu Gln Leu Ile Asp Leu
                515                 520                 525
```

```
Asn Thr Gly Val Arg Leu Lys Glu Ser Ala Gln Gln Gly Ile Gln Arg
            530                 535                 540

Tyr Gly Ile Tyr Glu Arg Glu Lys Asp Leu Val Val Ile Lys Ile Asp
545                 550                 555                 560

Ser Gly Lys Ala Lys Leu Gln Ile Leu Asp Lys Leu Glu Asn Leu Lys
                    565                 570                 575

Val Ile Ser Glu Ser Asn Phe Glu Ile Asn Lys Asn Ser Ser Leu Tyr
                580                 585                 590

Val Asp Ser Arg Met Ile Leu Val Val Lys Asp Asp Ser Asn Ala
                595                 600                 605

Trp Arg Leu Ala Lys Phe Ser Pro Lys Asn Leu Asp Glu Phe Ile Leu
            610                 615                 620

Ser Glu Asn Lys Ile Leu Pro Phe Thr Ser Phe Ala Val Arg Lys Asn
625                 630                 635                 640

Phe Ile Tyr Leu Gln Asp Glu Leu Lys Ser Leu Val Thr Leu Asp Val
                    645                 650                 655

Asn Thr Leu Lys Lys Val Lys
            660
```

(2) INFORMATION FOR SEQ ID NO:79:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:79:

CCGGTCACCC CATGGCTGCT TTAAAGTCTT TA                                  32

(2) INFORMATION FOR SEQ ID NO:80:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:80:

CCGGTCACCC CATGAATCTT GATAAAGCTC AG                                  32

(2) INFORMATION FOR SEQ ID NO:81:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:81:

CCGGTCACCC CATGGATGAA AAGCTTTTAA AAAGT                              35

(2) INFORMATION FOR SEQ ID NO:82:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:82:

CCGGTCACCC CCATGGTTGA GAAATTAGAT AAG                                 33

(2) INFORMATION FOR SEQ ID NO:83:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:83:

```
TTGGATCCGG TGACCCTTAA CTTTTTTTAA AG                              32
```

(2) INFORMATION FOR SEQ ID NO:84:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:84:

```
AAAGTAGAAG TTTTTGAATC CCATTTTCCA GTTTTTTT                        38
```

(2) INFORMATION FOR SEQ ID NO:85:

(i) SEQUENCE CHARACTERISTICS:
        (A) LENGTH: 825 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..825

(xi) SEQUENCE DESCRIPTION: SEQ ID NO:85:

```
ATG AAA AAA TAT TTA TTG GGA ATA GGT CTA ATA TTA GCC TTA ATA GCA     48
Met Lys Lys Tyr Leu Leu Gly Ile Gly Leu Ile Leu Ala Leu Ile Ala
 1               5                  10                  15

TGT AAG CAA AAT GTT AGC AGC CTT GAT GAA AAA AAT AGC GTT TCA GTA     96
Cys Lys Gln Asn Val Ser Ser Leu Asp Glu Lys Asn Ser Val Ser Val
            20                  25                  30

GAT TTA CCT GGT GGA ATG ACA GTT CTT GTA AGT AAA GAA AAA GAC AAA    144
Asp Leu Pro Gly Gly Met Thr Val Leu Val Ser Lys Glu Lys Asp Lys
        35                  40                  45

GAC GGT AAA TAC AGT CTA GAG GCA ACA GTA GAC AAG CTT GAG CTT AAA    192
Asp Gly Lys Tyr Ser Leu Glu Ala Thr Val Asp Lys Leu Glu Leu Lys
    50                  55                  60

GGA ACT TCT GAT AAA AAC AAC GGT TCT GGA ACA CTT GAA GGT GAA AAA    240
Gly Thr Ser Asp Lys Asn Asn Gly Ser Gly Thr Leu Glu Gly Glu Lys
65                  70                  75                  80

ACT GAC AAA AGT AAA GTA AAA TTA ACA ATT GCT GAT GAC CTA AGT CAA    288
Thr Asp Lys Ser Lys Val Lys Leu Thr Ile Ala Asp Asp Leu Ser Gln
                85                  90                  95

ACT AAA TTT GAA ATT TTC AAA GAA GAT GCC AAA ACA TTA GTA TCA AAA    336
Thr Lys Phe Glu Ile Phe Lys Glu Asp Ala Lys Thr Leu Val Ser Lys
           100                 105                 110

AAA GTA ACC CTT AAA GAC AAG TCA TCA ACA GAA GAA AAA TTC AAC GAA    384
Lys Val Thr Leu Lys Asp Lys Ser Ser Thr Glu Glu Lys Phe Asn Glu
       115                 120                 125

AAG GGT GAA ACA TCT GAA AAA ACA ATA GTA AGA GCA AAT GGA ACC AGA    432
Lys Gly Glu Thr Ser Glu Lys Thr Ile Val Arg Ala Asn Gly Thr Arg
   130                 135                 140
```

```
CTT GAA TAC ACA GAC ATA AAA AGC GAT GGA TCC GGA AAA GCT AAA GAA          480
Leu Glu Tyr Thr Asp Ile Lys Ser Asp Gly Ser Gly Lys Ala Lys Glu
145                 150                 155                 160

GTT TTA AAA GAC TTT ACT CTT GAA GGA ACT CTA GCT GCT GAC GGC AAA          528
Val Leu Lys Asp Phe Thr Leu Glu Gly Thr Leu Ala Ala Asp Gly Lys
                165                 170                 175

ACA ACA TTG AAA GTT ACA GAA GGC ACT GTT GTT TTA AGC AAG AAC ATT          576
Thr Thr Leu Lys Val Thr Glu Gly Thr Val Val Leu Ser Lys Asn Ile
        180                 185                 190

TTA AAA TCC GGA GAA ATA ACA GTT GCA CTT GAT GAC TCT GAC ACT ACT          624
Leu Lys Ser Gly Glu Ile Thr Val Ala Leu Asp Asp Ser Asp Thr Thr
            195                 200                 205

CAG GCT ACT AAA AAA ACT GGA AAA TGG GAT TCA AAA ACT TCT ACT TTA          672
Gln Ala Thr Lys Lys Thr Gly Lys Trp Asp Ser Lys Thr Ser Thr Leu
210                 215                 220

ACA ATT AGT GTT AAC AGC AAA AAA ACT ACA CAA CTT GTG TTT ACT AAA          720
Thr Ile Ser Val Asn Ser Lys Lys Thr Thr Gln Leu Val Phe Thr Lys
225                 230                 235                 240

CAA TAC ACA ATA ACT GTA AAA CAA TAC GAC TCC GCA GGT ACC AAT TTA          768
Gln Tyr Thr Ile Thr Val Lys Gln Tyr Asp Ser Ala Gly Thr Asn Leu
                245                 250                 255

GAA GGC ACA GCA GTC GAA ATT AAA ACA CTT GAT GAA CTT AAA AAC GCT          816
Glu Gly Thr Ala Val Glu Ile Lys Thr Leu Asp Glu Leu Lys Asn Ala
            260                 265                 270

TTA AAA TAA                                                              825
Leu Lys
        275
```

(2) INFORMATION FOR SEQ ID NO:86:

(i) SEQUENCE CHARACTERISTICS:
        (A) LENGTH: 274 amino acids
        (B) TYPE: amino acid
        (D) TOPOLOGY: linear (ii) MOLECULE TYPE: protein (xi) SEQUENCE DESCRIPTION: SEQ ID NO:86:

```
Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Gly Met Thr Val Leu Val Ser Lys Glu Lys Asp Lys
        35                  40                  45

Asp Gly Lys Tyr Ser Leu Glu Ala Thr Val Asp Lys Leu Glu Leu Lys
    50                  55                  60

Gly Thr Ser Asp Lys Asn Asn Gly Ser Gly Thr Leu Glu Gly Glu Lys
65                  70                  75                  80

Thr Asp Lys Ser Lys Val Lys Leu Thr Ile Ala Asp Asp Leu Ser Gln
                85                  90                  95

Thr Lys Phe Glu Ile Phe Lys Glu Asp Ala Lys Thr Leu Val Ser Lys
            100                 105                 110

Lys Val Thr Leu Lys Asp Lys Ser Ser Thr Glu Glu Lys Phe Asn Glu
        115                 120                 125

Lys Gly Glu Thr Ser Glu Lys Thr Ile Val Arg Ala Asn Gly Thr Arg
    130                 135                 140

Leu Glu Tyr Thr Asp Ile Lys Ser Asp Gly Ser Gly Lys Ala Lys Glu
145                 150                 155                 160
```

```
Val Leu Lys Asp Phe Thr Leu Glu Gly Thr Leu Ala Ala Asp Gly Lys
                165                 170                 175

Thr Thr Leu Lys Val Thr Glu Gly Thr Val Val Leu Ser Lys Asn Ile
            180                 185                 190

Leu Lys Ser Gly Glu Ile Thr Val Ala Leu Asp Asp Ser Asp Thr Thr
        195                 200                 205

Gln Ala Thr Lys Lys Thr Gly Lys Trp Asp Ser Lys Thr Ser Thr Leu
    210                 215                 220

Thr Ile Ser Val Asn Ser Lys Lys Thr Thr Gln Leu Val Phe Thr Lys
225                 230                 235                 240

Gln Tyr Thr Ile Thr Val Lys Gln Tyr Asp Ser Ala Gly Thr Asn Leu
                245                 250                 255

Glu Gly Thr Ala Val Glu Ile Lys Thr Leu Asp Glu Leu Lys Asn Ala
            260                 265                 270

Leu Lys (2) INFORMATION FOR SEQ ID NO:87:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:87:

AAAGTAGAAG TTTTTGAATT CCAAGCTGCA GTTTT                              35

(2) INFORMATION FOR SEQ ID NO:88:

(i) SEQUENCE CHARACTERISTICS:
        (A) LENGTH: 822 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..822

(xi) SEQUENCE DESCRIPTION: SEQ ID NO:88:

ATG AAA AAA TAT TTA TTG GGA ATA GGT CTA ATA TTA GCC TTA ATA GCA    48
Met Lys Lys Tyr Leu Leu Gly Ile Gly Leu Ile Leu Ala Leu Ile Ala
 1               5                  10                  15

TGC AAG CAA AAT GTT AGC AGC CTT GAT GAA AAA AAC AGC GCT TCA GTA    96
Cys Lys Gln Asn Val Ser Ser Leu Asp Glu Lys Asn Ser Ala Ser Val
                20                  25                  30

GAT TTG CCT GGT GAG ATG AAA GTT CTT GTA AGT AAA GAA AAA GAC AAA   144
Asp Leu Pro Gly Glu Met Lys Val Leu Val Ser Lys Glu Lys Asp Lys
            35                  40                  45

GAC GGT AAG TAC AGT CTA AAG GCA ACA GTA GAC AAG ATT GAG CTA AAA   192
Asp Gly Lys Tyr Ser Leu Lys Ala Thr Val Asp Lys Ile Glu Leu Lys
        50                  55                  60

GGA ACT TCT GAT AAA GAC AAT GGT TCT GGA GTG CTT GAA GGT ACA AAA   240
Gly Thr Ser Asp Lys Asp Asn Gly Ser Gly Val Leu Glu Gly Thr Lys
65                  70                  75                  80

GAT GAC AAA AGT AAA GCA AAA TTA ACA ATT GCT GAC GAT CTA AGT AAA   288
Asp Asp Lys Ser Lys Ala Lys Leu Thr Ile Ala Asp Asp Leu Ser Lys
                85                  90                  95
```

```
ACC ACA TTC GAA CTT TTA AAA GAA GAT GGC AAA ACA TTA GTG TCA AGA        336
Thr Thr Phe Glu Leu Leu Lys Glu Asp Gly Lys Thr Leu Val Ser Arg
        100                 105                 110

AAA GTA AGT TCT AGA GAC AAA ACA TCA ACA GAT GAA ATG TTC AAT GAA        384
Lys Val Ser Ser Arg Asp Lys Thr Ser Thr Asp Glu Met Phe Asn Glu
            115                 120                 125

AAA GGT GAA TTG TCT GCA AAA ACC ATG ACA AGA GAA AAT GGA ACC AAA        432
Lys Gly Glu Leu Ser Ala Lys Thr Met Thr Arg Glu Asn Gly Thr Lys
130                 135                 140

CTT GAA TAT ACA GAA ATG AAA AGC GAT GGA ACC GGA AAA GCT AAA GAA        480
Leu Glu Tyr Thr Glu Met Lys Ser Asp Gly Thr Gly Lys Ala Lys Glu
145                 150                 155                 160

GTT TTA AAA AAG TTT ACT CTT GAA GGA AAA GTA GCT AAT GAT AAA GTA        528
Val Leu Lys Lys Phe Thr Leu Glu Gly Lys Val Ala Asn Asp Lys Val
                165                 170                 175

ACA TTG GAA GTA AAA GAA GGA ACC GTT ACT TTA AGT AAG GAA ATT GCA        576
Thr Leu Glu Val Lys Glu Gly Thr Val Thr Leu Ser Lys Glu Ile Ala
                180                 185                 190

AAA TCT GGA GAA GTA ACA GTT GCT CTT AAT GAC ACT AAC ACT ACT CAG        624
Lys Ser Gly Glu Val Thr Val Ala Leu Asn Asp Thr Asn Thr Thr Gln
        195                 200                 205

GCT ACT AAA AAA ACT GGC GCA TGG GAT TCA AAA ACT TCT ACT TTA ACA        672
Ala Thr Lys Lys Thr Gly Ala Trp Asp Ser Lys Thr Ser Thr Leu Thr
210                 215                 220

ATT AGT GTT AAC AGC AAA AAA ACT ACA CAA CTT GTG TTT ACT AAA CAA        720
Ile Ser Val Asn Ser Lys Lys Thr Thr Gln Leu Val Phe Thr Lys Gln
225                 230                 235                 240

TAC ACA ATA ACT GTA AAA CAA TAC GAC TCC GCA GGT ACC AAT TTA GAA        768
Tyr Thr Ile Thr Val Lys Gln Tyr Asp Ser Ala Gly Thr Asn Leu Glu
                245                 250                 255

GGC ACA GCA GTC GAA ATT AAA ACA CTT GAT GAA CTT AAA AAC GCT TTA        816
Gly Thr Ala Val Glu Ile Lys Thr Leu Asp Glu Leu Lys Asn Ala Leu
                260                 265                 270

AAA TAA                                                                822
Lys
```

(2) INFORMATION FOR SEQ ID NO:89:

(i) SEQUENCE CHARACTERISTICS:
        (A) LENGTH: 273 amino acids
        (B) TYPE: amino acid
        (D) TOPOLOGY: linear (ii) MOLECULE TYPE: protein (xi) SEQUENCE DESCRIPTION: SEQ ID NO:89:

```
Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Ala Ser Val
                20                  25                  30

Asp Leu Pro Gly Glu Met Lys Val Leu Val Ser Lys Glu Lys Asp Lys
            35                  40                  45

Asp Gly Lys Tyr Ser Leu Lys Ala Thr Val Asp Lys Ile Glu Leu Lys
        50                  55                  60

Gly Thr Ser Asp Lys Asp Asn Gly Ser Gly Val Leu Glu Gly Thr Lys
65                  70                  75                  80

Asp Asp Lys Ser Lys Ala Lys Leu Thr Ile Ala Asp Leu Ser Lys
                85                  90                  95

Thr Thr Phe Glu Leu Leu Lys Glu Asp Gly Lys Thr Leu Val Ser Arg
            100                 105                 110
```

```
Lys Val Ser Ser Arg Asp Lys Thr Ser Thr Asp Glu Met Phe Asn Glu
        115                 120                 125

Lys Gly Glu Leu Ser Ala Lys Thr Met Thr Arg Glu Asn Gly Thr Lys
        130                 135                 140

Leu Glu Tyr Thr Glu Met Lys Ser Asp Gly Thr Gly Lys Ala Lys Glu
145                 150                 155                 160

Val Leu Lys Lys Phe Thr Leu Glu Gly Lys Val Ala Asn Asp Lys Val
                165                 170                 175

Thr Leu Glu Val Lys Glu Gly Thr Val Thr Leu Ser Lys Glu Ile Ala
        180                 185                 190

Lys Ser Gly Glu Val Thr Val Ala Leu Asn Asp Thr Asn Thr Thr Gln
        195                 200                 205

Ala Thr Lys Lys Thr Gly Ala Trp Asp Ser Lys Thr Ser Thr Leu Thr
210                 215                 220

Ile Ser Val Asn Ser Lys Lys Thr Thr Gln Leu Val Phe Thr Lys Gln
225                 230                 235                 240

Tyr Thr Ile Thr Val Lys Gln Tyr Asp Ser Ala Gly Thr Asn Leu Glu
                245                 250                 255

Gly Thr Ala Val Glu Ile Lys Thr Leu Asp Glu Leu Lys Asn Ala Leu
        260                 265                 270

Lys (2) INFORMATION FOR SEQ ID NO:90:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:90:

AAAGTGGAAG TTTTTGAATT CCAAGCTGCA GTTTTTTT                                38

(2) INFORMATION FOR SEQ ID NO:91:

(i) SEQUENCE CHARACTERISTICS:
        (A) LENGTH: 822 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..822

(xi) SEQUENCE DESCRIPTION: SEQ ID NO:91:

ATG AAA AAA TAT TTA TTG GGA ATA GGT CTA ATA TTA GCC TTA ATA GCA          48
Met Lys Lys Tyr Leu Leu Gly Ile Gly Leu Ile Leu Ala Leu Ile Ala
 1               5                  10                  15

TGT AAG CAA AAT GTT AGC AGC CTT GAC GAG AAA AAC AGC GTT TCA GTA          96
Cys Lys Gln Asn Val Ser Ser Leu Asp Glu Lys Asn Ser Val Ser Val
                20                  25                  30

GAT TTG CCT GGT GAA ATG AAA GTT CTT GTA AGC AAA GAA AAA AAC AAA         144
Asp Leu Pro Gly Glu Met Lys Val Leu Val Ser Lys Glu Lys Asn Lys
            35                  40                  45

GAC GGC AAG TAC GAT CTA ATT GCA ACA GTA GAC AAG CTT GAG CTT AAA         192
Asp Gly Lys Tyr Asp Leu Ile Ala Thr Val Asp Lys Leu Glu Leu Lys
        50                  55                  60
```

```
GGA ACT TCT GAT AAA AAC AAT GGA TCT GGA GTA CTT GAA GGC GTA AAA        240
Gly Thr Ser Asp Lys Asn Asn Gly Ser Gly Val Leu Glu Gly Val Lys
 65              70                  75                  80

GCT GAC AAA AGT AAA GTA AAA TTA ACA ATT TCT GAC GAT CTA GGT CAA        288
Ala Asp Lys Ser Lys Val Lys Leu Thr Ile Ser Asp Asp Leu Gly Gln
                 85                  90                  95

ACC ACA CTT GAA GTT TTC AAA GAA GAT GGC AAA ACA CTA GTA TCA AAA        336
Thr Thr Leu Glu Val Phe Lys Glu Asp Gly Lys Thr Leu Val Ser Lys
            100                 105                 110

AAA GTA ACT TCC AAA GAC AAG TCA TCA ACA GAA GAA AAA TTC AAT GAA        384
Lys Val Thr Ser Lys Asp Lys Ser Ser Thr Glu Glu Lys Phe Asn Glu
        115                 120                 125

AAA GGT GAA GTA TCT GAA AAA ATA ATA ACA AGA GCA GAC GGA ACC AGA        432
Lys Gly Glu Val Ser Glu Lys Ile Ile Thr Arg Ala Asp Gly Thr Arg
130                 135                 140

CTT GAA TAC ACA GGA ATT AAA AGC GAT GGA TCT GGA AAA GCT AAA GAG        480
Leu Glu Tyr Thr Gly Ile Lys Ser Asp Gly Ser Gly Lys Ala Lys Glu
145                 150                 155                 160

GTT TTA AAA GGC TAT GTT CTT GAA GGA ACT CTA ACT GCT GAA AAA ACA        528
Val Leu Lys Gly Tyr Val Leu Glu Gly Thr Leu Thr Ala Glu Lys Thr
                165                 170                 175

ACA TTG GTG GTT AAA GAA GGA ACT GTT ACT TTA AGC AAA AAT ATT TCA        576
Thr Leu Val Val Lys Glu Gly Thr Val Thr Leu Ser Lys Asn Ile Ser
            180                 185                 190

AAA TCT GGG GAA GTT TCA GTT GAA CTT AAT GAC ACT GAC AGT AGT GCT        624
Lys Ser Gly Glu Val Ser Val Glu Leu Asn Asp Thr Asp Ser Ser Ala
        195                 200                 205

GCT ACT AAA AAA ACT GCA GCT TGG AAT TCA AAA ACT TCC ACT TTA ACA        672
Ala Thr Lys Lys Thr Ala Ala Trp Asn Ser Lys Thr Ser Thr Leu Thr
    210                 215                 220

ATT AGT GTG AAT AGC CAA AAA ACC AAA AAC CTT GTA TTC ACA AAA GAA        720
Ile Ser Val Asn Ser Gln Lys Thr Lys Asn Leu Val Phe Thr Lys Glu
225                 230                 235                 240

GAC ACA ATA ACA GTA CAA AAA TAC GAC TCA GCA GGC ACC AAT CTA GAA        768
Asp Thr Ile Thr Val Gln Lys Tyr Asp Ser Ala Gly Thr Asn Leu Glu
                245                 250                 255

GGC AAA GCA GTC GAA ATT ACA ACA CTT AAA GAA CTT AAA AAC GCT TTA        816
Gly Lys Ala Val Glu Ile Thr Thr Leu Lys Glu Leu Lys Asn Ala Leu
            260                 265                 270

AAA TAA                                                                822
Lys (2) INFORMATION FOR SEQ ID NO:92:

(i) SEQUENCE CHARACTERISTICS:
        (A) LENGTH: 273 amino acids
        (B) TYPE: amino acid
        (D) TOPOLOGY: linear (ii) MOLECULE TYPE: protein (xi) SEQUENCE DESCRIPTION: SEQ ID NO:92:

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
                20                  25                  30

Asp Leu Pro Gly Glu Met Lys Val Leu Val Ser Lys Glu Lys Asn Lys
            35                  40                  45

Asp Gly Lys Tyr Asp Leu Ile Ala Thr Val Asp Lys Leu Glu Leu Lys
        50                  55                  60
```

```
Gly Thr Ser Asp Lys Asn Asn Gly Ser Gly Val Leu Glu Gly Val Lys
 65                  70                  75                  80

Ala Asp Lys Ser Lys Val Lys Leu Thr Ile Ser Asp Asp Leu Gly Gln
                 85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Arg Ala Asp Gly Thr Arg
130                 135                 140

Leu Glu Tyr Thr Gly Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Lys Thr Ser Thr Leu Thr
210                 215                 220

Ile Ser Val Asn Ser Gln Lys Thr Lys Asn Leu Val Phe Thr Lys Glu
225                 230                 235                 240

Asp Thr Ile Thr Val Gln Lys Tyr Asp Ser Ala Gly Thr Asn Leu Glu
                245                 250                 255

Gly Lys Ala Val Glu Ile Thr Thr Leu Lys Glu Leu Lys Asn Ala Leu
            260                 265                 270

Lys (2) INFORMATION FOR SEQ ID NO:93:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:93:

TAAAGTTGAA GTGCCTGCAT TCCAAGCTGC AGTTT                                35

(2) INFORMATION FOR SEQ ID NO:94:

(i) SEQUENCE CHARACTERISTICS:
        (A) LENGTH: 819 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..819

(xi) SEQUENCE DESCRIPTION: SEQ ID NO:94:

ATG AAA AAA TAT TTA TTG GGA ATA GGT CTA ATA TTA GCC TTA ATA GCA      48
Met Lys Lys Tyr Leu Leu Gly Ile Gly Leu Ile Leu Ala Leu Ile Ala
  1               5                  10                  15

TGT AAG CAA AAT GTT AGC AGC CTT GAC GAG AAA AAC AGC GTT TCA GTA      96
Cys Lys Gln Asn Val Ser Ser Leu Asp Glu Lys Asn Ser Val Ser Val
             20                  25                  30
```

```
GAT TTG CCT GGT GAA ATG AAA GTT CTT GTA AGC AAA GAA AAA AAC AAA      144
Asp Leu Pro Gly Glu Met Lys Val Leu Val Ser Lys Glu Lys Asn Lys
        35                  40                  45

GAC GGC AAG TAC GAT CTA ATT GCA ACA GTA GAC AAG CTT GAG CTT AAA      192
Asp Gly Lys Tyr Asp Leu Ile Ala Thr Val Asp Lys Leu Glu Leu Lys
 50                  55                  60

GGA ACT TCT GAT AAA AAC AAT GGA TCT GGA GTA CTT GAA GGC GTA AAA      240
Gly Thr Ser Asp Lys Asn Asn Gly Ser Gly Val Leu Glu Gly Val Lys
 65                  70                  75                  80

GCT GAC AAA AGT AAA GTA AAA TTA ACA ATT TCT GAC GAT CTA GGT CAA      288
Ala Asp Lys Ser Lys Val Lys Leu Thr Ile Ser Asp Asp Leu Gly Gln
             85                  90                  95

ACC ACA CTT GAA GTT TTC AAA GAA GAT GGC AAA ACA CTA GTA TCA AAA      336
Thr Thr Leu Glu Val Phe Lys Glu Asp Gly Lys Thr Leu Val Ser Lys
                100                 105                 110

AAA GTA ACT TCC AAA GAC AAG TCA TCA ACA GAA GAA AAA TTC AAT GAA      384
Lys Val Thr Ser Lys Asp Lys Ser Ser Thr Glu Glu Lys Phe Asn Glu
            115                 120                 125

AAA GGT GAA GTA TCT GAA AAA ATA ATA ACA AGA GCA GAC GGA ACC AGA      432
Lys Gly Glu Val Ser Glu Lys Ile Ile Thr Arg Ala Asp Gly Thr Arg
130                 135                 140

CTT GAA TAC ACA GGA ATT AAA AGC GAT GGA TCT GGA AAA GCT AAA GAG      480
Leu Glu Tyr Thr Gly Ile Lys Ser Asp Gly Ser Gly Lys Ala Lys Glu
145                 150                 155                 160

GTT TTA AAA GGC TAT GTT CTT GAA GGA ACT CTA ACT GCT GAA AAA ACA      528
Val Leu Lys Gly Tyr Val Leu Glu Gly Thr Leu Thr Ala Glu Lys Thr
                165                 170                 175

ACA TTG GTG GTT AAA GAA GGA ACT GTT ACT TTA AGC AAA AAT ATT TCA      576
Thr Leu Val Val Lys Glu Gly Thr Val Thr Leu Ser Lys Asn Ile Ser
            180                 185                 190

AAA TCT GGG GAA GTT TCA GTT GAA CTT AAT GAC ACT GAC AGT AGT GCT      624
Lys Ser Gly Glu Val Ser Val Glu Leu Asn Asp Thr Asp Ser Ser Ala
        195                 200                 205

GCT ACT AAA AAA ACT GCA GCT TGG AAT GCA GGC ACT TCA ACT TTA ACA      672
Ala Thr Lys Lys Thr Ala Ala Trp Asn Ala Gly Thr Ser Thr Leu Thr
    210                 215                 220

ATT ACT GTA AAC AAC AAA AAA ACT AAA GCC CTT GTA TTT ACA AAA CAA      720
Ile Thr Val Asn Asn Lys Lys Thr Lys Ala Leu Val Phe Thr Lys Gln
225                 230                 235                 240

GAC ACA ATT ACA TCA CAA AAA TAC GAC TCA GCA GGA ACC AAC TTG GAA      768
Asp Thr Ile Thr Ser Gln Lys Tyr Asp Ser Ala Gly Thr Asn Leu Glu
                245                 250                 255

GGC ACA GCA GTC GAA ATT AAA ACA CTT GAT GAA CTT AAA AAC GCT TTA      816
Gly Thr Ala Val Glu Ile Lys Thr Leu Asp Glu Leu Lys Asn Ala Leu
            260                 265                 270

AGA                                                                   819
Arg (2) INFORMATION FOR SEQ ID NO:95:

(i) SEQUENCE CHARACTERISTICS:
        (A) LENGTH: 273 amino acids
        (B) TYPE: amino acid
        (D) TOPOLOGY: linear (ii) MOLECULE TYPE: protein (xi) SEQUENCE DESCRIPTION: SEQ ID NO:95:

Met Lys Lys Tyr Leu Leu Gly Ile Gly Leu Ile Leu Ala Leu Ile Ala
 1               5                  10                  15
```

```
Cys Lys Gln Asn Val Ser Ser Leu Asp Glu Lys Asn Ser Val Ser Val
             20                  25                  30

Asp Leu Pro Gly Glu Met Lys Val Leu Val Ser Lys Glu Lys Asn Lys
         35                  40                  45

Asp Gly Lys Tyr Asp Leu Ile Ala Thr Val Asp Lys Leu Glu Leu Lys
     50                  55                  60

Gly Thr Ser Asp Lys Asn Asn Gly Ser Gly Val Leu Glu Gly Val Lys
 65                  70                  75                  80

Ala Asp Lys Ser Lys Val Lys Leu Thr Ile Ser Asp Asp Leu Gly Gln
                 85                  90                  95

Thr Thr Leu Glu Val Phe Lys Glu Asp Gly Lys Thr Leu Val Ser Lys
             100                 105                 110

Lys Val Thr Ser Lys Asp Lys Ser Ser Thr Glu Glu Lys Phe Asn Glu
         115                 120                 125

Lys Gly Glu Val Ser Glu Lys Ile Ile Thr Arg Ala Asp Gly Thr Arg
     130                 135                 140

Leu Glu Tyr Thr Gly Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
                 165                 170                 175

Thr Leu Val Val Lys Glu Gly Thr Val Thr Leu Ser Lys Asn Ile Ser
             180                 185                 190

Lys Ser Gly Glu Val Ser Val Glu Leu Asn Asp Thr Asp Ser Ser Ala
         195                 200                 205

Ala Thr Lys Lys Thr Ala Ala Trp Asn Ala Gly Thr Ser Thr Leu Thr
     210                 215                 220

Ile Thr Val Asn Asn Lys Lys Thr Lys Ala Leu Val Phe Thr Lys Gln
225                 230                 235                 240

Asp Thr Ile Thr Ser Gln Lys Tyr Asp Ser Ala Gly Thr Asn Leu Glu
                 245                 250                 255

Gly Thr Ala Val Glu Ile Lys Thr Leu Asp Glu Leu Lys Asn Ala Leu
             260                 265                 270

Arg (2) INFORMATION FOR SEQ ID NO:96:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:96:

CCCCAGATTT TGAAATCTTG CTTAAAACAA C                                31

(2) INFORMATION FOR SEQ ID NO:97:

(i) SEQUENCE CHARACTERISTICS:
        (A) LENGTH: 822 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..822

(xi) SEQUENCE DESCRIPTION: SEQ ID NO:97:
```

```
ATG AAA AAA TAT TTA TTG GGA ATA GGT CTA ATA TTA GCC TTA ATA GCA     48
Met Lys Lys Tyr Leu Leu Gly Ile Gly Leu Ile Leu Ala Leu Ile Ala
 1               5                  10                  15

TGT AAG CAA AAT GTT AGC AGC CTT GAT GAA AAA AAT AGC GTT TCA GTA     96
Cys Lys Gln Asn Val Ser Ser Leu Asp Glu Lys Asn Ser Val Ser Val
             20                  25                  30

GAT TTA CCT GGT GGA ATG ACA GTT CTT GTA AGT AAA GAA AAA GAC AAA    144
Asp Leu Pro Gly Gly Met Thr Val Leu Val Ser Lys Glu Lys Asp Lys
         35                  40                  45

GAC GGT AAA TAC AGT CTA GAG GCA ACA GTA GAC AAG CTT GAG CTT AAA    192
Asp Gly Lys Tyr Ser Leu Glu Ala Thr Val Asp Lys Leu Glu Leu Lys
     50                  55                  60

GGA ACT TCT GAT AAA AAC AAC GGT TCT GGA ACA CTT GAA GGT GAA AAA    240
Gly Thr Ser Asp Lys Asn Asn Gly Ser Gly Thr Leu Glu Gly Glu Lys
 65                  70                  75                  80

ACT GAC AAA AGT AAA GTA AAA TTA ACA ATT GCT GAT GAC CTA AGT CAA    288
Thr Asp Lys Ser Lys Val Lys Leu Thr Ile Ala Asp Asp Leu Ser Gln
                 85                  90                  95

ACT AAA TTT GAA ATT TTC AAA GAA GAT GCC AAA ACA TTA GTA TCA AAA    336
Thr Lys Phe Glu Ile Phe Lys Glu Asp Ala Lys Thr Leu Val Ser Lys
             100                 105                 110

AAA GTA ACC CTT AAA GAC AAG TCA TCA ACA GAA GAA AAA TTC AAC GAA    384
Lys Val Thr Leu Lys Asp Lys Ser Ser Thr Glu Glu Lys Phe Asn Glu
         115                 120                 125

AAG GGT GAA ACA TCT GAA AAA ACA ATA GTA AGA GCA AAT GGA ACC AGA    432
Lys Gly Glu Thr Ser Glu Lys Thr Ile Val Arg Ala Asn Gly Thr Arg
     130                 135                 140

CTT GAA TAC ACA GAC ATA AAA AGC GAT GGA TCC GGA AAA GCT AAA GAA    480
Leu Glu Tyr Thr Asp Ile Lys Ser Asp Gly Ser Gly Lys Ala Lys Glu
145                 150                 155                 160

GTT TTA AAA GAC TTT ACT CTT GAA GGA ACT CTA GCT GCT GAC GGC AAA    528
Val Leu Lys Asp Phe Thr Leu Glu Gly Thr Leu Ala Ala Asp Gly Lys
                 165                 170                 175

ACA ACA TTG AAA GTT ACA GAA GGC ACT GTT GTT TTA AGC AAG ATT TCA    576
Thr Thr Leu Lys Val Thr Glu Gly Thr Val Val Leu Ser Lys Ile Ser
             180                 185                 190

AAA TCT GGG GAA GTT TCA GTT GAA CTT AAT GAC ACT GAC AGT AGT GCT    624
Lys Ser Gly Glu Val Ser Val Glu Leu Asn Asp Thr Asp Ser Ser Ala
         195                 200                 205

GCT ACT AAA AAA ACT GCA GCT TGG AAT TCA AAA ACT TCC ACT TTA ACA    672
Ala Thr Lys Lys Thr Ala Ala Trp Asn Ser Lys Thr Ser Thr Leu Thr
     210                 215                 220

ATT AGT GTG AAT AGC CAA AAA ACC AAA AAC CTT GTA TTC ACA AAA GAA    720
Ile Ser Val Asn Ser Gln Lys Thr Lys Asn Leu Val Phe Thr Lys Glu
225                 230                 235                 240

GAC ACA ATA ACA GTA CAA AAA TAC GAC TCA GCA GGC ACC AAT CTA GAA    768
Asp Thr Ile Thr Val Gln Lys Tyr Asp Ser Ala Gly Thr Asn Leu Glu
                 245                 250                 255

GGC AAA GCA GTC GAA ATT ACA ACA CTT AAA GAA CTT AAA AAC GCT TTA    816
Gly Lys Ala Val Glu Ile Thr Thr Leu Lys Glu Leu Lys Asn Ala Leu
             260                 265                 270

AAA TAA                                                            822
Lys (2) INFORMATION FOR SEQ ID NO:98:

(i) SEQUENCE CHARACTERISTICS:
        (A) LENGTH: 273 amino acids
        (B) TYPE: amino acid
        (D) TOPOLOGY: linear
```

(ii) MOLECULE TYPE: protein (xi) SEQUENCE DESCRIPTION: SEQ ID NO:98:

Met Lys Lys Tyr Leu Leu Gly Ile Gly Leu Ile Leu Ala Leu Ile Ala
  1               5                  10                  15

Cys Lys Gln Asn Val Ser Ser Leu Asp Glu Lys Asn Ser Val Ser Val
             20                  25                  30

Asp Leu Pro Gly Gly Met Thr Val Leu Val Ser Lys Glu Lys Asp Lys
         35                  40                  45

Asp Gly Lys Tyr Ser Leu Glu Ala Thr Val Asp Lys Leu Glu Leu Lys
     50                  55                  60

Gly Thr Ser Asp Lys Asn Asn Gly Ser Gly Thr Leu Glu Gly Glu Lys
 65                  70                  75                  80

Thr Asp Lys Ser Lys Val Lys Leu Thr Ile Ala Asp Asp Leu Ser Gln
                 85                  90                  95

Thr Lys Phe Glu Ile Phe Lys Glu Asp Ala Lys Thr Leu Val Ser Lys
            100                 105                 110

Lys Val Thr Leu Lys Asp Lys Ser Ser Thr Glu Lys Phe Asn Glu
        115                 120                 125

Lys Gly Glu Thr Ser Glu Lys Thr Ile Val Arg Ala Asn Gly Thr Arg
    130                 135                 140

Leu Glu Tyr Thr Asp Ile Lys Ser Asp Gly Ser Gly Lys Ala Lys Glu
145                 150                 155                 160

Val Leu Lys Asp Phe Thr Leu Glu Gly Thr Leu Ala Ala Asp Gly Lys
                165                 170                 175

Thr Thr Leu Lys Val Thr Glu Gly Thr Val Val Leu Ser Lys Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Lys Thr Ser Thr Leu Thr
    210                 215                 220

Ile Ser Val Asn Ser Gln Lys Thr Lys Asn Leu Val Phe Thr Lys Glu
225                 230                 235                 240

Asp Thr Ile Thr Val Gln Lys Tyr Asp Ser Ala Gly Thr Asn Leu Glu
                245                 250                 255

Gly Lys Ala Val Glu Ile Thr Thr Leu Lys Glu Leu Lys Asn Ala Leu
            260                 265                 270

Lys (2) INFORMATION FOR SEQ ID NO:99:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:99:

CAAGTCTGGT TCCAATTTGC TCTTGTTATT AT                                    32

(2) INFORMATION FOR SEQ ID NO:100:

(i) SEQUENCE CHARACTERISTICS:
        (A) LENGTH: 822 base pairs
        (B) TYPE: nucleic acid
        (C) STRANDEDNESS: double
        (D) TOPOLOGY: linear (ix) FEATURE:
    (A) NAME/KEY: CDS
    (B) LOCATION: 1..822

(xi) SEQUENCE DESCRIPTION: SEQ ID NO:100:

| | | | | | | | | | | | | | | | | |
|---|---|---|---|---|---|---|---|---|---|---|---|---|---|---|---|---|
| ATG | AAA | AAA | TAT | TTA | TTG | GGA | ATA | GGT | CTA | ATA | TTA | GCC | TTA | ATA | GCA | 48 |
| Met | Lys | Lys | Tyr | Leu | Leu | Gly | Ile | Gly | Leu | Ile | Leu | Ala | Leu | Ile | Ala | |
| 1 | | | | 5 | | | | | 10 | | | | | 15 | | |
| TGT | AAG | CAA | AAT | GTT | AGC | AGC | CTT | GAT | GAA | AAA | AAT | AGC | GTT | TCA | GTA | 96 |
| Cys | Lys | Gln | Asn | Val | Ser | Ser | Leu | Asp | Glu | Lys | Asn | Ser | Val | Ser | Val | |
| | | | 20 | | | | | 25 | | | | | 30 | | | |
| GAT | TTA | CCT | GGT | GGA | ATG | ACA | GTT | CTT | GTA | AGT | AAA | GAA | AAA | GAC | AAA | 144 |
| Asp | Leu | Pro | Gly | Gly | Met | Thr | Val | Leu | Val | Ser | Lys | Glu | Lys | Asp | Lys | |
| | | 35 | | | | | 40 | | | | | 45 | | | | |
| GAC | GGT | AAA | TAC | AGT | CTA | GAG | GCA | ACA | GTA | GAC | AAG | CTT | GAG | CTT | AAA | 192 |
| Asp | Gly | Lys | Tyr | Ser | Leu | Glu | Ala | Thr | Val | Asp | Lys | Leu | Glu | Leu | Lys | |
| | 50 | | | | | 55 | | | | | 60 | | | | | |
| GGA | ACT | TCT | GAT | AAA | AAC | AAC | GGT | TCT | GGA | ACA | CTT | GAA | GGT | GAA | AAA | 240 |
| Gly | Thr | Ser | Asp | Lys | Asn | Asn | Gly | Ser | Gly | Thr | Leu | Glu | Gly | Glu | Lys | |
| 65 | | | | | 70 | | | | | 75 | | | | | 80 | |
| ACT | GAC | AAA | AGT | AAA | GTA | AAA | TTA | ACA | ATT | GCT | GAT | GAC | CTA | AGT | CAA | 288 |
| Thr | Asp | Lys | Ser | Lys | Val | Lys | Leu | Thr | Ile | Ala | Asp | Asp | Leu | Ser | Gln | |
| | | | 85 | | | | | 90 | | | | | 95 | | | |
| ACT | AAA | TTT | GAA | ATT | TTC | AAA | GAA | GAT | GCC | AAA | ACA | TTA | GTA | TCA | AAA | 336 |
| Thr | Lys | Phe | Glu | Ile | Phe | Lys | Glu | Asp | Ala | Lys | Thr | Leu | Val | Ser | Lys | |
| | | | | 100 | | | | | 105 | | | | | 110 | | |
| AAA | GTA | ACC | CTT | AAA | GAC | AAG | TCA | TCA | ACA | GAA | GAA | AAA | TTC | AAC | GAA | 384 |
| Lys | Val | Thr | Leu | Lys | Asp | Lys | Ser | Ser | Thr | Glu | Glu | Lys | Phe | Asn | Glu | |
| | | | 115 | | | | | 120 | | | | | 125 | | | |
| AAG | GGT | GAA | ACA | TCT | GAA | AAA | ACA | ATA | GTA | AGA | GCA | AAT | GGA | ACC | AGA | 432 |
| Lys | Gly | Glu | Thr | Ser | Glu | Lys | Thr | Ile | Val | Arg | Ala | Asn | Gly | Thr | Arg | |
| | 130 | | | | | 135 | | | | | 140 | | | | | |
| CTT | GAA | TAC | ACA | GAC | ATA | AAA | AGC | GAT | GGA | TCC | GGA | AAA | GCT | AAA | GAA | 480 |
| Leu | Glu | Tyr | Thr | Asp | Ile | Lys | Ser | Asp | Gly | Ser | Gly | Lys | Ala | Lys | Glu | |
| 145 | | | | | 150 | | | | | 155 | | | | | 160 | |
| GTT | TTA | AAA | GAC | TTT | ACT | CTT | GAA | GGA | ACT | CTA | GCT | GCT | GAC | GGC | AAA | 528 |
| Val | Leu | Lys | Asp | Phe | Thr | Leu | Glu | Gly | Thr | Leu | Ala | Ala | Asp | Gly | Lys | |
| | | | | 165 | | | | | 170 | | | | | 175 | | |
| ACA | ACA | TTG | AAA | GTT | ACA | GAA | GGC | ACT | GTT | GTT | TTA | AGC | AAG | ATT | TCA | 576 |
| Thr | Thr | Leu | Lys | Val | Thr | Glu | Gly | Thr | Val | Val | Leu | Ser | Lys | Ile | Ser | |
| | | | 180 | | | | | 185 | | | | | 190 | | | |
| AAA | TCT | GGG | GAA | GTT | TCA | GTT | GAA | CTT | AAT | GAC | ACT | GAC | AGT | AGT | GCT | 624 |
| Lys | Ser | Gly | Glu | Val | Ser | Val | Glu | Leu | Asn | Asp | Thr | Asp | Ser | Ser | Ala | |
| | | 195 | | | | | 200 | | | | | 205 | | | | |
| GCT | ACT | AAA | AAA | ACT | GCA | GCT | TGG | AAT | TCA | AAA | ACT | TCC | ACT | TTA | ACA | 672 |
| Ala | Thr | Lys | Lys | Thr | Ala | Ala | Trp | Asn | Ser | Lys | Thr | Ser | Thr | Leu | Thr | |
| | 210 | | | | | 215 | | | | | 220 | | | | | |
| ATT | AGT | GTG | AAT | AGC | CAA | AAA | ACC | AAA | AAC | CTT | GTA | TTC | ACA | AAA | GAA | 720 |
| Ile | Ser | Val | Asn | Ser | Gln | Lys | Thr | Lys | Asn | Leu | Val | Phe | Thr | Lys | Glu | |
| 225 | | | | | 230 | | | | | 235 | | | | | 240 | |
| GAC | ACA | ATA | ACA | GTA | CAA | AAA | TAC | GAC | TCA | GCA | GGC | ACC | AAT | CTA | GAA | 768 |
| Asp | Thr | Ile | Thr | Val | Gln | Lys | Tyr | Asp | Ser | Ala | Gly | Thr | Asn | Leu | Glu | |
| | | | | 245 | | | | | 250 | | | | | 255 | | |
| GGC | AAA | GCA | GTC | GAA | ATT | ACA | ACA | CTT | AAA | GAA | CTT | AAA | AAC | GCT | TTA | 816 |
| Gly | Lys | Ala | Val | Glu | Ile | Thr | Thr | Leu | Lys | Glu | Leu | Lys | Asn | Ala | Leu | |
| | | | 260 | | | | | 265 | | | | | 270 | | | |
| AAA | TAA | | | | | | | | | | | | | | | 822 |
| Lys | | | | | | | | | | | | | | | | |

(2) INFORMATION FOR SEQ ID NO:101:

(i) SEQUENCE CHARACTERISTICS:
       (A) LENGTH: 273 amino acids
       (B) TYPE: amino acid
       (D) TOPOLOGY: linear (ii) MOLECULE TYPE: protein (xi) SEQUENCE DESCRIPTION: SEQ ID NO:101:

```
Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
             20                  25                  30

Asp Leu Pro Gly Gly Met Thr Val Leu Val Ser Lys Glu Lys Asp Lys
         35                  40                  45

Asp Gly Lys Tyr Ser Leu Glu Ala Thr Val Asp Lys Leu Glu Leu Lys
     50                  55                  60

Gly Thr Ser Asp Lys Asn Asn Gly Ser Gly Thr Leu Glu Gly Glu Lys
 65                  70                  75                  80

Thr Asp Lys Ser Lys Val Lys Leu Thr Ile Ala Asp Asp Leu Ser Gln
             85                  90                  95

Thr Lys Phe Glu Ile Phe Lys Glu Asp Ala Lys Thr Leu Val Ser Lys
        100                 105                 110

Lys Val Thr Leu Lys Asp Lys Ser Ser Thr Glu Glu Lys Phe Asn Glu
    115                 120                 125

Lys Gly Glu Thr Ser Glu Lys Thr Ile Val Arg Ala Asn Gly Thr Arg
130                 135                 140

Leu Glu Tyr Thr Asp Ile Lys Ser Asp Gly Ser Gly Lys Ala Lys Glu
145                 150                 155                 160

Val Leu Lys Asp Phe Thr Leu Glu Gly Thr Leu Ala Ala Asp Gly Lys
                165                 170                 175

Thr Thr Leu Lys Val Thr Glu Gly Thr Val Val Leu Ser Lys Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Lys Thr Ser Thr Leu Thr
    210                 215                 220

Ile Ser Val Asn Ser Gln Lys Thr Lys Asn Leu Val Phe Thr Lys Glu
225                 230                 235                 240

Asp Thr Ile Thr Val Gln Lys Tyr Asp Ser Ala Gly Thr Asn Leu Glu
                245                 250                 255

Gly Lys Ala Val Glu Ile Thr Thr Leu Lys Glu Leu Lys Asn Ala Leu
            260                 265                 270

Lys
```

(2) INFORMATION FOR SEQ ID NO:102:

(i) SEQUENCE CHARACTERISTICS:
       (A) LENGTH: 41 base pairs
       (B) TYPE: nucleic acid
       (C) STRANDEDNESS: single
       (D) TOPOLOGY: linear (xi) SEQUENCE DESCRIPTION: SEQ ID NO:102:

GTTAAAGTGC TAGTACTGTC ATTCCAAGCT GCAGTTTTTT T                41

(2) INFORMATION FOR SEQ ID NO:103:

(i) SEQUENCE CHARACTERISTICS:
    (A) LENGTH: 822 base pairs
    (B) TYPE: nucleic acid
    (C) STRANDEDNESS: double
    (D) TOPOLOGY: linear (ix) FEATURE:
    (A) NAME/KEY: CDS
    (B) LOCATION: 1..822

(xi) SEQUENCE DESCRIPTION: SEQ ID NO:103:

```
ATG AAA AAA TAT TTA TTG GGA ATA GGT CTA ATA TTA GCC TTA ATA GCA        48
Met Lys Lys Tyr Leu Leu Gly Ile Gly Leu Ile Leu Ala Leu Ile Ala
 1               5                  10                  15

TGT AAG CAA AAT GTT AGC AGC CTT GAC GAG AAA AAC AGC GTT TCA GTA        96
Cys Lys Gln Asn Val Ser Ser Leu Asp Glu Lys Asn Ser Val Ser Val
             20                  25                  30

GAT TTG CCT GGT GAA ATG AAA GTT CTT GTA AGC AAA GAA AAA AAC AAA       144
Asp Leu Pro Gly Glu Met Lys Val Leu Val Ser Lys Glu Lys Asn Lys
         35                  40                  45

GAC GGC AAG TAC GAT CTA ATT GCA ACA GTA GAC AAG CTT GAG CTT AAA       192
Asp Gly Lys Tyr Asp Leu Ile Ala Thr Val Asp Lys Leu Glu Leu Lys
     50                  55                  60

GGA ACT TCT GAT AAA AAC AAT GGA TCT GGA GTA CTT GAA GGC GTA AAA       240
Gly Thr Ser Asp Lys Asn Asn Gly Ser Gly Val Leu Glu Gly Val Lys
 65                  70                  75                  80

GCT GAC AAA AGT AAA GTA AAA TTA ACA ATT TCT GAC GAT CTA GGT CAA       288
Ala Asp Lys Ser Lys Val Lys Leu Thr Ile Ser Asp Asp Leu Gly Gln
                 85                  90                  95

ACC ACA CTT GAA GTT TTC AAA GAA GAT GGC AAA ACA CTA GTA TCA AAA       336
Thr Thr Leu Glu Val Phe Lys Glu Asp Gly Lys Thr Leu Val Ser Lys
            100                 105                 110

AAA GTA ACT TCC AAA GAC AAG TCA TCA ACA GAA GAA AAA TTC AAT GAA       384
Lys Val Thr Ser Lys Asp Lys Ser Ser Thr Glu Glu Lys Phe Asn Glu
        115                 120                 125

AAA GGT GAA GTA TCT GAA AAA ATA ATA ACA AGA GCA GAC GGA ACC AGA       432
Lys Gly Glu Val Ser Glu Lys Ile Ile Thr Arg Ala Asp Gly Thr Arg
    130                 135                 140

CTT GAA TAC ACA GGA ATT AAA AGC GAT GGA TCT GGA AAA GCT AAA GAG       480
Leu Glu Tyr Thr Gly Ile Lys Ser Asp Gly Ser Gly Lys Ala Lys Glu
145                 150                 155                 160

GTT TTA AAA GGC TAT GTT CTT GAA GGA ACT CTA ACT GCT GAA AAA ACA       528
Val Leu Lys Gly Tyr Val Leu Glu Gly Thr Leu Thr Ala Glu Lys Thr
                165                 170                 175

ACA TTG GTG GTT AAA GAA GGA ACT GTT ACT TTA AGC AAA AAT ATT TCA       576
Thr Leu Val Val Lys Glu Gly Thr Val Thr Leu Ser Lys Asn Ile Ser
            180                 185                 190

AAA TCT GGG GAA GTT TCA GTT GAA CTT AAT GAC ACT GAC AGT AGT GCT       624
Lys Ser Gly Glu Val Ser Val Glu Leu Asn Asp Thr Asp Ser Ser Ala
        195                 200                 205

GCT ACT AAA AAA ACT GCA GCT TGG AAT GAC AGT ACT AGC ACT TTA ACA       672
Ala Thr Lys Lys Thr Ala Ala Trp Asn Asp Ser Thr Ser Thr Leu Thr
    210                 215                 220

ATT AGT GCT GAC AGC AAA AAA ACT AAA GAT TTG GTG TTC TTA ACA GAT       720
Ile Ser Ala Asp Ser Lys Lys Thr Lys Asp Leu Val Phe Leu Thr Asp
225                 230                 235                 240

GGT ACA ATT ACA GTA CAA CAA TAC AAC ACA GCT GGA ACC AGC CTA GAA       768
Gly Thr Ile Thr Val Gln Gln Tyr Asn Thr Ala Gly Thr Ser Leu Glu
                245                 250                 255
```

```
GGA TCA GCA AGT GAA ATT AAA AAT CTT TCA GAG CTT AAA AAC GCT TTA        816
Gly Ser Ala Ser Glu Ile Lys Asn Leu Ser Glu Leu Lys Asn Ala Leu
            260                 265                 270

AAA TAA                                                                822
Lys
```

(2) INFORMATION FOR SEQ ID NO:104:

(i) SEQUENCE CHARACTERISTICS:
        (A) LENGTH: 273 amino acids
        (B) TYPE: amino acid
        (D) TOPOLOGY: linear (ii) MOLECULE TYPE: protein (xi) SEQUENCE DESCRIPTION: SEQ ID NO:104:

```
Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
            35                  40                  45

Asp Gly Lys Tyr Asp Leu Ile Ala Thr Val Asp Lys Leu Glu Leu Lys
 50                  55                  60

Gly Thr Ser Asp Lys Asn Asn Gly Ser Gly Val Leu Glu Gly Val Lys
 65                  70                  75                  80

Ala Asp Lys Ser Lys Val Lys Leu Thr Ile Ser Asp Asp Leu Gly Gln
            85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
            115                 120                 125

Lys Gly Glu Val Ser Glu Lys Ile Ile Thr Arg Ala Asp Gly Thr Arg
130                 135                 140

Leu Glu Tyr Thr Gly Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
                180                 185                 190

Lys Ser Gly Glu Val Ser Val Glu Leu Asn Asp Thr Asp Ser Ser Ala
                195                 200                 205

Ala Thr Lys Lys Thr Ala Ala Trp Asn Asp Ser Thr Ser Thr Leu Thr
210                 215                 220

Ile Ser Ala Asp Ser Lys Lys Thr Lys Asp Leu Val Phe Leu Thr Asp
225                 230                 235                 240

Gly Thr Ile Thr Val Gln Gln Tyr Asn Thr Ala Gly Thr Ser Leu Glu
                245                 250                 255

Gly Ser Ala Ser Glu Ile Lys Asn Leu Ser Glu Leu Lys Asn Ala Leu
                260                 265                 270

Lys
```

(2) INFORMATION FOR SEQ ID NO:105:

(i) SEQUENCE CHARACTERISTICS:
        (A) LENGTH: 39 base pairs
        (B) TYPE: nucleic acid (C) STRANDEDNESS: single
            (D) TOPOLOGY: linear (xi) SEQUENCE DESCRIPTION: SEQ ID NO:105:

TGCAGATGTA ATCCCATCCG CCATTTTTAA AGCGTTTTT                                 39

(2) INFORMATION FOR SEQ ID NO:106:

(i) SEQUENCE CHARACTERISTICS:
            (A) LENGTH: 1401 base pairs
            (B) TYPE: nucleic acid
            (C) STRANDEDNESS: double
            (D) TOPOLOGY: linear (ix) FEATURE:
            (A) NAME/KEY: CDS
            (B) LOCATION: 1..1401

(xi) SEQUENCE DESCRIPTION: SEQ ID NO:106:

```
ATG AAA AAA TAT TTA TTG GGA ATA GGT CTA ATA TTA GCC TTA ATA GCA         48
Met Lys Lys Tyr Leu Leu Gly Ile Gly Leu Ile Leu Ala Leu Ile Ala
  1               5                  10                  15

TGT AAG CAA AAT GTT AGC AGC CTT GAC GAG AAA AAC AGC GTT TCA GTA         96
Cys Lys Gln Asn Val Ser Ser Leu Asp Glu Lys Asn Ser Val Ser Val
             20                  25                  30

GAT TTG CCT GGT GAA ATG AAA GTT CTT GTA AGC AAA GAA AAA AAC AAA        144
Asp Leu Pro Gly Glu Met Lys Val Leu Val Ser Lys Glu Lys Asn Lys
         35                  40                  45

GAC GGC AAG TAC GAT CTA ATT GCA ACA GTA GAC AAG CTT GAG CTT AAA        192
Asp Gly Lys Tyr Asp Leu Ile Ala Thr Val Asp Lys Leu Glu Leu Lys
 50                  55                  60

GGA ACT TCT GAT AAA AAC AAT GGA TCT GGA GTA CTT GAA GGC GTA AAA        240
Gly Thr Ser Asp Lys Asn Asn Gly Ser Gly Val Leu Glu Gly Val Lys
 65                  70                  75                  80

GCT GAC AAA AGT AAA GTA AAA TTA ACA ATT TCT GAC GAT CTA GGT CAA        288
Ala Asp Lys Ser Lys Val Lys Leu Thr Ile Ser Asp Asp Leu Gly Gln
                 85                  90                  95

ACC ACA CTT GAA GTT TTC AAA GAA GAT GGC AAA ACA CTA GTA TCA AAA        336
Thr Thr Leu Glu Val Phe Lys Glu Asp Gly Lys Thr Leu Val Ser Lys
            100                 105                 110

AAA GTA ACT TCC AAA GAC AAG TCA TCA ACA GAA GAA AAA TTC AAT GAA        384
Lys Val Thr Ser Lys Asp Lys Ser Ser Thr Glu Glu Lys Phe Asn Glu
        115                 120                 125

AAA GGT GAA GTA TCT GAA AAA ATA ATA ACA AGA GCA GAC GGA ACC AGA        432
Lys Gly Glu Val Ser Glu Lys Ile Ile Thr Arg Ala Asp Gly Thr Arg
    130                 135                 140

CTT GAA TAC ACA GGA ATT AAA AGC GAT GGA TCT GGA AAA GCT AAA GAG        480
Leu Glu Tyr Thr Gly Ile Lys Ser Asp Gly Ser Gly Lys Ala Lys Glu
145                 150                 155                 160

GTT TTA AAA GGC TAT GTT CTT GAA GGA ACT CTA ACT GCT GAA AAA ACA        528
Val Leu Lys Gly Tyr Val Leu Glu Gly Thr Leu Thr Ala Glu Lys Thr
                165                 170                 175

ACA TTG GTG GTT AAA GAA GGA ACT GTT ACT TTA AGC AAA AAT ATT TCA        576
Thr Leu Val Val Lys Glu Gly Thr Val Thr Leu Ser Lys Asn Ile Ser
            180                 185                 190

AAA TCT GGG GAA GTT TCA GTT GAA CTT AAT GAC ACT GAC AGT AGT GCT        624
Lys Ser Gly Glu Val Ser Val Glu Leu Asn Asp Thr Asp Ser Ser Ala
        195                 200                 205

GCT ACT AAA AAA ACT GCA GCT TGG AAT GAC AGT ACT AGC ACT TTA ACA        672
Ala Thr Lys Lys Thr Ala Ala Trp Asn Asp Ser Thr Ser Thr Leu Thr
    210                 215                 220
```

```
ATT AGT GCT GAC AGC AAA AAA ACT AAA GAT TTG GTG TTC TTA ACA GAT         720
Ile Ser Ala Asp Ser Lys Lys Thr Lys Asp Leu Val Phe Leu Thr Asp
225                 230                 235                 240

GGT ACA ATT ACA GTA CAA CAA TAC AAC ACA GCT GGA ACC AGC CTA GAA         768
Gly Thr Ile Thr Val Gln Gln Tyr Asn Thr Ala Gly Thr Ser Leu Glu
            245                 250                 255

GGA TCA GCA AGT GAA ATT AAA AAT CTT TCA GAG CTT AAA AAC GCT TTA         816
Gly Ser Ala Ser Glu Ile Lys Asn Leu Ser Glu Leu Lys Asn Ala Leu
        260                 265                 270

AAA ATG GCT AAT AAT TCA GGG AAA GAT GGG AAT ACA TCT GCA AAT TCT         864
Lys Met Ala Asn Asn Ser Gly Lys Asp Gly Asn Thr Ser Ala Asn Ser
    275                 280                 285

GCT GAT GAG TCT GTT AAA GGG CCT AAT CTT ACA GAA ATA AGT AAA AAA         912
Ala Asp Glu Ser Val Lys Gly Pro Asn Leu Thr Glu Ile Ser Lys Lys
290                 295                 300

ATT ACG GAT TCT AAT GCG GTT TTA CTT GCT GTG AAA GAG GTT GAA GCG         960
Ile Thr Asp Ser Asn Ala Val Leu Leu Ala Val Lys Glu Val Glu Ala
305                 310                 315                 320

TTG CTG TCA TCT ATA GAT GAA ATT GCT GCT AAA GCT ATT GGT AAA AAA        1008
Leu Leu Ser Ser Ile Asp Glu Ile Ala Ala Lys Ala Ile Gly Lys Lys
            325                 330                 335

ATA CAC CAA AAT AAT GGT TTG GAT ACC GAA TAT AAT CAC AAT GGA TCA        1056
Ile His Gln Asn Asn Gly Leu Asp Thr Glu Tyr Asn His Asn Gly Ser
        340                 345                 350

TTG TTA GCG GGA CGT TAT GCA ATA TCA ACC CTA ATA AAA CAA AAA TTA        1104
Leu Leu Ala Gly Arg Tyr Ala Ile Ser Thr Leu Ile Lys Gln Lys Leu
    355                 360                 365

GAT GGA TTG AAA AAT GAA GGA TTA AAG GAA AAA ATT GAT GCG GCT AAG        1152
Asp Gly Leu Lys Asn Glu Gly Leu Lys Glu Lys Ile Asp Ala Ala Lys
370                 375                 380

AAA TGT TCT GAA ACA TTT ACT AAT AAA TTA AAA GCA AAA CAC ACA GAT        1200
Lys Cys Ser Glu Thr Phe Thr Asn Lys Leu Lys Ala Lys His Thr Asp
385                 390                 395                 400

CTT GGT AAA GAA GGT GTT ACT GAT GCT GAT GCA AAA GAA GCC ATT TTA        1248
Leu Gly Lys Glu Gly Val Thr Asp Ala Asp Ala Lys Glu Ala Ile Leu
            405                 410                 415

AAA ACA AAT GGT ACT AAA ACT AAA GGT GCT GAA GAA CTT GGA AAA TTA        1296
Lys Thr Asn Gly Thr Lys Thr Lys Gly Ala Glu Glu Leu Gly Lys Leu
        420                 425                 430

TTT GAA TCA GTA GAG GTC TTG TCA AAA GCA GCT AAA GAG ATG CTT GCT        1344
Phe Glu Ser Val Glu Val Leu Ser Lys Ala Ala Lys Glu Met Leu Ala
    435                 440                 445

AAT TCA GTT AAA GAG CTT ACA AGC CCT GTT GTG GCA GAA AGT CCA AAA        1392
Asn Ser Val Lys Glu Leu Thr Ser Pro Val Val Ala Glu Ser Pro Lys
450                 455                 460

AAA CCT TAA                                                            1401
Lys Pro
465

(2) INFORMATION FOR SEQ ID NO:107:

(i) SEQUENCE CHARACTERISTICS:
        (A) LENGTH: 466 amino acids
        (B) TYPE: amino acid
        (D) TOPOLOGY: linear (ii) MOLECULE TYPE: protein (xi) SEQUENCE DESCRIPTION: SEQ ID NO:107:

Met Lys Lys Tyr Leu Leu Gly Ile Gly Leu Ile Leu Ala Leu Ile Ala
1               5                   10                  15
```

-continued

```
Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
        35                  40                  45

Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Thr Glu Glu Lys Phe Asn Glu
        115                 120                 125

Lys Gly Glu Val Ser Glu Lys Ile Ile Thr Arg Ala Asp Gly Thr Arg
    130                 135                 140

Leu Glu Tyr Thr Gly Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Asp Ser Thr Ser Thr Leu Thr
    210                 215                 220

Ile Ser Ala Asp Ser Lys Lys Thr Lys Asp Leu Val Phe Leu Thr Asp
225                 230                 235                 240

Gly Thr Ile Thr Val Gln Gln Tyr Asn Thr Ala Gly Thr Ser Leu Glu
                245                 250                 255

Gly Ser Ala Ser Glu Ile Lys Asn Leu Ser Glu Leu Lys Asn Ala Leu
            260                 265                 270

Lys Met Ala Asn Asn Ser Gly Lys Asp Gly Asn Thr Ser Ala Asn Ser
        275                 280                 285

Ala Asp Glu Ser Val Lys Gly Pro Asn Leu Thr Glu Ile Ser Lys Lys
    290                 295                 300

Ile Thr Asp Ser Asn Ala Val Leu Leu Ala Val Lys Glu Val Glu Ala
305                 310                 315                 320

Leu Leu Ser Ser Ile Asp Glu Ile Ala Ala Lys Ala Ile Gly Lys Lys
                325                 330                 335

Ile His Gln Asn Asn Gly Leu Asp Thr Glu Tyr Asn His Asn Gly Ser
            340                 345                 350

Leu Leu Ala Gly Arg Tyr Ala Ile Ser Thr Leu Ile Lys Gln Lys Leu
        355                 360                 365

Asp Gly Leu Lys Asn Glu Gly Leu Lys Glu Lys Ile Asp Ala Ala Lys
    370                 375                 380

Lys Cys Ser Glu Thr Phe Thr Asn Lys Leu Lys Ala Lys His Thr Asp
385                 390                 395                 400

Leu Gly Lys Glu Gly Val Thr Asp Ala Asp Ala Lys Glu Ala Ile Leu
                405                 410                 415

Lys Thr Asn Gly Thr Lys Thr Lys Gly Ala Glu Glu Leu Gly Lys Leu
            420                 425                 430
```

```
Phe Glu Ser Val Glu Val Leu Ser Lys Ala Ala Lys Glu Met Leu Ala
        435                 440                 445

Asn Ser Val Lys Glu Leu Thr Ser Pro Val Val Ala Glu Ser Pro Lys
        450                 455                 460

Lys Pro
465

(2) INFORMATION FOR SEQ ID NO:108:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:108:

GCTGCTAACA TTTTGCTTAG GTTTTTTTGG ACTTTC                                  36

(2) INFORMATION FOR SEQ ID NO:109:

(i) SEQUENCE CHARACTERISTICS:
        (A) LENGTH: 1401 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..1401

(xi) SEQUENCE DESCRIPTION: SEQ ID NO:109:

ATG AAA AAG AAT ACA TTA AGT GCG ATA TTA ATG ACT TTA TTT TTA TTT         48
Met Lys Lys Asn Thr Leu Ser Ala Ile Leu Met Thr Leu Phe Leu Phe
 1               5                  10                  15

ATA TCT TGT AAT AAT TCA GGG AAA GAT GGG AAT ACA TCT GCA AAT TCT         96
Ile Ser Cys Asn Asn Ser Gly Lys Asp Gly Asn Thr Ser Ala Asn Ser
                20                  25                  30

GCT GAT GAG TCT GTT AAA GGG CCT AAT CTT ACA GAA ATA AGT AAA AAA        144
Ala Asp Glu Ser Val Lys Gly Pro Asn Leu Thr Glu Ile Ser Lys Lys
            35                  40                  45

ATT ACG GAT TCT AAT GCG GTT TTA CTT GCT GTG AAA GAG GTT GAA GCG        192
Ile Thr Asp Ser Asn Ala Val Leu Leu Ala Val Lys Glu Val Glu Ala
        50                  55                  60

TTG CTG TCA TCT ATA GAT GAA ATT GCT GCT AAA GCT ATT GGT AAA AAA        240
Leu Leu Ser Ser Ile Asp Glu Ile Ala Ala Lys Ala Ile Gly Lys Lys
65                  70                  75                  80

ATA CAC CAA AAT AAT GGT TTG GAT ACC GAA TAT AAT CAC AAT GGA TCA        288
Ile His Gln Asn Asn Gly Leu Asp Thr Glu Tyr Asn His Asn Gly Ser
                85                  90                  95

TTG TTA GCG GGA CGT TAT GCA ATA TCA ACC CTA ATA AAA CAA AAA TTA        336
Leu Leu Ala Gly Arg Tyr Ala Ile Ser Thr Leu Ile Lys Gln Lys Leu
            100                 105                 110

GAT GGA TTG AAA AAT GAA GGA TTA AAG GAA AAA ATT GAT GCG GCT AAG        384
Asp Gly Leu Lys Asn Glu Gly Leu Lys Glu Lys Ile Asp Ala Ala Lys
        115                 120                 125

AAA TGT TCT GAA ACA TTT ACT AAT AAA TTA AAA GCA AAA CAC ACA GAT        432
Lys Cys Ser Glu Thr Phe Thr Asn Lys Leu Lys Ala Lys His Thr Asp
130                 135                 140

CTT GGT AAA GAA GGT GTT ACT GAT GCT GAT GCA AAA GAA GCC ATT TTA        480
Leu Gly Lys Glu Gly Val Thr Asp Ala Asp Ala Lys Glu Ala Ile Leu
145                 150                 155                 160
```

```
AAA ACA AAT GGT ACT AAA ACT AAA GGT GCT GAA GAA CTT GGA AAA TTA        528
Lys Thr Asn Gly Thr Lys Thr Lys Gly Ala Glu Glu Leu Gly Lys Leu
            165                 170                 175

TTT GAA TCA GTA GAG GTC TTG TCA AAA GCA GCT AAA GAG ATG CTT GCT        576
Phe Glu Ser Val Glu Val Leu Ser Lys Ala Ala Lys Glu Met Leu Ala
            180                 185                 190

AAT TCA GTT AAA GAG CTT ACA AGC CCT GTT GTG GCA GAA AGT CCA AAA        624
Asn Ser Val Lys Glu Leu Thr Ser Pro Val Val Ala Glu Ser Pro Lys
            195                 200                 205

AAA CCT AAG CAA AAT GTT AGC AGC CTT GAC GAG AAA AAC AGC GTT TCA        672
Lys Pro Lys Gln Asn Val Ser Ser Leu Asp Glu Lys Asn Ser Val Ser
210                 215                 220

GTA GAT TTG CCT GGT GAA ATG AAA GTT CTT GTA AGC AAA GAA AAA AAC        720
Val Asp Leu Pro Gly Glu Met Lys Val Leu Val Ser Lys Glu Lys Asn
225                 230                 235                 240

AAA GAC GGC AAG TAC GAT CTA ATT GCA ACA GTA GAC AAG CTT GAG CTT        768
Lys Asp Gly Lys Tyr Asp Leu Ile Ala Thr Val Asp Lys Leu Glu Leu
            245                 250                 255

AAA GGA ACT TCT GAT AAA AAC AAT GGA TCT GGA GTA CTT GAA GGC GTA        816
Lys Gly Thr Ser Asp Lys Asn Asn Gly Ser Gly Val Leu Glu Gly Val
            260                 265                 270

AAA GCT GAC AAA AGT AAA GTA AAA TTA ACA ATT TCT GAC GAT CTA GGT        864
Lys Ala Asp Lys Ser Lys Val Lys Leu Thr Ile Ser Asp Asp Leu Gly
            275                 280                 285

CAA ACC ACA CTT GAA GTT TTC AAA GAA GAT GGC AAA ACA CTA GTA TCA        912
Gln Thr Thr Leu Glu Val Phe Lys Glu Asp Gly Lys Thr Leu Val Ser
            290                 295                 300

AAA AAA GTA ACT TCC AAA GAC AAG TCA TCA ACA GAA GAA AAA TTC AAT        960
Lys Lys Val Thr Ser Lys Asp Lys Ser Ser Thr Glu Glu Lys Phe Asn
305                 310                 315                 320

GAA AAA GGT GAA GTA TCT GAA AAA ATA ATA ACA AGA GCA GAC GGA ACC       1008
Glu Lys Gly Glu Val Ser Glu Lys Ile Ile Thr Arg Ala Asp Gly Thr
            325                 330                 335

AGA CTT GAA TAC ACA GGA ATT AAA AGC GAT GGA TCT GGA AAA GCT AAA       1056
Arg Leu Glu Tyr Thr Gly Ile Lys Ser Asp Gly Ser Gly Lys Ala Lys
            340                 345                 350

GAG GTT TTA AAA GGC TAT GTT CTT GAA GGA ACT CTA ACT GCT GAA AAA       1104
Glu Val Leu Lys Gly Tyr Val Leu Glu Gly Thr Leu Thr Ala Glu Lys
            355                 360                 365

ACA ACA TTG GTG GTT AAA GAA GGA ACT GTT ACT TTA AGC AAA AAT ATT       1152
Thr Thr Leu Val Val Lys Glu Gly Thr Val Thr Leu Ser Lys Asn Ile
            370                 375                 380

TCA AAA TCT GGG GAA GTT TCA GTT GAA CTT AAT GAC ACT GAC AGT AGT       1200
Ser Lys Ser Gly Glu Val Ser Val Glu Leu Asn Asp Thr Asp Ser Ser
385                 390                 395                 400

GCT GCT ACT AAA AAA ACT GCA GCT TGG AAT GAC AGT ACT AGC ACT TTA       1248
Ala Ala Thr Lys Lys Thr Ala Ala Trp Asn Asp Ser Thr Ser Thr Leu
            405                 410                 415

ACA ATT AGT GCT GAC AGC AAA AAA ACT AAA GAT TTG GTG TTC TTA ACA       1296
Thr Ile Ser Ala Asp Ser Lys Lys Thr Lys Asp Leu Val Phe Leu Thr
            420                 425                 430

GAT GGT ACA ATT ACA GTA CAA CAA TAC AAC ACA GCT GGA ACC AGC CTA       1344
Asp Gly Thr Ile Thr Val Gln Gln Tyr Asn Thr Ala Gly Thr Ser Leu
            435                 440                 445

GAA GGA TCA GCA AGT GAA ATT AAA AAT CTT TCA GAG CTT AAA AAC GCT       1392
Glu Gly Ser Ala Ser Glu Ile Lys Asn Leu Ser Glu Leu Lys Asn Ala
            450                 455                 460

TTA AAA TAA                                                           1401
Leu Lys
465
```

(2) INFORMATION FOR SEQ ID NO:110:

(i) SEQUENCE CHARACTERISTICS:
        (A) LENGTH: 466 amino acids
        (B) TYPE: amino acid
        (D) TOPOLOGY: linear (ii) MOLECULE TYPE: protein (xi) SEQUENCE DESCRIPTION: SEQ ID NO:110:

```
Met Lys Lys Asn Thr Leu Ser Ala Ile Leu Met Thr Leu Phe Leu Phe
 1               5                  10                  15

Ile Ser Cys Asn Asn Ser Gly Lys Asp Gly Asn Thr Ser Ala Asn Ser
             20                  25                  30

Ala Asp Glu Ser Val Lys Gly Pro Asn Leu Thr Glu Ile Ser Lys Lys
         35                  40                  45

Ile Thr Asp Ser Asn Ala Val Leu Leu Ala Val Lys Glu Val Glu Ala
     50                  55                  60

Leu Leu Ser Ser Ile Asp Glu Ile Ala Ala Lys Ala Ile Gly Lys Lys
 65                  70                  75                  80

Ile His Gln Asn Asn Gly Leu Asp Thr Glu Tyr Asn His Asn Gly Ser
                 85                  90                  95

Leu Leu Ala Gly Arg Tyr Ala Ile Ser Thr Leu Ile Lys Gln Lys Leu
            100                 105                 110

Asp Gly Leu Lys Asn Glu Gly Leu Lys Glu Lys Ile Asp Ala Ala Lys
        115                 120                 125

Lys Cys Ser Glu Thr Phe Thr Asn Lys Leu Lys Ala Lys His Thr Asp
    130                 135                 140

Leu Gly Lys Glu Gly Val Thr Asp Ala Asp Ala Lys Glu Ala Ile Leu
145                 150                 155                 160

Lys Thr Asn Gly Thr Lys Thr Lys Gly Ala Glu Glu Leu Gly Lys Leu
                165                 170                 175

Phe Glu Ser Val Glu Val Leu Ser Lys Ala Ala Lys Glu Met Leu Ala
            180                 185                 190

Asn Ser Val Lys Glu Leu Thr Ser Pro Val Val Ala Glu Ser Pro Lys
        195                 200                 205

Lys Pro Lys Gln Asn Val Ser Ser Leu Asp Glu Lys Asn Ser Val Ser
    210                 215                 220

Val Asp Leu Pro Gly Glu Met Lys Val Leu Val Ser Lys Glu Lys Asn
225                 230                 235                 240

Lys Asp Gly Lys Tyr Asp Leu Ile Ala Thr Val Asp Lys Leu Glu Leu
                245                 250                 255

Lys Gly Thr Ser Asp Lys Asn Asn Gly Ser Gly Val Leu Glu Gly Val
            260                 265                 270

Lys Ala Asp Lys Ser Lys Val Lys Leu Thr Ile Ser Asp Asp Leu Gly
        275                 280                 285

Gln Thr Thr Leu Glu Val Phe Lys Glu Asp Gly Lys Thr Leu Val Ser
    290                 295                 300

Lys Lys Val Thr Ser Lys Asp Lys Ser Ser Thr Glu Glu Lys Phe Asn
305                 310                 315                 320

Glu Lys Gly Glu Val Ser Glu Lys Ile Ile Thr Arg Ala Asp Gly Thr
                325                 330                 335

Arg Leu Glu Tyr Thr Gly Ile Lys Ser Asp Gly Ser Gly Lys Ala Lys
            340                 345                 350
```

```
Glu Val Leu Lys Gly Tyr Val Leu Glu Gly Thr Leu Thr Ala Glu Lys
        355                 360                 365

Thr Thr Leu Val Val Lys Glu Gly Thr Val Thr Leu Ser Lys Asn Ile
        370                 375                 380

Ser Lys Ser Gly Glu Val Ser Val Glu Leu Asn Asp Thr Asp Ser Ser
385                 390                 395                 400

Ala Ala Thr Lys Lys Thr Ala Ala Trp Asn Asp Ser Thr Ser Thr Leu
                405                 410                 415

Thr Ile Ser Ala Asp Ser Lys Lys Thr Lys Asp Leu Val Phe Leu Thr
                420                 425                 430

Asp Gly Thr Ile Thr Val Gln Gln Tyr Asn Thr Ala Gly Thr Ser Leu
                435                 440                 445

Glu Gly Ser Ala Ser Glu Ile Lys Asn Leu Ser Glu Leu Lys Asn Ala
450                 455                 460

Leu Lys
465

(2) INFORMATION FOR SEQ ID NO:111:

(i) SEQUENCE CHARACTERISTICS:
        (A) LENGTH: 1720 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..1720

(xi) SEQUENCE DESCRIPTION: SEQ ID NO:111:

AAG CAA AAT GTT AGC AGC CTT GAC GAG AAA AAC AGC GTT TCA GTA GAT         48
Lys Gln Asn Val Ser Ser Leu Asp Glu Lys Asn Ser Val Ser Val Asp
 1               5                  10                  15

TTG CCT GGT GAA ATG AAA GTT CTT GTA AGC AAA GAA AAA AAC AAA GAC         96
Leu Pro Gly Glu Met Lys Val Leu Val Ser Lys Glu Lys Asn Lys Asp
                20                  25                  30

GGC AAG TAC GAT CTA ATT GCA ACA GTA GAC AAG CTT GAG CTT AAA GGA        144
Gly Lys Tyr Asp Leu Ile Ala Thr Val Asp Lys Leu Glu Leu Lys Gly
            35                  40                  45

ACT TCT GAT AAA AAC AAT GGA TCT GGA GTA CTT GAA GGC GTA AAA GCT        192
Thr Ser Asp Lys Asn Asn Gly Ser Gly Val Leu Glu Gly Val Lys Ala
        50                  55                  60

GAC AAA AGT AAA GTA AAA TTA ACA ATT TCT GAC GAT CTA GGT CAA ACC        240
Asp Lys Ser Lys Val Lys Leu Thr Ile Ser Asp Asp Leu Gly Gln Thr
 65                 70                  75                  80

ACA CTT GAA GTT TTC AAA GAA GAT GGC AAA ACA CTA GTA TCA AAA AAA        288
Thr Leu Glu Val Phe Lys Glu Asp Gly Lys Thr Leu Val Ser Lys Lys
                85                  90                  95

GTA ACT TCC AAA GAC AAG TCA TCA ACA GAA GAA AAA TTC AAT GAA AAA        336
Val Thr Ser Lys Asp Lys Ser Ser Thr Glu Glu Lys Phe Asn Glu Lys
                100                 105                 110

GGT GAA GTA TCT GAA AAA ATA ATA ACA AGA GCA GAC GGA ACC AGA CTT        384
Gly Glu Val Ser Glu Lys Ile Ile Thr Arg Ala Asp Gly Thr Arg Leu
            115                 120                 125

GAA TAC ACA GGA ATT AAA AGC GAT GGA TCT GGA AAA GCT AAA GAG GTT        432
Glu Tyr Thr Gly Ile Lys Ser Asp Gly Ser Gly Lys Ala Lys Glu Val
        130                 135                 140

TTA AAA GGC TAT GTT CTT GAA GGA ACT CTA ACT GCT GAA AAA ACA ACA        480
Leu Lys Gly Tyr Val Leu Glu Gly Thr Leu Thr Ala Glu Lys Thr Thr
145                 150                 155                 160
```

```
TTG GTG GTT AAA GAA GGA ACT GTT ACT TTA AGC AAA AAT ATT TCA AAA      528
Leu Val Val Lys Glu Gly Thr Val Thr Leu Ser Lys Asn Ile Ser Lys
            165                 170                 175

TCT GGG GAA GTT TCA GTT GAA CTT AAT GAC ACT GAC AGT AGT GCT GCT      576
Ser Gly Glu Val Ser Val Glu Leu Asn Asp Thr Asp Ser Ser Ala Ala
        180                 185                 190

ACT AAA AAA ACT GCA GCT TGG AAT TCA GGC ACT TCA ACT TTA ACA ATT      624
Thr Lys Lys Thr Ala Ala Trp Asn Ser Gly Thr Ser Thr Leu Thr Ile
            195                 200                 205

ACT GTA AAC AGT AAA AAA ACT AAA GAC CTT GTG TTT ACA AAA GAA AAC      672
Thr Val Asn Ser Lys Lys Thr Lys Asp Leu Val Phe Thr Lys Glu Asn
        210                 215                 220

ACA ATT ACA GTA CAA CAA TAC GAC TCA AAT GGC ACC AAA TTA GAG GGG      720
Thr Ile Thr Val Gln Gln Tyr Asp Ser Asn Gly Thr Lys Leu Glu Gly
225                 230                 235                 240

TCA GCA GTT GAA ATT ACA AAA CTT GAT GAA ATT AAA AAC GCT TTA AAA      768
Ser Ala Val Glu Ile Thr Lys Leu Asp Glu Ile Lys Asn Ala Leu Lys
                245                 250                 255

GGT CAC CCC ATG GAT GAA AAG CTT TTA AAA AGT AAA GAT GAT AAA GCA      816
Gly His Pro Met Asp Glu Lys Leu Leu Lys Ser Lys Asp Asp Lys Ala
            260                 265                 270

AGT AAA GAT GGT AAA GCC TTG GAT CTT GAT CGA GAA TTA AAT TCT AAA      864
Ser Lys Asp Gly Lys Ala Leu Asp Leu Asp Arg Glu Leu Asn Ser Lys
        275                 280                 285

GCT TCT AGC AAA GAA AAA AGT AAA GCC AAG GAA GAA GAA ATA ACC AAG      912
Ala Ser Ser Lys Glu Lys Ser Lys Ala Lys Glu Glu Glu Ile Thr Lys
    290                 295                 300

GGT AAG TCA CAG AAA AGC TTA GGC GAT TTG AAT AAT GAT GAA AAT CTT      960
Gly Lys Ser Gln Lys Ser Leu Gly Asp Leu Asn Asn Asp Glu Asn Leu
305                 310                 315                 320

ATG ATG CCA GAA GAT CAA AAA TTA CCT GAG GTT AAA AAA TTA GAT AGC     1008
Met Met Pro Glu Asp Gln Lys Leu Pro Glu Val Lys Lys Leu Asp Ser
                325                 330                 335

AAA AAA GAA TTT AAA CCT GTT TCT GAG GTT GAG AAA TTA GAT AAG ATT     1056
Lys Lys Glu Phe Lys Pro Val Ser Glu Val Glu Lys Leu Asp Lys Ile
            340                 345                 350

TTC AAG TCT AAT AAC AAT GTT GGA GAA TTA TCA CCG TTA GAT AAA TCT     1104
Phe Lys Ser Asn Asn Asn Val Gly Glu Leu Ser Pro Leu Asp Lys Ser
        355                 360                 365

TCT TAT AAA GAC ATT GAT TCA AAA GAG GAG ACA GTT AAT AAA GAT GTT     1152
Ser Tyr Lys Asp Ile Asp Ser Lys Glu Glu Thr Val Asn Lys Asp Val
    370                 375                 380

AAT TTG CAA AAG ACT AAG CCT CAG GTT AAA GAC CAA GTT ACT TCT TTG     1200
Asn Leu Gln Lys Thr Lys Pro Gln Val Lys Asp Gln Val Thr Ser Leu
385                 390                 395                 400

AAT GAA GAT TTG ACT ACT ATG TCT ATA GAT TCC AGT AGT CCT GTA TTT     1248
Asn Glu Asp Leu Thr Thr Met Ser Ile Asp Ser Ser Ser Pro Val Phe
                405                 410                 415

TTA GAG GTT ATT GAT CCA ATT ACA AAT TTA GGA ACT CTT CAA CTT ATT     1296
Leu Glu Val Ile Asp Pro Ile Thr Asn Leu Gly Thr Leu Gln Leu Ile
            420                 425                 430

GAT TTA AAT ACT GGT GTT AGG CTT AAA GAA AGC ACT CAG CAA GGC ATT     1344
Asp Leu Asn Thr Gly Val Arg Leu Lys Glu Ser Thr Gln Gln Gly Ile
        435                 440                 445

CAG CGG TAT GGA ATT TAT GAA CGT GAA AAA GAT TTG GTT GTT ATT AAA     1392
Gln Arg Tyr Gly Ile Tyr Glu Arg Glu Lys Asp Leu Val Val Ile Lys
    450                 455                 460

ATG GAT TCA GGA AAA GCT AAG CTT CAG ATA CTT GAT AAA CTT GAA AAT     1440
Met Asp Ser Gly Lys Ala Lys Leu Gln Ile Leu Asp Lys Leu Glu Asn
465                 470                 475                 480
```

```
TTA AAA GTG GTA TCA GAG TCT AAT TTT GAG ATT AAT AAA AAT TCA TCT        1488
Leu Lys Val Val Ser Glu Ser Asn Phe Glu Ile Asn Lys Asn Ser Ser
                485                 490                 495

CTT TAT GTT GAT TCT AAA ATG ATT TTA GTA GCT GTT AGG GAT AAA GAT        1536
Leu Tyr Val Asp Ser Lys Met Ile Leu Val Ala Val Arg Asp Lys Asp
                500                 505                 510

AGT AGT AAT GAT TGG AGA TTG GCC AAA TTT TCT CCT AAA AAT TTA GAT        1584
Ser Ser Asn Asp Trp Arg Leu Ala Lys Phe Ser Pro Lys Asn Leu Asp
                515                 520                 525

GAG TTT ATT CTT TCA GAG AAT AAA ATT ATG CCT TTT ACT AGC TTT TCT        1632
Glu Phe Ile Leu Ser Glu Asn Lys Ile Met Pro Phe Thr Ser Phe Ser
        530                 535                 540

GTG AGA AAA AAT TTT ATT TAT TTG CAA GAT GAG TTT AAA AGT CTA GTT        1680
Val Arg Lys Asn Phe Ile Tyr Leu Gln Asp Glu Phe Lys Ser Leu Val
545                 550                 555                 560

ATT TTA GAT GTA AAT ACT TTA AAA AAA GTT AAG GGT CAC C                  1720
Ile Leu Asp Val Asn Thr Leu Lys Lys Val Lys Gly His
                565                 570
```

(2) INFORMATION FOR SEQ ID NO:112:

(i) SEQUENCE CHARACTERISTICS:
        (A) LENGTH: 573 amino acids
        (B) TYPE: amino acid
        (D) TOPOLOGY: linear (ii) MOLECULE TYPE: protein (xi) SEQUENCE DESCRIPTION: SEQ ID NO:112:

```
Lys Gln Asn Val Ser Ser Leu Asp Glu Lys Asn Ser Val Ser Val Asp
 1               5                  10                  15

Leu Pro Gly Glu Met Lys Val Leu Val Ser Lys Glu Lys Asn Lys Asp
                20                  25                  30

Gly Lys Tyr Asp Leu Ile Ala Thr Val Asp Lys Leu Glu Leu Lys Gly
            35                  40                  45

Thr Ser Asp Lys Asn Asn Gly Ser Gly Val Leu Glu Gly Val Lys Ala
        50                  55                  60

Asp Lys Ser Lys Val Lys Leu Thr Ile Ser Asp Asp Leu Gly Gln Thr
65                  70                  75                  80

Thr Leu Glu Val Phe Lys Glu Asp Gly Lys Thr Leu Val Ser Lys Lys
                85                  90                  95

Val Thr Ser Lys Asp Lys Ser Ser Thr Glu Glu Lys Phe Asn Glu Lys
                100                 105                 110

Gly Glu Val Ser Glu Lys Ile Ile Thr Arg Ala Asp Gly Thr Arg Leu
            115                 120                 125

Glu Tyr Thr Gly Ile Lys Ser Asp Gly Ser Gly Lys Ala Lys Glu Val
        130                 135                 140

Leu Lys Gly Tyr Val Leu Glu Gly Thr Leu Thr Ala Glu Lys Thr Thr
145                 150                 155                 160

Leu Val Val Lys Glu Gly Thr Val Thr Leu Ser Lys Asn Ile Ser Lys
                165                 170                 175

Ser Gly Glu Val Ser Val Glu Leu Asn Asp Thr Asp Ser Ser Ala Ala
            180                 185                 190

Thr Lys Lys Thr Ala Ala Trp Asn Ser Gly Thr Ser Thr Leu Thr Ile
        195                 200                 205

Thr Val Asn Ser Lys Lys Thr Leu Asp Leu Val Phe Thr Lys Glu Asn
210                 215                 220
```

```
Thr Ile Thr Val Gln Gln Tyr Asp Ser Asn Gly Thr Lys Leu Glu Gly
225                 230                 235                 240

Ser Ala Val Glu Ile Thr Lys Leu Asp Glu Ile Lys Asn Ala Leu Lys
            245                 250                 255

Gly His Pro Met Asp Glu Lys Leu Leu Lys Ser Lys Asp Lys Ala
            260                 265                 270

Ser Lys Asp Gly Lys Ala Leu Asp Leu Asp Arg Glu Leu Asn Ser Lys
        275                 280                 285

Ala Ser Ser Lys Glu Lys Ser Lys Ala Lys Glu Glu Ile Thr Lys
290                 295                 300

Gly Lys Ser Gln Lys Ser Leu Gly Asp Leu Asn Asn Asp Glu Asn Leu
305                 310                 315                 320

Met Met Pro Glu Asp Gln Lys Leu Pro Glu Val Lys Lys Leu Asp Ser
            325                 330                 335

Lys Lys Glu Phe Lys Pro Val Ser Glu Val Lys Leu Asp Lys Ile
            340                 345                 350

Phe Lys Ser Asn Asn Asn Val Gly Glu Leu Ser Pro Leu Asp Lys Ser
            355                 360                 365

Ser Tyr Lys Asp Ile Asp Ser Lys Glu Glu Thr Val Asn Lys Asp Val
        370                 375                 380

Asn Leu Gln Lys Thr Lys Pro Gln Val Lys Asp Gln Val Thr Ser Leu
385                 390                 395                 400

Asn Glu Asp Leu Thr Thr Met Ser Ile Asp Ser Ser Pro Val Phe
            405                 410                 415

Leu Glu Val Ile Asp Pro Ile Thr Asn Leu Gly Thr Leu Gln Leu Ile
            420                 425                 430

Asp Leu Asn Thr Gly Val Arg Leu Lys Glu Ser Thr Gln Gln Gly Ile
            435                 440                 445

Gln Arg Tyr Gly Ile Tyr Glu Arg Glu Lys Asp Leu Val Val Ile Lys
            450                 455                 460

Met Asp Ser Gly Lys Ala Lys Leu Gln Ile Leu Asp Lys Leu Glu Asn
465                 470                 475                 480

Leu Lys Val Val Ser Glu Ser Asn Phe Glu Ile Asn Lys Asn Ser Ser
                485                 490                 495

Leu Tyr Val Asp Ser Lys Met Ile Leu Val Ala Val Arg Asp Lys Asp
                500                 505                 510

Ser Ser Asn Asp Trp Arg Leu Ala Lys Phe Ser Pro Lys Asn Leu Asp
            515                 520                 525

Glu Phe Ile Leu Ser Glu Asn Lys Ile Met Pro Phe Thr Ser Phe Ser
            530                 535                 540

Val Arg Lys Asn Phe Ile Tyr Leu Gln Asp Glu Phe Lys Ser Leu Val
545                 550                 555                 560

Ile Leu Asp Val Asn Thr Leu Lys Lys Val Lys Gly His
                565                 570
```

(2) INFORMATION FOR SEQ ID NO:113:

(i) SEQUENCE CHARACTERISTICS:
        (A) LENGTH: 1180 base pairs
        (B) TYPE: nucleic acid
        (C) STRANDEDNESS: double
        (D) TOPOLOGY: linear (ix) FEATURE:
   (A) NAME/KEY: CDS
   (B) LOCATION: 1..1180

(xi) SEQUENCE DESCRIPTION: SEQ ID NO:113:

```
GCA CAA AAA GGT GCT GAG TCA ATT GGT TCT CAA AAA GAA AAT GAT CTA        48
Ala Gln Lys Gly Ala Glu Ser Ile Gly Ser Gln Lys Glu Asn Asp Leu
 1               5                  10                  15

AAC CTT GAA GAC TCT AGT AAA AAA TCA CAT CAA AAC GCT AAA CAA GAC        96
Asn Leu Glu Asp Ser Ser Lys Lys Ser His Gln Asn Ala Lys Gln Asp
             20                  25                  30

CTT CCT GCG GTG ACA GAA GAC TCA GTG TCT TTG TTT AAT GGT AAT AAA       144
Leu Pro Ala Val Thr Glu Asp Ser Val Ser Leu Phe Asn Gly Asn Lys
         35                  40                  45

ATT TTT GTA AGC AAA GAA AAA AAT AGC TCC GGC AAA TAT GAT TTA AGA       192
Ile Phe Val Ser Lys Glu Lys Asn Ser Ser Gly Lys Tyr Asp Leu Arg
 50                  55                  60

GCA ACA ATT GAT CAG GTT GAA CTT AAA GGA ACT TCC GAT AAA AAC AAT       240
Ala Thr Ile Asp Gln Val Glu Leu Lys Gly Thr Ser Asp Lys Asn Asn
 65                  70                  75                  80

GGT TCT GGA ACC CTT GAA GGT TCA AAG CCT GAC AAG AGT AAA GTA AAA       288
Gly Ser Gly Thr Leu Glu Gly Ser Lys Pro Asp Lys Ser Lys Val Lys
             85                  90                  95

TTA ACA GTT TCT GCT GAT TTA AAC ACA GTA ACC TTA GAA GCA TTT GAT       336
Leu Thr Val Ser Ala Asp Leu Asn Thr Val Thr Leu Glu Ala Phe Asp
            100                 105                 110

GCC AGC AAC CAA AAA ATT TCA AGT AAA GTT ACT AAA AAA CAG GGG TCA       384
Ala Ser Asn Gln Lys Ile Ser Ser Lys Val Thr Lys Lys Gln Gly Ser
        115                 120                 125

ATA ACA GAG GAA ACT CTC AAA GCT AAT AAA TTA GAC TCA AAG AAA TTA       432
Ile Thr Glu Glu Thr Leu Lys Ala Asn Lys Leu Asp Ser Lys Lys Leu
130                 135                 140

ACA AGA TCA AAC GGA ACT ACA CTT GAA TAC TCA CAA ATA ACA GAT GCT       480
Thr Arg Ser Asn Gly Thr Thr Leu Glu Tyr Ser Gln Ile Thr Asp Ala
145                 150                 155                 160

GAC AAT GCT ACA AAA GCA GTA GAA ACT CTA AAA AAT AGC ATT AAG CTT       528
Asp Asn Ala Thr Lys Ala Val Glu Thr Leu Lys Asn Ser Ile Lys Leu
                165                 170                 175

GAA GGA AGT CTT GTA GTC GGA AAA ACA ACA GTG GAA ATT AAA GAA GGT       576
Glu Gly Ser Leu Val Val Gly Lys Thr Thr Val Glu Ile Lys Glu Gly
            180                 185                 190

ACT GTT ACT CTA AAA AGA GAA ATT GAA AAA GAT GGA AAA GTA AAA GTC       624
Thr Val Thr Leu Lys Arg Glu Ile Glu Lys Asp Gly Lys Val Lys Val
        195                 200                 205

TTT TTG AAT GAC ACT GCA GGT TCT AAC AAA AAA ACA GGT AAA TGG GAA       672
Phe Leu Asn Asp Thr Ala Gly Ser Asn Lys Lys Thr Gly Lys Trp Glu
210                 215                 220

GAC AGT ACT AGC ACT TTA ACA ATT AGT GCT GAC AGC AAA AAA ACT AAA       720
Asp Ser Thr Ser Thr Leu Thr Ile Ser Ala Asp Ser Lys Lys Thr Lys
225                 230                 235                 240

GAT TTG GTG TTC TTA ACA GAT GGT ACA ATT ACA GTA CAA CAA TAC AAC       768
Asp Leu Val Phe Leu Thr Asp Gly Thr Ile Thr Val Gln Gln Tyr Asn
                245                 250                 255

ACA GCT GGA ACC AGC CTA GAA GGA TCA GCA AGT GAA ATT AAA AAT CTT       816
Thr Ala Gly Thr Ser Leu Glu Gly Ser Ala Ser Glu Ile Lys Asn Leu
            260                 265                 270

TCA GAG CTT AAA AAC GCT TTA AAA GGT CAC CCC ATG GCT CAA TAT AAC       864
Ser Glu Leu Lys Asn Ala Leu Lys Gly His Pro Met Ala Gln Tyr Asn
        275                 280                 285
```

```
CAA ATG CAC ATG TTA TCA AAC AAA TCT GCT TCT CAA AAT GTA AGA ACA      912
Gln Met His Met Leu Ser Asn Lys Ser Ala Ser Gln Asn Val Arg Thr
    290                 295                 300

GCT GAA GAG CTT GGA ATG CAG CCT GCA AAA ATT AAC ACA CCA GCA TCA      960
Ala Glu Glu Leu Gly Met Gln Pro Ala Lys Ile Asn Thr Pro Ala Ser
305                 310                 315                 320

CTT TCA GGG CTT CAA GCG TCT TGG ACT TTA AGA GTT CAT GTT GGA GCA     1008
Leu Ser Gly Leu Gln Ala Ser Trp Thr Leu Arg Val His Val Gly Ala
                325                 330                 335

ACC CAA GAT GAA GCT ATT GCT GTA AAT ATT TAT GCA GCT AAT GTT GCA     1056
Thr Gln Asp Glu Ala Ile Ala Val Asn Ile Tyr Ala Ala Asn Val Ala
            340                 345                 350

AAT CTT TTC TCT GGT GAG GGA GCT CAA ACT GCT CAG GCT GCA CCG GTT     1104
Asn Leu Phe Ser Gly Glu Gly Ala Gln Thr Ala Gln Ala Ala Pro Val
        355                 360                 365

CAA GAG GGT GTT CAA CAG GAA GGA GCT CAA CAG CCA GCA CCT GCT ACA     1152
Gln Glu Gly Val Gln Gln Glu Gly Ala Gln Gln Pro Ala Pro Ala Thr
    370                 375                 380

GCA CCT TCT CAA GGC GGA GTT GGT CAC C                                1180
Ala Pro Ser Gln Gly Gly Val Gly His
385                 390

(2) INFORMATION FOR SEQ ID NO:114:

(i) SEQUENCE CHARACTERISTICS:
        (A) LENGTH: 393 amino acids
        (B) TYPE: amino acid
        (D) TOPOLOGY: linear (ii) MOLECULE TYPE: protein (xi) SEQUENCE DESCRIPTION: SEQ ID NO:114:

Ala Gln Lys Gly Ala Glu Ser Ile Gly Ser Gln Lys Glu Asn Asp Leu
1               5                   10                  15

Asn Leu Glu Asp Ser Ser Lys Lys Ser His Gln Asn Ala Lys Gln Asp
            20                  25                  30

Leu Pro Ala Val Thr Glu Asp Ser Val Ser Leu Phe Asn Gly Asn Lys
        35                  40                  45

Ile Phe Val Ser Lys Glu Lys Asn Ser Ser Gly Lys Tyr Asp Leu Arg
    50                  55                  60

Ala Thr Ile Asp Gln Val Glu Leu Lys Gly Thr Ser Asp Lys Asn Asn
65                  70                  75                  80

Gly Ser Gly Thr Leu Glu Gly Ser Lys Pro Asp Lys Ser Lys Val Lys
                85                  90                  95

Leu Thr Val Ser Ala Asp Leu Asn Thr Val Thr Leu Glu Ala Phe Asp
            100                 105                 110

Ala Ser Asn Gln Lys Ile Ser Ser Lys Val Thr Lys Gln Gly Ser
        115                 120                 125

Ile Thr Glu Glu Thr Leu Lys Ala Asn Lys Leu Asp Ser Lys Lys Leu
    130                 135                 140

Thr Arg Ser Asn Gly Thr Thr Leu Glu Tyr Ser Gln Ile Thr Asp Ala
145                 150                 155                 160

Asp Asn Ala Thr Lys Ala Val Glu Thr Leu Lys Asn Ser Ile Lys Leu
                165                 170                 175

Glu Gly Ser Leu Val Val Gly Lys Thr Thr Val Glu Ile Lys Glu Gly
            180                 185                 190

Thr Val Thr Leu Lys Arg Glu Ile Glu Lys Asp Gly Lys Val Lys Val
        195                 200                 205
```

```
Phe Leu Asn Asp Thr Ala Gly Ser Asn Lys Lys Thr Gly Lys Trp Glu
    210                 215                 220

Asp Ser Thr Ser Thr Leu Thr Ile Ser Ala Asp Ser Lys Lys Thr Lys
225                 230                 235                 240

Asp Leu Val Phe Leu Thr Asp Gly Thr Ile Thr Val Gln Gln Tyr Asn
                245                 250                 255

Thr Ala Gly Thr Ser Leu Glu Gly Ser Ala Ser Glu Ile Lys Asn Leu
            260                 265                 270

Ser Glu Leu Lys Asn Ala Leu Lys Gly His Pro Met Ala Gln Tyr Asn
        275                 280                 285

Gln Met His Met Leu Ser Asn Lys Ser Ala Ser Gln Asn Val Arg Thr
    290                 295                 300

Ala Glu Glu Leu Gly Met Gln Pro Ala Lys Ile Asn Thr Pro Ala Ser
305                 310                 315                 320

Leu Ser Gly Leu Gln Ala Ser Trp Thr Leu Arg Val His Val Gly Ala
                325                 330                 335

Thr Gln Asp Glu Ala Ile Ala Val Asn Ile Tyr Ala Ala Asn Val Ala
            340                 345                 350

Asn Leu Phe Ser Gly Glu Gly Ala Gln Thr Ala Gln Ala Ala Pro Val
        355                 360                 365

Gln Glu Gly Val Gln Gln Glu Gly Ala Gln Gln Pro Ala Pro Ala Thr
    370                 375                 380

Ala Pro Ser Gln Gly Gly Val Gly His
385                 390

(2) INFORMATION FOR SEQ ID NO:115:

(i) SEQUENCE CHARACTERISTICS:
        (A) LENGTH: 1363 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..1363

(xi) SEQUENCE DESCRIPTION: SEQ ID NO:115:

GCA CAA AAA GGT GCT GAG TCA ATT GGT TCT CAA AAA GAA AAT GAT CTA         48
Ala Gln Lys Gly Ala Glu Ser Ile Gly Ser Gln Lys Glu Asn Asp Leu
1               5                   10                  15

AAC CTT GAA GAC TCT AGT AAA AAA TCA CAT CAA AAC GCT AAA CAA GAC         96
Asn Leu Glu Asp Ser Ser Lys Lys Ser His Gln Asn Ala Lys Gln Asp
            20                  25                  30

CTT CCT GCG GTG ACA GAA GAC TCA GTG TCT TTG TTT AAT GGT AAT AAA        144
Leu Pro Ala Val Thr Glu Asp Ser Val Ser Leu Phe Asn Gly Asn Lys
        35                  40                  45

ATT TTT GTA AGC AAA GAA AAA AAT AGC TCC GGC AAA TAT GAT TTA AGA        192
Ile Phe Val Ser Lys Glu Lys Asn Ser Ser Gly Lys Tyr Asp Leu Arg
    50                  55                  60

GCA ACA ATT GAT CAG GTT GAA CTT AAA GGA ACT TCC GAT AAA AAC AAT        240
Ala Thr Ile Asp Gln Val Glu Leu Lys Gly Thr Ser Asp Lys Asn Asn
65                  70                  75                  80

GGT TCT GGA ACC CTT GAA GGT TCA AAG CCT GAC AAG AGT AAA GTA AAA        288
Gly Ser Gly Thr Leu Glu Gly Ser Lys Pro Asp Lys Ser Lys Val Lys
                85                  90                  95

TTA ACA GTT TCT GCT GAT TTA AAC ACA GTA ACC TTA GAA GCA TTT GAT        336
Leu Thr Val Ser Ala Asp Leu Asn Thr Val Thr Leu Glu Ala Phe Asp
            100                 105                 110
```

```
GCC AGC AAC CAA AAA ATT TCA AGT AAA GTT ACT AAA AAA CAG GGG TCA        384
Ala Ser Asn Gln Lys Ile Ser Ser Lys Val Thr Lys Lys Gln Gly Ser
        115                 120                 125

ATA ACA GAG GAA ACT CTC AAA GCT AAT AAA TTA GAC TCA AAG AAA TTA        432
Ile Thr Glu Glu Thr Leu Lys Ala Asn Lys Leu Asp Ser Lys Lys Leu
    130                 135                 140

ACA AGA TCA AAC GGA ACT ACA CTT GAA TAC TCA CAA ATA ACA GAT GCT        480
Thr Arg Ser Asn Gly Thr Thr Leu Glu Tyr Ser Gln Ile Thr Asp Ala
145                 150                 155                 160

GAC AAT GCT ACA AAA GCA GTA GAA ACT CTA AAA AAT AGC ATT AAG CTT        528
Asp Asn Ala Thr Lys Ala Val Glu Thr Leu Lys Asn Ser Ile Lys Leu
            165                 170                 175

GAA GGA AGT CTT GTA GTC GGA AAA ACA ACA GTG GAA ATT AAA GAA GGT        576
Glu Gly Ser Leu Val Val Gly Lys Thr Thr Val Glu Ile Lys Glu Gly
        180                 185                 190

ACT GTT ACT CTA AAA AGA GAA ATT GAA AAA GAT GGA AAA GTA AAA GTC        624
Thr Val Thr Leu Lys Arg Glu Ile Glu Lys Asp Gly Lys Val Lys Val
    195                 200                 205

TTT TTG AAT GAC ACT GCA GGT TCT AAC AAA AAA ACA GGT AAA TGG GAA        672
Phe Leu Asn Asp Thr Ala Gly Ser Asn Lys Lys Thr Gly Lys Trp Glu
210                 215                 220

GAC AGT ACT AGC ACT TTA ACA ATT AGT GCT GAC AGC AAA AAA ACT AAA        720
Asp Ser Thr Ser Thr Leu Thr Ile Ser Ala Asp Ser Lys Lys Thr Lys
225                 230                 235                 240

GAT TTG GTG TTC TTA ACA GAT GGT ACA ATT ACA GTA CAA CAA TAC AAC        768
Asp Leu Val Phe Leu Thr Asp Gly Thr Ile Thr Val Gln Gln Tyr Asn
            245                 250                 255

ACA GCT GGA ACC AGC CTA GAA GGA TCA GCA AGT GAA ATT AAA AAT CTT        816
Thr Ala Gly Thr Ser Leu Glu Gly Ser Ala Ser Glu Ile Lys Asn Leu
        260                 265                 270

TCA GAG CTT AAA AAC GCT TTA AAA GGT CAC CCC ATG GCT CAA TAT AAC        864
Ser Glu Leu Lys Asn Ala Leu Lys Gly His Pro Met Ala Gln Tyr Asn
    275                 280                 285

CAA ATG CAC ATG TTA TCA AAC AAA TCT GCT TCT CAA AAT GTA AGA ACA        912
Gln Met His Met Leu Ser Asn Lys Ser Ala Ser Gln Asn Val Arg Thr
290                 295                 300

GCT GAA GAG CTT GGA ATG CAG CCT GCA AAA ATT AAC ACA CCA GCA TCA        960
Ala Glu Glu Leu Gly Met Gln Pro Ala Lys Ile Asn Thr Pro Ala Ser
305                 310                 315                 320

CTT TCA GGG CTT CAA GCG TCT TGG ACT TTA AGA GTT CAT GTT GGA GCA       1008
Leu Ser Gly Leu Gln Ala Ser Trp Thr Leu Arg Val His Val Gly Ala
            325                 330                 335

ACC CAA GAT GAA GCT ATT GCT GTA AAT ATT TAT GCA GCT AAT GTT GCA       1056
Thr Gln Asp Glu Ala Ile Ala Val Asn Ile Tyr Ala Ala Asn Val Ala
        340                 345                 350

AAT CTT TTC TCT GGT GAG GGA GCT CAA ACT GCT CAG GCT GCA CCG GTT       1104
Asn Leu Phe Ser Gly Glu Gly Ala Gln Thr Ala Gln Ala Ala Pro Val
    355                 360                 365

CAA GAG GGT GTT CAA CAG GAA GGA GCT CAA CAG CCA GCA CCT GCT ACA       1152
Gln Glu Gly Val Gln Gln Glu Gly Ala Gln Gln Pro Ala Pro Ala Thr
370                 375                 380

GCA CCT TCT CAA GGC GGA GTT AAT TCT CCT GTT AAT GTT ACA ACT ACA       1200
Ala Pro Ser Gln Gly Gly Val Asn Ser Pro Val Asn Val Thr Thr Thr
385                 390                 395                 400

GTT GAT GCT AAT ACA TCA CTT GCT AAA ATT GAA AAT GCT ATT AGA ATG       1248
Val Asp Ala Asn Thr Ser Leu Ala Lys Ile Glu Asn Ala Ile Arg Met
            405                 410                 415

ATA AGT GAT CAA AGG GCA AAT TTA GGT GCT TTC CAA AAT AGA CTT GAA       1296
Ile Ser Asp Gln Arg Ala Asn Leu Gly Ala Phe Gln Asn Arg Leu Glu
        420                 425                 430
```

```
TCT ATA AAG AAT AGT ACT GAG TAT GCA ATT GAA AAT CTA AAA GCA TCT         1344
Ser Ile Lys Asn Ser Thr Glu Tyr Ala Ile Glu Asn Leu Lys Ala Ser
    435                 440                 445

TAT GCT CAA ATA GGT CAC C                                                1363
Tyr Ala Gln Ile Gly His
    450
```

(2) INFORMATION FOR SEQ ID NO:116:

(i) SEQUENCE CHARACTERISTICS:
        (A) LENGTH: 454 amino acids
        (B) TYPE: amino acid
        (D) TOPOLOGY: linear (ii) MOLECULE TYPE: protein (xi) SEQUENCE DESCRIPTION: SEQ ID NO:116:

```
Ala Gln Lys Gly Ala Glu Ser Ile Gly Ser Gln Lys Glu Asn Asp Leu
  1               5                  10                  15

Asn Leu Glu Asp Ser Ser Lys Lys Ser His Gln Asn Ala Lys Gln Asp
             20                  25                  30

Leu Pro Ala Val Thr Glu Asp Ser Val Ser Leu Phe Asn Gly Asn Lys
         35                  40                  45

Ile Phe Val Ser Lys Glu Lys Asn Ser Ser Gly Lys Tyr Asp Leu Arg
     50                  55                  60

Ala Thr Ile Asp Gln Val Glu Leu Lys Gly Thr Ser Asp Lys Asn Asn
 65                  70                  75                  80

Gly Ser Gly Thr Leu Glu Gly Ser Lys Pro Asp Lys Ser Lys Val Lys
                 85                  90                  95

Leu Thr Val Ser Ala Asp Leu Asn Thr Val Thr Leu Glu Ala Phe Asp
            100                 105                 110

Ala Ser Asn Gln Lys Ile Ser Ser Lys Val Thr Lys Gln Gly Ser
            115                 120                 125

Ile Thr Glu Glu Thr Leu Lys Ala Asn Lys Leu Asp Ser Lys Lys Leu
        130                 135                 140

Thr Arg Ser Asn Gly Thr Thr Leu Glu Tyr Ser Gln Ile Thr Asp Ala
145                 150                 155                 160

Asp Asn Ala Thr Lys Ala Val Glu Thr Leu Lys Asn Ser Ile Lys Leu
                165                 170                 175

Glu Gly Ser Leu Val Val Gly Lys Thr Thr Val Glu Ile Lys Glu Gly
            180                 185                 190

Thr Val Thr Leu Lys Arg Glu Ile Glu Lys Asp Gly Lys Val Lys Val
        195                 200                 205

Phe Leu Asn Asp Thr Ala Gly Ser Asn Lys Lys Thr Gly Lys Trp Glu
    210                 215                 220

Asp Ser Thr Ser Thr Leu Thr Ile Ser Ala Asp Ser Lys Lys Thr Lys
225                 230                 235                 240

Asp Leu Val Phe Leu Thr Asp Gly Thr Ile Thr Val Gln Gln Tyr Asn
                245                 250                 255

Thr Ala Gly Thr Ser Leu Glu Gly Ser Ala Ser Glu Ile Lys Asn Leu
            260                 265                 270

Ser Glu Leu Lys Asn Ala Leu Lys Gly His Pro Met Ala Gln Tyr Asn
        275                 280                 285

Gln Met His Met Leu Ser Asn Lys Ser Ala Ser Gln Asn Val Arg Thr
    290                 295                 300
```

-continued

```
Ala Glu Glu Leu Gly Met Gln Pro Ala Lys Ile Asn Thr Pro Ala Ser
305                 310                 315                 320

Leu Ser Gly Leu Gln Ala Ser Trp Thr Leu Arg Val His Val Gly Ala
            325                 330                 335

Thr Gln Asp Glu Ala Ile Ala Val Asn Ile Tyr Ala Ala Asn Val Ala
            340                 345                 350

Asn Leu Phe Ser Gly Glu Gly Ala Gln Thr Ala Gln Ala Ala Pro Val
            355                 360                 365

Gln Glu Gly Val Gln Gln Glu Gly Ala Gln Pro Ala Pro Ala Thr
370                 375                 380

Ala Pro Ser Gln Gly Gly Val Asn Ser Pro Val Asn Val Thr Thr Thr
385                 390                 395                 400

Val Asp Ala Asn Thr Ser Leu Ala Lys Ile Glu Asn Ala Ile Arg Met
                405                 410                 415

Ile Ser Asp Gln Arg Ala Asn Leu Gly Ala Phe Gln Asn Arg Leu Glu
            420                 425                 430

Ser Ile Lys Asn Ser Thr Glu Tyr Ala Ile Glu Asn Leu Lys Ala Ser
            435                 440                 445

Tyr Ala Gln Ile Gly His
    450
```

(2) INFORMATION FOR SEQ ID NO:117:

(i) SEQUENCE CHARACTERISTICS:
        (A) LENGTH: 1141 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..1141

(xi) SEQUENCE DESCRIPTION: SEQ ID NO:117:

```
GCA CAA AAA GGT GCT GAG TCA ATT GGT TCT CAA AAA GAA AAT GAT CTA      48
Ala Gln Lys Gly Ala Glu Ser Ile Gly Ser Gln Lys Glu Asn Asp Leu
 1               5                  10                  15

AAC CTT GAA GAC TCT AGT AAA AAA TCA CAT CAA AAC GCT AAA CAA GAC      96
Asn Leu Glu Asp Ser Ser Lys Lys Ser His Gln Asn Ala Lys Gln Asp
                20                  25                  30

CTT CCT GCG GTG ACA GAA GAC TCA GTG TCT TTG TTT AAT GGT AAT AAA     144
Leu Pro Ala Val Thr Glu Asp Ser Val Ser Leu Phe Asn Gly Asn Lys
             35                  40                  45

ATT TTT GTA AGC AAA GAA AAA AAT AGC TCC GGC AAA TAT GAT TTA AGA     192
Ile Phe Val Ser Lys Glu Lys Asn Ser Ser Gly Lys Tyr Asp Leu Arg
 50                  55                  60

GCA ACA ATT GAT CAG GTT GAA CTT AAA GGA ACT TCC GAT AAA AAC AAT     240
Ala Thr Ile Asp Gln Val Glu Leu Lys Gly Thr Ser Asp Lys Asn Asn
 65                  70                  75                  80

GGT TCT GGA ACC CTT GAA GGT TCA AAG CCT GAC AAG AGT AAA GTA AAA     288
Gly Ser Gly Thr Leu Glu Gly Ser Lys Pro Asp Lys Ser Lys Val Lys
                 85                  90                  95

TTA ACA GTT TCT GCT GAT TTA AAC ACA GTA ACC TTA GAA GCA TTT GAT     336
Leu Thr Val Ser Ala Asp Leu Asn Thr Val Thr Leu Glu Ala Phe Asp
            100                 105                 110

GCC AGC AAC CAA AAA ATT TCA AGT AAA GTT ACT AAA AAA CAG GGG TCA     384
Ala Ser Asn Gln Lys Ile Ser Ser Lys Val Thr Lys Lys Gln Gly Ser
        115                 120                 125
```

| | | |
|---|---|---|
| ATA ACA GAG GAA ACT CTC AAA GCT AAT AAA TTA GAC TCA AAG AAA TTA<br>Ile Thr Glu Glu Thr Leu Lys Ala Asn Lys Leu Asp Ser Lys Lys Leu<br>130                       135                       140 | | 432 |

```
ATA ACA GAG GAA ACT CTC AAA GCT AAT AAA TTA GAC TCA AAG AAA TTA      432
Ile Thr Glu Glu Thr Leu Lys Ala Asn Lys Leu Asp Ser Lys Lys Leu
            130                 135                 140

ACA AGA TCA AAC GGA ACT ACA CTT GAA TAC TCA CAA ATA ACA GAT GCT      480
Thr Arg Ser Asn Gly Thr Thr Leu Glu Tyr Ser Gln Ile Thr Asp Ala
145                 150                 155                 160

GAC AAT GCT ACA AAA GCA GTA GAA ACT CTA AAA AAT AGC ATT AAG CTT      528
Asp Asn Ala Thr Lys Ala Val Glu Thr Leu Lys Asn Ser Ile Lys Leu
                165                 170                 175

GAA GGA AGT CTT GTA GTC GGA AAA ACA ACA GTG GAA ATT AAA GAA GGT      576
Glu Gly Ser Leu Val Val Gly Lys Thr Thr Val Glu Ile Lys Glu Gly
            180                 185                 190

ACT GTT ACT CTA AAA AGA GAA ATT GAA AAA GAT GGA AAA GTA AAA GTC      624
Thr Val Thr Leu Lys Arg Glu Ile Glu Lys Asp Gly Lys Val Lys Val
        195                 200                 205

TTT TTG AAT GAC ACT GCA GGT TCT AAC AAA AAA ACA GGT AAA TGG GAA      672
Phe Leu Asn Asp Thr Ala Gly Ser Asn Lys Lys Thr Gly Lys Trp Glu
210                 215                 220

GAC AGT ACT AGC ACT TTA ACA ATT AGT GCT GAC AGC AAA AAA ACT AAA      720
Asp Ser Thr Ser Thr Leu Thr Ile Ser Ala Asp Ser Lys Lys Thr Lys
225                 230                 235                 240

GAT TTG GTG TTC TTA ACA GAT GGT ACA ATT ACA GTA CAA CAA TAC AAC      768
Asp Leu Val Phe Leu Thr Asp Gly Thr Ile Thr Val Gln Gln Tyr Asn
                245                 250                 255

ACA GCT GGA ACC AGC CTA GAA GGA TCA GCA AGT GAA ATT AAA AAT CTT      816
Thr Ala Gly Thr Ser Leu Glu Gly Ser Ala Ser Glu Ile Lys Asn Leu
            260                 265                 270

TCA GAG CTT AAA AAC GCT TTA AAA GGT CAC CCC ATG GCT TCT CAA AAT      864
Ser Glu Leu Lys Asn Ala Leu Lys Gly His Pro Met Ala Ser Gln Asn
        275                 280                 285

GTA AGA ACA GCT GAA GAG CTT GGA ATG CAG CCT GCA AAA ATT AAC ACA      912
Val Arg Thr Ala Glu Glu Leu Gly Met Gln Pro Ala Lys Ile Asn Thr
290                 295                 300

CCA GCA TCA CTT TCA GGG CTT CAA GCG TCT TGG ACT TTA AGA GTT CAT      960
Pro Ala Ser Leu Ser Gly Leu Gln Ala Ser Trp Thr Leu Arg Val His
305                 310                 315                 320

GTT GGA GCA ACC CAA GAT GAA GCT ATT GCT GTA AAT ATT TAT GCA GCT     1008
Val Gly Ala Thr Gln Asp Glu Ala Ile Ala Val Asn Ile Tyr Ala Ala
                325                 330                 335

AAT GTT GCA AAT CTT TTC TCT GGT GAG GGA GCT CAA ACT GCT CAG GCT     1056
Asn Val Ala Asn Leu Phe Ser Gly Glu Gly Ala Gln Thr Ala Gln Ala
            340                 345                 350

GCA CCG GTT CAA GAG GGT GTT CAA CAG GAA GGA GCT CAA CAG CCA GCA     1104
Ala Pro Val Gln Glu Gly Val Gln Gln Glu Gly Ala Gln Gln Pro Ala
        355                 360                 365

CCT GCT ACA GCA CCT TCT CAA GGC GGA GTT GGT CAC C                   1141
Pro Ala Thr Ala Pro Ser Gln Gly Gly Val Gly His
370                 375                 380
```

(2) INFORMATION FOR SEQ ID NO:118:

(i) SEQUENCE CHARACTERISTICS:
        (A) LENGTH: 380 amino acids
        (B) TYPE: amino acid
        (D) TOPOLOGY: linear (ii) MOLECULE TYPE: protein (xi) SEQUENCE DESCRIPTION: SEQ ID NO:118:

```
Ala Gln Lys Gly Ala Glu Ser Ile Gly Ser Gln Lys Glu Asn Asp Leu
 1               5                  10                  15
```

-continued

```
Asn Leu Glu Asp Ser Ser Lys Lys Ser His Gln Asn Ala Lys Gln Asp
             20                  25                  30

Leu Pro Ala Val Thr Glu Asp Ser Val Ser Leu Phe Asn Gly Asn Lys
         35                  40                  45

Ile Phe Val Ser Lys Glu Lys Asn Ser Ser Gly Lys Tyr Asp Leu Arg
     50                  55                  60

Ala Thr Ile Asp Gln Val Glu Leu Lys Gly Thr Ser Asp Lys Asn Asn
 65                  70                  75                  80

Gly Ser Gly Thr Leu Glu Gly Ser Lys Pro Asp Lys Ser Lys Val Lys
             85                  90                  95

Leu Thr Val Ser Ala Asp Leu Asn Thr Val Thr Leu Glu Ala Phe Asp
            100                 105                 110

Ala Ser Asn Gln Lys Ile Ser Ser Lys Val Thr Lys Lys Gln Gly Ser
            115                 120                 125

Ile Thr Glu Glu Thr Leu Lys Ala Asn Lys Leu Asp Ser Lys Lys Leu
        130                 135                 140

Thr Arg Ser Asn Gly Thr Thr Leu Glu Tyr Ser Gln Ile Thr Asp Ala
145                 150                 155                 160

Asp Asn Ala Thr Lys Ala Val Glu Thr Leu Lys Asn Ser Ile Lys Leu
                165                 170                 175

Glu Gly Ser Leu Val Val Gly Lys Thr Thr Val Glu Ile Lys Glu Gly
            180                 185                 190

Thr Val Thr Leu Lys Arg Glu Ile Glu Lys Asp Gly Lys Val Lys Val
        195                 200                 205

Phe Leu Asn Asp Thr Ala Gly Ser Asn Lys Lys Thr Gly Lys Trp Glu
    210                 215                 220

Asp Ser Thr Ser Thr Leu Thr Ile Ser Ala Asp Ser Lys Lys Thr Lys
225                 230                 235                 240

Asp Leu Val Phe Leu Thr Asp Gly Thr Ile Thr Val Gln Gln Tyr Asn
                245                 250                 255

Thr Ala Gly Thr Ser Leu Glu Gly Ser Ala Ser Glu Ile Lys Asn Leu
            260                 265                 270

Ser Glu Leu Lys Asn Ala Leu Lys Gly His Pro Met Ala Ser Gln Asn
        275                 280                 285

Val Arg Thr Ala Glu Glu Leu Gly Met Gln Pro Ala Lys Ile Asn Thr
290                 295                 300

Pro Ala Ser Leu Ser Gly Leu Gln Ala Ser Trp Thr Leu Arg Val His
305                 310                 315                 320

Val Gly Ala Thr Gln Asp Glu Ala Ile Ala Val Asn Ile Tyr Ala Ala
                325                 330                 335

Asn Val Ala Asn Leu Phe Ser Gly Glu Gly Ala Gln Thr Ala Gln Ala
            340                 345                 350

Ala Pro Val Gln Glu Gly Val Gln Gln Glu Gly Ala Gln Gln Pro Ala
        355                 360                 365

Pro Ala Thr Ala Pro Ser Gln Gly Gly Val Gly His
370                 375                 380
```

(2) INFORMATION FOR SEQ ID NO:119:

(i) SEQUENCE CHARACTERISTICS:
        (A) LENGTH: 1324 base pairs
        (B) TYPE: nucleic acid
        (C) STRANDEDNESS: double
        (D) TOPOLOGY: linear (ix) FEATURE:
    (A) NAME/KEY: CDS
    (B) LOCATION: 1..1324

(xi) SEQUENCE DESCRIPTION: SEQ ID NO:119:

| | | | | | | | | | | | | | | | | |
|---|---|---|---|---|---|---|---|---|---|---|---|---|---|---|---|---|
| GCA | CAA | AAA | GGT | GCT | GAG | TCA | ATT | GGT | TCT | CAA | AAA | GAA | AAT | GAT | CTA | 48 |
| Ala | Gln | Lys | Gly | Ala | Glu | Ser | Ile | Gly | Ser | Gln | Lys | Glu | Asn | Asp | Leu | |
| 1 | | | | 5 | | | | | 10 | | | | | 15 | | |
| AAC | CTT | GAA | GAC | TCT | AGT | AAA | AAA | TCA | CAT | CAA | AAC | GCT | AAA | CAA | GAC | 96 |
| Asn | Leu | Glu | Asp | Ser | Ser | Lys | Lys | Ser | His | Gln | Asn | Ala | Lys | Gln | Asp | |
| | | | 20 | | | | | 25 | | | | | 30 | | | |
| CTT | CCT | GCG | GTG | ACA | GAA | GAC | TCA | GTG | TCT | TTG | TTT | AAT | GGT | AAT | AAA | 144 |
| Leu | Pro | Ala | Val | Thr | Glu | Asp | Ser | Val | Ser | Leu | Phe | Asn | Gly | Asn | Lys | |
| | | 35 | | | | | 40 | | | | | 45 | | | | |
| ATT | TTT | GTA | AGC | AAA | GAA | AAA | AAT | AGC | TCC | GGC | AAA | TAT | GAT | TTA | AGA | 192 |
| Ile | Phe | Val | Ser | Lys | Glu | Lys | Asn | Ser | Ser | Gly | Lys | Tyr | Asp | Leu | Arg | |
| | 50 | | | | | 55 | | | | | 60 | | | | | |
| GCA | ACA | ATT | GAT | CAG | GTT | GAA | CTT | AAA | GGA | ACT | TCC | GAT | AAA | AAC | AAT | 240 |
| Ala | Thr | Ile | Asp | Gln | Val | Glu | Leu | Lys | Gly | Thr | Ser | Asp | Lys | Asn | Asn | |
| 65 | | | | | 70 | | | | | 75 | | | | | 80 | |
| GGT | TCT | GGA | ACC | CTT | GAA | GGT | TCA | AAG | CCT | GAC | AAG | AGT | AAA | GTA | AAA | 288 |
| Gly | Ser | Gly | Thr | Leu | Glu | Gly | Ser | Lys | Pro | Asp | Lys | Ser | Lys | Val | Lys | |
| | | | | 85 | | | | | 90 | | | | | 95 | | |
| TTA | ACA | GTT | TCT | GCT | GAT | TTA | AAC | ACA | GTA | ACC | TTA | GAA | GCA | TTT | GAT | 336 |
| Leu | Thr | Val | Ser | Ala | Asp | Leu | Asn | Thr | Val | Thr | Leu | Glu | Ala | Phe | Asp | |
| | | | | 100 | | | | | 105 | | | | | 110 | | |
| GCC | AGC | AAC | CAA | AAA | ATT | TCA | AGT | AAA | GTT | ACT | AAA | AAA | CAG | GGG | TCA | 384 |
| Ala | Ser | Asn | Gln | Lys | Ile | Ser | Ser | Lys | Val | Thr | Lys | Lys | Gln | Gly | Ser | |
| | | 115 | | | | | 120 | | | | | 125 | | | | |
| ATA | ACA | GAG | GAA | ACT | CTC | AAA | GCT | AAT | AAA | TTA | GAC | TCA | AAG | AAA | TTA | 432 |
| Ile | Thr | Glu | Glu | Thr | Leu | Lys | Ala | Asn | Lys | Leu | Asp | Ser | Lys | Lys | Leu | |
| | 130 | | | | | 135 | | | | | 140 | | | | | |
| ACA | AGA | TCA | AAC | GGA | ACT | ACA | CTT | GAA | TAC | TCA | CAA | ATA | ACA | GAT | GCT | 480 |
| Thr | Arg | Ser | Asn | Gly | Thr | Thr | Leu | Glu | Tyr | Ser | Gln | Ile | Thr | Asp | Ala | |
| 145 | | | | | 150 | | | | | 155 | | | | | 160 | |
| GAC | AAT | GCT | ACA | AAA | GCA | GTA | GAA | ACT | CTA | AAA | AAT | AGC | ATT | AAG | CTT | 528 |
| Asp | Asn | Ala | Thr | Lys | Ala | Val | Glu | Thr | Leu | Lys | Asn | Ser | Ile | Lys | Leu | |
| | | | | 165 | | | | | 170 | | | | | 175 | | |
| GAA | GGA | AGT | CTT | GTA | GTC | GGA | AAA | ACA | ACA | GTG | GAA | ATT | AAA | GAA | GGT | 576 |
| Glu | Gly | Ser | Leu | Val | Val | Gly | Lys | Thr | Thr | Val | Glu | Ile | Lys | Glu | Gly | |
| | | | 180 | | | | | 185 | | | | | 190 | | | |
| ACT | GTT | ACT | CTA | AAA | AGA | GAA | ATT | GAA | AAA | GAT | GGA | AAA | GTA | AAA | GTC | 624 |
| Thr | Val | Thr | Leu | Lys | Arg | Glu | Ile | Glu | Lys | Asp | Gly | Lys | Val | Lys | Val | |
| | | 195 | | | | | 200 | | | | | 205 | | | | |
| TTT | TTG | AAT | GAC | ACT | GCA | GGT | TCT | AAC | AAA | AAA | ACA | GGT | AAA | TGG | GAA | 672 |
| Phe | Leu | Asn | Asp | Thr | Ala | Gly | Ser | Asn | Lys | Lys | Thr | Gly | Lys | Trp | Glu | |
| | 210 | | | | | 215 | | | | | 220 | | | | | |
| GAC | AGT | ACT | AGC | ACT | TTA | ACA | ATT | AGT | GCT | GAC | AGC | AAA | AAA | ACT | AAA | 720 |
| Asp | Ser | Thr | Ser | Thr | Leu | Thr | Ile | Ser | Ala | Asp | Ser | Lys | Lys | Thr | Lys | |
| 225 | | | | | 230 | | | | | 235 | | | | | 240 | |
| GAT | TTG | GTG | TTC | TTA | ACA | GAT | GGT | ACA | ATT | ACA | GTA | CAA | CAA | TAC | AAC | 768 |
| Asp | Leu | Val | Phe | Leu | Thr | Asp | Gly | Thr | Ile | Thr | Val | Gln | Gln | Tyr | Asn | |
| | | | | 245 | | | | | 250 | | | | | 255 | | |
| ACA | GCT | GGA | ACC | AGC | CTA | GAA | GGA | TCA | GCA | AGT | GAA | ATT | AAA | AAT | CTT | 816 |
| Thr | Ala | Gly | Thr | Ser | Leu | Glu | Gly | Ser | Ala | Ser | Glu | Ile | Lys | Asn | Leu | |
| | | | 260 | | | | | 265 | | | | | 270 | | | |
| TCA | GAG | CTT | AAA | AAC | GCT | TTA | AAA | GGT | CAC | CCC | ATG | GCT | TCT | CAA | AAT | 864 |
| Ser | Glu | Leu | Lys | Asn | Ala | Leu | Lys | Gly | His | Pro | Met | Ala | Ser | Gln | Asn | |
| | | 275 | | | | | 280 | | | | | 285 | | | | |

```
GTA AGA ACA GCT GAA GAG CTT GGA ATG CAG CCT GCA AAA ATT AAC ACA      912
Val Arg Thr Ala Glu Glu Leu Gly Met Gln Pro Ala Lys Ile Asn Thr
    290                 295                 300

CCA GCA TCA CTT TCA GGG CTT CAA GCG TCT TGG ACT TTA AGA GTT CAT      960
Pro Ala Ser Leu Ser Gly Leu Gln Ala Ser Trp Thr Leu Arg Val His
305                 310                 315                 320

GTT GGA GCA ACC CAA GAT GAA GCT ATT GCT GTA AAT ATT TAT GCA GCT     1008
Val Gly Ala Thr Gln Asp Glu Ala Ile Ala Val Asn Ile Tyr Ala Ala
                325                 330                 335

AAT GTT GCA AAT CTT TTC TCT GGT GAG GGA GCT CAA ACT GCT CAG GCT     1056
Asn Val Ala Asn Leu Phe Ser Gly Glu Gly Ala Gln Thr Ala Gln Ala
            340                 345                 350

GCA CCG GTT CAA GAG GGT GTT CAA CAG GAA GGA GCT CAA CAG CCA GCA     1104
Ala Pro Val Gln Glu Gly Val Gln Gln Glu Gly Ala Gln Gln Pro Ala
        355                 360                 365

CCT GCT ACA GCA CCT TCT CAA GGC GGA GTT AAT TCT CCT GTT AAT GTT     1152
Pro Ala Thr Ala Pro Ser Gln Gly Gly Val Asn Ser Pro Val Asn Val
370                 375                 380

ACA ACT ACA GTT GAT GCT AAT ACA TCA CTT GCT AAA ATT GAA AAT GCT     1200
Thr Thr Thr Val Asp Ala Asn Thr Ser Leu Ala Lys Ile Glu Asn Ala
385                 390                 395                 400

ATT AGA ATG ATA AGT GAT CAA AGG GCA AAT TTA GGT GCT TTC CAA AAT     1248
Ile Arg Met Ile Ser Asp Gln Arg Ala Asn Leu Gly Ala Phe Gln Asn
                405                 410                 415

AGA CTT GAA TCT ATA AAG AAT AGT ACT GAG TAT GCA ATT GAA AAT CTA     1296
Arg Leu Glu Ser Ile Lys Asn Ser Thr Glu Tyr Ala Ile Glu Asn Leu
            420                 425                 430

AAA GCA TCT TAT GCT CAA ATA GGT CAC C                                1324
Lys Ala Ser Tyr Ala Gln Ile Gly His
        435                 440

(2) INFORMATION FOR SEQ ID NO:120:

(i) SEQUENCE CHARACTERISTICS:
         (A) LENGTH: 441 amino acids
         (B) TYPE: amino acid
         (D) TOPOLOGY: linear (ii) MOLECULE TYPE: protein (xi) SEQUENCE DESCRIPTION: SEQ ID NO:120:

Ala Gln Lys Gly Ala Glu Ser Ile Gly Ser Gln Lys Glu Asn Asp Leu
1               5                   10                  15

Asn Leu Glu Asp Ser Ser Lys Lys Ser His Gln Asn Ala Lys Gln Asp
            20                  25                  30

Leu Pro Ala Val Thr Glu Asp Ser Val Ser Leu Phe Asn Gly Asn Lys
        35                  40                  45

Ile Phe Val Ser Lys Glu Lys Asn Ser Ser Gly Lys Tyr Asp Leu Arg
    50                  55                  60

Ala Thr Ile Asp Gln Val Glu Leu Lys Gly Thr Ser Asp Lys Asn Asn
65                  70                  75                  80

Gly Ser Gly Thr Leu Glu Gly Ser Lys Pro Asp Lys Ser Lys Val Lys
                85                  90                  95

Leu Thr Val Ser Ala Asp Leu Asn Thr Val Thr Leu Glu Ala Phe Asp
            100                 105                 110

Ala Ser Asn Gln Lys Ile Ser Ser Lys Val Thr Lys Lys Gln Gly Ser
        115                 120                 125

Ile Thr Glu Glu Thr Leu Lys Ala Asn Lys Leu Asp Ser Lys Lys Leu
    130                 135                 140
```

```
Thr Arg Ser Asn Gly Thr Thr Leu Glu Tyr Ser Gln Ile Thr Asp Ala
145                 150                 155                 160

Asp Asn Ala Thr Lys Ala Val Glu Thr Leu Lys Asn Ser Ile Lys Leu
            165                 170                 175

Glu Gly Ser Leu Val Val Gly Lys Thr Thr Val Glu Ile Lys Glu Gly
            180                 185                 190

Thr Val Thr Leu Lys Arg Glu Ile Glu Lys Asp Gly Lys Val Lys Val
        195                 200                 205

Phe Leu Asn Asp Thr Ala Gly Ser Asn Lys Lys Thr Gly Lys Trp Glu
    210                 215                 220

Asp Ser Thr Ser Thr Leu Thr Ile Ser Ala Asp Ser Lys Lys Thr Lys
225                 230                 235                 240

Asp Leu Val Phe Leu Thr Asp Gly Thr Ile Thr Val Gln Gln Tyr Asn
                245                 250                 255

Thr Ala Gly Thr Ser Leu Glu Gly Ser Ala Ser Glu Ile Lys Asn Leu
            260                 265                 270

Ser Glu Leu Lys Asn Ala Leu Lys Gly His Pro Met Ala Ser Gln Asn
            275                 280                 285

Val Arg Thr Ala Glu Glu Leu Gly Met Gln Pro Ala Lys Ile Asn Thr
290                 295                 300

Pro Ala Ser Leu Ser Gly Leu Gln Ala Ser Trp Thr Leu Arg Val His
305                 310                 315                 320

Val Gly Ala Thr Gln Asp Glu Ala Ile Ala Val Asn Ile Tyr Ala Ala
                325                 330                 335

Asn Val Ala Asn Leu Phe Ser Gly Glu Gly Ala Gln Thr Ala Gln Ala
            340                 345                 350

Ala Pro Val Gln Glu Gly Val Gln Gln Glu Gly Ala Gln Gln Pro Ala
            355                 360                 365

Pro Ala Thr Ala Pro Ser Gln Gly Gly Val Asn Ser Pro Val Asn Val
            370                 375                 380

Thr Thr Thr Val Asp Ala Asn Thr Ser Leu Ala Lys Ile Glu Asn Ala
385                 390                 395                 400

Ile Arg Met Ile Ser Asp Gln Arg Ala Asn Leu Gly Ala Phe Gln Asn
                405                 410                 415

Arg Leu Glu Ser Ile Lys Asn Ser Thr Glu Tyr Ala Ile Glu Asn Leu
                420                 425                 430

Lys Ala Ser Tyr Ala Gln Ile Gly His
            435                 440

(2) INFORMATION FOR SEQ ID NO:121:

(i) SEQUENCE CHARACTERISTICS:
        (A) LENGTH: 1765 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..1765

(xi) SEQUENCE DESCRIPTION: SEQ ID NO:121:

GCA CAA AAA GGT GCT GAG TCA ATT GGT TCT CAA AAA GAA AAT GAT CTA    48
Ala Gln Lys Gly Ala Glu Ser Ile Gly Ser Gln Lys Glu Asn Asp Leu
  1               5                  10                  15

AAC CTT GAA GAC TCT AGT AAA AAA TCA CAT CAA AAC GCT AAA CAA GAC    96
Asn Leu Glu Asp Ser Ser Lys Lys Ser His Gln Asn Ala Lys Gln Asp
             20                  25                  30
```

-continued

```
CTT CCT GCG GTG ACA GAA GAC TCA GTG TCT TTG TTT AAT GGT AAT AAA       144
Leu Pro Ala Val Thr Glu Asp Ser Val Ser Leu Phe Asn Gly Asn Lys
         35                  40                  45

ATT TTT GTA AGC AAA GAA AAA AAT AGC TCC GGC AAA TAT GAT TTA AGA       192
Ile Phe Val Ser Lys Glu Lys Asn Ser Ser Gly Lys Tyr Asp Leu Arg
 50                  55                  60

GCA ACA ATT GAT CAG GTT GAA CTT AAA GGA ACT TCC GAT AAA AAC AAT       240
Ala Thr Ile Asp Gln Val Glu Leu Lys Gly Thr Ser Asp Lys Asn Asn
 65                  70                  75                  80

GGT TCT GGA ACC CTT GAA GGT TCA AAG CCT GAC AAG AGT AAA GTA AAA       288
Gly Ser Gly Thr Leu Glu Gly Ser Lys Pro Asp Lys Ser Lys Val Lys
                 85                  90                  95

TTA ACA GTT TCT GCT GAT TTA AAC ACA GTA ACC TTA GAA GCA TTT GAT       336
Leu Thr Val Ser Ala Asp Leu Asn Thr Val Thr Leu Glu Ala Phe Asp
             100                 105                 110

GCC AGC AAC CAA AAA ATT TCA AGT AAA GTT ACT AAA AAA CAG GGG TCA       384
Ala Ser Asn Gln Lys Ile Ser Ser Lys Val Thr Lys Lys Gln Gly Ser
         115                 120                 125

ATA ACA GAG GAA ACT CTC AAA GCT AAT AAA TTA GAC TCA AAG AAA TTA       432
Ile Thr Glu Glu Thr Leu Lys Ala Asn Lys Leu Asp Ser Lys Lys Leu
     130                 135                 140

ACA AGA TCA AAC GGA ACT ACA CTT GAA TAC TCA CAA ATA ACA GAT GCT       480
Thr Arg Ser Asn Gly Thr Thr Leu Glu Tyr Ser Gln Ile Thr Asp Ala
145                 150                 155                 160

GAC AAT GCT ACA AAA GCA GTA GAA ACT CTA AAA AAT AGC ATT AAG CTT       528
Asp Asn Ala Thr Lys Ala Val Glu Thr Leu Lys Asn Ser Ile Lys Leu
                 165                 170                 175

GAA GGA AGT CTT GTA GTC GGA AAA ACA ACA GTG GAA ATT AAA GAA GGT       576
Glu Gly Ser Leu Val Val Gly Lys Thr Thr Val Glu Ile Lys Glu Gly
             180                 185                 190

ACT GTT ACT CTA AAA AGA GAA ATT GAA AAA GAT GGA AAA GTA AAA GTC       624
Thr Val Thr Leu Lys Arg Glu Ile Glu Lys Asp Gly Lys Val Lys Val
         195                 200                 205

TTT TTG AAT GAC ACT GCA GGT TCT AAC AAA AAA ACA GGT AAA TGG GAA       672
Phe Leu Asn Asp Thr Ala Gly Ser Asn Lys Lys Thr Gly Lys Trp Glu
     210                 215                 220

GAC AGT ACT AGC ACT TTA ACA ATT AGT GCT GAC AGC AAA AAA ACT AAA       720
Asp Ser Thr Ser Thr Leu Thr Ile Ser Ala Asp Ser Lys Lys Thr Lys
225                 230                 235                 240

GAT TTG GTG TTC TTA ACA GAT GGT ACA ATT ACA GTA CAA CAA TAC AAC       768
Asp Leu Val Phe Leu Thr Asp Gly Thr Ile Thr Val Gln Gln Tyr Asn
                 245                 250                 255

ACA GCT GGA ACC AGC CTA GAA GGA TCA GCA AGT GAA ATT AAA AAT CTT       816
Thr Ala Gly Thr Ser Leu Glu Gly Ser Ala Ser Glu Ile Lys Asn Leu
             260                 265                 270

TCA GAG CTT AAA AAC GCT TTA AAA GGT CAC CCC ATG GGA AAT AAT TCA       864
Ser Glu Leu Lys Asn Ala Leu Lys Gly His Pro Met Gly Asn Asn Ser
         275                 280                 285

GGG AAA GAT GGG AAT ACA TCT GCA AAT TCT GCT GAT GAG TCT GTT AAA       912
Gly Lys Asp Gly Asn Thr Ser Ala Asn Ser Ala Asp Glu Ser Val Lys
     290                 295                 300

GGG CCT AAT CTT ACA GAA ATA AGT AAA AAA ATT ACG GAT TCT AAT GCG       960
Gly Pro Asn Leu Thr Glu Ile Ser Lys Lys Ile Thr Asp Ser Asn Ala
305                 310                 315                 320

GTT TTA CTT GCT GTG AAA GAG GTT GAA GCG TTG CTG TCA TCT ATA GAT      1008
Val Leu Leu Ala Val Lys Glu Val Glu Ala Leu Leu Ser Ser Ile Asp
                 325                 330                 335
```

```
GAA ATT GCT GCT AAA GCT ATT GGT AAA AAA ATA CAC CAA AAT AAT GGT      1056
Glu Ile Ala Ala Lys Ala Ile Gly Lys Lys Ile His Gln Asn Asn Gly
                340                 345                 350

TTG GAT ACC GAA TAT AAT CAC AAT GGA TCA TTG TTA GCG GGA CGT TAT      1104
Leu Asp Thr Glu Tyr Asn His Asn Gly Ser Leu Leu Ala Gly Arg Tyr
            355                 360                 365

GCA ATA TCA ACC CTA ATA AAA CAA AAA TTA GAT GGA TTG AAA AAT GAA      1152
Ala Ile Ser Thr Leu Ile Lys Gln Lys Leu Asp Gly Leu Lys Asn Glu
        370                 375                 380

GGA TTA AAG GAA AAA ATT GAT GCG GCT AAG AAA TGT TCT GAA ACA TTT      1200
Gly Leu Lys Glu Lys Ile Asp Ala Ala Lys Lys Cys Ser Glu Thr Phe
385                 390                 395                 400

ACT AAT AAA TTA AAA GAA AAA CAC ACA GAT CTT GGT AAA GAA GGT GTT      1248
Thr Asn Lys Leu Lys Glu Lys His Thr Asp Leu Gly Lys Glu Gly Val
                405                 410                 415

ACT GAT GCT GAT GCA AAA GAA GCC ATT TTA AAA ACA AAT GGT ACT AAA      1296
Thr Asp Ala Asp Ala Lys Glu Ala Ile Leu Lys Thr Asn Gly Thr Lys
            420                 425                 430

ACT AAA GGT GCT GAA GAA CTT GGA AAA TTA TTT GAA TCA GTA GAG GTC      1344
Thr Lys Gly Ala Glu Glu Leu Gly Lys Leu Phe Glu Ser Val Glu Val
        435                 440                 445

TTG TCA AAA GCA GCT AAA GAG ATG CTT GCT AAT TCA GTT AAA GAG CTT      1392
Leu Ser Lys Ala Ala Lys Glu Met Leu Ala Asn Ser Val Lys Glu Leu
450                 455                 460

ACA AGC CCT GTT GTG GCA GAA AGT CCA AAA AAA CCT GGT ACC ATG GCT      1440
Thr Ser Pro Val Val Ala Glu Ser Pro Lys Lys Pro Gly Thr Met Ala
465                 470                 475                 480

CAA TAT AAC CAA ATG CAC ATG TTA TCA AAC AAA TCT GCT TCT CAA AAT      1488
Gln Tyr Asn Gln Met His Met Leu Ser Asn Lys Ser Ala Ser Gln Asn
                485                 490                 495

GTA AGA ACA GCT GAA GAG CTT GGA ATG CAG CCT GCA AAA ATT AAC ACA      1536
Val Arg Thr Ala Glu Glu Leu Gly Met Gln Pro Ala Lys Ile Asn Thr
            500                 505                 510

CCA GCA TCA CTT TCA GGG CTT CAA GCG TCT TGG ACT TTA AGA GTT CAT      1584
Pro Ala Ser Leu Ser Gly Leu Gln Ala Ser Trp Thr Leu Arg Val His
        515                 520                 525

GTT GGA GCA ACC CAA GAT GAA GCT ATT GCT GTA AAT ATT TAT GCA GCT      1632
Val Gly Ala Thr Gln Asp Glu Ala Ile Ala Val Asn Ile Tyr Ala Ala
        530                 535                 540

AAT GTT GCA AAT CTT TTC TCT GGT GAG GGA GCT CAA ACT GCT CAG GCT      1680
Asn Val Ala Asn Leu Phe Ser Gly Glu Gly Ala Gln Thr Ala Gln Ala
545                 550                 555                 560

GCA CCG GTT CAA GAG GGT GTT CAA CAG GAA GGA GCT CAA CAG CCA GCA      1728
Ala Pro Val Gln Glu Gly Val Gln Gln Glu Gly Ala Gln Gln Pro Ala
                565                 570                 575

CCT GCT ACA GCA CCT TCT CAA GGC GGA GTT GGT CAC C                    1765
Pro Ala Thr Ala Pro Ser Gln Gly Gly Val Gly His
            580                 585
```

(2) INFORMATION FOR SEQ ID NO:122:

(i) SEQUENCE CHARACTERISTICS:
        (A) LENGTH: 588 amino acids
        (B) TYPE: amino acid
        (D) TOPOLOGY: linear (ii) MOLECULE TYPE: protein (xi) SEQUENCE DESCRIPTION: SEQ ID NO:122:

```
Ala Gln Lys Gly Ala Glu Ser Ile Gly Ser Gln Lys Glu Asn Asp Leu
 1               5                  10                  15
```

-continued

```
Asn Leu Glu Asp Ser Ser Lys Lys Ser His Gln Asn Ala Lys Gln Asp
             20                  25                  30

Leu Pro Ala Val Thr Glu Asp Ser Val Ser Leu Phe Asn Gly Asn Lys
         35                  40                  45

Ile Phe Val Ser Lys Glu Lys Asn Ser Ser Gly Lys Tyr Asp Leu Arg
     50                  55                  60

Ala Thr Ile Asp Gln Val Glu Leu Lys Gly Thr Ser Asp Lys Asn Asn
 65                  70                  75                  80

Gly Ser Gly Thr Leu Glu Gly Ser Lys Pro Asp Lys Ser Lys Val Lys
                 85                  90                  95

Leu Thr Val Ser Ala Asp Leu Asn Thr Val Thr Leu Glu Ala Phe Asp
            100                 105                 110

Ala Ser Asn Gln Lys Ile Ser Ser Lys Val Thr Lys Gln Gly Ser
        115                 120                 125

Ile Thr Glu Glu Thr Leu Lys Ala Asn Lys Leu Asp Ser Lys Lys Leu
    130                 135                 140

Thr Arg Ser Asn Gly Thr Thr Leu Glu Tyr Ser Gln Ile Thr Asp Ala
145                 150                 155                 160

Asp Asn Ala Thr Lys Ala Val Glu Thr Leu Lys Asn Ser Ile Lys Leu
                165                 170                 175

Glu Gly Ser Leu Val Val Gly Lys Thr Thr Val Glu Ile Lys Glu Gly
                180                 185                 190

Thr Val Thr Leu Lys Arg Glu Ile Glu Lys Asp Gly Lys Val Lys Val
            195                 200                 205

Phe Leu Asn Asp Thr Ala Gly Ser Asn Lys Lys Thr Gly Lys Trp Glu
    210                 215                 220

Asp Ser Thr Ser Thr Leu Thr Ile Ser Ala Asp Ser Lys Lys Thr Lys
225                 230                 235                 240

Asp Leu Val Phe Leu Thr Asp Gly Thr Ile Thr Val Gln Gln Tyr Asn
                245                 250                 255

Thr Ala Gly Thr Ser Leu Glu Gly Ser Ala Ser Glu Ile Lys Asn Leu
            260                 265                 270

Ser Glu Leu Lys Asn Ala Leu Lys Gly His Pro Met Gly Asn Asn Ser
        275                 280                 285

Gly Lys Asp Gly Asn Thr Ser Ala Asn Ser Ala Asp Glu Ser Val Lys
    290                 295                 300

Gly Pro Asn Leu Thr Glu Ile Ser Lys Lys Ile Thr Asp Ser Asn Ala
305                 310                 315                 320

Val Leu Leu Ala Val Lys Glu Val Glu Ala Leu Leu Ser Ser Ile Asp
                325                 330                 335

Glu Ile Ala Ala Lys Ala Ile Gly Lys Lys Ile His Gln Asn Asn Gly
            340                 345                 350

Leu Asp Thr Glu Tyr Asn His Asn Gly Ser Leu Leu Ala Gly Arg Tyr
        355                 360                 365

Ala Ile Ser Thr Leu Ile Lys Gln Lys Leu Asp Gly Leu Lys Asn Glu
    370                 375                 380

Gly Leu Lys Glu Lys Ile Asp Ala Ala Lys Lys Cys Ser Glu Thr Phe
385                 390                 395                 400

Thr Asn Lys Leu Lys Glu Lys His Thr Asp Leu Gly Lys Glu Gly Val
                405                 410                 415

Thr Asp Ala Asp Ala Lys Glu Ala Ile Leu Lys Thr Asn Gly Thr Lys
            420                 425                 430
```

```
Thr Lys Gly Ala Glu Glu Leu Gly Lys Leu Phe Glu Ser Val Glu Val
        435                 440                 445
Leu Ser Lys Ala Ala Lys Glu Met Leu Ala Asn Ser Val Lys Glu Leu
        450                 455                 460
Thr Ser Pro Val Val Ala Glu Ser Pro Lys Lys Pro Gly Thr Met Ala
465                 470                 475                 480
Gln Tyr Asn Gln Met His Met Leu Ser Asn Lys Ser Ala Ser Gln Asn
                    485                 490                 495
Val Arg Thr Ala Glu Glu Leu Gly Met Gln Pro Ala Lys Ile Asn Thr
            500                 505                 510
Pro Ala Ser Leu Ser Gly Leu Gln Ala Ser Trp Thr Leu Arg Val His
            515                 520                 525
Val Gly Ala Thr Gln Asp Glu Ala Ile Ala Val Asn Ile Tyr Ala Ala
        530                 535                 540
Asn Val Ala Asn Leu Phe Ser Gly Glu Gly Ala Gln Thr Ala Gln Ala
545                 550                 555                 560
Ala Pro Val Gln Glu Gly Val Gln Gln Glu Gly Ala Gln Gln Pro Ala
                    565                 570                 575
Pro Ala Thr Ala Pro Ser Gln Gly Gly Val Gly His
            580                 585
```

(2) INFORMATION FOR SEQ ID NO:123:

(i) SEQUENCE CHARACTERISTICS:
  (A) LENGTH: 704 base pairs
  (B) TYPE: nucleic acid
  (C) STRANDEDNESS: double
  (D) TOPOLOGY: linear (xi) SEQUENCE DESCRIPTION: SEQ ID NO:123:

```
CTACTGTTAA GTTTATTTTT ATTGCTCTCA ATATCTTGTT CTTTAGATAA TGAAGGTGTA      60
AACTCAAAAG ATTACGAGTC AAAAAAACAG AGTATACTAG GTGAATTAAA TCAGCTATTG     120
GGGCAAACTA CAAATTCACT AAAAGAAGCA AAAAATACAA CAGATAATTT AAATGCATCA     180
AATGAGGCAA ATAAAGTTGT AGAAGCAGTT ATAAGTGTGG TTAATTTAAT TTCATCTGCT     240
GCAGATCAGG TAAAAGGTCA ACAACAAATA TGCACGATTT AGCTCAAATG GCAGAAATAG     300
ATTTAGAAAA AATAAAGGAA TCTAGTGATA AAGTAATAGT TGCGGCTAAT GTTGCGAAAG     360
AAGCATATAA CCTTACTAAA GCAGTAGAAC AAAAATATGCA AAAACTGTAC AAAGAGCAAG     420
AAGAGCAACT AAAACACTAT CTGATTCTGA TGAAACAGAA CGAGTTTCTG ATGAAATAAA     480
ACAAGCTAAA GAGGCTGTAG AAATAGCTTG GAAAGCCACA GTAAAAGTAA AAGATGAGTT     540
AATTGATGTA GAAAATGCAG TCAAAGAGGC ATTGGATAAA ATAAAGACAG AAACCGCGAA     600
CAATACAAAA CTTACAGATA TAGAAGAAGT AGCAGAGTTA GTATTACAGA TAGCCAAAAA     660
TGTAGCGGAA ATAGCGCAAG AAGTTGTGGC CTTGTTAAAT ACTT                      704
```

(2) INFORMATION FOR SEQ ID NO:124:

(i) SEQUENCE CHARACTERISTICS:
  (A) LENGTH: 704 base pairs
  (B) TYPE: nucleic acid
  (C) STRANDEDNESS: double
  (D) TOPOLOGY: linear (xi) SEQUENCE DESCRIPTION: SEQ ID NO:124:

```
CTACTGTTAA GTTTATTTTT ATTGCTCTCA ATATCTTGTT ATTTAGATAA TGAAGGTGTA      60
AACTCAAAAG ATTACGAGTC AAAAAAACAG AGTATACTAG GTGAATTAAA TCAGCTATTG     120
```

```
GGGCAAACTA CAAATTCACT AAAAGAAGCA AAAAATACAA CAGATAATTT AAATGCATCA    180

AATGAGGCAA ATAAAGTTGT AGAAGCAGTT ATAAGTGTGG TTAATTTAAT TTCATCTGCT    240

GCAGATCAGG TAAAAGGTCA ACAACAAATA TGCACGATTT AGCTCAAATG GCAGAAATAG    300

ATTTAGAAAA AATAAAGGAA TCTAGTGATA AAGTAATAGT TGCGGCTAAT GTTGCGAAAG    360

AAGCATATAA CCTTACTAAA GCAGTAGAAC AAAATATGCA AAAACTGTAC AAAGAGCAAG    420

AAGAGCAACT AAAACACTAT CTGATTCTGA TGAAACAGAA CGAGTTTCTG ATGAAATAAA    480

ACAAGCTAAA GAGGCTGTAG AAATAGCTTG GAAAGCCACA GTAAAGTAA AAGATGAGTT     540

AATTGATGTA GAAAATGCAG TCAAAGAGGC ATTGGATAAA ATAAAGACAG AAACCGCGAA    600

CAATACAAAA CTTACAGATA TAGAAGAAGT AGCAGAGTTA GTATTACAAA TAGCCAAAAA    660

TGTAGCGGAA ATAGCGCAAG AAGTTGTGGC CTTGTTAAAT ACTT                     704
```

(2) INFORMATION FOR SEQ ID NO:125:

(i) SEQUENCE CHARACTERISTICS:
        (A) LENGTH: 704 base pairs
        (B) TYPE: nucleic acid
        (C) STRANDEDNESS: double
        (D) TOPOLOGY: linear (xi) SEQUENCE DESCRIPTION: SEQ ID NO:125:

```
CTACTGCTAA GTTTATTTTT ATTGCTCTCA ATATCTGGTT CTTTAGATAA TGAAGGTGTA     60

AACTCAAAAG ATTACGAGTC AAAAAAACAG AGTATACTAG GTGAATTAAA TCAGCTATTG    120

GGGCAAACTA CAAATTCACT AAAAGAAGCA AAAAATACAA CAGATAATTT AAATGCATCA    180

AATGAGGCAA ATAAAGTTGT AGAAGCAGTT ATAAGTGTGG TTAATTTAAT TTCATCTGCT    240

GCAGATCAGG TGAAAGGTCA ACAACAAATA TGCACGATTT AGCTCAAATG GCAGAAATAG    300

ATTTAGAAAA AATAAAGGAA TCTAGTGATA AAGTAATAGT TGCGGCTAAT GTTGCGAAAG    360

AAGCATATAA CCTTACTAAA GCAGTAGAAC AAAATATGCA AAAACTGTAC AAAGAGCAAG    420

AAGAGCAACT AAAACACTAT CTGATTCTGA TGAAGCAGAA CGAGTTTCTG ATGAAATAAA    480

ACAAGCTAAA GAGGCTGTAG AAATAGCTTG GAAAGCCACA GTAAAAGTAA AAGATGAGTT    540

AATTGATGTA GAAAATGCAG TCAAAGAGGC ATTGGATAAA ATAAAGACAG AAACCGCGAA    600

CAATACAAAA CTTACAGATA TAGAAGAAGT AGCAGAGTTA GTATTACAAA TAGCCAAAAA    660

TGTAGCGGAA ATAGCGCAAG AAGTTGTGGC CTTGTTAAAT ACTT                     704
```

(2) INFORMATION FOR SEQ ID NO:126:

(i) SEQUENCE CHARACTERISTICS:
        (A) LENGTH: 704 base pairs
        (B) TYPE: nucleic acid
        (C) STRANDEDNESS: double
        (D) TOPOLOGY: linear (xi) SEQUENCE DESCRIPTION: SEQ ID NO:126:

```
CTACTGTTAA GTTTATTTTT ATTGCTCTCA ATATCTTGTT CTTTAGATAA TGAAGGTGTA     60

AGCTCAAAAG ATTACGAGTC AAAAAAACAG AGTATACTAG GTGAATTAAA TCAGCTATTG    120

GGGCAAACTA CAAATTCACT AAAAGAAGCA AAAAATACAA CAGATAATTT AAATGCATCA    180

AATGAGGCAA ATAAAGTTGT AGAAGCAGTT ATAAGTGTGG TTAATTTAAT TTCATCTGCT    240

GCAGATCAGG TGAAAGGTCA ACAACAAATA TGCACGATTT AGCTCAAATG GCAGAAATAG    300

ATTTAGAAAA AATAAAGGAA TCTAGTGATA AAGTAATAGT TGCGGCTAAT GTTGCGAAAG    360
```

```
AAGCATATAA CCTTACTAAA GCAGTAGAAC AAAATATGCA AAAACTGTAC AAAGAGCAAG      420

AAGAGCAACT AAAACACTAT CTGATTCTGA TGAAGCAGAA CGAGTTTCTG ATGAAATAAA      480

ACAAGCTAAA GAGGCTGTAG AAATAGCTTG GAAAGCCACA GTAAAAGTAA AAGATGAGTT      540

AATTGATGTA GAAAATGCAG TCAAAGAGGC ATTGGATAAA ATAAAGACAG GAACCGCGAA      600

CAATACAAAA CTTACAGATA TAGAAGAAGT AGCAGAGTTA GTATTACAAA TAGCCAAAAA      660

TGTAGCGGAA ATAGCGCAAG AAGTTGTGGC CTTGTTAAAT ACTT                      704
```

(2) INFORMATION FOR SEQ ID NO:127:

(i) SEQUENCE CHARACTERISTICS:
        (A) LENGTH: 1011 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..1011

(xi) SEQUENCE DESCRIPTION: SEQ ID NO:127:

```
ATG ATT ATC AAT CAT AAT ACA TCA GCT ATT AAT GCT TCA AGA AAT AAT         48
Met Ile Ile Asn His Asn Thr Ser Ala Ile Asn Ala Ser Arg Asn Asn
  1               5                  10                  15

GGC ATT AAC GCT GCT AAT CTT AGT AAA ACT CAA GAA AAG CTT TCT AGT         96
Gly Ile Asn Ala Ala Asn Leu Ser Lys Thr Gln Glu Lys Leu Ser Ser
                 20                  25                  30

GGC TAC AGA ATT AAT CGA GCT TCT GAT GAT GCT GCT GGC ATG GGA GTT        144
Gly Tyr Arg Ile Asn Arg Ala Ser Asp Asp Ala Ala Gly Met Gly Val
             35                  40                  45

TCT GGT AAG ATT AAT GCT CAA ATA AGA GGT TTG TCA CAA GCT TCT AGA        192
Ser Gly Lys Ile Asn Ala Gln Ile Arg Gly Leu Ser Gln Ala Ser Arg
         50                  55                  60

AAT ACT TCA AAG GCT ATT AAT TTT ATT CAG ACA ACA GAA GGG AAT TTA        240
Asn Thr Ser Lys Ala Ile Asn Phe Ile Gln Thr Thr Glu Gly Asn Leu
 65                  70                  75                  80

AAT GAA GTA GAA AAA GTC TTA GTA AGA ATG AAG GAA TTG GCA GTT CAA        288
Asn Glu Val Glu Lys Val Leu Val Arg Met Lys Glu Leu Ala Val Gln
                 85                  90                  95

TCA GGT AAC GGC ACA TAT TCA GAT GCA GAC AGA GGT TCT ATA CAA ATT        336
Ser Gly Asn Gly Thr Tyr Ser Asp Ala Asp Arg Gly Ser Ile Gln Ile
                100                 105                 110

GAA ATA GAG CAA CTT ACA GAC GAA ATT AAT AGA ATT GCT GAT CAA GCT        384
Glu Ile Glu Gln Leu Thr Asp Glu Ile Asn Arg Ile Ala Asp Gln Ala
            115                 120                 125

CAA TAT AAC CAA ATG CAC ATG TTA TCA AAC AAA TCT GCT TCT CAA AAT        432
Gln Tyr Asn Gln Met His Met Leu Ser Asn Lys Ser Ala Ser Gln Asn
        130                 135                 140

GTA AGA ACA GCT GAA GAG CTT GGA ATG CAG CCT GCA AAA ATT AAC ACA        480
Val Arg Thr Ala Glu Glu Leu Gly Met Gln Pro Ala Lys Ile Asn Thr
145                 150                 155                 160

CCA GCA TCA CTT TCA GGG CTT CAA GCG TCT TGG ACT TTA AGA GTT CAT        528
Pro Ala Ser Leu Ser Gly Leu Gln Ala Ser Trp Thr Leu Arg Val His
                165                 170                 175

GTT GGA GCA ACC CAA GAT GAA GCT ATT GCT GTA AAT ATT TAT GCA GCT        576
Val Gly Ala Thr Gln Asp Glu Ala Ile Ala Val Asn Ile Tyr Ala Ala
                180                 185                 190

AAT GTT GCA AAT CTT TTC TCT GGT GAG GGA GCT CAA ACT GCT CAG GCT        624
Asn Val Ala Asn Leu Phe Ser Gly Glu Gly Ala Gln Thr Ala Gln Ala
            195                 200                 205
```

```
GCA CCG GTT CAA GAG GGT GTT CAA CAG GAA GGA GCT CAA CAG CCA GCA    672
Ala Pro Val Gln Glu Gly Val Gln Gln Glu Gly Ala Gln Gln Pro Ala
    210                 215                 220

CCT GCT ACA GCA CCT TCT CAA GGC GGA GTT AAT TCT CCT GTT AAT GTT    720
Pro Ala Thr Ala Pro Ser Gln Gly Gly Val Asn Ser Pro Val Asn Val
225                 230                 235                 240

ACA ACT ACA GTT GAT GCT AAT ACA TCA CTT GCT AAA ATT GAA AAT GCT    768
Thr Thr Thr Val Asp Ala Asn Thr Ser Leu Ala Lys Ile Glu Asn Ala
                245                 250                 255

ATT AGA ATG ATA AGT GAT CAA AGG GCA AAT TTA GGT GCT TTC CAA AAT    816
Ile Arg Met Ile Ser Asp Gln Arg Ala Asn Leu Gly Ala Phe Gln Asn
            260                 265                 270

AGA CTT GAA TCT ATA AAG AAT AGT ACT GAG TAT GCA ATT GAA AAT CTA    864
Arg Leu Glu Ser Ile Lys Asn Ser Thr Glu Tyr Ala Ile Glu Asn Leu
        275                 280                 285

AAA GCA TCT TAT GCT CAA ATA AAA GAT GCT ACA ATG ACA GAT GAG GTT    912
Lys Ala Ser Tyr Ala Gln Ile Lys Asp Ala Thr Met Thr Asp Glu Val
    290                 295                 300

GTA GCA GCA ACA ACT AAT ATG ATT TTA ACA CAA TCT GCA ATG GCA ATG    960
Val Ala Ala Thr Thr Asn Met Ile Leu Thr Gln Ser Ala Met Ala Met
305                 310                 315                 320

ATT GCG CAG GCT AAT CAA GTT CCC CAA TAT GTT TTG TCA TTG CTT AGA   1008
Ile Ala Gln Ala Asn Gln Val Pro Gln Tyr Val Leu Ser Leu Leu Arg
                325                 330                 335

TAA                                                               1011
```

(2) INFORMATION FOR SEQ ID NO:128:

(i) SEQUENCE CHARACTERISTICS:
        (A) LENGTH: 336 amino acids
        (B) TYPE: amino acid
        (D) TOPOLOGY: linear (ii) MOLECULE TYPE: protein (xi) SEQUENCE DESCRIPTION: SEQ ID NO:128:

```
Met Ile Ile Asn His Asn Thr Ser Ala Ile Asn Ala Ser Arg Asn Asn
 1               5                  10                  15

Gly Ile Asn Ala Ala Asn Leu Ser Lys Thr Gln Glu Lys Leu Ser Ser
                20                  25                  30

Gly Tyr Arg Ile Asn Arg Ala Ser Asp Asp Ala Ala Gly Met Gly Val
            35                  40                  45

Ser Gly Lys Ile Asn Ala Gln Ile Arg Gly Leu Ser Gln Ala Ser Arg
        50                  55                  60

Asn Thr Ser Lys Ala Ile Asn Phe Ile Gln Thr Thr Glu Gly Asn Leu
65                  70                  75                  80

Asn Glu Val Glu Lys Val Leu Val Arg Met Lys Glu Leu Ala Val Gln
                85                  90                  95

Ser Gly Asn Gly Thr Tyr Ser Asp Ala Asp Arg Gly Ser Ile Gln Ile
                100                 105                 110

Glu Ile Glu Gln Leu Thr Asp Glu Ile Asn Arg Ile Ala Asp Gln Ala
            115                 120                 125

Gln Tyr Asn Gln Met His Met Leu Ser Asn Lys Ser Ala Ser Gln Asn
        130                 135                 140

Val Arg Thr Ala Glu Glu Leu Gly Met Gln Pro Ala Lys Ile Asn Thr
145                 150                 155                 160

Pro Ala Ser Leu Ser Gly Leu Gln Ala Ser Trp Thr Leu Arg Val His
                165                 170                 175
```

```
Val Gly Ala Thr Gln Asp Glu Ala Ile Ala Val Asn Ile Tyr Ala Ala
            180                 185                 190

Asn Val Ala Asn Leu Phe Ser Gly Glu Gly Ala Gln Thr Ala Gln Ala
        195                 200                 205

Ala Pro Val Gln Glu Gly Val Gln Gln Glu Gly Ala Gln Gln Pro Ala
    210                 215                 220

Pro Ala Thr Ala Pro Ser Gln Gly Gly Val Asn Ser Pro Val Asn Val
225                 230                 235                 240

Thr Thr Thr Val Asp Ala Asn Thr Ser Leu Ala Lys Ile Glu Asn Ala
                245                 250                 255

Ile Arg Met Ile Ser Asp Gln Arg Ala Asn Leu Gly Ala Phe Gln Asn
            260                 265                 270

Arg Leu Glu Ser Ile Lys Asn Ser Thr Glu Tyr Ala Ile Glu Asn Leu
        275                 280                 285

Lys Ala Ser Tyr Ala Gln Ile Lys Asp Ala Thr Met Thr Asp Glu Val
    290                 295                 300

Val Ala Ala Thr Thr Asn Met Ile Leu Thr Gln Ser Ala Met Ala Met
305                 310                 315                 320

Ile Ala Gln Ala Asn Gln Val Pro Gln Tyr Val Leu Ser Leu Leu Arg
                325                 330                 335

(2) INFORMATION FOR SEQ ID NO:129:

(i) SEQUENCE CHARACTERISTICS:
        (A) LENGTH: 1008 base pairs
        (B) TYPE: nucleic acid
        (C) STRANDEDNESS: double
        (D) TOPOLOGY: linear (xi) SEQUENCE DESCRIPTION: SEQ ID NO:129:

ATGATTATCA ATCATAATAC ATCAGCTATT AATGCTTCAA GAAATAATGG CATTAACGCT     60

GCTAATCTTA GTAAAACTCA AGAAAAGCTT TCTAGTGGGT ACAGAATTAA TCGAGCTTCT    120

GATGATGCTG CTGGCATGGG AGTTTCTGGT AAGATTAATG CTCAAATAAG AGGTTTGTCA    180

CAAGCTTCTA GAAATACTTC AAAGGCTATT AATTTTATTC AGACAACAGA AGGGAATTTA    240

AATGAAGTAG AAAAAGTCTT AGTAAGAATG AAGGAATTGG CAGTTCAATC AGGTAACGGC    300

ACATATTCAG ATGCAGACAG AGGTTCTATA CAAATTGAAA TAGAGCAACT TACAGACGAA    360

ATTAATAGAA TTGCTGATCA AGCTCAATAT AACCAAATGC ACATGTTATC AAACAAATCT    420

GCTTCTCAAA ATGTAAGAAC AGCTGAAGAG CTTGGAATGC AGCCTGCAAA AATTAACACA    480

CCAGCATCAC TTTCAGGGTC TCAAGCGTCT TGGACTTTAA GAGTTCATGT TGGAGCAAAC    540

CAAGATGAAG CTATTGCTGT AAATATTTAT GCAGCTAATG TTGCAAATCT TTTCTCTGGT    600

GAGGGAGCTC AAACTGCTCA GGCTGCACCG GTTCAAGAGG GTGTTCAACA GGAAGGAGCT    660

CAACAGCCAG CACCTGCTAC AGCACCTTCT CAAGGCGGAG TTAATTCTCC TGTTAATGTT    720

ACAACTACAG TTGATGCTAA TACATCACTT GCTAAAATTG AAAATGCTAT TAGAATGATA    780

AGTGATCAAA GGGCAAATTT AGGTGCTTTC CAAAATAGAC TTGAATCTAT AAAGAATAGT    840

ACTGAGTATG CAATTGAAAA TCTAAAAGCA TCTTATGCTC AAATAAAAGA TGCTACAATG    900

ACAGATGAGG TTGTAGCAGC AACAACTAAT AGTATTTTAA CACAATCTGC AATGGCAATG    960

ATTGCGCAGG CTAATCAAGT TCCCCAATAT GTTTTGTCAT TGCTTAGA              1008
```

(2) INFORMATION FOR SEQ ID NO:130:

(i) SEQUENCE CHARACTERISTICS:
        (A) LENGTH: 1008 base pairs
        (B) TYPE: nucleic acid
        (C) STRANDEDNESS: double
        (D) TOPOLOGY: linear (xi) SEQUENCE DESCRIPTION: SEQ ID NO:130:

```
ATGATTATCA ATCATAATAC ATCAGCTATT AATGCTTCAA GAAATAATGC CATTAATGCT      60
GCTAATCTTA GTAAAACCCA AGAGAAGCTT TCTAGTGGTT ACAGAATTAA TCGAGCTTCT     120
GATGATGCTG CTGGTATGGG GGTTTCTGGC AAGATTAATG CTCAAATAAG AGGCTTATCA     180
CAAGCTTCTA GAAACACTTC AAAAGCTATC AATTTTATTC AGACAACAGA AGGAAATTTA     240
AATGAAGTAG AAAAAGTTTT AGTAAGAATG AAAGAATTAG CAGTTCAATC AGGTAACGGA     300
ACGTATTCAG ACTCAGACAG AGGTTCTATA CAGATTGAAA TAGAGCAACT TACAGACGAA     360
ATTAATAGAA TTGCTGATCA GGCTCAATAT AACCAAATGC ACATGTTGTC AAACAAATCT     420
GCTTCCCAAA ATGTAAAAAC AGCTGAAGAG CTTGGAATGC AGCCTGCAAA AATTAACACA     480
CCAGCATCAC TTTCAGGATC TCAAGCTTCT TGGACTTTAA GAGTTCATGT GGGAGCAAAT     540
CAAGATGAAG CAATTGCTGT AAATATTTAT TCAGCTAATG TTGCAAATCT TTTTGCTGGT     600
GAGGGAGCTC AAGCTGCTCA GGCTGCACCT GTTCAAGAGG GTGCTCAAGA AGAAGGAGCT     660
CAGCAACCAA CACCTGCTAC AGCACCTACT CAAGGTGGAG TTAATTCTCC TGTTAATGTT     720
ACAACCACAG TTGATGCTAA TACATCACTT GCTAAAATAG AAAATGCTAT TAGAATGATA     780
AGTGATCAAA GAGCAAATTT AGGTGCTTTC CAAAATAGAC TTGAATCTAT AAAGAATAGC     840
ACTGAGTATG CTATTGAAAA TCTAAAAGCA TCTTATGCTC AAATAAAAGA TGCTACAATG     900
ACAGATGAGG TTGTAGCAGC TACAACTAAT AGTATTTTAA CTCAATCTGC AATGGCAATG     960
ATTGCACAGG CTAATCAAGT TCCTCAATAT GTTTTGTCAT TGCTTAGA              1008
```

(2) INFORMATION FOR SEQ ID NO:131:

(i) SEQUENCE CHARACTERISTICS:
        (A) LENGTH: 1008 base pairs
        (B) TYPE: nucleic acid
        (C) STRANDEDNESS: double
        (D) TOPOLOGY: linear (xi) SEQUENCE DESCRIPTION: SEQ ID NO:131:

```
ATGATTATCA ATCATAATAC ATCAGCTATT AATGCTTCAA GAAATAATGC CATTAATGCT      60
GCTAATCTTA GTAAAACCCA AGAGAAGCCT TCTAGTGGTT ACAGAATTAA TCGAGCTTCT     120
GATGATGCTG CTGGTATGGG GGTTTCTGGC AAGATTAATG CTCAAATAAG AGGCTTATCA     180
CAAGCTTCTA GAAACACTTC AAAAGCTATC AATTTTATTC AGACAACAGA AGGAAATTTA     240
AATGAAGTAG AAAAAGTTTT AGTAAGAATG AAAGAATTAG CAGTTCAATC AGGTAACGGA     300
ACGTATTCAG ACTCAGACAG AGGTTCTATA CAGATTGAAA TAGAGCAACT TACAGACGAA     360
ATTAATAGAA TTGCTGATCA GGCTCAATAT AACCAAATGC ACATGTTGTC AAACAAATCT     420
GCTTCCCAAA ATGTAAAAAC AGCTGAAGAG CTTGGAATGC AGCCTGCAAA AATTAACACA     480
CCAGCATCAC TTTCAGGATC TCAAGCTTCT TGGACTTTAA GAGTTCATGT GGGAGCAAAT     540
CAAGATGAAG CAATTGCTGT AAATATTTAT TCAGCTAATG TTGCAAATCT TTTTGCTGGT     600
GAGGGAGCTC AAGCTGCTCA GGCTGCACCT GTTCAAGAGG GTGCTCAAGA AGAAGGAGCT     660
```

-continued

```
CAGCAACCAA CACCTGCTAC AGCACCTACT CAAGGTGGAG TTAATTCTCC TGTTAATGTT      720

ACAACCACAG TTGATGCTAA TACATCACTT GCTAAAATAG AAAATGCTAT TAGAATGATA      780

AGTGATCAAA GAGCAAATTT AGGTGCTTTC CAAAATAGAC TTGAATCTAT AAAGAATAGC      840

ACTGAGTATG CTATTGAAAA TCTAAAAGCA TCTTATGCTC AAATAAAAGA TGCTACAATG      900

ACAGATGAGG TTGTAGCAGC TACAACTAAA AGTATTTTAA CTCAATCTGC AATGGCAATG      960

ATTGCACAGG CTAATCAAGT TCCTCAATAT GTTTTGTCAT TGCTTAGA                  1008
```

(2) INFORMATION FOR SEQ ID NO:132:

(i) SEQUENCE CHARACTERISTICS:
        (A) LENGTH: 822 base pairs
        (B) TYPE: nucleic acid
        (C) STRANDEDNESS: double
        (D) TOPOLOGY: linear (xi) SEQUENCE DESCRIPTION: SEQ ID NO:132:

```
ATGAAAAAAT ATTTATTGGG AATAGGTCTA ATATTAGCCT TAATAGCATG TAAGCAAAAT       60

GTTAGCAGCC TTGACGAGAA AAACAGCGTT TCAGTAGATT TGCCTGGTGA AATGAAAGTT      120

CTTGTAAGCA AGAAAAAAA CAAAGACGGC AAGTACGATC TAATTGCAAC AGTAGACAAG       180

CTTGAGCTTA AAGGAACTTC TGATAAAAAC AATGGATCTG GAGTACTTGA AGGCGTAAAA      240

GCTGACAAAA GTAAAGTAAA ATTAACAATT TCTGACGATC TAGGTCAAAC CACACTTGAA      300

GTTTTCAAAG AAGATGGCAA AACACTAGTA TCAAAAAAAG TAACTTCCAA AGACAAGTCA      360

TCAACAGAAG AAAAATTCAA TGAAAAGGT GAAGTATCTG AAAAAATAAT AACAAGAGCA       420

GACGGAACCA GACTTGAATA CACAGGAATT AAAAGCGATG GATCTGGAAA AGCTAAAGAG      480

GTTTTAAAAG CTATGTTCT TGAAGGAACT CTAACTGCTG AAAAAACAAC ATTGGTGGTT       540

AAAGAAGGAA CTGTTACTTT AAGCAAAAAT ATTTCAAAAT CTGGGGAAGT TTCAGTTGAA      600

CTTAATGACA CTGACAGTAG TGCTGCTACT AAAAAAACTG CAGCTTGGAA TTCAGGCACT      660

TCAACTTTAA CAATTACTGT AAACAGTAAA AAAACTAAAG ACCTTGTGTT TACAAAAGAA      720

AACACAATTA CAGTACAACA ATACGACTCA AATGGCACCA AATTAGAGGG GTCAGCAGTT      780

GAAATTACAA AACTTGATGA AATTAAAAAC GCTTTAAAAT AA                         822
```

(2) INFORMATION FOR SEQ ID NO:133:

(i) SEQUENCE CHARACTERISTICS:
        (A) LENGTH: 822 base pairs
        (B) TYPE: nucleic acid
        (C) STRANDEDNESS: double
        (D) TOPOLOGY: linear (xi) SEQUENCE DESCRIPTION: SEQ ID NO:133:

```
ATGAAAAAAT ATTTATTGGG AATAGGTCTA ATATTAGCCT TAATAGCATG TAAGCAAAAT       60

GTTAGCAGCC TTGACGAGAA AAACAGCGTT TCAGTAGATT TGCCTGGTGA AATGAACGTT      120

CTTGTAAGCA AGAAAAAAA CAAAGACGGC AAGTACGATC TAATTGCAAC AGTAGACAAG       180

CTTGAGCTTA AAGGAACTTC TGATAAAAAC AATGGATCTG GAGTACTTGA AGGCGTAAAA      240

GCTGACAAAA GTAAAGTAAA ATTAACAATT TCTGACGATC TAGGTCAAAC CACACTTGAA      300

GTTTTCAAAG AAGATGGCAA AACACTAGTA TCAAAAAAAG TAACTTCCAA AGACAAGTCA      360

TCAACAGAAG AAAAATTCAA TGAAAAGGT GAAGTATCTG AAAAAATAAT AACAAGAGCA       420

GACGGAACCA GACTTGAATA CACAGAAATT AAAAGCGATG GATCTGGAAA AGCTAAAGAG      480

GTTTTAAAAG CTATGTTCT TGAAGGAACT CTAACTGCTG AAAAAACAAC ATTGGTGGTT       540
```

```
AAAGAAGGAA CTGTTACTTT AAGCAAAAAT ATTTCAAAAT CTGGGGAAGT TTCAGTTGAA      600

CTTAATGACA CTGACAGTAG TGCTGCTACT AAAAAAACTG CAGCTTGGAA TTCAGGCACT      660

TCAACTTTAA CAATTACTGT AAACAGTAAA AAAACTAAAG ACCTTGTGTT TACAAAAGAA      720

AACACAATTA CAGTACAACA ATACGACTCA AATGGCACCA AATTAGAGGG GTCAGCAGTT     780

GAAATTACAA AACTTGATGA AATTAAAAAC GCTTTAAAAT AA                        822

(2) INFORMATION FOR SEQ ID NO:134:

(i) SEQUENCE CHARACTERISTICS:
        (A) LENGTH: 822 base pairs
        (B) TYPE: nucleic acid
        (C) STRANDEDNESS: double
        (D) TOPOLOGY: linear (xi) SEQUENCE DESCRIPTION: SEQ ID NO:134:

ATGAAAAAAT ATTTATTGGG AATAGGTCTA ATATTAGCCT TAATAGCATG TAAGCAAAAT       60

GTTAGCAGCC TTGACGAGAA AAACAGCGTT TCAGTAGATT TGCCTGGTGA AATGAACGTT     120

CTTGTAAGCA AAGAAAAAAA CAAAGACGGC AAGTACGATC TAATTGCAAC AGTAGACAAG     180

CTTGAGCTTA AAGGAACTTC TGATAAAAAC AATGGATCTG GAGTACTTGA AGGCGTAAAA     240

GCTGACAAAA GTAAAGTAAA ATTAACAATT TCTGACGATC TAGGTCAAAC CACACTTGAA     300

GTTTTCAAAG AAGATGGCAA AACACTAGTA TCAAAAAAAG TAACTTCCAA AGACAAGTCA     360

TCAACAGAAG AAAAATTCAA TGAAAAAGGT GAAGTATCTG AAAAAATAAT AACAAGAGCA     420

GACGGAACCA GACTTGAATA CACAGAAATT AAAAGCGATG GATCTGGAAA AGCTAAAGAG     480

GTTTTAAAAA GCTATGTTCT TGAAGGAACT TTAACTGCTG AAAAAACAAC ATTGGTGGTT     540

AAAGAAGGAA CTGTTACTTT AAGCAAAAAT ATTTCAAAAT CTGGGGAAGT TTCAGTTGAA      600

CTTAATGACA CTGACAGTAG TGCTGCTACT AAAAAAACTG CAGCTTGGAA TTCAGGCACT      660

TCAACTTTAA CAATTACTGT AAACAGTAAA AAAACTAAAG ACCTTGTGTT TACAAAAGAA      720

AACACAATTA CAGTACAACA ATACGACTCA AATGGCACCA AATTAGAGGG GTCAGCAGTT     780

GAAATTACAA AACTTGATGA AATTAAAAAC GCTTTAAAAT AA                        822

(2) INFORMATION FOR SEQ ID NO:135:

(i) SEQUENCE CHARACTERISTICS:
        (A) LENGTH: 821 base pairs
        (B) TYPE: nucleic acid
        (C) STRANDEDNESS: double
        (D) TOPOLOGY: linear (xi) SEQUENCE DESCRIPTION: SEQ ID NO:135:

ATGAAAAAAT ATTTATTGGG AATAGGTCTA ATATTAGCCT TAATAGCATG TAAGCAAAAT       60

GTTAGCAGCC TTGATGAGAA AAACAGCGTT TCAGTAGATT TACCTGGTGA AATGAAAGTT     120

CTTGTAAGCA AAGAAAAAGA CAAAGATGGT AAATACAGTC TAATGGCAAC AGTAGACAAG     180

CTAGAGCTTA AAGGAACTTC TGATAAAAGC AACGGTTCTG GAACACTTGA AGGTGAAAAA     240

TCTGACAAAA GTAAAGCAAA ATTAACAATT TCTGAAGATC TAAGTAAAAC CACATTTGAA     300

ATTTTCAAAG AAGATGGCAA AACATTAGTA TCAAAAAAAG TAAATTCTAA AGATAAGTCA     360

TCAATAGAAG AAAAATTCAA CGCAAAAGGT GAATTATCTG AAAAACAAT ACTAAGAGCA     420

AACGGAACCA GGCTTGAATA CACAGAAATA AAAAGCGATG GAACCGGAAA AGCTAAAGAA     480

GCTTTAAAAG ACTTTGCTCT TGAAGGAACT CTAGCTGCCG ACAAAACAAC ATTGAAAGTT     540
```

```
ACAGAAGGCA CTGTTGTTTT AAGCAAACAC ATTCCAAACT CTGGAGAAAT AACAGTTGAG      600

CTTAATGACT CTAACTCTAC TCAGGCTACT AAAAAAACTG GAAAATGGGA TTCAAATACT      660

TCCACTTTAA CAATTAGTGT GAATAGCAAA AAAACTAAAA ACATTGTATT TACAAAAGAA      720

GACACAATAA CAGTACAAAA ATACGACTCA GCAGGCACCA ATCTAGAAGG CAACGCAGTC      780

GAAATTAAAA CACTTGATGA ACTTAAAAAC GCTTTAAAAT A                          821
```

(2) INFORMATION FOR SEQ ID NO:136:

(i) SEQUENCE CHARACTERISTICS:
        (A) LENGTH: 821 base pairs
        (B) TYPE: nucleic acid
        (C) STRANDEDNESS: double
        (D) TOPOLOGY: linear (xi) SEQUENCE DESCRIPTION: SEQ ID NO:136:

```
ATGAAAAAAT ATTTATTGGG AATAGGTCTA ATATTAGCCT TAATAGCATG TAAGCAAAAT       60

GTTAGCAGCC TTGATGAAAA AAATAGCGTT TCAGTAGATT TACCTGGTGG AATGAAAGTT      120

CTTGTAAGTA AAGAAAAAGA CAAAGATGGT AAATACAGTC TAATGGCAAC AGTAGAAAAG      180

CTTGAGCTTA AAGGAACTTC TGATAAAAAC AACGGTTCTG GAACACTTGA AGGTGAAAAA      240

ACTGACAAAA GTAAAGTAAA ATTAACAATT GCTGAGGATC TAAGTAAAAC CACATTTGAA      300

ATCTTCAAAG AAGATGGCAA ACATTAGTA TCGAAAAAAG TAACCCTTAA AGACAAGTCA       360

TCAACAGAAG AAAAATTCAA CGAAAAGGGT GAAATATCTG AAAAAACAAT AGTAAGAGCA      420

AATGGAACCA GACTTGAATA CACAGACATA AAAAGCGATA AACCGGAAA AGCTAAAGAA       480

GTTTTAAAAG ACTTTACTCT TGAAGGAACT CTAGCTGCTG ACGGCAAAAC AACATTGAAA      540

GTTACAGAGG GCACTGTTAC TTTAAGCAAG AACATTTCAA AATCCGGAGA ATAACAGTT       600

GCACTTGATG ACACTGACTC TAGCGGCAAT AAAAAATCCG GAACATGGGA TTCAGGTACT      660

TCTACTTTAA CAATTAGTAA AAACAGACAA AAAACTAAAC AACTTGTATT CACAAAAGAA      720

GACACAATAA CAGTACAAAA CTACGACTCA GCAGGCACCA ATCTAGAAGG CAAAGCAGTC      780

GAAATTACAA CACTTAAAGA ACTTAAAAAC GCTTTAAAAT A                          821
```

(2) INFORMATION FOR SEQ ID NO:137:

(i) SEQUENCE CHARACTERISTICS:
        (A) LENGTH: 825 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..825

(xi) SEQUENCE DESCRIPTION: SEQ ID NO:137:

```
ATG AAA AAA TAT TTA TTG GGA ATA GGT CTA ATA TTA GCC TTA ATA GCA        48
Met Lys Lys Tyr Leu Leu Gly Ile Gly Leu Ile Leu Ala Leu Ile Ala
 1               5                  10                  15

TGT AAG CAA AAT GTT AGC AGC CTT GAT GAA AAA AAT AGC GTT TCA GTA        96
Cys Lys Gln Asn Val Ser Ser Leu Asp Glu Lys Asn Ser Val Ser Val
                 20                  25                  30

GAT TTA CCT GGT GGA ATG ACA GTT CTT GTA AGT AAA GAA AAA GAC AAA       144
Asp Leu Pro Gly Gly Met Thr Val Leu Val Ser Lys Glu Lys Asp Lys
             35                  40                  45

GAC GGT AAA TAC AGT CTA GAG GCA ACA GTA GAC AAG CTT GAG CTT AAA       192
```

```
                Asp Gly Lys Tyr Ser Leu Glu Ala Thr Val Asp Lys Leu Glu Leu Lys
                 50                  55                  60

GGA ACT TCT GAT AAA AAC AAC GGT TCT GGA ACA CTT GAA GGT GAA AAA                240
Gly Thr Ser Asp Lys Asn Asn Gly Ser Gly Thr Leu Glu Gly Glu Lys
 65                  70                  75                  80

ACT GAC AAA AGT AAA GTA AAA TTA ACA ATT GCT GAT GAC CTA AGT CAA                288
Thr Asp Lys Ser Lys Val Lys Leu Thr Ile Ala Asp Asp Leu Ser Gln
                 85                  90                  95

ACT AAA TTT GAA ATT TTC AAA GAA GAT GCC AAA ACA TTA GTA TCA AAA                336
Thr Lys Phe Glu Ile Phe Lys Glu Asp Ala Lys Thr Leu Val Ser Lys
            100                 105                 110

AAA GTA ACC CTT AAA GAC AAG TCA TCA ACA GAA GAA AAA TTC AAC GAA                384
Lys Val Thr Leu Lys Asp Lys Ser Ser Thr Glu Glu Lys Phe Asn Glu
            115                 120                 125

AAG GGT GAA ACA TCT GAA AAA ACA ATA GTA AGA GCA AAT GGA ACC AGA                432
Lys Gly Glu Thr Ser Glu Lys Thr Ile Val Arg Ala Asn Gly Thr Arg
        130                 135                 140

CTT GAA TAC ACA GAC ATA AAA AGC GAT GGA TCC GGA AAA GCT AAA GAA                480
Leu Glu Tyr Thr Asp Ile Lys Ser Asp Gly Ser Gly Lys Ala Lys Glu
145                 150                 155                 160

GTT TTA AAA GAC TTT ACT CTT GAA GGA ACT CTA GCT GCT GAC GGC AAA                528
Val Leu Lys Asp Phe Thr Leu Glu Gly Thr Leu Ala Ala Asp Gly Lys
                165                 170                 175

ACA ACA TTG AAA GTT ACA GAA GGC ACT GTT GTT TTA AGC AAG AAC ATT                576
Thr Thr Leu Lys Val Thr Glu Gly Thr Val Val Leu Ser Lys Asn Ile
            180                 185                 190

TTA AAA TCC GGA GAA ATA ACA GTT GCA CTT GAT GAC TCT GAC ACT ACT                624
Leu Lys Ser Gly Glu Ile Thr Val Ala Leu Asp Asp Ser Asp Thr Thr
            195                 200                 205

CAG GCT ACT AAA AAA ACT GGA AAA TGG GAT TCA AAT ACT TCC ACT TTA                672
Gln Ala Thr Lys Lys Thr Gly Lys Trp Asp Ser Asn Thr Ser Thr Leu
        210                 215                 220

ACA ATT AGT GTG AAT AGC AAA AAA ACT AAA AAC ATT GTA TTT ACA AAA                720
Thr Ile Ser Val Asn Ser Lys Lys Thr Lys Asn Ile Val Phe Thr Lys
225                 230                 235                 240

GAA GAC ACA ATA ACA GTA CAA AAA TAC GAC TCA GCA GGC ACC AAT CTA                768
Glu Asp Thr Ile Thr Val Gln Lys Tyr Asp Ser Ala Gly Thr Asn Leu
                245                 250                 255

GAA GGC AAC GCA GTC GAA ATT AAA ACA CTT GAT GAA CTT AAA AAC GCT                816
Glu Gly Asn Ala Val Glu Ile Lys Thr Leu Asp Glu Leu Lys Asn Ala
            260                 265                 270

TTA AAA TAA                                                                    825
Leu Lys
        275

(2) INFORMATION FOR SEQ ID NO:138:

(i) SEQUENCE CHARACTERISTICS:
        (A) LENGTH: 274 amino acids
        (B) TYPE: amino acid
        (D) TOPOLOGY: linear (ii) MOLECULE TYPE: protein (xi) SEQUENCE DESCRIPTION: SEQ ID NO:138:

Met Lys Lys Tyr Leu Leu Gly Ile Gly Leu Ile Leu Ala Leu Ile Ala
  1               5                  10                  15

Cys Lys Gln Asn Val Ser Ser Leu Asp Glu Lys Asn Ser Val Ser Val
                 20                  25                  30

Asp Leu Pro Gly Gly Met Thr Val Leu Val Ser Lys Glu Lys Asp Lys
            35                  40                  45
```

```
Asp Gly Lys Tyr Ser Leu Glu Ala Thr Val Asp Lys Leu Glu Leu Lys
        50                  55                  60

Gly Thr Ser Asp Lys Asn Asn Gly Ser Gly Thr Leu Glu Gly Glu Lys
 65                  70                  75                  80

Thr Asp Lys Ser Lys Val Lys Leu Thr Ile Ala Asp Asp Leu Ser Gln
                85                  90                  95

Thr Lys Phe Glu Ile Phe Lys Glu Asp Ala Lys Thr Leu Val Ser Lys
            100                 105                 110

Lys Val Thr Leu Lys Asp Lys Ser Ser Thr Glu Glu Lys Phe Asn Glu
            115                 120                 125

Lys Gly Glu Thr Ser Glu Lys Thr Ile Val Arg Ala Asn Gly Thr Arg
    130                 135                 140

Leu Glu Tyr Thr Asp Ile Lys Ser Asp Gly Ser Gly Lys Ala Lys Glu
145                 150                 155                 160

Val Leu Lys Asp Phe Thr Leu Glu Gly Thr Leu Ala Ala Asp Gly Lys
                165                 170                 175

Thr Thr Leu Lys Val Thr Glu Gly Thr Val Val Leu Ser Lys Asn Ile
            180                 185                 190

Leu Lys Ser Gly Glu Ile Thr Val Ala Leu Asp Asp Ser Asp Thr Thr
    195                 200                 205

Gln Ala Thr Lys Lys Thr Gly Lys Trp Asp Ser Asn Thr Ser Thr Leu
210                 215                 220

Thr Ile Ser Val Asn Ser Lys Leu Thr Lys Asn Ile Val Phe Thr Lys
225                 230                 235                 240

Glu Asp Thr Ile Thr Val Gln Lys Tyr Asp Ser Ala Gly Thr Asn Leu
                245                 250                 255

Glu Gly Asn Ala Val Glu Ile Lys Thr Leu Asp Glu Leu Lys Asn Ala
            260                 265                 270

Leu Lys
```

(2) INFORMATION FOR SEQ ID NO:139:

(i) SEQUENCE CHARACTERISTICS:
        (A) LENGTH: 822 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..822

(xi) SEQUENCE DESCRIPTION: SEQ ID NO:139:

```
ATG AAA AAA TAT TTA TTG GGA ATA GGT CTA ATA TTA GCC TTA ATA GCA      48
Met Lys Lys Tyr Leu Leu Gly Ile Gly Leu Ile Leu Ala Leu Ile Ala
 1               5                  10                  15

TGC AAG CAA AAT GTT AGC AGC CTT GAT GAA AAA AAC AGC GCT TCA GTA      96
Cys Lys Gln Asn Val Ser Ser Leu Asp Glu Lys Asn Ser Ala Ser Val
            20                  25                  30

GAT TTG CCT GGT GAG ATG AAA GTT CTT GTA AGT AAA GAA AAA GAC AAA     144
Asp Leu Pro Gly Glu Met Lys Val Leu Val Ser Lys Glu Lys Asp Lys
        35                  40                  45

GAC GGT AAG TAC AGT CTA AAG GCA ACA GTA GAC AAG ATT GAG CTA AAA     192
Asp Gly Lys Tyr Ser Leu Lys Ala Thr Val Asp Lys Ile Glu Leu Lys
 50                  55                  60
```

```
GGA ACT TCT GAT AAA GAC AAT GGT TCT GGA GTG CTT GAA GGT ACA AAA         240
Gly Thr Ser Asp Lys Asp Asn Gly Ser Gly Val Leu Glu Gly Thr Lys
 65              70                  75                  80

GAT GAC AAA AGT AAA GCA AAA TTA ACA ATT GCT GAC GAT CTA AGT AAA         288
Asp Asp Lys Ser Lys Ala Lys Leu Thr Ile Ala Asp Asp Leu Ser Lys
                 85                  90                  95

ACC ACA TTC GAA CTT TTA AAA GAA GAT GGC AAA ACA TTA GTG TCA AGA         336
Thr Thr Phe Glu Leu Leu Lys Glu Asp Gly Lys Thr Leu Val Ser Arg
            100                 105                 110

AAA GTA AGT TCT AGA GAC AAA ACA TCA ACA GAT GAA ATG TTC AAT GAA         384
Lys Val Ser Ser Arg Asp Lys Thr Ser Thr Asp Glu Met Phe Asn Glu
        115                 120                 125

AAA GGT GAA TTG TCT GCA AAA ACC ATG ACA AGA GAA AAT GGA ACC AAA         432
Lys Gly Glu Leu Ser Ala Lys Thr Met Thr Arg Glu Asn Gly Thr Lys
130                 135                 140

CTT GAA TAT ACA GAA ATG AAA AGC GAT GGA ACC GGA AAA GCT AAA GAA         480
Leu Glu Tyr Thr Glu Met Lys Ser Asp Gly Thr Gly Lys Ala Lys Glu
145                 150                 155                 160

GTT TTA AAA AAG TTT ACT CTT GAA GGA AAA GTA GCT AAT GAT AAA GTA         528
Val Leu Lys Lys Phe Thr Leu Glu Gly Lys Val Ala Asn Asp Lys Val
                165                 170                 175

ACA TTG GAA GTA AAA GAA GGA ACC GTT ACT TTA AGT AAG GAA ATT GCA         576
Thr Leu Glu Val Lys Glu Gly Thr Val Thr Leu Ser Lys Glu Ile Ala
            180                 185                 190

AAA TCT GGA GAA GTA ACA GTT GCT CTT AAT GAC ACT AAC ACT ACT CAG         624
Lys Ser Gly Glu Val Thr Val Ala Leu Asn Asp Thr Asn Thr Thr Gln
        195                 200                 205

GCT ACT AAA AAA ACT GGC GCA TGG GAT TCA AAA ACT TCT ACT TTA ACA         672
Ala Thr Lys Lys Thr Gly Ala Trp Asp Ser Lys Thr Ser Thr Leu Thr
210                 215                 220

ATT AGT GTT AAC AGC AAA AAA ACT ACA CAA CTT GTG TTT ACT AAA CAA         720
Ile Ser Val Asn Ser Lys Lys Thr Thr Gln Leu Val Phe Thr Lys Gln
225                 230                 235                 240

GAC ACA ATA ACT GTA CAA AAA TAC GAC TCC GCA GGT ACC AAT TTA GAA         768
Asp Thr Ile Thr Val Gln Lys Tyr Asp Ser Ala Gly Thr Asn Leu Glu
                245                 250                 255

GGC ACA GCA GTC GAA ATT AAA ACA CTT GAT GAA CTT AAA AAC GCT TTA         816
Gly Thr Ala Val Glu Ile Lys Thr Leu Asp Glu Leu Lys Asn Ala Leu
            260                 265                 270

AAA TAA                                                                  822
Lys (2) INFORMATION FOR SEQ ID NO:140:

(i) SEQUENCE CHARACTERISTICS:
        (A) LENGTH: 273 amino acids
        (B) TYPE: amino acid
        (D) TOPOLOGY: linear (ii) MOLECULE TYPE: protein (xi) SEQUENCE DESCRIPTION: SEQ ID NO:140:

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Ala Ser Val
                20                  25                  30

Asp Leu Pro Gly Glu Met Lys Val Leu Val Ser Lys Glu Lys Asp Lys
            35                  40                  45

Asp Gly Lys Tyr Ser Leu Lys Ala Thr Val Asp Lys Ile Glu Leu Lys
        50                  55                  60
```

```
Gly Thr Ser Asp Lys Asp Asn Gly Ser Gly Val Leu Glu Gly Thr Lys
 65                  70                  75                  80

Asp Asp Lys Ser Lys Ala Lys Leu Thr Ile Ala Asp Asp Leu Ser Lys
                 85                  90                  95

Thr Thr Phe Glu Leu Leu Lys Glu Asp Gly Lys Thr Leu Val Ser Arg
            100                 105                 110

Lys Val Ser Ser Arg Asp Lys Ser Thr Asp Glu Met Phe Asn Glu
        115                 120                 125

Lys Gly Glu Leu Ser Ala Lys Thr Met Thr Arg Glu Asn Gly Thr Lys
    130                 135                 140

Leu Glu Tyr Thr Glu Met Lys Ser Asp Gly Thr Gly Lys Ala Lys Glu
145                 150                 155                 160

Val Leu Lys Lys Phe Thr Leu Glu Gly Lys Val Ala Asn Asp Lys Val
                165                 170                 175

Thr Leu Glu Val Lys Glu Gly Thr Val Thr Leu Ser Lys Glu Ile Ala
            180                 185                 190

Lys Ser Gly Glu Val Thr Val Ala Leu Asn Asp Thr Asn Thr Thr Gln
        195                 200                 205

Ala Thr Lys Lys Thr Gly Ala Trp Asp Ser Lys Thr Ser Thr Leu Thr
    210                 215                 220

Ile Ser Val Asn Ser Lys Lys Thr Thr Gln Leu Val Phe Thr Lys Gln
225                 230                 235                 240

Asp Thr Ile Thr Val Gln Lys Tyr Asp Ser Ala Gly Thr Asn Leu Glu
                245                 250                 255

Gly Thr Ala Val Glu Ile Lys Thr Leu Asp Glu Leu Lys Asn Ala Leu
            260                 265                 270

Lys (2) INFORMATION FOR SEQ ID NO:141:

(i) SEQUENCE CHARACTERISTICS:
        (A) LENGTH: 822 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..822

(xi) SEQUENCE DESCRIPTION: SEQ ID NO:141:

ATG AAA AAA TAT TTA TTG GGA ATA GGT CTA ATA TTA GCC TTA ATA GCA      48
Met Lys Lys Tyr Leu Leu Gly Ile Gly Leu Ile Leu Ala Leu Ile Ala
  1               5                  10                  15

TGC AAG CAA AAT GTT AGC AGC CTT GAT GAA AAA AAC AGC GCT TCA GTA      96
Cys Lys Gln Asn Val Ser Ser Leu Asp Glu Lys Asn Ser Ala Ser Val
             20                  25                  30

GAT TTG CCT GGT GAG ATG AAA GTT CTT GTA AGT AAA GAA AAA GAC AAA     144
Asp Leu Pro Gly Glu Met Lys Val Leu Val Ser Lys Glu Lys Asp Lys
         35                  40                  45

GAC GGT AAG TAC AGT CTA AAG GCA ACA GTA GAC AAG ATT GAG CTA AAA     192
Asp Gly Lys Tyr Ser Leu Lys Ala Thr Val Asp Lys Ile Glu Leu Lys
     50                  55                  60

GGA ACT TCT GAT AAA GAC AAT GGT TCT GGA GTG CTT GAA GGT ACA AAA     240
Gly Thr Ser Asp Lys Asp Asn Gly Ser Gly Val Leu Glu Gly Thr Lys
 65                  70                  75                  80
```

```
GAT GAC AAA AGT AAA GCA AAA TTA ACA ATT GCT GAC GAT CTA AGT AAA      288
Asp Asp Lys Ser Lys Ala Lys Leu Thr Ile Ala Asp Asp Leu Ser Lys
            85                  90                  95

ACC ACA TTC GAA CTT TTA AAA GAA GAT GGC AAA ACA TTA GTG TCA AGA      336
Thr Thr Phe Glu Leu Leu Lys Glu Asp Gly Lys Thr Leu Val Ser Arg
       100                 105                 110

AAA GTA AGT TCT AGA GAC AAA ACA TCA ACA GAT GAA ATG TTC AAT GAA      384
Lys Val Ser Ser Arg Asp Lys Thr Ser Thr Asp Glu Met Phe Asn Glu
            115                 120                 125

AAA GGT GAA TTG TCT GCA AAA ACC ATG ACA AGA GAA AAT GGA ACC AAA      432
Lys Gly Glu Leu Ser Ala Lys Thr Met Thr Arg Glu Asn Gly Thr Lys
130                 135                 140

CTT GAA TAT ACA GAA ATG AAA AGC GAT GGA ACC GGA AAA GCT AAA GAA      480
Leu Glu Tyr Thr Glu Met Lys Ser Asp Gly Thr Gly Lys Ala Lys Glu
145                 150                 155                 160

GTT TTA AAA AAG TTT ACT CTT GAA GGA AAA GTA GCT AAT GAT AAA GTA      528
Val Leu Lys Lys Phe Thr Leu Glu Gly Lys Val Ala Asn Asp Lys Val
            165                 170                 175

ACA TTG GAA GTA AAA GAA GGA ACC GTT ACT TTA AGT AAG GAA ATT TCA      576
Thr Leu Glu Val Lys Glu Gly Thr Val Thr Leu Ser Lys Glu Ile Ser
            180                 185                 190

AAA TCT GGG GAA GTT TCA GTT GAA CTT AAT GAC ACT GAC AGT AGT GCT      624
Lys Ser Gly Glu Val Ser Val Glu Leu Asn Asp Thr Asp Ser Ser Ala
        195                 200                 205

GCT ACT AAA AAA ACT GCA GCT TGG AAT TCA AAA ACT TCC ACT TTA ACA      672
Ala Thr Lys Lys Thr Ala Ala Trp Asn Ser Lys Thr Ser Thr Leu Thr
    210                 215                 220

ATT AGT GTG AAT AGC CAA AAA ACC AAA AAC CTT GTA TTC ACA AAA GAA      720
Ile Ser Val Asn Ser Gln Lys Thr Lys Asn Leu Val Phe Thr Lys Glu
225                 230                 235                 240

GAC ACA ATA ACA GTA CAA AAA TAC GAC TCA GCA GGC ACC AAT CTA GAA      768
Asp Thr Ile Thr Val Gln Lys Tyr Asp Ser Ala Gly Thr Asn Leu Glu
            245                 250                 255

GGC AAA GCA GTC GAA ATT ACA ACA CTT AAA GAA CTT AAA AAC GCT TTA      816
Gly Lys Ala Val Glu Ile Thr Thr Leu Lys Glu Leu Lys Asn Ala Leu
            260                 265                 270

AAA TAA                                                              822
Lys (2) INFORMATION FOR SEQ ID NO:142:

(i) SEQUENCE CHARACTERISTICS:
        (A) LENGTH: 273 amino acids
        (B) TYPE: amino acid
        (D) TOPOLOGY: linear (ii) MOLECULE TYPE: protein (xi) SEQUENCE DESCRIPTION: SEQ ID NO:142:

Met Lys Lys Tyr Leu Leu Gly Ile Gly Leu Ile Leu Ala Leu Ile Ala
  1               5                  10                  15

Cys Lys Gln Asn Val Ser Ser Leu Asp Glu Lys Asn Ser Ala Ser Val
                 20                  25                  30

Asp Leu Pro Gly Glu Met Lys Val Leu Ser Lys Glu Lys Asp Lys
             35                  40                  45

Asp Gly Lys Tyr Ser Leu Lys Ala Thr Val Asp Lys Ile Glu Leu Lys
         50                  55                  60

Gly Thr Ser Asp Lys Asp Asn Gly Ser Gly Val Leu Glu Gly Thr Lys
 65                  70                  75                  80
```

```
Asp Asp Lys Ser Lys Ala Lys Leu Thr Ile Ala Asp Asp Leu Ser Lys
            85                  90                  95

Thr Thr Phe Glu Leu Leu Lys Glu Asp Gly Lys Thr Leu Val Ser Arg
           100                 105                 110

Lys Val Ser Ser Arg Asp Lys Thr Ser Thr Asp Glu Met Phe Asn Glu
           115                 120                 125

Lys Gly Glu Leu Ser Ala Lys Thr Met Thr Arg Glu Asn Gly Thr Lys
           130                 135                 140

Leu Glu Tyr Thr Glu Met Lys Ser Asp Gly Thr Gly Lys Ala Lys Glu
145                 150                 155                 160

Val Leu Lys Lys Phe Thr Leu Glu Gly Lys Val Ala Asn Asp Lys Val
               165                 170                 175

Thr Leu Glu Val Lys Glu Gly Thr Val Thr Leu Ser Lys Glu Ile Ser
           180                 185                 190

Lys Ser Gly Glu Val Ser Val Glu Leu Asn Asp Thr Asp Ser Ser Ala
           195                 200                 205

Ala Thr Lys Lys Thr Ala Ala Trp Asn Ser Lys Thr Ser Thr Leu Thr
           210                 215                 220

Ile Ser Val Asn Ser Gln Lys Thr Lys Asn Leu Val Phe Thr Lys Glu
225                 230                 235                 240

Asp Thr Ile Thr Val Gln Lys Tyr Asp Ser Ala Gly Thr Asn Leu Glu
               245                 250                 255

Gly Lys Ala Val Glu Ile Thr Thr Leu Lys Glu Leu Lys Asn Ala Leu
           260                 265                 270

Lys
```

(2) INFORMATION FOR SEQ ID NO:143:

(i) SEQUENCE CHARACTERISTICS:
        (A) LENGTH: 822 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..822

(xi) SEQUENCE DESCRIPTION: SEQ ID NO:143:

```
ATG AAA AAA TAT TTA TTG GGA ATA GGT CTA ATA TTA GCC TTA ATA GCA      48
Met Lys Lys Tyr Leu Leu Gly Ile Gly Leu Ile Leu Ala Leu Ile Ala
 1               5                  10                  15

TGT AAG CAA AAT GTT AGC AGC CTT GAC GAG AAA AAC AGC GTT TCA GTA      96
Cys Lys Gln Asn Val Ser Ser Leu Asp Glu Lys Asn Ser Val Ser Val
            20                  25                  30

GAT TTG CCT GGT GAA ATG AAA GTT CTT GTA AGC AAA GAA AAA AAC AAA     144
Asp Leu Pro Gly Glu Met Lys Val Leu Val Ser Lys Glu Lys Asn Lys
        35                  40                  45

GAC GGC AAG TAC GAT CTA ATT GCA ACA GTA GAC AAG CTT GAG CTT AAA     192
Asp Gly Lys Tyr Asp Leu Ile Ala Thr Val Asp Lys Leu Glu Leu Lys
    50                  55                  60

GGA ACT TCT GAT AAA AAC AAT GGA TCT GGA GTA CTT GAA GGC GTA AAA     240
Gly Thr Ser Asp Lys Asn Asn Gly Ser Gly Val Leu Glu Gly Val Lys
65                  70                  75                  80

GCT GAC AAA AGT AAA GTA AAA TTA ACA ATT TCT GAC GAT CTA GGT CAA     288
Ala Asp Lys Ser Lys Val Lys Leu Thr Ile Ser Asp Asp Leu Gly Gln
                85                  90                  95
```

```
ACC ACA CTT GAA GTT TTC AAA GAA GAT GGC AAA ACA CTA GTA TCA AAA        336
Thr Thr Leu Glu Val Phe Lys Glu Asp Gly Lys Thr Leu Val Ser Lys
            100                 105                 110

AAA GTA ACT TCC AAA GAC AAG TCA TCA ACA GAA GAA AAA TTC AAT GAA        384
Lys Val Thr Ser Lys Asp Lys Ser Ser Thr Glu Glu Lys Phe Asn Glu
            115                 120                 125

AAA GGT GAA GTA TCT GAA AAA ATA ATA ACA AGA GCA AAT GGA ACC AAA        432
Lys Gly Glu Val Ser Glu Lys Ile Ile Thr Arg Ala Asn Gly Thr Lys
130                 135                 140

CTT GAA TAT ACA GAA ATG AAA AGC GAT GGA ACC GGA AAA GCT AAA GAA        480
Leu Glu Tyr Thr Glu Met Lys Ser Asp Gly Thr Gly Lys Ala Lys Glu
145                 150                 155                 160

GTT TTA AAA AAG TTT ACT CTT GAA GGA AAA GTA GCT AAT GAT AAA GTA        528
Val Leu Lys Lys Phe Thr Leu Glu Gly Lys Val Ala Asn Asp Lys Val
                165                 170                 175

ACA TTG GAA GTA AAA GAA GGA ACC GTT ACT TTA AGT AAG GAA ATT TCA        576
Thr Leu Glu Val Lys Glu Gly Thr Val Thr Leu Ser Lys Glu Ile Ser
            180                 185                 190

AAA TCT GGG GAA GTT TCA GTT GAA CTT AAT GAC ACT GAC AGT AGT GCT        624
Lys Ser Gly Glu Val Ser Val Glu Leu Asn Asp Thr Asp Ser Ser Ala
            195                 200                 205

GCT ACT AAA AAA ACT GCA GCT TGG AAT TCA AAA ACT TCC ACT TTA ACA        672
Ala Thr Lys Lys Thr Ala Ala Trp Asn Ser Lys Thr Ser Thr Leu Thr
210                 215                 220

ATT AGT GTG AAT AGC CAA AAA ACC AAA AAC CTT GTA TTC ACA AAA GAA        720
Ile Ser Val Asn Ser Gln Lys Thr Lys Asn Leu Val Phe Thr Lys Glu
225                 230                 235                 240

GAC ACA ATA ACA GTA CAA AAA TAC GAC TCA GCA GGC ACC AAT CTA GAA        768
Asp Thr Ile Thr Val Gln Lys Tyr Asp Ser Ala Gly Thr Asn Leu Glu
                245                 250                 255

GGC AAA GCA GTC GAA ATT ACA ACA CTT AAA GAA CTT AAA AAC GCT TTA        816
Gly Lys Ala Val Glu Ile Thr Thr Leu Lys Glu Leu Lys Asn Ala Leu
            260                 265                 270

AAA TAA                                                                822
Lys (2) INFORMATION FOR SEQ ID NO:144:

(i) SEQUENCE CHARACTERISTICS:
        (A) LENGTH: 273 amino acids
        (B) TYPE: amino acid
        (D) TOPOLOGY: linear (ii) MOLECULE TYPE: protein (xi) SEQUENCE DESCRIPTION: SEQ ID NO:144:

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
                20                  25                  30

Asp Leu Pro Gly Glu Met Lys Val Leu Val Ser Lys Glu Lys Asn Lys
            35                  40                  45

Asp Gly Lys Tyr Asp Leu Ile Ala Thr Val Asp Lys Leu Glu Leu Lys
        50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
                100                 105                 110
```

-continued

```
Lys Val Thr Ser Lys Asp Lys Ser Ser Thr Glu Glu Lys Phe Asn Glu
        115             120             125

Lys Gly Glu Val Ser Glu Lys Ile Ile Thr Arg Ala Asn Gly Thr Lys
        130             135             140

Leu Glu Tyr Thr Glu Met Lys Ser Asp Gly Thr Gly Lys Ala Lys Glu
145             150             155                     160

Val Leu Lys Lys Phe Thr Leu Glu Gly Lys Val Ala Asn Asp Lys Val
                165             170                 175

Thr Leu Glu Val Lys Glu Gly Thr Val Thr Leu Ser Lys Glu Ile Ser
            180             185             190

Lys Ser Gly Glu Val Ser Val Glu Leu Asn Asp Thr Asp Ser Ser Ala
        195             200             205

Ala Thr Lys Lys Thr Ala Ala Trp Asn Ser Lys Thr Ser Thr Leu Thr
    210             215             220

Ile Ser Val Asn Ser Gln Lys Thr Lys Asn Leu Val Phe Thr Lys Glu
225             230             235             240

Asp Thr Ile Thr Val Gln Lys Tyr Asp Ser Ala Gly Thr Asn Leu Glu
                245             250             255

Gly Lys Ala Val Glu Ile Thr Thr Leu Lys Glu Leu Lys Asn Ala Leu
            260             265             270

Lys
```

CHIMERIC PROTEINS COMPRISING BORRELIA POLYPEPTIDES AND USES THEREFOR

RELATED APPLICATION

This application is a continuation-in-part of U.S. Ser. No. 08/148,191 filed Nov. 1, 1993, now abandoned. The entire teachings of this application are incorporated herein by reference.

GOVERNMENT SUPPORT

The work described herein was supported in part by grants from the Centers for Disease Control (U50/CCU206608), the National Institutes of Health (RO1AI32454), and the state of New York. The United States Government has certain rights in the invention.

BACKGROUND OF THE INVENTION

Lyme borreliosis is the most common tick-borne infectious disease in North America, Europe, and northern Asia. The causative bacterial agent of this disease, Borrelia burgdorferi, was first isolated and cultivated in 1982 (Burgdorferi, W. A. et al., Science 216: 1317–1319 (1982); Steere, A. R. et al., N. Engl. J. Med. 308: 733–740 (1983)). With that discovery, a wide array of clinical syndromes, described in both the European and American literature since the early 20th century, could be attributed to infection by B. burgdorferi (Afzelius, A., Acta Derm. Venereol. 2: 120–125 (1921); Bannwarth, A., Arch. Psychiatr. Nervenkrankh. 117: 161–185 (1944); Garin, C. and A. Bujadouz, J. Med. Lyon 71: 765–767 (1922); Herxheimer, K. and K. Hartmann, Arch. Dermatol. Syphilol. 61: 57–76, 255–300 (1902)).

The immune response to B. burgdorferi is characterized by an early, prominent, and persistent humoral response to the end of lagellar protein, p41 (fla), and to a protein constituent of the protoplasmic cylinder, p93 (Szczepanski, A., and J. L. Benach, Microbiol. Rev. 55:21 (1991)). The p41 flagellin antigen is an immunodominant protein; however, it shares significant homology with flagellins of other microorganisms and therefore is highly cross reactive. The p93 antigen is the largest immunodominant antigen of B. burgdorferi. Both the p41 and p93 proteins are physically cryptic antigens, sheathed from the immune system by an outer membrane whose major protein constituents are the outer surface proteins A and B (OspA and OspB). OspA is a basic lipoprotein of approximately 31 kd, which is encoded on a large linear plasmid along with OspB, a basic lipoprotein of approximately 34 kd (Szczepanski, A., and J. L. Benach, Microbiol. Rev. 55:21 (1991)). Analysis of isolates of B. burgdorferi obtained from North America and Europe has demonstrated that OspA has antigenic variability, and that several distinct groups can be serologically and genotypically defined (Wilske, B., et al., World J. Microbiol. 7: 130 (1991)). Other Borrelia proteins demonstrate similar antigenic variability. Surprisingly, the immune response to these outer surface proteins tends to occur late in the disease, if at all (Craft, J. E. et al., J. Clin Invest. 78: 934–939 (1986); Dattwyler, R. J. and B. J. Luft, Rheum. Clin. North Am. 15: 727–734 (1989)). Furthermore, patients acutely and chronically infected with B. burgdorferi respond variably to the different antigens, including OspA, OspB, OspC, OspD, p39, p41 and p93.

Vaccines against Lyme borreliosis have been attempted. Mice immunized with a recombinant form of OspA are protected from challenge with the same strain of B. burgdorferi from which the protein was obtained (Fikrig, E., et al., Science 250: 553–556 (1990)). Furthermore, passively transferred anti-OspA monoclonal antibodies (Mabs) have been shown to be protective in mice, and vaccination with a recombinant protein induced protective immunity against subsequent infection with the homologous strain of B.burgdorferi (Simon, M. M., et al., J. Infect. Dis. 164: 123 (1991)). Unfortunately, immunization with a protein from one strain does not necessarily confer resistance to a heterologous strain (Fikrig, E. et al., J. Immunol. 7: 2256–1160 (1992)), but rather, is limited to the homologous 'species' from which the protein was prepared. Furthermore, immunization with a single protein from a particular strain of Borrelia will not confer resistance to that strain in all individuals. There is considerable variation displayed in OspA and OspB, as well as p93, including the regions conferring antigenicity. Therefore, the degree and frequency of protection from vaccination with a protein from a single strain depend upon the response of the immune system to the particular variation, as well as the frequency of genetic variation in B. burgdorferi. Currently, a need exists for a vaccine which provides immunogenicity across species and to more epitopes within a species, as well as immunogenicity against more than one protein.

SUMMARY OF THE INVENTION

The current invention pertains to chimeric Borrelia proteins which include two or more antigenic Borrelia polypeptides which do not occur naturally (in nature) in the same protein in Borrelia, as well as the nucleic acids encoding such chimeric proteins. The antigenic polypeptides incorporated in the chimeric proteins are derived from any Borrelia protein from any strain of Borrelia, and include outer surface protein (Osp) A, OspB, OspC, OspD, p12, p39, p41, p66, and p93. The proteins from which the antigenic polypeptides are derived can be from the same strain of Borrelia, from different strains, or from combinations of proteins from the same and from different strains. If the proteins from which the antigenic polypeptides are derived are OspA or OspB, the antigenic polypeptides can be derived from either the portion of the OspA or OspB protein present between the amino terminus and the conserved tryptophan of the protein (referred to as a proximal portion), or the portion of the OspA or OspB protein present between the conserved tryptophan of the protein and the carboxy terminus (referred to as a distal portion). Particular chimeric proteins, and the nucleotide sequences encoding them, are set forth in FIGS. 23–37 and 43–46.

The chimeric proteins of the current invention provide antigenic polypeptides of a variety of Borrelia strains and/or proteins within a single protein. Such proteins are particularly useful in immunodiagostic assays to detect the presence of antibodies to native Borrelia in potentially infected individuals as well as to measure T-cell reactivity, and can therefore be used as immunodiagnostic reagents. The chimeric proteins of the current invention are additionally useful as vaccine immunogens against Borrelia infection.

For a better understanding of the present invention together with other and further objects, reference is made to the following description, taken together with the accompanying drawings.

BRIEF DESCRIPTION OF THE DRAWINGS

FIG. 2 is a comparison of the antigenic domains depicted in FIG. 1, for OspA in nine strains of *B. burgdorferi*.

FIG. 4 depicts the amino acid alignment of residues 200 through 220 for OspAs from strains B31 and K48 as well as for the site-directed mutants 613, 625, 640, 613/625, and 613/640. Arrow indicates Trp216. Amino acid changes are underlined.

FIG. 7A and FIG. 7B depict the nucleic acid sequence of OspA-B31 (SEQ ID NO. 6), and the encoded protein sequence (SEQ ID NO. 7).

FIG. 8A, FIG. 8B and FIG. 8C depict the nucleic acid sequence of OspA-K48 (SEQ ID NO. 8), and the encoded protein sequence (SEQ ID NO. 9).

FIG. 9A, FIG. 9B and FIG. 9C depict the nucleic acid sequence of OspA-PGau (SEQ ID NO. 10), and the encoded protein sequence (SEQ ID NO. 11).

FIG. 10A, FIG. 10B and FIG. 10C depict the nucleic acid sequence of OspA-25015 (SEQ ID NO. 12), and the encoded protein sequence (SEQ ID NO. 13).

FIG. 11A, FIG. 11B and FIG. 11C depict the nucleic acid sequence of OspB-B31 (SEQ ID NO. 21), and the encoded protein sequence (SEQ ID NO. 22).

FIG. 12A and FIG. 12B depict the nucleic acid sequence of OspC-B31 (SEQ ID NO. 29), and the encoded protein sequence (SEQ ID NO. 30).

FIG. 13A and FIG. 13B depict the nucleic acid sequence of OspC-K48 (SEQ ID NO. 31), and the encoded protein sequence (SEQ ID NO. 32).

FIG. 14A and FIG. 14B depict the nucleic acid sequence of OspC-PKo (SEQ ID NO. 33), and the encoded protein sequence (SEQ ID NO. 34).

FIG. 15A and FIG. 15B depict the nucleic acid sequence of OspC-pTrob (SEQ ID NO. 35) and the encoded protein sequence (SEQ ID NO. 36).

FIG. 16A, FIG. 16B, FIG. 16C, FIG. 16D and FIG. 16E depict the nucleic acid sequence of p93-B31 (SEQ ID NO. 65) and the encoded protein sequence (SEQ ID NO. 66).

FIG. 17 depicts the nucleic acid sequence of p93-K48 (SEQ ID NO. 67).

FIG. 18 depicts the nucleic acid sequence of p93-PBo (SEQ ID NO. 69).

FIG. 19 depicts the nucleic acid sequence of p93-pTrob (SEQ ID NO. 71).

FIG. 20 depicts the nucleic acid sequence of p93-pGau (SEQ ID NO. 73).

FIG. 21 depicts the nucleic acid sequence of p93-25015 (SEQ ID NO. 75).

FIG. 22 depicts the nucleic acid sequence of p93-pKo (SEQ ID NO. 77).

FIG. 23A, FIG. 23B and FIG. 23C depict the nucleic acid sequence of the OspA-K48/OspA-PGau chimer (SEQ ID NO. 85) and the encoded chimeric protein sequence (SEQ ID NO. 86).

FIG. 24A, FIG. 24B and FIG. 24C depict the nucleic acid sequence of the OspA-B31/OspA-PGau chimer (SEQ ID NO. 88) and the encoded chimeric protein sequence (SEQ ID NO. 89).

FIG. 25A and FIG. 25B depict the nucleic acid sequence of the OspA-B31/OspA-K48 chimer (SEQ ID NO. 91) and the encoded chimeric protein sequence (SEQ ID NO. 92).

FIG. 26A, FIG. 26B and FIG. 26C depict the nucleic acid sequence of the OspA-B31/OspA-25015 chimer (SEQ ID NO. 94) and the encoded chimeric protein sequence (SEQ ID NO. 95).

FIG. 27A, FIG. 27B and FIG. 27C depict the nucleic acid sequence of the OspA-K48/OspA-B31/OspA-K48 chimer (SEQ ID NO. 97) and the encoded chimeric protein sequence (SEQ ID NO. 98).

FIG. 28A, FIG. 28B and FIG. 28C depict the nucleic acid sequence of the OspA-B31/OspA-K48/OspA-B31/OspA-K48 chimer (SEQ ID NO. 100) and the encoded chimeric protein sequence (SEQ ID NO. 101).

FIG. 29A, FIG. 29B and FIG. 29C depict the nucleic acid sequence of the OspA-B31/OspB-B31 chimer (SEQ ID NO. 103) and the encoded chimeric protein sequence (SEQ ID NO. 104).

FIG. 30A, FIG. 30B, FIG. 30C and FIG. 30D depict the nucleic acid sequence of the OspA-B31/OspB-B31/OspC-B31 chimer (SEQ ID NO. 106) and the encoded chimeric protein sequence (SEQ ID NO. 107).

FIG. 31A, FIG. 31B, FIG. 31C and FIG. 31D depict the nucleic acid sequence of the OspC-B31/OspA-B31/OspB-B31 chimer (SEQ ID NO. 109) and the encoded chimeric protein sequence (SEQ ID NO. 110).

FIG. 32A, FIG. 32B, FIG. 32C, FIG. 32D and FIG. 32E depict the nucleic acid sequence of the OspA-B31/p93-B31 chimer (SEQ ID NO. 111) and the encoded chimeric protein sequence (SEQ ID NO. 112).

FIG. 33A, FIG. 33B, FIG. 33C and FIG. 33D depict the nucleic acid sequence of the OspB-B31/p41-B31 (122–234) chimer (SEQ ID NO. 113) and the encoded chimeric protein sequence (SEQ ID NO. 114).

FIG. 34A, FIG. 34B, FIG. 34C and FIG. 34D depict the nucleic acid sequence of the OspB-B31/p41-B31 (122–295) chimer (SEQ ID NO. 115) and the encoded chimeric protein sequence (SEQ ID NO. 116).

FIG. 35A, FIG. 35B and FIG. 35C depict the nucleic acid sequence of the OspB-B31/p41-B31 (140–234) chimer (SEQ ID NO. 117) and the encoded chimeric protein sequence (SEQ ID NO. 118).

FIG. 36A, FIG. 36B, FIG. 36C and 36D depict the nucleic acid sequence of the OspB-B31/p41-B31 (140–295) chimer (SEQ ID NO. 119) and the encoded chimeric protein sequence (SEQ ID NO. 120).

FIG. 37A, FIG. 37B, FIG. 37C, FIG. 37D and FIG. 37E depict the nucleic acid sequence of the OspB-B31/p41-B31 (122–234)/OspC-B31 chimer (SEQ ID NO. 121) and the encoded chimeric protein sequence (SEQ ID NO. 122).

FIG. 38A, FIG. 38B, FIG. 38C and FIG. 38D depict an alignment of the nucleic acid sequences for OspC-B31 (SEQ ID NO. 29), OspC-PKo (SEQ ID NO. 33), OspC-pTrob (SEQ ID NO. 35), and OspC-K48 (SEQ ID NO. 31). Nucleic acids which are identical to those in the lead nucleic acid sequence (here, OspC-B31) are represented by a period (.); differing nucleic acids are shown in lower case letters.

FIG. 39A, FIG. 39B, FIG. 39C and FIG. 39D depict an alignment of the nucleic acid sequences for OspD-pBO (SEQ ID NO. 123), OspD-PGau (SEq ID NO. 124), OspD-DK29 (SEQ ID NO. 125), and OspD-K48 (SEQ ID NO. 126). Nucleic acids which are identical to those in the lead nucleic acid sequence (here, OspD-pBo) are represented by a period (.); differing nucleic acids are shown in lower case letters.

FIG. 40A, FIG. 40B and FIG. 40C depict the nucleic acid sequence of p41-B31 (SEq ID NO. 127) and then encoded protein sequence (SEQ ID NO. 128).

FIG. 41A, FIG. 41B, FIG. 41C, FIG. 41D, FIG. 41E, FIG. 41F, FIG. 41G and FIG. 41H depict an alignment of the nucleic acid sequences for p41-B31 (SEQ ID NO. 127), p41-pKal (SEQ ID NO. 129), p41-PGau (SEQ ID NO. 51), p41-PBo (SEQ ID NO. 130), p41-DK29 (SEQ ID NO. 53), and p41-PKo (SEQ ID NO. 131). Nucleic acids which are identical to those in the lead nucleic acid sequence (here, p41-B31) are represented by a period (.); differing nucleic acids are shown in lower case letters.

FIG. 42A, FIG. 42B, FIG. 42C, FIG. 42D, FIG. 42E, FIG. 42F, FIG. 42G, FIG. 42H, FIG. 42I, FIG. 42J, FIG. 42K, FIG. 42L, FIG. 42M, FIG. 42N, FIG. 42O and FIG. 42P depict an alignment of the nucleic acid sequences for OspA-B31 (SEQ ID NO. 6), OspA-pKa1 (SEQ ID NO. 132), OspA-N40 (SEQ ID NO. 133), OspA-ZS7 (SEQ ID NO. 134), OspA-25015 (SEQ ID NO. 12), OspA-pTrob (SEQ ID NO. 135), OspA-K48 (SEQ ID NO. 8), OspA-Hei (SEQ ID NO. 136), OspA-DK29 (SEQ ID NO. 49), OSpA-Ip90 (SEQ ID NO. 50), OspA-pBo (Seq ID NO. 55), OspA-Ip3 (SEQ ID NO. 56), OspA-PKo (SEQ ID NO. 57), OspA-ACAI (SEQ ID NO. 58), and OspA-PGau (SEQ ID NO. 10). Nucleic acids which are identical to those in the lead nucleic acid sequence (here, OspA-B31) are represented by a period (.); differing nucleic acids are shown in lower case letters.

FIG. 43A and FIG. 43B depict the nucleic acid sequence of the OspA-Tro/OspA-Bo chimer (SEQ ID NO. 137) and the encoded chimeric protein sequence (SEQ ID NO. 138).

FIG. 44A and FIG. 44B depict the nucleic acid sequence of the OspA-PGau/OspA-Bo chimer (SEQ ID NO. 139) and the encoded chimeric protein sequence (SEQ ID NO. 140).

FIG. 45A and FIG. 45B depict the nucleic acid sequence of the OspA-B31/OspA-PGau/OspA-B31/OspA-K48 chimer (SEQ ID NO. 141) and the encoded chimeric protein sequence (SEQ ID NO. 142).

FIG. 46A and FIG. 46B depict the nucleic acid sequence of the OspA-PGau/OspA-B31/OspA-K48 chimer (SEQ ID NO. 143) and the encoded chimeric protein sequence (SEQ ID NO. 144).

DETAILED DESCRIPTION OF THE INVENTION

Figure 1:
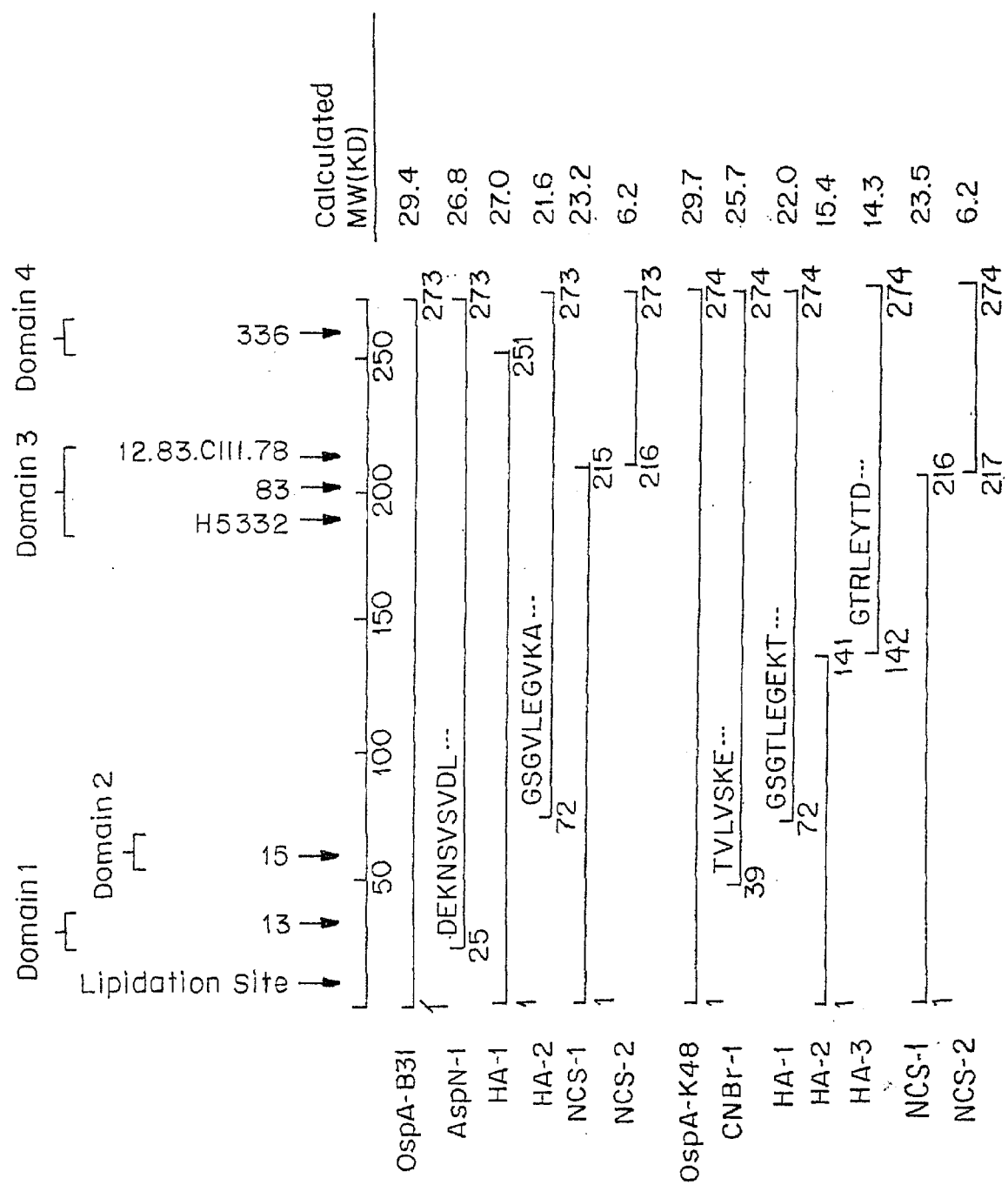
FIG. 1 summarizes peptides and antigenic domains localized by proteolytic and chemical fragmentation of OspA.

The current invention pertains to chimeric proteins comprising antigenic Borrelia polypeptides which do not occur in nature in the same Borrelia protein. The chimeric proteins are a combination of two or more antigenic polypeptides derived from Borrelia proteins. The antigenic polypeptides can be derived from different proteins from the same species of Borrelia, or different proteins from different Borrelia species, as well as from corresponding proteins from different species. As used herein, the term "chimeric protein" describes a protein comprising two or more polypeptides which are derived from corresponding and/or non-corresponding native Borrelia protein. A polypeptide "derived from" a native Borrelia protein is a polypeptide which has an amino acid sequence the same as an amino acid sequence present in a Borrelia protein, an amino acid sequence equivalent to the amino acid sequence of a naturally occurring Borrelia protein, or an amino acid sequence substantially similar to the amino acid sequence of a naturally occurring Borrelia protein (e.g., differing by few amino acids) such as when a nucleic acid encoding a protein is subjected to site-directed mutagenesis. "Corresponding" proteins are equivalent proteins from different species or strains of Borrelia, such as outer surface protein A (OspA) from strain B31 and OspA from strain K48. The invention additionally pertains to nucleic acids encoding these chimeric proteins.

As described below, Applicants have identified two separate antigenic domains of OspA and OspB which flank the sole conserved tryptophan present in OspA and in OspB. These domains share cross-reactivity with different genospecies of Borrelia. The precise amino acids responsible for antigenic variability were determined through site-directed mutagenesis, so that proteins with specific amino acid substitutions are available for the development of chimeric proteins. Furthermore, Applicants have identified immunologically important hypervariable domains in OspA proteins, as described below in Example 2. The first hypervariable domain of interest for chimeric proteins, Domain A, includes amino acid residues 120–140 of OspA, the second hypervariable domain, Domain B, includes residues 150–180 and the third hypervariable domain, Domain C, includes residues 200–216 or 217 (depending on the position of the sole conserved tryptophan residue in the OspA of that particular species of Borrelia) (see FIG. 3). In addition, Applicants have sequenced the genes for several Borrelia proteins.

These discoveries have aided in the development of novel recombinant Borrelia proteins which include two or more amino acid regions or sequences which do not occur in the same Borrelia protein in nature. The recombinant proteins comprise polypeptides from a variety of Borrelia proteins, including, but not limited to, OspA, OspB, ospC, OspD, p12, p39, p41, p66, and p93. Antigenically relevant polypeptides from each of a number of proteins are combined into a single chimeric protein.

In one embodiment of the current invention, chimers are now available which include antigenic polypeptides flanking a tryptophan residue. The antigenic polypeptides are derived from either the proximal portion from the tryptophan (the portion of the OspA or OspB protein present between the amino terminus and the conserved tryptophan of the protein), or the distal portion from the tryptophan (the portion of the OspA or OspB protein present between the conserved tryptophan of the protein and the carboxy terminus) in OspA and/or OspB. The resultant chimers can be OspA-OspA chimers (i.e., chimers incorporating polypeptides derived from OspA from different strains of Borrelia), OspA-OspB chimers, or OspB-OspB chimers, and are constructed such that amino acid residues amino-proximal to an invariant tryptophan are from one protein and residues carboxy-proximal to the invariant tryptophan are from the other protein. For example, one available chimer consists of a polypeptide derived from the amino-proximal region of OspA from strain B31, followed by the tryptophan residue, followed by a polypeptide derived from the carboxy-proximal region of OspA from strain K48 (SEQ ID NO. 92). Another available chimer includes a polypeptide derived from the amino-proximal region of OspA from strain B31, and a polypeptide derived from the carboxy-proximal region of OspB from strain B31 (SEQ ID NO. 104). If the polypeptide proximal to the tryptophan of these chimeric proteins is derived from OspA, the proximal polypeptide can be further subdivided into the three hypervariable domains (Domains A, B, and C), each of which can be derived from OspA from a different strain of Borrelia. These chimeric proteins can further comprise antigenic polypeptides from another protein, in addition to the antigenic polypeptides flanking the tryptophan residue.

In another embodiment of the current invention, chimeric proteins are available which incorporate antigenic domains of two or more Borrelia proteins, such as Osp proteins (Osp A, B, C and/or D) as well as p12, p39, p41, p66, and/or p93.

The chimers described herein can be produced so that they are highly soluble, hyper-produced in *E. coli,* and non-lipidated. In addition, the chimeric proteins can be designed to end in an affinity tag (His-tag) to facilitate purification. The recombinant proteins described herein have been constructed to maintain high levels of antigenicity. In addition, recombinant proteins specific for the various genospecies of Borrelia that cause Lyme disease are now available, because the genes from each of the major genospecies have been sequenced; the sequences are set forth below. These recombinant proteins with their novel biophysical and antigenic properties will be important diagnostic reagent and vaccine candidates.

The chimeric proteins of the current invention are advantageous in that they retain specific reactivity to monoclonal and polyclonal antibodies against wild-type Borrelia proteins, are immunogenic, and inhibit the growth or induce lysis of Borrelia in vitro. Furthermore, in some embodiments, the proteins provide antigenic domains of two or more Borrelia strains and/or proteins within a single protein. Such proteins are particularly useful in immunodiagostic assays. For example, proteins of the present invention can be used as reagents in assays to detect the presence of antibodies to native Borrelia in potentially infected individuals. These proteins can also be used as immunodiagnostic reagents, such as in dot blots, Western blots, enzyme linked immunosorbed assays, or agglutination assays. The chimeric proteins of the present invention can be produced by known techniques, such as by recombinant methodology, polymerase chain reaction, or mutagenesis.

Furthermore, the proteins of the current invention are useful as vaccine immunogens against Borrelia infection. Because Borrelia has been shown to be clonal, a protein comprising antigenic polypeptides from a variety of Borrelia proteins and/or species, will provide immunoprotection for a considerable time when used in a vaccine. The lack of significant intragenic recombination, a process which might rapidly generate novel epitopes with changed antigenic properties, ensures that Borrelia can only change antigenic type by accumulating mutational change, which is slow when compared with recombination in generating different antigenic types. The chimeric protein can be combined with a physiologically acceptable carrier and administered to a vertebrate animal through standard methods (e.g., intravenously or intramuscularly, for example).

The current invention is illustrated by the following Examples, which are not to be construed to be limiting in any way.

EXAMPLE 1

Purification of *Borrelia burgorferi* Outer Surface Protein A and Analysis of Antibody Binding Domains This example details a method for the purification of large amounts of native outer surface protein A (OspA) to homogeneity, and describes mapping of the antigenic specificities of several anti-OspA MAbs. OspA was purified to homogeneity by exploiting its resistance to trypsin digestion. Intrinsic labeling with $^{14}C$-palmitic acid confirmed that OspA was lipidated, and partial digestion established lipidation at the amino-terminal cysteine of the molecule.

The reactivity of seven anti-OspA murine monoclonal antibodies to nine different Borrelia isolates was ascertained by Western blot analysis. Purified OspA was fragmented by enzymatic or chemical cleavage, and the monoclonal antibodies were able to define four distinct immunogenic domains (see FIG. 1). Domain 3, which included residues 190–220 of OspA, was reactive with protective antibodies known to agglutinate the organism in vitro, and included distinct specificities, some of which were not restricted to a genotype of *B. burgdorferi.*

A. Purification of Native OspA

Detergent solubilization of *B. burgdorferi* strips the outer surface proteins and yields partially-purified preparations containing both OspA and outer surface protein B (Osp B) (Barbour, A. G. et al., *Infect. Immun.* 52 (5): 549–554 (1986); Coleman, J. L. and J. L. Benach, *J Infect. Dis.* 155 (4): 756–765 (1987); Cunningham, T. M. et al., *Ann. NY Acad. Sci.* 539: 376–378 (1988); Brandt, M. E. et al., *Infect. Immun.* 58: 983–991 (1990); Sambri, V. and R. Cevenini, *Microbiol.* 14:307–314 (1991)). Although both OspA and OspB are sensitive to proteinase K digestion, in contrast to OspB, OspA is resistant to cleavage by trypsin (Dunn, J. et al., *Prot. Exp. Purif.* 1: 159–168 (1990); Barbour, A. G. et al., *Infect. Immun.* 45:94–100 (1984)). The relative insensitivity to trypsin is surprising in view of the fact that Osp A has a high (16% for B31) lysine content, and may relate to the relative configuration of Osp A and B in the outer membrane.

Intrinsic Radiolabeling of Borrelia

Labeling for lipoproteins was performed as described by Brandt et al. (*Infect. Immun.* 58:983–991 (1990)). $^{14}C$-palmitic acid (ICN, Irvine, Calif.) was added to the BSK II media to a final concentration of 0.5 μCi per milliliter (ml). Organisms were cultured at 34° C. in this medium until a density of $10^8$ cells per ml was achieved.

Purification of OspA Protein from Borrelia Strain B31

*Borrelia burgdorferi,* either $^{14}C$-palmitic acid-labeled or unlabeled, were harvested and washed as described (Brandt, M. E. et al., *Infect. Immun.* 58:983–991 (1990)). Whole organisms were trypsinized according to the protocol of Barbour et al. (*Infect. Immun.* 45:94–100 (1984)) with some modifications. The pellet was suspended in phosphate buffered saline (PBS, 10 mM, pH 7.2), containing 0.8% tosyl-L-phenylalanine chloromethyl ketone (TPCK)-treated trypsin (Sigma, St. Louis, Mo.), the latter at a ratio of 1 μg per $10^8$ cells. Reaction was carried out at 25° C. for 1 hour, following which the cells were centrifuged. The pellet was washed in PBS with 100 μg/ml phenylmethylsulfonyl fluoride (PMSF). Triton X-114 partitioning of the pellet was carried out as described by Brandt et al. (*Infect. Immun.* 58:983–991 (1990)). Following trypsin treatment, cells were resuspended in ice-cold 2% (v/v) Triton X-114 in PBS at $10^9$ cells per ml. The suspension was rotated overnight at 4° C., and the insoluble fraction removed as a pellet after centrifugation at 10,000×g for 15 minutes at 4° C. The supernatant (soluble fraction) was incubated at 37° C. for 15 minutes and centrifuged at room temperature at 1000×g for 15 minutes to separate the aqueous and detergent phases. The aqueous phase was decanted, and ice cold PBS added to the lower Triton phase, mixed, warmed to 37° C., and again centrifuged at 1000×g for 15 minutes. Washing was repeated twice more. Finally, detergent was removed from the preparation using a spin column of Bio-beads SM2 (BioRad, Melville, N.Y.) as described (Holloway, P. W., *Anal. Biochem.* 53:304–308 (1973)).

Ion exchange chromatography was carried out as described by Dunn et al. (*Prot. Exp. Purif.* 1: 159–168 (1990)) with minor modifications. Crude OspA was dissolved in buffer A (1% Triton X-100, 10 mM phosphate buffer (pH 5.0)) and loaded onto a SP Sepharose resin (Pharmacia, Piscataway, N.J.), pre-equilibrated with buffer A at 25° C. After washing the column with 10 bed-volumes of buffer A, the bound OspA was eluted with buffer B (1% Triton X-100, 10 mM phosphate buffer (pH 8.0)). OspA fractions were detected by protein assay using the BCA method (Pierce, Rockford, Ill.), or as radioactivity when intrinsically labeled material was fractionated. Triton X-100 was removed using a spin column of Bio-beads SM2.

This method purifies OspA from an outer surface membrane preparation. In the absence of trypsin-treatment, OspA and B were the major components of the soluble fraction obtained after Triton partitioning of strain B31. In contrast, when Triton extraction was carried out after trypsin-treatment, the OspB band is not seen. Further purification of OspA-B31 on a SP Sepharose column resulted in a single band by SDS-PAGE. The yield following removal of detergent was approximately 2 mg per liter of culture. This method of purification of OspA, as described herein for strain B31, can be used for other isolates of Borrelia as well. For strains such as strain K48, which lack OspB, trypsin treatment can be omitted.

Lipidation site of OspA-B31

$^{14}$C-palmitic acid labeled OspA from strain B31 was purified as described above and partially digested with endoproteinase Asp-N (data not shown). Following digestion, a new band of lower molecular weight was apparent by SDS-PAGE, found by direct amino-terminal sequencing to begin at $Asp_{25}$. This band had no trace of radioactivity by autoradiography (data not shown). OspA and B contain a signal sequence (L-X-Y-C) similar to the consensus described for lipoproteins of *E. coli,* and it has been predicted that the lipidation site of OspA and B should be the amino-terminal cysteine (Brandt, M. E. et al., *Infect. Immun* 58: 983–991 (1990)). The results presented herein support this prediction.

B. Comparison of OspA Antibody Binding Regions in Nine Strains of *Borrelia burgdorferi*

The availability of the amino acid sequenced for OspA from a number of different isolates, combined with peptide mapping and Western blot analysis, permitted the identification of the antigenic domains recognized by monoclonal antibodies (MAbs) and allowed inference of the key amino acid residues responsible for specific antibody reactivity.

Strains of *Borrelia burgdorferi*

Nine strains of Borrelia, including seven European strains and two North American strains, were used in this study of antibody binding domains of several proteins. Information concerning the strains is summarized in Table I, below.

TABLE I

Representative Borrelia Strains

| Strain | Location and Source | Reference for Strain |
| --- | --- | --- |
| K48 | Czechoslovakia, *Ixodes ricinus* | none |
| PGau | Germany, human ACA | Wilske, B. et al., J. Clin. Microbiol. 32:340–350 (1993) |
| DK29 | Denmark, human EM | Wilske, B. et al. |
| PKo | Germany, human EM | Wilske, B. et al. |
| PTrob | Germany, human skin | Wilske, B. et al. |
| Ip3 | Khabarovsk, Russia, *I. persulcatus* | Asbrink, E. et al., Acta Derm. Venereol. 64: 506–512 (1984) |
| Ip90 | Khabarovsk, Russia, *I. persulcatus* | Asbrink, E. et al. |
| 25015 | Millbrook, NY, *I. persulcatus* | Barbour, A. G. et al., Curr. Microbiol. 8:123–126 (1983) |
| B31 | Shelter Island, NY, *I. scapularis* | Luft, B. J. et al., Infect. Immun. 60: 4309–4321 (1992); ATCC 35210 |
| PKa1 | Germany, human CSF | Wilske, B. et al. |
| ZS7 | Freiburg, Germany, *I. ricinus* | Wallich, R. et al., Nucl. Acids Res. 17: 8864 (1989) |
| N40 | Westchester Co., NY | Fikrig, E. et al., Science 250:553–556 (1990) |
| PHei | Germany, human CSF | Wilske, B. et al. |
| ACAI | Sweden, human ACA | Luft, B. J. et al., FEMS Microbiol. Lett. 93:73–68 (1992) |
| PBo | Germany, human CSF | Wilske, B. et al. |

ACA = patient with acrodermatitis chronica atrophicans;
EM = patient with erythema migrans;
CSF = cerebrospinal fluid of patient with Lyme disease Strains K48, PGau and DK29 were supplied by R. Johnson, University of Minnesota; PKo and pTrob were provided by B. Wilske and V. Preac-Mursic of the Pettenkhofer Institute, Munich, Germany; and Ip3 and Ip90 were supplied by L. Mayer of the Center for Disease Control, Atlanta, Ga. The North American strains included strain 25015, provided by J. Anderson of the Connecticut Department of Agriculture; and strain B31 (ATCC 35210).

Monoclonal Antibodies

Seven monoclonal antibodies (MAbs) were utilized in this study. Five of the MAbs (12, 13, 15, 83 and 336) were produced from hybridomas cloned and subcloned as previously described (Schubach, W. H., et al., *Infect. Immun.* 59(6):1911–1915 (1991)). MAb H5332 (Barbour, A. G. et al., *Infect. Immun.* 41:795–804 (1983)) was a gift from Drs. Alan Barbour, University of Texas, and MAb CIII.78 (Sears, J. E. et al., *J. Immunol.* 147(6):1995–2000 (1991)) was a gift from Richard A. Flavell, Yale University. MAbs 12 and 15 were raised against whole sonicated B3; MAb 336 was produced against whole PGau; and MAbs 13 and 83 were raised to a truncated form of OspA cloned from the K48 strain and expressed in *E. coli* using the T7 RNA polymerase system (McGrath, B. C. et al., *Vaccines,* Cold Spring Harbor Laboratory Press, Plainview, N.Y., pp. 365–370 (1993)). All MAbs were typed as being Immunoglobulin G (IgG).

Methods of Protein Cleavage, Western Blotting, and Amino-Terminal Sequencing

Prediction of the various cleavage sites was achieved by knowledge of the primary amino acid sequence derived from the full nucleotide sequences of OspA, many of which are currently available (see Table II, below). Cleavage sites can also be predicted based on the peptide sequence of OspA, which can be determined by standard techniques after isolation and purification of OspA by the method described above. Cleavage of several OspA isolates was conducted to determine the localization of monoclonal antibody binding of the proteins.

Hydroxylamine-HCl (HA), N-chlorosuccinimide (NCS), and cyanogen bromide cleavage of OspA followed the methods described by Bornstein (*Biochem.* 9 (12) :2408–2421 (1970)), Shechter et al., (*Biochem.* 15 (23) :5071–5075 (1976)), and Gross (in Hirs, C. H. W. (ed): *Methods in Enzymology,* (N. Y. Acad. Press), 11:238–255 (1967)) respectively. Protease cleavage by endoproteinase, Asp-N (Boehringer Mannheim, Indianapolis, Ind.), was performed as described by Cleveland D. W. et al., (*J. Biol. Chem.* 252:1102–1106 (1977)). Ten micrograms of OspA were used for each reaction. The ratio of enzyme to OspA was approximately 1 to 10 (w/w).

Proteins and peptides generated by cleavage were separated by SDS-polyacrylamide gel electrophoresis (SDS-PAGE) (Laemmli, U. K., *Nature* (London) 227:680–685 (1970)), and electroblotted onto immobilon Polyvinylidine Difluoride (PVDF) membranes (Ploskal, M. G. et al., *Biotechniques* 4:272–283 (1986)). They were detected by amido black staining or by immunostaining with murine MAbs, followed by alkaline phosphatase-conjugated goat antimouse IgG. Specific binding was detected using a 5-bromo-4-chloro-3-indolylphosphate (BCIP)/nitroblue tetrazolium (NBT) developer system (KPL Inc., Gathersburg, Md.).

In addition, amino-terminal amino acid sequence analysis was carried out on several cleavage products, as described by Luft et al. (*Infect. Immun.* 57:3637–3645 (1989)). Amido black stained bands were excised from PVDF blots and sequenced by Edman degradation using a Biosystems model 475A sequenator with model 120A PTH analyzer and model 900A control/data analyzer.

Cleavage Products of Outer Surface Protein A Isolates

Purified OspA-B31, labeled with $^{14}$C-palmitic acid, was fragmented with hydroxylamine-HCl (HA) into two peptides, designated HA1 and HA2 (data not shown). The HA1 band migrated at 27 KD and retained its radioactivity, indicating that the peptide included the lipidation site at the N-terminus of the molecule (data not shown). From the predicted cleavage point, HA1 should correspond to residues 1 to 251 of OspA-B31. HA2 had a MW of 21.6 KD by SDS-PAGE, with amino-terminal sequence analysis showing it to begin at Gly72, i.e. residues 72 to 273 of OspA-B31. By contrast, HA cleaved OspA-K48 into three peptides, designated HA1, HA2, and HA3 with apparent MWs of 22KD, 16 KD and 12 KD, respectively. Amino-terminal sequencing showed HA1 to start at Gly72, and HA3 at Gly142. HA2 was found to have a blocked amino-terminus, as was observed for the full-length OspA protein. HA1, 2 and 3 of OspA-K48 were predicted to be residues 72–274, 1 to 141 and 142 to 274, respectively.

N-Chlorosuccinimide (NCS) cleaves tryptophan (W), which is at residue 216 of OspA-B31 or residue 217 of OspA-K48 (data not shown). NCS cleaved OspA-B31 into 2 fragments, NCS1, with MW of 23 KD, residues 1–216 of the protein, and NCS2 with a MW of 6.2 KD, residues 217 to 273 (data not shown). Similarly, K48 OspA was divided into 2 pieces, NCS1 residues 1–217, and NCS2 residues 218 to 274 (data not shown).

Cleavage of OspA by cyanogen bromide (CNBr) occurs at the carboxy side of methionine, residue 39. The major fragment, CNBr1, has a MW of 25.7 KD, residues 39–274 by amino-terminal amino acid sequence analysis (data not shown). CNBr2 (about 4 KD) could not be visualized by amido black staining; instead, lightly stained bands of about 20 KD MW were seen. These bands reacted with anti-OspA MAbs, and most likely were degradation products due to cleavage by formic acid.

Determination of Antibody Binding Domains for Anti-OspA Monoclonal Antibodies

The cleavage products of OspA-B31 and OspA-K48 were analyzed by Western blot to assess their ability to bind to the six different MAbs. Preliminary Western blot analysis of the cleavage products demonstrated that strains K48 and DK29 have similar patterns of reactivity, as do IP3, PGau and PKo. The OspA of strain PTrob was immunologically distinct from the others, being recognized only by MAb 336. MAb 12 recognized only the two North American strains, B31 and 25015. When the isolates were separated into genogroups, it was remarkable that all the MAbs, except MAb 12, crossed over to react with multiple genogroups.

MAb12, specific for OspA-B31, bound to both HA1 and HA2 of OspA-B31. However, cleavage of OspA-B31 by NCS at residue Trp216 created fragments which did not react with MAb12, suggesting that the relevant domain is near or is structurally dependent upon the integrity of this residue (data not shown). MAb 13 bound only to OspA-K48, and to peptides containing the amino-terminus of that molecule (e.g. HA2; NCS1). It did not bind to CNBr1 residues 39 to 274. Thus the domain recognized by MAb13 is in the amino-terminal end of OspA-K48, near Met38.

MAb15 reacts with the OspA of both the B31 and K48 strains, and to peptides containing the N-terminus of OspA, such as HA1 of OspA-B31 and NCS1, but not to peptides HA2 of OspA-B31 and HA1 of OspA-K48 (data not shown). Both peptides include residue 72 to the C-terminus of the molecules. MAb5 bound to CNBr1 of OspA-K48, indicating the domain for this antibody to be residues 39 to 72, specifically near Gly72 (data not shown).

MAb83 binds to OspA-K48, and to peptides containing the C-terminal portion of the molecule, such as HA1. They do not bind to HA2 of OspA-K48, most likely because the C-terminus of HA2 of OspA-K48 ends at 141. Similar to MAb12 and OspA-B31, binding of MAbs 83 and CIII.78 is eliminated by cleavage of OspA at the tryptophan residue. Thus binding of MAbs 12, 83 and CIII.78 to OspA depends on the structural integrity of the Trp$_{216}$ residue, which appears to be critical for antigenicity. Also apparent is that, although these MAbs bind to a common antigenic domain, the precise epitopes which they recognize are distinct from one another given the varying degrees of cross-reactivity to these MAbs among strains.

Although there is similar loss of binding activity of MAb336 with cleavage at Trp$_{216}$, this MAb does not bind to HA1 of OspA-B31, suggesting the domain for this antibody includes the carboxy-terminal end of the molecule, inclusive of residues 251 to 273. Low MW peptides, such as HA3 (10 KD) and NCS2 (6KD), of OspA-K48 do not bind this MAb on Western blots. In order to confirm this observation, we tested binding of the 6 MAbs with a recombinant fusion construct p3A/EC that contains a trpE leader protein fused with residues 217 to 273 of OspA-B31 (Schubach, W. H. et al., *Infect. Immun.* 59(6): 1911–1915 (1991)). Only MAb336 reacted with this construct (data not shown). Peptides and antigenic domains localized by fragmentation of OspA are summarized in FIG. 1.

Mapping of Domains to Define the Molecular Basis for the Serotype Analysis

To define the molecular basis for the serotype analysis of OspA, we compared the derived amino acid sequences of OspA for the nine isolates (FIG. 2). At the amino terminus of the protein, these predictions can be more precise given the relatively small number of amino acid substitutions in this region compared to the carboxy terminus. Domain 1, which is recognized by MAb13, includes residues Leu34 to Leu41. MAb13 only binds to the OspA of species K48, DK29 and IP90. Within this region, residue 37 is variable, however Gly37 is conserved amongst the three reactive strains. When Gly37 is changed to Glu37, as it is in OspA of strains B31, pTrob, PGau, and PKo, MAb13 does not recognize the protein (data not shown). By similar analysis, it can be seen that Asp70 is a crucial residue for Domain 2, which includes residues 65 to 75 and is recognized by MAb15. Domain 3 is reactive with MAbs H5332, 12 and 83, and includes residues 190–220. It is clear that significant heterogeneity exists between MAbs reactive with this domain, and that more than one conformational epitope must be contained within the sequence. Domain 4 binds MAb336, and includes residues 250 to 270. In this region, residue 266 is variable and therefore may be an important determinant. It is apparent, however, that other determinants of the reactivity of this monoclonal antibody reside in the region comprising amino acids 217–250. Furthermore, the structural integrity of Trp216 is essential for antibody reactivity in the intact protein. Finally, it is important to stress that FIG. 2 indicates only the locations of the domains, and does not necessarily encompass the entire domain. Exact epitopes are being analyzed by site-directed mutagenesis of specific residues.

Overall, evidence suggests that the N-terminal portion is not the immunodominant domain of OspA, possibly by virtue of its lipidation, and the putative function of the lipid moiety in anchoring the protein to the outer envelope. The C-terminal end is immunodominant and includes domains that account in part for structural heterogeneity (Wilske, B. et al., *Med. Microbiol. Immunol.* 181: 191–207 (1992)), and may provide epitopes for antibody neutralization (Sears, J. E. et al., *J. Immunol.* 147(6): 1995–2000 (1991)), and relate to other activities, such as the induction of T-cell proliferation (Shanafel, M. M., et al., *J. Immunol.* 148: 218–224 (1992)). There are common epitopes in the carboxy-end of the protein that are shared among genospecies which may have immunoprotective potential (Wilske, B., et al., *Med. Microbiol. Immunol.* 181: 191–207 (1992)).

Prediction of secondary structure on the basis of hydropathy analysis and circular dichroism and fluorescence spectroscopy measurements (McGrath, B. C., et al., *Vaccines,* Cold Spring Harbor Laboratory Press, Plainview, N.Y.; pp. 365–370 (1993)) suggest domains 3 and 4 to be in a region of the molecule with a propensity to form alpha-helix, whereas domains 1 and 2 occur in regions predicted to be beta-sheets (see FIG. 1). These differences may distinguish domains in accessibility to antibody or to reactive T-cells (Shanafel, M. M. et al., *J. Immunol.* 148: 218–224 (1992)). Site-directed mutagenesis of specific epitopes, as described below in Example 2, aids in identifying exact epitopes.

EXAMPLE 2

Identification of an Immunologically Important Hypervariable Domain of the Manor Outer Surface Protein A of Borrelia This Example describes epitope mapping studies using chemically cleaved OspA and TrpE-OspA fusion proteins. The studies indicate a hypervariable region surrounding the single conserved tryptophan residue of OspA (at residue 216, or in some cases 217), as determined by a moving window population analysis of OspA from fifteen European and North American isolates of Borrelia. The hypervariable region is important for immune recognition.

Site-directed mutagenesis was also conducted to examine the hypervariable regions more closely. Fluorescence and circular dichroism spectroscopy have indicated that the conserved tryptophan is part of an alpha-helical region in which the tryptophan is buried in a hydrophobic environment (McGrath, B. C., et al., *Vaccines,* Cold Spring Harbor Laboratory Press, Plainview, N.Y.; pp. 365–370 (1993)). More polar amino acid side-chains flanking the tryptophan are likely to be exposed to the hydrophilic solvent. The hypervariability of these solvent-exposed residues among the various strains of Borrelia suggested that these amino acid residues-may contribute to the antigenic variation in OspA. Therefore, site-directed mutagenesis was performed to replace some of the potentially exposed amino acid side chains in the protein from one strain with the analogous residues of a second strain. The altered proteins were then analyzed by Western Blot using monoclonal antibodies which bind OspA on the surface of the intact, non-mutated spirochete. The results indicated that certain specific amino acid changes near the tryptophan can abolish reactivity of OspA to these monoclonal antibodies.

A. Verification of Clustered Polymorphisms in Outer Surface Protein A Sequences

Cloning and sequencing of the OspA protein from fifteen European and North American isolates (described above in Table I) demonstrated that amino acid polymorphism is not randomly distributed throughout the protein; rather, polymorphism tended to be clustered in three regions of OspA. The analysis was carried out by plotting the moving, weighted average polymorphism of a window (a fixed length subsection of the total sequence) as it is slid along the sequence. The window size in this analysis was thirteen amino acids, based upon the determination of the largest number of significantly deviating points as established by the method of Tajima (*J. Mol. Evol.* 33: 470–473 (1991)). The average weighted polymorphism was calculated by summing the number of variant alleles for each site. Polymorphism calculations were weighted by the severity of amino acid replacement (Dayhoff, M. O. et al., in: Dayhoff, M. O. (ed.) *Atlas of Protein Sequence and Structure NBRF,* Washington, Vol. 5, Suppl. 3: 345 (1978)). The sum was normalized by the window size and plotted. The amino acid sequence position corresponds to a window that encompasses amino acids 1 through 13. Bootstrap resampling was used to generate 95% confidence intervals on the sliding window analysis. Since Borrelia has been shown to be clonal, the bootstrap analysis should give a reliable estimate of the expected variance out of polymorphism calculations. The bootstrap was iterated five hundred times at each position, and the mean was calculated from the sum of all positions. The clonal nature of Borrelia ensures that the stochastic variance that results from differing genealogical histories of the sequence positions (as would be expected if recombination were prevalent) will be minimized.

Figure 3:
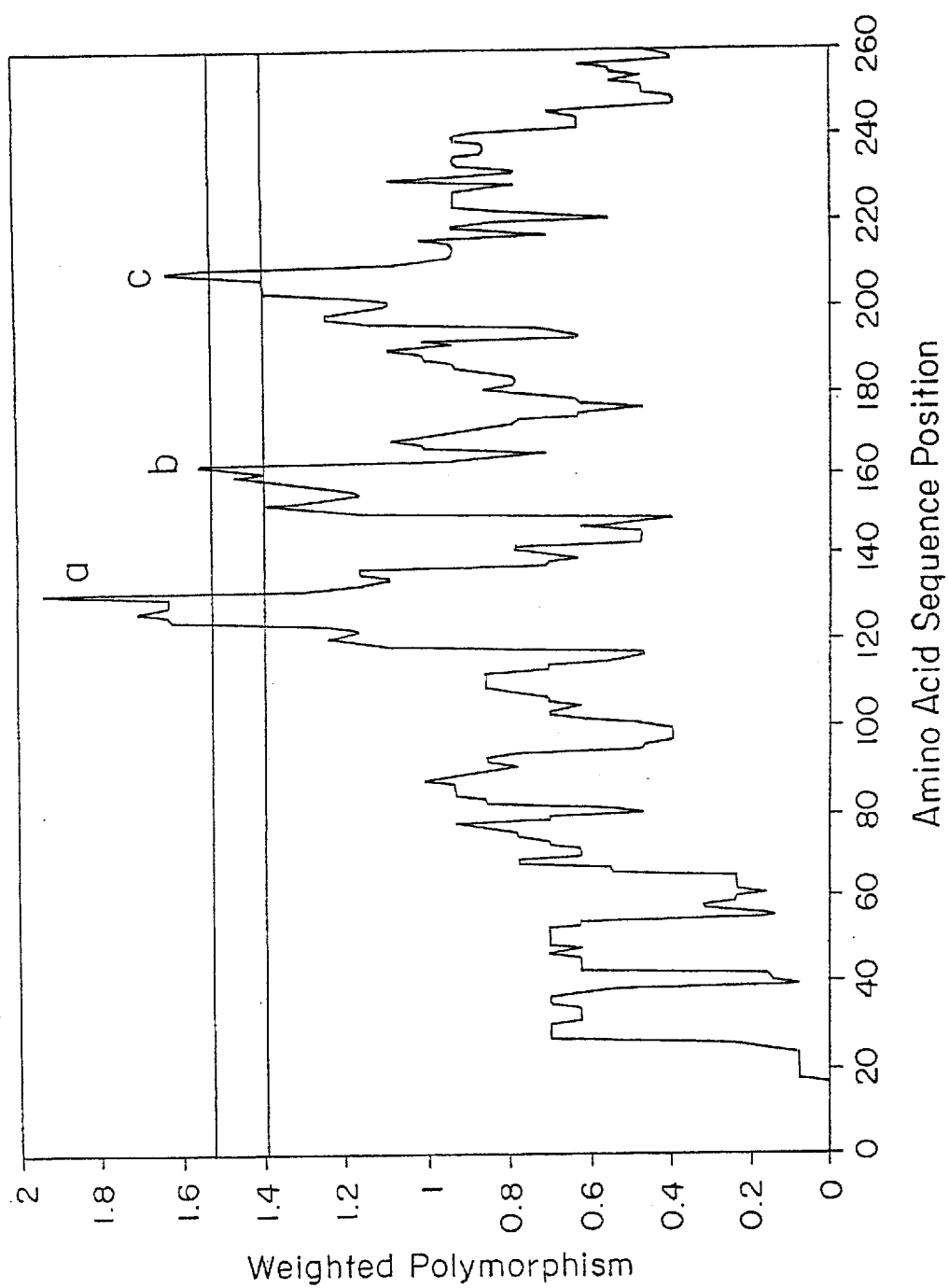
FIG. 3 is a graph depicting a plot of weighted polymorphism versus amino acid position among 14 OspA variants. The marked peaks are: a) amino acids 132–145; b) amino acids 163–177; c) amino acids 208–221. The lower dotted line at polymorphism value 1.395 demarcates statistically significant excesses of polymorphism at p=0.05. The upper dotted line at 1.520 is the same, except that the first 29 amino acids at the monomorphic N-terminus have been removed from the original analysis.
Figure 5:
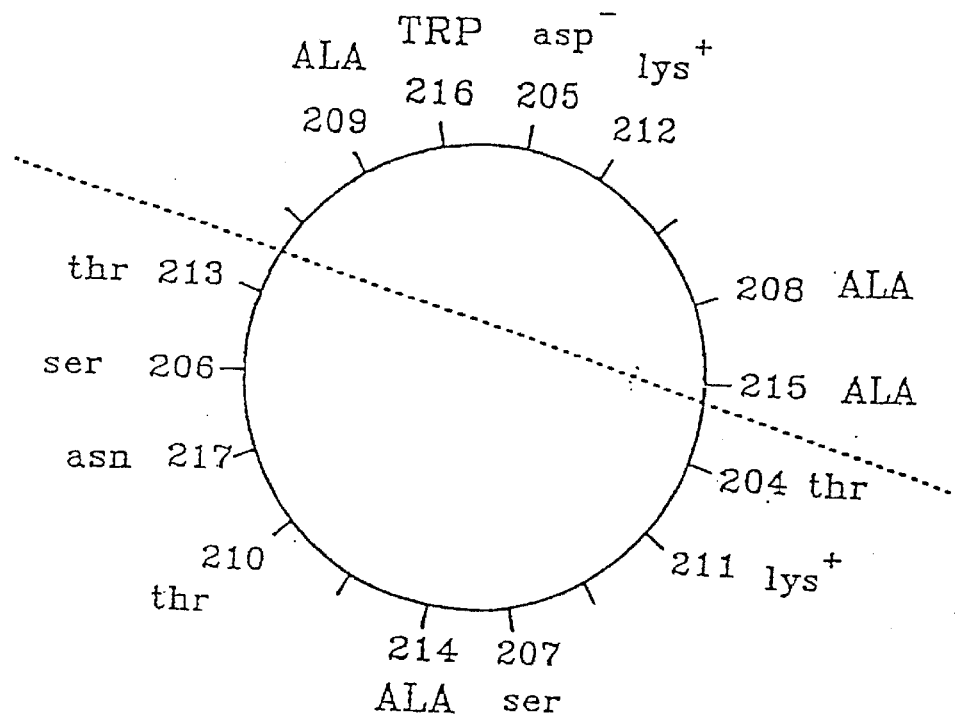
FIG. 5 is a helical wheel projection of residues 204–217 of B31 OspA. Capital letters indicate hydrophobic residues; lower case letters indicate hydrophilic residues; +/− indicate positively/negatively charged residues. Dashed line indicates division of the alpha-helix into hydrophobic arc (above the line) and polar arc (below the line). Adapted from France et al. (*Biochem. Biophys. Acta* 1120: 59 (1992)).
Figure 6:
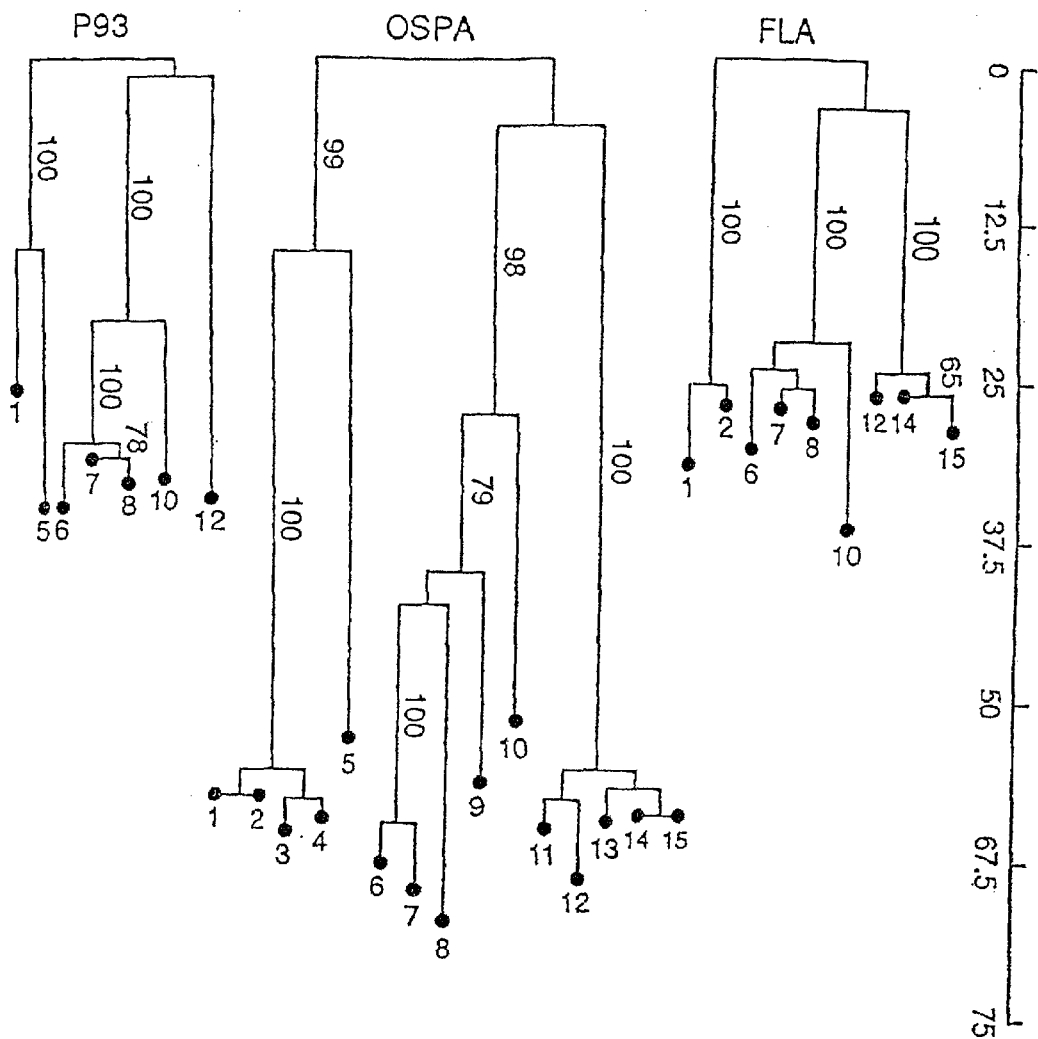
FIG. 6 depicts a phylogenic tree for strains of Borrelia described in Table I. The strains are as follows: 1=B31; 2=Pka1; 3=ZS7; 4=N40; 5=25015; 6=K48; 7=DK29; 8=PHei; 9=Ip90; 10=PTrob; 11=ACAI; 12=PGau; 13=Ip3; 14=PBo; 15=PKo.

This test verified that the three regions around the observed peaks all have significant excesses of polymorphism. Excesses of polymorphism were observed in the regions including amino acid residues 132–145, residues 163–177, and residues 208–221 (FIG. 3). An amino acid alignment between residues 200 and 220 for B31, K48 and the four site-directed mutants is shown in FIG. 4. The amino acid 208–221 region includes the region of OspA which has been modeled as an oriented alpha-helix in which the single tryptophan residue at amino acid 216 is buried in a hydrophobic pocket, thereby exposing more polar amino acids to the solvent (FIG. 5) (France, L. L., et al., *Biochem. Biophys. Acta* 1120: 59 (1992)). These potentially solvent-exposed residues showed considerable variability among the OspAs from various strains and may be an important component of OspA antigenic variation. For the purposes of generating chimeric proteins, the hypervariable domains of interest are Domain A, which includes amino acid residues 120–140 of OspA; Domain B, which includes residues 150–180; and Domain C, which includes residues 200–216 or 217.

B. Site-Directed Mutagenesis of the Hypervariable Region

Site-directed mutagenesis was performed to convert residues within the 204–219 domain of the recombinant B31 OspA to the analogous residues of a European OspA variant, K48. In the region of OspA between residues 204 and 219, which includes the helical domain (amino acids 204–217), there are seven amino acid differences between OspA-B31 and OspA-K48. Three oligonucleotides were generated, each containing nucleotide changes which would incorporate K48 amino acids at their analogous positions in the B31 OspA protein. The oligos used to create the site-directed mutants were:

5'-CTTAATGACTCTGACACTAGTGC-3' (#613, which converts threonine at position 204 to serine, and serine at 206 to threonine (Thr204-Ser, Thr206-Ser)) (SEQ ID NO. 1);

5'-GCTACTAAAAAAACCGGGAAATGGAATTCA-3' (#625, which converts alanine at 214 to glycine, and alanine at 215 to lysine (Ala214-Gly, Ala215-Lys)) (SEQ ID NO. 2); and 5'-GCAGCTTGGGATTCAAAAACATCCACTTTAACA-3' (#640, which converts asparagine at 217 to aspartate, and glycine at 219 to lysine (Asn217-Asp, Gly219-Lys)) (SEQ ID NO. 3).

Site-directed mutagenesis was carried out by performing mutagenesis with pairs of the above oligos. Three site-directed mutants were created, each with two changes: OspA 613 (Thr204-Ser, Thr206-Ser), OspA 625 (Ala214-Gly, Ala215-Lys), and 640 (Asn217-Asp, Gly219-Lys). There were also two proteins with four changes: OspA 613/625 (Thr204-Ser, Thr206-Ser, Ala214-Gly, Ala215-Lys) and OspA 613/640 (Thr204-Ser, Thr206-Ser, Asn217-Asp, Gly219-Lys).

Specificity of Antibody Binding to Epitopes of the Non-mutated Hypervariable Region Monoclonal antibodies that agglutinate spirochetes, including several which are neutralizing in vitro, recognize epitopes that map to the hypervariable region around Trp216 (Barbour, A. G. et al., *Infect. and Immun.* 41: 759 (1983); Schubach, W. H. et al., *Infect. and Immun.* 59: 1911 (1991)). Western Blot analysis demonstrated that chemical cleavage of OspA from the B31 strain at Trp 216 abolishes reactivity of the protein with the agglutinating Mab 105, a monoclonal raised against B31 spirochetes (data not shown). The reagent, n-chlorosuccinimide (NCS), cleaves OspA at the Trp 216, forming a 23.2 kd fragment and a 6.2 kd peptide which is not retained on the Imobilon-P membrane after transfer. The uncleaved material binds Mab 105; however, the 23.2 kd fragment is unreactive. Similar Western blots with a TrpE-OspA fusion protein containing the carboxy-terminal portion of the OspA protein demonstrated that the small 6.2 kd piece also fails to bind Mab 105 (Schubach, W. H. et al., *Infect. and Immun.* 59: 1911 (1991)).

Monoclonal antibodies H5332 and H3TS (Barbour, A. G. et al., *Infect. and Immun.* 41: 759 (1983)) have been shown by immunofluorescence to decorate the surface of fixed spirochetes (Wilske, B. et al., *World J. Microbiol.* 7: 130 (1991)). These monoclonals also inhibit the growth of the organism in culture. Epitope mapping with fusion proteins has confirmed that the epitopes which bind these Mabs are conformationally determined and reside in the carboxy half of the protein. Mab H5332 is cross-reactive among all of the known phylogenetic groups, whereas Mab H3TS and Mab 105 seem to be specific to the B31 strain to which they were raised. Like Mab 105, the reactivities of H5332 and H3TS to OspA are abrogated by fragmentation of the protein at Trp216(data not shown). Mab 336 was raised to whole spirochetes of the strain P/Gau. It cross-reacts to OspA from group 1 (the group to which B31 belongs) but not to group 2 (of which K48 is a member). Previous studies using fusion proteins and chemical cleavage have indicated that this antibody recognizes a domain of OspA in the region between residues 217 and 273 (data not shown). All of these Mabs will agglutinate the B31 spirochete.

Western Blot Analysis of Antibody Binding to Mutated Hypervariable Regions

Mabs were used for Western Blot analysis of the site-directed OspA mutants induced in *E.coli* using the T7 expression system (Dunn, J. J. et al., *Protein Expression and Purification* 1: 159 (1990)). *E. coli* cells carrying Pet9c plasmids having a site-directed OspA mutant insert were induced at mid-log phase growth with IPTG for four hours at 37° C. Cell lysates were made by boiling an aliquot of the induced cultures in SDS gell loading dye, and this material was then loaded onto a 12% SDS gell (BioRad mini-Protean II), and electrophoresed. The proteins were then transferred to Imobilon-P membranes (Millipore) 70V, 2 hour at 4° C. using the BioRad mini transfer system. Western analysis was carried out as described by Schubach et al. (*Infect. Immun.* 59: 1911 (1991)).

Western Blot analysis indicated that only the 625 mutant (Ala214-Gly and Ala215-Lys) retained binding to the agglutinating monoclonal H3TS (data not shown). However, the 613/625 mutant which has additional alterations to the amino terminus of Trp216 (Ser204-Thr and Thr206-Ser) did not bind this monoclonal. Both 640 and 613/640 OspAs which have the Asn217-Asp and Gly219-Lys changes on the carboxy-terminal side of Trp216 also failed to bind Mab H3TS. This indicated that the epitope of the B31 OspA which binds H3TS is comprised of amino acid side-chains on both sides of Trp216.

The 613/625 mutant failed to bind Mabs 105 and H5332, while the other mutants retained their ability to bind these Mabs. This is important in light of the data using fusion proteins that indicate that Mab 105 behaves more like Mab H3TS in terms of its serotype specificity and binding to OspA (Wilske, B. et al., *Med. Microbiol. Immunol.* 181: 191 (1992)). The 613/625 protein has, in addition to the differences at residues Thr204 and Ser206, changes immediately amino-terminal to Trp216 (Ala214-Gly and Ala215-Lys). The abrogation of reactivity of Mabs 105 and H5332 to this protein indicated that the epitopes of OspA which bind these monoclonals are comprised of residues on the amino-terminal side of Trp216.

The two proteins carrying the Asn217-Asp and Gly219-Lys replacements on the carboxy-terminal side of Trp216 (OspAs 640 and 613/640) retained binding to Mabs 105 and H5332; however, they failed to react with Mab 336, a monoclonal which has been mapped with TrpE-OspA fusion proteins and by chemical cleavage to a more carboxy-terminal domain. This result may explain why Mab 336 failed to recognize the K48-type of OspA (Group 2).

It is clear that amino acids Ser204 and Thr206 play an important part in the agglutinating epitopes in the region of the B31 OspA flanking Trp216. Replacement of these two residues altered the epitopes of OspA that bind Mabs 105, H3TS and H5332. The ability of the 640 changes alone to abolish reactivity of Mab 336 indicated that Thr204 and Ser206 are not involved in direct interaction with Mab 336.

The results indicated that the epitopes of OspA which are available to Mabs that agglutinate spirochetes are comprised at least in part by amino acids in the immediate vicinity of Trp216. Since recent circular dichroism analysis indicated that the structures of B31 and K48 OspA differ very little within this domain, it is unlikely that the changes made by mutation have radically altered the overall structure of the OspA protein (France, L. L. et al., *Biochem. Biophys. Acta* 1120: 59 (1992); and France et al., *Biochem. Biophys Acta,* submitted (1993)). This hypothesis is supported by the finding that the recombinant, mutant OspAs exhibit the same high solubility and purification properties as the parent B31 protein (data not shown).

In summary, amino acid side-chains at Ser204 and Thr206 are important for many of the agglutinating epitopes. However, a limited set of conservative changes at these sites were not sufficient to abolish binding of all of the agglutinating Mabs. These results suggested that the agglutinating epitopes of OspA are distinct, yet may have some overlap. The results also supported the hypothesis that the surface-exposed epitope around Trp216 which is thought to be important for immune recognition and neutralization is a conformationally-determined and complex domain of OspA.

EXAMPLE 3

Borrelia Strains and Proteins

Proteins and genes from any strain of Borrelia can be utilized in the current invention. Representative strains are summarized in Table I, above.

A. Genes Encoding Borrelia Proteins

The chimeric peptides of the current invention can comprise peptides derived from any Borrelia proteins. Representative proteins include OspA, OspB, OspC, OspD, p12, p39, p41 (fla), p66, and p93. Nucleic acid sequences encoding several Borrelia proteins are presently available (see Table II, below); alternatively, nucleic acid sequences encoding Borrelia proteins can be isolated and characterized using methods such as those described below.

TABLE II

References for Nucleic Acid Sequences for Several Proteins of Various Borrelia Strains

| Strain | p93 | OspA | p41 (fla) |
|---|---|---|---|
| K48 | X69602 (SID 67) | X62624 (SID 8) | X69610 (SID 49) |
| PGau | SID 73 | X62387 (SID 10) | X69612 (SID 51) |
| DK29 | — | X63412 (SID 137) | X69608 (SID 53) |
| PKo | X69803 (SID 77) | X65599 (SID 141) | X69613 (SID 131) |
| PTrob | X69604 (SID 71) | X65598 (SID 135) | X69614 (SID 55) |
| Ip3 | — | X70365 (SID 140) | — |
| Ip90 | ND | Kryuchechnikov, V. N. et al., J.Microbiol. Epid. Immunobiol. 12:41–44 (1988) (SID 138) | |
| 25015 | X70365 (SID 75) | Fikrig, E. S. et al., J. Immunol. 7:2256–2260 1992) SID 12) | — |
| B31 | Perng, G. C. et al., Infect. Immun. 59:2070– 74 (1992); Luft, B. J. et al., Infect. Immun. 60:4309–4321 (1992) (SID 65) | Bergstrom, S. et al., Mol. Microbiol. 3:479–486 (1989) (SID 6) | Gassmann, G. S. et al., Nucl. Acids Res. 17: 3590 (1989) (SID 127) |
| PKa1 | — | X69606 (SID 132) | X69611 (SID 129) |
| ZS7 | — | Jonsson, M. et al., Infect. Immun. 60:1845–1853 (1992) (SID 134) | — |
| N40 | — | Kryuchechnikov, V. N. et al. (SID 133) | — |
| PHei | — | X65600 (SID 136) | — |
| ACAI | — | Kryuchechnikov, V. N. et al. (SID 142) | — |
| PBo | X69601 (SID 69) | X65605 (SID 139) | X69610 (SID 130) |

Numbers with an "X" prefix are GenBank data base accession numbers.
SID = SEQ ID NO.

B. Isolation of Borrelia Genes

Nucleic acid sequences encoding full length, lipidated proteins from known Borrelia strains were isolated using the polymerase chain reaction (PCR) as described below. In addition, nucleic acid sequences were generated which encoded truncated proteins (proteins in which the lipidation signal has been removed, such as by eliminating the nucleic acid sequence encoding the first 18 amino acids, resulting in non-lipidated proteins). Other proteins were generated which encoded polypeptides of a particular gene (i.e., encoding a segment of the protein which has a different number of amino acids than the protein does in nature). Using similar methods as those described below, primers can be generated from known nucleic acid sequences encoding Borrelia proteins and used to isolate other genes encoding Borrelia proteins. Primers can be designed to amplify all of a gene, as well as to amplify a nucleic acid sequence encoding truncated protein sequences, such as described below for OspC, or nucleic acid sequences encoding a polypeptide derived from a Borrelia protein. Primers can also be designed to incorporate unique restriction enzyme cleavage sites into the amplified nucleic acid sequences. Sequence analysis of the amplified nucleic acid sequences can then be performed using standard techniques.

Cloning and Sequencing of OspA Genes and Relevant Nucleic Acid Sequences

Borrelia OspA sequences were isolated in the following manner: 100 µl reaction mixtures containing 50 mM KCl, 10 mM TRIS-HCl (pH 8,3), 1.5 mM $MgCl_2$, 200 µM each NTP, 2.5 units of TaqI DNA polymerase (Amplitaq, Perkin-Elmer/Cetus) and 100 pmol each of the 5' and 3' primers (described below) were used. Amplification was performed in a Perkin-Elmer/Cetus thermal cycler as described (Schubach, W. H. et al., *Infect. Immun.* 59:1811–1915 (1991)). The amplicon was visualized on an agarose gel by ethidium bromide staining. Twenty nanograms of the chloroform-extracted PCR product were cloned directly into the PC-TA vector (Invitrogen) by following the manufacturer's instructions. Recombinant colonies containing the amplified fragment were selected, the plasmids were prepared, and the nucleic acid sequence of each OspA was determined by the dideoxy chain-termination technique using the Sequenase kit (United States Biochemical). Directed sequencing was performed with M13 primers followed by OspA-specific primers derived from sequences, previously obtained with M13 primers.

Because the 5' and 3' ends of the OspA gene are highly conserved (Fikrig, E. S. et al., *J. Immunol.* 7:2256–2260 (1992); Bergstrom, S. et al., *Mol. Microbiol.* 3: 479–486 (1989); Zumstein, G. et al., *Med. Microbiol. Immunol.* 181: 57–70 (1992)), the 5' and 3' primers for cloning can be based upon any known OspA sequences. For example, the following primers based upon the OspA nucleic acid sequence from strain B31 were used:

5'-GGAGAATATATTATGAAA-3' (−12 to +6) (SEQ ID NO. 4); and

5'-CTCCTTATTTTAAAGCG-3' (+826 to +809) (SEQ ID NO. 5).

(Schubach, W. H. et al., *Infect. Immun* 59:1811–1915 (1991)).

OspA genes isolated in this manner include those for strains B31, K48, PGau, and 25015; the nucleic acid sequences are depicted in the sequence listing as SEQ ID NO. 6 (OspA-B31), SEQ ID NO. 8 (OspA-K48), SEQ ID NO. 10 (OspA-PGau), and SEQ ID NO. 12 (OspA-25015). An alignment of these and other OspA nucleic acid sequences is shown in FIG. 42. The amino acid sequences of the proteins encoded by these nucleic acid sequences are represented as SEQ ID NO. 7 (OspA-B31), SEQ ID NO. 9 (OspA-K48), SEQ ID NO. 11 (OspA-PGau), and SEQ ID NO. 13 (OspA-25015).

The following primers were used to generate specific nucleic acid sequences of the OspA gene, to be used to generate chimeric nucleic acid sequences (as described in Example 4):

5'-GTCTGCAAAAACCATGACAAG-3' (plus strand primer #369) (SEQ ID NO. 14);

5'-GTCATCAACAGAAGAAAAATTC-3' (plus strand primer #357) (SEQ ID NO 15);

5'-CCGGATCCATATGAAAAAATATTTATTGGG-3' (plus strand primer #607) (SEQ ID NO. 16);

5'-CCGGGATCCATATGGCTAAGCAAAATGTTAGC-3' (plus strand primer #584) (SEQ ID NO. 17);

5'-GCGTTCAAGTACTCCAGA-3' (minus strand primer #200) (SEQ ID NO. 18);

5'-GATATCTAGATCTTATTTTAAAGCGTT-3' (minus strand primer #586) (SEQ ID NO. 19); and 5'-GGATCCGGTGACCTTTTAAAGCGTTTTTAAT-3' (minus strand primer #1169) (SEQ ID NO. 20).

Cloning and Sequencing of OspB

Similar methods were also used to isolate OspB genes. One OspB genes isolated is represented as SEQ ID NO. 21 (OspB-B31); its encoded amino acid sequence is SEQ ID NO. 22.

The following primers were used to generate specific nucleic acid sequences of the OspB gene, to be used in generation of chimeric nucleic acid sequences (see Example 4):

5'-GGTACAATTACAGTACAA-3' (plus strand primer #721) (SEQ ID NO. 23);

5'-CCGAGAATCTCATATGGCACAAAAAGGTGCTGA GTCAATTGG-3' (plus strand primer #1105) (SEQ ID NO. 24);

5'-CCGATATCGGATCCTATTTTAAAGCGTTTTTAAG C-3' (minus strand primer #1106) (SEQ ID NO. 25); and 5'-GGATCCGGTGACCTTTTAAAGCGTTTTTAAG-3' (minus strand primer #1170) (SEQ ID NO. 26).

Cloning and Sequencing of OspC

Similar methods were also used to isolate OspC genes. The following primers were used to isolate entire OspC genes from Borrelia strains B31, K48, PKO, and pTrob:

5'-GTGCGCGACCATATGAAAAAGAATACATTAAGT GCG-3' (plus strand primer having Nde1 site combined with start codon) (SEQ ID NO. 27), and 5'-GTCGGCGGATCCTTAAGGTTTTTTTGGACTTTCT GC-3' (minus strand primer having BamH1 site followed by stop codon) (SEQ ID NO. 28).

The nucleic acid sequences of the OspC genes were then determined by the dideoxy chain-termination technique using the Sequenase kit (United States Biochemical). OspC genes isolated and sequenced in this manner include those for strains B31, K48, PKo, and Tro; the nucleic acid sequences are depicted in the sequence listing as SEQ ID NO. 29 (OspC-B31), SEQ ID NO. 31 (OspC-K48), SEQ ID NO. 33 (OspC-PKo), and SEQ ID NO. 35 (OspC-Tro). An alignment of these sequences is shown in FIG. 38. The amino acid sequences of the proteins encoded by these nucleic acid sequences are represented as SEQ ID NO. 30 (OspC-B31), SEQ ID NO. 32 (OspC-K48), SEQ ID NO. 34 (OspC-PKo), and SEQ ID NO. 36 (OspC-Tro).

Truncated OspC genes were generated using other primers. These primers were designed to amplify nucleic acid sequences, derived from the OspC gene, that lacked the nucleic acids encoding the signal peptidase sequence of the full-length protein. The primers corresponded to bp 58–75 of the natural protein, with a codon for Met-Ala attached ahead. For strain B31, the following primer was used:

5'-GTGCGCGACCATATGGCTAATAATTCAGGGAAA GAT-3' (SEQ ID NO. 37).

For strain PKo,

5,'-GTGCGCGACCATATGGCTAGTAATTCAGGGAAA GGT-3' (SEQ ID NO. 38) was used.

For strains pTrob and K48,

5'-GTGCGCGACCATATGGCTAATAATTCAGGTGGG GAT-3 (SEQ ID NO. 39) was used.

Additional primers were also designed to amplify nucleic acids encoding particular polypeptides, for use in creation of chimeric nucleic acid sequences (see Example 4). These primers included:

5'-CTTGGAAAATTATTTGAA-3' (plus strand primer #520) (SEQ ID NO. 40);

5'-CACGGTCACCCCATGGGAAATAATTCAGGGAA AGG-3' (plus strand primer #58) (SEQ ID NO. 41);

5'-TATAGATGACAGCAACGC-3' (minus strand primer #207) (SEQ ID NO. 42); and

5'-CCGGTGACCCCATGGTACCAGGTTTTTTTGGACT TTCTGC-3' (minus strand primer #636) (SEQ ID NO. 43).

Cloning and Sequencing of OspD

Similar methods can be used to isolate OspD genes. An alignment of four OspD nucleic acid sequences (from strains pBo, PGau, DK29, and K48) is shown in FIG. 39.

Cloning and Sequencing of p12

The p12 gene was similarly identified. Primers used to clone the entire p12 gene included:

5'-CCGGATCCATATGGTTAAAAAAATAATATTTATT TC-3' (forward primer #757) (SEQ ID NO. 44); and 5'-GATATCTAGATCTTTAATTGCTCTGCTCACTCTC TTC-3' (reverse primer #758) (SEQ ID NO. 45).

To amplify a truncated p12 gene (one in which the transcribed protein is non-lipidated, and begins at amino acid 18 of the native sequence), the following primers were used:

5'-CCGGGATCCATATGGCTAGTGCAATTGGTCGTGG-3' (forward primer #759) (SEQ ID NO. 46); and primer #758 (SEQ ID NO. 45).

Cloning and Sequencing of p41 (fla)

A similar approach was used to clone and sequence genes encoding the p41 (fla) protein. The p41 sequences listed in Table II with GenBank accession numbers were isolated using the following primers from strain B31:
5'-ATGATTATCAATCATAAT-3' (+1 to +18) (SEQ ID NO. 47); and
5'-TCTGAACAATGACAAAAC-3' (+1008 to +991) (SEQ ID NO. 48).

The nucleic acid sequences of p41 isolated in this manner are depicted in the sequence listing as SEQ ID NO. 51 (p41-PGau), and SEQ ID NO. 53 (p41-DK29). An alignment of several p41 nucleic acid sequences, including those for strains B31, pKa1, PGau, pBo, DK29, and pKo, is shown in FIG. 41. The amino acid sequences of the proteins encoded by these nucleic acid sequences are represented as SEQ ID NO. 50 (p41-K48), SEQ ID NO. 52 (p41-PGau), SEQ ID NO. 54 (p41-DK29), SEQ ID NO. 56 (p41-PTrob), and SEQ ID NO. 58 (p41-PHei).

Other primers were designed to amplify nucleic acid sequences encoding polypeptides of p41, to be used in chimeric nucleic acid sequences. These primers included:
5'-TTGGATCCGGTCACCCCATGGCTCAATATAACC AATG-3' (minus strand primer #122) (SEQ ID NO. 59);
5'-TTGGATCCGGTCACCCCATGGCTTCTCAAAAT GTAAG-3' (plus strand primer #140) (SEQ ID NO. 60);
5'-TTGGATCCGGTGACCAACTCCGCCTTGAGAAGG-3' (minus strand primer #234) (SEQ ID NO. 61); and
5'-TTGGATCCGGTGACCTATTTGAGCATAAGATGC-3' (minus strand primer #141) (SEQ ID NO. 62).

Cloning and Sequencing of p93

The same approach was also used to clone and sequence p93 protein. Genes encoding p93, as listed in Table II with GenBank accession numbers, were isolated by this method with the following primers from strain B31:
5'-GGTGAATTTAGTTGGTAAGG-3' (−54 to −35) (SEQ ID NO. 63); and
5'-CACCAGTTTCTTTAAGCTGCTCCTGC-3' (+1117 to +1092) (SEQ ID NO. 64).

The nucleic acid sequences of p93 isolated in this manner are depicted in the sequence listing as SEQ ID NO. 65 (p93-B31), SEQ ID NO. 67 (p93-K48) SEQ ID NO. 69 (p93-PBo), SEQ ID NO. 71 (p93-PTrob), SEQ ID NO. 73 (p93-PGau), SEQ ID NO. 75 (p93-25015), and SEQ ID NO. 77 (p93-PKo). The amino acid sequences of the proteins encoded by these nucleic acid sequences are represented as SEQ ID NO. 66 (p93-B31), SEQ ID NO. 68 (p93-K48) SEQ ID NO. 70 (p93-PBo), SEQ ID NO. 72 (p93-PTrob), SEQ ID NO. 74 (p93-PGau), SEQ ID NO. 76 (p93-25015), and SEQ ID NO. 78 (p93-PKo).

Other primers were used to amplify nucleic acid sequences encoding polypeptides of p93 to be used in generating chimeric nucleic acid sequences. These primers included:
5'-CCGGTCACCCCATGGCTGCTTTAAAGTCTTTA-3' (plus strand primer #475) (SEQ ID NO. 79);
5'-CCGGTCACCCCATGAATCTTGATAAAGCTCAG-3' (plus strand primer #900) (SEQ ID NO. 80);
5'-CCGGTCACCCCATGGATGAAAAGCTTTTAAAA AGT-3' (plus strand primer #1168) (SEQ ID NO. 81);
5'-CCGGTCACCCCATGGTTGAGAAATTAGATAAG-3' (plus strand primer #1423) (SEQ ID NO. 82); and
5'-TTGGATCCGGTGACCCTTAACTTTTTTTAAAG-3' (minus strand primer #2100) (SEQ ID NO. 83).

C. Expression of Proteins from Borrelia Genes

The nucleic acid sequences described above can be incorporated into expression plasmids, using standard techniques, and transfected into compatible host cells in order to express the proteins encoded by the nucleic acid sequences. As an example, the expression the p12 gene and the isolation of p12 protein is set forth.

Amplification of the p12 nucleic acid sequence was conducted with primers that included a NdeI restriction site into the nucleic acid sequence. The PCR product was extracted with phenol/chloroform and precipitated with ethanol. The precipitated product was digested and ligated into an expression plasmid as follows: 15 μl (approximately 1 μg) of PCR DNA was combined with 2 μl 10× restriction buffer for NdeI (Gibco/BRL), 1 μl NdeI (Gibco/BRL), and 2 μl distilled water, and incubated overnight at 37° C. This mixture was subsequently combined with 3 μl 10× buffer (buffer 3, New England BioLabs), 1 μl BamHI (NEB), and 6 μl distilled water, and incubated at 370° for two hours. The resultant material was purified by preparative gel electrophoresis using low melting point agarose, and the band was visualized under long wave ultraviolet light and excised from the gel. The gel slice was treated with Gelase using conditions recommended by the manufacturer (Epicentre Technologies). The resulting DNA pelled was resuspended in 25–50 μl of 10 mM TRIS-CL (pH 8.0) and 1 mM EDTA (TE). An aliquot of this material was ligated into the Pet9c expression vector (Dunn, J. J. et al., *Protein Expression and Purification* 1: 159 (1990)).

To ligate the material into the Pet9c expression vector, 20–50 ng of p12 nucleic acid sequences cut and purified as described above was combined with 5 μl 10 One-Phor-All (OPA) buffer (Pharmacia), 30–60 ng Pet9c cut with NdeI and BamHI, 2.5 μl 20 mM ATP, 2 μl T4 DNA ligase (Pharmacia) diluted 1:5 in 1×OPA buffer, and sufficient distilled water to bring the final volume to 50 μl. The mixture was incubated at 12° C. overnight.

The resultant ligations were transformed into competent DH5-alpha cells and plated on nutrient agar plates containing 50 μg/ml kanamycin and incubated overnight at 37° C. DH5-alpha is used as a "storage strain" for T7 expression clones, because it is RecA deficient, so that recombination and concatenation are not problematic, and because it lacks the T7 RNA polymerase gene necessary to express the cloned gene. The use of this strain allows for cloning of potentially toxic gene products while minimizing the chance of deletion and/or rearrangement of the desired genes. Other cell lines having similar properties may also be used.

Kanamycin resistant colonies were single-colony purified on nutrient agar plates supplemented with kanamycin at 50 μg/ml. A colony from each isolate was inoculated into 3–5 ml of liquid medium containing 50 μg/ml kanamycin, and incubated at 37° C. without agitation. Plasmid DNA was obtained from 1 ml of each isolate using a hot alkaline lysis procedure (Mantiatis, T. et al., *Molecular Cloning: A Laboratory Manual,* cold Spring Harbor Laboratory, Cold Spring Harbor, N.Y. (1982)).

Plasmid DNA was digested with EcoRI and BglII in the following manner: 15 μl plasmid DNA was combined with 2 μl 10× buffer 3 (NEB), 1μ EcoRI (NEB), 1 μl BglII (NEB) and 1 μl distilled water, and incubated for two hours at 37° C. The entire reaction mixture was electrophoresed on an analytical agarose gel. Plasmids carrying the p12 insert were identified by the presence of a band corresponding to 925 base-pairs (full length p12) or 875 base-pairs (nonlipidated p12). One or two plasmid DNAs from the full length and nonlipidated p12 clones in Pet9c were used to transform BL21 DE3 pLysS to kanamycin resistance as described by Studier et al. (*Methods in Enzymology,* Goeddel, D. (Ed.), Academic Press, 185: 60–89 (1990)). One or two transformants of the full length and nonlipidated clones were single-colony purified on nutrient plates containing 25 μg/ml chloramphenicol (to maintain pLysS) and 50 μg/ml kanamycin at 37° C. One colony of each isolate was inoculated into liquid medium supplemented with chloramphenicol and kanamycin and incubated overnight at 37° C. The overnight culture was subcultured the following morning into 500 ml of liquid broth with chloramphenicol (25 µg/ml) and kanamycin (50 µg/ml) and grown with aeration at 37° C. in an orbital air-shaker until the absorbance at 600 nm reached 0.4–0.7. Isopropyl-thio-galactoside (IPTG) was added to a final concentration of 0.5 mM, for induction, and the culture was incubated for 3–4 hours at 37° as before. The induced cells were pelleted by centrifugation and resuspended in 25 ml of 20 mM NaPO$_4$ (pH 7.7). A small aliquot was removed for analysis by gel electrophoresis. Expressing clones produced proteins which migrated at the 12 kDa position.

A crude cell lysate was prepared from the culture as described for recombinant OspA by Dunn, J. J. et al., (*Protein Expression and Purification* 1: 159 (1990)). The crude lysate was first passed over a Q-sepharose column (Pharmacia) which had been pre-equilibrated in Buffer A: 10 mM NaPO$_4$ (pH 7.7), 10 mM NaCl, 0.5 mM PMSF. The column was washed with 10 mM NaPO$_4$, 50 mM NaCl and 0.5 mM PMSF and then p12 was eluted in 10 mM NaPO$_4$, 0.5 mM PMSF with a NaCl gradient from 50–400 mM. p12 eluted approximately halfway through the gradient between 100 and 200 mM NaCl. The peak fractions were pooled and dialyzed against 10 mM NaPo4 (pH 7.7), 10 mM NaCl, 0.5 mM PMSF. The protein was then concentrated and applied to a Sephadex G50 gel filtration column of approximately 50 ml bed volume (Pharmacia), in 10 mM NaPO$_4$, 200 mM NaCl, 0.5 mM PMSF. p12 would typically elute shortly after the excluded volume marker. Peak fractions were determined by running small aliquots of all fractions on a gel. The p12 peak was pooled and stored in small aliquots at −20° C.

EXAMPLE 4

Generation of Chimeric Nucleic Acid Sequences and Chimeric Proteins

A. General Protocol for Creation of Chimeric Nucleic Acid Sequences

The megaprimer method of site directed mutagenesis and its modification were used to generate chimeric nucleic acid sequences (Sarkar and Sommer, *Biotechniques* 8(4): 404–407 (1990); Aiyar, A. and J. Leis, *Biotechniques* 14(3): 366–369 (1993)). A 5' primer for the first genomic template and a 3' fusion oligo are used to amplify the desired region. The fusion primer consists of a 3' end of the first template (DNA that encodes the amino-proximal polypeptide of the fusion protein), coupled to a 5' end of the second template (DNA that encodes the carboxy-proximal polypeptide of the fusion protein).

The PCR amplifications are performed using Taq DNA polymerase, 10×PCR buffer, and MgCl$_2$ (Promega Corp., Madison, Wis.), and Ultrapure dNTPs (Pharmacia, Piscataway, N.J.). One µg of genomic template 1, 5µ of 10 µM 5' oligo and 5 µl of 10 µM fusion oligo are combined with the following reagents at indicated final concentrations: 10× Buffer-Mg FREE (1×), MgCl$_2$ (2 mM), dNTP mix (200 µM each dNTP), Taq DNA polymerase (2.5 units), water to bring final volume to 100 µl. A Thermal Cycler (Perkin Elmer Cetus, Norwalk, Conn.) is used to amplify under the following conditions: 35 cycles at 95° C. for one minute, 55° C. for two minutes, and 720° for three minutes. This procedure results in a "megaprimer".

The resulting megaprimer is run on a 1×TAE, 4% low-melt agarose gel. The megaprimer band is cut from the gel and purified using the Promega Magic PCR Preps DNA purification system. Purified megaprimer is then used in a second PCR step. One µg of genomic template 2, approximately 0.5 µg of the megaprimer, and 5µ of 10 µM 3' oligo are added to a cocktail of 10× buffer, MgCl$_2$, dNTPs and Taq at the same final concentrations as noted above, and brought to 100 µl with water. PCR conditions are the same as above. The fusion product resulting from this amplification is also purified using the Promega Magic PCR Preps DNA purification system.

The fusion product is then ligated into TA vector and transformed into *E. coli* using the Invitrogen (San Diego, Calif.) TA Cloning Kit. Approximately 50 ng of PCR fusion product is ligated to 50 ng of PCRII vector with 1× Ligation Buffer, 4 units of T4 ligase, and brought to 10 N1 with water. This ligated product mixture is incubated at 12° C. overnight (approximately 14 hours). Two µl of the ligation product mixture is added to 50 µl competent INC F' cells and 2µ beta mercaptoethanol. The cells are then incubated for 30 minutes, followed by heat shock treatment at 42° C. for 60 seconds, and an ice quenching for two minutes. 450 µl of warmed SOC media is then added to the cells, resulting in a transformed cell culture which is incubated at 37° C. for one hour with slight shaking. 50 µl of the transformed cell culture is plated on LB+50 µg/µl ampicillin plates and incubated overnight at 37° C. Single white colonies are picked and added to individual overnight cultures containing 3 ml LB with ampicillin (50 µg/µl).

The individual overnight cultures are prepared using Promega's Magic Miniprep DNA purification system. A small amount of the resulting DNA is cut using a restriction digest as a check. DNA sequencing is then performed to check the sequence of the fusion nucleic acid sequence, using the United States Biochemical (Cleveland, Ohio) Sequenase Version 2.0 DNA sequencing kit. Three to five µg of plasmid DNA is used per reaction. 2 µl 2M NaOH/2 mM EDTA are added to the DNA, and the volume is brought to 20 µl with water. The mixture is then incubated at room temperature for five minutes. 7 µl water, 3µl 3M NaAc, 75 µl EtOH are added. The resultant mixture is mixed by vortex and incubated for ten minutes at −70° C., and then subjected to microfugation. After microfuge for ten minutes, the supernatant is aspirated off, and the pellet is dried in the speed vac for 30 second. 6 µl water, 2 µl annealing buffer, and 2 µl of 10 µM of the appropriate oligo is then added. This mixture is incubated for 10 minutes at 37° C. and then allowed to stand at room temperature for 10 minutes. Subsequently, 5.5 µl of label cocktail (described above) is added to each sample of the mixture, which are incubated at room temperature for an additional five minutes. 3.5 µl labeled DNA is then added to each sample which is then incubated for five minutes at 37° C. 4 µl stop solution is added to each well. The DNA is denatured at 95° for two minutes, and then placed on ice.

Clones with the desired fusion nucleic acid sequences are then recloned in frame in the pEt expression system in the lipidated (full length) and non-lipidated (truncated, i.e., without first 17 amino acids) forms. The product is amplified using restriction sites contained in the PCR primers. The vector and product are cut with the same enzymes and ligated together with T4 ligase. The resultant plasmid is transformed into competent *E. coli* using standard transformation techniques. Colonies are screened as described earlier and positive clones are transformed into expression cells, such as *E. coli* BL21, for protein expression with IPTG for induction. The expressed protein in its bacterial culture lysate form and/or purified form is then injected in mice for antibody production. The mice are bled, and the sera collected for agglutination, in vitro growth inhibition, and complement-dependent and -independent lysis tests.

B. Specific Chimeric Nucleic Acid Sequences

Various chimeric nucleic acid sequences were generated. The nucleic acid sequences are described as encoding polypeptides from Borrelia proteins. The chimeric nucleic acid sequences are produced such that the nucleic acid sequence encoding one polypeptide is in the same reading frame as the nucleic acid sequence encoding the next polypeptide in the chimeric protein sequence encoded by the chimeric nucleic acid sequence. The proteins are listed sequentially (in order of presence of the encoding sequence) in the description of the chimeric nucleic acid sequence. For example, if a chimeric nucleic acid sequence consists of bp 1–650 from OspA-1 and bp 651–820 from OspA-2 were sequenced, the sequence of the chimer would include the first 650 base pairs from OspA-1 followed immediately by base pairs 651–820 of OspA-2.

OspA-K48/OspA-PGau A chimer of OspA from strain K48 (OspA-K48) and OspA from strain PGau (OspA-PGau) was generated using the method described above. This chimeric nucleic acid sequence included bp 1–654 from OspA-K48, followed by bp 655–820 from OspA-PGau. Primers used included: the amino-terminal sequence of OspA primer #607 (SEQ ID NO. 16); the fusion primer, 5'-AAAGTAGAAGTTTTTGAATCCCATTTTCCAGTTT TTTT-3' (minus strand primer #668–654) (SEQ ID NO. 84); the carboxy-terminal sequence of OspA primer #586 (SEQ ID NO. 19); and the sequence primers #369 (SEQ ID NO. 14) and #357 (SEQ ID NO. 15). The chimeric nucleic acid sequence is presented as SEQ ID NO. 85; the chimeric protein encoded by this chimeric nucleic acid sequence is presented as SEQ ID NO. 86.

OspA-B31/OspA-PGau A chimer of OspA from strain B31 (OspA-B31) and OspA from strain PGau (OspA-PGau) was generated using the method described above. This chimeric nucleic acid sequence included bp 1–651 from OspA-B31, followed by bp 652–820 from OspA-PGau. Primers used included: the fusion primer, 5'-AAAGTAGAAGTTTTTGAATTCCAAGCTGCAGTT TT-3' (minus strand primer #668–651) (SEQ ID NO. 87); and the sequence primer, #369 (SEQ ID NO. 14). The chimeric nucleic acid sequence is presented as SEQ ID NO. 88; the chimeric protein encoded by this chimeric nucleic acid sequence is presented as SEQ ID NO. 89.

OspA-B31/OspA-K48 A chimer of OspA from strain B31 (OspA-B31) and OspA from strain K48 (OspA-K48) was generated using the method described above. This chimeric nucleic acid sequence included bp 1–651 from OspA-B31, followed by bp 652–820 from OspA-K48. Primers used included: the fusion primer, 5'-AAAGTGGAAGTTTTTGAATTCCAAGCTGCAGTT TTTTT-3' (minus strand primer #671–651) (SEQ ID NO. 90); and the sequence primer, #369 (SEQ ID NO. 14). The chimeric nucleic acid sequence is presented as SEQ ID NO. 91; the chimeric protein encoded by this chimeric nucleic acid sequence is presented as SEQ ID NO. 92.

OspA-B31/OspA-25015 A chimer of OspA from strain B31 (OspA-B31) and OspA from strain 25015 (OspA-25015) was generated using the method described above. This chimeric nucleic acid sequence included bp 1–651 from OspA-B31, followed by bp 652–820 from OspA-25015. Primers used included: the fusion primer, 5'-TAAAGTTGAAGTGCCTGCATTCCAAGCTGCAGT TT-3' (SEQ ID NO. 93). The chimeric nucleic acid sequence is presented as SEQ ID NO. 94; the chimeric protein encoded by this chimeric nucleic acid sequence is presented as SEQ ID NO. 95.

OspA-K48/OspA-B31/OspA-K48 A chimer of OspA from strain B31 (OspA-B31) and OspA from strain K48 (OspA-K48) was generated using the method described above. This chimeric nucleic acid sequence included bp 1–570 from OspA-B31, followed by bp 570–651 from OspA-B31, followed by bp 650–820 from OspA-K48. Primers used included: the fusion primer, 5'-CCCCAGATTTTGAAATCTTGCTTAAAACAAC-3' (SEQ ID NO. 96); and the sequence primer, #357 (SEQ ID NO. 15). The chimeric nucleic acid sequence is presented as SEQ ID NO. 97; the chimeric protein encoded by this chimeric nucleic acid sequence is presented as SEQ ID NO. 98.

OspA-B31/OspA-K48/OspA-B31/OspA-K48 A chimer of OspA from strain B31 (OspA-B31) and OspA from strain K48 (OspA-K48) was generated using the method described above. This chimeric nucleic acid sequence included bp 1–420 from OspA-B31, followed by 420–570 from OspA-K48, followed by bp 570–650 from OspA-B31, followed by bp 651–820 from OspA-K48. Primers used included: the fusion primer, 5'-CAAGTCTGGTTCCAATTTGCTCTTGTTATTAT-3' (minus strand primer #436–420) (SEQ ID NO. 99); and the sequence primer, #357 (SEQ ID NO. 15). The chimeric nucleic acid sequence is presented as SEQ ID NO. 100; the chimeric protein encoded by this chimeric nucleic acid sequence is presented as SEQ ID NO. 101.

OspA-B31/OspB-B31 A chimer of OspA and OspB from strain B31 (OspA-B31, OspB-B31) was generated using the method described above. The chimeric nucleic acid sequence included bp 1–651 from OspA-B31, followed by bp 652–820 from OspB-B31. Primers used included: the fusion primer, 5'-GTTAAAGTGCTAGTACTGTCATTCCAAGCTGCA GTTTTTTT-3' (minus strand primer #740–651) (SEQ ID NO. 102); the carboxy-terminal sequence of OspB primer #1106 (SEQ ID NO. 25); and the sequence primer #357 (SEQ ID NO. 15). The chimeric nucleic acid sequence is presented as SEQ ID NO. 103; the chimeric protein encoded by this chimeric nucleic acid sequence is presented as SEQ ID NO. 104.

OspA-B31/OspB-B31/OspC-B31 A chimer of OspA, OspB and OspC from strain B31 (OspA-B31, OspB-B31, and OspC-B31) was generated using the method described above. The chimeric nucleic acid sequence included bp 1–650 from OspA-B31, followed by bp 652–820 from OspB-B31, followed by bp 74–630 of OspC-B31. Primers used included: the fusion primer, 5'-TGCAGATGTAATCCCATCCGCCATTTTTAAAGCG TTTTT-3' (SEQ ID NO. 105); and the carboxy-terminal sequence of OspC primer (SEQ ID NO. 28). The chimeric nucleic acid sequence is presented as SEQ ID NO. 106; the chimeric protein encoded by this chimeric nucleic acid sequence is presented as SEQ ID NO. 107.

OspC-B31/OspA-B31/OspB-B31 A chimer of OspA, OspB and OspC from strain B31 (OspA-B31, OspB-B31, and OspC-B31) was generated using the method described above. The chimeric nucleic acid sequence included bp 1–630 from OspC-B31, followed by bp 52–650 from OspA-B31, followed by bp 650–820 of OspB-B31. Primers used included: the amino-terminal sequence of OspC primer having SEQ ID NO. 27; the fusion primer, 5'-GCTGCTAACATTTTGCTTAGGTTTTTTTGGACTT TC-3' (minus strand primer #69–630) (SEQ ID NO. 108); and the sequence primers #520 (SEQ ID NO. 40) and #200 (SEQ ID NO. 18). The chimeric nucleic acid sequence is presented as SEQ ID NO. 109; the chimeric protein encoded by this chimeric nucleic acid sequence is presented as SEQ ID NO. 110.

Additional Chimeric Nucleic Acid Sequences

Using the methods described above, other chimeric nucleic acid sequences were produced. These chimeric nucleic acid sequences, and the proteins encoded, are summarized in Table 3.

TABLE III

Chimeric Nucleic acid Sequences and the Encoded Proteins

| Chimers Generated (base pairs) | SEQ ID NO. (nt) | SEQ ID NO. (protein) |
|---|---|---|
| OspA (52–882)/p93 (1168–2100) | 111 | 112 |
| OspB (45–891)/p41 (122–234) | 113 | 114 |
| OspB (45–891)/p41 (122–295) | 115 | 116 |
| OspB (45–891)/p41 (140–234) | 117 | 118 |
| OspB (45–891)/p41 (140–295) | 119 | 120 |
| OspB (45–891)/p41 (122–234)/ OspC (58–633) | 121 | 122 |
| OspA-Tro/OspA-Bo | 137 | 138 |
| OspA-PGau/OspA-Bo | 139 | 140 |
| OspA-B31/OspA-PGau/OspA-B31/ OspA-K48 | 141 | 142 |
| OspA-PGau/OspA-B31/OspA-K48 | 143 | 144 |

C. Purification of Proteins Generated by Chimeric Nucleic Acid Sequences

The chimeric nucleic acid sequences described above, as well as chimeric nucleic acid sequences produced by the methods described above, are used to produce chimeric proteins encoded by the nucleic acid sequences. Standard methods, such as those described above in Example 3, concerning the expression of proteins from Borrelia genes, can be used to express the proteins in a compatible host organism. The chimeric proteins can then be isolated and purified using standard techniques.

If the chimeric protein is soluble, it can be purified on a Sepharose column. Insoluble proteins can be solubilized in guanidine and purified on a Ni++ column; alternatively, they can be solubilized in 10 mM $NaPO_4$ with 0.1–1% TRIXON×114, and subsequently purified over an S column (Pharmacia). Lipidated proteins were generally purified by the latter method. Solubility was determined by separating both soluble and insoluble fractions of cell lysate on a 12% PAGE gel, and checking for the localization of the protein by Coomasie staining, or by Western blotting with monoclonal antibodies directed to an antigenic polypeptide of the chimeric protein.

Equivalents

Those skilled in the art will recognize, or be able to ascertain using no more than routine experimentation, many equivalents to the specific embodiments of the invention described herein. Such equivalents are intended to be encompassed in the scope of the following claims.

What is claimed is:

1. A protein having an amino acid sequence selected from the group consisting of: SEQ ID NO. 86, SEQ ID NO. 89, SEQ ID NO. 92, SEQ ID NO. 95, SEQ ID NO. 98, SEQ ID NO. 101, SEQ ID NO. 104, SEQ ID NO. 107, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 138, SEQ ID NO. 140, SEQ ID NO. 142, and SEQ ID NO. 144.

2. A chimeric protein comprising two polypeptides derived from outer surface protein A from different Lyme Disease causing strains of Borrelia wherein the first polypeptide comprises outer surface protein A from the N-terminus to and including a conserved tryptophan and the second polypeptide comprises outer surface protein A from the conserved tryptophan to the C-terminus of the protein wherein said first polypeptide and said second polypeptide are from different strains of Lyme Disease causing Borrelia and wherein the amino acid sequence of said chimeric protein is not the same as the amino acid sequence of either outer surface protein A from which said first polypeptide and said second polypeptide are obtained and wherein each polypeptide retains antigenicity in the chimeric protein.

3. The chimeric protein of claim 2, wherein the polypeptides are derived from two genospecies of Lyme Disease causing Borrelia.

4. A chimeric OspA protein comprising
   a) a first polypeptide, comprising outer surface protein A from the N-terminus to and including a conserved tryptophan, wherein said first polypeptide includes hypervariable regions comprising residues 120 through 140, residues 150 through 180, and residues 200 through 217, and
   b) a second polypeptide comprising outer surface protein A from the conserved tryptophan to the C-terminus of the protein;

wherein the Lyme disease causing strain of Borrelia from which at least one of the group consisting of: any one of said hypervariable regions and said second polypeptide differs from the Lyme disease causing strain of Borrelia from which the remainder of said first polypeptide is obtained, and wherein the hypervariable region comprising residues 200 through 217 and said second polypeptide are from different Lyme disease causing strains of Borrelia, and wherein the amino acid sequence of said chimeric OspA protein is not the same as the amino acid sequence of any outer surface protein A from which said first polypeptide and said second polypeptide are obtained and wherein the chimeric protein retains antigenicity representative of the OspA protein of the parent Borrelia strains.

5. The chimeric protein of claim 4, wherein at least two of the polypeptides within the chimeric protein are from different genospecies of Borrelia.

* * * * *

UNITED STATES PATENT AND TRADEMARK OFFICE
CERTIFICATE OF CORRECTION

PATENT NO. : 6,248,562 B1
DATED : June 19, 2001
INVENTOR(S) : John J. Dunn and Benjamin J. Luft It is certified that error appears in the above-identified patent and that said Letters Patent is hereby corrected as shown below:

Column 3,
Line 41, delete "OspA-25015 (SEQ ID NO.12)" and insert -- the OspA-B31/OspA-25015 chimer (SEQ ID NO. 94) --;
Line 42, delete "13" and insert -- 95 --.

Column 5,
Line 53, delete "141" and insert -- 143 --;
Line 54, delete "142" and insert -- 144 --;
Line 57, delete "143" and insert -- 141 --;
Line 58, delete "144" and insert -- 142 --.

Column 17,
Line 51, delete "(SID 49)";
Line 53, delete "137" and insert -- 49 --;
Line 54, delete "141" and insert -- 57 --;
Line 56, delete "(SID 55)";
Line 57, delete "140" and insert -- 56 --;
Line 61, delete "138" and insert -- 50 --.

Column 18,
Line 20, delete "142" and insert -- 58 --;
Line 21, delete "139" and insert -- 55 --.

Column 21,
Line 13, delete "SEQ ID NO. 50 (p41-K48),";
Lines 14 and 15, delete ",SEQ ID NO. 56 (p41-PTrob), and SEQ ID NO. 58 (p41-PHei)".

UNITED STATES PATENT AND TRADEMARK OFFICE
CERTIFICATE OF CORRECTION

PATENT NO. : 6,248,562 B1
DATED : June 19, 2001
INVENTOR(S) : John J. Dunn and Benjamin J. Luft It is certified that error appears in the above-identified patent and that said Letters Patent is hereby corrected as shown below:

Column 27,
Line 21, delete "141" and insert -- 143 --, and delete "142" and insert -- 144 --;
Line 23, delete "143" and insert -- 141 --, and delete "144" and insert -- 142 --.

Signed and Sealed this

Twenty-third Day of April, 2002

Attest:

JAMES E. ROGAN
Attesting Officer *Director of the United States Patent and Trademark Office*

UNITED STATES PATENT AND TRADEMARK OFFICE
CERTIFICATE OF CORRECTION

| | | |
|---|---|---|
| PATENT NO. | : 6,248,562 B1 | Page 1 of 1 |
| APPLICATION NO. | : 08/235836 | |
| DATED | : June 19, 2001 | |
| INVENTOR(S) | : John J. Dunn and Benjamin J. Luft | |

It is certified that error appears in the above-identified patent and that said Letters Patent is hereby corrected as shown below:

Column 1, line 16, after "New York" add "and with Government support under contract number DE-AC02-98CH10886, awarded by the U.S. Department of Energy"

Signed and Sealed this

Twenty-third Day of August, 2011

David J. Kappos
*Director of the United States Patent and Trademark Office*